US012528761B2

(12) United States Patent
von Geldern et al.

(10) Patent No.: US 12,528,761 B2
(45) Date of Patent: Jan. 20, 2026

(54) THYROMIMETICS

(71) Applicant: Autobahn Therapeutics, Inc., San Diego, CA (US)

(72) Inventors: Thomas von Geldern, Richmond, IL (US); Bradley Backes, San Francisco, CA (US); Brian Andrew Stearns, San Diego, CA (US); Jill Melissa Baccei, San Diego, CA (US); Jason Randall Harris, San Diego, CA (US)

(73) Assignee: AUTOBAHN THERAPEUTICS, INC., San Diego, CA (US)

( * ) Notice: Subject to any disclaimer, the term of this patent is extended or adjusted under 35 U.S.C. 154(b) by 363 days.

(21) Appl. No.: 18/002,037

(22) PCT Filed: Jun. 17, 2021

(86) PCT No.: PCT/US2021/037862

§ 371 (c)(1),
(2) Date: Dec. 15, 2022

(87) PCT Pub. No.: WO2021/257851

PCT Pub. Date: Dec. 23, 2021

(65) Prior Publication Data

US 2023/0242471 A1 Aug. 3, 2023

Related U.S. Application Data

(60) Provisional application No. 63/040,453, filed on Jun. 17, 2020.

(51) Int. Cl.

| | |
|---|---|
| ***C07C 59/56*** | (2006.01) |
| ***C07C 229/20*** | (2006.01) |
| ***C07C 237/20*** | (2006.01) |
| ***C07C 317/46*** | (2006.01) |

(52) U.S. Cl.

CPC ............ *C07C 59/56* (2013.01); *C07C 229/20* (2013.01); *C07C 237/20* (2013.01); *C07C 317/46* (2013.01)

(58) Field of Classification Search

CPC ...... C07C 59/56; C07C 229/20; C07C 237/20

See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,652,441 | A | 3/1987 | Okada et al. |
| 4,675,189 | A | 6/1987 | Kent et al. |
| 4,677,191 | A | 6/1987 | Tanaka et al. |
| 4,723,027 | A | 2/1988 | Stoutamire et al. |
| 4,728,721 | A | 3/1988 | Yamamoto et al. |
| 4,741,897 | A | 5/1988 | Andrews et al. |
| 4,917,893 | A | 4/1990 | Okada et al. |
| 4,992,445 | A | 2/1991 | Lawter et al. |
| 5,001,139 | A | 3/1991 | Lawter et al. |
| 5,023,252 | A | 6/1991 | Hseih |
| 5,466,569 | A | 11/1995 | Eber et al. |
| 5,616,345 | A | 4/1997 | Geoghegan et al. |
| 5,883,294 | A | 3/1999 | Scanlan et al. |
| 6,054,485 | A | 4/2000 | Schwartz et al. |
| 6,107,517 | A | 8/2000 | Scanlan et al. |
| 6,236,946 | B1 | 5/2001 | Scanlan et al. |
| 6,441,015 | B2 | 8/2002 | Aspnes et al. |
| 6,787,652 | B1 | 9/2004 | Dow et al. |
| 7,288,571 | B2 | 10/2007 | Hangeland et al. |
| 7,302,347 | B2 | 11/2007 | Baxter et al. |
| 7,915,261 | B2 | 3/2011 | Ishii et al. |
| 7,919,494 | B2 | 4/2011 | Ishii et al. |
| 7,919,495 | B2 | 4/2011 | Ishii et al. |
| 9,562,012 | B2 | 2/2017 | Tanis et al. |
| 9,701,650 | B2 | 7/2017 | Scanlan et al. |
| 10,130,643 | B2 | 11/2018 | Cable et al. |
| 10,226,438 | B2 | 3/2019 | Scanlan et al. |
| 10,392,356 | B2 | 8/2019 | Scanlan et al. |
| 10,544,075 | B2 | 1/2020 | Scanlan et al. |
| 10,870,616 | B2 | 12/2020 | Scanlan et al. |
| 11,104,654 | B2 | 8/2021 | Scanlan et al. |
| 11,325,886 | B2 | 5/2022 | Scanlan et al. |
| 11,510,887 | B2 | 11/2022 | Scanlan et al. |
| 11,578,032 | B2 | 2/2023 | Scanlan |
| 11,613,517 | B2 | 3/2023 | Scanlan et al. |
| 11,780,825 | B2 | 10/2023 | Zhou et al. |
| 2003/0203898 | A1 | 10/2003 | Haning et al. |
| 2003/0215434 | A1 | 11/2003 | Khan et al. |

(Continued)

FOREIGN PATENT DOCUMENTS

| | | | |
|---|---|---|---|
| CN | 1882327 | A | 12/2006 |
| CN | 101180097 | A | 5/2008 |

(Continued)

OTHER PUBLICATIONS

Lian et al, Jun. 11, 2020, CA Doc No. 173:90753, p. 1-2. (Year: 2020).*

U.S. Appl. No. 17/780,465 Office Action dated Dec. 27, 2024.

Actis et al., Small molecule inhibitors of PCNA/PIP-box interaction suppress translesion DNA synthesis. Bioorg Med Chem. 21(7):1972-1977 (2013).

Alonso-Merino et al., Thyroid hormones inhibit TGF-beta signaling and attenuate fibrotic responses. PNAS USA 113(24):E3451-E3460 (2016).

Ashraf et al., Synthesis, characterization and in vitro hydrolysis studies of ester and amide prodrugs of dexibuprofen. Medicinal Chemistry Research 21:3361-3368 (2012).

Balkwill et al., Smoldering and polarized inflammation in the initiation and promotion of malignant disease. Cancer Cell 7(3):211-217 (2005).

(Continued)

*Primary Examiner* — Adam C Milligan
*Assistant Examiner* — Karen Cheng
(74) *Attorney, Agent, or Firm* — WILSON SONSINI GOODRICH & ROSATI

(57) ABSTRACT

Compounds provided herein function as thyromimetics and have utility for treating diseases such as neurodegenerative disorders and fibrotic diseases. Pharmaceutical compositions containing such compounds are also provided, as are methods of their preparation.

14 Claims, No Drawings

(56) References Cited

U.S. PATENT DOCUMENTS

| | | | |
|---|---|---|---|
| 2004/0157844 | A1 | 8/2004 | Dow et al. |
| 2005/0282872 | A1 | 12/2005 | Hangeland et al. |
| 2007/0021407 | A1 | 1/2007 | Boyle et al. |
| 2008/0124280 | A1 | 5/2008 | Mousa et al. |
| 2008/0221170 | A1 | 9/2008 | Roberts et al. |
| 2009/0028925 | A1 | 1/2009 | Erion et al. |
| 2009/0062330 | A1 | 3/2009 | Kalafer et al. |
| 2009/0105347 | A1 | 4/2009 | Scanlan et al. |
| 2009/0232879 | A1 | 9/2009 | Cable et al. |
| 2009/0306225 | A1 | 12/2009 | Lichter et al. |
| 2009/0318514 | A1 | 12/2009 | Garcia Collazo et al. |
| 2010/0099608 | A1 | 4/2010 | Browning |
| 2010/0216771 | A1 | 8/2010 | Li |
| 2010/0303934 | A1 | 12/2010 | Soumyanath et al. |
| 2011/0178134 | A1 | 7/2011 | Jaehne et al. |
| 2012/0004166 | A1 | 1/2012 | Keil et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1 | 9/2014 | Fujii et al. |
| 2016/0081955 | A1 | 3/2016 | Scanlan et al. |
| 2016/0199309 | A1 | 7/2016 | Mousa et al. |
| 2016/0244418 | A1 | 8/2016 | Scanlan et al. |
| 2017/0007589 | A1 | 1/2017 | Ding et al. |
| 2017/0226154 | A1 | 8/2017 | Evans et al. |
| 2018/0057472 | A1 | 3/2018 | Scanlan et al. |
| 2019/0175531 | A1 | 6/2019 | Scanlan et al. |
| 2019/0210950 | A1 | 7/2019 | Scanlan et al. |
| 2020/0163930 | A1 | 5/2020 | Jerzak et al. |
| 2020/0181103 | A1 | 6/2020 | Scanlan et al. |
| 2020/0361849 | A1 | 11/2020 | Von Geldern et al. |
| 2020/0405669 | A1 | 12/2020 | Scanlan et al. |
| 2021/0002208 | A1 | 1/2021 | Scanlan |
| 2021/0053917 | A1 | 2/2021 | Von Geldern et al. |
| 2021/0087137 | A1 | 3/2021 | Scanlan et al. |
| 2021/0230146 | A1 | 7/2021 | Zhou et al. |
| 2023/0048992 | A1 | 2/2023 | Von et al. |
| 2023/0242473 | A1 | 8/2023 | Von Geldern et al. |
| 2023/0242492 | A1 | 8/2023 | Von Geldern et al. |
| 2023/0348364 | A1 | 11/2023 | Backes et al. |

FOREIGN PATENT DOCUMENTS

| | | | | |
|---|---|---|---|---|
| CN | 101189248 | A | | 5/2008 |
| CN | 101547898 | A | | 9/2009 |
| CN | 101600450 | A | | 12/2009 |
| CN | 101610774 | A | | 12/2009 |
| CN | 101848712 | A | | 9/2010 |
| CN | 107848940 | A | | 3/2018 |
| EP | 1148054 | B1 | | 11/2005 |
| EP | 3259246 | A1 | | 12/2017 |
| JP | S59116256 | A | | 7/1984 |
| JP | H09301917 | A | | 11/1997 |
| JP | 2001114768 | A | | 4/2001 |
| JP | 2001226359 | A | | 8/2001 |
| JP | 2002053564 | A | | 2/2002 |
| JP | 2004512303 | A | | 4/2004 |
| JP | 2004517037 | A | | 6/2004 |
| JP | 2008542301 | A | | 11/2008 |
| JP | 2008545711 | A | | 12/2008 |
| JP | 2012106996 | A | | 6/2012 |
| JP | 2016517884 | A | | 6/2016 |
| PE | 20180021 | A1 | | 1/2018 |
| RU | 2007148927 | A | | 7/2009 |
| WO | WO-9321146 | A1 | | 10/1993 |
| WO | WO-9900353 | A1 | | 1/1999 |
| WO | WO-0039077 | A2 | | 7/2000 |
| WO | WO-0073292 | A1 | | 12/2000 |
| WO | WO-0160784 | A1 | | 8/2001 |
| WO | WO-0190053 | A1 | | 11/2001 |
| WO | WO-0200167 | A2 | | 1/2002 |
| WO | WO-0234260 | A1 | | 5/2002 |
| WO | WO-02072539 | A1 | | 9/2002 |
| WO | WO-02081426 | A1 | | 10/2002 |
| WO | WO-2004043939 | A1 | | 5/2004 |
| WO | WO-2006031922 | A2 | | 3/2006 |
| WO | WO-2006128056 | A2 | | 11/2006 |
| WO | WO-2006128058 | A2 | | 11/2006 |
| WO | WO-2007110226 | A1 | | 10/2007 |
| WO | WO-2007132475 | A1 | | 11/2007 |
| WO | WO-2008125724 | A1 | | 10/2008 |
| WO | WO-2013006734 | A1 | | 1/2013 |
| WO | WO-2014078892 | A1 | | 5/2014 |
| WO | WO-2014178892 | A1 | | 11/2014 |
| WO | WO-2014178931 | A1 | | 11/2014 |
| WO | WO-2015188015 | A1 | | 12/2015 |
| WO | WO-2016134292 | A1 | | 8/2016 |
| WO | WO-2017015360 | A1 | | 1/2017 |
| WO | WO-2017201320 | A1 | | 11/2017 |
| WO | WO-2018032012 | A1 | | 2/2018 |
| WO | WO-2018208707 | A1 | | 11/2018 |
| WO | WO-2019160980 | A1 | | 8/2019 |
| WO | WO2020117962 | | * | 6/2020 |
| WO | WO-2020118564 | A1 | | 6/2020 |
| WO | WO-2020123861 | A1 | | 6/2020 |
| WO | WO-2020169069 | A1 | | 8/2020 |
| WO | WO-2020180624 | A1 | | 9/2020 |
| WO | WO-2020227549 | A1 | | 11/2020 |
| WO | WO-2021108549 | A1 | | 6/2021 |
| WO | WO-2021247847 | A1 | | 12/2021 |
| WO | WO-2021257804 | A1 | | 12/2021 |
| WO | WO-2021257834 | A1 | | 12/2021 |
| WO | WO-2021257851 | A1 | | 12/2021 |

OTHER PUBLICATIONS

Bastin et al. Salt selection and optimisation procedures for pharmaceutical new chemical entities. Organic Process Research & Development 4(5):427-435 (2000).

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4):154-157 (2004).

Baxter et al., Selective modulation of thyroid hormone receptor action. J. Steroid Biochem. Mol. Bio. 76:31-42 (2001).

Belikov. Pharmaceutical Chemistry: Manual. Moscow: MEDpress-inform (pp. 27-29) (2007).

Berge et al. Pharmaceutical Salts. Journal of Pharmaceutical Sciences 66(1):1-19 (Jan. 1977).

Berkenstam et al., The thyroid hormone mimetic compound KB2115 lowers plasma LDL cholesterol and stimulates bile acid synthesis without cardiac effects in humans. PNAS USA 105(2):663-667 (2008).

Bernal et al., Action of thyroid hormone in brain. J Endocrinol Invest. 25(3):268-288 (2002).

Bernal et al., Thyroid hormone receptors in brain development and function. Nat Clin Pract Endocrinol Metab. 3(3):249-259 (2007).

Biondi et al., Hypothyroidism as a risk factor for cardiovascular disease. Endocrine 24:1-13 (2004).

Boger et al., Fatty acid amide hydrolase substrate specificity. Bioorg Med Chem Lett. 10(23):2613-2616 (2000).

Borngraeber et al. Ligand Selectivity by Seeking Hydrophobicity in Thyroid Hormone Receptor. PNAS USA 100(26):15358-15363 (2003).

Boymond et al., Preparation of highly functionalized grignard reagents by an iodine-magnesium exchange reaction and its application in solid-phase synthesis. Angew Chem Int Ed Engl. 37(12):1701-1703 (1998).

Calza et al., Thyroid hormone and remyelination in adult central nervous system: a lesson from an inflammatory-demyelinating disease. Brain Res Brain Res Rev. 48(2):339-346 (2005).

Chiellini et al., A high-affinity subtype-selective agonist ligand for the thyroid hormone receptor. Chemistry and Biology 5(6):299-306 (1998).

Chiellini et al., Synthesis and biological activity of novel thyroid hormone analogues: 5'-aryl substituted GC-1 derivatives. Bioorg Med Chem. 10(2):333-346 (2002).

(56) References Cited

OTHER PUBLICATIONS

Cravatt et al., Supersensitivity to anandamide and enhanced endogenous cannabinoid signaling in mice lacking fatty acid amide hydrolase. Proc Natl Acad Sci U S A 98(16):9371-9376 (2001).
Dell'Acqua et al., Functional and molecular evidence of myelin- and neuroprotection by thyroid hormone administration in experimental allergic encephalomyelitis. Neuropathol Appl Neurobiol. 38(5):454-470 (2012).
Devereaux et al., Increasing thyromimetic potency through halogen substitution. ChemMedChem. 11(21):2459-2465 (2016).
D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).
Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Elbers et al. Thyroid Hormone Mimetics: the Past, Current Status and Future Challenges. Cur Atheroscler Rep 18(3):14 (2016).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. PNAS USA 104(39):15490-15495 (2007).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould et al. Salt Selection for Basic Drugs. Int J. Pharm. 33:201-217 (1986).
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
Hashimoto et al., Design and synthesis of complementing ligands for mutant thyroid hormone receptor TRbeta(R320H): a tailor-made approach toward the treatment of resistance to thyroid hormone. Bioorg Med Chem. 13(11):3627-3639 (2005).
Johnson, Demyelinating diseases, in: The Infectious Etiology of Chronic Diseases: Defining the Relationship, Enhancing the Research, and Mitigating the Effects: Workshop Summary. Institute of Medicine (US) Forum on Microbial Threats; Knobler SL, O'Connor S, Lemon SM, et al., editors. Washington (DC): National Academies Press (US); 45-52 (2004).
Jorgensen. Thyroid hormones and analogues. II. Structure-activity relationships. Hormonal Proteins and Peptides; Li, C. H., Ed.; Academic Press: New York 6:107-204 (1978).
Kavirajan et al., Efficacy and adverse effects of cholinesterase inhibitors and memantine in vascular dementia: a meta-analysis of randomised controlled trials. Lancet Neurol. 6(9):782-792 (2007).
Koenning et al., Myelin gene regulatory factor is required for maintenance of myelin and mature oligodendrocyte identity in the adult CNS. J Neurosci. 32(36):12528-12542 (2012).
Krogsgaard-Larsen et al. Chapter 4: Design and application of prodrugs. Textbook of Drug Designing and Discovery, US, Taylor & Francis Inc (3rd Ed.) (pp. P460-514).
Lee et al., Drug transporters in the central nervous system: brain barriers and brain parenchyma considerations. Pharmacological Review 53(4):569-596 (2001).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Malm et al., Recent advances in the development of agonists selective for beta1-type thyroid hormone receptor. Mini Rev Med Chem. 7(1):79-86 (2007).
Mandal et al., Pd-C-induced catalytic transfer hydrogenation with triethylsilane. Journal of Organic Chemistry 72(17):6599-6601 (2007).
Martin et al. The proliferating cell nuclear antigen regulates retinoic acid receptor transcriptional activity through direct protein-protein interaction. Nucleic Acids Res. 33(13):4311-21 (2005).
Massague. TGFbeta signalling in context. Nat Rev Mol Cell Biol. 13(10):616-630 (2012).
Meinig et al., Structure-activity relationships of central nervous system penetration by fatty acid amide hydrolase (FAAH)-targeted thyromimetic prodrugs. ACS Med Chem Lett. 10(1):111-116 (2018).
Meinig et al., Targeting fatty-acid amide hydrolase with prodrugs for CNS-selective therapy. ACS Chem Neurosci. 8(11):2468-2476 (2017).
Miller et al., Primary-progressive multiple sclerosis. Lance Neurol. 6:903-912 (2007).
Miyabara et al., Thyroid hormone receptor-beta-selective agonist GC-24 spares skeletal muscle type I to II fiber shift. Cell Tissue Res. 321(2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'Shea et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
Patani et al. Bioisosterism: A Rational Approach in Drug Design. Chem. Rev. 96:3147-3176 (1996).
PCT/CN2018/120634 International Search Report and Written Opinion dated Sep. 11, 2019.
PCT/US2016/018732 International Search Report and Written Opinion dated Jun. 1, 2016.
PCT/US2017/033388 International Search Report and Written Opinion dated Aug. 16, 2017.
PCT/US2019/017881 International Search Report and Written Opinion dated May 13, 2019.
PCT/US2019/019576 International Search Report and Written Opinion dated May 13, 2019.

(56) References Cited

OTHER PUBLICATIONS

PCT/US2019/066066 International Search Report and Written Opinion dated Mar. 5, 2020.
PCT/US2020/020199 International Search Report and Written Opinion dated May 14, 2020.
PCT/US2020/062229 International Invitation to Pay Additional Fees dated Jan. 27, 2021.
PCT/US2020/062229 International Search Report and Written Opinion dated Mar. 24, 2021.
PCT/US2021/035679 International Invitation to Pay Additional Fees dated Aug. 16, 2021.
PCT/US2021/035679 International Search Report and Written Opinion dated Oct. 29, 2021.
PCT/US2021/037788 International Invitation to Pay Additional Fees dated Aug. 30, 2021.
PCT/US2021/037788 International Search Report and Written Opinion dated Nov. 10, 2021.
PCT/US2021/037833 International Invitation to Pay Additional Fees dated Aug. 30, 2021.
PCT/US2021/037833 International Search Report and Written Opinion dated Nov. 17, 2021.
PCT/US2021/037862 International Invitation to Pay Additional Fees dated Aug. 30, 2021.
PCT/US2021/037862 International Search Report and Written Opinion dated Nov. 17, 2021.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
Pubchem Compound Record for CID 140404356, 2-[3,5-Dichloro-4-[(2-chloro-4-hydroxyphenyl)methyl]phenyl]-4,5-dihydro-1,2,4-triazin-3-one; https://pubchem.ncbi.nlm.nih.gov/compound/140404356 (2019).
Pubchem Compound Record for CID 142030791, 4-[(2,6-Dimethyl-4-pyrrolidin-1-ylphenyl)methyl]-2-propan-2-ylphenol; https://pubchem.ncbi.nlm.nih.gov/compound/142030791 (2019).
PubChem SID 235918886 [ https://pubchem.ncbi.nlm.nih.gov/substance/ 235918886] (2015).
PubChem SID 319635332 [ https://pubchem.ncbi.nlm.nih.gov/substance/319635332 ] (2016).
Pubmed Compound Record for CID 132562601, 2-(4-(3-(1-(2H3)Methyl-(2,2,2-2H3)ethyl)-4-hydroxybenzyl)-3,5-dlmethylphenoxy)acetic acid. U.S. National Library of Medicine https://pubchem.ncbi.nlm.nih.gov/compound/132562601 (2018).
Pubmed Compound Record for CID 132562602, 2-(4-(3-Isopropyl-4-hydroxy(alpha-3H)benzyl)-3,5-dimethylphenoxy)acetic acid. U.S. National Library of Medicine https://pubchem.ncbi.nlm.nih.gov/compound/132562602 (2018).
Reichel et al., The role of blood-brain barrier studies in the pharmaceutical industry. Curr Drug Metab. 7(2):183-203 (2006).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term=Scanlan&rank=1).
Scanlan. Sobetirome: a case history of bench-to-clinic drug discovery and development. Heart Fail Rev 15:177-182 (2010).
Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).
Tangdenpaisal et al., Synthesis of the thyroid hormone analog GC-1 via Bi(OTf)3-catalyzed benzylation. Tetrahedron 70:6789-6795 (2014).
Taub et al., Lipid lowering in healthy volunteers treated with multiple doses of MGL-3196, a liver-targeted thyroid hormone receptor-beta agonist. Atherosclerosis 230(2):373-380 (2013).
Tegeli et al. Synthesis and evaluation of amide prodrugs of mefenamic acid. International Journal of Chemical Sciences 12(3):1033-1043.
Thyroid. Abstract from poster presented at the 87th Annual Meeting of the American Thyroid Association (Oct. 18-22, 2017).
Trost et al., The thyroid hormone receptor-beta-selective agonist GC-1 differentially affects plasma lipids and cardiac activity. Endocrinology 141(9):3057-3064 (2000).
U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/updated Mar. 1, 2021].
Valadares et al. Role of halogen bonds in thyroid hormone receptor selectivity: pharmacophore-based 3D-QSSR studies. J Chem Inf Model 49(11):2606-2616 (2009).
Varga et al., Antitransforming growth factor-beta therapy in fibrosis: recent progress and implications for systemic sclerosis. Curr Opin Rheumatol. 20(6):720-728 (2008).
Vattakatuchery et al., Acetylcholinesterase inhibitors in cognitive impairment in Huntington's disease: A brief review. 3(3):62-64 (2013).
Ye et al, Thyroid receptor ligands. 1. Agonist ligands selective for the thyroid receptor beta1. J Med Chem. 46(9):1580-1588 (2003).
Yen., Physiological and molecular basis of thyroid hormone action. Physiological Reviews 81(3):1097-1142 (2001).
Yoshihara et al., A designed antagonist of the thyroid hormone receptor. Bioorg Med Chem Lett. 11(21):2821-2825 (2001).
Yoshihara et al., Structural determinants of selective thyromimetics. J Med Chem. 46(14):3152-3161 (2003).
Zhang et al., Thyroid hormone potentially benefits multiple sclerosis via facilitating remyelination. Mol Neurobiol. 53(7):4406-4416 (2016).
U.S. Appl. No. 18/002,035 Office Action dated Jul. 18, 2025.

* cited by examiner

THYROMIMETICS

CROSS-REFERENCE

This application claims benefit of U.S. Provisional Patent Application No. 63/040,453, filed on Jun. 17, 2020 which is incorporated herein by reference in its entirety.

BACKGROUND

Technical Field

The invention relates to thyromimetic compounds and to products containing the same, as well as to methods of their use and preparation.

Description of the Related Art

Thyroid hormone (TH) is a key signal for oligodendrocyte differentiation and myelin formation during development, and also stimulates remyelination in adult models of multiple sclerosis (MS) (Calzà et al., *Brain Res Revs* 48:339-346, 2005). However, TH is not an acceptable long-term therapy due to the limited therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm et al., *Mini Rev Med Chem* 7:79-86, 2007). These receptors are expressed in two major forms with heterogenous tissue distributions and overlapping but distinct sets of target genes (Yen, *Physiol Rev* 81:1097-1142, 2001). TRα is enriched in the heart, brain, and bone while TRβ is enriched in the liver (O'Shea et al., *Nucl Recept Signal* 4:e011, 2006).

It has also been reported that TH can inhibit the transforming growth factor beta (TGF-β) signaling, and, therefore, attenuate fibrotic responses (Alonso-Merino et al., *Proc Natl Acad Sci USA.* 113(24):E3451-60, 2016). TGF-β is a cytokine with pleiotropic effects in tissue homeostasis that plays a key role in pathological processes such as fibrosis (Massagué, *Nat Rev Mol Cell Biol.* 13(10):616-630, 2012). By inhibiting TGF-β signalling, TR ligands or agonists could have beneficial effects to block the progression of fibrotic diseases, such as idiopathic pulmonary fibrosis (IPF) or systemic sclerosis (Varga et al., *Curr Opin Rheumatol.* 20(6): 720-728, 2008).

Developing selective thyromimetics has been challenging due to the high sequence homology of thyroid hormone receptor subtypes; namely, only one amino acid residue on the internal surface of the ligand binding domain cavity varies between the α1 and β1 forms. Despite this challenge, several groups have reported TRβ-selective agonists. Scanlan et al. identified GC-1 (sobetirome) as one of the first potent analogs to demonstrate significant TRβ-selectivity in vitro (Chiellini et al., *Chem Biol* 5:299-306, 1998; Yoshihara et al., *J Med Chem* 46:3152-3161, 2003) and in vivo (Trost et al., *Endocrinology* 141:3057-3064, 2000; Grover et al., *Endocrinology* 145:1656-1661, 2004; Baxter et al., *Trends Endocrinol Metab* 15:154-157, 2004). As used herein, the term "sobetirome" refers to a synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1. Metabasis employs a similar core with a novel liver-targeting prodrug strategy in MB07811 (Erion et al., *PNAS* 104(39), 15490-15495, 2007). Madrigal has reported TRβ-selective activity in vivo for MGL-3196 (Taub et al., *Atherosclerosis* 230(2):373-380, 2013). KaroBio has reported on eprotirome (KB2115; Berkenstam et al., *PNAS* 105(2):663-668, 2008) and KB-141 (Ye et al., *J Med Chem* 46:1580-1588, 2003), both of which demonstrate improved TRβ-selectivity in vitro. Further studies from this group highlight additional selective compounds (Hangeland et al., *BMCL* 14:3549-3553, 2004). Two TRβ-selective agonists, identified as SKL-12846 and SKL-13784, have been reported to accumulate in the liver and to reduce cholesterol levels in rodents (Takahashi et al., *BMC* 22(1):488-498, 2014; *Xenobiotica* 2015, 1-9). Kissei has also reported selective compounds (Shiohara et al., *BMC* 20(11), 3622-3634, 2012).

While progress has been made in this field, there remains a need in the art for further selective thyromimetic compounds, as well as to products containing the same, and for methods related to their use and preparation.

BRIEF SUMMARY

Disclosed herein are compounds according to Formula I:

(I)

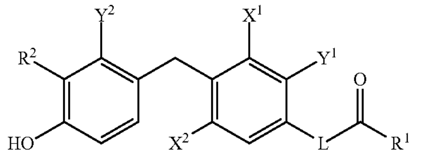

or a pharmaceutically acceptable isomer, racemate, tautomer, hydrate, solvate, isotope, or salt thereof, wherein L, $X^1$, $X^2$, $Y^1$, $Y^2$, $R^1$, and $R^2$ are as defined below.

In an embodiment, a pharmaceutical composition is provided comprising a compound having the structure of Formula (I), or a pharmaceutically acceptable isomer, racemate, tautomer, hydrate, solvate, isotope, or salt thereof, in combination with a pharmaceutically acceptable carrier, diluent, or excipient. In an embodiment, the pharmaceutical composition is for use in treating a neurodegenerative disorder including neurodegenerative disorders classified as a demyelinating disease such as X-linked adrenoleukodystrophy or multiple sclerosis. In another embodiment, the pharmaceutical composition is for use in treating a medical condition associated increased activity of TGF-β, such as a fibrotic disease.

In an embodiment, a method is provided for treating a neurodegenerative disorder in a subject in need thereof, comprising administering a compound having the structure of Formula (I), or a pharmaceutically acceptable salt or composition comprising the same. In some aspects, the neurodegenerative disorder can be classified as a demyelinating disease such as X-linked adrenoleukodystrophy or multiple sclerosis.

In another embodiment, a method is provided for treating a medical condition associated with over-expression of TGF-β in a subject in need thereof, comprising administering a compound having the structure of Formula (I), or a pharmaceutically acceptable salt or composition comprising the same. In some aspects, the medical condition associated with over-expression of TGF-β is a fibrotic disease.

DETAILED DESCRIPTION

As mentioned above, the invention relates to thyromimetic compounds, to products comprising the same, and to methods for their use and synthesis.

In one embodiment, compounds are provided having the structure of Formula (I):

(I)

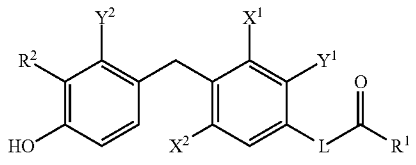

or a pharmaceutically acceptable isomer, racemate, tautomer, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
L is $-J^1-L'-J^2-$;
L' is ab sent or L' is lower alkenyl, lower alkynyl, —NH—, —NHC(O)—, —O—, —C(O)—, —OC(O)—, or $—S(O)_t—$;
$J^1$ is $—(CR_2)_m—$;
$J^2$ is $—(CR_2)_n—$;
m is 0-6;
n is 0-6;
t is 0-2;
each R is, independently, H, lower alkyl, $—NH_2$, or halo;
$R^1$ is $—NR^{1a}R^{1b}$ or $—OR^{1c}$;
$R^{1a}$ and $R^{1b}$ are each, independently, H, lower alkyl, lower alkenyl, lower alkynyl, $—OR^a$, $—NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl; and
$R^2$ is lower alkyl, lower alkenyl, carbocycle, heterocycle, carbocyclealkyl, or heterocyclealkyl;
wherein L', $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", $—S(O)_2R'$ or $—S(O)_2OR'$, wherein R' and R" are each, independently, H, lower alkyl, or lower haloalkyl;
wherein at least one of $X^1$ or $X^2$ is lower alkenyl, lower haloalkyl, or halo when $R^1$ is $—OR^{1c}$, L' is absent, m is 0, n is 0, 1, or 2, and $R^2$ is isopropyl;
wherein at least one of $X^1$ or $X^2$ is lower alkenyl, lower haloalkyl, or halo when $R^1$ is $—OR^{1c}$, L' is vinyl, m is 0, n is 0, and $R^2$ is isopropyl; or
wherein at least one of $X^1$ or $X^2$ is lower alkenyl, lower haloalkyl, or halo when $R^1$ is $—OR^{1c}$, L' is —NHC(O)—, m is 0, and n is 0 or 1; and
wherein at least one R is lower alkyl, $—NH_2$, or halo when L' is —O—, m is 0, n is 1, and $R^2$ is isopropyl or benzyl.

The acid compounds of the present invention ($R^1=—OR^{1c}$ and $R^{1c}$=H) are active agonists selectively activating the TRβ receptor. The amide compounds of the present invention ($R^1=—NR^{1a}R^{1b}$) may act as substrates for the specific hydrolase enzyme fatty acid-amide hydrolase (FAAH), which cleaves the amide, liberating the thyromimetic. Thus, prodrug conversion to drug is enhanced in tissues that express high levels of FAAH such as the central nervous system. FIG. 1 indicates that the amide prodrugs Compound 16 and 17 provides markedly higher brain levels of the parent acid Compound 15, than can be achieved by dosing Compound 15 itself. The ester compounds of the present invention ($R^1=—OR^{1c}$ and $R^{1c}\neq$H) are also prodrugs, typically processed through the action of esterases which may exist selectively in specific tissues.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of straight chain lower alkyl groups include, but are not limited to, methyl, ethyl, n-propyl, n-butyl, n-pentyl-, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "lower alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, isopropenyl, butenyl, pentenyl, and hexenyl.

As used herein, "lower alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of lower alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to —OH.

"Cyano" refers to —CN.

"Lower haloalkyl" refers to a lower alkyl as defined above with one or more hydrogen atoms replaced with halogen. Examples of lower haloalkyl groups include, but are not limited to, $—CF_3$, $—CHF_2$, and the like.

"Lower alkoxy" refers to a lower alkyl as defined above joined byway of an oxygen atom (i.e., —O-(lower alkyl). Examples of lower alkoxy groups include, but are not limited to, methoxy, ethoxy, n-propoxy, n-butoxy, isopropoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, $—OCF_3$, $—OCHF_2$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Carbocyclyl," "carbocycle," or "carbocyclic" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above.

"Carbocyclealkyl" are alkyl groups as defined above in which a hydrogen or carbon bond of the alkyl group is replaced with a bond to a carbocycle group as defined above. Examples of carbocyclealkyl groups include, but are not limited to, cy clopropylmethyl, cyclobutylmethyl, benzyl, and the like.

"Heterocyclyl," "heterocycle," or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, —CN, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclealkyl" are alkyl groups as defined above in which a hydrogen or carbon bond of the alkyl group is replaced with a bond to a heterocycle group as defined above.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

In one embodiment, compounds are provided having the structure of Formula (I), or a pharmaceutically acceptable isomer, racemate, hydrate, solvate, isotope, or salt thereof, wherein $R^2$ is lower alkyl optionally substituted with one or more halo, —CN, —OR', —NR'R'', =O, =S, —$S(O)_2R'$ or —$S(O)_2OR'$, wherein R' and R'' are each, independently, H, lower alkyl, or lower haloalkyl. In another embodiment, $R^2$ is unsubstituted lower alkyl. In a more specific embodiment, $R^2$ is methyl, ethyl, propyl, isopropyl, or butyl.

In one embodiment, compounds are provided having the structure of Formula (I), or a pharmaceutically acceptable isomer, racemate, tautomer, hydrate, solvate, isotope, or salt thereof, wherein $R^1$ is —$NR^{1a}R^{1b}$.

In one embodiment, compounds are provided having the structure of Formula (I), or a pharmaceutically acceptable isomer, racemate, tautomer, hydrate, solvate, isotope, or salt thereof, wherein $R^1$ is —$OR^{1c}$.

In one embodiment, compounds are provided having the structure of Formula (I), or a pharmaceutically acceptable isomer, racemate, tautomer, hydrate, solvate, isotope, or salt thereof, wherein L' is absent.

In one embodiment, compounds are provided having the structure of Formula (I-A):

(I-A)

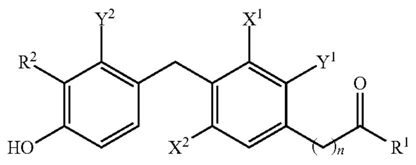

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

n is 0-3;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2R'$ or —$S(O)_2OR'$, wherein R' and R" are each, independently, H, lower alkyl, or lower haloalkyl; and wherein at least one of $X^1$ or $X^2$ is lower alkenyl, lower haloalkyl, or halo when $R^1$ is —$OR^{1c}$, n is 0, 1, or 2, and $R^2$ is isopropyl.

In one embodiment, compounds are provided having the structure of Formula (I-A-1):

(I-A-1)

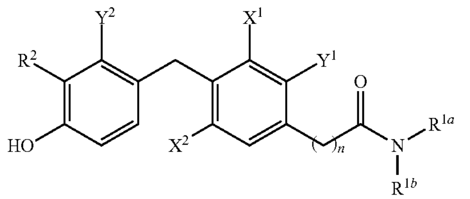

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

n is 0-3;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle; and $R^2$ is lower alkyl, lower alkenyl, carbocycle, heterocycle, carbocyclealkyl, or heterocyclealkyl;

wherein $R^{1a}$, $R^{1b}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2R'$ or —$S(O)_2OR'$, wherein R' and R" are each, independently, H, lower alkyl, or lower haloalkyl;

In one embodiment, compounds are provided having the structure of Formula (I-A-2):

(I-A-2)

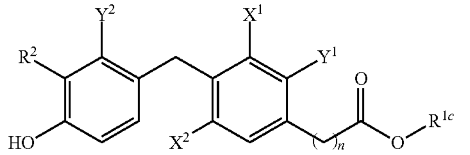

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

n is 0-3;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", —$S(O)_2R'$ or —$S(O)_2$ OR', wherein R' and R" are each, independently, H, lower alkyl, or lower haloalkyl; and wherein at least one of $X^1$ or $X^2$ is lower alkenyl, lower haloalkyl, or halo when n is 0, 1, or 2 and $R^2$ is isopropyl.

In one embodiment, compounds are provided having the structure of Formula (I), or a pharmaceutically acceptable isomer, racemate, tautomer, hydrate, solvate, isotope, or salt thereof, wherein L' is lower alkenyl.

In one embodiment, compounds are provided having the structure of Formula (I-B):

(I-B)

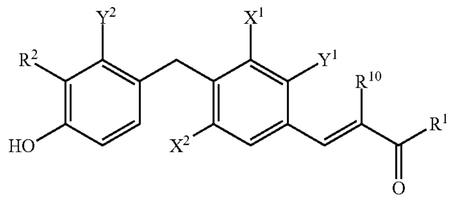

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

$R^2$ is lower alkyl, lower alkenyl, carbocycle, heterocycle, carbocyclealkyl, or heterocyclealkyl; and $R^{10}$ is H, lower alkyl, lower haloalkyl, —C(O)OR', or —C(O)NR'R";

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2R'$ or —$S(O)_2OR'$, and wherein R' and R" are each, independently, H, lower alkyl, or lower haloalkyl; and wherein at least one of $X^1$ or $X^2$ is lower alkenyl, lower haloalkyl, or halo when $R^1$ is —$OR^{1c}$ and $R^2$ is isopropyl.

In one embodiment, compounds are provided having the structure of Formula (I-B-1):

(I-B-1)

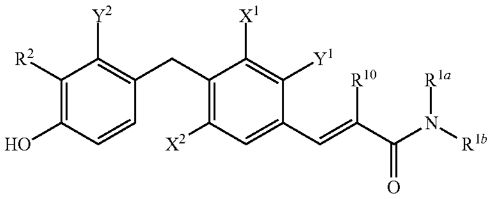

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^2$ is lower alkyl, lower alkenyl, carbocycle, heterocycle, carbocyclealkyl, or heterocyclealkyl; and $R^{10}$ is H, lower alkyl, lower haloalkyl, —C(O)OR', or —C(O)NR'R";

wherein $R^{1a}$, $R^{1b}$, and $R^2$ are each, independently, optionally substituted with one or more halo, lower alkyl, lower halo alkyl, —CN, —OR', —NR'R", =O, =S, —C(O)OR', —C(O)NR'R", —$S(O)_2R'$ or —$S(O)_2OR'$, and wherein R' and R" are each, independently, H, lower alkyl, or lower haloalkyl.

In one embodiment, compounds are provided having the structure of Formula (I-B-2):

(I-B-2)

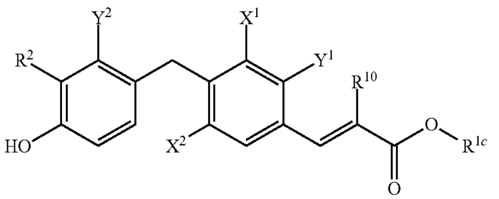

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^{1c}$ is H, lower alkyl, carbocycle, heterocycle, carbocyclealkyl, or heterocyclealkyl;

$R^2$ is lower alkyl, lower alkenyl, carbocycle, heterocycle, carbocyclealkyl, or heterocyclealkyl; and $R^{10}$ is H, lower alkyl, lower haloalkyl, —C(O)OR', or —C(O)NR'R";

wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", —$S(O)_2R'$ or —$S(O)_2$ OR', and wherein R' and R" are each, independently, H, lower alkyl, or lower haloalkyl; and wherein at least one of $X^1$ or $X^2$ is lower alkenyl, lower haloalkyl, or halo when $R^2$ is isopropyl.

In one embodiment, compounds are provided having the structure of Formula (I), or a pharmaceutically acceptable isomer, racemate, tautomer, hydrate, solvate, isotope, or salt thereof, wherein L' is lower alkynyl.

In one embodiment, compounds are provided having the structure of Formula (I-C):

(I-C)

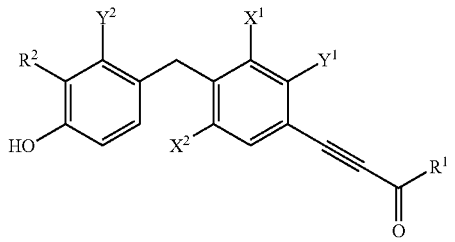

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2R'$ or —$S(O)_2OR'$, wherein R' and R" are each, independently, H, lower alkyl, or lower haloalkyl.

In one embodiment, compounds are provided having the structure of Formula (I-C-1):

(I-C-1)

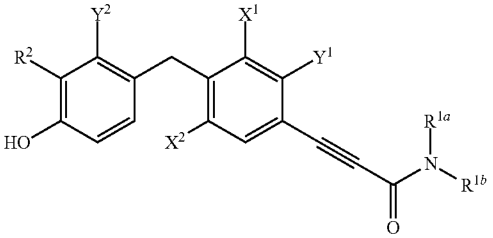

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle; $R^2$ is lower alkyl, lower alkenyl, carbocycle, heterocycle, carbocyclealkyl, or heterocyclealkyl;

wherein $R^{1a}$, $R^{1b}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2$R' or —$S(O)_2$OR', wherein R' and R" are each, independently, H, lower alkyl, or lower haloalkyl.

In one embodiment, compounds are provided having the structure of Formula (I-C-2):

(I-C-2)

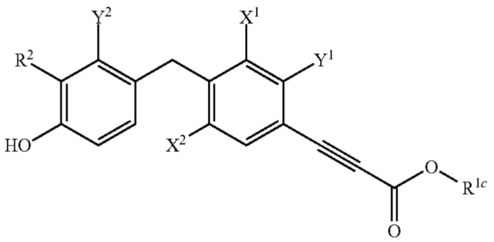

or a pharmaceutically acceptable isomer, racemate, tautomer, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
$R^{1c}$ is H, lower alkyl, carbocycle, heterocycle, carbocyclealkyl, or heterocyclealkyl; and
$R^2$ is lower alkyl, lower alkenyl, carbocycle, heterocycle, carbocyclealkyl, or heterocyclealkyl;
wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", —$S(O)_2$R' or —$S(O)_2$OR', wherein R' and R" are each, independently, H, lower alkyl, or lower haloalkyl.

In one embodiment, compounds are provided having the structure of Formula (I), or a pharmaceutically acceptable isomer, racemate, tautomer, hydrate, solvate, isotope, or salt thereof, wherein L' is —NH—.

In one embodiment, compounds are provided having the structure of Formula (I-D):

(I-D)

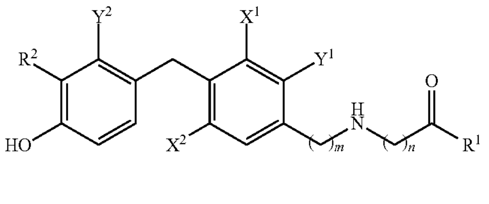

or a pharmaceutically acceptable isomer, racemate, tautomer, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
m is 0 or 1;
n is 1 or 2;

$R^1$ is —$NR^{1a}R^{1b}$ or —$OR^{1c}$;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl; and
$R^2$ is lower alkyl, lower alkenyl, carbocycle, heterocycle, carbocyclealkyl, or heterocyclealkyl;
wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2$R' or —$S(O)_2$OR', wherein R' and R" are each, independently, H, lower alkyl, or lower haloalkyl.

In one embodiment, compounds are provided having the structure of Formula (I-D-1):

(I-D-1)

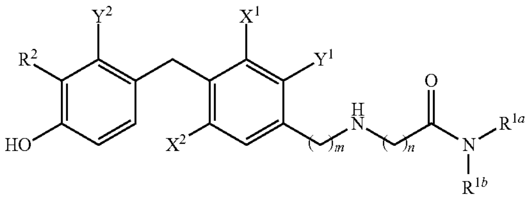

or a pharmaceutically acceptable isomer, racemate, tautomer, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
m is 0 or 1;
n is 1 or 2;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^2$ is lower alkyl, lower alkenyl, carbocycle, heterocycle, carbocyclealkyl, or heterocyclealkyl;
wherein $R^{1a}$, $R^{1b}$, and $R^2$ are each, independently, optionally substituted with one or more halo, lower alkyl, lower haloalkyl, —CN, —OR', —NR'R", =O, =S, —C(O)OR', —C(O)NR'R", —$S(O)_2$R' or —$S(O)_2$OR', wherein R' and R" are each, independently, H, lower alkyl, or lower haloalkyl.

In one embodiment, compounds are provided having the structure of Formula (I-D-2):

(I-D-2)

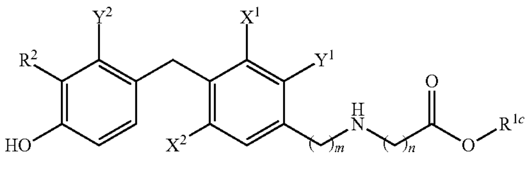

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

m is 0 or 1;

n is 1 or 2;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", —S(O)$_2$R' or —S(O)$_2$OR', wherein R' and R" are each, independently, H, lower alkyl, or lower haloalkyl.

In one embodiment, compounds are provided having the structure of Formula (I), or a pharmaceutically acceptable isomer, racemate, tautomer, hydrate, solvate, isotope, or salt thereof, wherein L' is —NHC(O)—.

In one embodiment, compounds are provided having the structure of Formula (I-E):

(I-E)

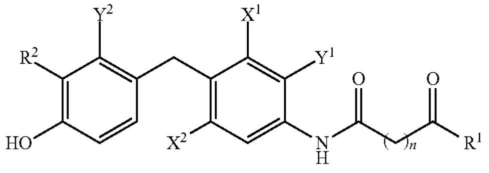

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

n is 0, 1, or 2;

$R^1$ is —NR$^{1a}$R$^{1b}$ or —OR$^{1c}$;

$R^{1a}$ and $R^{1b}$ are each, independently, H, lower alkyl, lower alkenyl, lower alkynyl, —OR$^a$, —NR$^a$R$^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", —S(O)$_2$R' or —S(O)$_2$OR', wherein R' and R" are each, independently, H, lower alkyl, or lower haloalkyl; and wherein at least one of $X^1$ or $X^2$ is lower alkenyl, lower haloalkyl, or halo when $R^1$ is —OR$^{1c}$.

In one embodiment, compounds are provided having the structure of Formula (I-E-1):

(I-E-1)

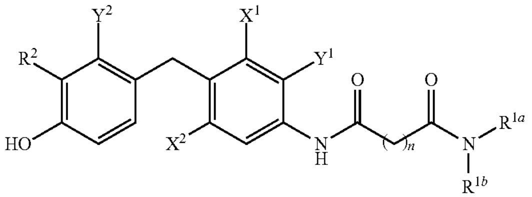

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

n is 0, 1, or 2;

$R^{1a}$ and $R^{1b}$ are each, independently, H, lower alkyl, lower alkenyl, lower alkynyl, —OR$^a$, —NR$^a$R$^b$, carbocycle, carbocyclealkyl, heterocycle, or heterocyclealkyl, or $R^{1a}$ and $R^{1b}$ taken together with the nitrogen atom to which they are attached form heterocycle;

$R^2$ is lower alkyl, lower alkenyl, carbocycle, heterocycle, carbocyclealkyl, or heterocyclealkyl;

wherein $R^{1a}$, $R^{1b}$, and $R^2$ are each, independently, optionally substituted with one or more halo, lower alkyl, lower haloalkyl, —CN, —OR', —NR'R", =O, =S, —C(O)OR', —C(O)NR'R", —S(O)$_2$R' or —S(O)$_2$OR', wherein R' and R" are each, independently, H, lower alkyl, or lower haloalkyl.

In one embodiment, compounds are provided having the structure of Formula (I-E-2):

(I-E-2)

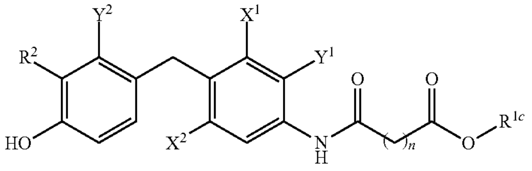

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

n is 0, 1, or 2;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", —S(O)$_2$R' or —S(O)$_2$OR', wherein R' and R" are each, independently, H, lower alkyl, or lower haloalkyl; and wherein at least one of $X^1$ or $X^2$ is lower alkenyl, lower haloalkyl, or halo.

In one embodiment, compounds are provided having the structure of Formula (I), or a pharmaceutically acceptable isomer, racemate, tautomer, hydrate, solvate, isotope, or salt thereof, wherein L' is —O—.

In one embodiment, compounds are provided having the structure of Formula (I-F):

(I-F)

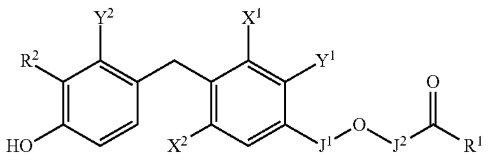

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$J^1$ is $-(CH_2)_m-$;

$J^2$ is $-(CR_2)_n-$;

m is 0 or 1;

n is 1-4;

each R is, independently, H, lower alkyl, $-NH_2$, or halo;

$R^1$ is $-NR^{1a}R^{1b}$ or $-OR^{1c}$;

$R^{1a}$ and $R^{1b}$ are each, independently, H, lower alkyl, lower alkenyl, lower alkynyl, $-OR^a$, $-NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", $-S(O)_2R'$ or $-S(O)_2OR'$, wherein R' and R" are each, independently, H, lower alkyl, or lower haloalkyl; and wherein at least one R is lower alkyl when m is 0, n is 1, and $R^2$ is isopropyl or benzyl.

In one embodiment, compounds are provided having the structure of Formula (I-F-1):

(I-F-1)

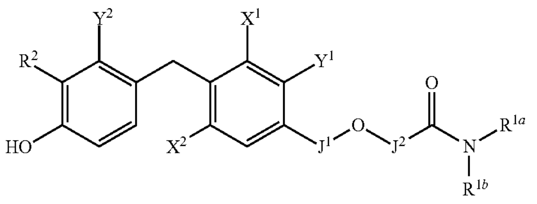

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$J^1$ is $-(CH_2)_m-$;

$J^2$ is $-(CR_2)_n-$;

m is 0 or 1;

n is 1-4;

each R is, independently, H, lower alkyl, $-NH_2$, or halo;

$R^{1a}$ and $R^{1b}$ are each, independently, H, lower alkyl, lower alkenyl, lower alkynyl, $-OR^a$, $-NR^aR^b$, carbocycle, carbocyclealkyl, heterocycle, or heterocyclealkyl, or $R^{1a}$ and $R^{1b}$ taken together with the nitrogen atom to which they are attached form heterocycle; and $R^2$ is lower alkyl, lower alkenyl, carbocycle, heterocycle, carbocyclealkyl, or heterocyclealkyl;

wherein $R^{1a}$, $R^{1b}$, and $R^2$ are each, independently, optionally substituted with one or more halo, lower alkyl, lower haloalkyl, —CN, —OR', —NR'R", =O, =S, —C(O)OR', —C(O)NR'R", $-S(O)_2R'$ or $-S(O)_2OR'$, wherein R' and R" are each, independently, H, lower alkyl, or lower haloalkyl; and wherein at least one R is lower alkyl when m is 0, n is 1, and $R^2$ is isopropyl or benzyl.

In one embodiment, compounds are provided having the structure of Formula (I-F-2):

(I-F-2)

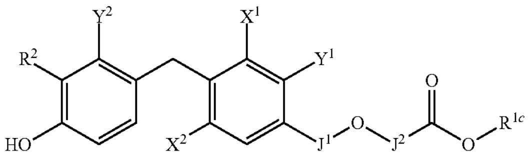

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$J^1$ is $-(CH_2)_m-$;

$J^2$ is $-(CR_2)_n-$;

m is 0 or 1;

n is 1-4;

each R is, independently, H, lower alkyl, $-NH_2$, or halo;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", $-S(O)_2R'$ or $-S(O)_2OR'$, wherein R' and R" are each, independently, H, lower alkyl, or lower haloalkyl; and wherein at least one R is lower alkyl when m is 0, n is 1, and $R^2$ is isopropyl or benzyl.

In one embodiment, compounds are provided having the structure of any one of Formula (I-F), Formula (I-F-1), or Formula (I-F-2), or a pharmaceutically acceptable isomer, racemate, tautomer, hydrate, solvate, isotope, or salt thereof, wherein m is 0 and n is 1. In one embodiment, m is 1 and n is 1. In another embodiment, m is 0 or 1 and n is 2, 3, or 4.

In one embodiment, compounds are provided having the structure of Formula (I), or a pharmaceutically acceptable isomer, racemate, tautomer, hydrate, solvate, isotope, or salt thereof, wherein L' is —C(O)—.

In one embodiment, compounds are provided having the structure of Formula (I), or a pharmaceutically acceptable isomer, racemate, tautomer, hydrate, solvate, isotope, or salt thereof, wherein L' is —OC(O)—.

In one embodiment, compounds are provided having the structure of Formula (I), or a pharmaceutically acceptable isomer, racemate, tautomer, hydrate, solvate, isotope, or salt thereof, wherein L' is $—S(O)_t—$.

In one embodiment, compounds are provided having the structure of Formula (I-G):

(I-G)

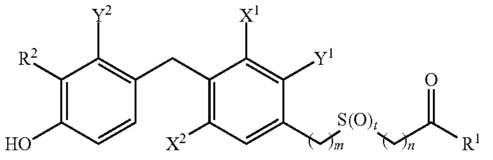

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

m is 0 or 1;

n is 1, 2, or 3;

t is 0, 1, or 2;

$R^1$ is $—NR^{1a}R^{1b}$ or $—OR^{1c}$;

$R^{1a}$ and $R^{1b}$ are each, independently, H, lower alkyl, lower alkenyl, lower alkynyl, $—OR^a$, $—NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O)OR', —C(O)NR'R", $—S(O)_2R'$ or $—S(O)_2OR'$, wherein R' and R" are each, independently, H, lower alkyl, or lower haloalkyl.

In one embodiment, compounds are provided having the structure of Formula (I-G-1):

(I-G-1)

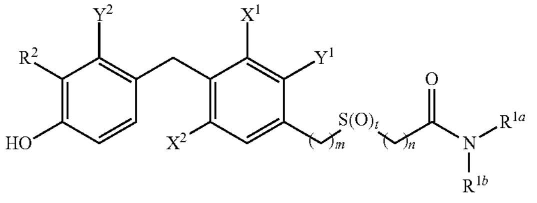

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

m is 0 or 1;

n is 1, 2, or 3;

t is 0, 1, or 2;

$R^{1a}$ and $R^{1b}$ are each, independently, H, lower alkyl, lower alkenyl, lower alkynyl, $—OR^a$, $—NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^2$ is lower alkyl, lower alkenyl, carbocycle, heterocycle, carbocyclealkyl, or heterocyclealkyl;

wherein $R^{1a}$, $R^{1b}$, and $R^2$ are each, independently, optionally substituted with one or more halo, lower alkyl, lower haloalkyl, —CN, —OR', —NR'R", =O, =S, —C(O)OR', —C(O)NR'R", $—S(O)_2R'$ or $—S(O)_2OR'$, wherein R' and R" are each, independently, H, lower alkyl, or lower haloalkyl.

In one embodiment, compounds are provided having the structure of Formula (I-G-2):

(I-G-2)

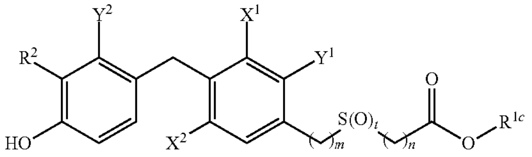

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

m is 0 or 1;

n is 1, 2, or 3;

t is 0, 1, or 2;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1c}$ and $R^2$ are each, independently, optionally substituted with one or more halo, lower alkyl, lower haloalkyl, —CN, —OR', —NR'R", =O, =S, —C(O)OR', —C(O)NR'R", $—S(O)_2R'$ or $—S(O)_2OR'$, wherein R' and R" are each, independently, H, lower alkyl, or lower haloalkyl.

In one embodiment, compounds are provided having the structure of any one of Formula (I), Formula (I-G), Formula (I-G-1), or Formula (I-G-2), or a pharmaceutically acceptable isomer, racemate, tautomer, hydrate, solvate, isotope, or salt thereof, wherein t is 0. In one embodiment, t is 1. In another embodiment, t is 2.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is lower alkyl optionally substituted with one or more halo, —CN, —OR', —NR'R", =O, =S, $—S(O)_2R'$ or $—S(O)_2OR'$, wherein R' and R" are each, independently, H, lower alkyl, or lower haloalkyl. In one embodiment, $R^2$ is unsubstituted lower alkyl. In another embodiment, $R^2$ is methyl, ethyl, propyl, or butyl. In one embodiment, $R^2$ is isopropyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is carbocyclealkyl or heterocyclealkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is arylalkyl or heteroaralkyl having the structure of Formula (i);

(i)

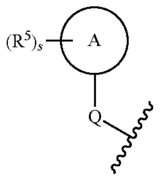

wherein:

A is aryl or heteroaryl;

Q is —$C(R^{3a}R^{4a})$— or —$C(R^{3a}R^{4a})$—$C(R^{3b}R^{4b})$—;

$R^{3a}$, $R^{4a}$, $R^{3b}$, and $R^{4b}$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl or $R^{3a}$ and $R^{4a}$, together, or $R^{3b}$ and $R^{4b}$, together, form ═O or ═S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^a$ and $R^b$ are each, independently, H, lower alkyl, or lower haloalkyl;

s is 0-5;

wherein $R^{3a}$, $R^{3b}$, $R^{4a}$, $R^{4b}$, $R^5$, $R^a$, and $R^b$ are each, independently, optionally substituted with one or more halo, —CN, —OR', —NR'R'', ═O, ═S, —$S(O)_2R'$ or —$S(O)_2OR'$, wherein R' and R'' are each, independently, H, lower alkyl, or lower haloalkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is arylalkyl or heteroaralkyl having the structure of Formula (i):

(i)

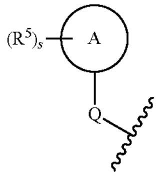

wherein Q is —$C(R^{3a}R^{4a})$— and $R^{3a}$, $R^{4a}$, $R^{3b}$, and $R^{4b}$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^{3a}$ and $R^{4a}$, together, form ═O or ═S. In one embodiment, $R^{3a}$ is H or lower alkyl and $R^{4a}$ is H or lower alkyl. In another embodiment, $R^{3a}$ is H and $R^{4a}$ is H. In one embodiment, $R^{3a}$ and $R^{4a}$, together, form ═O.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is arylalkyl or heteroaralkyl having the structure of Formula (i);

(i)

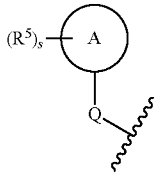

wherein Q is —$C(R^{3a}R^{4a})$—$C(R^{3b}R^{4b})$— and $R^{3a}$ and $R^{4a}$, $R^{3b}$, and $R^{4b}$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^{3a}$ and $R^{4a}$, together, or $R^{3b}$ and $R^{4b}$, together, form ═O or ═S.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is arylalkyl or heteroaralkyl having the structure of Formula (i);

(i)

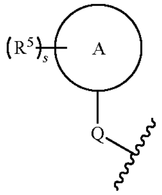

wherein A is a 6-membered aryl or 6-membered heteroaryl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ has the structure of Formula (ii):

(ii)

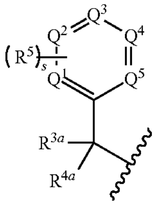

wherein $Q^1$, $Q^2$, $Q^3$, $Q^4$, and $Q^5$ are each, independently, CH, $CR^5$, or N.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is arylalkyl having the structure of Formula (i):

(i)

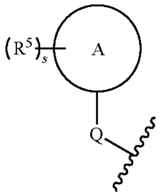

wherein A is phenyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is arylalkyl having the structure of Formula (iii):

(iii)

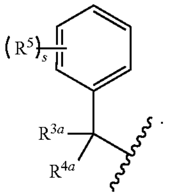

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ is carbocycle or heterocycle.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ has the structure of Formula (iv):

(iv)

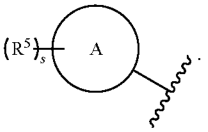

wherein:

A is aryl or heteroaryl;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^a$ and $R^b$ are each, independently, H, lower alkyl, or lower haloalkyl; and s is 0-5;

wherein $R^5$, $R^a$, and $R^b$ are each, independently, optionally substituted with one or more halo, —CN, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), or Formula (I-G-2), or a pharmaceutically acceptable isomer, racemate, tautomer, hydrate, solvate, isotope, or salt thereof, wherein $R^2$ has the structure of Formula (iv):

(iv)

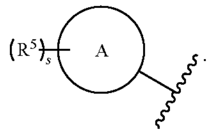

wherein A is phenyl.

In one embodiment, compounds are provided having the structure of Formula (II):

(II)

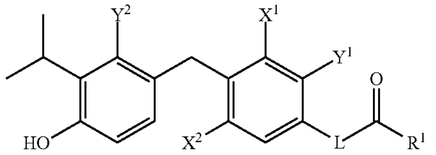

or a pharmaceutically acceptable isomer, racemate, tautomer, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
L is $-J^1$-L'-$J^2$-;
L' is ab sent or L' is lower alkenyl, lower alkynyl, —NH—, —NHC(O)—, —O—, —C(O)—, —OC(O)—, or $—S(O)_t—$;
$J^1$ is $—(CR_2)_m—$;
$J^2$ is $—(CR_2)_n—$;
m is 0-6;
n is 0-6;
t is 0-2;
each R is, independently, H, lower alkyl, $—NH_2$, or halo;
$R^1$ is $—NR^{1a}R^{1b}$ or $—OR^{1c}$;
$R^{1a}$ and $R^{1b}$ are each, independently, H, lower alkyl, lower alkenyl, lower alkynyl, $—OR^a$, $—NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl; and
wherein L', $R^{1a}$, $R^{1b}$, and $R^{1c}$ are each, independently, optionally substituted with one or more halo, lower alkyl, lower haloalkyl, —CN, —OR', —NR'R", =O, =S, —C(O)OR', —C(O)NR'R", $—S(O)_2R'$ or $—S(O)_2OR'$, wherein R' and R" are each, independently, H, lower alkyl, or lower haloalkyl;
wherein at least one of $X^1$ or $X^2$ is lower alkenyl, lower haloalkyl, or halo:
when $R^1$ is $—OR^{1c}$, L' is absent, m is 0, and n is 0, 1, or 2;
when $R^1$ is $—OR^{1c}$, L' is vinyl, m is 0, and n is 0; or
when $R^1$ is $—OR^{1c}$, L' is —NHC(O)—, m is 0, and n is 0 or 1; and
wherein at least one R is lower alkyl, $—NH_2$, or halo when L' is —O—, m is 0, and n is 1.

In one embodiment, compounds are provided having the structure of Formula (III):

(III)

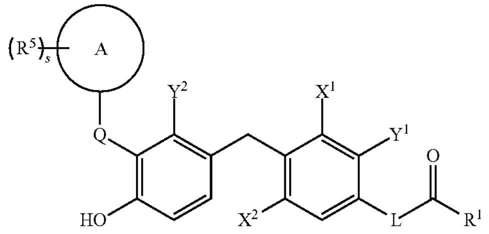

or a pharmaceutically acceptable isomer, racemate, tautomer, hydrate, solvate, isotope, or salt thereof, wherein:

A is aryl or heteroaryl;
$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
Q is $—C(R^{3a}R^{4a})—$ or $—C(R^{3a}R^{4a})—C(R^{3b}R^{4b})—$;
L is $-J^1$-L'-$J^2$-;
L' is absent or L' is lower alkenyl, lower alkynyl, —NH—, —NHC(O)—, —O—, —C(O)—, —OC(O)—, or $—S(O)_t—$;
$J^1$ is $—(CR_2)_m—$;
$J^2$ is $—(CR_2)_n—$;
m is 0-6;
n is 0-6;
s is 0-5;
t is 0-2;
each R is, independently, H, lower alkyl, $—NH_2$, or halo;
$R^1$ is $—NR^{1a}R^{1b}$ or $—OR^{1c}$;
$R^{1a}$ and $R^{1b}$ are each, independently, H, lower alkyl, lower alkenyl, lower alkynyl, $—OR^a$, $—NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl; and
$R^{3a}$, $R^{4a}$, $R^{3b}$, and $R^{4b}$ are each, independently, H, halo, —CN, lower alkyl, lower alkenyl, lower alkynyl, lower haloalkyl, $—OR^a$, $—NR^aR^b$, carbocycle, heterocycle, carbocyclealkyl, or heterocyclealkyl,
or $R^{3a}$ and $R^{4a}$, together, or $R^{3b}$ and $R^{4b}$, together, form =O or =S;
each $R^5$ is, independently, halo, —CN, lower alkyl, lower alkenyl, lower alkynyl, lower haloalkyl, carbocycle, heterocycle, carbocyclealkyl, heterocyclealkyl, $—OR^a$, $—NR^aR^b$, $—C(O)R^a$, $—C(O)OR^a$, $—C(O)NR^aR^b$, $—NR^aC(O)R^b$, $—S(O)_2R^a$, or $—S(O)_2OR^a$;
$R^a$ and $R^b$ are each, independently, H, lower alkyl, or lower haloalkyl;
wherein $R^{1a}$, $R^{1b}$, $R^{1c}$, $R^{3a}$, $R^{3b}$, $R^{4a}$, $R^{4b}$, $R^5$, $R^a$, and $R^b$ are each, independently, optionally substituted with one or more halo, —CN, —OR', —NR'R", =O, =S, $—S(O)_2R'$ or $—S(O)_2OR'$, wherein R' and R" are each, independently, H, lower alkyl, or lower haloalkyl;

wherein at least one of $X^1$ or $X^2$ is lower alkenyl, lower haloalkyl, or halo when $R^1$ is —$OR^{1c}$, L' is —NHC(O)—, m is 0, and n is 0 or 1; and wherein at least one R is lower alkyl, —$NH_2$, or halo when L' is —O—, m is 0, n is 1, s is 0, and -Q-A is benzyl.

In one embodiment, compounds are provided having the structure of Formula (IV):

(IV)

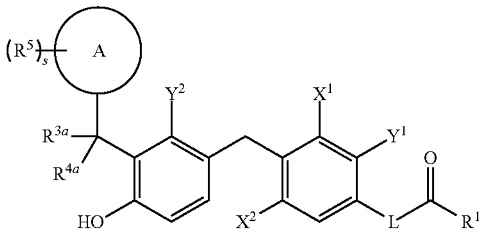

or a pharmaceutically acceptable isomer, racemate, tautomer, hydrate, solvate, isotope, or salt thereof, wherein:

A is aryl or heteroaryl;

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

L is -$J^1$-L'-$J^2$-;

L' is absent or L' is lower alkenyl, lower alkynyl, —NH—, —NHC(O)—, —O—, —C(O)—, —OC(O)—, or —$S(O)_t$—;

$J^1$ is —$(CR_2)_m$—;

$J^2$ is —$(CR_2)_n$—;

m is 0-6;

n is 0-6;

s is 0-5;

t is 0-2;

each R is, independently, H, lower alkyl, —$NH_2$, or halo;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^{3a}$ and $R^{4a}$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^{3a}$ and $R^{4a}$, together, form ═O or ═S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^a$ and $R^b$ are each, independently, H, lower alkyl, or lower haloalkyl;

wherein $R^{1a}$, $R^{1b}$, $R^{1c}$, $R^{3a}$, $R^{4a}$, $R^5$, $R^a$, and $R^b$ are each, independently, optionally substituted with one or more halo, —CN, —OR', —NR'R", ═O, ═S, —$S(O)_2$R' or —$S(O)_2$OR', wherein R' and R" are each, independently, H, lower alkyl, or lower haloalkyl;

wherein at least one of $X^1$ or $X^2$ is lower alkenyl, lower haloalkyl, or halo when $R^1$ is —$OR^{1c}$, L' is —NHC(O)—, m is 0, and n is 0 or 1; and wherein at least one R is lower alkyl, —$NH_2$, or halo when L' is —O—, m is 0, n is 1, s is 0, $R^{3a}$ is H, $R^{4a}$ is H, and A is phenyl.

In one embodiment, compounds are provided having the structure of Formula (V):

(V)

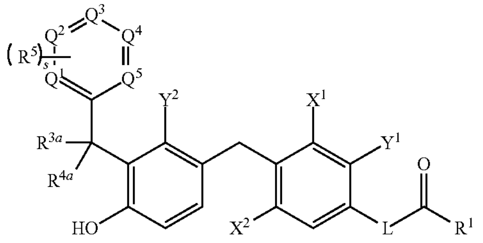

or a pharmaceutically acceptable isomer, racemate, tautomer, hydrate, solvate, isotope, or salt thereof, wherein:

$Q^1$, Q $Q^3$, $Q^4$, and $Q^5$ are each, independently, CH, $CR^5$, or N;

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

L is -$J^1$-L'-$J^2$-;

L' is absent or L' is lower alkenyl, lower alkynyl, —NH—, —NHC(O)—, —O—, —C(O)—, —OC(O)—, or —$S(O)_t$—;

$J^1$ is —$(CR_2)_m$—;

$J^2$ is —$(CR_2)_n$—;

m is 0-6;

n is 0-6;

s is 0-5;

t is 0-2;

each R is, independently, H, lower alkyl, —$NH_2$, or halo;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^{3a}$ and $R^{4a}$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^{3a}$ and $R^{4a}$, together, form ═O or ═S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^a$ and $R^b$ are each, independently, H, lower alkyl, or lower haloalkyl;

wherein $R^{1a}$, $R^{1b}$, $R^{1c}$, $R^{3a}$, $R^{4a}$, $R^5$, $R^a$, and $R^b$ are each, independently, optionally substituted with one or more halo, —CN, —OR', —NR'R", ═O, ═S, —$S(O)_2R'$ or —$S(O)_2OR'$, wherein R' and R" are each, independently, H, lower alkyl, or lower haloalkyl;

wherein at least one of $X^1$ or $X^2$ is lower alkenyl, lower haloalkyl, or halo when $R^1$ is —$OR^{1c}$, L' is —NHC(O)—, m is 0, and n is 0 or 1; and wherein at least one R is lower alkyl, —$NH_2$, or halo when L' is —O—, m is 0, n is 1, $R^{3a}$ is H, $R^{4a}$ is H, and $Q^1$, $Q^2$, $Q^3$, $Q^4$, and $Q^5$ are each CH.

In one embodiment, compounds are provided having the structure of Formula (VI):

(VI)

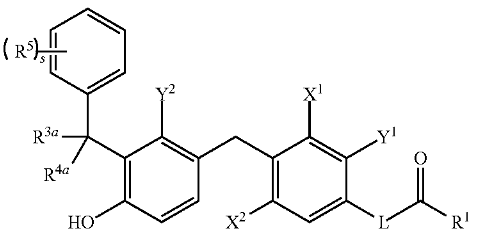

or a pharmaceutically acceptable isomer, racemate, tautomer, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

L is $-J^1-L'-J^2-$;

L' is ab sent or L' is lower alkenyl, lower alkynyl, —NH—, —NHC(O)—, —O—, —C(O)—, —OC(O)—, or —$S(O)_t$—;

$J^1$ is —$(CR_2)_m$—;

$J^2$ is —$(CR_2)_n$—;

m is 0-6;

n is 0-6;

s is 0-5;

t is 0-2;

each R is, independently, H, lower alkyl, —$NH_2$, or halo;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^{3a}$ and $R^{4a}$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^{3a}$ and $R^{4a}$, together, form ═O or ═S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^a$ and $R^b$ are each, independently, H, lower alkyl, or lower haloalkyl;

wherein $R^{1a}$, $R^{1b}$, $R^{1c}$, $R^{3a}$, $R^{4a}$, $R^5$, $R^a$, and $R^b$ are each, independently, optionally substituted with one or more halo, —CN, —OR', —NR'R", ═O, ═S, —$S(O)_2R'$ or —$S(O)_2OR'$, wherein R' and R" are each, independently, H, lower alkyl, or lower haloalkyl;

wherein at least one of $X^1$ or $X^2$ is lower alkenyl, lower haloalkyl, or halo when $R^1$ is —$OR^{1c}$, L' is —NHC(O)—, m is 0, and n is 0 or 1; and wherein at least one R is lower alkyl, —$NH_2$, or halo when L' is —O—, m is 0, n is 1, s is 0, $R^{3a}$ is H, and $R^{4a}$ is H.

In one embodiment, compounds are provided having the structure of Formula (VII):

(VII)

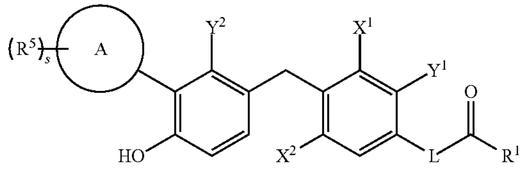

or a pharmaceutically acceptable isomer, racemate, tautomer, hydrate, solvate, isotope, or salt thereof, wherein:

A is aryl or heteroaryl;

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

L is $-J^1-L'-J^2-$;

L' is absent or L' is lower alkenyl, lower alkynyl, —NH—, —NHC(O)—, —O—, —C(O)—, —OC(O)—, or —$S(O)_t$—;

$J^1$ is —$(CR_2)_m$—;

$J^2$ is —$(CR_2)_n$—;

m is 0-6;

n is 0-6;

s is 0-5;

t is 0-2;

each R is, independently, H, lower alkyl, —$NH_2$, or halo;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^a$ and $R^b$ are each, independently, H, lower alkyl, or lower haloalkyl;

wherein $R^{1a}$, $R^{1b}$, $R^{1c}$, $R^5$, $R^a$, and $R^b$ are each, independently, optionally substituted with one or more halo, —CN, —OR', —NR'R", ═O, ═S, —$S(O)_2R'$ or —$S(O)_2OR'$, wherein R' and R" are each, independently, H, lower alkyl, or lower haloalkyl.

In one embodiment, compounds are provided having the structure of Formula (VIII):

(VII)

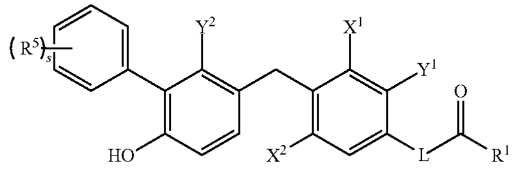

or a pharmaceutically acceptable isomer, racemate, tautomer, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ is H, —CN, halogen, lower alkyl, or lower alkoxy;
$Y^2$ is H, —CN, halogen, lower alkyl, or lower alkoxy;
L is $-J^1-L'-J^2-$;
L' is ab sent or L' is lower alkenyl, lower alkynyl, —NH—, —NHC(O)—, —O—, —C(O)—, —OC(O)—, or $—S(O)_t—$;
$J^1$ is $—(CR_2)_m—$;
$J^2$ is $—(CR_2)_n—$;
m is 0-6;
n is 0-6;
s is 0-5;
t is 0-2;
each R is, independently, H, lower alkyl, $—NH_2$, or halo;
$R^1$ is $—NR^{1a}R^{1b}$ or $—OR^{1c}$;
$R^{1a}$ and $R^{1b}$ are each, independently, H, lower alkyl, lower alkenyl, lower alkynyl, $—OR^a$, $—NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl; and
each $R^5$ is, independently, halo, —CN, lower alkyl, lower alkenyl, lower alkynyl, lower haloalkyl, carbocycle, heterocycle, carbocyclealkyl, heterocyclealkyl, $—OR^a$, $—NR^aR^b$, $—C(O)R^a$, $—C(O)OR^a$, $—C(O)NR^aR^b$, $—NR^aC(O)R^b$, $—S(O)_2R^a$, or $—S(O)_2OR^a$;
$R^a$ and $R^b$ are each, independently, H, lower alkyl, or lower haloalkyl;
wherein $R^{1a}$, $R^{1b}$, $R^{1c}$, $R^5$, $R^a$, and $R^b$ are each, independently, optionally substituted with one or more halo, —CN, —OR', —NR'R", =O, =S, $—S(O)_2R'$ or $—S(O)_2OR'$, wherein R' and R" are each, independently, H, lower alkyl, or lower haloalkyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^1$ is $—NR^{1a}R^{1b}$.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^1$ is $—OR^{1c}$.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is absent. In one embodiment, L' is absent, m is 0, n is 0-3, and each R is, independently, H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is lower alkenyl. In one embodiment, L' is $—CH=CR^{10}—$ and $R^{10}$ is H, lower alkyl, lower haloalkyl, —C(O)OR', or —C(O)NR'R".

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is lower alkynyl. In one embodiment, L' is —C≡C—.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is —NH—. In one embodiment, L' is —NH—, m is 0 or 1, and n is 1 or 2. In one embodiment, L' is —NH— and each R is, independently, H. In one embodiment, L' is —NH—, m is 0 or 1, n is 1 or 2, and each R is, independently, H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is —NHC(O)—. In one embodiment, L' is —NHC(O)— and m is 0 and n is 0 or 1.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is —O—. In one embodiment, L' is —O—, $J^1$ is $—(CH_2)_m—$, $J^2$ is $—(CR_2)_n—$, m is 0 or 1, n is 1-4, and each R is, independently, H, lower alkyl, $—NH_2$, or halo. In one embodiment, L' is —O—, m is 0 and n is 1. In another embodiment, L' is —O—, $J^1$ is $—(CH_2)_m—$, $J^2$ is $—(CR_2)_n—$, m is 0, n is 1, and each R is, independently, H, lower alkyl, $—NH_2$, or halo. In one embodiment, L' is —O—, m is 1 and n is 1. In another embodiment, L' is —O—, $J^1$ is $—(CH_2)_m—$, $J^2$ is $—(CR_2)_n—$, m is 1, n is 1, and each R is, independently, H, lower alkyl, $—NH_2$, or halo. In one embodiment, L' is —O—, m is 0 or 1, and n is 2, 3, or 4. In another embodiment, L' is —O—, $J^1$ is $—(CH_2)_m—$, $J^2$ is $—(CR_2)_n—$, m is 0 or 1, n is 2, 3, or 4, and each R is, independently, H, lower alkyl, $—NH_2$, or halo.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is —C(O)—. In one embodiment, L' is —C(O)—, m is 0 or 1, n is 1, and each R is, independently, H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is —OC(O)—. In one embodiment, L' is —OC(O)—, m is 0 or 1, n is 1, and each R is, independently, H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein L' is —$S(O)_t$—. In one embodiment, t is 0. In one embodiment, t is 1. In another embodiment, t is 2. In one embodiment, L' is —$S(O)_t$—, m is 0 or 1, n is 1, and each R is, independently, H. In one embodiment, L' is —$S(O)_t$—, t is 0, m is 0 or 1, n is 1, and each R is, independently, H. In one embodiment, L' is —$S(O)_t$—, t is 1, m is 0 or 1, n is 1, and each R is, independently, H. In one embodiment, L' is —$S(O)_t$—, t is 2, m is 0 or 1, n is 1, and each R is, independently, H.

In one embodiment, compounds are provided having the structure of any one of Formula (III), Formula (IV), Formula (V), or Formula (VI), or a pharmaceutically acceptable isomer, racemate, tautomer, hydrate, solvate, isotope, or salt thereof, wherein $R^{3a}$ is H.

In one embodiment, compounds are provided having the structure of any one of Formula (III), Formula (IV), Formula (V), or Formula (VI), or a pharmaceutically acceptable isomer, racemate, tautomer, hydrate, solvate, isotope, or salt thereof, wherein $R^{3a}$ is carbocycle. In one embodiment, $R^{3a}$ is cyclopropyl or cyclobutyl.

In one embodiment, compounds are provided having the structure of any one of Formula (III), Formula (IV), Formula (V), or Formula (VI), or a pharmaceutically acceptable isomer, racemate, tautomer, hydrate, solvate, isotope, or salt thereof, wherein $R^{3a}$ is lower alkyl. In one embodiment, $R^{3a}$ is methyl, ethyl, or propyl.

In one embodiment, compounds are provided having the structure of any one of Formula (III), Formula (IV), Formula (V), or Formula (VI), or a pharmaceutically acceptable isomer, racemate, tautomer, hydrate, solvate, isotope, or salt thereof, wherein $R^{3a}$ is —$OR^a$. In one embodiment, $R^a$ is H. In one embodiment, $R^a$ is lower alkyl. In a more specific embodiment, $R^a$ is methyl.

In one embodiment, compounds are provided having the structure of any one of Formula (I), Formula (I-A), Formula (I-A-1), Formula (I-B), Formula (I-B-1), Formula (I-C), Formula (I-C-1), Formula (I-D), Formula (I-D-1), Formula (I-E), Formula (I-E-1), Formula (I-F), Formula (I-F-1), Formula (I-G), Formula (I-G-1), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1a}$ is H.

In one embodiment, compounds are provided having the structure of any one of Formula (I), Formula (I-A), Formula (I-A-1), Formula (I-B), Formula (I-B-1), Formula (I-C), Formula (I-C-1), Formula (I-D), Formula (I-D-1), Formula (I-E), Formula (I-E-1), Formula (I-F), Formula (I-F-1), Formula (I-G), Formula (I-G-1), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1a}$ is lower alkyl. In one embodiment, $R^{1a}$ is methyl.

In one embodiment, compounds are provided having the structure of any one of Formula (I), Formula (I-A), Formula (I-A-1), Formula (I-B), Formula (I-B-1), Formula (I-C), Formula (I-C-1), Formula (I-D), Formula (I-D-1), Formula (I-E), Formula (I-E-1), Formula (I-F), Formula (I-F-1), Formula (I-G), Formula (I-G-1), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1a}$ is carbocycle, carbocyclealkyl, heterocycle, or heterocyclealkyl. In one embodiment, $R^{1a}$ is carbocycle. In one embodiment, $R^{1a}$ is carbocyclealkyl. In one embodiment, $R^{1a}$ is heterocycle. In one embodiment, $R^{1a}$ is heteroaryl. In one embodiment, $R^{1a}$ is heterocyclealkyl.

In one embodiment, compounds are provided having the structure of any one of Formula (I), Formula (I-A), Formula (I-A-1), Formula (I-B), Formula (I-B-1), Formula (I-C), Formula (I-C-1), Formula (I-D), Formula (I-D-1), Formula (I-E), Formula (I-E-1), Formula (I-F), Formula (I-F-1), Formula (I-G), Formula (I-G-1), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1b}$ is H.

In one embodiment, compounds are provided having the structure of any one of Formula (I), Formula (I-A), Formula (I-A-1), Formula (I-B), Formula (I-B-1), Formula (I-C), Formula (I-C-1), Formula (I-D), Formula (I-D-1), Formula (I-E), Formula (I-E-1), Formula (I-F), Formula (I-F-1), Formula (I-G), Formula (I-G-1), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1b}$ is lower alkyl. In one embodiment, $R^{1b}$ is methyl.

In one embodiment, compounds are provided having the structure of any one of Formula (I), Formula (I-A), Formula (I-A-1), Formula (I-B), Formula (I-B-1), Formula (I-C), Formula (I-C-1), Formula (I-D), Formula (I-D-1), Formula (I-E), Formula (I-E-1), Formula (I-F), Formula (I-F-1), Formula (I-G), Formula (I-G-1), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1a}$ is methyl and $R^{1b}$ is H. In another embodiment, $R^{1a}$ is methyl and $R^{1b}$ is methyl.

In one embodiment, compounds are provided having the structure of any one of Formula (I), Formula (I-A), Formula (I-A-2), Formula (I-B), Formula (I-B-2), Formula (I-C), Formula (I-C-2), Formula (I-D), Formula (I-D-2), Formula (I-E), Formula (I-E-2), Formula (I-F), Formula (I-F-2), Formula (I-G), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1c}$ is H.

In one embodiment, compounds are provided having the structure of any one of Formula (I), Formula (I-A), Formula (I-A-2), Formula (I-B), Formula (I-B-2), Formula (I-C), Formula (I-C-2), Formula (I-D), Formula (I-D-2), Formula (I-E), Formula (I-E-2), Formula (I-F), Formula (I-F-2), Formula (I-G), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $R^{1c}$ is lower alkyl. In one embodiment, $R^{1c}$ is methyl or ethyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is lower alkyl. In one embodiment, $X^1$ is methyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is halo. In one embodiment, $X^1$ is Cl or Br. In one embodiment, $X^1$ is Cl. In one embodiment, $X^1$ is Br.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is lower haloalkyl. In one embodiment, $X^1$ is $—CF_3$, $—CHF_2$, or $—CH_2F$. In one embodiment, $X^1$ is $—CF_3$.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is lower alkenyl. In one embodiment, $X^1$ is vinyl or isopropenyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is lower alkyl. In one embodiment, $X^2$ is methyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is halo. In one embodiment, $X^2$ is Cl or Br. In another embodiment, $X^2$ is Cl. In another embodiment, $X^2$ is Br.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is lower haloalkyl. In one embodiment, $X^2$ is $—CF_3$, $—CHF_2$, or $—CH_2F$. In one embodiment, $X^2$ is $—CF_3$.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is lower alkenyl. In one embodiment, $X^2$ is vinyl or isopropenyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is lower alkyl. In one embodiment, at least one $R^5$ is lower alkyl substituted with —OR'. In one embodiment, R' is H. In another embodiment, R' is lower alkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is lower haloalkyl. In one embodiment, at least one $R^5$ is $—CF_3$, $—CHF_2$, or $—CH_2F$. In one embodiment, at least one $R^5$ is $—CF_3$.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$OR^a$. In one embodiment, $R^a$ is lower alkyl. In another embodiment, $R^a$ is lower haloalkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$C(O)R^a$. In one embodiment, $R^a$ is lower alkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$NR^aC(O)R^b$. In one embodiment, $R^a$ is H. In one embodiment, $R^b$ is lower alkyl. In another embodiment, $R^b$ is methyl. In one embodiment, $R^a$ is H and $R^b$ is lower alkyl. In another embodiment, $R^a$ is H and $R^b$ is methyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$C(O)OR^a$. In one embodiment, $R^a$ is lower alkyl. In another embodiment, $R^a$ is methyl or ethyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$S(O)_2R^a$. In one embodiment, $R^a$ is lower alkyl. In another embodiment, $R^a$ is methyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is halo. In one embodiment, at least one $R^5$ is F.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —CN.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is halogen. In one embodiment, $Y^1$ is F or Cl. In one embodiment, $Y^1$ is F. In another embodiment, $Y^1$ is Cl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is —CN.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkyl. In one embodiment, $Y^1$ is methyl, ethyl, or isopropyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkoxy. In one embodiment, $Y^1$ is methoxy.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is halogen. In one embodiment, $Y^2$ is F or Cl. In one embodiment, $Y^2$ is F. In another embodiment, $Y^2$ is Cl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is —CN.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is lower alkyl. In one embodiment, $Y^2$ is methyl, ethyl, or isopropyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is lower alkoxy. In one embodiment, $Y^2$ is methoxy.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is F and $Y^2$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is Cl and $Y^2$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is —CN and $Y^2$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkyl and $Y^2$ is H. In one embodiment, $Y^1$ is methyl and $Y^2$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkoxy and $Y^2$ is H. In one embodiment, $Y^1$ is methoxy and $Y^2$ is H.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is F.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is Cl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is —CN.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is lower alkyl.

In one embodiment, compounds are provided having the structure of any one of Formula (I), Formula (I-A), Formula (I-A-1), Formula (I-A-2), Formula (I-B), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is lower alkoxy.

In one embodiment, compounds are provided having the structure of any one of Formula (I), Formula (I-A), Formula (I-A-1), Formula (I-A-2), Formula (I-B3), Formula (I-B-1), Formula (I-B-2), Formula (I-C), Formula (I-C-1), Formula (I-C-2), Formula (I-D), Formula (I-D-1), Formula (I-D-2), Formula (I-E), Formula (I-E-1), Formula (I-E-2), Formula (I-F), Formula (I-F-1), Formula (I-F-2), Formula (I-G), Formula (I-G-1), Formula (I-G-2), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is F and $Y^2$ is F.

Representative compounds of Formula (I), and Formulas (II) through (VIII) as applicable, include the compounds listed in Table 1 below, as well as pharmaceutically acceptable salts thereof. To this end, representative compounds are identified herein by their respective "Compound Number", which is sometimes abbreviated as "Compound No.", "Cmpd. No." or "No."

TABLE 1

REPRESENTATIVE COMPOUNDS

| Cmpd No | Structure | Name |
|---|---|---|
| 1 | 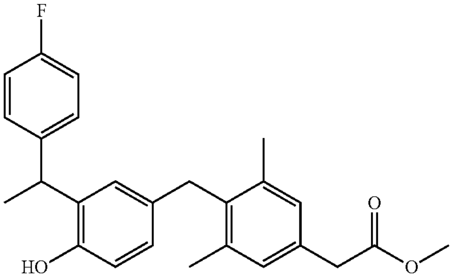 [SMILES: COC(=O)Cc1cc(C)c(Cc2ccc(O)c(C(C)c3ccc(F)cc3)c2)c(C)c1] | methyl 2-(4-(3-(1-(4-fluorophenyl)ethyl)-4-hydroxybenzyl)-3,5-dimethylphenyl)acetate |

TABLE 1-continued

| REPRESENTATIVE COMPOUNDS | | |
|---|---|---|
| Cmpd No | Structure | Name |
| 2 | 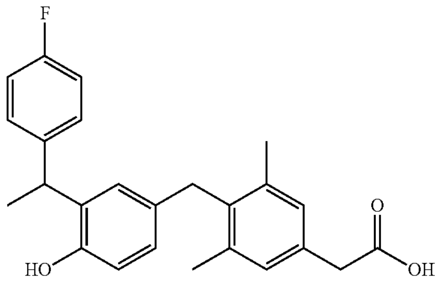 [SMILES: Cc1cc(CC(=O)O)cc(C)c1Cc1ccc(O)c(C(C)c2ccc(F)cc2)c1] | 2-(4-(3-(1-(4-fluorophenyl)ethyl)-4-hydroxybenzyl)-3,5-dimethylphenyl)acetic acid |
| 3 | 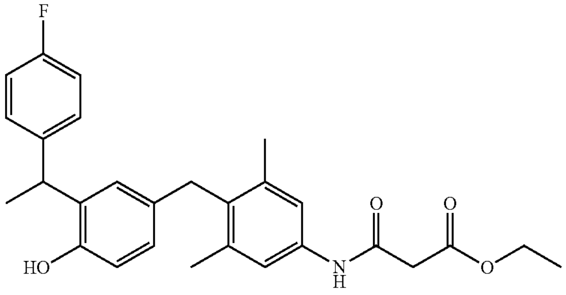 [SMILES: CCOC(=O)CC(=O)Nc1cc(C)c(Cc2ccc(O)c(C(C)c3ccc(F)cc3)c2)c(C)c1] | ethyl 3-((4-(3-(1-(4-fluorophenyl)ethyl)-4-hydroxybenzyl)-3,5-dimethylphenyl)amino)-3-oxopropanoate |
| 4 | 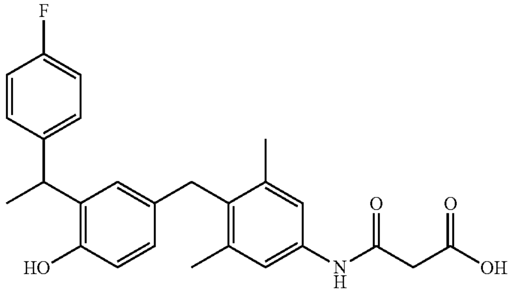 [SMILES: Cc1cc(NC(=O)CC(=O)O)cc(C)c1Cc1ccc(O)c(C(C)c2ccc(F)cc2)c1] | 3-((4-(3-(1-(4-fluorophenyl)ethyl)-4-hydroxybenzyl)-3,5-dimethylphenyl)amino)-3-oxopropanoic acid |
| 5 | 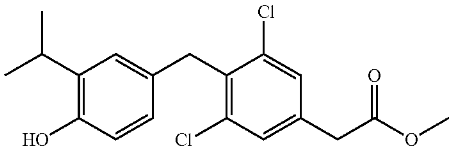 [SMILES: COC(=O)Cc1cc(Cl)c(Cc2ccc(O)c(C(C)C)c2)c(Cl)c1] | methyl 2-(3,5-dichloro-4-(4-hydroxy-3-isopropylbenzyl)phenyl)acetate |
| 6 | 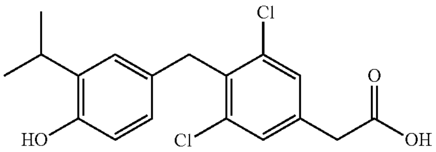 | 2-(3,5-dichloro-4-(4-hydroxy-3-isopropylbenzyl)phenyl)acetic acid |
| 7 | 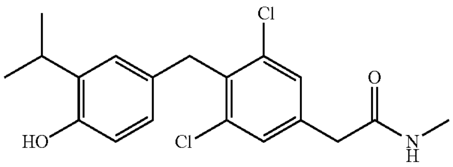 [SMILES: CNC(=O)Cc1cc(Cl)c(Cc2ccc(O)c(C(C)C)c2)c(Cl)c1] | 2-(3,5-dichloro-4-(4-hydroxy-3-isopropylbenzyl)phenyl)-N-methylacetamide |

TABLE 1-continued

REPRESENTATIVE COMPOUNDS

| Cmpd No | Structure | Name |
| --- | --- | --- |
| 8 | 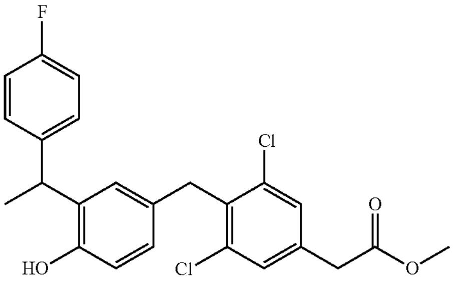 [SMILES: COC(=O)Cc1cc(Cl)c(Cc2ccc(O)c(C(C)c3ccc(F)cc3)c2)c(Cl)c1] | methyl 2-(3,5-dichloro-4-(3-(1-(4-fluorophenyl)ethyl)-4-hydroxybenzyl)phenyl)acetate |
| 9 | 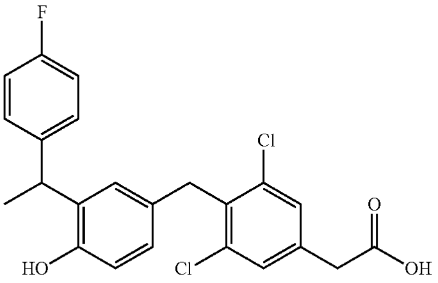 [SMILES: CC(c1ccc(F)cc1)c1cc(Cc2c(Cl)cc(CC(=O)O)cc2Cl)ccc1O] | 2-(3,5-dichloro-4-(3-(1-(4-fluorophenyl)ethyl)-4-hydroxybenzyl)phenyl)acetic acid |
| 10 | 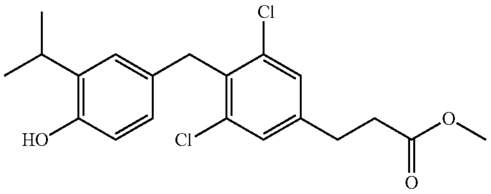 [SMILES: COC(=O)CCc1cc(Cl)c(Cc2ccc(O)c(C(C)C)c2)c(Cl)c1] | methyl 3-(3,5-dichloro-4-(4-hydroxy-3-isopropylbenzyl)phenyl)propanoate |
| 11 | 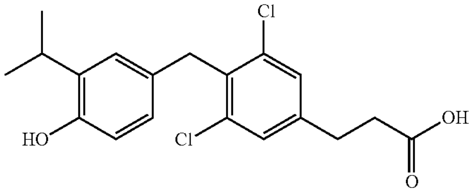 [SMILES: CC(C)c1cc(Cc2c(Cl)cc(CCC(=O)O)cc2Cl)ccc1O] | 3-(3,5-dichloro-4-(4-hydroxy-3-isopropylbenzyl)phenyl)propanoic acid |
| 12 | 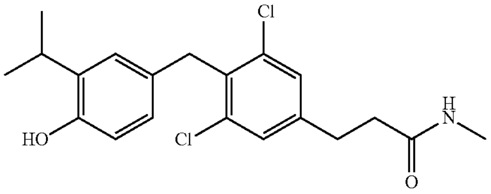 [SMILES: CNC(=O)CCc1cc(Cl)c(Cc2ccc(O)c(C(C)C)c2)c(Cl)c1] | 3-(3,5-dichloro-4-(4-hydroxy-3-isopropylbenzyl)phenyl)-N-methylpropanamide |
| 13 | 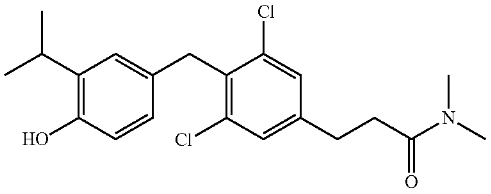 [SMILES: CC(C)c1cc(Cc2c(Cl)cc(CCC(=O)N(C)C)cc2Cl)ccc1O] | 3-(3,5-dichloro-4-(4-hydroxy-3-isopropylbenzyl)phenyl)-N,N-dimethylpropanamide |
| 14 | 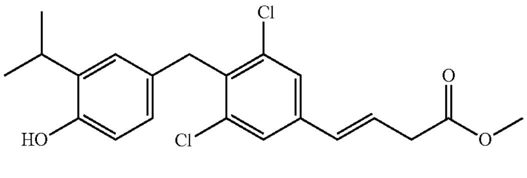 [SMILES: COC(=O)C/C=C/c1cc(Cl)c(Cc2ccc(O)c(C(C)C)c2)c(Cl)c1] | methyl (E)-4-(3,5-dichloro-4-(4-hydroxy-3-isopropylbenzyl)phenyl)but-3-enoate |

TABLE 1-continued

REPRESENTATIVE COMPOUNDS

| Cmpd No | Structure | Name |
|---|---|---|
| 15 | 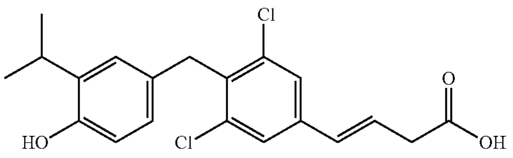 [SMILES: CC(C)c1cc(Cc2c(Cl)cc(/C=C/CC(=O)O)cc2Cl)ccc1O] | (E)-4-(3,5-dichloro-4-(4-hydroxy-3-isopropylbenzyl)phenyl)but-3-enoic acid |
| 16 | 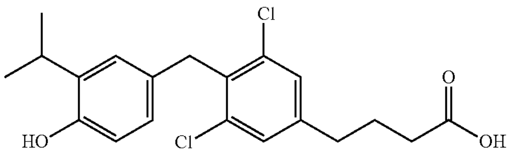 | 4-(3,5-dichloro-4-(4-hydroxy-3-isopropylbenzyl)phenyl)butanoic acid |
| 17 | 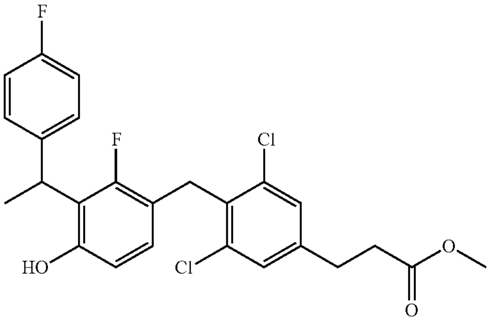 [SMILES: COC(=O)CCc1cc(Cl)c(Cc2ccc(O)c(C(C)c3ccc(F)cc3)c2F)c(Cl)c1] | methyl 3-(3,5-dichloro-4-(2-fluoro-3-(1-(4-fluorophenyl)ethyl)-4-hydroxybenzyl)phenyl)propanoate |
| 18 | 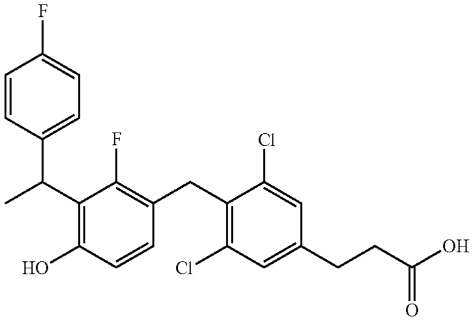 [SMILES: CC(c1ccc(F)cc1)c1c(O)ccc(Cc2c(Cl)cc(CCC(=O)O)cc2Cl)c1F] | 3-(3,5-dichloro-4-(2-fluoro-3-(1-(4-fluorophenyl)ethyl)-4-hydroxybenzyl)phenyl)propanoic acid |
| 19 | 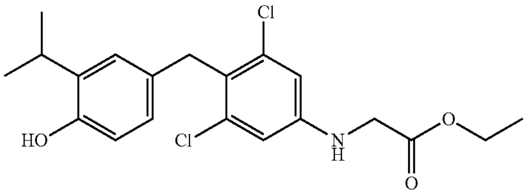 [SMILES: CCOC(=O)CNc1cc(Cl)c(Cc2ccc(O)c(C(C)C)c2)c(Cl)c1] | ethyl (3,5-dichloro-4-(4-hydroxy-3-isopropylbenzyl)phenyl)glycinate |
| 20 | 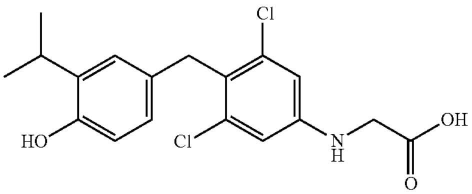 [SMILES: CC(C)c1cc(Cc2c(Cl)cc(NCC(=O)O)cc2Cl)ccc1O] | (3,5-dichloro-4-(4-hydroxy-3-isopropylbenzyl)phenyl)glycine |

TABLE 1-continued

| REPRESENTATIVE COMPOUNDS | | |
|---|---|---|
| Cmpd No | Structure | Name |
| 21 | 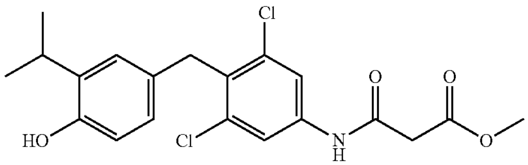 [SMILES: COC(=O)CC(=O)Nc1cc(Cl)c(Cc2ccc(O)c(C(C)C)c2)c(Cl)c1] | methyl 3-((3,5-dichloro-4-(4-hydroxy-3-isopropylbenzyl)phenyl)amino)-3-oxopropanoate |
| 22 | 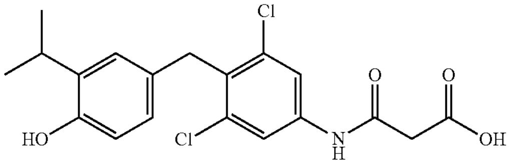 [SMILES: CC(C)c1cc(Cc2c(Cl)cc(NC(=O)CC(=O)O)cc2Cl)ccc1O] | 3-((3,5-dichloro-4-(4-hydroxy-3-isopropylbenzyl)phenyl)amino)-3-oxopropanoic acid |
| 23 | 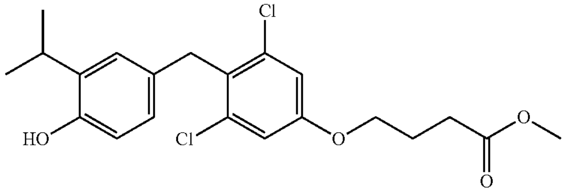 [SMILES: COC(=O)CCCOc1cc(Cl)c(Cc2ccc(O)c(C(C)C)c2)c(Cl)c1] | methyl 4-(3,5-dichloro-4-(4-hydroxy-3-isopropylbenzyl)phenoxy)butanoate |
| 24 | 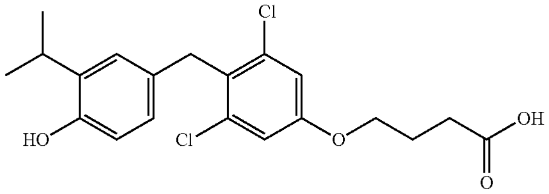 [SMILES: CC(C)c1cc(Cc2c(Cl)cc(OCCCC(=O)O)cc2Cl)ccc1O] | 4-(3,5-dichloro-4-(4-hydroxy-3-isopropylbenzyl)phenoxy)butanoic acid |
| 25 | 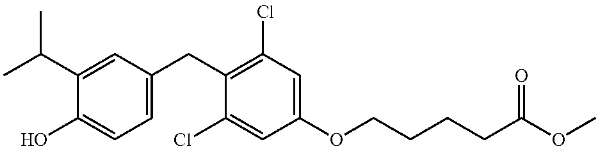 [SMILES: COC(=O)CCCCOc1cc(Cl)c(Cc2ccc(O)c(C(C)C)c2)c(Cl)c1] | methyl 5-(3,5-dichloro-4-(4-hydroxy-3-isopropylbenzyl)phenoxy) pentanoate |
| 26 | 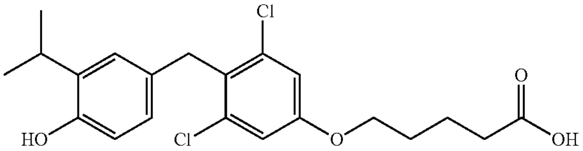 [SMILES: CC(C)c1cc(Cc2c(Cl)cc(OCCCCC(=O)O)cc2Cl)ccc1O] | 5-(3,5-dichloro-4-(4-hydroxy-3-isopropylbenzyl)phenoxy)pentanoic acid |
| 27 | 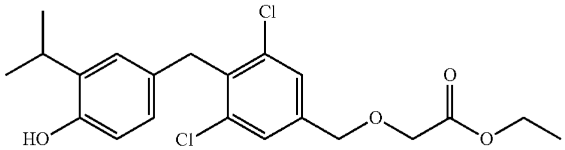 [SMILES: CCOC(=O)COCc1cc(Cl)c(Cc2ccc(O)c(C(C)C)c2)c(Cl)c1] | ethyl 2-((3,5-dichloro-4-(4-hydroxy-3-isopropylbenzyl)benzyl)oxy)acetate |
| 28 | 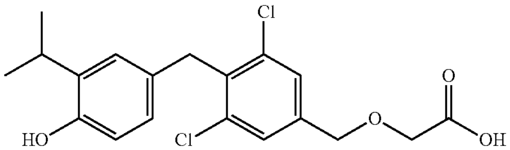 | 2-((3,5-dichloro-4-(4-hydroxy-3-isopropylbenzyl)benzyl)oxy)acetic acid |

TABLE 1-continued

| REPRESENTATIVE COMPOUNDS | | |
|---|---|---|
| Cmpd No | Structure | Name |
| 29 | 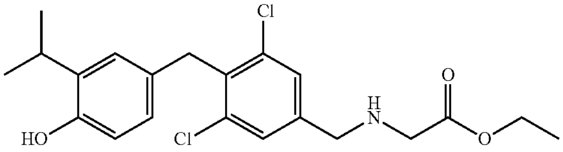 [SMILES: CCOC(=O)CNCc1cc(Cl)c(Cc2ccc(O)c(C(C)C)c2)c(Cl)c1] | ethyl (3,5-dichloro-4-(4-hydroxy-3-isopropylbenzyl)benzyl)glycinate |
| 30 | 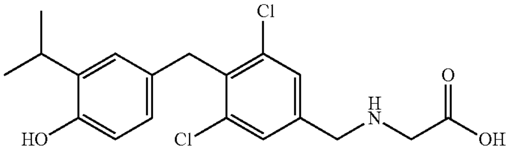 [SMILES: CC(C)c1cc(Cc2c(Cl)cc(CNCC(=O)O)cc2Cl)ccc1O] | (3,5-dichloro-4-(4-hydroxy-3-isopropylbenzyl)benzyl)glycine |
| 31 | 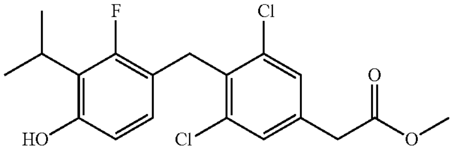 [SMILES: COC(=O)Cc1cc(Cl)c(Cc2ccc(O)c(C(C)C)c2F)c(Cl)c1] | methyl 2-(3,5-dichloro-4-(2-fluoro-4-hydroxy-3-isopropylbenzyl)phenyl)acetate |
| 32 | 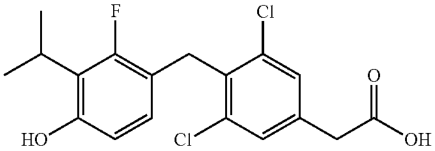 [SMILES: CC(C)c1c(O)ccc(Cc2c(Cl)cc(CC(=O)O)cc2Cl)c1F] | 2-(3,5-dichloro-4-(2-fluoro-4-hydroxy-3-isopropylbenzyl)phenyl)acetic acid |
| 33 | 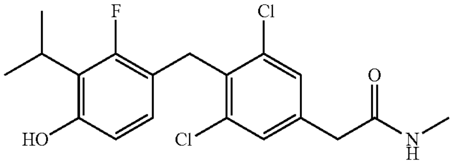 [SMILES: CNC(=O)Cc1cc(Cl)c(Cc2ccc(O)c(C(C)C)c2F)c(Cl)c1] | 2-(3,5-dichloro-4-(2-fluoro-4-hydroxy-3-isopropylbenzyl)phenyl)-N-methylacetamide |
| 34 | 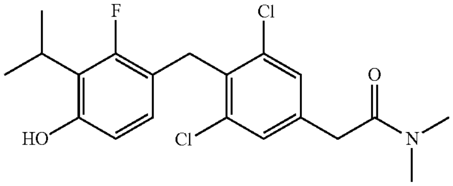 [SMILES: CC(C)c1c(O)ccc(Cc2c(Cl)cc(CC(=O)N(C)C)cc2Cl)c1F] | 2-(3,5-dichloro-4-(2-fluoro-4-hydroxy-3-isopropylbenzyl)phenyl)-N,N-dimethylacetamide |
| 35 | 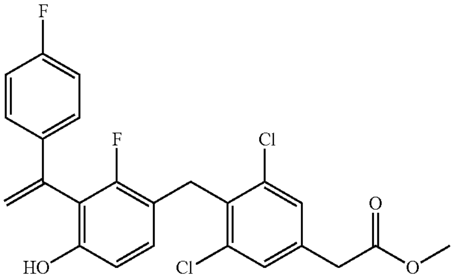 [SMILES: C=C(c1ccc(F)cc1)c1c(O)ccc(Cc2c(Cl)cc(CC(=O)OC)cc2Cl)c1F] | methyl 2-(3,5-dichloro-4-(2-fluoro-3-(1-(4-fluorophenyl)vinyl)-4-hydroxybenzyl)phenyl)acetate |

TABLE 1-continued

| REPRESENTATIVE COMPOUNDS | | |
|---|---|---|
| Cmpd No | Structure | Name |
| 36 | 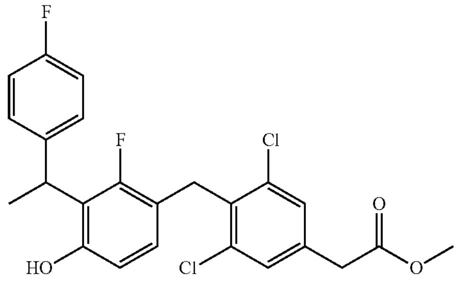 [SMILES: COC(=O)Cc1cc(Cl)c(Cc2ccc(O)c(C(C)c3ccc(F)cc3)c2F)c(Cl)c1] | methyl 2-(3,5-dichloro-4-(2-fluoro-3-(1-(4-fluorophenyl)ethyl)-4-hydroxybenzyl)phenyl)acetate |
| 37 | 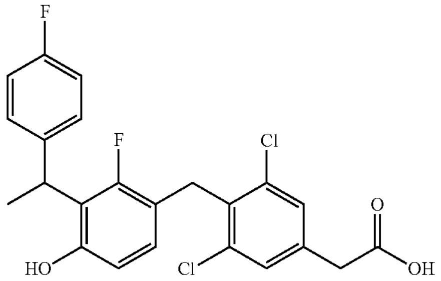 [SMILES: CC(c1ccc(F)cc1)c1c(O)ccc(Cc2c(Cl)cc(CC(=O)O)cc2Cl)c1F] | 2-(3,5-dichloro-4-(2-fluoro-3-(1-(4-fluorophenyl)ethyl)-4-hydroxybenzyl)phenyl)acetic acid |
| 38 | 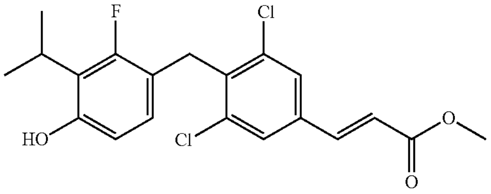 [SMILES: COC(=O)/C=C/c1cc(Cl)c(Cc2ccc(O)c(C(C)C)c2F)c(Cl)c1] | methyl (E)-3-(3,5-dichloro-4-(2-fluoro-4-hydroxy-3-isopropylbenzyl)phenyl)acrylate |
| 39 | 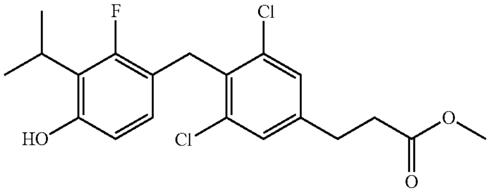 [SMILES: COC(=O)CCc1cc(Cl)c(Cc2ccc(O)c(C(C)C)c2F)c(Cl)c1] | methyl 3-(3,5-dichloro-4-(2-fluoro-4-hydroxy-3-isopropylbenzyl)phenyl)propanoate |
| 40 | 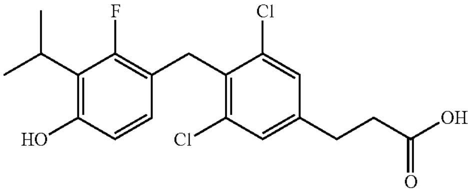 [SMILES: CC(C)c1c(O)ccc(Cc2c(Cl)cc(CCC(=O)O)cc2Cl)c1F] | 3-(3,5-dichloro-4-(2-fluoro-4-hydroxy-3-isopropylbenzyl)phenyl)propanoic acid |
| 41 | 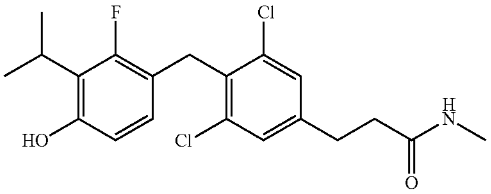 [SMILES: CNC(=O)CCc1cc(Cl)c(Cc2ccc(O)c(C(C)C)c2F)c(Cl)c1] | 3-(3,5-dichloro-4-(2-fluoro-4-hydroxy-3-isopropylbenzyl)phenyl)-N-methylpropanamide |

TABLE 1-continued

| REPRESENTATIVE COMPOUNDS | | |
|---|---|---|
| Cmpd No | Structure | Name |
| 42 | 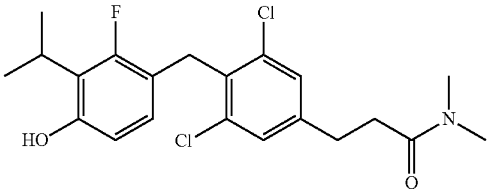 [SMILES: CC(C)c1c(O)ccc(Cc2c(Cl)cc(CCC(=O)N(C)C)cc2Cl)c1F] | 3-(3,5-dichloro-4-(2-fluoro-4-hydroxy-3-isopropylbenzyl)phenyl)-N,N-dimethylpropanamide |
| 43 | 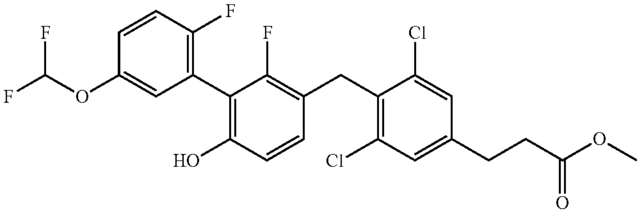 [SMILES: COC(=O)CCc1cc(Cl)c(Cc2ccc(O)c(-c3cc(OC(F)F)ccc3F)c2F)c(Cl)c1] | methyl 3-(3,5-dichloro-4-((5'-(difluoromethoxy)-2,2'-difluoro-6-hydroxy-[1,1'-biphenyl]-3-yl)methyl)phenyl)propanoate |
| 44 | 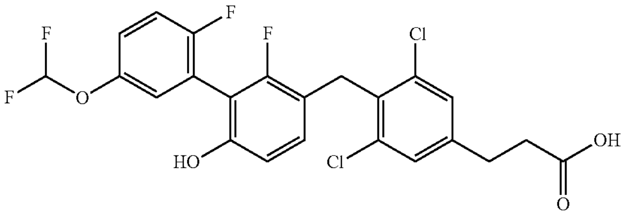 [SMILES: O=C(O)CCc1cc(Cl)c(Cc2ccc(O)c(-c3cc(OC(F)F)ccc3F)c2F)c(Cl)c1] | 3-(3,5-dichloro-4-((5'-(difluoromethoxy)-2,2'-difluoro-6-hydroxy-[1,1'-biphenyl]-3-yl)methyl)phenyl)propanoic acid |
| 45 | 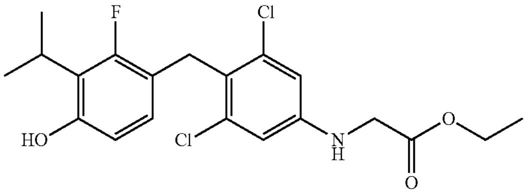 [SMILES: CCOC(=O)CNc1cc(Cl)c(Cc2ccc(O)c(C(C)C)c2F)c(Cl)c1] | ethyl (3,5-dichloro-4-(2-fluoro-4-hydroxy-3-isopropylbenzyl)phenyl)glycinate |
| 46 | 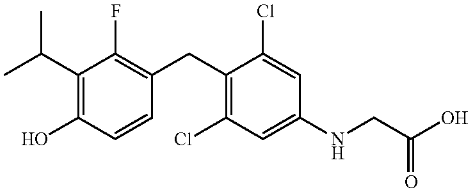 [SMILES: CC(C)c1c(O)ccc(Cc2c(Cl)cc(NCC(=O)O)cc2Cl)c1F] | (3,5-dichloro-4-(2-fluoro-4-hydroxy-3-isopropylbenzyl)phenyl)glycine |
| 47 | 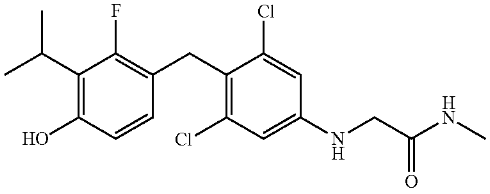 [SMILES: CNC(=O)CNc1cc(Cl)c(Cc2ccc(O)c(C(C)C)c2F)c(Cl)c1] | 2-((3,5-dichloro-4-(2-fluoro-4-hydroxy-3-isopropylbenzyl)phenyl)amino)-N-methylacetamide |
| 48 | 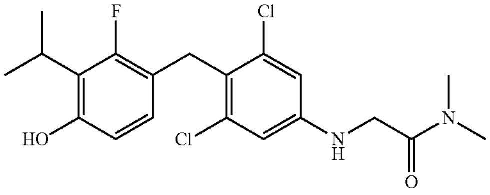 [SMILES: CC(C)c1c(O)ccc(Cc2c(Cl)cc(NCC(=O)N(C)C)cc2Cl)c1F] | 2-((3,5-dichloro-4-(2-fluoro-4-hydroxy-3-isopropylbenzyl)phenyl)amino)-N,N-dimethylacetamide |

TABLE 1-continued

| REPRESENTATIVE COMPOUNDS | | |
|---|---|---|
| Cmpd No | Structure | Name |
| 49 | 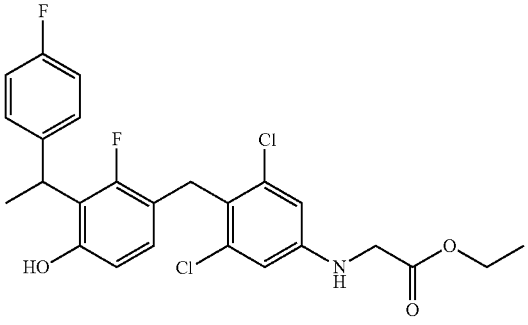 [SMILES: CCOC(=O)CNc1cc(Cl)c(Cc2ccc(O)c(C(C)c3ccc(F)cc3)c2F)c(Cl)c1] | ethyl (3,5-dichloro-4-(2-fluoro-3-(1-(4-fluorophenyl)ethyl)-4-hydroxybenzyl)phenyl)glycinate |
| 50 | 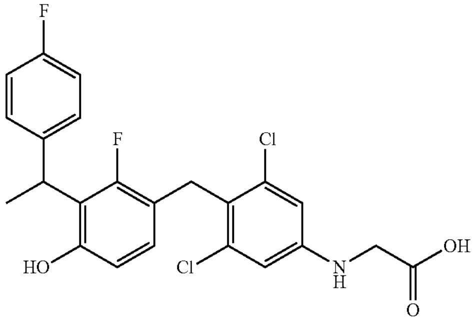 [SMILES: CC(c1ccc(F)cc1)c1c(O)ccc(Cc2c(Cl)cc(NCC(=O)O)cc2Cl)c1F] | (3,5-dichloro-4-(2-fluoro-3-(1-(4-fluorophenyl)ethyl)-4-hydroxybenzyl)phenyl)glycine |
| 51 | 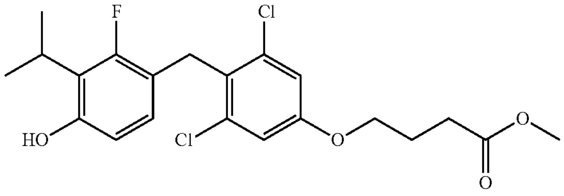 [SMILES: COC(=O)CCCOc1cc(Cl)c(Cc2ccc(O)c(C(C)C)c2F)c(Cl)c1] | methyl 4-(3,5-dichloro-4-(2-fluoro-4-hydroxy-3-isopropylbenzyl)phenoxy)butanoate |
| 52 | 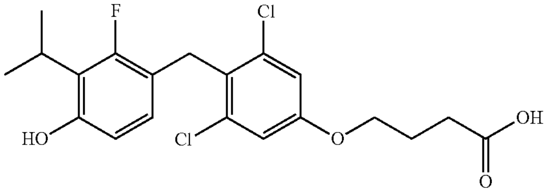 [SMILES: CC(C)c1c(O)ccc(Cc2c(Cl)cc(OCCCC(=O)O)cc2Cl)c1F] | 4-(3,5-dichloro-4-(2-fluoro-4-hydroxy-3-isopropylbenzyl)phenoxy)butanoic acid |
| 53 | 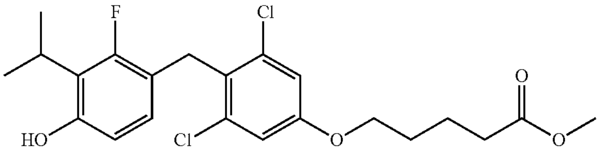 [SMILES: COC(=O)CCCCOc1cc(Cl)c(Cc2ccc(O)c(C(C)C)c2F)c(Cl)c1] | methyl 5-(3,5-dichloro-4-(2-fluoro-4-hydroxy-3-isopropylbenzyl)phenoxy)pentanoate |
| 54 | 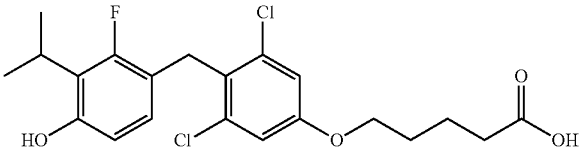 [SMILES: CC(C)c1c(O)ccc(Cc2c(Cl)cc(OCCCCC(=O)O)cc2Cl)c1F] | 5-(3,5-dichloro-4-(2-fluoro-4-hydroxy-3-isopropylbenzyl)phenoxy)pentanoic acid |

TABLE 1-continued

| Cmpd No | Structure | Name |
| --- | --- | --- |
| REPRESENTATIVE COMPOUNDS | | |
| 55 | 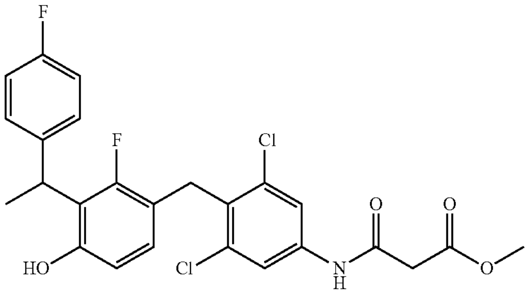 [SMILES: COC(=O)CC(=O)Nc1cc(Cl)c(Cc2ccc(O)c(C(C)c3ccc(F)cc3)c2F)c(Cl)c1] | methyl 3-((3,5-dichloro-4-(2-fluoro-3-(1-(4-fluorophenyl)ethyl)-4-hydroxybenzyl)phenyl)amino)-3-oxopropanoate |
| 56 | 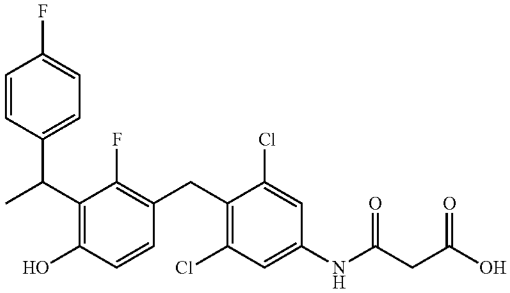 [SMILES: CC(c1ccc(F)cc1)c1c(O)ccc(Cc2c(Cl)cc(NC(=O)CC(=O)O)cc2Cl)c1F] | 3-((3,5-dichloro-4-(2-fluoro-3-(1-(4-fluorophenyl)ethyl)-4-hydroxybenzyl)phenyl)amino)-3-oxopropanoic acid |
| 57 | 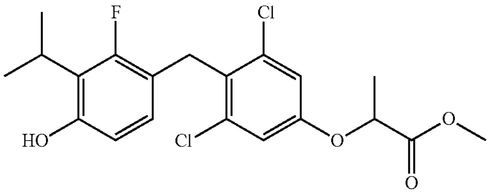 [SMILES: COC(=O)C(C)Oc1cc(Cl)c(Cc2ccc(O)c(C(C)C)c2F)c(Cl)c1] | methyl 2-(3,5-dichloro-4-(2-fluoro-4-hydroxy-3-isopropylbenzyl)phenoxy)propanoate |
| 58 | 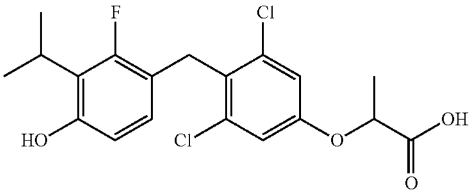 [SMILES: CC(Oc1cc(Cl)c(Cc2ccc(O)c(C(C)C)c2F)c(Cl)c1)C(=O)O] | 2-(3,5-dichloro-4-(2-fluoro-4-hydroxy-3-isopropylbenzyl)phenoxy)propanoic acid |
| 59 | 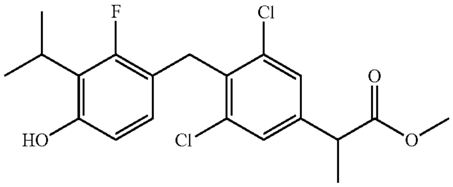 [SMILES: COC(=O)C(C)c1cc(Cl)c(Cc2ccc(O)c(C(C)C)c2F)c(Cl)c1] | methyl 2-(3,5-dichloro-4-(2-fluoro-4-hydroxy-3-isopropylbenzyl)phenyl)propanoate |
| 60 | 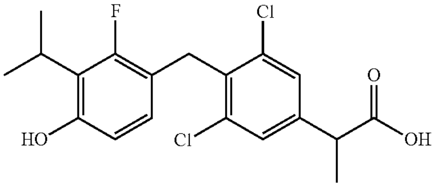 [SMILES: CC(C)c1c(O)ccc(Cc2c(Cl)cc(C(C)C(=O)O)cc2Cl)c1F] | 2-(3,5-dichloro-4-(2-fluoro-4-hydroxy-3-isopropylbenzyl)phenyl)propanoic acid |

TABLE 1-continued

| REPRESENTATIVE COMPOUNDS | | |
|---|---|---|
| Cmpd No | Structure | Name |
| 61 | 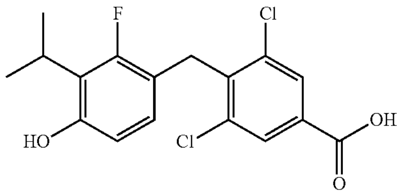 [SMILES: CC(C)c1c(O)ccc(Cc2c(Cl)cc(C(=O)O)cc2Cl)c1F] | 3,5-dichloro-4-(2-fluoro-4-hydroxy-3-isopropylbenzyl)benzoic acid |
| 62 | 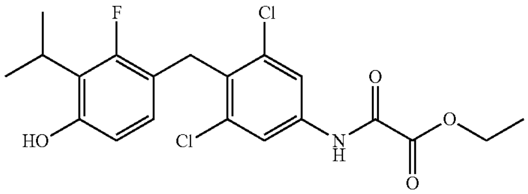 [SMILES: CCOC(=O)C(=O)Nc1cc(Cl)c(Cc2ccc(O)c(C(C)C)c2F)c(Cl)c1] | ethyl 2-((3,5-dichloro-4-(2-fluoro-4-hydroxy-3-isopropylbenzyl)phenyl)amino)-2-oxoacetate |
| 63 | 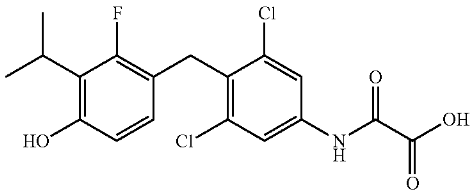 [SMILES: CC(C)c1c(O)ccc(Cc2c(Cl)cc(NC(=O)C(=O)O)cc2Cl)c1F] | 2-((3,5-dichloro-4-(2-fluoro-4-hydroxy-3-isopropylbenzyl)phenyl)amino)-2-oxoacetic acid |
| 64 | 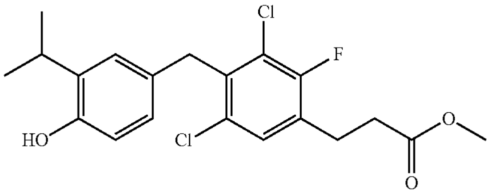 [SMILES: COC(=O)CCc1cc(Cl)c(Cc2ccc(O)c(C(C)C)c2)c(Cl)c1F] | methyl 3-(3,5-dichloro-2-fluoro-4-(4-hydroxy-3-isopropylbenzyl)phenyl)propanoate |
| 65 | 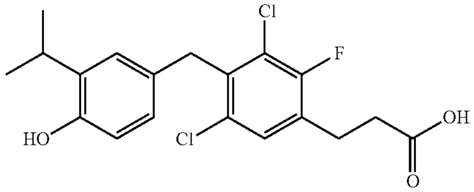 [SMILES: CC(C)c1cc(Cc2c(Cl)cc(CCC(=O)O)c(F)c2Cl)ccc1O] | 3-(3,5-dichloro-2-fluoro-4-(4-hydroxy-3-isopropylbenzyl)phenyl)propanoic acid |
| 66 | 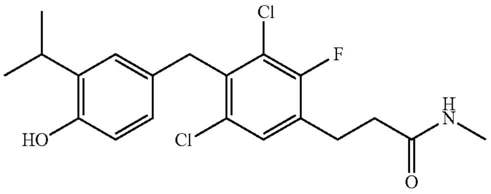 [SMILES: CNC(=O)CCc1cc(Cl)c(Cc2ccc(O)c(C(C)C)c2)c(Cl)c1F] | 3-(3,5-dichloro-2-fluoro-4-(4-hydroxy-3-isopropylbenzyl)phenyl)-N-methylpropanamide |
| 67 | 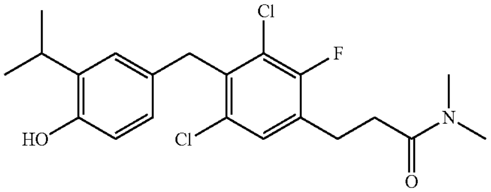 [SMILES: CC(C)c1cc(Cc2c(Cl)cc(CCC(=O)N(C)C)c(F)c2Cl)ccc1O] | 3-(3,5-dichloro-2-fluoro-4-(4-hydroxy-3-isopropylbenzyl)phenyl)-N,N-dimethylpropanamide |

TABLE 1-continued

REPRESENTATIVE COMPOUNDS

| Cmpd No | Structure | Name |
|---|---|---|
| 68 | 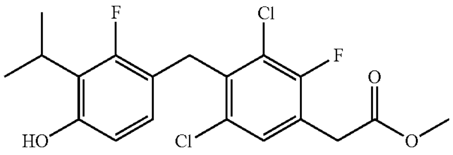 [SMILES: COC(=O)Cc1cc(Cl)c(Cc2ccc(O)c(C(C)C)c2F)c(Cl)c1F] | methyl 2-(3,5-dichloro-2-fluoro-4-(2-fluoro-4-hydroxy-3-isopropylbenzyl)phenyl)acetate |
| 69 | 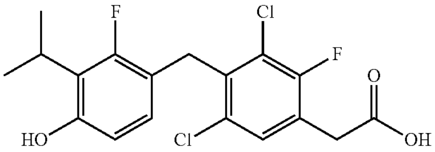 [SMILES: CC(C)c1c(O)ccc(Cc2c(Cl)cc(CC(=O)O)c(F)c2Cl)c1F] | 2-(3,5-dichloro-2-fluoro-4-(2-fluoro-4-hydroxy-3-isopropylbenzyl)phenyl)acetic acid |
| 70 | 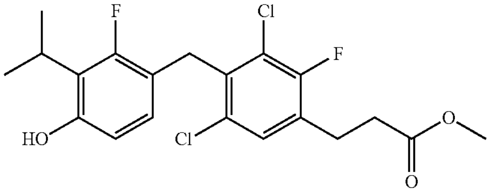 [SMILES: COC(=O)CCc1cc(Cl)c(Cc2ccc(O)c(C(C)C)c2F)c(Cl)c1F] | methyl 3-(3,5-dichloro-2-fluoro-4-(2-fluoro-4-hydroxy-3-isopropylbenzyl)phenyl)propanoate |
| 71 | 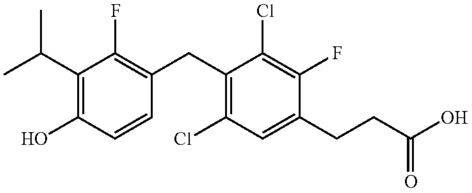 [SMILES: CC(C)c1c(O)ccc(Cc2c(Cl)cc(CCC(=O)O)c(F)c2Cl)c1F] | 3-(3,5-dichloro-2-fluoro-4-(2-fluoro-4-hydroxy-3-isopropylbenzyl)phenyl)propanoic acid |
| 72 | 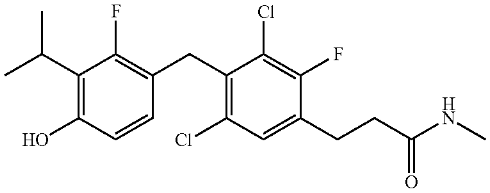 [SMILES: CNC(=O)CCc1cc(Cl)c(Cc2ccc(O)c(C(C)C)c2F)c(Cl)c1F] | 3-(3,5-dichloro-2-fluoro-4-(2-fluoro-4-hydroxy-3-isopropylbenzyl)phenyl)-N-methylpropanamide |
| 73 | 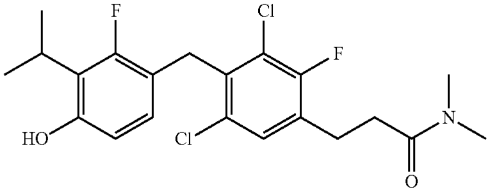 [SMILES: CC(C)c1c(O)ccc(Cc2c(Cl)cc(CCC(=O)N(C)C)c(F)c2Cl)c1F] | 3-(3,5-dichloro-2-fluoro-4-(2-fluoro-4-hydroxy-3-isopropylbenzyl)phenyl)-N,N-dimethylpropanamide |
| 74 | 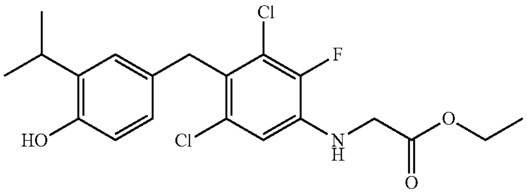 [SMILES: CCOC(=O)CNc1cc(Cl)c(Cc2ccc(O)c(C(C)C)c2)c(Cl)c1F] | ethyl (3,5-dichloro-2-fluoro-4-(4-hydroxy-3-isopropylbenzyl)phenyl)glycinate |
| 75 | 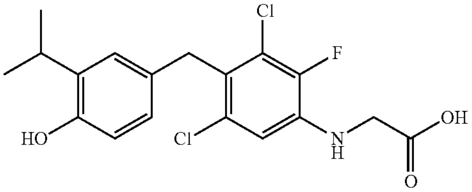 [SMILES: CC(C)c1cc(Cc2c(Cl)cc(NCC(=O)O)c(F)c2Cl)ccc1O] | (3,5-dichloro-2-fluoro-4-(4-hydroxy-3-isopropylbenzyl)phenyl)glycine |

TABLE 1-continued

| REPRESENTATIVE COMPOUNDS | | |
|---|---|---|
| Cmpd No | Structure | Name |
| 76 | 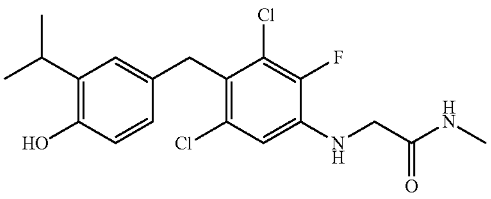 | 2-((3,5-dichloro-2-fluoro-4-(4-hydroxy-3-isopropylbenzyl)phenyl)amino)-N-methylacetamide |
| 77 | 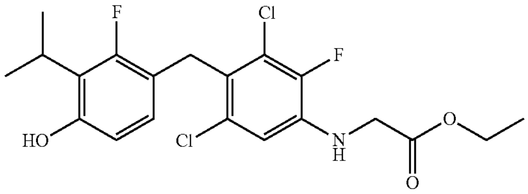 [SMILES: CCOC(=O)CNc1cc(Cl)c(Cc2ccc(O)c(C(C)C)c2F)c(Cl)c1F] | ethyl (3,5-dichloro-2-fluoro-4-(2-fluoro-4-hydroxy-3-isopropylbenzyl)phenyl)glycinate |
| 78 | 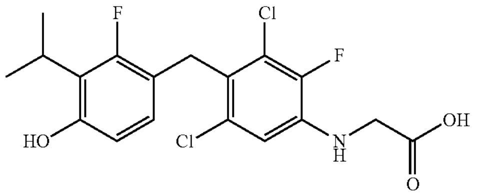 | (3,5-dichloro-2-fluoro-4-(2-fluoro-4-hydroxy-3-isopropylbenzyl)phenyl)glycine |
| 79 | 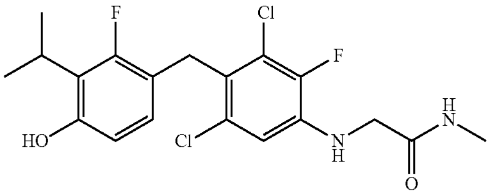 [SMILES: CNC(=O)CNc1cc(Cl)c(Cc2ccc(O)c(C(C)C)c2F)c(Cl)c1F] | 2-((3,5-dichloro-2-fluoro-4-(2-fluoro-4-hydroxy-3-isopropylbenzyl)phenyl)amino)-N-methylacetamide |
| 80 | 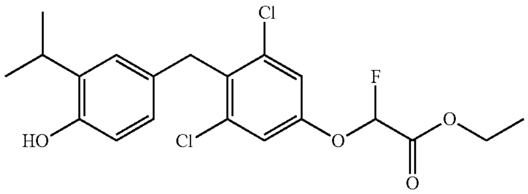 [SMILES: CCOC(=O)C(F)Oc1cc(Cl)c(Cc2ccc(O)c(C(C)C)c2)c(Cl)c1] | ethyl 2-(3,5-dichloro-4-(4-hydroxy-3-isopropylbenzyl)phenoxy)-2-fluoroacetate |
| 81 | 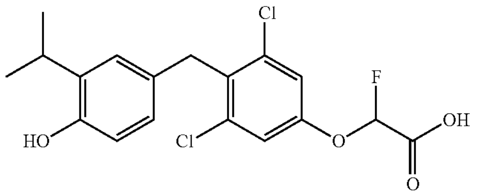 [SMILES: CC(C)c1cc(Cc2c(Cl)cc(OC(F)C(=O)O)cc2Cl)ccc1O] | 2-(3,5-dichloro-4-(4-hydroxy-3-isopropylbenzyl)phenoxy)-2-fluoroacetic acid |
| 82 | 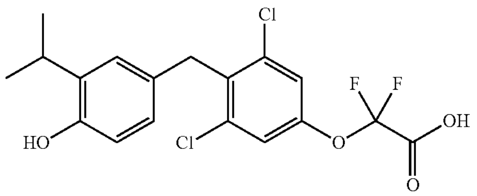 [SMILES: CC(C)c1cc(Cc2c(Cl)cc(OC(F)(F)C(=O)O)cc2Cl)ccc1O] | 2-(3,5-dichloro-4-(4-hydroxy-3-isopropylbenzyl)phenoxy)-2,2-difluoroacetic acid |

TABLE 1-continued

| REPRESENTATIVE COMPOUNDS | | |
|---|---|---|
| Cmpd No | Structure | Name |
| 83 | 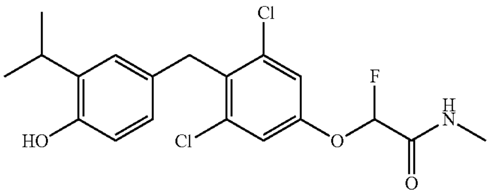 [SMILES: CNC(=O)C(F)Oc1cc(Cl)c(Cc2ccc(O)c(C(C)C)c2)c(Cl)c1] | 2-(3,5-dichloro-4-(4-hydroxy-3-isopropylbenzyl)phenoxy)-2-fluoro-N-methylacetamide |
| 84 | 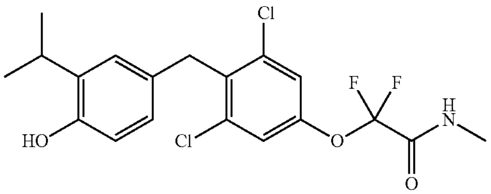 [SMILES: CNC(=O)C(F)(F)Oc1cc(Cl)c(Cc2ccc(O)c(C(C)C)c2)c(Cl)c1] | 2-(3,5-dichloro-4-(4-hydroxy-3-isopropylbenzyl)phenoxy)-2,2-difluoro-N-methylacetamide |
| 85 | 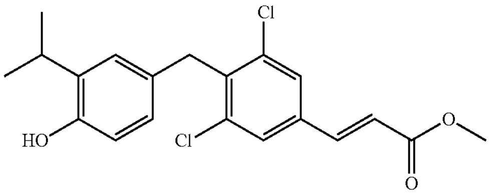 [SMILES: COC(=O)/C=C/c1cc(Cl)c(Cc2ccc(O)c(C(C)C)c2)c(Cl)c1] | methyl (E)-3-(3,5-dichloro-4-(4-hydroxy-3-isopropylbenzyl)phenyl)acrylate |
| 86 | 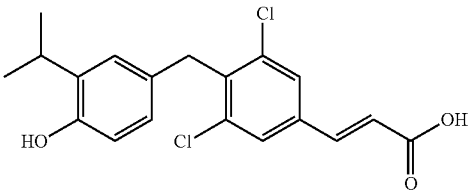 [SMILES: CC(C)c1cc(Cc2c(Cl)cc(/C=C/C(=O)O)cc2Cl)ccc1O] | (E)-3-(3,5-dichloro-4-(4-hydroxy-3-isopropylbenzyl)phenyl)acrylic acid |
| 87 | 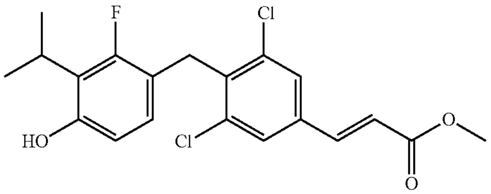 [SMILES: COC(=O)/C=C/c1cc(Cl)c(Cc2ccc(O)c(C(C)C)c2F)c(Cl)c1] | methyl (E)-3-(3,5-dichloro-4-(2-fluoro-4-hydroxy-3-isopropylbenzyl)phenyl)acrylate |
| 88 | 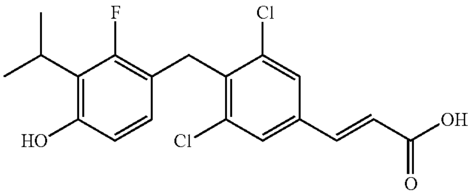 | (E)-3-(3,5-dichloro-4-(2-fluoro-4-hydroxy-3-isopropylbenzyl)phenyl)acrylic acid |
| 89 | 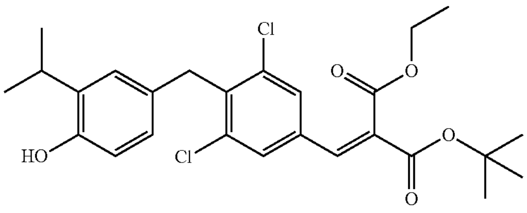 [SMILES: CCOC(=O)/C(=C\c1cc(Cl)c(Cc2ccc(O)c(C(C)C)c2)c(Cl)c1)C(=O)OC(C)(C)C] | 1-(tert-butyl) 3-ethyl (E)-2-(3,5-dichloro-4-(4-hydroxy-3-isopropylbenzyl)benzylidene)malonate |

TABLE 1-continued

| REPRESENTATIVE COMPOUNDS | | |
|---|---|---|
| Cmpd No | Structure | Name |
| 90 | 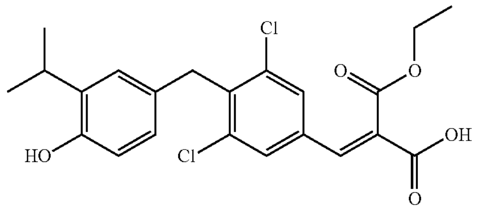 [SMILES: CCOC(=O)/C(=C\c1cc(Cl)c(Cc2ccc(O)c(C(C)C)c2)c(Cl)c1)C(=O)O] | (Z)-3-(3,5-dichloro-4-(4-hydroxy-3-isopropylbenzyl)phenyl)-2-(ethoxycarbonyl)acrylic acid |
| 91 | 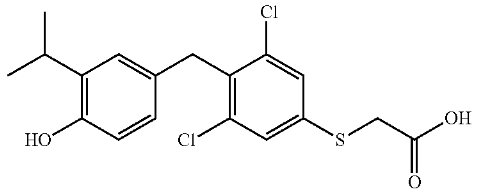 | 2-((3,5-dichloro-4-(4-hydroxy-3-isopropylbenzyl)phenyl)thio)acetic acid |
| 92 | 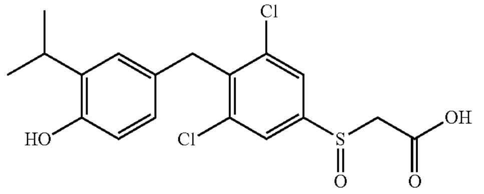 [SMILES: CC(C)c1cc(Cc2c(Cl)cc(S(=O)CC(=O)O)cc2Cl)ccc1O] | 2-((3,5-dichloro-4-(4-hydroxy-3-isopropylbenzyl)phenyl)sulfinyl)acetic acid |
| 93 | 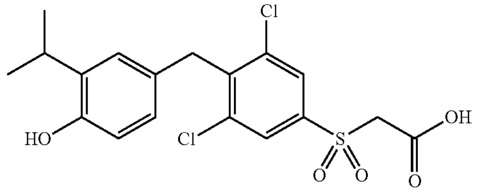 [SMILES: CC(C)c1cc(Cc2c(Cl)cc(S(=O)(=O)CC(=O)O)cc2Cl)ccc1O] | 2-((3,5-dichloro-4-(4-hydroxy-3-isopropylbenzyl)phenyl)sulfonyl) acetic acid |
| 94 | 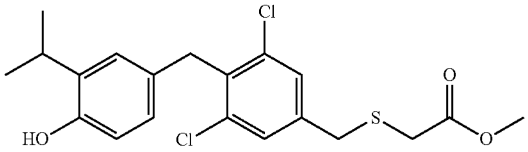 [SMILES: COC(=O)CSCc1cc(Cl)c(Cc2ccc(O)c(C(C)C)c2)c(Cl)c1] | methyl 2-((3,5-dichloro-4-(4-hydroxy-3-isopropylbenzyl)benzyl)thio)acetate |
| 95 | 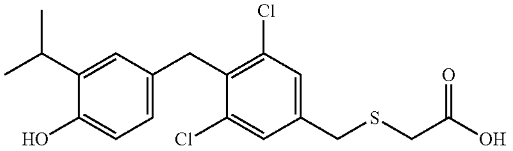 [SMILES: CC(C)c1cc(Cc2c(Cl)cc(CSCC(=O)O)cc2Cl)ccc1O] | 2-((3,5-dichloro-4-(4-hydroxy-3-isopropylbenzyl)benzyl)thio)acetic acid |
| 96 | 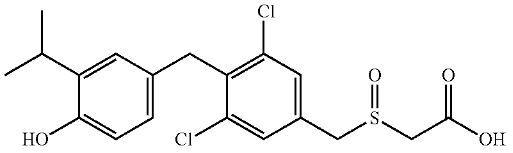 [SMILES: CC(C)c1cc(Cc2c(Cl)cc(CS(=O)CC(=O)O)cc2Cl)ccc1O] | 2-((3,5-dichloro-4-(4-hydroxy-3-isopropylbenzyl)benzyl)sulfinyl)acetic acid |
| 97 | 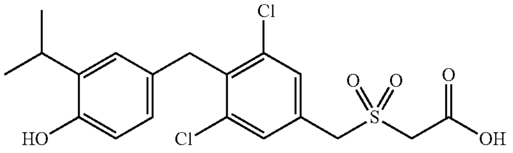 [SMILES: CC(C)c1cc(Cc2c(Cl)cc(CS(=O)(=O)CC(=O)O)cc2Cl)ccc1O] | 2-((3,5-dichloro-4-(4-hydroxy-3-isopropylbenzyl)benzyl)sulfonyl)acetic acid |

TABLE 1-continued

| REPRESENTATIVE COMPOUNDS | | |
|---|---|---|
| Cmpd No | Structure | Name |
| 98 | 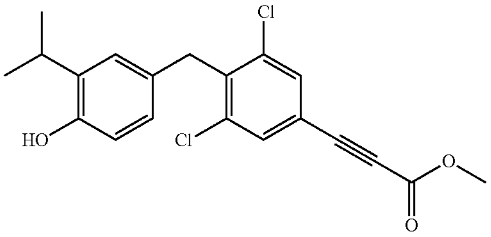 [SMILES: COC(=O)C#Cc1cc(Cl)c(Cc2ccc(O)c(C(C)C)c2)c(Cl)c1] | methyl 3-(3,5-dichloro-4-(4-hydroxy-3-isopropylbenzyl)phenyl) propiolate |
| 99 | 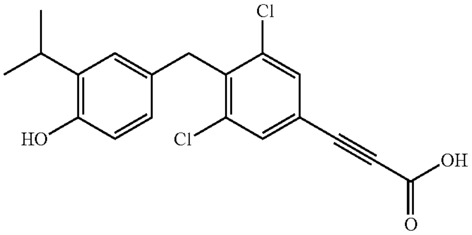 [SMILES: CC(C)c1cc(Cc2c(Cl)cc(C#CC(=O)O)cc2Cl)ccc1O] | 3-(3,5-dichloro-4-(4-hydroxy-3-isopropylbenzyl)phenyl)propiolic acid |
| 100 | 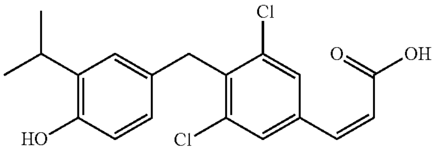 [SMILES: CC(C)c1cc(Cc2c(Cl)cc(/C=C\C(=O)O)cc2Cl)ccc1O] | (Z)-3-(3,5-dichloro-4-(4-hydroxy-3-isopropylbenzyl)phenyl)acrylic acid |
| 101 | 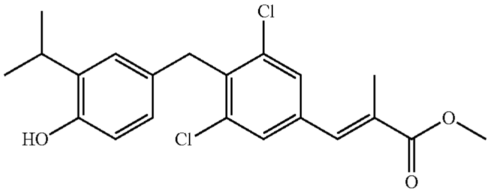 [SMILES: COC(=O)/C(C)=C/c1cc(Cl)c(Cc2ccc(O)c(C(C)C)c2)c(Cl)c1] | methyl (E)-3-(3,5-dichloro-4-(4-hydroxy-3-isopropylbenzyl)phenyl)-2-methylacrylate |
| 102 | 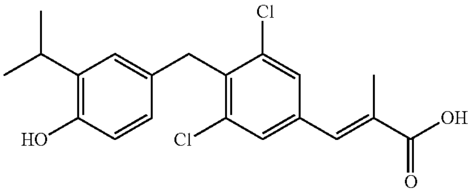 [SMILES: C/C(=C\c1cc(Cl)c(Cc2ccc(O)c(C(C)C)c2)c(Cl)c1)C(=O)O] | (E)-3-(3,5-dichloro-4-(4-hydroxy-3-isopropylbenzyl)phenyl)-2-methylacrylic acid |
| 103 | 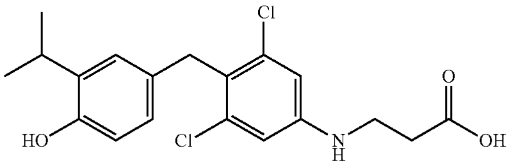 [SMILES: CC(C)c1cc(Cc2c(Cl)cc(NCCC(=O)O)cc2Cl)ccc1O] | 3-((3,5-dichloro-4-(4-hydroxy-3-isopropylbenzyl)phenyl)amino)propanoic acid |
| 104 | 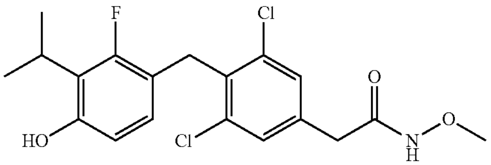 [SMILES: CONC(=O)Cc1cc(Cl)c(Cc2ccc(O)c(C(C)C)c2F)c(Cl)c1] | 2-(3,5-dichloro-4-(2-fluoro-4-hydroxy-3-isopropylbenzyl)phenyl)-N-methoxyacetamide |

TABLE 1-continued

| REPRESENTATIVE COMPOUNDS | | |
|---|---|---|
| Cmpd No | Structure | Name |
| 105 | 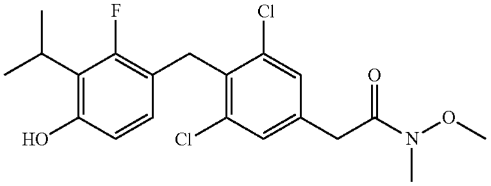 [SMILES: CON(C)C(=O)Cc1cc(Cl)c(Cc2ccc(O)c(C(C)C)c2F)c(Cl)c1] | 2-(3,5-dichloro-4-(2-fluoro-4-hydroxy-3-isopropylbenzyl)phenyl)-N-methoxy-N-methylacetamide |
| 106 | 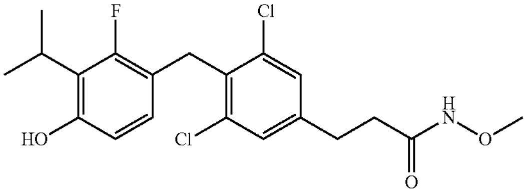 | 3-(3,5-dichloro-4-(2-fluoro-4-hydroxy-3-isopropylbenzyl)phenyl)-N-methoxypropanamide |
| 107 | 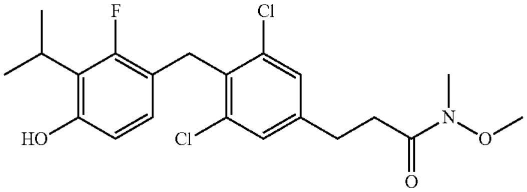 [SMILES: CON(C)C(=O)CCc1cc(Cl)c(Cc2ccc(O)c(C(C)C)c2F)c(Cl)c1] | 3-(3,5-dichloro-4-(2-fluoro-4-hydroxy-3-isopropylbenzyl)phenyl)-N-methoxy-N-methylpropanamide |
| 108 | 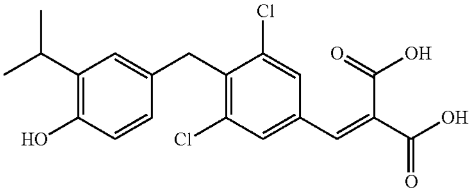 [SMILES: CC(C)c1cc(Cc2c(Cl)cc(C=C(C(=O)O)C(=O)O)cc2Cl)ccc1O] | 2-(3,5-dichloro-4-(4-hydroxy-3-isopropylbenzyl)benzylidene)malonic acid |
| 109 | 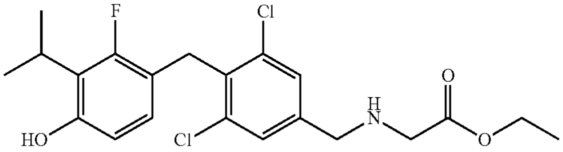 [SMILES: CCOC(=O)CNCc1cc(Cl)c(Cc2ccc(O)c(C(C)C)c2F)c(Cl)c1] | ethyl (3,5-dichloro-4-(2-fluoro-4-hydroxy-3-isopropylbenzyl)benzyl)glycinate |
| 110 | 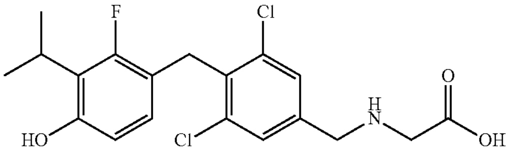 [SMILES: CC(C)c1c(O)ccc(Cc2c(Cl)cc(CNCC(=O)O)cc2Cl)c1F] | (3,5-dichloro-4-(2-fluoro-4-hydroxy-3-isopropylbenzyl)benzyl)glycine |
| 111 | 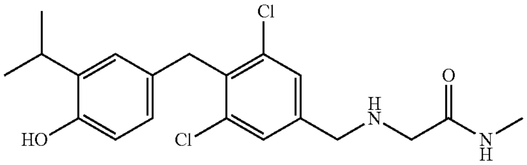 [SMILES: CNC(=O)CNCc1cc(Cl)c(Cc2ccc(O)c(C(C)C)c2)c(Cl)c1] | 2-((3,5-dichloro-4-(4-hydroxy-3-isopropylbenzyl)benzyl)amino)-N-methylacetamide |
| 112 | 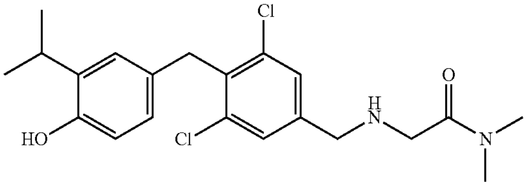 [SMILES: CC(C)c1cc(Cc2c(Cl)cc(CNCC(=O)N(C)C)cc2Cl)ccc1O] | 2-((3,5-dichloro-4-(4-hydroxy-3-isopropylbenzyl)benzyl)amino)-N,N-dimethylacetamide |

TABLE 1-continued

| REPRESENTATIVE COMPOUNDS | | |
|---|---|---|
| Cmpd No | Structure | Name |
| 113 | 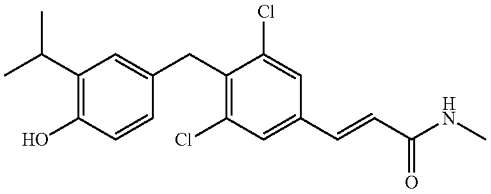 [SMILES: CNC(=O)/C=C/c1cc(Cl)c(Cc2ccc(O)c(C(C)C)c2)c(Cl)c1] | (E)-3-(3,5-dichloro-4-(4-hydroxy-3-isopropylbenzyl)phenyl)-N-methylacrylamide |
| 114 | 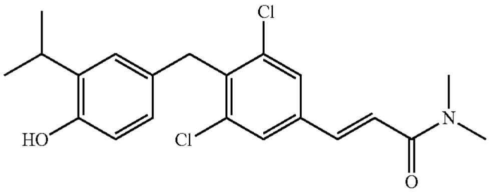 [SMILES: CC(C)c1cc(Cc2c(Cl)cc(/C=C/C(=O)N(C)C)cc2Cl)ccc1O] | (E)-3-(3,5-dichloro-4-(4-hydroxy-3-isopropylbenzyl)phenyl)-N,N-dimethylacrylamide |
| 115 | 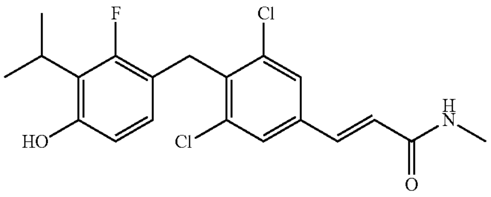 [SMILES: CNC(=O)/C=C/c1cc(Cl)c(Cc2ccc(O)c(C(C)C)c2F)c(Cl)c1] | (E)-3-(3,5-dichloro-4-(2-fluoro-4-hydroxy-3-isopropylbenzyl)phenyl)-N-methylacrylamide |
| 116 | 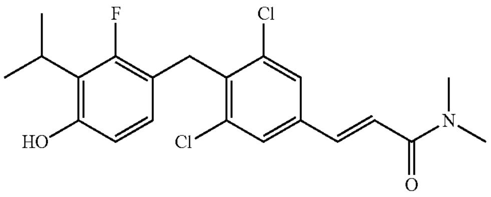 [SMILES: CC(C)c1c(O)ccc(Cc2c(Cl)cc(/C=C/C(=O)N(C)C)cc2Cl)c1F] | (E)-3-(3,5-dichloro-4-(2-fluoro-4-hydroxy-3-isopropylbenzyl)phenyl)-N,N-dimethylacrylamide |
| 117 | 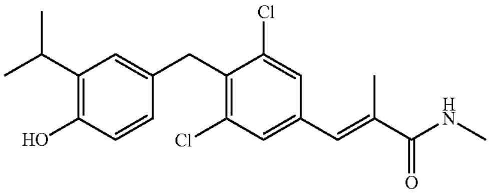 [SMILES: CNC(=O)/C(C)=C/c1cc(Cl)c(Cc2ccc(O)c(C(C)C)c2)c(Cl)c1] | (E)-3-(3,5-dichloro-4-(4-hydroxy-3-isopropylbenzyl)phenyl)-N,2-dimethylacrylamide |
| 118 | 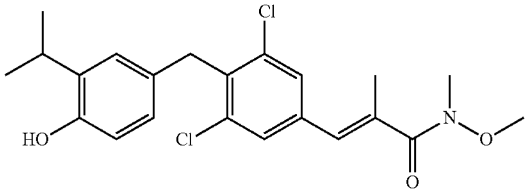 [SMILES: CON(C)C(=O)/C(C)=C/c1cc(Cl)c(Cc2ccc(O)c(C(C)C)c2)c(Cl)c1] | (E)-3-(3,5-dichloro-4-(4-hydroxy-3-isopropylbenzyl)phenyl)-N-methoxy-N,2-dimethylacrylamide |
| 119 | 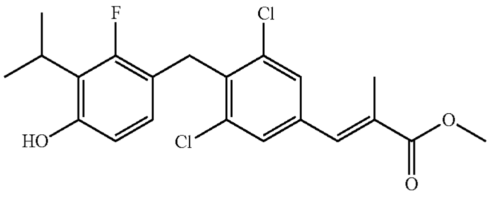 [SMILES: COC(=O)/C(C)=C/c1cc(Cl)c(Cc2ccc(O)c(C(C)C)c2F)c(Cl)c1] | methyl (E)-3-(3,5-dichloro-4-(2-fluoro-4-hydroxy-3-isopropylbenzyl)phenyl)-2-methylacrylate |

TABLE 1-continued

| REPRESENTATIVE COMPOUNDS | | |
|---|---|---|
| Cmpd No | Structure | Name |
| 120 | 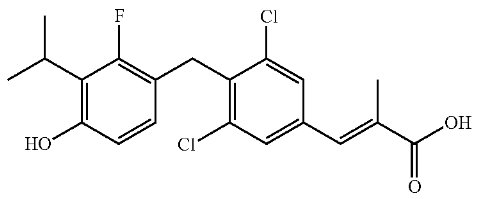 [SMILES: C/C(=C\c1cc(Cl)c(Cc2ccc(O)c(C(C)C)c2F)c(Cl)c1)C(=O)O] | (E)-3-(3,5-dichloro-4-(2-fluoro-4-hydroxy-3-isopropylbenzyl)phenyl)-2-methylacrylic acid |
| 121 | 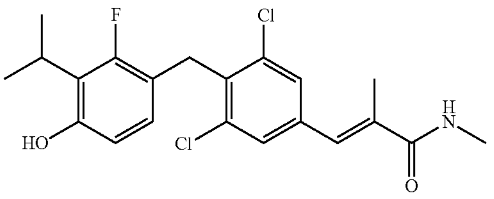 [SMILES: CNC(=O)/C(C)=C/c1cc(Cl)c(Cc2ccc(O)c(C(C)C)c2F)c(Cl)c1] | (E)-3-(3,5-dichloro-4-(2-fluoro-4-hydroxy-3-isopropylbenzyl)phenyl)-N,2-dimethylacrylamide |
| 122 | 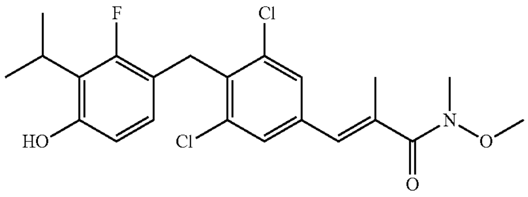 [SMILES: CON(C)C(=O)/C(C)=C/c1cc(Cl)c(Cc2ccc(O)c(C(C)C)c2F)c(Cl)c1] | (E)-3-(3,5-dichloro-4-(2-fluoro-4-hydroxy-3-isopropylbenzyl)phenyl)-N-methoxy-N,2-dimethylacrylamide |
| 123 | 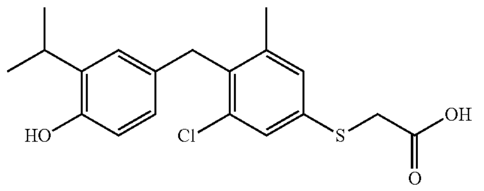 [SMILES: Cc1cc(SCC(=O)O)cc(Cl)c1Cc1ccc(O)c(C(C)C)c1] | (3-chloro-4-(4-hydroxy-3-isopropylbenzyl)-5-methylbenzyl)glycine |
| 124 | 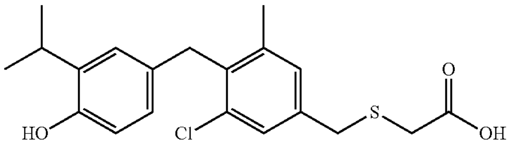 [SMILES: Cc1cc(CSCC(=O)O)cc(Cl)c1Cc1ccc(O)c(C(C)C)c1] | 2-((3-chloro-4-(4-hydroxy-3-isopropylbenzyl)-5-methylbenzyl)thio)acetic acid |
| 125 | 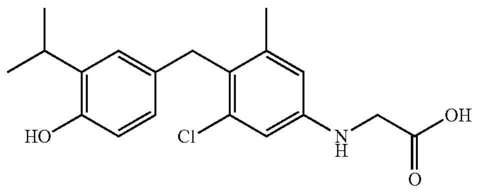 [SMILES: Cc1cc(NCC(=O)O)cc(Cl)c1Cc1ccc(O)c(C(C)C)c1] | (3-chloro-4-(4-hydroxy-3-isopropylbenzyl)-5-methylphenyl)glycine |
| 126 | 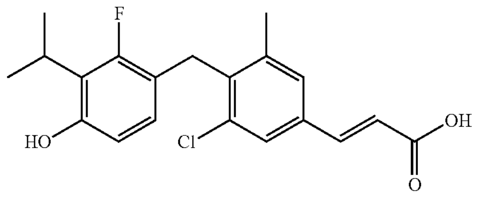 [SMILES: Cc1cc(/C=C/C(=O)O)cc(Cl)c1Cc1ccc(O)c(C(C)C)c1F] | (E)-3-(3-chloro-4-(2-fluoro-4-hydroxy-3-isopropylbenzyl)-5-methylphenyl)acrylic acid |

TABLE 1-continued

| REPRESENTATIVE COMPOUNDS | | |
|---|---|---|
| Cmpd No | Structure | Name |
| 127 | 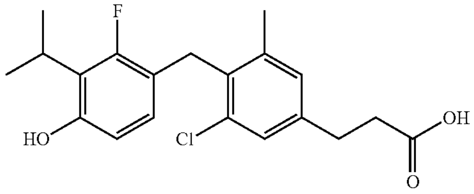 [SMILES: Cc1cc(CCC(=O)O)cc(Cl)c1Cc1ccc(O)c(C(C)C)c1F] | 3-(3-chloro-4-(2-fluoro-4-hydroxy-3-isopropylbenzyl)-5-methylphenyl)propanoic acid |
| 128 | 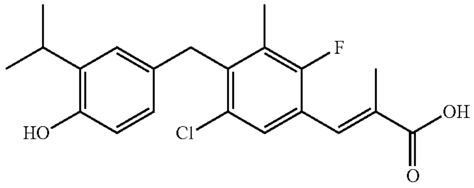 [SMILES: C/C(=C\c1cc(Cl)c(Cc2ccc(O)c(C(C)C)c2)c(C)c1F)C(=O)O] | (E)-3-(5-chloro-2-fluoro-4-(4-hydroxy-3-isopropylbenzyl)-3-methylphenyl)-2-methylacrylic acid |
| 129 | 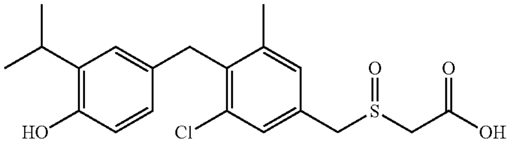 [SMILES: Cc1cc(CS(=O)CC(=O)O)cc(Cl)c1Cc1ccc(O)c(C(C)C)c1] | 2-((3-chloro-4-(4-hydroxy-3-isopropylbenzyl)-5-methylbenzyl)sulfinyl)acetic acid |
| 130 | 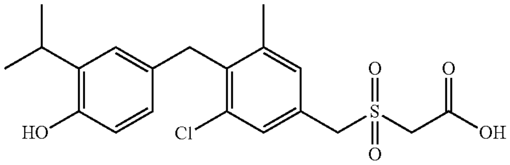 [SMILES: Cc1cc(CS(=O)(=O)CC(=O)O)cc(Cl)c1Cc1ccc(O)c(C(C)C)c1] | 2-((3-chloro-4-(4-hydroxy-3-isopropylbenzyl)-5-methylbenzyl)sulfonyl)acetic acid |
| 131 | 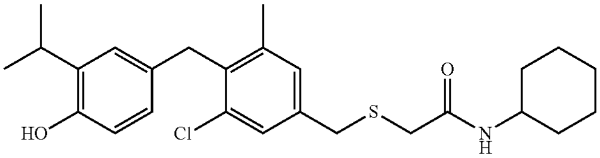 [SMILES: Cc1cc(CSCC(=O)NC2CCCCC2)cc(Cl)c1Cc1ccc(O)c(C(C)C)c1] | 2-((3-chloro-4-(4-hydroxy-3-isopropylbenzyl)-5-methylbenzyl)thio)-N-cyclohexylacetamide |
| 132 | 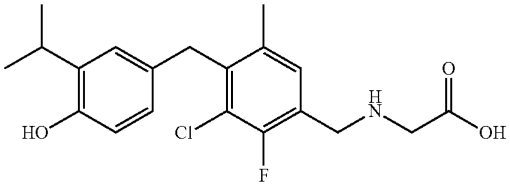 [SMILES: Cc1cc(CNCC(=O)O)c(F)c(Cl)c1Cc1ccc(O)c(C(C)C)c1] | (3-chloro-2-fluoro-4-(4-hydroxy-3-isopropylbenzyl)-5-methylbenzyl)glycine |
| 133 | 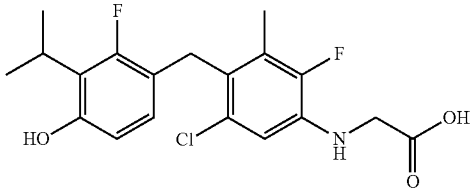 [SMILES: Cc1c(F)c(NCC(=O)O)cc(Cl)c1Cc1ccc(O)c(C(C)C)c1F] | (5-chloro-2-fluoro-4-(2-fluoro-4-hydroxy-3-isopropylbenzyl)-3-methylphenyl)glycine |
| 134 | 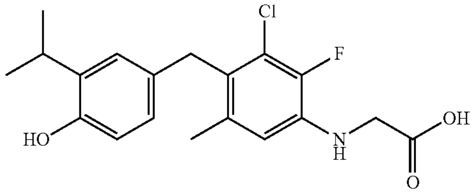 [SMILES: Cc1cc(NCC(=O)O)c(F)c(Cl)c1Cc1ccc(O)c(C(C)C)c1] | (3-chloro-2-fluoro-4-(4-hydroxy-3-isopropylbenzyl)-5-methylphenyl)glycine |

TABLE 1-continued

| Cmpd No | Structure | Name |
|---|---|---|
| REPRESENTATIVE COMPOUNDS | | |
| 135 | 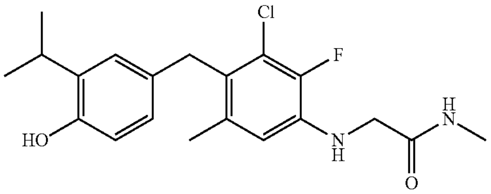 [SMILES: CNC(=O)CNc1cc(C)c(Cc2ccc(O)c(C(C)C)c2)c(Cl)c1F] | 2-((3-chloro-2-fluoro-4-(4-hydroxy-3-isopropylbenzyl)-5-methylphenyl)amino)-N-methylacetamide |
| 136 | 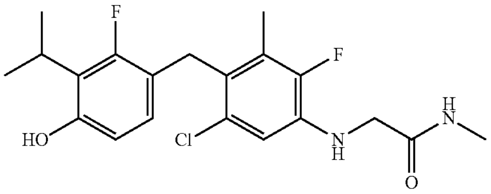 [SMILES: CNC(=O)CNc1cc(Cl)c(Cc2ccc(O)c(C(C)C)c2F)c(C)c1F] | 2-((5-chloro-2-fluoro-4-(2-fluoro-4-hydroxy-3-isopropylbenzyl)-3-methylphenyl)amino)-N-methylacetamide |
| 137 | 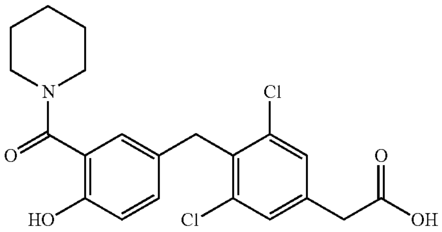 [SMILES: O=C(O)Cc1cc(Cl)c(Cc2ccc(O)c(C(=O)N3CCCCC3)c2)c(Cl)c1] | 2-(3,5-dichloro-4-(4-hydroxy-3-(piperidine-1-carbonyl)benzyl)phenyl)acetic acid |
| 138 | 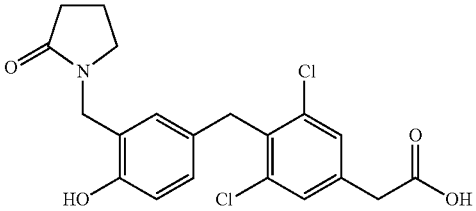 [SMILES: O=C(O)Cc1cc(Cl)c(Cc2ccc(O)c(CN3CCCC3=O)c2)c(Cl)c1] | 2-(3,5-dichloro-4-(4-hydroxy-3-((2-oxopyrrolidin-1-yl)methyl)benzyl)phenyl)acetic acid |
| 139 | 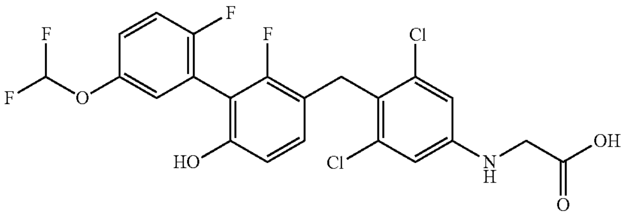 [SMILES: O=C(O)CNc1cc(Cl)c(Cc2ccc(O)c(-c3cc(OC(F)F)ccc3F)c2F)c(Cl)c1] | (3,5-dichloro-4-((5'-(difluoromethoxy)-2,2'-difluoro-6-hydroxy-[1,1'-biphenyl]-3-yl)methyl)phenyl)glycine |
| 140 | 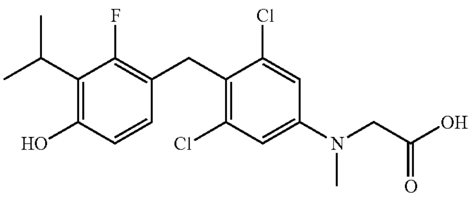 [SMILES: CC(C)c1c(O)ccc(Cc2c(Cl)cc(N(C)CC(=O)O)cc2Cl)c1F] | N-(3,5-dichloro-4-(2-fluoro-4-hydroxy-3-isopropylbenzyl)phenyl)-N-methylglycine |
| 141 | 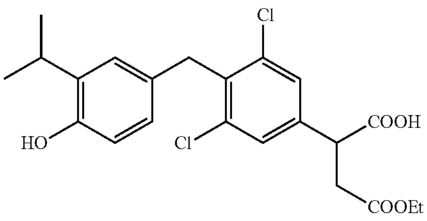 [SMILES: CCOC(=O)CC(C(=O)O)c1cc(Cl)c(Cc2ccc(O)c(C(C)C)c2)c(Cl)c1] | 2-(3,5-dichloro-4-(4-hydroxy-3-isopropylbenzyl)phenyl)-4-ethoxy-4-oxobutanoic acid |

TABLE 1-continued

REPRESENTATIVE COMPOUNDS

| Cmpd No | Structure | Name |
|---|---|---|
| 142 | 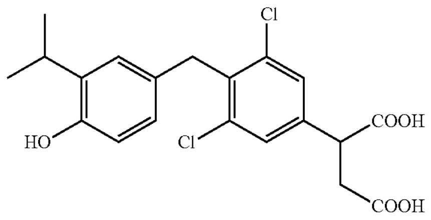 [SMILES: CC(C)c1cc(Cc2c(Cl)cc(C(CC(=O)O)C(=O)O)cc2Cl)ccc1O] | 2-(3,5-dichloro-4-(4-hydroxy-3-isopropylbenzyl)phenyl)succinic acid |
| 143 | 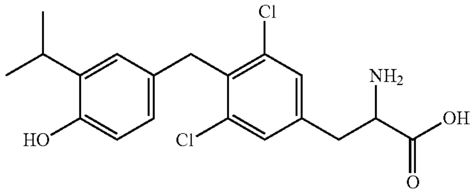 [SMILES: CC(C)c1cc(Cc2c(Cl)cc(CC(N)C(=O)O)cc2Cl)ccc1O] | 2-amino-3-(3,5-dichloro-4-(4-hydroxy-3-isopropylbenzyl)phenyl)propanoic acid |
| 144 | 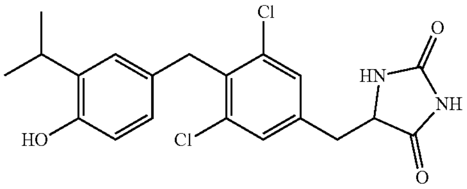 [SMILES: CC(C)c1cc(Cc2c(Cl)cc(CC3NC(=O)NC3=O)cc2Cl)ccc1O] | 5-(3,5-dichloro-4-(4-hydroxy-3-isopropylbenzyl)benzyl)imidazolidine-2,4-dione |
| 145 | 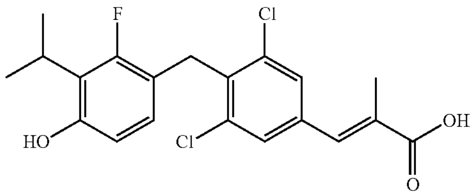 [SMILES: C/C(=C\c1cc(Cl)c(Cc2ccc(O)c(C(C)C)c2F)c(Cl)c1)C(=O)O] | (E)-3-(3,5-dichloro-4-(2-fluoro-4-hydroxy-3-isopropylbenzyl)phenyl)-2-methylacrylic acid |
| 146 | 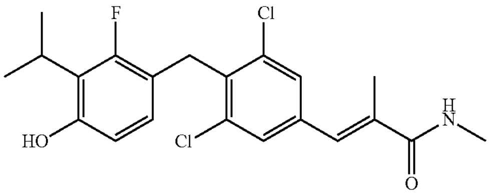 [SMILES: CNC(=O)/C(C)=C/c1cc(Cl)c(Cc2ccc(O)c(C(C)C)c2F)c(Cl)c1] | (E)-3-(3,5-dichloro-4-(2-fluoro-4-hydroxy-3-isopropylbenzyl)phenyl)-N,2-dimethylacrylamide |
| 147 | 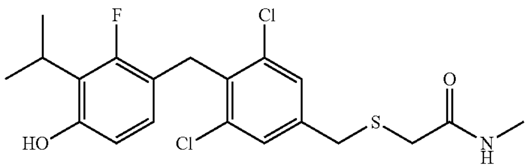 [SMILES: CNC(=O)CSCc1cc(Cl)c(Cc2ccc(O)c(C(C)C)c2F)c(Cl)c1] | 2-((3,5-dichloro-4-(2-fluoro-4-hydroxy-3-isopropylbenzyl)benzyl)thio)-N-methylacetamide |
| 148 | 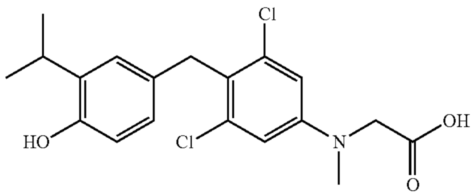 [SMILES: CC(C)c1cc(Cc2c(Cl)cc(N(C)CC(=O)O)cc2Cl)ccc1O] | N-(3,5-dichloro-4-(4-hydroxy-3-isopropylbenzyl)phenyl)-N-methylglycine |

TABLE 1-continued

REPRESENTATIVE COMPOUNDS

| Cmpd No | Structure | Name |
|---|---|---|
| 149 | 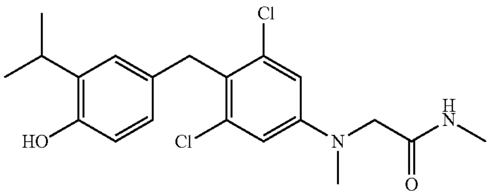 [SMILES: CNC(=O)CN(C)c1cc(Cl)c(Cc2ccc(O)c(C(C)C)c2)c(Cl)c1] | 2-((3,5-dichloro-4-(4-hydroxy-3-isopropylbenzyl)phenyl)(methyl)amino)-N-methylacetamide |
| 150 | 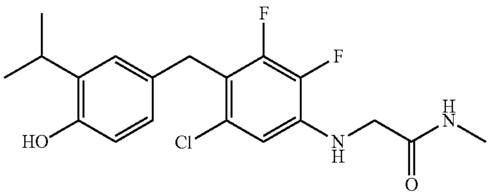 [SMILES: CNC(=O)CNc1cc(Cl)c(Cc2ccc(O)c(C(C)C)c2)c(F)c1F] | 2-((5-chloro-2,3-difluoro-4-(4-hydroxy-3-isopropylbenzyl)phenyl)amino)-N-methylacetamide |
| 151 | 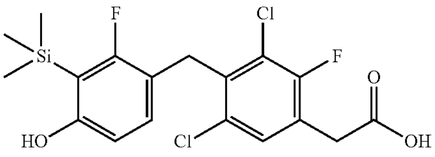 [SMILES: C[Si](C)(C)c1c(O)ccc(Cc2c(Cl)cc(CC(=O)O)c(F)c2Cl)c1F] | 2-(3,5-dichloro-2-fluoro-4-(2-fluoro-4-hydroxy-3-(trimethylsilyl)benzyl)phenyl)acetic acid |
| 152 | 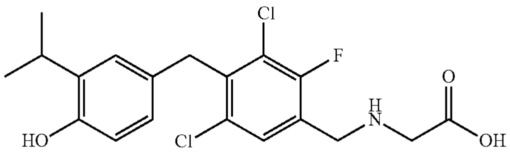 [SMILES: CC(C)c1cc(Cc2c(Cl)cc(CNCC(=O)O)c(F)c2Cl)ccc1O] | (3,5-dichloro-2-fluoro-4-(4-hydroxy-3-isopropylbenzyl)benzyl)glycine |
| 153 | 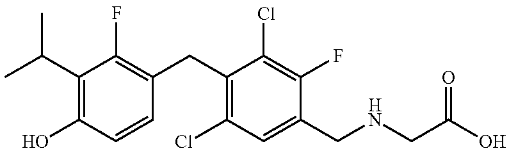 [SMILES: CC(C)c1c(O)ccc(Cc2c(Cl)cc(CNCC(=O)O)c(F)c2Cl)c1F] | (3,5-dichloro-2-fluoro-4-(2-fluoro-4-hydroxy-3-isopropylbenzyl)benzyl)glycine |
| 154 | 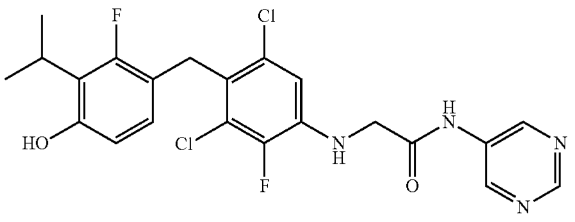 [SMILES: CC(C)c1c(O)ccc(Cc2c(Cl)cc(NCC(=O)Nc3cncnc3)c(F)c2Cl)c1F] | 2-((3,5-dichloro-2-fluoro-4-(2-fluoro-4-hydroxy-3-isopropylbenzyl)phenyl)amino)-N-(pyrimidin-5-yl)acetamide |
| 155 | 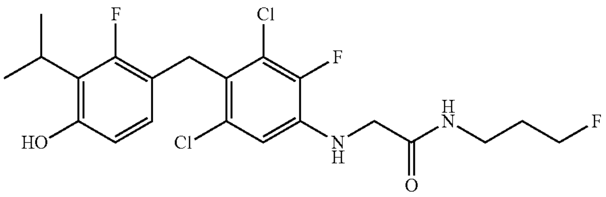 [SMILES: CC(C)c1c(O)ccc(Cc2c(Cl)cc(NCC(=O)NCCCF)c(F)c2Cl)c1F] | 2-((3,5-dichloro-2-fluoro-4-(2-fluoro-4-hydroxy-3-isopropylbenzyl)phenyl)amino)-N-(3-fluoropropyl)acetamide |
| 156 | 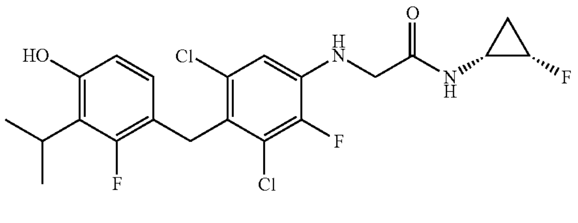 [SMILES: CC(C)c1c(O)ccc(Cc2c(Cl)cc(NCC(=O)N[C@@H]3C[C@@H]3F)c(F)c2Cl)c1F] | 2-((3,5-dichloro-2-fluoro-4-(2-fluoro-4-hydroxy-3-isopropylbenzyl)phenyl)amino)-N-((1R,2S)-2-fluorocyclopropyl)acetamide |

TABLE 1-continued

| REPRESENTATIVE COMPOUNDS | | |
|---|---|---|
| Cmpd No | Structure | Name |
| 157 | 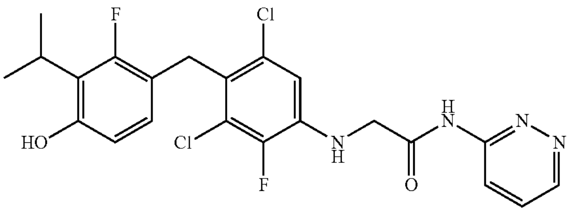 [SMILES: CC(C)c1c(O)ccc(Cc2c(Cl)cc(NCC(=O)Nc3cccnn3)c(F)c2Cl)c1F] | 2-((3,5-dichloro-2-fluoro-4-(2-fluoro-4-hydroxy-3-isopropylbenzyl)phenyl)amino)-N-(pyridazin-3-yl)acetamide |
| 158 | 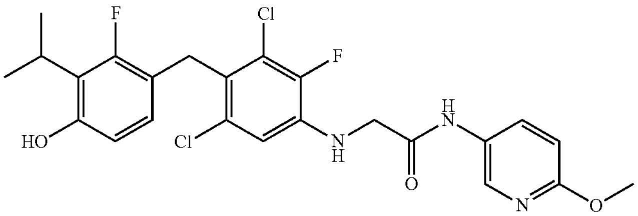 [SMILES: COc1ccc(NC(=O)CNc2cc(Cl)c(Cc3ccc(O)c(C(C)C)c3F)c(Cl)c2F)cn1] | 2-((3,5-dichloro-2-fluoro-4-(2-fluoro-4-hydroxy-3-isopropylbenzyl)phenyl)amino)-N-(6-methoxypyridin-3-yl)acetamide |
| 159 | 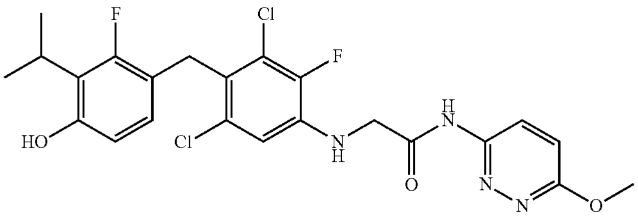 [SMILES: COc1ccc(NC(=O)CNc2cc(Cl)c(Cc3ccc(O)c(C(C)C)c3F)c(Cl)c2F)nn1] | 2-((3,5-dichloro-2-fluoro-4-(2-fluoro-4-hydroxy-3-isopropylbenzyl)phenyl)amino)-N-(6-methoxypyridazin-3-yl)acetamide |
| 160 | 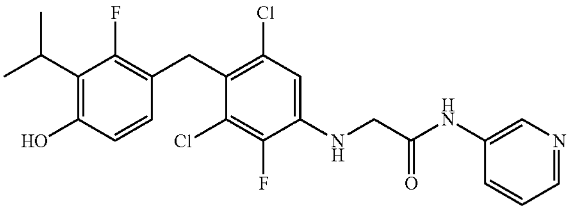 | 2-((3,5-dichloro-2-fluoro-4-(2-fluoro-4-hydroxy-3-isopropylbenzyl)phenyl)amino)-N-(pyridin-3-yl)acetamide |
| 161 | 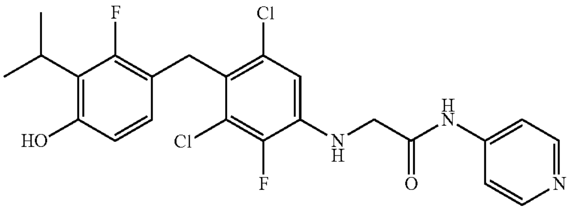 | 2-((3,5-dichloro-2-fluoro-4-(2-fluoro-4-hydroxy-3-isopropylbenzyl)phenyl)amino)-N-(pyridin-4-yl)acetamide |
| 162 | 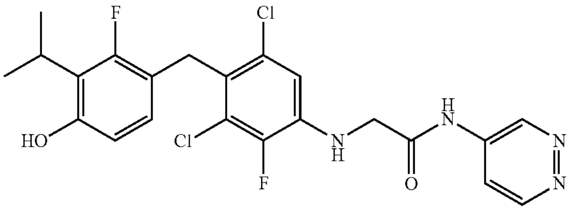 | 2-((3,5-dichloro-2-fluoro-4-(2-fluoro-4-hydroxy-3-isopropylbenzyl)phenyl)amino)-N-(pyridazin-4-yl)acetamide |
| 163 | 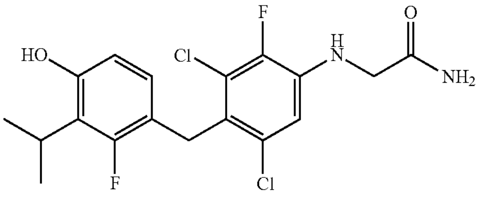 [SMILES: CC(C)c1c(O)ccc(Cc2c(Cl)cc(NCC(N)=O)c(F)c2Cl)c1F] | 2-((3,5-dichloro-2-fluoro-4-(2-fluoro-4-hydroxy-3-isopropylbenzyl)phenyl)amino)acetamide |

TABLE 1-continued

| REPRESENTATIVE COMPOUNDS | | |
|---|---|---|
| Cmpd No | Structure | Name |
| 164 | 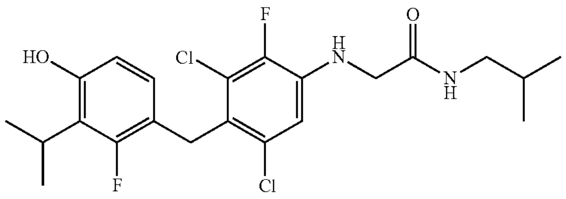 [SMILES: CC(C)CNC(=O)CNc1cc(Cl)c(Cc2ccc(O)c(C(C)C)c2F)c(Cl)c1F] | 2-((3,5-dichloro-2-fluoro-4-(2-fluoro-4-hydroxy-3-isopropylbenzyl)phenyl)amino)-N-isobutylacetamide |
| 165 | 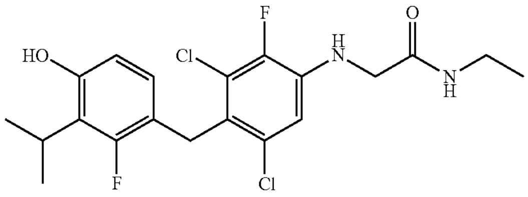 [SMILES: CCNC(=O)CNc1cc(Cl)c(Cc2ccc(O)c(C(C)C)c2F)c(Cl)c1F] | 2-((3,5-dichloro-2-fluoro-4-(2-fluoro-4-hydroxy-3-isopropylbenzyl)phenyl)amino)-N-ethylacetamide |
| 166 | 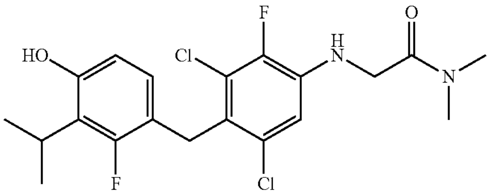 [SMILES: CC(C)c1c(O)ccc(Cc2c(Cl)cc(NCC(=O)N(C)C)c(F)c2Cl)c1F] | 2-((3,5-dichloro-2-fluoro-4-(2-fluoro-4-hydroxy-3-isopropylbenzyl)phenyl)amino)-N,N-dimethylacetamide |
| 167 | 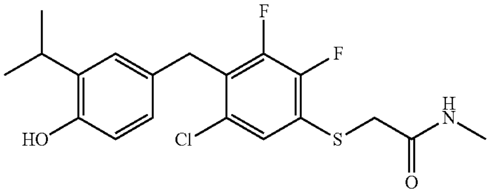 [SMILES: CNC(=O)CSc1cc(Cl)c(Cc2ccc(O)c(C(C)C)c2)c(F)c1F] | 2-((5-chloro-2,3-difluoro-4-(4-hydroxy-3-isopropylbenzyl)phenyl)thio)-N-methylacetamide |
| 168 | 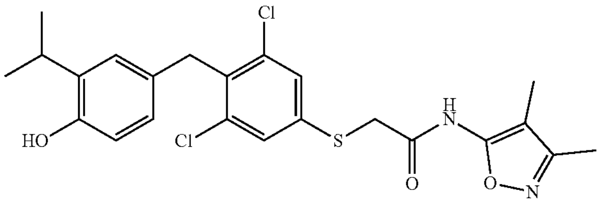 [SMILES: Cc1noc(NC(=O)CSc2cc(Cl)c(Cc3ccc(O)c(C(C)C)c3)c(Cl)c2)c1C] | 2-((3,5-dichloro-4-(4-hydroxy-3-isopropylbenzyl)phenyl)thio)-N-(3,4-dimethylisoxazol-5-yl)acetamide |
| 169 | 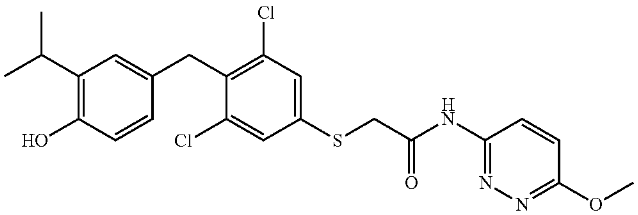 [SMILES: COc1ccc(NC(=O)CSc2cc(Cl)c(Cc3ccc(O)c(C(C)C)c3)c(Cl)c2)nn1] | 2-((3,5-dichloro-4-(4-hydroxy-3-isopropylbenzyl)phenyl)thio)-N-(6-methoxypyridazin-3-yl)acetamide |
| 170 | 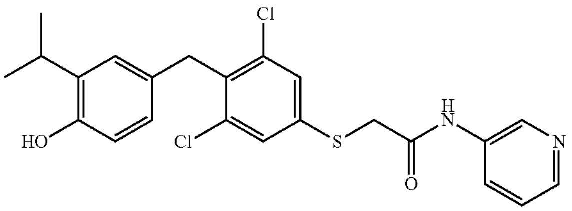 | 2-((3,5-dichloro-4-(4-hydroxy-3-isopropylbenzyl)phenyl)thio)-N-(pyridin-3-yl)acetamide |

TABLE 1-continued

| REPRESENTATIVE COMPOUNDS | | |
|---|---|---|
| Cmpd No | Structure | Name |
| 171 | 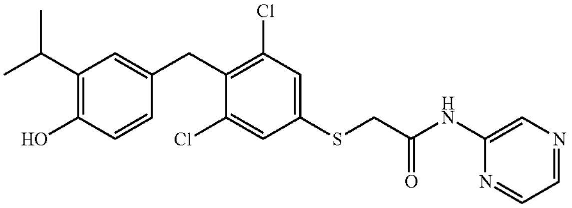 [SMILES: CC(C)c1cc(Cc2c(Cl)cc(SCC(=O)Nc3cnccn3)cc2Cl)ccc1O] | 2-((3,5-dichloro-4-(4-hydroxy-3-isopropylbenzyl)phenyl)thio)-N-(pyrazin-2-yl)acetamide |
| 172 | 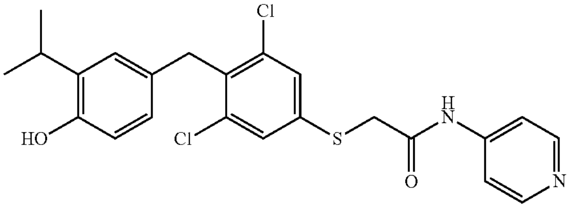 [SMILES: CC(C)c1cc(Cc2c(Cl)cc(SCC(=O)Nc3ccncc3)cc2Cl)ccc1O] | 2-((3,5-dichloro-4-(4-hydroxy-3-isopropylbenzyl)phenyl)thio)-N-(pyridin-4-yl)acetamide |
| 173 | 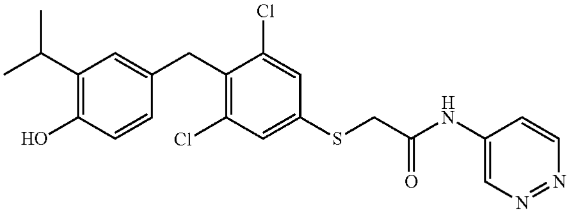 [SMILES: CC(C)c1cc(Cc2c(Cl)cc(SCC(=O)Nc3ccnnc3)cc2Cl)ccc1O] | 2-((3,5-dichloro-4-(4-hydroxy-3-isopropylbenzyl)phenyl)thio)-N-(pyridazin-4-yl)acetamide |
| 174 | 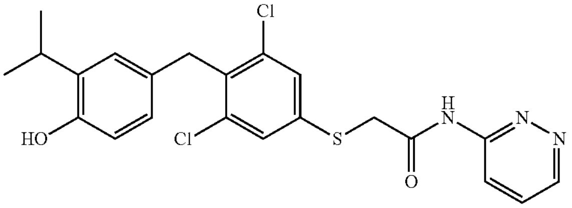 [SMILES: CC(C)c1cc(Cc2c(Cl)cc(SCC(=O)Nc3cccnn3)cc2Cl)ccc1O] | 2-((3,5-dichloro-4-(4-hydroxy-3-isopropylbenzyl)phenyl)thio)-N-(pyridazin-3-yl)acetamide |
| 175 | 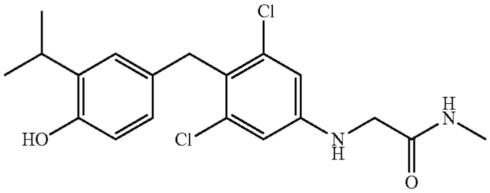 [SMILES: CNC(=O)CNc1cc(Cl)c(Cc2ccc(O)c(C(C)C)c2)c(Cl)c1] | 2-((3,5-dichloro-4-(4-hydroxy-3-isopropylbenzyl)phenyl)amino)-N-methylacetamide |
| 177 | 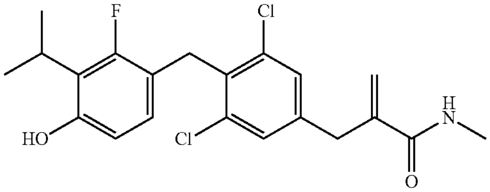 [SMILES: C=C(Cc1cc(Cl)c(Cc2ccc(O)c(C(C)C)c2F)c(Cl)c1)C(=O)NC] | 2-(3,5-dichloro-4-(2-fluoro-4-hydroxy-3-isopropylbenzyl)benzyl)-N-methylacrylamide |
| 178 | 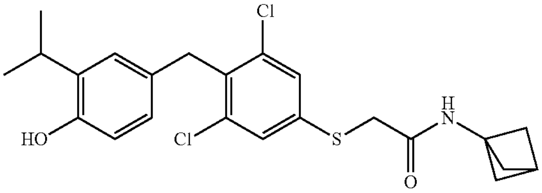 [SMILES: CC(C)c1cc(Cc2c(Cl)cc(SCC(=O)NC34CC(C3)C4)cc2Cl)ccc1O] | N-(bicyclo[1.1.1]pentan-1-yl)-2-((3,5-dichloro-4-(4-hydroxy-3-isopropylbenzyl)phenyl)thio)acetamide |

TABLE 1-continued

| REPRESENTATIVE COMPOUNDS | | |
|---|---|---|
| Cmpd No | Structure | Name |
| 179 | 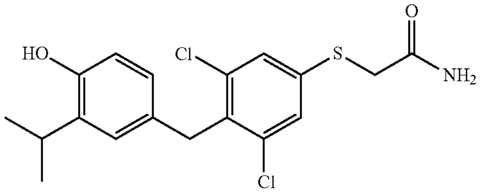 [SMILES: CC(C)c1cc(Cc2c(Cl)cc(SCC(N)=O)cc2Cl)ccc1O] | 2-((3,5-dichloro-4-(4-hydroxy-3-isopropylbenzyl)phenyl)thio)acetamide |
| 180 | 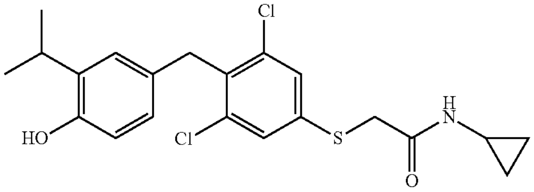 [SMILES: CC(C)c1cc(Cc2c(Cl)cc(SCC(=O)NC3CC3)cc2Cl)ccc1O] | N-cyclopropyl-2-((3,5-dichloro-4-(4-hydroxy-3-isopropylbenzyl)phenyl)thio)acetamide |
| 181 | 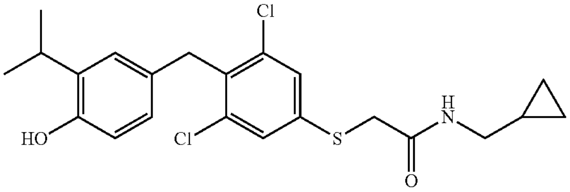 [SMILES: CC(C)c1cc(Cc2c(Cl)cc(SCC(=O)NCC3CC3)cc2Cl)ccc1O] | N-(cyclopropylmethyl)-2-((3,5-dichloro-4-(4-hydroxy-3-isopropylbenzyl)phenyl)thio)acetamide |
| 182 | 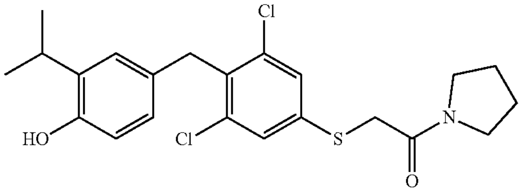 [SMILES: CC(C)c1cc(Cc2c(Cl)cc(SCC(=O)N3CCCC3)cc2Cl)ccc1O] | 2-((3,5-dichloro-4-(4-hydroxy-3-isopropylbenzyl)phenyl)thio)-1-(pyrrolidin-1-yl)ethan-1-one |
| 183 | 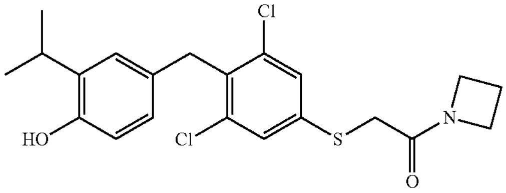 [SMILES: CC(C)c1cc(Cc2c(Cl)cc(SCC(=O)N3CCC3)cc2Cl)ccc1O] | 1-(azetidin-1-yl)-2-((3,5-dichloro-4-(4-hydroxy-3-isopropylbenzyl)phenyl)thio)ethan-1-one |
| 184 | 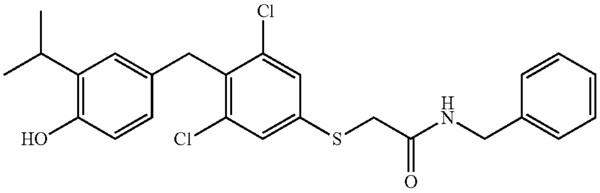 [SMILES: CC(C)c1cc(Cc2c(Cl)cc(SCC(=O)NCc3ccccc3)cc2Cl)ccc1O] | N-benzyl-2-((3,5-dichloro-4-(4-hydroxy-3-isopropylbenzyl)phenyl)thio)acetamide |
| 185 | 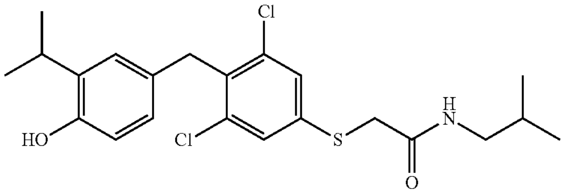 [SMILES: CC(C)CNC(=O)CSc1cc(Cl)c(Cc2ccc(O)c(C(C)C)c2)c(Cl)c1] | 2-((3,5-dichloro-4-(4-hydroxy-3-isopropylbenzyl)phenyl)thio)-N-isobutylacetamide |

TABLE 1-continued

| REPRESENTATIVE COMPOUNDS | | |
|---|---|---|
| Cmpd No | Structure | Name |
| 186 | 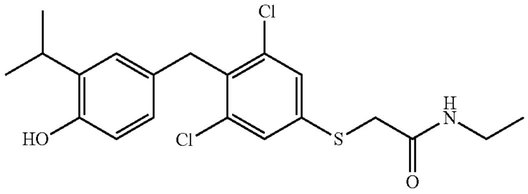 [SMILES: CCNC(=O)CSc1cc(Cl)c(Cc2ccc(O)c(C(C)C)c2)c(Cl)c1] | 2-((3,5-dichloro-4-(4-hydroxy-3-isopropylbenzyl)phenyl)thio)-N-ethylacetamide |
| 187 | 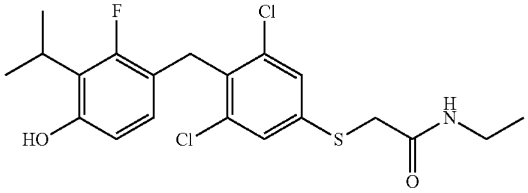 [SMILES: CCNC(=O)CSc1cc(Cl)c(Cc2ccc(O)c(C(C)C)c2F)c(Cl)c1] | 2-((3,5-dichloro-4-(2-fluoro-4-hydroxy-3-isopropylbenzyl)phenyl)thio)-N-ethylacetamide |
| 188 | 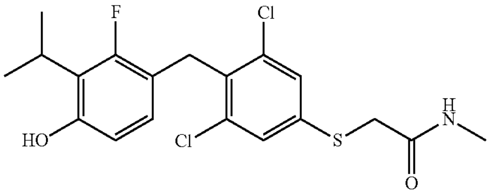 | 2-((3,5-dichloro-4-(2-fluoro-4-hydroxy-3-isopropylbenzyl)phenyl)thio)-N-methylacetamide |
| 189 | 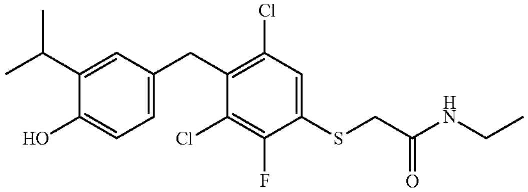 [SMILES: CCNC(=O)CSc1cc(Cl)c(Cc2ccc(O)c(C(C)C)c2)c(Cl)c1F] | 2-((3,5-dichloro-2-fluoro-4-(4-hydroxy-3-isopropylbenzyl)phenyl)thio)-N-ethylacetamide |
| 190 | 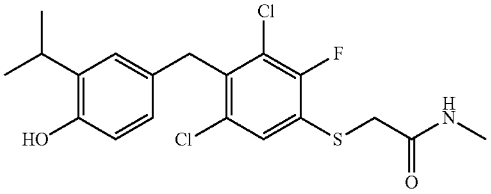 [SMILES: CNC(=O)CSc1cc(Cl)c(Cc2ccc(O)c(C(C)C)c2)c(Cl)c1F] | 2-((3,5-dichloro-2-fluoro-4-(4-hydroxy-3-isopropylbenzyl)phenyl)thio)-N-methylacetamide |
| 191 | 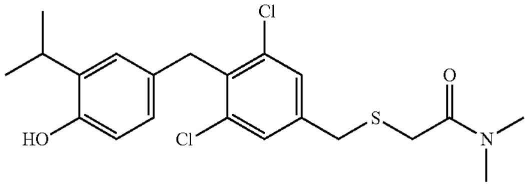 [SMILES: CC(C)c1cc(Cc2c(Cl)cc(CSCC(=O)N(C)C)cc2Cl)ccc1O] | 2-((3,5-dichloro-4-(4-hydroxy-3-isopropylbenzyl)benzyl)thio)-N,N-dimethylacetamide |
| 193 | 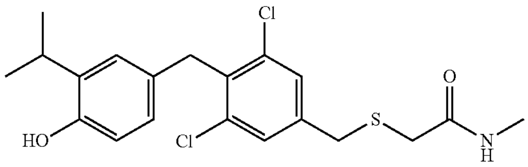 [SMILES: CNC(=O)CSCc1cc(Cl)c(Cc2ccc(O)c(C(C)C)c2)c(Cl)c1] | 2-((3,5-dichloro-4-(4-hydroxy-3-isopropylbenzyl)benzyl)thio)-N-methylacetamide |

TABLE 1-continued

REPRESENTATIVE COMPOUNDS

| Cmpd No | Structure | Name |
|---|---|---|
| 194 | 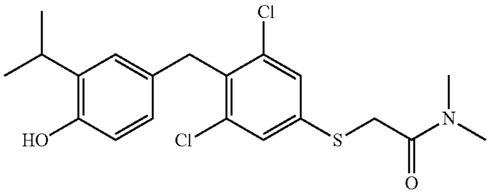 | 2-((3,5-dichloro-4-(4-hydroxy-3-isopropylbenzyl)phenyl)thio)-N,N-dimethylacetamide |
| 195 | 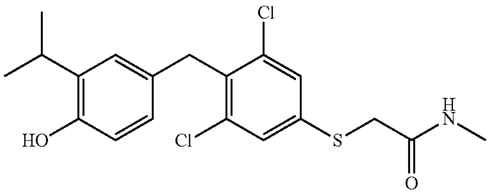 [SMILES: CNC(=O)CSc1cc(Cl)c(Cc2ccc(O)c(C(C)C)c2)c(Cl)c1] | 2-((3,5-dichloro-4-(4-hydroxy-3-isopropylbenzyl)phenyl)thio)-N-methylacetamide |
| 196 | 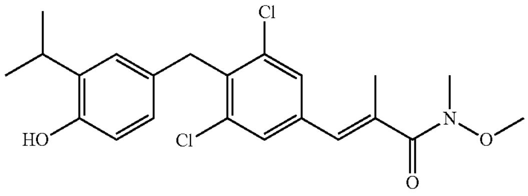 [SMILES: CON(C)C(=O)/C(C)=C/c1cc(Cl)c(Cc2ccc(O)c(C(C)C)c2)c(Cl)c1] | (E)-3-(3,5-dichloro-4-(4-hydroxy-3-isopropylbenzyl)phenyl)-N-methoxy-N,2-dimethylacrylamide |
| 197 | 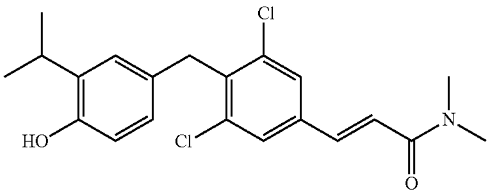 [SMILES: CC(C)c1cc(Cc2c(Cl)cc(/C=C/C(=O)N(C)C)cc2Cl)ccc1O] | (E)-3-(3,5-dichloro-4-(4-hydroxy-3-isopropylbenzyl)phenyl)-N,N-dimethylacrylamide |
| 198 | 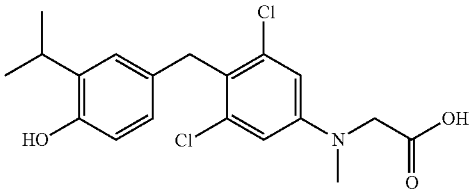 [SMILES: CC(C)c1cc(Cc2c(Cl)cc(N(C)CC(=O)O)cc2Cl)ccc1O] | N-(3,5-dichloro-4-(4-hydroxy-3-isopropylbenzyl)phenyl)-N-methylglycine |
| 199 | 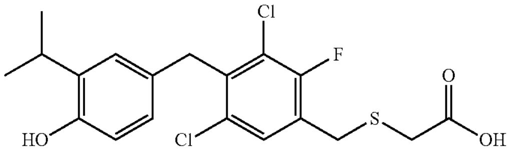 [SMILES: CC(C)c1cc(Cc2c(Cl)cc(CSCC(=O)O)c(F)c2Cl)ccc1O] | 2-((3,5-dichloro-2-fluoro-4-(4-hydroxy-3-isopropylbenzyl)benzyl)thio)acetic acid |
| 200 | 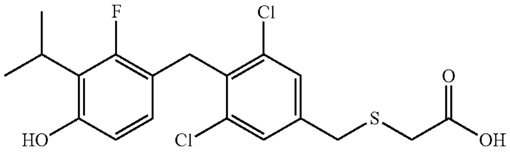 [SMILES: CC(C)c1c(O)ccc(Cc2c(Cl)cc(CSCC(=O)O)cc2Cl)c1F] | 2-((3,5-dichloro-4-(2-fluoro-4-hydroxy-3-isopropylbenzyl)benzyl)thio)acetic acid |
| 201 | 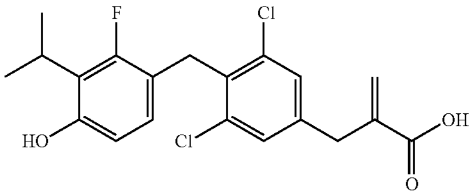 [SMILES: C=C(Cc1cc(Cl)c(Cc2ccc(O)c(C(C)C)c2F)c(Cl)c1)C(=O)O] | 2-(3,5-dichloro-4-(2-fluoro-4-hydroxy-3-isopropylbenzyl)benzyl)acrylic acid |

TABLE 1-continued

REPRESENTATIVE COMPOUNDS

| Cmpd No | Structure | Name |
|---|---|---|
| 203 | 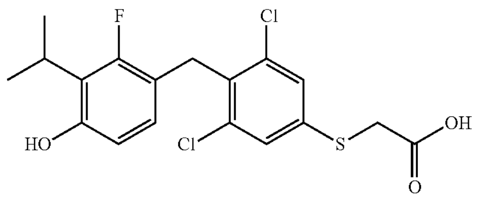 | 2-((3,5-dichloro-4-(2-fluoro-4-hydroxy-3-isopropylbenzyl)phenyl)thio)acetic acid |
| 204 | 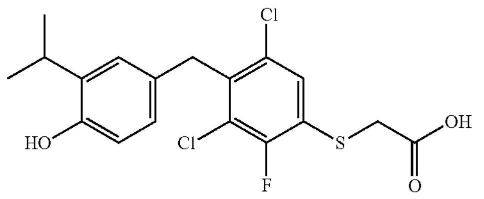 [SMILES: CC(C)c1cc(Cc2c(Cl)cc(SCC(=O)O)c(F)c2Cl)ccc1O] | 2-((3,5-dichloro-2-fluoro-4-(4-hydroxy-3-isopropylbenzyl)phenyl)thio)acetic acid |
| 205 | 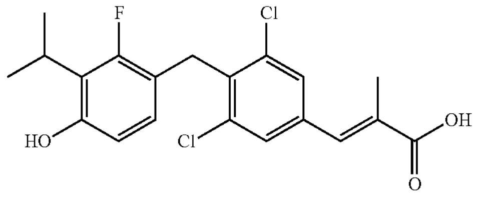 [SMILES: C/C(=C\c1cc(Cl)c(Cc2ccc(O)c(C(C)C)c2F)c(Cl)c1)C(=O)O] | (E)-3-(3,5-dichloro-4-(2-fluoro-4-hydroxy-3-isopropylbenzyl)phenyl)-2-methylacrylic acid |
| 206 | 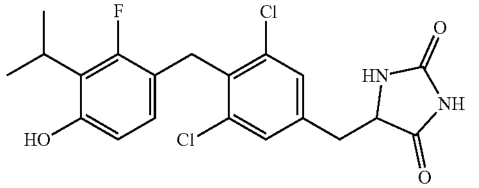 [SMILES: CC(C)c1c(O)ccc(Cc2c(Cl)cc(CC3NC(=O)NC3=O)cc2Cl)c1F] | 5-(3,5-dichloro-4-(2-fluoro-4-hydroxy-3-isopropylbenzyl)benzyl)imidazolidine-2,4-dione |
| 207 | 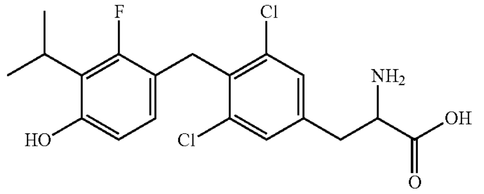 [SMILES: CC(C)c1c(O)ccc(Cc2c(Cl)cc(CC(N)C(=O)O)cc2Cl)c1F] | 2-amino-3-(3,5-dichloro-4-(2-fluoro-4-hydroxy-3-isopropylbenzyl)phenyl)propanoic acid |
| 208 | 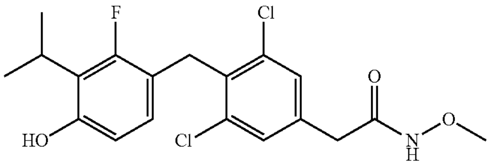 [SMILES: CONC(=O)Cc1cc(Cl)c(Cc2ccc(O)c(C(C)C)c2F)c(Cl)c1] | 2-(3,5-dichloro-4-(2-fluoro-4-hydroxy-3-isopropylbenzyl)phenyl)-N-methoxyacetamide |
| 209 | 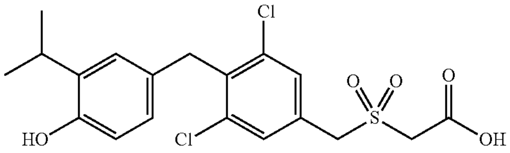 [SMILES: CC(C)c1cc(Cc2c(Cl)cc(CS(=O)(=O)CC(=O)O)cc2Cl)ccc1O] | 2-((3,5-dichloro-4-(4-hydroxy-3-isopropylbenzyl)benzyl)sulfonyl)acetic acid |
| 210 | 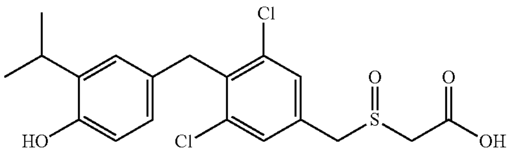 [SMILES: CC(C)c1cc(Cc2c(Cl)cc(CS(=O)CC(=O)O)cc2Cl)ccc1O] | 2-((3,5-dichloro-4-(4-hydroxy-3-isopropylbenzyl)benzyl)sulfinyl)acetic acid |

TABLE 1-continued

| REPRESENTATIVE COMPOUNDS | | |
|---|---|---|
| Cmpd No | Structure | Name |
| 211 | 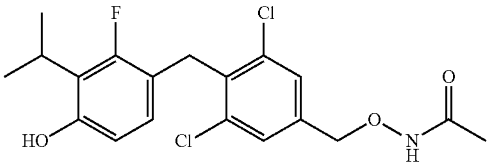 [SMILES: CC(=O)NOCc1cc(Cl)c(Cc2ccc(O)c(C(C)C)c2F)c(Cl)c1] | N-((3,5-dichloro-4-(2-fluoro-4-hydroxy-3-isopropylbenzyl)benzyl)oxy)acetamide |
| 212 | 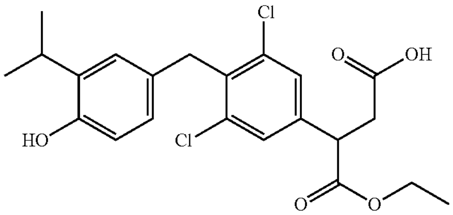 [SMILES: CCOC(=O)C(CC(=O)O)c1cc(Cl)c(Cc2ccc(O)c(C(C)C)c2)c(Cl)c1] | 3-(3,5-dichloro-4-(4-hydroxy-3-isopropylbenzyl)phenyl)-4-ethoxy-4-oxobutanoic acid |
| 213 | 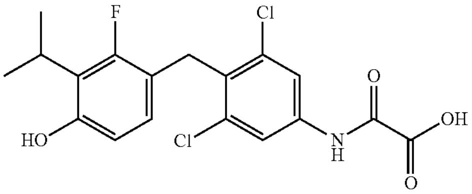 [SMILES: CC(C)c1c(O)ccc(Cc2c(Cl)cc(NC(=O)C(=O)O)cc2Cl)c1F] | 2-((3,5-dichloro-4-(2-fluoro-4-hydroxy-3-isopropylbenzyl)phenyl)amino)-2-oxoacetic acid |
| 214 | 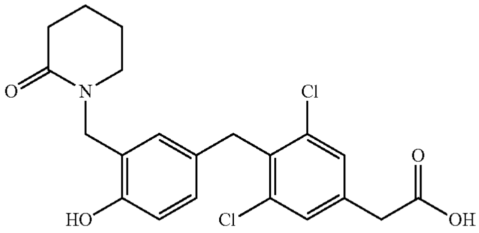 [SMILES: O=C(O)Cc1cc(Cl)c(Cc2ccc(O)c(CN3CCCCC3=O)c2)c(Cl)c1] | 2-(3,5-dichloro-4-(4-hydroxy-3-((2-oxopiperidin-1-yl)methyl)benzyl)phenyl)acetic acid |
| 215 | 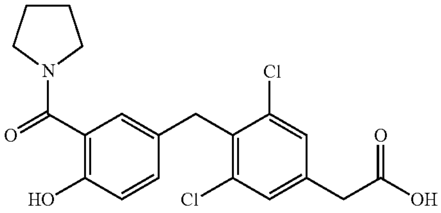 [SMILES: O=C(O)Cc1cc(Cl)c(Cc2ccc(O)c(C(=O)N3CCCC3)c2)c(Cl)c1] | 2-(3,5-dichloro-4-(4-hydroxy-3-(pyrrolidine-1-carbonyl)benzyl)phenyl)acetic acid |
| 216 | 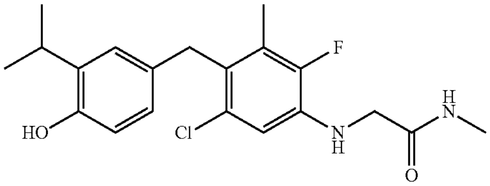 [SMILES: CNC(=O)CNc1cc(Cl)c(Cc2ccc(O)c(C(C)C)c2)c(C)c1F] | 2-((5-chloro-2-fluoro-4-(4-hydroxy-3-isopropylbenzyl)-3-methylphenyl)amino)-N-methylacetamide |
| 217 | 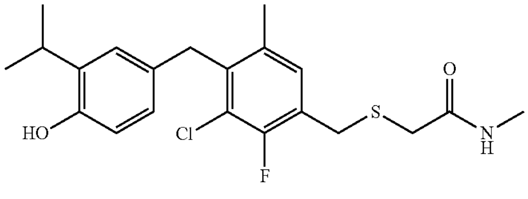 [SMILES: CNC(=O)CSCc1cc(C)c(Cc2ccc(O)c(C(C)C)c2)c(Cl)c1F] | 2-((3-chloro-2-fluoro-4-(4-hydroxy-3-isopropylbenzyl)-5-methylbenzyl)thio)-N-methylacetamide |

TABLE 1-continued

| REPRESENTATIVE COMPOUNDS | | |
|---|---|---|
| Cmpd No | Structure | Name |
| 218 | 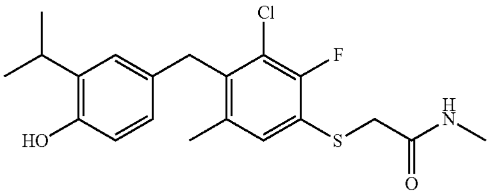 [SMILES: CNC(=O)CSc1cc(C)c(Cc2ccc(O)c(C(C)C)c2)c(Cl)c1F] | 2-((3-chloro-2-fluoro-4-(4-hydroxy-3-isopropylbenzyl)-5-methylphenyl)thio)-N-methylacetamide |
| 219 | 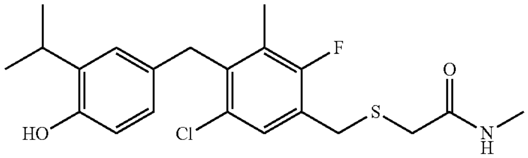 [SMILES: CNC(=O)CSCc1cc(Cl)c(Cc2ccc(O)c(C(C)C)c2)c(C)c1F] | 2-((5-chloro-2-fluoro-4-(4-hydroxy-3-isopropylbenzyl)-3-methylbenzyl)thio)-N-methylacetamide |
| 220 | 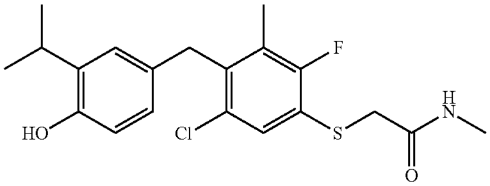 [SMILES: CNC(=O)CSc1cc(Cl)c(Cc2ccc(O)c(C(C)C)c2)c(C)c1F] | 2-((5-chloro-2-fluoro-4-(4-hydroxy-3-isopropylbenzyl)-3-methylphenyl)thio)-N-methylacetamide |
| 221 | 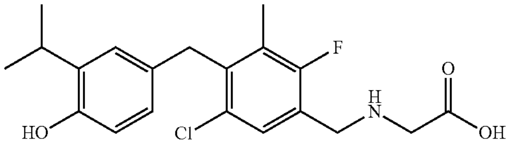 [SMILES: Cc1c(F)c(CNCC(=O)O)cc(Cl)c1Cc1ccc(O)c(C(C)C)c1] | (5-chloro-2-fluoro-4-(4-hydroxy-3-isopropylbenzyl)-3-methylbenzyl)glycine |
| 222 | 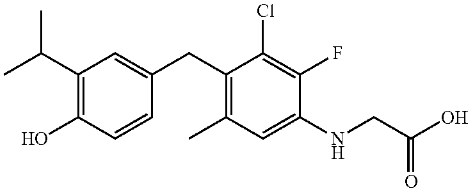 [SMILES: Cc1cc(NCC(=O)O)c(F)c(Cl)c1Cc1ccc(O)c(C(C)C)c1] | (3-chloro-2-fluoro-4-(4-hydroxy-3-isopropylbenzyl)-5-methylphenyl)glycine |
| 223 | 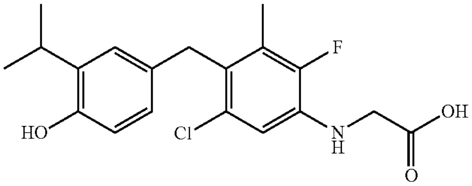 [SMILES: Cc1c(F)c(NCC(=O)O)cc(Cl)c1Cc1ccc(O)c(C(C)C)c1] | (5-chloro-2-fluoro-4-(4-hydroxy-3-isopropylbenzyl)-3-methylphenyl)glycine |
| 224 | 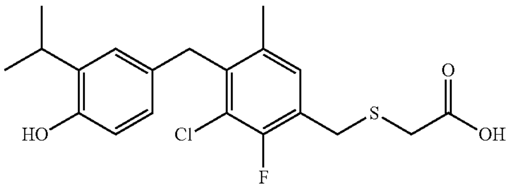 [SMILES: Cc1cc(CSCC(=O)O)c(F)c(Cl)c1Cc1ccc(O)c(C(C)C)c1] | 2-((3-chloro-2-fluoro-4-(4-hydroxy-3-isopropylbenzyl)-5-methylbenzyl)thio)acetic acid |
| 225 | 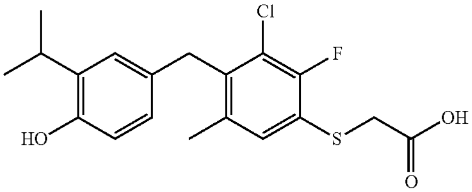 [SMILES: Cc1cc(SCC(=O)O)c(F)c(Cl)c1Cc1ccc(O)c(C(C)C)c1] | 2-((3-chloro-2-fluoro-4-(4-hydroxy-3-isopropylbenzyl)-5-methylphenyl)thio)acetic acid |

TABLE 1-continued

| REPRESENTATIVE COMPOUNDS | | |
|---|---|---|
| Cmpd No | Structure | Name |
| 226 | 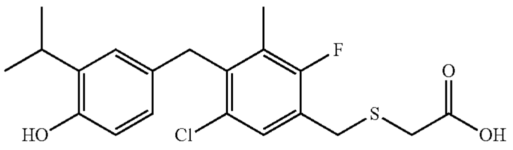 [SMILES: Cc1c(F)c(CSCC(=O)O)cc(Cl)c1Cc1ccc(O)c(C(C)C)c1] | 2-((5-chloro-2-fluoro-4-(4-hydroxy-3-isopropylbenzyl)-3-methylbenzyl)thio)acetic acid |
| 227 | 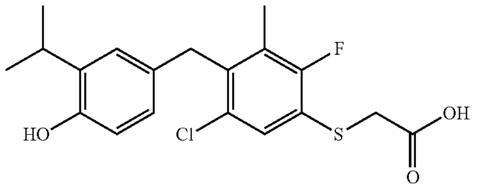 [SMILES: Cc1c(F)c(SCC(=O)O)cc(Cl)c1Cc1ccc(O)c(C(C)C)c1] | 2-((5-chloro-2-fluoro-4-(4-hydroxy-3-isopropylbenzyl)-3-methylphenyl)thio)acetic acid |
| 228 | 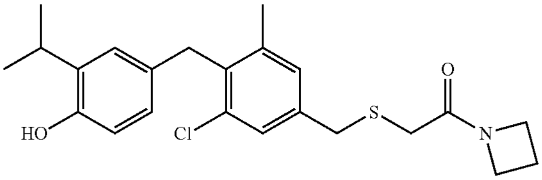 [SMILES: Cc1cc(CSCC(=O)N2CCC2)cc(Cl)c1Cc1ccc(O)c(C(C)C)c1] | 1-(azetidin-1-yl)-2-((3-chloro-4-(4-hydroxy-3-isopropylbenzyl)-5-methylbenzyl)thio)ethan-1-one |
| 229 | 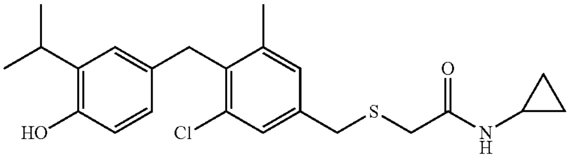 [SMILES: Cc1cc(CSCC(=O)NC2CC2)cc(Cl)c1Cc1ccc(O)c(C(C)C)c1] | 2-((3-chloro-4-(4-hydroxy-3-isopropylbenzyl)-5-methylbenzyl)thio)-N-cyclopropylacetamide |
| 230 | 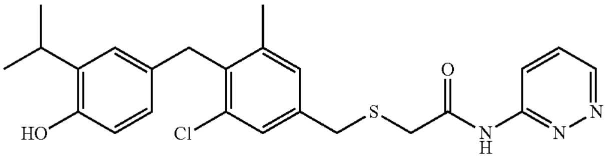 [SMILES: Cc1cc(CSCC(=O)Nc2cccnn2)cc(Cl)c1Cc1ccc(O)c(C(C)C)c1] | 2-((3-chloro-4-(4-hydroxy-3-isopropylbenzyl)-5-methylbenzyl)thio)-N-(pyridazin-3-yl)acetamide |
| 231 | 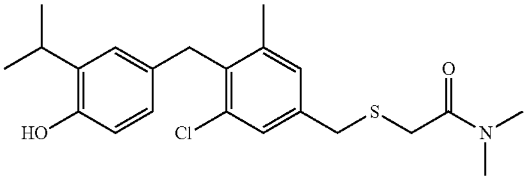 [SMILES: Cc1cc(CSCC(=O)N(C)C)cc(Cl)c1Cc1ccc(O)c(C(C)C)c1] | 2-((3-chloro-4-(4-hydroxy-3-isopropylbenzyl)-5-methylbenzyl)thio)-N,N-dimethylacetamide |
| 232 | 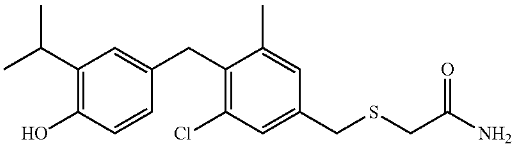 [SMILES: Cc1cc(CSCC(N)=O)cc(Cl)c1Cc1ccc(O)c(C(C)C)c1] | 2-((3-chloro-4-(4-hydroxy-3-isopropylbenzyl)-5-methylbenzyl)thio)acetamide |
| 233 | 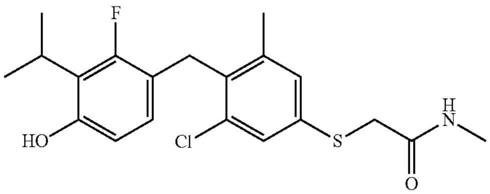 [SMILES: CNC(=O)CSc1cc(C)c(Cc2ccc(O)c(C(C)C)c2F)c(Cl)c1] | 2-((3-chloro-4-(2-fluoro-4-hydroxy-3-isopropylbenzyl)-5-methylphenyl)thio)-N-methylacetamide |

TABLE 1-continued

| REPRESENTATIVE COMPOUNDS | | |
|---|---|---|
| Cmpd No | Structure | Name |
| 234 | 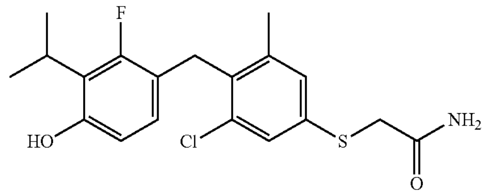 [SMILES: Cc1cc(SCC(N)=O)cc(Cl)c1Cc1ccc(O)c(C(C)C)c1F] | 2-((3-chloro-4-(2-fluoro-4-hydroxy-3-isopropylbenzyl)-5-methylphenyl)thio)acetamide |
| 235 | 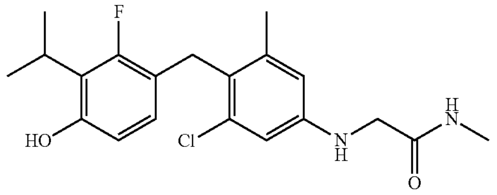 [SMILES: CNC(=O)CNc1cc(C)c(Cc2ccc(O)c(C(C)C)c2F)c(Cl)c1] | 2-((3-chloro-4-(2-fluoro-4-hydroxy-3-isopropylbenzyl)-5-methylphenyl)amino)-N-methylacetamide |
| 236 | 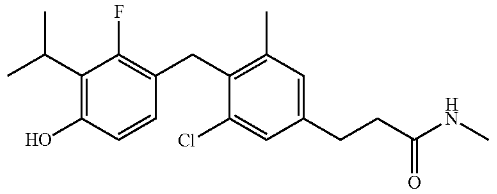 [SMILES: CNC(=O)CCc1cc(C)c(Cc2ccc(O)c(C(C)C)c2F)c(Cl)c1] | 3-(3-chloro-4-(2-fluoro-4-hydroxy-3-isopropylbenzyl)-5-methylphenyl)-N-methylpropanamide |
| 237 | 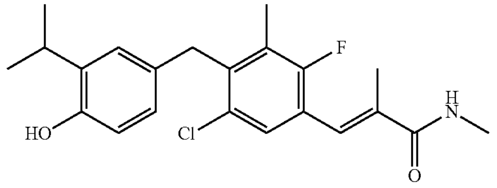 [SMILES: CNC(=O)/C(C)=C/c1cc(Cl)c(Cc2ccc(O)c(C(C)C)c2)c(C)c1F] | (E)-3-(5-chloro-2-fluoro-4-(4-hydroxy-3-isopropylbenzyl)-3-methylphenyl)-N,2-dimethylacrylamide |
| 238 | 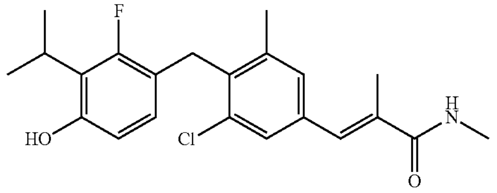 [SMILES: CNC(=O)/C(C)=C/c1cc(C)c(Cc2ccc(O)c(C(C)C)c2F)c(Cl)c1] | (E)-3-(3-chloro-4-(2-fluoro-4-hydroxy-3-isopropylbenzyl)-5-methylphenyl)-N,2-dimethylacrylamide |
| 239 | 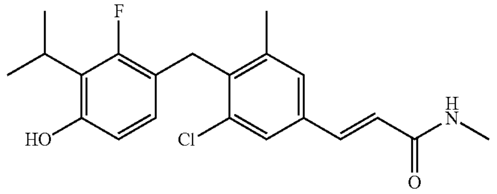 [SMILES: CNC(=O)/C=C/c1cc(C)c(Cc2ccc(O)c(C(C)C)c2F)c(Cl)c1] | (E)-3-(3-chloro-4-(2-fluoro-4-hydroxy-3-isopropylbenzyl)-5-methylphenyl)-N-methylacrylamide |
| 240 | 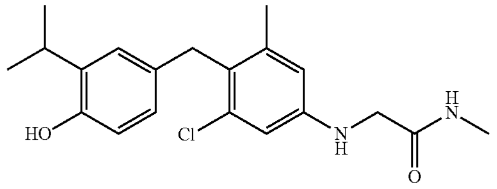 [SMILES: CNC(=O)CNc1cc(C)c(Cc2ccc(O)c(C(C)C)c2)c(Cl)c1] | 2-((3-chloro-4-(4-hydroxy-3-isopropylbenzyl)-5-methylphenyl)amino)-N-methylacetamide |

TABLE 1-continued

REPRESENTATIVE COMPOUNDS

| Cmpd No | Structure | Name |
|---|---|---|
| 241 | 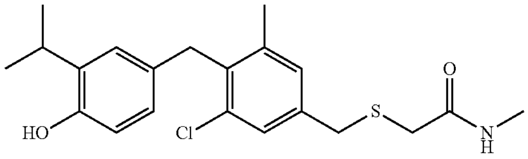 [SMILES: CNC(=O)CSCc1cc(C)c(Cc2ccc(O)c(C(C)C)c2)c(Cl)c1] | 2-((3-chloro-4-(4-hydroxy-3-isopropylbenzyl)-5-methylbenzyl)thio)-N-methylacetamide |
| 242 | 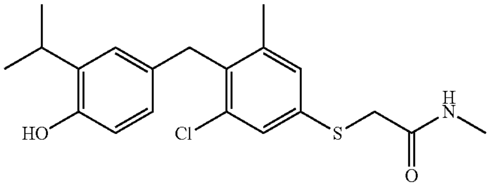 [SMILES: CNC(=O)CSc1cc(C)c(Cc2ccc(O)c(C(C)C)c2)c(Cl)c1] | 2-((3-chloro-4-(4-hydroxy-3-isopropylbenzyl)-5-methylphenyl)thio)-N-methylacetamide |
| 244 | 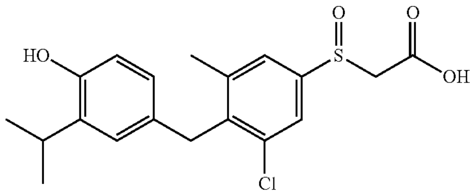 [SMILES: Cc1cc(S(=O)CC(=O)O)cc(Cl)c1Cc1ccc(O)c(C(C)C)c1] | 2-((3-chloro-4-(4-hydroxy-3-isopropylbenzyl)-5-methylphenyl)sulfinyl)acetic acid |
| 245 | 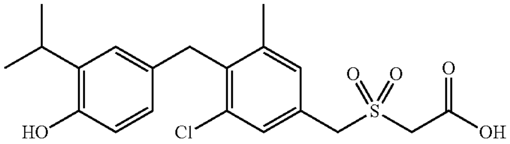 [SMILES: Cc1cc(CS(=O)(=O)CC(=O)O)cc(Cl)c1Cc1ccc(O)c(C(C)C)c1] | 2-((3-chloro-4-(4-hydroxy-3-isopropylbenzyl)-5-methylbenzyl)sulfonyl)acetic acid |
| 246 | 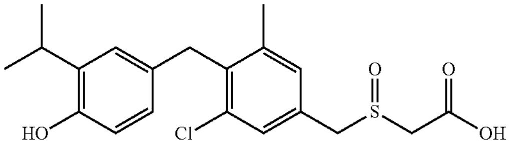 [SMILES: Cc1cc(CS(=O)CC(=O)O)cc(Cl)c1Cc1ccc(O)c(C(C)C)c1] | 2-((3-chloro-4-(4-hydroxy-3-isopropylbenzyl)-5-methylbenzyl)sulfinyl)acetic acid |
| 247 | 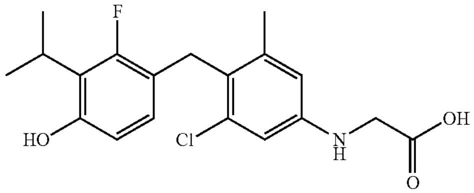 [SMILES: Cc1cc(NCC(=O)O)cc(Cl)c1Cc1ccc(O)c(C(C)C)c1F] | (3-chloro-4-(2-fluoro-4-hydroxy-3-isopropylbenzyl)-5-methylphenyl)glycine |
| 248 | 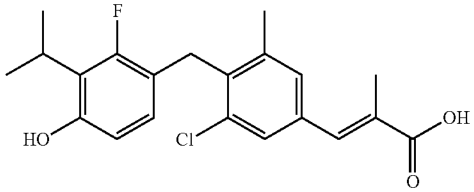 [SMILES: C/C(=C\c1cc(C)c(Cc2ccc(O)c(C(C)C)c2F)c(Cl)c1)C(=O)O] | (E)-3-(3-chloro-4-(2-fluoro-4-hydroxy-3-isopropylbenzyl)-5-methylphenyl)-2-methylacrylic acid |
| 249 | 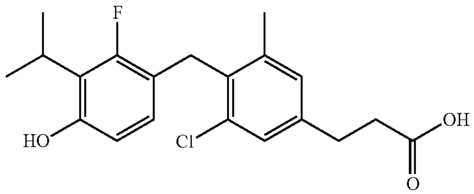 [SMILES: Cc1cc(CCC(=O)O)cc(Cl)c1Cc1ccc(O)c(C(C)C)c1F] | 3-(3-chloro-4-(2-fluoro-4-hydroxy-3-isopropylbenzyl)-5-methylphenyl)propanoic acid |

TABLE 1-continued

| Cmpd No | Structure | Name |
| --- | --- | --- |
| REPRESENTATIVE COMPOUNDS | | |
| 250 | 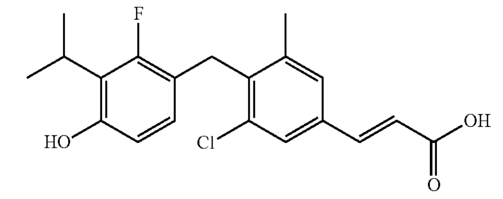 [SMILES: Cc1cc(/C=C/C(=O)O)cc(Cl)c1Cc1ccc(O)c(C(C)C)c1F] | (E)-3-(3-chloro-4-(2-fluoro-4-hydroxy-3-isopropylbenzyl)-5-methylphenyl)acrylic acid |
| 251 | 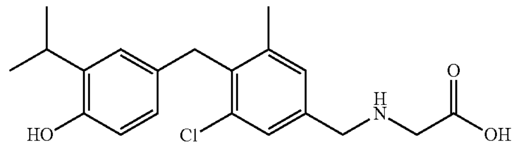 [SMILES: Cc1cc(CNCC(=O)O)cc(Cl)c1Cc1ccc(O)c(C(C)C)c1] | (3-chloro-4-(4-hydroxy-3-isopropylbenzyl)-5-methylbenzyl)glycine |

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "tautomer" refers to each of two or more structural isomers that readily interconvert in equilibrium by migration of an atom or group within the molecule. A tautomer commonly arises from a proton shift from one atom of a molecule to another atom of the same molecule. The present invention includes tautomers of compounds of Formula (I).

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), tromethamine (tris-hydroxymethyl methylamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semisolid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy,* $21^{st}$ Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the *Physicians' Desk Reference*, incorporated herein by reference.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the neurodegenerative disease is a demyelinating disease. In another embodiment, the demyelinating disease is a chronic demyelinating disease. In yet another embodiment, the demyelinating disease is or is associated with a X-linked genetic disorder, leukodystrophy, dementia, tauopathy, or ischaemic stroke. In another embodiment, the demyelinating disease is or is associated with adult Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, or Zellweger syndrome. In one embodiment, the demyelinating disease is or is associated with multiple sclerosis, MCT8 deficiency, X-linked adrenoleukodystrophy (ALD), amyotrophic lateral sclerosis (ALS), Alzheimer's disease, frontotemporal dementia, or lacunar stroke.

As used herein, the term "neurodegenerative disease" refers to any type of disease that is characterized by the progressive deterioration of the nervous system.

As used herein, the term "demyelinating disease" refers to any disease or medical condition of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused b y an infectious agent, an autoimmune response, a toxic agent or traumatic injury. In other cases, the cause of the demyelinating disease is unknown ("idiopathic") or develops from a combination of factors.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including for example, "leukoencephalopathy with vanishing white matter" and "toxic leukoencephalopathy." Leukoencephalopathies are leukodystrophy-like diseases.

As used herein, the term "tauopathy" refers to tau-related disorders or conditions, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

In yet another embodiment, a method of treating a subject having a X-linked genetic disorder is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the X-linked genetic disorder is MCT8 deficiency or X-linked adrenoleukodystrophy (ALD).

In another embodiment, a method of treating a subject having a leukodystrophy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the leukodystrophy is adrenoleukodystrophy (ALD), adrenomyeloneuropathy (AMN), cerebral form of adrenoleukodystrophy (cALD), metachromatic leukodystrophy (MLD), Canavan's disease, or Krabbe disease (globoid leukodystrophy). As used herein, the term "adrenomyeloneuropathy" or "AMN" refers to an adult variant of X-linked adrenoleukodystrophy, characterized by ABCD1 gene mutation, that results in impaired peroxisome function with accumulation of very long chain fatty acids (VLCFA) and demyelination.

In one embodiment, a method of treating a subject having a tauopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the tauopathy is Alzheimer's disease, frontotemporal dementia, primary age-related tauopathy (PART), Pick's disease, or frontotemporal dementia and parkinsonism linked to chromosome 17 (FTDP-17).

In yet another embodiment, a method of treating a subject having an ischaemic stroke is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ischaemic stroke is lacunar stroke (also called "lacunar infarct"). In another embodiment, the present method is used to treat a subject suffering from a lacunar stroke syndrome (LACS).

In another embodiment, a method of treating a subject having adult Refsum disease, infantile Refsum disease, Alexander disease, Alzheimer's disease, balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In one embodiment, the demyelinating disease is multiple sclerosis. In another embodiment, the demyelinating disease is X-linked adrenoleukodystrophy (ALD).

In another embodiment, a method of treating a subject having an amyotrophic lateral sclerosis (ALS) disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ALS is sporadic or familial ALS, or ALS with Superoxide dismutase-1 mutation.

In one embodiment, a method of treating a subject having a medical condition associated with increased activity of TGF-β is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the medical condition associated with increased activity of TGF-β is a fibrotic disease. In another embodiment, the fibrotic disease is or is associated with nonalcoholic steatohepatitis (NASH), idiopathic pulmonary fibrosis (IPF), systemic scleroderma, or Alport syndrome. As used herein, the term "Alport syndrome" refers to a hereditary disorder caused by mutations in the a3a4a5(IV) collagen network genes resulting in structural defects in the glomerular basement membrane (GBM) early during development leading subsequently to the breakdown of the filtration barrier, development of renal fibrosis and kidney failure.

As used herein, the term "fibrotic disease" refers to a condition, disease or disorder that is amenable to treatment by administration of a compound having anti-fibrotic activity. Fibrotic diseases include, but are not limited to, pulmonary fibrosis, including idiopathic pulmonary fibrosis (IPF) and pulmonary fibrosis from a known etiology, liver fibrosis, and renal-fibrosis. Other exemplary fibrotic diseases include musculoskeletal fibrosis, cardiac fibrosis, post-surgical adhesions, scleroderma, glaucoma, and skin lesions such as keloids.

In another embodiment, a method of treating a subject having NASH, NAFLD, NAFLD with hyperlipidemia, alcoholic liver disease/alcoholic steatohepatitis, liver fibrosis associated with viral infection (HBV, HCV), fibrosis associated with cholestatic diseases (primary biliary cholangitis, primary sclerosing cholangitis), (familial) hypercholesterolemia, dyslipidemia, genetic lipid disorders, cirrhosis, alcohol-induced fibrosis, hemochromatosis, glycogen storage diseases, alpha-1 antitrypsin deficiency, autoimmune hepatitis, Wilson's disease, Crigler-Najjar Syndrome, lysosomal acid lipase deficiency, liver disease in cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Alport syndrome, diabetic nephropathy, FSGS, fibrosis associated with IgA nephropathy, chronic kidney diseases (CKD), post AKI, HIV associated CKD, chemotherapy induced CKD, CKD associated with nephrotoxic agents, nephrogenic systemic fibrosis, tubulointerstitial fibrosis, glomerulosclerosis, or polycystic kidney disease (PKD) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having IPF, ILD, pulmonary fibrosis, pulmonary fibrosis associated with autoimmune diseases like rheumatoid arthritis, scleroderma or Sjogren's syndrome, asthma-related pulmonary fibrosis, COPD, asbestos or silica induced PF, silicosis, respiratory bronchiolitis, Idiopathic interstitial pneumonias (IIP), Idiopathic nonspecific interstitial pneumonia, Respiratory bronchiolitis-interstitial lung disease, desquamative interstitial pneumonia, acute interstitial pneumonia, Rare IIPs: Idiopathic lymphoid interstitial pneumonia, idiopathic pleuroparenchymal fibroelastosis, unclassifiable idiopathic interstitial pneumonias, hypersensitivity pneumonitis, radiation-induced lung injury, progressive massive fibrosis—pneumoconiosis, bronchiectasis, byssinosis, chronic respiratory disease, chronic obstructive pulmonary disease (COPD), emphysema, pulmonary arterial hypertension (PAH), or Cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scleroderma/systemic sclerosis, graft versus host disease, hypertrophic scars, keloids, nephrogenic systemic fibrosis, *Porphyria cutanea tarda*, restrictive dermopathy, Dupuytren's contracture, dermal fibrosis, nephrogenic systemic fibrosis/nephrogenic fibrosing dermopathy, mixed connective tissue disease, scleromyxedema, eosinophilic fasciitis, fibrosis caused by exposure to chemicals or physical agents. GvHD induced fibrosis, Scleredoma adultorum, Lipodermatosclerosis, or Progeroid disorders (progeria, acrogeria, Werner's syndrome) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having atrial fibrosis, endomyocardial fibrosis, cardiac fibrosis, atherosclerosis, restenosis, or arthrofibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having mediastinal fibrosis, myelofibrosis, post-polycythemia vera myelofibrosis, or post essential thrombocythemia is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Crohn's disease, retroperitoneal fibrosis, intestinal fibrosis, fibrosis in inflammatory bowel disease, ulcerative colitis, GI fibrosis due to cystic fibrosis, or pancreatic fibrosis due to pancreatitis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having endometrial fibrosis, uterine fibroids, or Peyronie's disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having macular degeneration, diabetic retinopathy, retinal fibrovascular diseases, or vitreal retinopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scarring associated with trauma (surgical complications, chemotherapeutics drug-induced fibrosis, radiation induced fibrosis) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

As used herein, the term "administration" refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "chronic" refers to a medical disorder or condition that persists overtime or is frequently recurring.

Compounds having the structure of Formulas (I), (II), (III), (IV), (V), (VI), (VII), and (VIII) can be synthesized using standard synthetic techniques known to those skilled in the art. For example, compounds of the present invention can be synthesized using appropriately modified synthetic procedures set forth in Schemes 1-23 below.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures, or higher if reactions are run in sealed vessels). A given reaction may be carried out in one solvent or a mixture of more than one solvent. Depending on the particular reaction, suitable solvents for a particular work-up following the reaction may be employed.

Scheme 1.

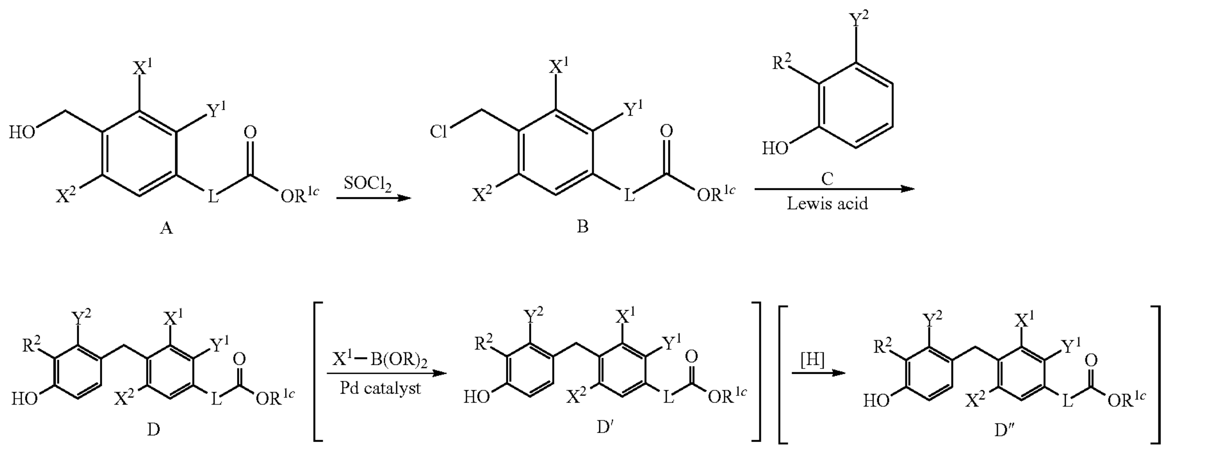

Compounds D of the present invention can be prepared according to Scheme 1. Referring to Scheme 1, hydroxymethyl derivative (A) is activated (for example, through reaction with thionyl chloride, or oxalyl chloride, or p-toluenesulfonylchloride, or the like) to give a chloromethyl derivative (B) (or the corresponding tosylate, or mesylate, or bromomethyl analog or the like), which is condensed with a 2-substituted phenol (C) in the presence of a Lewis acid (like zinc chloride, or aluminum chloride, or the like) to give an ester (D). Alternatively, intermediate alcohol (A) can be reacted directly with phenol (C) in the presence of a protic acid (for example using sulfuric acid, or the like), or a Lewis acid (for example boron trifluoride etherate, or the like). In cases in which $X^1$ is a bromide or iodide, D can be reacted under Suzuki coupling conditions (for example using a boronic acid, or boronate reagent, or the like in the presence of Palladium catalysts $Pd(OAc)_2$, or $Pd(dppf)Cl_2$, or the like) to produce alkyl, alkenyl, or alkynyl products (D'). In cases where $X^1$ is an alkene or alkyne, subsequent hydrogenation (for example using Pd—C catalyst, or the like under a hydrogen atmosphere, or the like) can provide the corresponding alkyl-substituted (D").

Scheme 2.

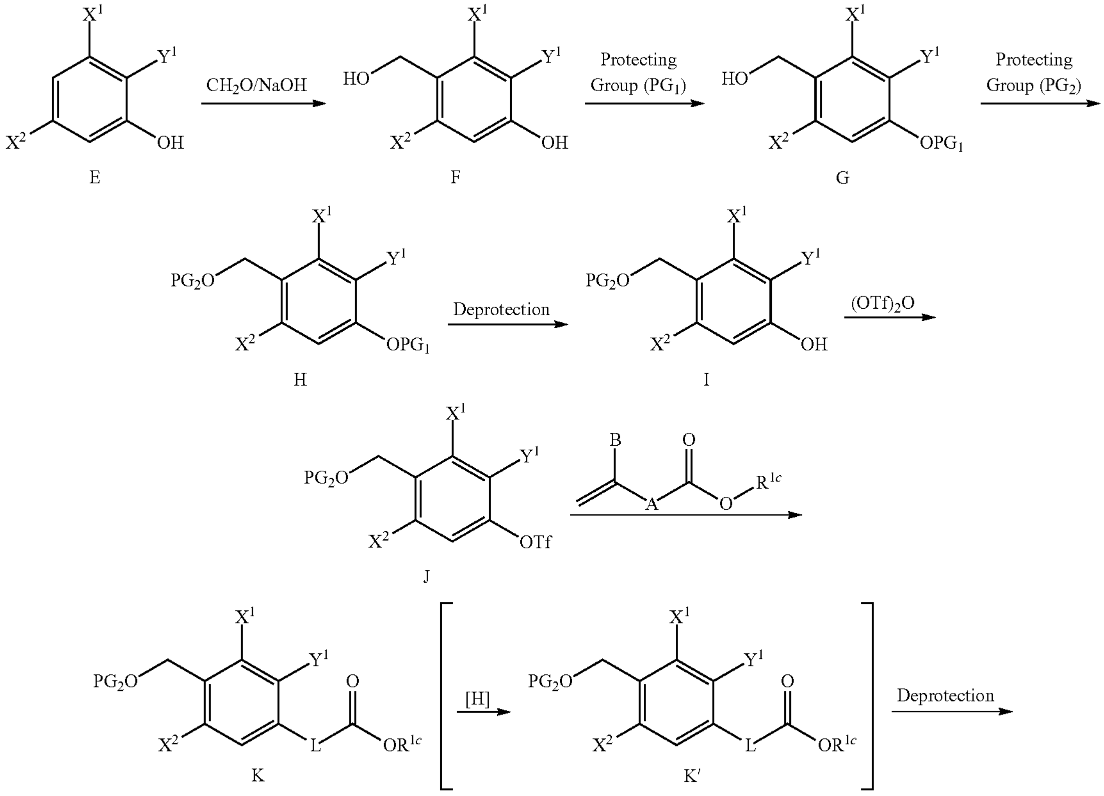

-continued

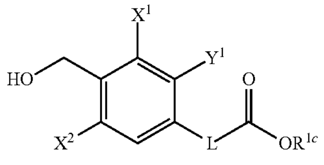

A

Hydroxymethyl derivatives (A) of the present invention can be prepared according to Scheme 2. Referring to Scheme 2, a di- or tri-substituted phenol (E) (for example, 3,5-dichlorophenol, or 2-fluoro-3,5-dichlorophenol, or the like) is reacted with a formaldehyde equivalent (for example, aqueous formaldehyde, or paraformaldehyde, or dimethoxymethane, or the like) to give a hydroxymethyl derivative (F). The phenolic residue of F is selectively protected (for example, as the corresponding benzyl ether, using benzyl bromide and base, or the like) to give intermediate G. Hydroxymethyl intermediate G is protected on the remaining hydroxyl group (for example, as the tert-butyldimethyl silyl ether, using tert-butyldimethyl silyl chloride and imidazole, or the like) to give di-protected intermediate H. The phenolic residue is selectively deprotected (for example, with palladium catalyst, under a hydrogen atmosphere, when the protecting group is a benzyl ether) to give phenol (I). Phenol (I) is subsequently activated (for example, as the triflate using triflic anhydride, or the like and pyridine, or the like) to give intermediate J, which is reacted with an alkene (for example, using methyl prop-2-enoate, or the like) under Heck arylation conditions (for example, in the presence of a Palladium catalyst like $Pd(OAc)_2$) to provide alkene (K). Subsequently, hydrogenation of K (for example, using Pd—C catalyst under a hydrogen atmosphere) can provide the corresponding saturated alkane (K'). Both intermediates K and K' can be further deprotected (for example using HF in pyridine, or the like, in the case where $PG_2$ is a TBS group) to give hydroxymethyl derivatives (A) of the present invention.

Scheme 3.

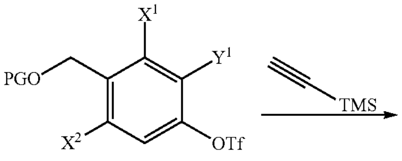

J

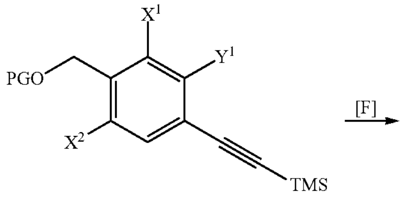

L

-continued

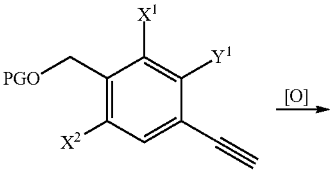

M

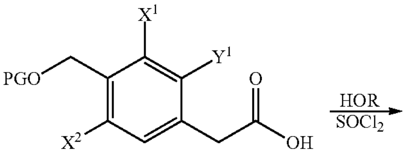

N

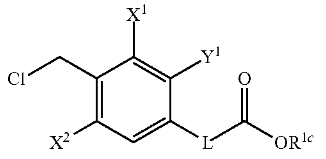

B

Chloromethyl derivatives (B) of the present invention can be prepared according to Scheme 3. Referring to Scheme 3, intermediate J (as prepared in Scheme 2) is coupled to ethynyltrimethylsilane under Sogonashira conditions (for example, using $Pd(PPh_3Cl_2/CuI$, or the like) to give alkyne (L) that can be deprotected with a fluoride ion source (for example, using tetrabutylammonium fluoride, or the like) to give intermediate M. Terminal alkyne oxidation (for example, employing 4-methyl-1-oxido-pyridin-1-ium, or the like and $[Rh(cod)Cl]_2$ or the like) gives acid N, that can be concomitantly deprotected and chlorinated at the benzylic position with ester formation (for example, using $SOCl_2$, or the like and methanol, or the like when the protecting group is a tert-butyldimethyl silyl ether, or the like) to give chloromethyl derivatives (B) of the present invention. Alternatively the transformation from N to B can be accomplished in several steps.

Scheme 4.

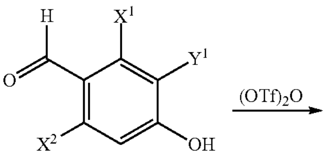

O

-continued

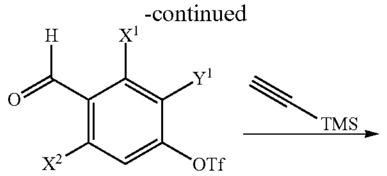

P

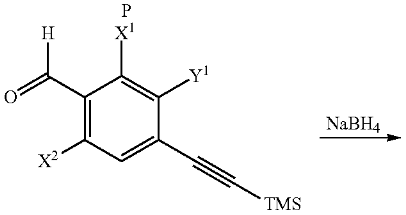

Q

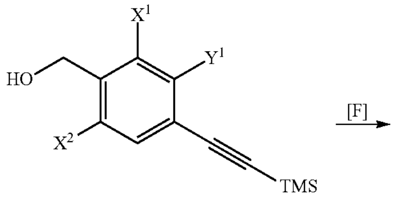

R

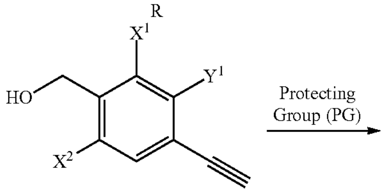

S

-continued

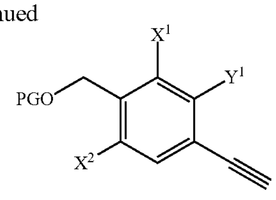

M

Alkynyl derivatives (M) of the present invention can be prepared according to Scheme 4. Referring to Scheme 4, a di- or tri-substituted aldehyde phenol (O) (for example using 3,5-dimethyl-4-formylphenol, or the like) is activated (for example, as the triflate, or the like using triflic anhydride, or the like and pyridine, or the like) to give intermediate P, which is coupled to ethynyltrimethylsilane under Sogonashira conditions (for example, using Pd($PPh_3Cl_2$/CuI, or the like) to give alkyne (Q). Intermediate Q is selectively reduced (for example, using sodium borohydride, or the like) to give alcohol (R), and deprotected with a fluoride ion source (for example, using tetrabutylammonium fluoride, or the like) to give intermediate S. Alcohol S is protected (for example, as the tert-butyldimethyl silyl ether, or the like using tert-butyldimethyl silyl chloride, or the like and imidazole, or the like) to give an alkynyl derivative (M) of the present invention.

Scheme 5.

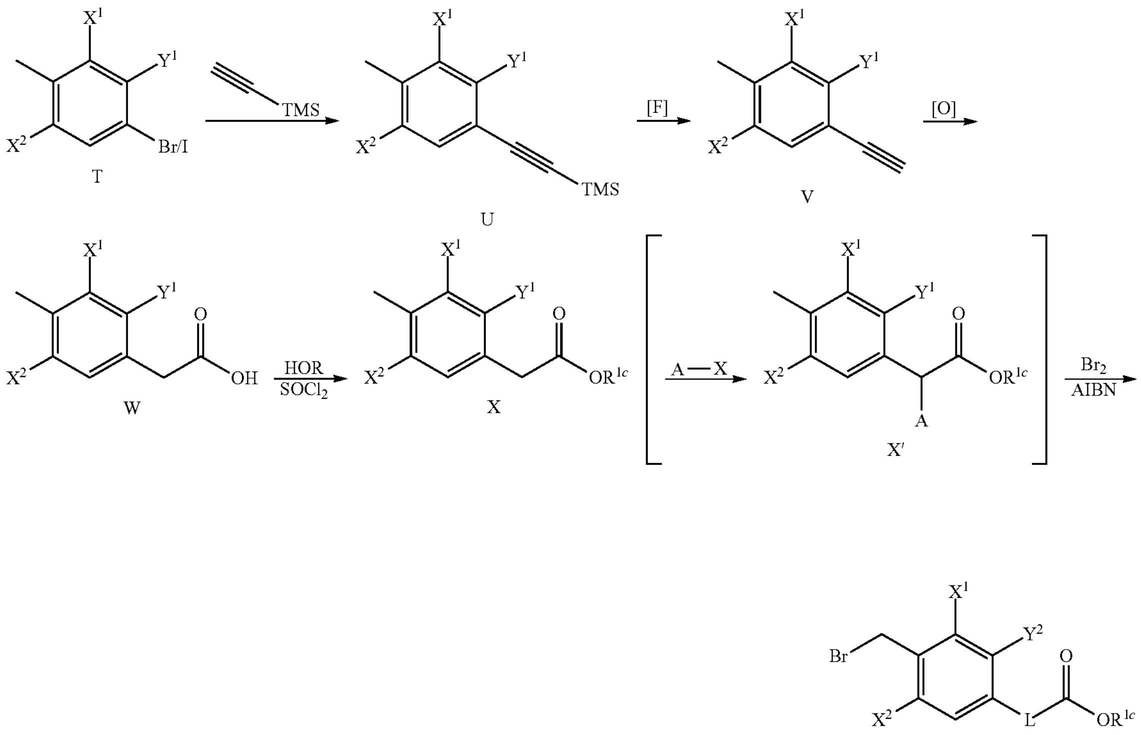

B

Bromomethyl intermediates B of the present invention can be prepared according to Scheme 5. Referring to Scheme 5, a tri- or tetra-substituted toluene for which one substituent is a bromine or iodide (T) (for example, 3,5-chloro-4-methyl-1-bromobenzene, or the like) is coupled to ethynyltrimethylsilane under Sogonashira conditions (for example, using $Pd(PPh_3Cl_2/CuI$, or the like) to give alkyne (U) that can be deprotected with a fluoride ion source (for example, using tetrabutylammonium fluoride, or the like) to give intermediate V. Terminal alkyne oxidation (for example, employing 4-methyl-1-oxido-pyridin-1-ium, or the like and $[Rh(cod)Cl]_2$, or the like) gives acetate W, that can be subjected to ester forming conditions (for example, using $SOCl_2$, or the like and methanol, or the like) to give intermediate X. Acetate ester (X) can be alkylated (for example, with base and iodomethane, or the like) to give substituted ester (X'). Intermediates X and X' can be brominated (for example, using N-bromosuccinimide (NBS), or the like and radical initiator azobisisobutyronitrile (AIBN), or the like) to provide bromomethyl intermediates B of the present invention.

Scheme 6.

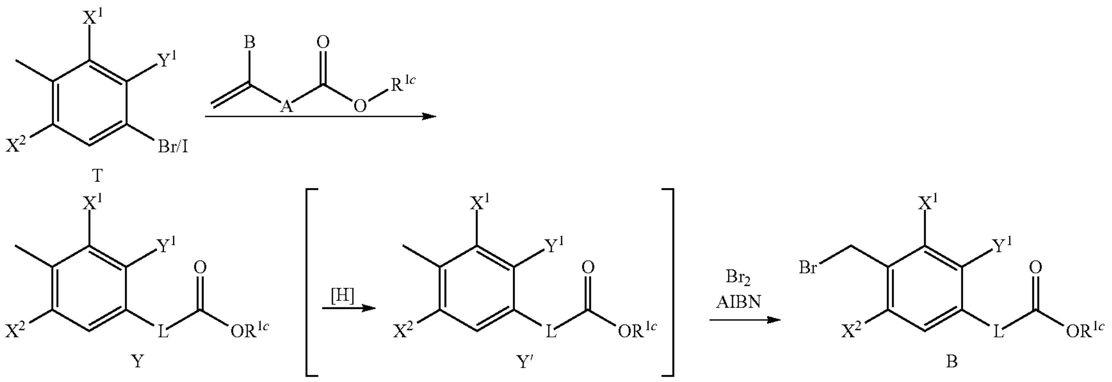

Alternatively, bromomethyl derivatives (B) of the present invention can be prepared according to Scheme 6. Referring to Scheme 6, a tri- or tetra-substituted toluene for which one substituent is a bromine or iodide (T) (for example, using 3,5-chloro-4-methyl-1-bromobenzene, or the like) is coupled under Heck conditions (for example, using palladium catalyst $Pd(OAc)_2$, or the like) to provide alkene (Y). Subsequently, alkene (Y) can be hydrogenated (for example, using Pd—C catalyst or the like under a hydrogen atmosphere, or the like) to provide the corresponding saturated alkane (Y'). Intermediates Y and Y' can be brominated (for example, using N-bromosuccinimide (NBS), or the like and radical initiator azobisisobutyronitrile (AIBN), or the like) to provide bromomethyl derivatives (B) of the present invention.

Scheme 7.

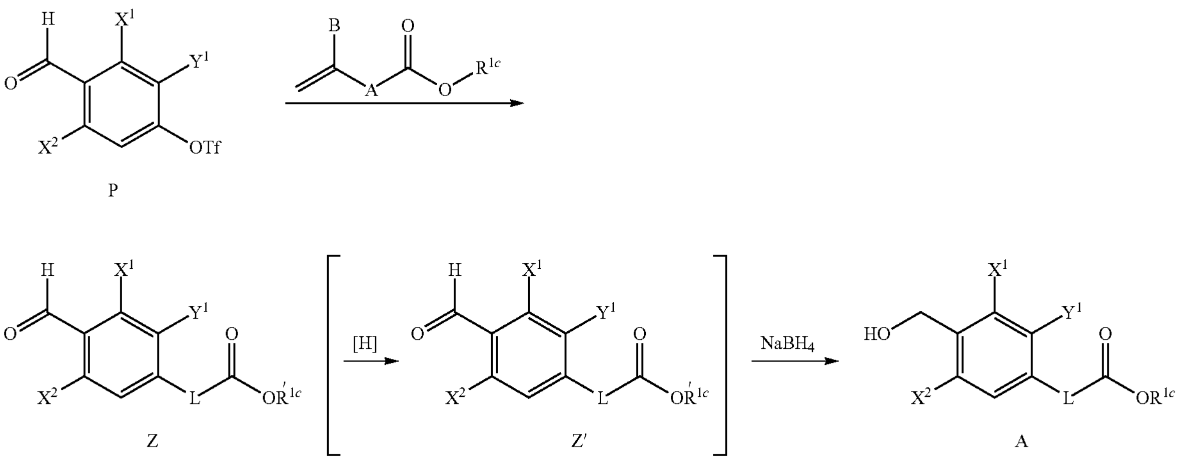

Hydroxymethyl derivatives (A) of the present invention can be prepared according to Scheme 7. Referring to Scheme 7, intermediate P (as prepared in Scheme 4) is coupled under Heck conditions (for example, using a palladium catalyst like $Pd(OAc)_2$ or the like) to provide alkene (Z). Subsequently, hydrogenation (for example using Pd—C catalyst, or the like under a hydrogen atmosphere, or the like) can provide the corresponding saturated alkane (Z'). Intermediates Z and Z' can be reduced (for example, using sodium borohydride, or the like) to provide hydroxymethyl derivatives (A) of the present invention.

Scheme 8.

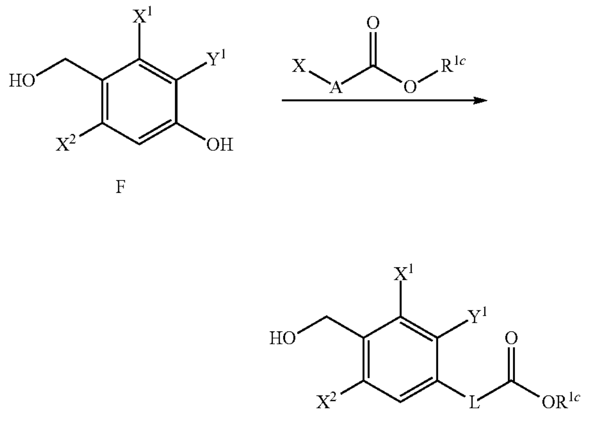

F

A

Hydroxymethyl derivatives (A) of the present invention can be prepared according to Scheme 8. Referring to Scheme 8, phenol intermediate F (as prepared in Scheme 2) can be alkylated with an activated ester-containing moiety (for example, using methyl 4-bromobutyrate, or the like in the presence of base, or the like) to provide hydroxymethyl derivative (A) of the present invention.

Scheme 9.

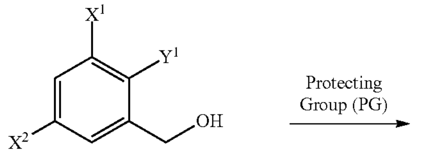

AA

-continued

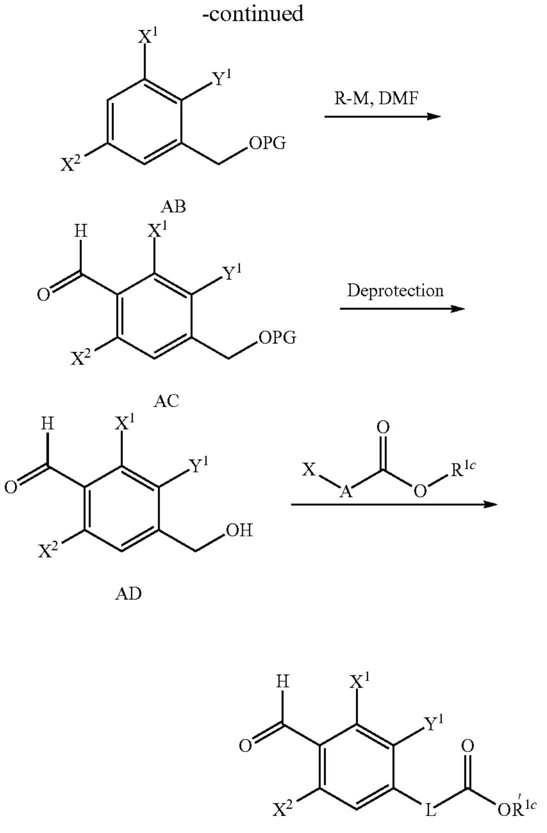

AB

AC

AD

Z

Aldehyde derivatives (Z) of the present invention can be prepared according to Scheme 9. Referring to Scheme 9, di- or tri-substituted benzyl alcohol intermediate AA is protected (for example, as the tert-butyldimethyl silyl ether, or the like using tert-butyldimethyl silyl chloride, or the like and imidazole, or the like) to give intermediate AB. Intermediate AB is metallated (for example, using isopropylmagnesium bromide or n-butyllithium, or the like), then quenched with DMF to give aldehyde (AC), which is subsequently deprotected (for example, by treatment with tetra-n-butylammonium fluoride, or the like when the protecting group is a tert-butyldimethyl silyl ether, or the like) to give intermediate AD. Aldehyde intermediate AD can be reacted with an activated ester-containing moiety (for example, using methyl bromoacetate, or the like) in the presence of base, to provide aldehyde derivatives (Z) of the present invention.

Scheme 10.

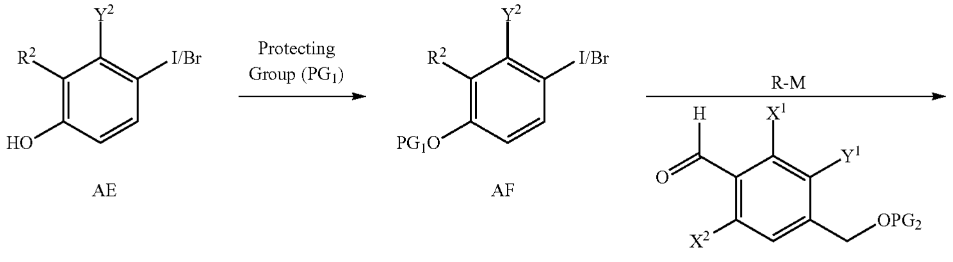

AE

AF

AC

-continued

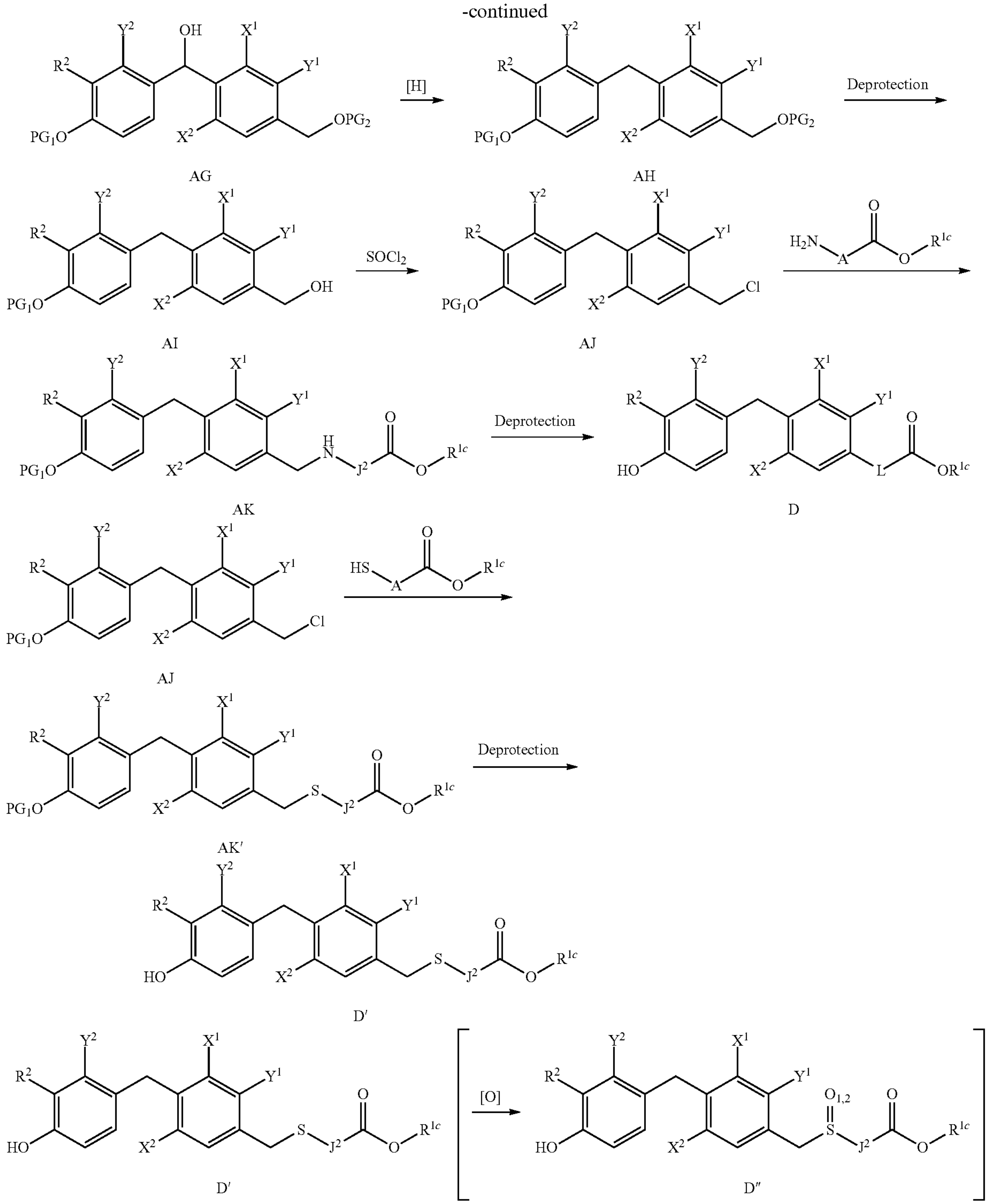

Compounds D of the present invention can be prepared according to Scheme 10. Referring to Scheme 10, 4-halophenol intermediate AE is masked with an appropriate protecting group (for example, treatment with methoxymethyl chloride, or the like to provide MOM-protection, or the like) to give intermediate AF. Intermediate AF can be metallated (for example, using isopropylmagnesium bromide or n-butyllithium, or the like) and condensed with aldehyde intermediate AC (for example, obtained commercially, or synthesized according to Scheme 9, or the like), to give alcohol (AG). Intermediate AG can be deoxygenated under hydrogenolysis conditions (for example, by treatment with trifluoroacetic acid, or the like and triethylsilane, or the like) to provide intermediate AH. Protected hydroxymethyl alcohol (AH) is unmasked (for example, by treatment with tetra-n-butylammonium fluoride, or the like when the protecting group is a tert-butyl dimethyl silyl ether, or the like) to give intermediate AI. Hydroxymethyl alcohol (AI) can be activated (for example, through reaction with thionyl chloride, or oxalyl chloride, or p-toluenesulfonylchloride, or the like) to give chloromethyl derivative (AJ) that can be displaced by an amino ester nucleophile (for example, using methyl glycinate, or the like) to give compound (AK). Intermediate AK can be deprotected (for example, using trifluoroacetic acid, or the like when the protecting group is a methoxy methyl ether, or the like) to give compounds (D) of the present invention. Alternatively, intermediate AJ can be displaced with a thiol-containing ester nucleophile (for example, using methyl thioglycolate, or the like) to provide intermediate AK'. Intermediate AK' can be deprotected (for example, using trifluoroacetic acid, or the like when the protecting group is a methoxy methyl ether, or the like) to give sulfide (D') of the present invention. The thioether product (D') can be further oxidized (for example, using m-CPBA or $H_2O_2$ or the like) to give sulfone and sulfoxide products (D'') of the present invention.

Scheme 11.

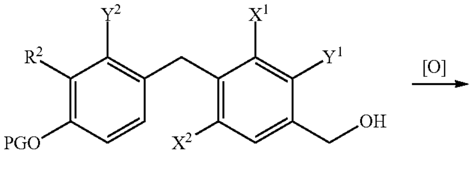

AI

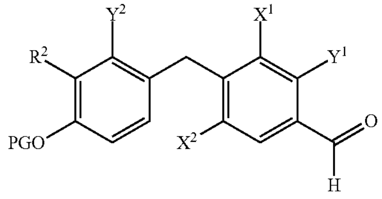

AL

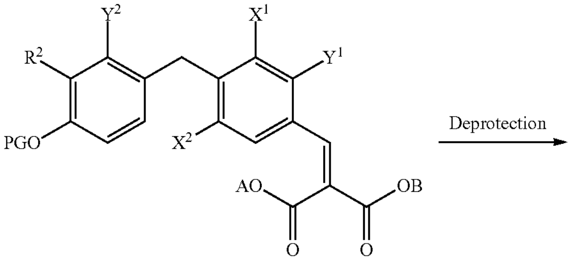

AM

-continued

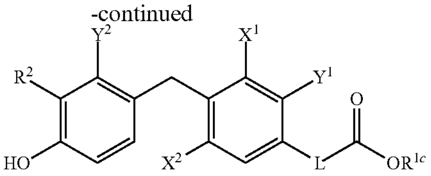

D

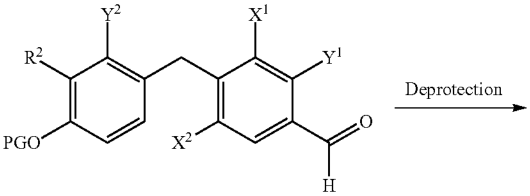

AL

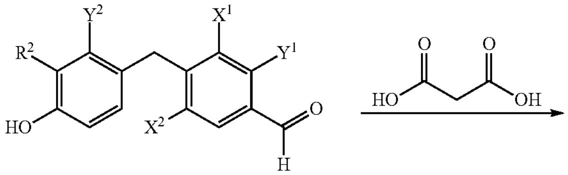

AN

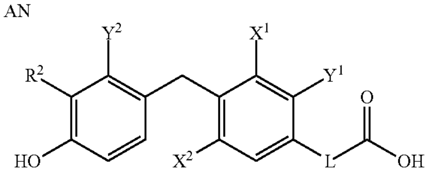

AO

Compounds D and AO of the present invention can be prepared according to Scheme 11. Referring to Scheme 11, hydroxymethyl intermediate AI (for example, as prepared in Scheme 10, or the like) is oxidized (for example, using Dess-Martin conditions, or the like) to give aldehyde (AL) that is condensed (for example, using piperidine base, or the like) with a differentially protected malonic acid (for example, using tert-butyl ethyl malonate, or the like) to give di-ester AM. Intermediate AM is deprotected (for example, using trifluoroacetic acid, or the like when the protecting group is a methoxy methyl ether, or the like) to give compounds D of the present invention. Aldehyde intermediate AL can be deprotected (for example, using hydrochloric acid, or the like when the protecting group is a methoxy methyl ether, or the like) to give intermediate AN, and condensed with malonic acid (for example, using piperidine base, or the like and catalytic L-homoserine, or the like) to give compounds AO of the present invention.

Scheme 12.

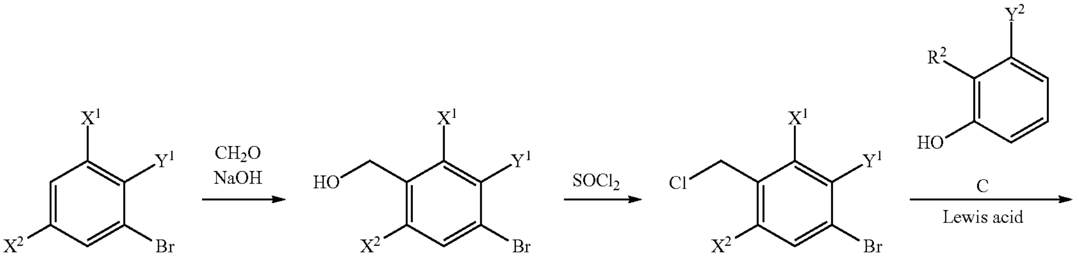

AP AQ AR

-continued
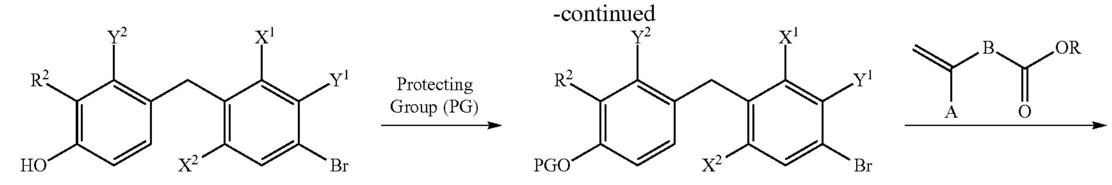
AS AT
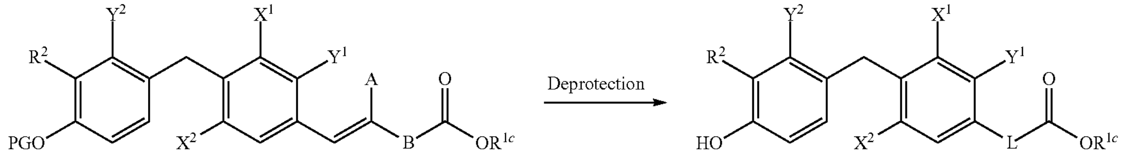
AU D
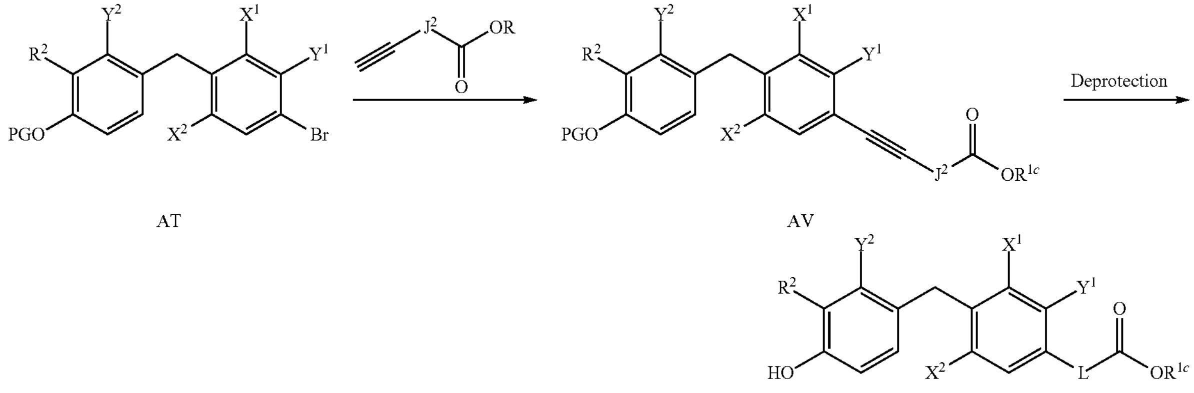
AT AV
D′
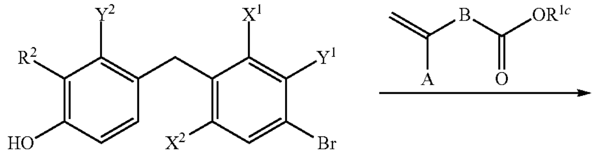
AS
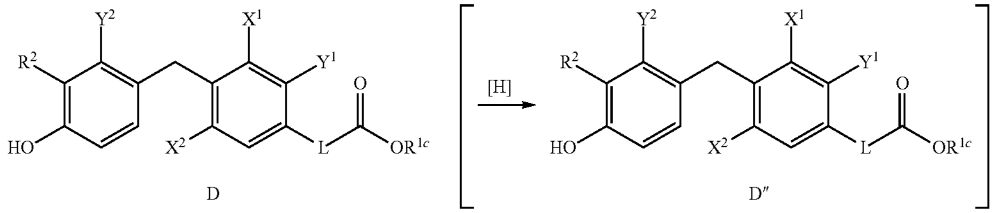
D D″
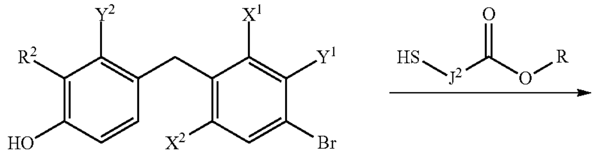
AS
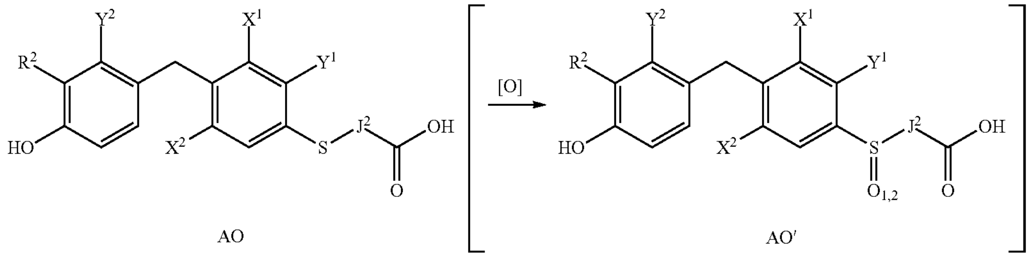
AO AO′

Compounds D and AO of the present invention can be prepared according to Scheme 12. Referring to Scheme 12, a di- or tri-substituted bromobenzene intermediate AP (for example, using 3,5-dichloro bromobenzene) is reacted with a formaldehyde equivalent (for example, aqueous formaldehyde, or paraformaldehyde, or dimethoxymethane, or the like) to give a hydroxymethyl derivative (AQ), that is activated (for example, through reaction with thionyl chloride, or oxalyl chloride, or p-toluenesulfonylchloride, or the like) to give a chloromethyl derivative (AR). Intermediate AR is condensed with a 2-substituted phenol (C) in the presence of a Lewis acid (for example zinc chloride, or aluminum chloride, or the like) to give phenol (AS), that is masked with a protecting group (for example, as the 2-tetrahydropyranyl ether, or the like using 3,4-dihydropyran, or the like and acid treatment, or the like) to give bromine (AT). Intermediate AT is coupled under Heck conditions (for example, in the presence of palladium catalyst $Pd(OAc)_2$, or the like) to provide alkene (AU) that can be deprotected (for example, using tosylic acid, or the like and methanol, or the like when the protecting group is a tetrahydropyranyl ether, or the like) to give compounds D of the current invention. Bromine (AT) can be coupled with an alkyne under Sogonashira conditions (for example, using $Pd(PPh_3Cl_2$, or the like and $Et_3N$, or the like) to give alkyne (AV), that can be deprotected (for example, using tosylic acid, or the like and methanol, or the like) when the protecting group is a tetrahydropyranyl ether, or the like) to give compounds D' of the current invention. Alternatively, intermediate AS can be coupled under Heck conditions (for example, in the presence of palladium catalyst $Pd(OAc)_2$, or the like) to provide compounds D' of the current invention. Subsequently, hydrogenation (for example using Pd—C catalyst, or the like under a hydrogen atmosphere, or the like) can provide the corresponding saturated alkane compounds D" of the current invention. Intermediate AS can be reacted with a thiol-containing ester nucleophile and base (for example, using methyl thioglycolate, or the like) to provide compounds AO of the present invention. Thioether compounds AO can be further oxidized (for example, using m-CPBA or $H_2O_2$, or the like) to give sulfone and sulfoxide compounds AO' of the present invention.

Scheme 13.

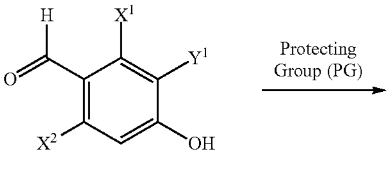

O

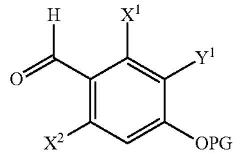

AW

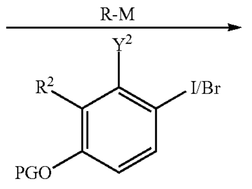

AF

-continued

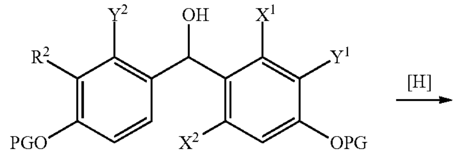

AX

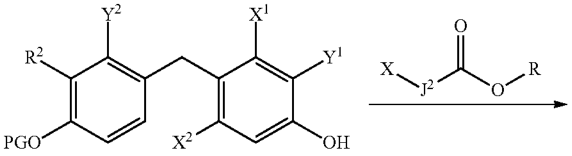

AY

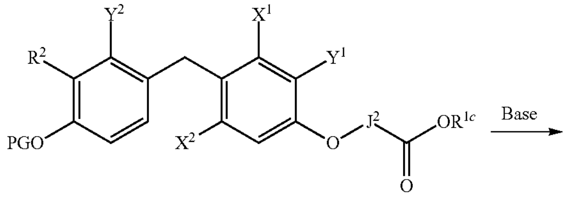

AZ

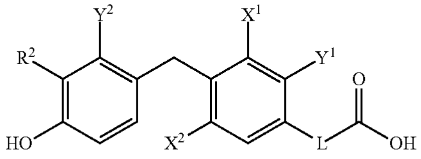

AO

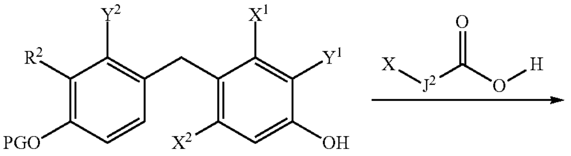

AY

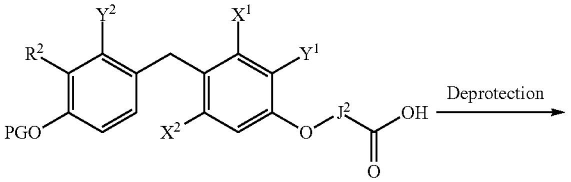

AAA

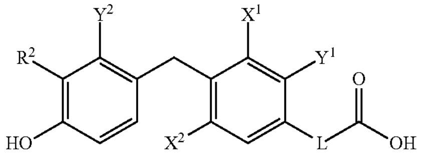

AO

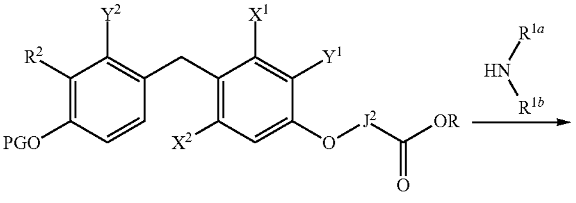

AZ

-continued

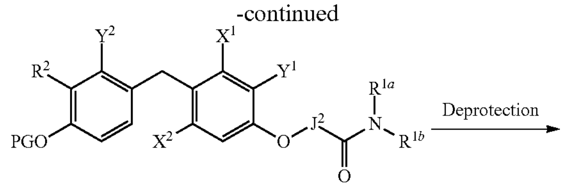

AAB

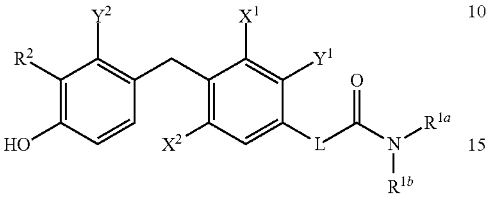

AAC

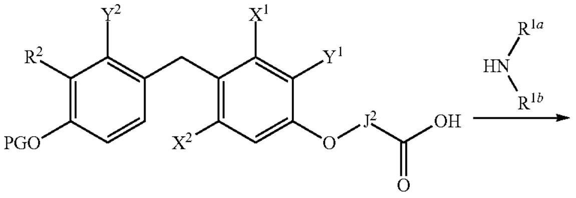

AAA

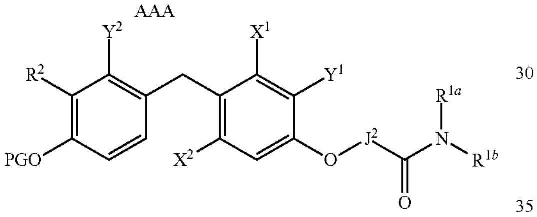

AAB

Compounds AO and AAC of the present invention can be prepared according to Scheme 13. Referring to Scheme 13, di- or tri-substituted hydroxybenzaldehyde (O) is masked with an appropriate protecting group (for example, treatment with benzyl chloride, or the like to provide a benzyl ether, or the like) to give intermediate AW. Intermediate AF is metallated (for example, using isopropylmagnesium bromide or n-butyllithium, or the like) and condensed with aldehyde intermediate AW (for example, obtained commercially or synthesized according to Scheme 9, or the like), to give alcohol (AX). Intermediate AX can be deoxygenated with concomitant deprotection of the phenol (for example, under hydrogenolysis conditions using Pd—C catalyst, or the like when the phenol protecting group is a benzyl ether, or the like) to provide phenol (AY). Intermediate AY can be alkylated with an activated ester-containing moiety (for example, using ethyl 2-fluoro-2-bromoacetate, or the like) in the presence of base to give ester (AZ), that is treated with basic conditions to concomitantly deprotect the phenol and hydrolyze the ester (for example, using potassium carbonate, or the like in aqueous DMF, or the like when the ester is an ethyl group, or the like and the phenol protecting group is a tertbutyldimethylsilyl ether, or the like) to give compounds OA of the present invention. Phenol intermediate A can alkylated with an activated acid-containing moiety (for example, using ethyl 2,2-difluoro-2-bromoacetic acid, or the like) in the presence of base to give acid (AAA), that is deprotected (for example, by treatment with tetra-n-butylammonium fluoride, or the like when the protecting group is a tert-butyl dimethyl silyl ether, or the like) to give compounds OA of the present invention. Either esters (AZ), or acids (AAA) may be heated with an amine $R^{2a}R^{2b}NH$ (for example, methylamine, or propylamine, or 2-sulfonylethylamine, or the like) to give amides (AAB), that can be deprotected (for example, using Pd—C catalyst, or the like under a hydrogen atmosphere, or the like when the phenol protecting group is benzyl ether, or the like) to give compounds AAC of the present invention. Alternatively, acid (AAA) can be converted to an amide (AAB) by condensing with the corresponding amine (for example, using methylamine, or propylamine, or 2-sulfonylethylamine, or the like) in the presence of a coupling agent (for example, using DDC or EDCI, or the like), or by forming an activated intermediate (for example, the corresponding acid chloride using thionyl chloride, or the like).

Scheme 14.

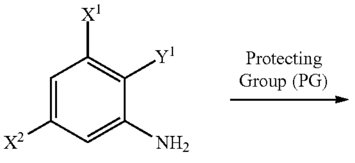

AAD

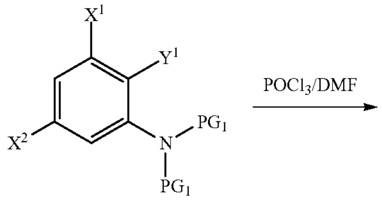

AAE

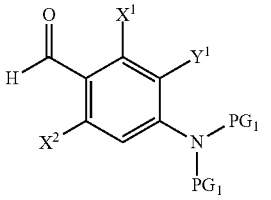

AAF

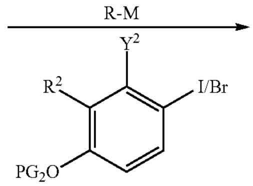

AF

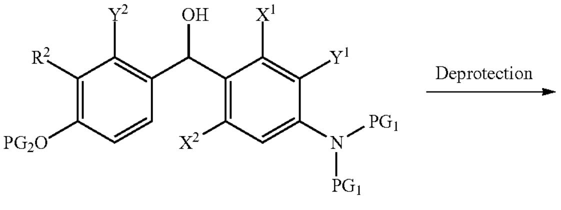

AAG

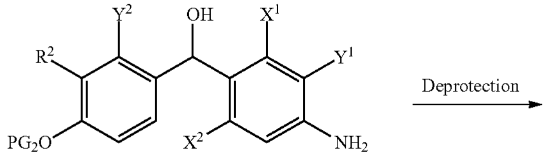

AAH

-continued

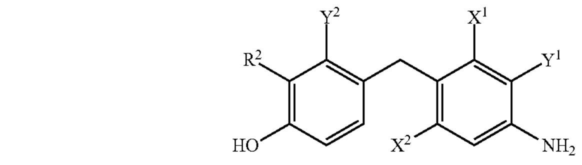

AAI

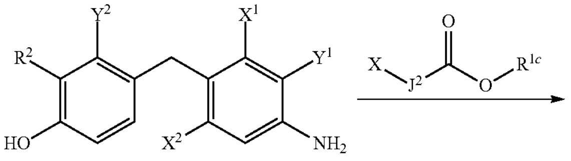

AAI

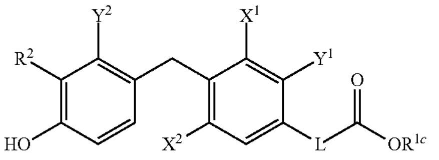

D

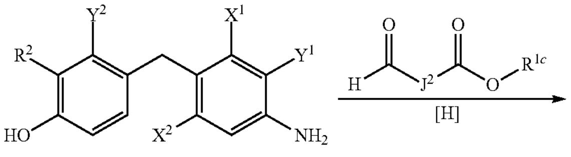

AAI

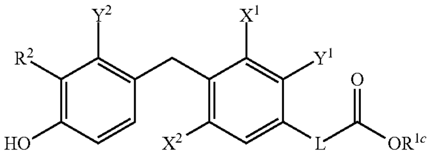

D'

-continued

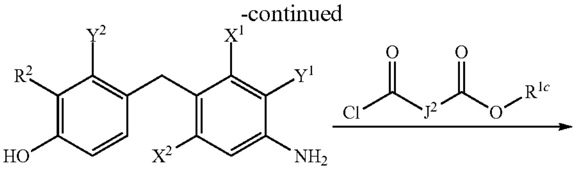

AAI

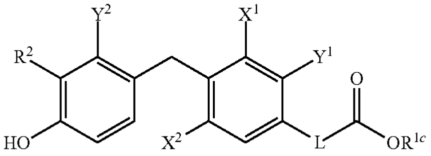

D''

Compounds D of the present invention can be prepared according to Scheme 14. Referring to Scheme 14, a di- or tri-substituted aniline (for example, using 3,5-dichloroaniline, or the like) is di-protected (for example, with benzyl bromide, or the like and base to give the dibenzyl aniline, or the like) to provide intermediate AAE, that can be formylated (for example, using Vilsmeier-Haack conditions of DMF and $POCl_3$, or the like) to give aldehyde (AAF). Intermediate AF is metallated (for example, using isopropylmagnesium bromide or n-butyllithium, or the like) and condensed with aldehyde intermediate AAF to give alcohol (AAG). The aniline of intermediate AAG is unmasked (for example, using Pd—C, or the like and an atmosphere of hydrogen, or the like) to provide aniline (AAH), that can be deoxygenated with concomitant deprotection of the phenol (for example, by treatment with trifluoroacetic acid, or the like and triethylsilane, or the like when the protecting group is a methoxymethyl ether, or the like) to give key intermediate AAI. Aniline (AAI) can be alkylated with an activated ester-containing compound (for example, using methyl bromoacetate, or the like) to give compounds D of the present invention. Aniline (AAI) can be reductively aminated with an aldehyde-containing ester (for example, under hydrogenolysis conditions with Pd—C catalyst, or the like after condensation with methyl 3-formylpropionate, or the like) to provide compounds D' of the present invention. Additionally, aniline (AAI) can be acylated with an acyl group-containing ester and base (for example, using ethyl chlorooxoacetate, or the like) to provide compounds D" of the present invention.

Scheme 15.

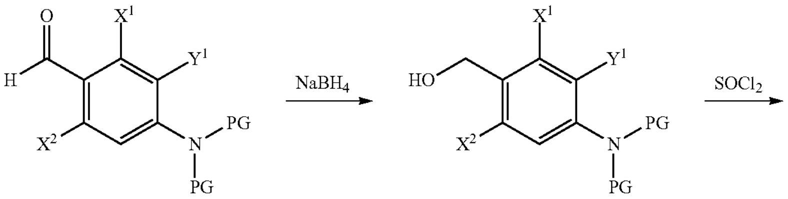

AAF AAJ

-continued

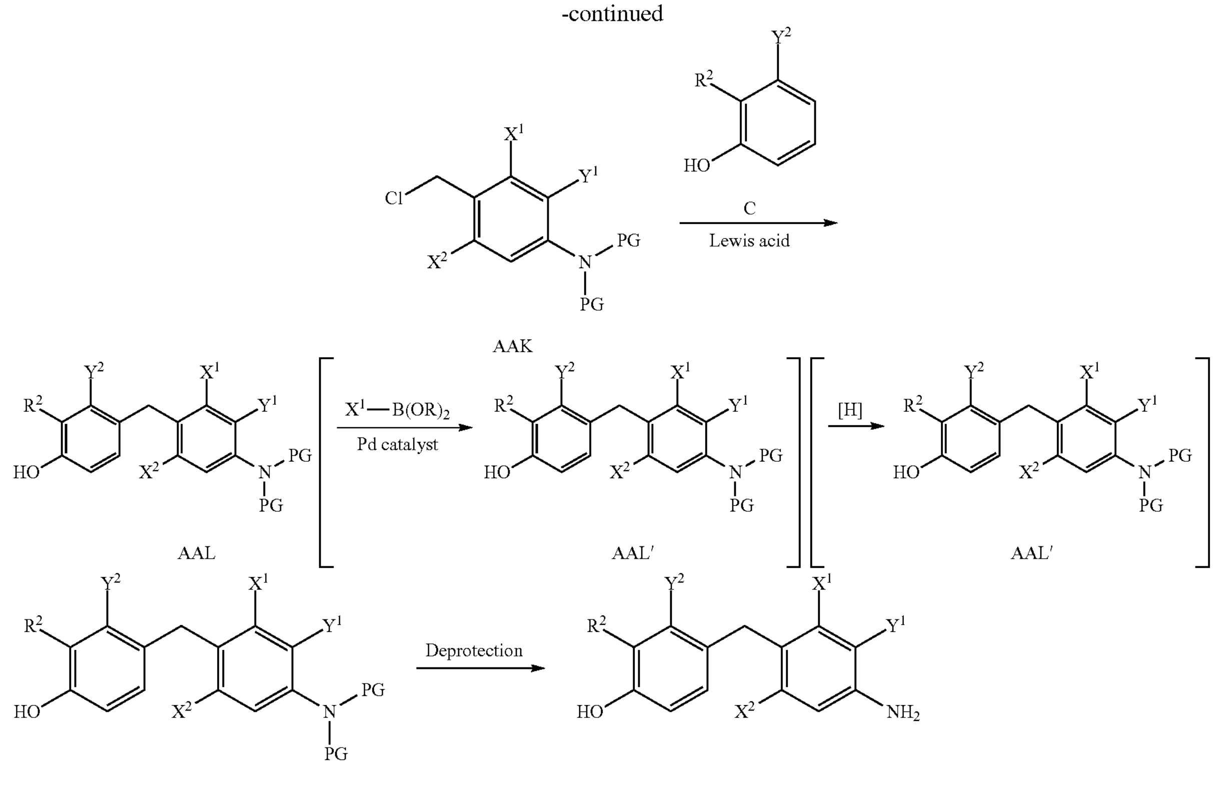

AAF AAI

Compounds AAL and AAI of the present invention can be prepared according to Scheme 15. Referring to Scheme 15, aldehyde intermediate AAF (for example, as prepared in Scheme 14, or the like) is reduced (for example, with sodium borohydride, or the like) to give hydroxymethyl intermediate AAJ, that is activated (for example, through reaction with thionyl chloride, or oxalyl chloride, or p-toluenesulfonylchloride, or the like) to give chloromethyl derivative (AAK) (or the corresponding tosylate, or mesylate, or bromomethyl analog, or the like), which is condensed with a 2-substituted phenol (C) in the presence of a Lewis acid (for example, using zinc chloride or aluminum chloride, or the like) to give intermediate AAL. Alternatively, intermediate alcohol AAJ can be reacted directly with phenol (C) in the presence of a protic acid (for example, using sulfuric acid, or the like), or a Lewis acid (for example, using boron trifluoride etherate, or the like) to give intermediate AAL. In cases in which $R^1$ is a bromide or iodide, Intermediate AAI can be reacted under Suzuki coupling conditions (for example, using a boronic acid or boronate reagent, or the like in the presence of $Pd(OAc)_2$ or $Pd(dppf)Cl_2$, or the like), to produce alkyl, alkenyl, alkynyl or aryl products (AAL'). In cases where $R^1$ is an alkene or alkyne, subsequent hydrogenation (for example, using Pd—C catalyst, or the like under a hydrogen atmosphere, or the like) can provide the corresponding alkyl-substituted (AAL"). Additionally, intermediates AAL can be deprotected (for example, with palladium on carbon, or the like, under a hydrogen atmosphere, or the like) to give compounds AAI of the current invention.

Scheme 16.

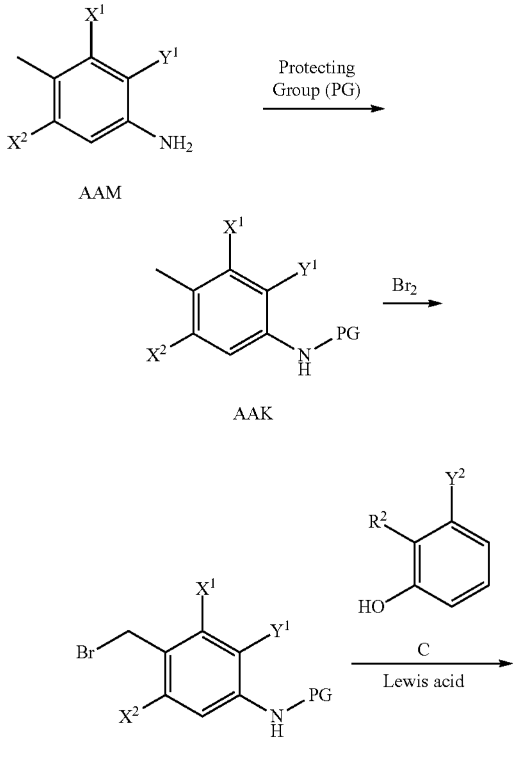

AAO

-continued

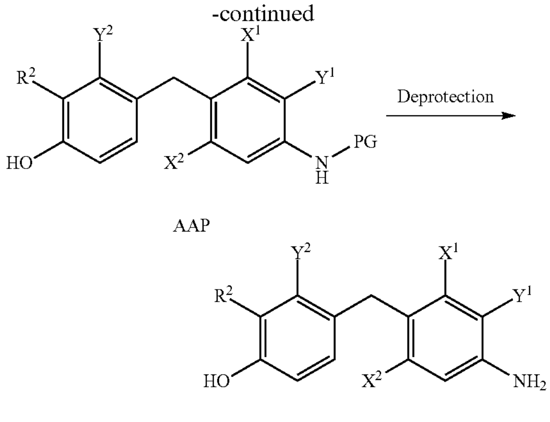

AAP

AAI

Alternatively, compounds AAI of the present invention can be prepared according to Scheme 16. Referring to Scheme 16, aniline (AAM) is protected (for example, using acetyl chloride, or the like to give the acetamide, or the like) and brominated (for example, using bromine, or the like and free radical initiator benzoic peroxyanhydride, or the like) to give bromomethyl intermediate AAO, that is condensed with a 2-substituted phenol (C) in the presence of a Lewis acid (for example, zinc chloride or aluminum chloride, or the like) to give intermediate AAP. Phenol (AAP) is deprotected (for example, with sodium hydroxide, or the like when the protecting group is acetamide, or the like) to give compounds AAI of the present invention.

Scheme 17.

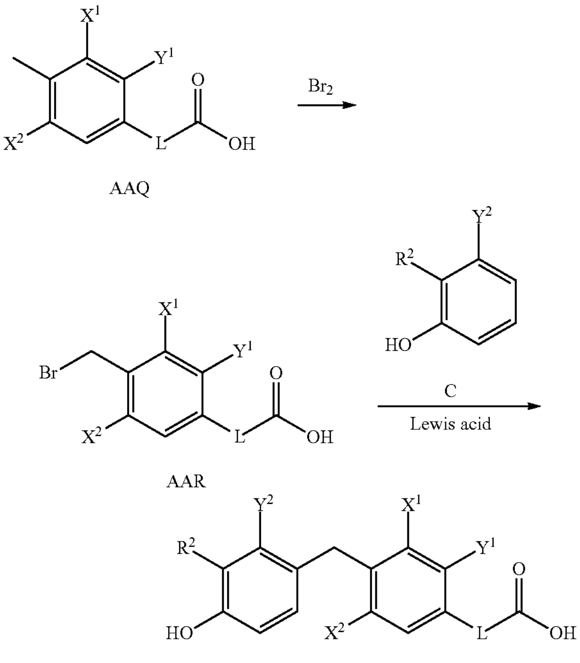

AAQ

AAR

AO

Compounds AO of the present invention can be prepared according to Scheme 17. Referring to Scheme 17, a tri- or tetra-substituted benzoic acid-containing a para methyl group (AAQ) (for example, using 3,5-4-methyl benzoic acid or the like) is brominated (for example, using bromine, or the like and free radical initiator benzoic peroxy anhydride, or the like) to give bromomethyl intermediate AAR, that is condensed with a 2-substituted phenol (C) in the presence of a Lewis acid for example zinc chloride, or aluminum chloride, or the like) to give compounds AO of the present invention.

Scheme 18.

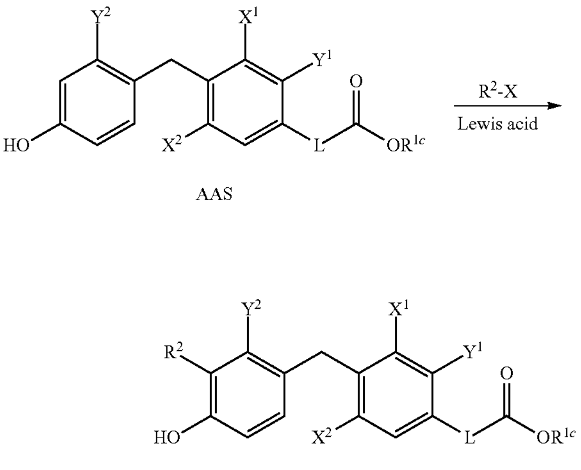

AAS

D

Compounds D of the present invention can be prepared according to Scheme 18. Referring to Scheme 18, phenol intermediate AAS is then reacted with a reactive halides (for example, p-fluorobenzyl chloride, or 1-(1-chloroethyl)-4-fluoro-benzene, or 2,4-difluorobenzyl alcohol, or the like) in the presence of a Lewis acid (for example, Zinc chloride, or Aluminum chloride, or boron trifluoride etherate, or the like) to give a 3'-alkylated compounds D of the current invention.

Scheme 19.

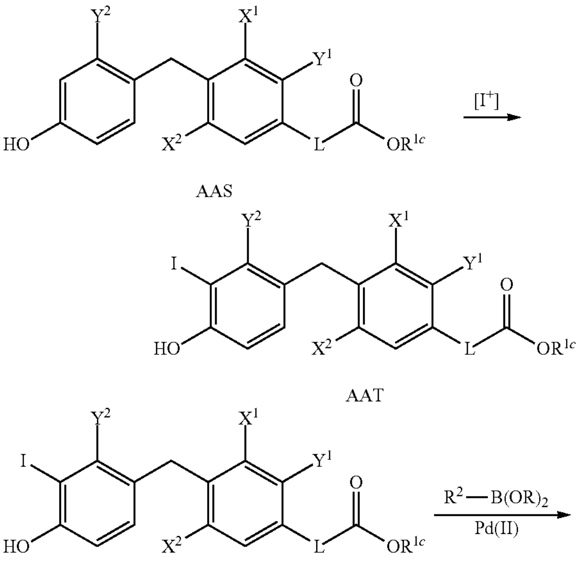

AAS

AAT

AAT

-continued

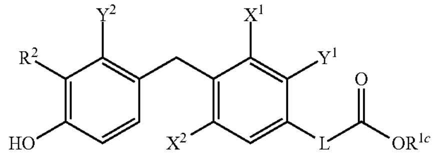

D

Compounds D of the present invention can be prepared according to Scheme 19. Referring to Scheme 19, phenol (AAS) is ortho-iodinated (for example, using N-iodosuccinimide or solid iodine or the like) to provide intermediate AAT, that is reacted with a boronic acid (or boronate) under various Suzuki conditions to provide compounds D of the present invention.

Scheme 20.

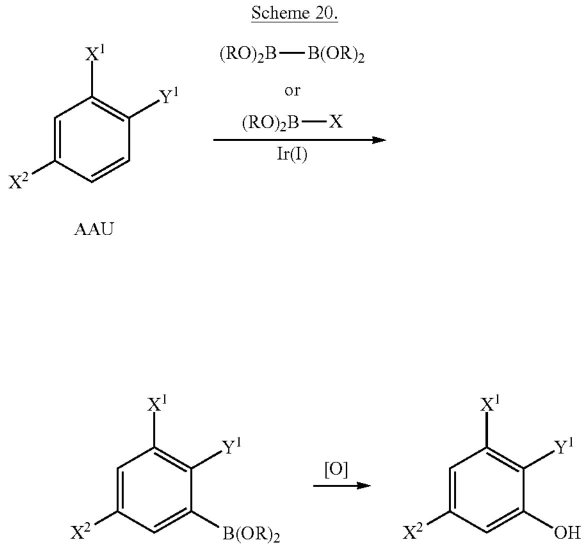

AAU

AAV

E

Phenols (E) of the present invention may be commercially available, or may be prepared according to Scheme 20. Referring to Scheme 20, di- or -tri-substituted arenes (AAU) may be oxidatively borolated (for example, using an activated borylating agent like (bis-pinacolato)diboron, or the like in the presence of an active metal catalyst (1,5-cyclooctadiene) (methoxy)iridium(I) dimer, or the like) to give the corresponding boronate (AAV). Oxidative deborylation of AAV (for example, using hydrogen peroxide solution) provides the corresponding phenol (E).

Scheme 21.

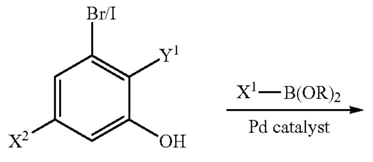

AAW

-continued

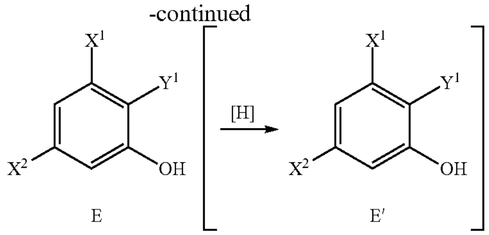

E

E'

An alternative approach to the preparation of key intermediate phenols (E) is described in Scheme 21. Referring to Scheme 21, di- or tri-substituted phenols (AAW) having one substituent as bromine or iodine may be reacted under Suzuki coupling conditions (for example using a boronic acid or boronate reagent, or the like in the presence of a Palladium catalyst like $Pd(OAc)_2$ or $Pd(dppf)Cl_2$ or the like) to produce alkyl, alkenyl, or alkynyl products (E). In the case where $X^1$ is an alkene or alkyne, subsequent hydrogenation (for example, using Pd—C catalyst, or the like under a hydrogen atmosphere, or the like) can provide the corresponding alkyl-substituted (E').

Scheme 22.

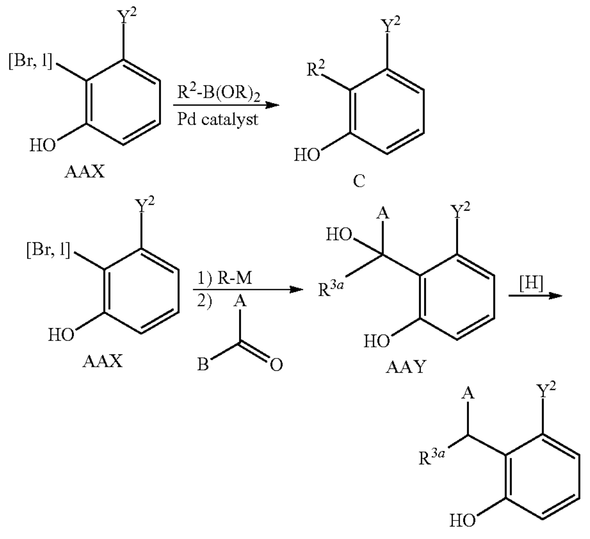

AAX

C

AAX

AAY

C

Substituted phenols (C) of the present invention may be prepared as indicated in Scheme 22. Referring to Scheme 22, a 2-halophenol (AAX) (for example, 2-bromophenol or 2-bromo-3-fluorophenol, or the like) may be condensed with a boronic acid or ester under Suzuki conditions For example, in the presence of a palladium catalyst, or the like) to give 2-substituted phenols (C). In the case where the $R^2$ group is an alkene or alkyne, subsequent hydrogenation (for example, using Pd—C catalyst, or the like under a hydrogen atmosphere, or the like) can provide the corresponding alkyl-substituted phenols(C). Alternatively, a 2-halophenol (C) (for example, like 2-bromophenol, or 2-bromo-3-fluorophenol, or the like) may be metallated (for example, using isopropylmagnesium bromide or n-butyllithium, or the like) then condensed with an aldehyde or ketone, to give an intermediate like (AAY). Deoxygenation of (AAY) under hydrogenolysis conditions (for example, using hydrogen gas, or the like in the presence of a palladium or platinum catalyst or the like, or under reductive-deoxygenation conditions in the presence of a reducing agent triethylsilane or the like, in the presence of an acid like TFA or the like) produces substituted phenol (C).

The compounds and intermediates produced according to the methods of the invention may require purification. Purification of organic compounds is well known to a person skilled in the art and there may be several ways of purifying Scheme 23.

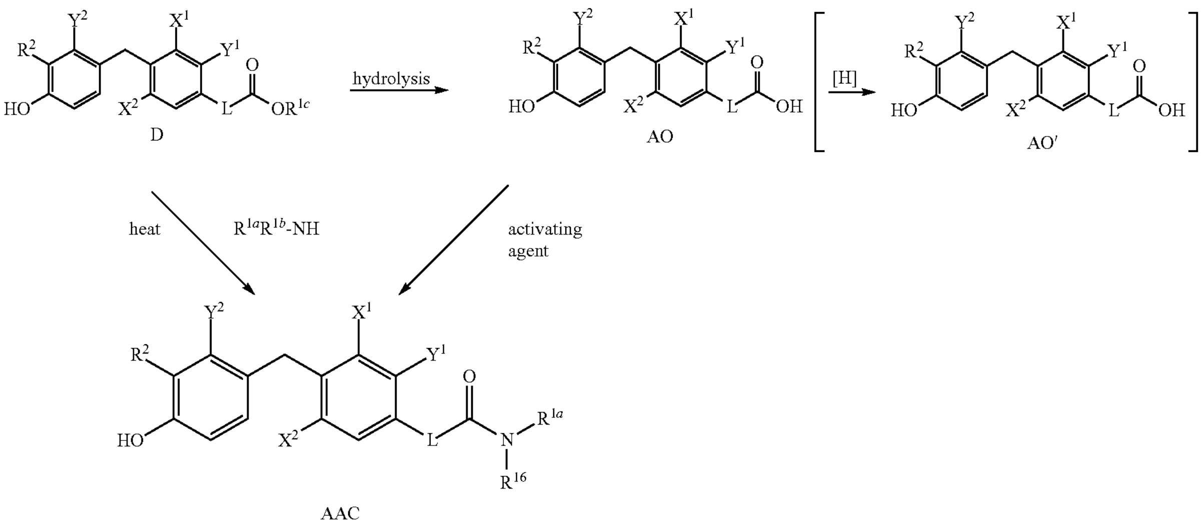

Compounds AO and AAC of the present invention may be prepared as indicated in Scheme 22. Referring to Scheme 22, hydrolysis of the ester group of intermediate D (for example, using aqueous sodium hydroxide (if $R^2$ is methyl) or TFA (if $R^2$ is t-butyl), or the like) provides compounds AO of the present invention. In the case where the $R^1$ or L group of AO contains an alkene or alkyne, subsequent hydrogenation (for example, using Pd—C catalyst, or the like under a hydrogen atmosphere, or the like) can provide the corresponding alkane or alkene compounds AO' of the present invention. If desired, esters (D), or acids (AO) may be heated with an amine $R^{2a}R^{2b}NH$ (for example, methylamine, or propylamine, or 2-sulfonylethylamine, or the like) to give compounds AAC of the present invention. Alternatively, acids (AO) can be converted to amides AAC of the current invention by condensing with the corresponding amine (for example, using methylamine, or propylamine, or 2-sulfonylethylamine, or the like) in the presence of a coupling agent (for example, using DDC or EDCI, or the like), or by forming an activated intermediate of AO (for example, the corresponding acid chloride using thionyl chloride, or the like), followed by amine treatment.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All reagents, for which the synthesis is not described in the experimental part, are either commercially available, or are known compounds or may be formed from known compounds by known methods by a person skilled in the art.

the same compound. In some cases, no purification may be necessary. In some cases, the compounds may be purified by crystallization. In some cases, impurities may be stirred out using a suitable solvent.

In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by Prep-HPLC (normal-phase or reversed-phase) using methods as described. Prep-HPLC purification by reverse phase HPLC was performed using gradients of acetonitrile in aqueous TFA or an equivalent HPLC system such as Methanol in aqueous ammonium acetate.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

All the starting materials and reagents are commercially available and were used as is. $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in partsper-million using conventional abbreviations for designation of major peaks: e.g. s, singlet; d, doublet; t, triplet; q, quartet; dd, doublet of doublets; dt, doublet of triplets; m, multiplet; br, broad.

Chemical names were generated using the ChemDraw naming software (Version 17.0.0.206) by PerkinElmer Informatics, Inc. In some cases, generally accepted names and generally accepted acronyms for commercially available reagents were used in place of names generated by the naming software.

Intermediate A1

Synthesis of 4-formyl-3,5-dimethylphenyl trifluoromethanesulfonate (A1)

A1

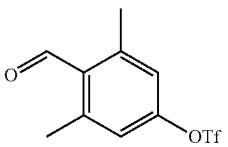

To a solution of 4-hydroxy-2,6-dimethylbenzaldehyde (10.0 g, 66.6 mmol, 1.0 eq) and pyridine (10.5 g, 133 mmol, 2.0 eq) in DCM (150 mL) at 0° C. was added $Tf_2O$ (22.5 g, 79.9 mmol, 1.2 eq). The mixture was stirred at 0° C. for 2 h. Water (200 mL) and DCM (200 mL) were added and the organic phase was washed with brine (200 mL), dried over $Na_2SO_4$ and concentrated in vacuo to afford Intermediate A1 (16.0 g, 85.1% yield) as a yellow liquid.

Intermediate A2

Synthesis of 2,6-dimethyl-4-((trimethylsilyl)ethynyl)benzaldehyde (A2)

A2

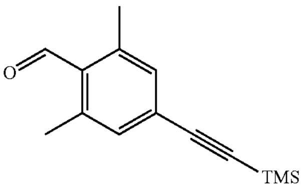

A mixture of A1 (16.0 g, 56.7 mmol, 1.0 eq), ethynyl (trimethyl)silane (6.7 g, 68 mmol, 1.2 eq), $Pd(PPh_3)_2Cl_2$ (2.0 g, 2.8 mmol, 0.05 eq), CuI (110 mg, 0.57 mmol, 0.01 eq) and triethylamine (11.5 g, 113 mmol, 2 eq) in DMF (200 mL) was stirred at 100° C. for 2 h. Water (100 mL) was added and the mixture was extracted with EtOAc (50 mL*2). The combined organic phase was washed with brine (100 mL), dried over $Na_2SO_4$, concentrated in vacuo and purified by silica gel column chromatography (pet. ether) to afford Intermediate A2 (9.0 g, 68% yield) as a brown liquid.

$^1H$ NMR: (400 MHz, DMSO-$d_6$) δ 10.42 (d, J=1.2 Hz, 1H), 7.20 (s, 2H), 2.47 (s, 6H), 0.19 (d, J=0.8 Hz, 9H).

Intermediate A3

Synthesis of (2,6-dimethyl-4-((trimethylsilyl)ethynyl)phenyl)methanol (A3)

A3

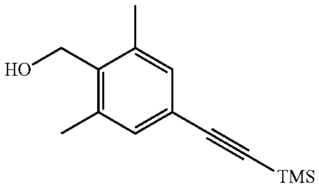

To a 0° C. solution of A2 (5.0 g, 21 mmol, 1.0 eq) in THF (80 mL), $NaBH_4$ (862 mg, 22.8 mmol, 1.05 eq) was added in portions, and the mixture was stirred 2 h. The reaction was quenched with $NH_4Cl$ (80 mL) and extracted with EtOAc (50 mL*2). The combined organic phase was washed with brine (50 mL*2), dried over $Na_2SO_4$, concentrated in vacuo and purified by silica gel column chromatography (pet. ether/EtOAc=10/1 to 3/1) to afford Intermediate A3 (4.5 g, 90% yield) as a light yellow solid.

$^1H$ NMR: (400 MHz, DMSO-$d_6$) δ 7.10 (s, 2H), 4.78 (t, J=5.2 Hz, 1H), 4.45 (d, J=5.2 Hz, 2H), 2.32 (s, 6H), 0.21 (s, 9H).

Intermediate A4

Synthesis of (4-ethynyl-2,6-dimethylphenyl)methanol (A4)

A4

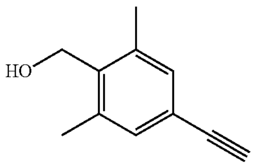

To a solution of A3 (4.5 g, 19.36 mmol, 1.0 eq) in THF (50 mL) was added TBAF (1 M in THF, 23 mL, 23 mmol, 1.2 eq) and the mixture was stirred at rt for 1 h. Water (100 mL) was added and the mixture was extracted with EtOAc (30 mL*2). The combined organic phase was washed with brine (50 mL), dried over $Na_2SO_4$, concentrated in vacuo and purified by silica gel column chromatography (pet. ether) to afford Intermediate A4 (2.5 g, 810% yield) as a light yellow solid.

$^1H$ NMR: (400 MHz, DMSO-$d_6$) δ 7.11 (s, 2H), 4.77 (t, J=5.2 Hz, 1H), 4.46 (d, J=5.2 Hz, 2H), 4.06 (s, 1H), 2.33 (s, 6H).

Intermediate A5

Synthesis of tert-butyl((4-ethynyl-2,6-dimethylbenzyl)oxy)dimethylsilane (A5)

A5

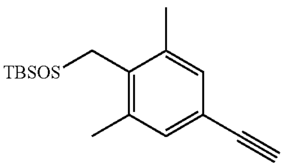

To a solution of A4 (2.5 g, 16 mmol, 1.0 eq) and imidazole (1.3 g, 19 mmol, 1.2 eq) in DCM (30 mL) at rt was added TBSCl (2.6 g, 17 mmol, 1.1 eq) and the mixture was stirred overnight. The mixture was filtered, and the filtrate diluted with DCM (20 mL). Water (50 mL) was added, the organic phase was separated, and the aqueous phase was extracted with DCM (10 mL*3). The combined organic phase was washed with brine (30 mL), dried over $Na_2SO_4$ and concentrated in vacuo to afford Intermediate A5 (4.0 g, 93% yield) as a yellow solid.

$^1$H NMR: (400 MHz, DMSO-$d_6$) δ 7.13 (s, 2H), 4.65 (s, 2H), 4.08 (s, 1H), 2.31 (s, 6H), 0.87 (s, 9H), 0.08 (d, J=0.8 Hz, 6H).

Intermediate A6

Synthesis of 2-(4-(((tert-butyldimethylsilyl)oxy) methyl)-3,5-dimethylphenyl)acetic acid (A6)

A6

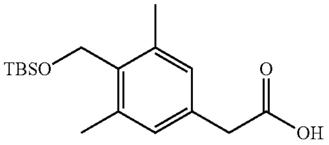

To a solution of A5 (6.0 g, 22 mmol, 1.0 eq) and 4-picoline N-oxide (4.8 g, 44 mmol, 2.0 eq) in MeCN (80 mL) at rt were added $[Rh(cod)Cl]_2$ (526 mg, 1.09 mmol, 0.05 eq), tris(4-fluorophenyl)phosphane (1.4 g, 4.4 mmol, 0.2 eq) and water (3.94 mL), and the mixture was stirred at 60° C. overnight. The pH of the mixture was adjusted to pH=9 with aqueous $NaHCO_3$, extracted with ether (40 mL*2), and the combined organic phase was discarded. The aqueous phase was adjusted to pH=3-4 with aqueous HCl (3N), and extracted with EtOAc (30 mL*2). The combined organic phase was washed with brine (50 mL), dried over $Na_2SO_4$, and concentrated in vacuo to afford Intermediate A6 (3.5 g, 52% yield) as a yellow solid.

$^1$H NMR: (400 MHz, DMSO-$d_6$) δ 12.25 (s, 1H), 6.88 (s, 2H), 4.64 (s, 2H), 3.44 (s, 2H), 2.30 (s, 6H), 0.87 (s, 9H), 0.09 (s, 6H).

Intermediate A7

Synthesis of methyl 2-(4-(hydroxymethyl)-3,5-dimethylphenyl)acetate (A7)

A7

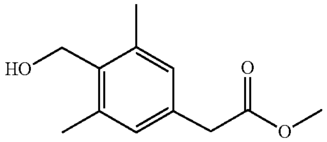

To a solution of A6 (3.5 g, 11 mmol, 1.0 eq) in methanol (50 mL) was added $SOCl_2$ (2.0 g, 17 mmol, 1.5 eq) and the mixture was refluxed for 2 h. The mixture was concentrated in vacuo, water (50 mL) was added, and the mixture was extracted with EtOAc (30 mL*2). The combined organic phase was concentrated in vacuo to afford crude Intermediate A7 (2.2 g, 92% yield) that was used in next reaction without purification.

Intermediate A8

Synthesis of methyl 2-(4-(chloromethyl)-3,5-dimethylphenyl)acetate (A8)

A8

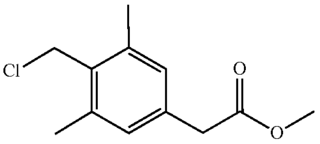

To a solution of A7 (2.2 g, 11 mmol, 1.0 eq) in DCM (30 mL) at rt was added $SOCl_2$ (1.9 g, 16 mmol, 1.5 eq). The mixture was stirred at rt for 1 h and then concentrated in vacuo to afford crude Intermediate A7 (2.2 g, 92% yield) as a yellow liquid.

$^1$H NMR: (400 MHz, DMSO-$d_6$) δ 6.95 (s, 2H), 4.76 (s, 2H), 3.60 (d, J=2.8 Hz, 3H), 3.58 (s, 2H), 2.35 (s, 6H).

Intermediate A9

Synthesis of N,N-dibenzyl-3,5-dimethylaniline (A9)

A9

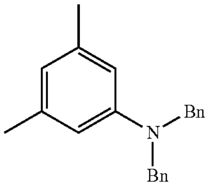

A solution of 3,5-dimethylaniline (10 g, 83 mmol, 1.0 eq) and benzyl bromide (42 g, 250 mmol, 3.0 eq) in DMF (100 mL) was cooled to 0° C. NaH (5.94 g, 248 mmol, 3.0 eq) was added in portions and the reaction was stirred at rt overnight. Water (500 mL) was carefully added and the mixture was extracted with EtOAc (200 mL*2). The combined organic phase was washed with water (500 mL) and brine (500 mL), dried over $Na_2SO_4$ and concentrated in vacuo. The residue was triturated with EtOAc/hexane: 1/10 (50 mL), and the resulting solid was collected by filtration and dried in vacuo to afford Intermediate A9 (24.0 g, 96.4% yield) as a light brown solid.

TLC: Pet. ether/EtOAc=2/1 (v/v), Rf=0.6

$^1$H NMR: (400 MHz, DMSO-$d_6$) δ 7.37 (s, 4H), 7.21 (s, 6H), 6.34 (s, 2H), 6.25 (s, 1H), 4.62 (s, 4H), 2.09 (s, 6H).

Intermediate A10

Synthesis of 4-(dibenzylamino)-2,6-dimethylbenzaldehyde (A10)

A10

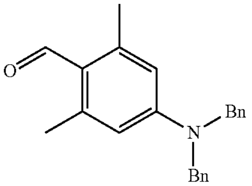

To a solution of A9 (24.0 g, 79.6 mmol, 1.0 eq) in DMF (100 mL) was added dropwise $POCl_3$ (36.6 g, 239 mmol, 3.0 eq) and the reaction mixture was stirred at 90° C. overnight. The reaction was cooled to rt, poured into $NaHCO_3$ (aq) (400 mL), and extracted with EtOAc (100 mL*2). The combined organic phase was washed with brine (400 mL), dried over $Na_2SO_4$, and concentrated in vacuo. The residue was purified by silica gel column chromatography (pet. ether/EtOAc=30/1 to 5/1) to afford Intermediate A10 (21.0 g, 77.2% yield) as a light brown solid.

TLC: Pet. ether/EtOAc=2/1 (v/v), Rf=0.15

$^1H$ NMR: (400 MHz, DMSO-$d_6$) δ 10.18 (s, 1H), 7.32 (s, 4H), 7.25 (s, 6H), 6.46 (s, 2H), 4.77 (s, 4H), 2.41 (s, 6H).

Intermediate A11

Synthesis of (4-(dibenzylamino)-2,6-dimethylphenyl)methanol (A11)

A11

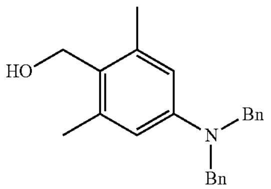

A solution of A10 (17.6 g, 53.4 mmol, 1.0 eq) in THE (100 mL) was cooled to 0° C. and $NaBH_4$ (3.0 g, 80 mmol, 3.0 eq) was added in one portion. The reaction was stirred at rt for 1 h, then quenched with water (300 mL), and extracted with EtOAc (100 mL*2). The combined organic phase was washed with brine (200 mL), dried over $Na_2SO_4$ and concentrated in vacuo. The residue was purified by silica gel column chromatography (pet. ether/EtOAc=10/1 to 3/1) to afford Intermediate A11 (12.0 g, 67.7% yield) as a yellow solid.

TLC: Pet. ether/EtOAc=1/1 (v/v), Rf=0.10

$^1H$ NMR: (400 MHz, DMSO-$d_6$) δ 7.33 (s, 4H), 7.25-7.19 (m, 6H), 6.35 (s, 2H), 4.62 (s, 4H), 4.33 (s, 3H), 2.17 (s, 6H).

Intermediate A12

Synthesis of N,N-dibenzyl-4-(chloromethyl)-3,5-dimethylaniline (A12)

A12

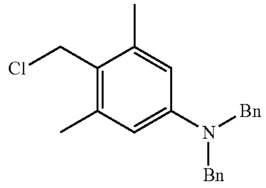

A solution of All (350 mg, 1.05 mmol, 1.0 eq) in DCM (5 mL) was added catalytic DMF and $SOCl_2$ (250 mg, 2.1 mmol, 2.0 eq). The reaction was stirred at rt for 30 min then concentrated in vacuo to afford Intermediate A12 (360 mg, 98% yield) as a yellow solid.

TLC: Pet. ether/EtOAc=1/1 (v/v), Rf=0.85.

Intermediate A13

Synthesis of ((3,5-dichloro-4-methylphenyl)ethynyl) trimethylsilane (A13)

A13

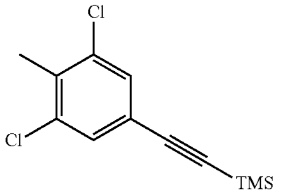

A solution of 5-bromo-1,3-dichloro-2-methylbenzene (10.0 g, 41.7 mmol, 1.0 eq), ethynyl(trimethyl)silane (6.1 g, 63 mmol, 1.5 eq), $Pd(PPh_3)_2Cl_2$ (1.5 g, 2.1 mmol, 0.05 eq), triethylamine (8.4 g, 83 mmol, 2.0 eq) and CuI (8.0 mg, 42 μmol, 0.001 eq) in DMF (100 mL) was stirred at 100° C. for 2 h. Water (100 mL) was added and the mixture was extracted with EtOAc (50 mL*2). The combined organic phase was washed with brine (50 mL), dried over $Na_2SO_4$ and concentrated in vacuo. The residue was purified by silica gel column chromatography (pet. ether) to afford Intermediate A13 (11 g, 98% yield) as a brown oil.

TLC: Pet. ether, Rf=0.95

$^1H$ NMR: (400 MHz, DMSO-$d_6$) δ 7.53 (s, 2H), 2.41 (s, 3H), 0.23 (s, 9H).

Intermediate A14

Synthesis of 1,3-dichloro-5-ethynyl-2-methylbenzene (A14)

A14

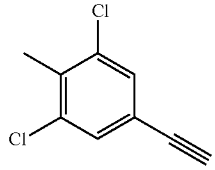

To a solution of A13 (10.5 g, 40.8 mmol, 1.0 eq) in THF (100 mL) was added TBAF (1.0 M in THF, 49 mmol, 49 mL, 1.2 eq) and the reaction was stirred at rt for 1 h. Water (100 mL) was added and the mixture was extracted with EtOAc (50 mL*2). The combined organic phase was washed with brine (50 mL*2), dried over $Na_2SO_4$ and concentrated in vacuo. The residue was purified by silica gel column chromatography (pet. ether) to afford Intermediate A14 (6.0 g, 79% yield) as a light yellow solid.

TLC: Pet. ether, Rf=0.94

$^1H$ NMR: (400 MHz, DMSO-$d_6$) δ 7.55 (s, 2H), 4.39 (d, J=1.2 Hz, 1H), 2.41 (s, 3H).

Intermediate A15

Synthesis of 2-(3,5-dichloro-4-methylphenyl)acetic acid (A15)

A15

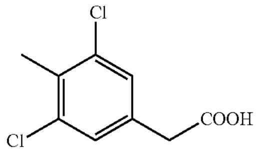

To a solution of A14 (6.0 g, 32 mmol, 1.0 eq), 4-methylpyridine-N-oxide (7.1 g, 65 mmol, 2.0 eq) in MeCN (70 mL) and water (6 mL) at rt was added Chloro(1,5-cyclooctadiene)rhodium(I) dimer (780 mg, 1.62 mmol, 0.05 eq) and tris(4-fluorophenyl)phosphane (2.0 g, 6.5 mmol, 0.2 eq). The reaction was stirred at 60° C. overnight, cooled, then the mixture was adjusted pH=9 with aqueous $NaHCO_3$ and washed with ether (40 mL*2). The aqueous phase was then adjusted to pH=3-4 with aqueous HCl (3N), and extracted with EtOAc (30 mL*2). The combined organic extract was washed with brine (50 mL), dried over $Na_2SO_4$ and concentrated in vacuo to afford Intermediate A15 (3.8 g, 53% yield) as a white solid.

TLC: DCM/MeOH=5/1 (v/v), Rf=0.42

$^1$H NMR: (400 MHz, DMSO-$d_6$) δ 7.35 (s, 2H), 3.60 (s, 2H), 2.37 (s, 3H).

Intermediate A16

Synthesis of methyl 2-(3,5-dichloro-4-methylphenyl)acetate (A16)

A16

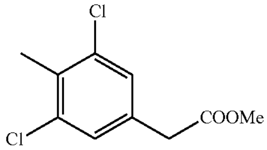

To a solution of A15 (3.8 g, 14 mmol, 1.0 eq) in MeOH (40 mL) was added $SOCl_2$ (2.4 g, 21 mmol, 1.5 eq) and the reaction was refluxed 2 h. The mixture was concentrated in vacuo, water (20 mL) was added, and the mixture was extracted with EtOAc (15 mL*2). The combined organic phase was washed with brine (20 mL), dried over $Na_2SO_4$ and concentrated in vacuo to afford Intermediate A16 (3.0 g, 94% yield) as a white solid.

TLC: Pet. ether/EtOAc=5/1 (v/v), Rf=0.51

$^1$H NMR: (400 MHz, DMSO-$d_6$) δ 7.38 (s, 2H), 3.71 (s, 2H), 3.62 (s, 3H), 2.38 (s, 3H).

Intermediate A17

Synthesis of methyl 2-(4-(bromomethyl)-3,5-dichlorophenyl)acetate (A17)

A17

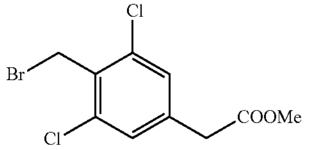

To a solution of A16 (3.0 g, 13 mmol, 1.0 eq) in $CCl_4$ (30 mL) at rt was added benzoyl peroxide (160 mg, 0.64 mmol, 0.05 eq), and N-bromosuccinimide (2.3 g, 13 mmol, 1.0 eq). The reaction was stirred at 80° C. for 1.5 h, then cooled to rt and filtered. The filtrate was diluted with DCM (15 mL), water (15 mL) was added, and the mixture extracted with DCM (15 mL*3). The combined organic phase was washed with brine (30 mL), dried over $Na_2SO_4$, concentrated in vacuo. The residue was purified by silica gel column chromatography (pet. ether/EtOAc=100/1 to 40/1) to afford Intermediate A17 (2.0 g, 50% yield) as a light yellow solid.

TLC: Pet. ether/EtOAc=5/1 (v/v), Rf=0.48

$^1$H NMR: (400 MHz, DMSO-$d_6$) δ 7.48 (s, 2H), 4.77 (s, 2H), 3.77 (s, 2H), 3.63 (s, 3H).

Intermediate A18

Synthesis of methyl (E)-3-(3,5-dichloro-4-methylphenyl)acrylate (A18)

A18

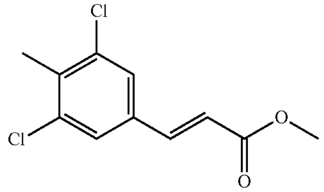

To a mixture of 5-bromo-1,3-dichloro-2-methylbenzene (3.0 g, 12.50 mmol, 1.0 eq), $Pd(OAc)_2$ (1.25 mmol, 0.1 eq) and $K_2CO_3$ (3.5 g, 25 mmol, 2.0 eq) in DMF (30 mL) was added methyl acrylate (1.6 g, 19 mmol, 1.5 eq). The mixture was stirred at 110° C. overnight, then water (50 mL) was added and the mixture was extracted with EtOAc (20 mL*3). The combined organic phase was washed with brine (30 mL), dried over $Na_2SO_4$ and concentrated under reduced pressure. The crude material was purified by silica gel column chromatography (EtOAc/pet. ether=1/100 to 1/30) to afford Intermediate A18 (2.3 g, 74% yield) as a white solid.

TLC: EtOAc/pet. ether=1/30 (v/v), Rf=0.60

LCMS: T=3.144 min, [M+1]=245.1

$^1$H NMR: (400 MHz, DMSO-$d_6$) δ 7.88 (s, 2H), 7.60 (d, J=16.0 Hz, 1H), 6.79 (d, J=16.0 Hz, 1H), 3.73 (s, 3H), 2.43 (s, 3H).

Intermediate A19

Synthesis of methyl 3-(3,5-dichloro-4-methylphenyl)propanoate (A19)

A19

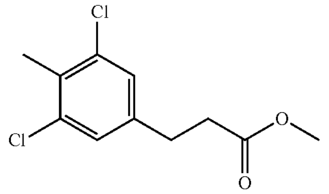

To a solution of A18 (2.2 g, 9.0 mmol) in THF (20 mL) was added Pd/C (10%, 1.0 g), and the mixture was stirred at rt overnight under 1 atm $H_2$. The mixture was filtered, water (50 mL) was added to the filtrate, and the mixture was extracted with EtOAc (20 mL*3). The combined organic phase was washed with brine (50 mL), dried over $Na_2SO_4$ and concentrated in vacuo to afford crude Intermediate A19 (2.2 g, 99% yield) as a white solid.

TLC: EtOAc/pet. ether=1/20 (v/v), Rf=0.70

$^1$H NMR: (400 MHz, DMSO-$d_6$) δ 7.32 (s, 2H), 3.60 (s, 3H), 2.82 (t, J=7.4 Hz, 2H), 2.66 (t, J=7.4 Hz, 2H), 2.35 (s, 3H).

Intermediate A20

Synthesis of methyl 3-(4-(bromomethyl)-3,5-dichlorophenyl)propanoate (A20)

A20

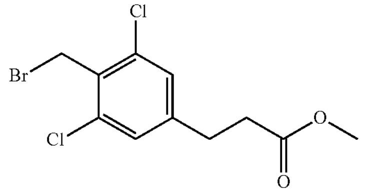

To a mixture of A19 (1.0 g, 4.0 mmol, 1.0 eq) and N-bromosuccinimide (720 mg, 4.05 mmol, 1.0 eq) in $CCl_4$ (10.0 mL) at rt was added AIBN (133 mg, 809 μmol, 0.2 eq). The reaction was stirred at 90° C. for 2 h then water (50 mL) was added, and mixture extracted with DCM (15 mL*3). The combined organic phase was washed with brine (30 mL), dried over $Na_2SO_4$ and concentrated in vacuo. The crude material was purified by silica gel column chromatography (EtOAc/pet. ether=1/100 to 1/30) to afford Intermediate A20 (400 mg, 30.3% yield) as a light yellow oil.

TLC: EtOAc/pet. ether=1/20 (v/v), Rf=0.55.

Intermediate A21

Synthesis of 5-bromo-2-(bromomethyl)-1,3-dichlorobenzene (A21)

A21

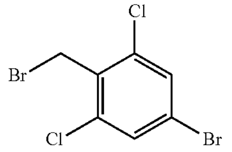

To a solution of 1,3-dichloro-2-methylbenzene (20.0 g, 83.4 mmol, 1.0 eq) in $CCl_4$ (250 mL) at rt were added benzoyl peroxide (1.0 g, 4.17 mmol, 0.05 eq) and N-bromosuccinimide (14.8 g, 83.4 mmol, 1.0 eq). The reaction was stirred at 60° C. for 1 h, then water (60 mL) was added and the mixture was extracted with DCM (100 mL*3). The combined organic phase was washed with brine (100 mL), dried over $Na_2SO_4$ and concentrated under reduced pressure. The crude material was purified by silica gel flash column flash chromatography (pet. ether) to afford Intermediate A21 (17.7 g, 66.6% yield) as a white solid.

$^1$H NMR: (400 MHz, DMSO-$d_6$) δ 7.85 (s, 2H), 4.74 (s, 2H).

Intermediate A22

Synthesis of 3,5-dichloro-4-formylphenyl trifluoromethanesulfonate (A22)

A22

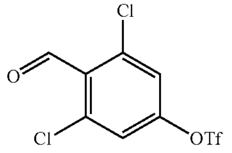

To a solution of 2,6-dichloro-4-hydroxybenzaldehyde (5.0 g, 26 mmol, 1.0 eq) in DCM (70 mL) at 0° C. were added pyridine (4.2 mL, 524 mmol, 2.0 eq) and trifluoromethanesulfonic anhydride (4.4 mL, 26 mmol, 1.0 eq). The mixture was stirred at 0° C. for 6 h and was then washed with brine (100 mL), dried over $Na_2SO_4$ and concentrated in vacuo to afford Intermediate A22 (8.2 g, 97% yield) as a colorless oil.

$^1$H NMR: (400 MHz, DMSO-$d_6$) δ 10.30 (s, 1H), 8.01 (s, 2H).

Intermediate A23

Synthesis of methyl (E)-3-(3,5-dichloro-4-formylphenyl)acrylate (A23)

A23

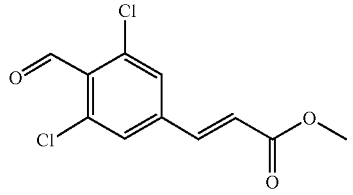

To a solution of A22 (8.2 g, 254 mmol, 1.0 eq) in DMF (100 mL) at rt were added 1,3-bis(diphenylphosphino)propane (dppp) (0.60 g, 1.4 mmol, 0.06 eq), $Pd(OAc)_2$ (0.30 g, 1.3 mmol, 0.05 eq), $Et_3N$ (10.2 g, 102 mmol, 4.0 eq) and methyl acrylate (2.6 g, 31 mmol, 1.2 eq). The mixture was stirred at 100° C. for 1.5 h, then diluted with water (100 mL) and extracted with EtOAc (20 mL*3). The combined organic phase was washed with water (100 mL*3) and brine (50 mL), dried over $Na_2SO_4$ and concentrated under reduced pressure. The crude product was purified by silica gel column chromatography (pet. ether/EtOAc=10/1) to afford Intermediate A23 (2.2 g, 33% yield) as a light yellow solid.

$^1H$ NMR: (400 MHz, DMSO-$d_6$) δ 10.34 (s, 1H), 8.03 (s, 2H), 7.66 (d, J=16.0 Hz, 1H), 6.97 (d, J=16.0 Hz, 1H), 3.75 (s, 3H).

Intermediate A24

Synthesis of methyl 3-(3,5-dichloro-4-formylphenyl)propanoate (A24)

A24

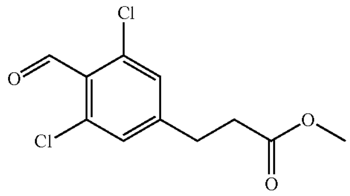

To a solution of A23 (2.2 g, 8.5 mmol) in THF (40 mL) at rt was added Pd/C (10% w/w, 0.3 g). The mixture was stirred at rt under 1 atm $H_2$ for 4 h and then filtered through Celite. The filtrate was concentrated under reduce pressure to afford Intermediate A24 (2.2 g, 99% yield) as a colorless oil.

$^1H$ NMR: (400 MHz, DMSO-$d_6$) δ 10.32 (s, 1H), 7.52 (s, 2H), 3.58 (s, 3H), 2.90 (t, J=7.6 Hz, 2H), 2.72 (t, J=7.6 Hz, 2H).

Intermediate A25

Synthesis of methyl 3-(3,5-dichloro-4-(hydroxymethyl)phenyl)propanoate (A25)

A25

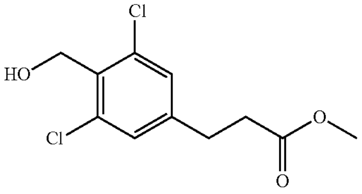

To a solution of A24 (2.3 g, 8.8 mmol, 1.0 eq) in THF (30 mL) at 0° C. was added $NaBH_4$ (0.30 g, 8.8 mmol, 1.0 eq). The mixture was stirred at 0° C. for 2 h, then diluted with water (30 mL) and extracted with EtOAc (10 mL*3). The combined organic phase was washed with brine (10 mL), dried over $Na_2SO_4$ and concentrated under reduced pressure. The crude product was purified by silica gel column chromatography (pet. ether/EtOAc=1/10) to afford Intermediate A25 (0.80 g, 35% yield) as a colorless oil.

$^1H$ NMR: (400 MHz, DMSO-$d_6$) δ 7.34 (s, 2H), 5.15 (t, J=5.2 Hz, 1H), 4.63 (d, J=5.2 Hz, 2H), 3.58 (s, 3H), 2.83 (t, J=7.2 Hz, 2H), 2.67 (t, J=7.6 Hz, 2H).

Intermediate A26

Synthesis of methyl 3-(3,5-dichloro-4-(chloromethyl)phenyl)propanoate (A26)

A26

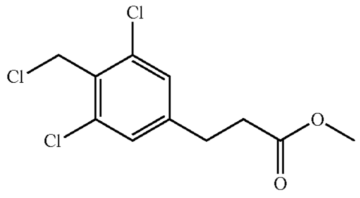

To a solution of A25 (700 mg, 2.66 mmol, 1.0 eq) in DCM (10 mL) at 0° C. was added $SOCl_2$ (316 mg, 2.66 mmol, 1.0 eq). The mixture was stirred at rt for 2 h, diluted with DCM (20 mL) and concentrated under reduced pressure to afford Intermediate A26 (700 mg, 93.4% yield) as a yellow oil.

Intermediate A27

Synthesis of N,N-dibenzyl-3,5-dichloroaniline (A27)

A27

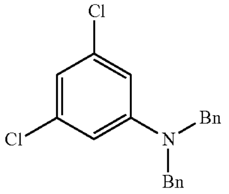

A solution of 3,5-dichloroaniline (10.0 g, 61.7 mmol, 1.0 eq) and benzyl bromide (31.7 g, 185 mmol, 3.0 eq) in DMF (100 mL) was cooled to 0° C. and NaH (4.4 g, 190 mmol, 3.0 eq) was added in portions. The reaction was stirred at rt overnight, then water (500 mL) was carefully added and the mixture was extracted with EtOAc (200 mL*2). The combined organic phase was washed with water (500 mL) and brine (500 mL), dried over $Na_2SO_4$ and concentrated in vacuo. The residue was purified by silica gel column chromatography (pet. ether/EtOAc=100/1 to 10/1) to afford Intermediate A27 (20.0 g, 96.7% yield) as a yellow solid.

TLC: Pet. ether/EtOAc=5/1 (v/v), Rf=0.7

$^1H$ NMR: (400 MHz, DMSO-$d_6$) δ 7.38-7.32 (m, 6H), 7.29-7.22 (m, 7H), 6.68 (t, J=1.6 Hz, 1H), 6.63 (d, J=1.6 Hz, 2H), 4.75 (s, 4H).

Intermediate A28

Synthesis of 2,6-dichloro-4-(dibenzylamino)benzaldehyde (A28)

A28

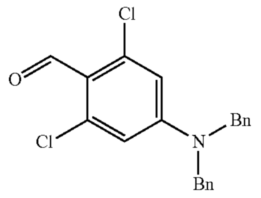

A solution of A27 (20.0 g, 58.4 mmol, 1.0 eq) in DMF (200 mL) was added dropwise to $POCl_3$ (26.9 g, 175 mmol, 3.0 eq). The reaction mixture was stirred at 80° C. for 4 h, then cooled to rt and poured into sat. aq. $NaHCO_3$ solution (400 mL) and extracted with EtOAc (100 mL*2). The combined organic phase was washed with brine (400 mL), dried over $Na_2SO_4$ and concentrated in vacuo. The residue was purified by silica gel column chromatography (pet. ether/EtOAc=30/1 to 5/1) to afford Intermediate A28 (17.7 g, 81.8% yield) as a yellow solid.

TLC: Pet. ether/EtOAc=5/1 (v/v), Rf=0.5

$^1$H NMR: (400 MHz, DMSO-$d_6$) δ 10.12 (s, 1H), 7.37 (m, 4H), 7.25 (m, 6H), 6.79 (s, 2H), 4.88 (s, 4H).

Intermediate A29

Synthesis of (2,6-dichloro-4-(dibenzylamino)phenyl)methanol (A29)

A29

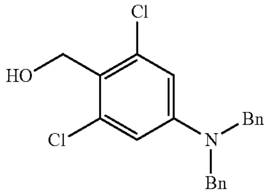

A solution of A28 (3.0 g, 8.1 mmol, 1.0 eq) in THE (30 mL) was cooled to 0° C. and $NaBH_4$ (3.0 g, 11 mmol, 1.3 eq) was added in portions. The reaction was stirred at rt for 1 h, then quenched with water (300 mL) and extracted with EtOAc (100 mL*2). The combined organic phase was washed with brine (200 mL), dried over $Na_2SO_4$ and concentrated in vacuo to afford Intermediate A29 (2.9 g, 98% yield) as a yellow oil.

TLC: Pet. ether/EtOAc=5/1 (v/v), Rf=0.30

LCMS: T=4.408 min, [M+1]=372.1.

Intermediate A30

Synthesis of N,N-dibenzyl-3,5-dichloro-4-(chloromethyl)aniline (A30)

A30

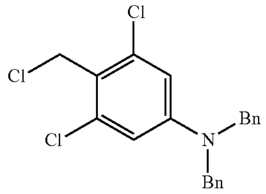

To a solution of A29 (500 mg, 1.34 mmol, 1.0 eq) in DCM (5.0 mL) at 0° C. was added dropwise, $SOCl_2$ (320 mg, 2.69 mmol, 2.0 eq). The reaction was stirred at rt for 4 h, then concentrated in vacuo to afford Intermediate A30 (500 mg, 95.3% yield) that was used without purification.

TLC: Pet. ether/EtOAc=5/1 (v/v), Rf=0.40.

Intermediate A31

Synthesis of methyl 4-(3,5-dichloro-4-(hydroxymethyl)phenoxy)butanoate (A31)

A31

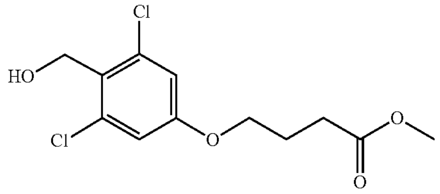

To a solution of 3,5-dichloro-4-(hydroxymethyl)phenol (1.34 g, 6.94 mmol, 1.0 eq) in DMF (10 mL) were added methyl 4-bromobutanoate (1.26 g, 6.94 mmol, 1.0 eq) and $K_2CO_3$ (1.06 g, 7.64 mmol, 1.1 eq). The mixture was stirred at 50° C. overnight, then water (100 mL) was added, and the mixture was extracted with EtOAc (30 mL*2). The combined organic phase was washed with water (2*50 mL) and brine (50 mL), dried over $Na_2SO_4$ and concentrated under reduced pressure. The crude product was purified by silica gel column chromatography (pet. ether/EtOAc=5:1) to afford Intermediate A31 (1.4 g, 69% yield) as a white solid.

TLC: DCM/MeOH=1/1 (v/v), Rf=0.5

$^1$H NMR: (400 MHz, DMSO-$d_6$) δ 7.07-6.99 (m, 2H), 5.04 (s, 1H), 4.60 (d, J=5.2 Hz, 2H), 4.03 (t, J=6.4 Hz, 2H), 3.60 (s, 3H), 2.45 (t, J=7.3 Hz, 2H), 1.97-1.89 (m, 2H).

Intermediate A32

Synthesis of methyl 4-(3,5-dichloro-4-(chloromethyl)phenoxy)butanoate (A32)

A32

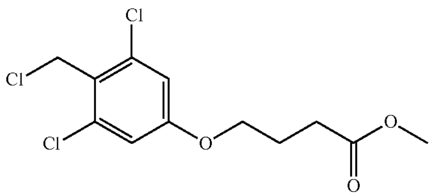

To a solution of A31 (1.4 g, 4.8 mmol, 1.0 eq) in DCM (10 mL) at 0° C. was added dropwise $SOCl_2$ (1.70 g, 14.3 mmol, 3.0 eq). The mixture was stirred at rt for 3 h and was then concentrated in vacuo. The residue was triturated with n-hexane (15 mL) to afford Intermediate A32 (1.3 g, 87% yield) as a white solid.

TLC: EtOAc/pet. ether=1/1 (v/v), Rf=0.8

$^1$H NMR: (400 MHz, DMSO-$d_6$) δ 7.15 (s, 2H), 4.85 (s, 2H), 4.06 (s, 2H), 3.60 (s, 3H), 2.44 (s, 2H), 1.94 (s, 2H).

Intermediate A33

Synthesis of methyl 5-(3,5-dichloro-4-(hydroxymethyl)phenoxy)pentanoate (A33)

A33

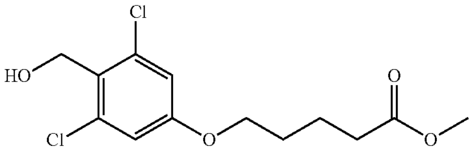

To a solution of 3,5-dichloro-4-(hydroxymethyl)phenol (2.0 g, 6.9 mmol, 1.0 eq) in DMF (6 mL) at rt were added $K_2CO_3$ (1.1 g, 7.6 mmol, 1.1 eq) and methyl 5-bromopentanoate (1.4 g, 6.9 mmol, 1.0 eq). The mixture was stirred at 50° C. overnight, then diluted with water (80 mL) and extracted with EtOAc (30 mL*3). The combined organic phase was washed with water (20 ml*3) and brine (20 mL*2), dried over $Na_2SO_4$ and concentrated under reduced pressure. The crude product was purified by silica gel column chromatography (PE/EtOAc=20/1 to 8/1) to afford Intermediate A33 (1.5 g, 70% yield) as an off-white solid.

TLC: EtOAc/pet. ether=1/10, Rf=0.34

LCMS: T=3.73 min; [M−1]=441.0.

Intermediate A34

Synthesis of methyl 5-(3,5-dichloro-4-(chloromethyl)phenoxy)pentanoate (A34)

A34

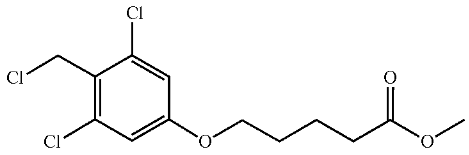

To a solution of A33 (1.5 g, 4.98 mmol, 1.0 eq) in DCM (15 mL) at 0° C. was added dropwise, $SOCl_2$ (0.90 g, 7.3 mmol, 1.5 eq). The mixture was stirred at rt, then concentrated under reduce pressure. The crude product was triturated with hexane and dried to afford Intermediate A34 (1.0 g, 63% yield) as a light yellow solid. The product was used directly in the next step without further purification.

TLC: EtOAc/pet. ether=1/10, Rf=0.60.

Intermediate A35

Synthesis of tert-butyl((3,5-dichlorobenzyl)oxy)dimethylsilane (A35)

A35

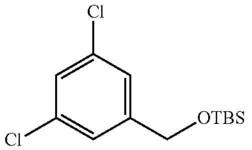

To a solution of (3,5-dichlorophenyl)methanol (6.0 g, 34 mmol, 1.0 eq) in DCM (60 mL) at 0° C. were added imidazole (3.5 g, 51 mmol, 1.5 eq) and TBSCl (7.7 g, 51 mmol, 1.5 eq). The reaction was stirred at rt for 2 h and was then washed with water (50 mL) and brine (50 mL). The organic phase was dried over $Na_2SO_4$ and concentrated in vacuo to afford Intermediate A35 (9.8 g, 99% yield) as a colorless oil.

TLC: EtOAc/pet. ether-1/20, Rf=0.74

$^1$H NMR: (400 MHz, DMSO-$d_6$) δ 7.47 (d, J=2.0 Hz, 1H), 7.32 (s, 2H), 4.72 (s, 2H), 0.90 (s, 9H), 0.08 (s, 6H).

Intermediate A36

Synthesis of 4-(((tert-butyldimethylsilyl)oxy)methyl)-2,6-dichlorobenzaldehyde (A36)

A36

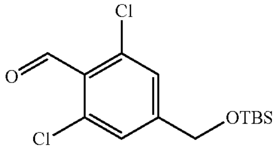

A solution of A35 (9.8 g, 34 mmol, 1.0 eq) in THE (100 mL) was cooled to −78° C. and n-BuLi (2.5 M, 14 mL, 34 mmol, 1.0 eq) was added dropwise. The mixture was stirred at −78° C. for 30 min, then DMF (3.0 g, 41 mmol) was added dropwise and the reaction stirred at −78° C. for an additional 2 h. The reaction was quenched with saturated aqueous $NH_4Cl$ (10 mL) and extracted with EtOAc (20 mL*2). The combined organic phase was washed with brine (20 mL), dried over $Na_2SO_4$ and concentrated in vacuo to afford Intermediate A36 (10.5 g, 97.1% yield) as a yellow solid.

TLC: EtOAc/pet. ether=1/20, Rf=0.82

$^1$H NMR: (400 MHz, DMSO-$d_6$) δ 10.34 (s, 1H), 7.32 (s, 2H), 4.79 (s, 2H), 0.91 (s, 12H), 0.10 (s, 6H).

Intermediate A37

Synthesis of 2,6-dichloro-4-(hydroxymethyl)benzaldehyde (A37)

A37

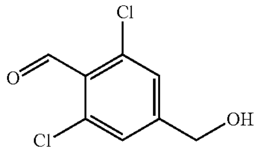

To a solution of A36 (11 g, 33 mmol, 1.0 eq) in THE (50 mL) was added TBAF (1 M, 49 mL, 49 mmol, 1.5 eq) and the reaction was stirred at rt for 30 min. Water (50 mL) was added and the mixture was extracted with EtOAc (50 mL*2). The combined organic phase was washed with brine (50 mL), dried over $Na_2SO_4$ and concentrated in vacuo to afford Intermediate A37 (6.7 g, 99% yield) as a yellow solid.

TLC: EtOAc/pet. ether=1/10, Rf=0.44

$^1$H NMR: (400 MHz, DMSO-$d_6$) δ 10.35 (s, 1H), 7.51 (s, 2H), 5.60 (s, 1H), 4.58 (s, 2H).

Intermediate A38

Synthesis of ethyl 2-((3,5-dichloro-4-formylbenzyl)oxy)acetate (A38)

A38

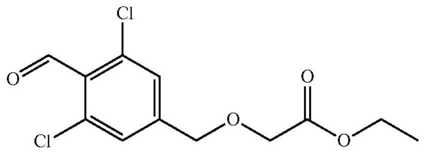

To a solution of A37 (4.1 g, 20 mmol, 1.0 eq) in DMF (35 mL) at 0° C. was added LiHMDS (1 M, 20 mL, 20 mmol, 1.0 eq). The mixture was stirred at rt for 30 min, then ethyl 2-bromoacetate (4.3 g, 26 mmol, 1.3 eq) was added and the reaction was stirred at rt overnight. Water (300 mL) was added and the mixture was extracted with EtOAc (100 mL*2). The combined organic phase was washed with water (50 mL*3) and brine (50 mL), dried over $Na_2SO_4$ and concentrated in vacuo. The crude product was purified by silica gel column chromatography (pet. ether/EtOAc=30:1) to afford Intermediate A38 (380 mg, 6.4% yield) as a colorless oil.

TLC: EtOAc/pet. ether=1/10, Rf=0.56

$^1$H NMR: (400 MHz, DMSO-$d_6$) δ 10.36 (s, 1H), 7.58 (s, 2H), 4.64 (s, 2H), 4.25 (s, 2H), 4.18-4.13 (m, 2H), 1.21 (d, J=7.1 Hz, 3H).

Intermediate A39

Synthesis of ethyl 2-((3,5-dichloro-4-(hydroxymethyl)benzyl)oxy)acetate (A39)

A39

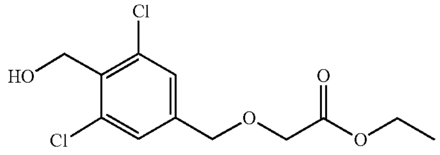

To a solution of A38 (380 mg, 1.3 mmol, 1.0 eq) in methanol (5 mL) was added $NaBH_4$ (56 mg, 1.5 mmol, 1.15 eq) in portions. The mixture was stirred at rt for 30 min then the mixture was concentrated in vacuo. Aqueous, saturated $NH_4Cl$ (10 mL) was added, and the mixture was extracted with EtOAc (20 mL*2). The combined organic phase was washed with brine (20 mL), dried over $Na_2SO_4$ and concentrated in vacuo to afford Intermediate A39 (220 mg, 58% yield) as a colorless oil.

TLC: EtOAc/pet. ether=1/10, Rf=0.23.

Intermediate A40

Synthesis of ethyl 2-((3,5-dichloro-4-(chloromethyl)benzyl)oxy)acetate (A40)

A40

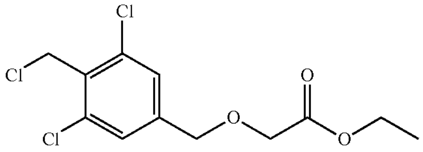

To a solution of A39 (220 mg, 0.75 mmol, 1.0 eq) in DCM (3 mL) at 0° C. was added thionyl chloride (179 mg, 1.50 mmol, 2.0 eq) and the reaction was stirred at rt for 2 h. The mixture was concentrated under reduced pressure to afford Intermediate A40 (220 mg, 94.10% yield) as a yellow solid which was used directly in the next step without purification.

TLC: EtOAc/pet. ether=1/10, Rf=0.78.

Intermediate A41

Synthesis of methyl (E)-3-(4-(bromomethyl)-3,5-dichlorophenyl)acrylate (A41)

A41

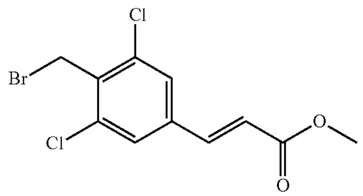

To a mixture of A18 (500 mg, 2.04 mmol, 1.0 eq) and N-bromosuccinimide (363 mg, 2.04 mmol, 1.0 eq) in $CCl_4$ (10.0 mL) at rt was added benzoyl peroxide (25 mg, 100 μmol, 0.05 eq). The reaction was stirred at 90° C. for 2 h, then water (50 mL) was added, and the mixture extracted with DCM (15 mL*3). The combined organic phase was washed with brine (30 mL), dried over $Na_2SO_4$ and concentrated in vacuo. The crude material was purified by silica gel column chromatography (EtOAc/pet. ether=1/100 to 1/30) to afford Intermediate A41 (120 mg, 18.2% yield) as a light yellow oil.

TLC: EtOAc/pet. ether=1/20 (v/v), Rf=0.55

$^1$H NMR: (400 MHz, DMSO-$d_6$) δ 7.98 (s, 2H), 7.62 (d, J=16.0 Hz, 1H), 6.88 (d, J=16.0 Hz, 1H), 4.79 (s, 2H), 3.74 (s, 3H).

Intermediate A42

Synthesis of methyl 2-(3,5-dichloro-4-(hydroxymethyl)phenoxy)propanoate (A42)

A42

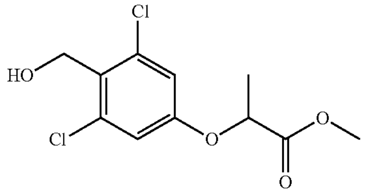

A solution of 3,5-dichloro-4-(hydroxymethyl)phenol (1.1 g, 5.6 mmol, 1.0 eq), methyl 2-bromopropanoate (0.93 g, 5.6 mmol, 1.0 eq) and $K_2CO_3$ (0.93 g, 6.7 mmol, 1.2 eq) in DMF (10 mL) was stirred overnight at rt. The reaction mixture was diluted with EtOAc (100 mL) and filtered, then the filtrate was washed with water (50 mL*2) and brine (50 mL*2), dried over $Na_2SO_4$ and concentrated under reduce pressure. The crude product was purified through silica gel column flash chromatography (EtOAc/pet. ether=1/5) to afford Intermediate A42 (670 mg, 42.9% yield) as a light yellow solid.

TLC: EtOAc/pet. ether=1/10, Rf=0.50

$^1$H NMR: (400 MHz, DMSO-$d_6$) δ 7.04 (s, 2H), 5.19 (q, J=6.7 Hz, 1H), 5.09 (t, J=5.3 Hz, 1H), 4.60 (d, J=5.3 Hz, 2H), 3.68 (s, 3H), 1.50 (d, J=6.8 Hz, 3H).

Intermediate A43

Synthesis of methyl 2-(3,5-dichloro-4-(chloromethyl)phenoxy)propanoate (A43)

A43

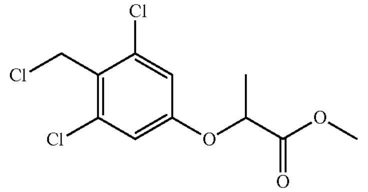

To a solution of A42 (670 mg, 2.4 mmol, 1.0 eq) in DCM (15 mL) at rt was added $SOCl_2$ (570 mg, 4.8 mmol, 2.0 eq). After 3 h the reaction mixture was concentrated under reduced pressure to afford Intermediate A43 (703 mg, 98.4% yield) as a white solid.

TLC: EtOAc/pet. ether=1/10, Rf=0.60.

Intermediate A44

Synthesis of methyl 2-(3,5-dichloro-4-methylphenyl)propanoate (A44)

A44

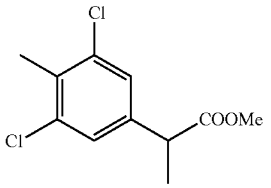

A solution of A16 (230 mg, 0.99 mmol, 1.0 eq) in THE (5 mL) was cooled to 0° C., t-BuOK (118 mg, 1.05 mmol, 1.05 eq) was added and the reaction was stirred at 0° C. for 20 min. $CH_3I$ (140 mg, 0.99 mmol, 1.0 eq) was added, and the reaction was stirred at 0° C. for an additional 1 h. The reaction was quenched with $NH_4Cl$ (sat. aq., 10 mL) and extracted with EtOAc (10 mL*2). The combined organic phase was washed with brine (30 mL), dried over $Na_2SO_4$ and concentrated in vacuo to afford crude Intermediate A44 (240 mg, 97.1% yield), that was used in the next step without further purification.

$^1$H NMR: (400 MHz, DMSO-$d_6$) δ 7.37 (s, 2H), 3.85 (d, J=7.2 Hz, 1H), 3.60 (s, 3H), 2.37 (s, 3H), 1.38 (d, J=6.8 Hz, 3H).

Intermediate A45

Synthesis of methyl 2-(4-(bromomethyl)-3,5-dichlorophenyl)propanoate (A45)

A45

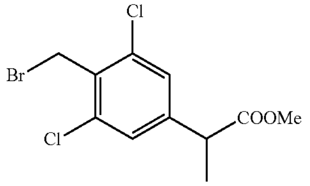

To a solution of A44 (1.4 g, 5.80 mmol, 1.0 eq) in $CCl_4$ (30 mL) was added N-bromosuccinimide (1.1 g, 6.1 mmol, 1.05 eq) and benzoyl peroxide (0.10 g, 0.46 mmol, 0.08 eq). The mixture was stirred at reflux for 1 h, then cooled to rt and concentrated in vacuo. The residue was purified by silica gel column chromatography (pet. ether/EtOAc=100/1 to 50/1) and Prep-TLC (pet. ether/EtOAc=10/1) to afford Intermediate A45 (300 mg, 16% yield) as a light yellow oil.

$^1$H NMR: (400 MHz, DMSO-$d_6$) δ 7.24 (dd, J=8.8, 2.0 Hz, 1H), 7.12 (t, J=8.4 Hz, 1H), 5.36 (t, J=5.6 Hz, 1H), 4.91 (s, 2H), 4.50 (d, J=6.0 Hz, 2H), 4.16 (q, J=7.2 Hz, 2H), 1.20 (t, J=7.2 Hz, 3H).

Intermediate A46

Synthesis of 4-(bromomethyl)-3,5-dichlorobenzoic acid (A46)

A46

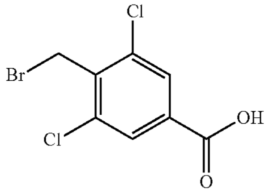

To a solution of 3,5-dichloro-4-methylbenzoic acid (500 mg, 2.44 mmol, 1.0 eq) in $CCl_4$ (10 mL) were added N-bromosuccinimide (477 mg, 2.68 mmol, 1.1 eq) and benzoyl peroxide (7.5 mg, 122 μmol, 0.05 eq) and the reaction was heated to reflux overnight. After cooling, the mixture was diluted with DCM (20 mL) and washed with water (20 mL). The organic phase was concentrated in vacuo to afford Intermediate A46 (475 mg, 68.6% yield) as a yellow solid.

Intermediate A47

Synthesis of (4-(benzyloxy)-2,6-dichloro-3-fluoro-phenyl)methanol (A47)

A47

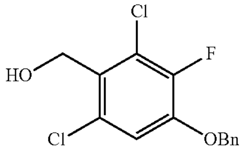

To a solution of 3,5-dichloro-2-fluoro-4-(hydroxymethyl) phenol (24.6 g, 117 mmol, 1.0 eq) in DMF (100 mL) at rt were added $K_2CO_3$ (20.9 g, 152 mmol, 1.3 eq) and benzyl bromide (21.1 g, 124 mmol, 15 mL, 1.1 eq). The reaction was stirred at rt for 16 h, then the reaction was poured into water (20 mL), and extracted with EtOAc (30 mL*3). The combined organic fractions were concentrated in vacuo and purified by silica gel column chromatography (pet. ether: EtOAc=2:1) to afford Intermediate A47 (25.4 g, 72.4% yield) as a white solid.

$^1$H NMR: (400 MHz, DMSO) δ 7.51-7.30 (m, 6H), 5.27 (s, 2H), 5.19 (td, J=5.2, 1.2 Hz, 1H), 4.62 (d, J=5.2 Hz, 2H).

Intermediate A48

Synthesis of ((4-(benzyloxy)-2,6-dichloro-3-fluo-robenzyl)oxy)(tert-butyl)dimethylsilane (A48)

A48

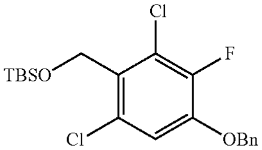

To a solution of A47 (25 g, 84 mmol, 1.0 eq) in DCM (100 mL) at rt were added imidazole (11.5 g, 169 mmol, 1.0 eq) and TBSCl (13.5 g, 89 mmol, 1.1 eq). The reaction was stirred at rt for 1 h, then the reaction mixture was poured into water (20 mL), and extracted with DCM (30 mL*3). The combined organic phase was concentrated to afford Intermediate A48 (34.2 g, 97.6% yield) as a white solid.

$^1$H NMR: (400 MHz, DMSO) δ 7.50-7.34 (m, 6H), 5.27 (s, 2H), 4.80 (s, 2H), 0.87 (s, 9H), 0.09 (s, 6H).

Intermediate A49

Synthesis of 4-(((tert-butyldimethylsilyl)oxy) methyl)-3,5-dichloro-2-fluorophenol (A49)

A49

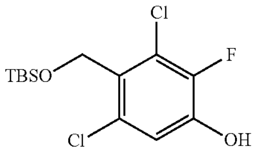

To a solution of A48 (34.2 g, 82.3 mmol) in THE (200 mL) at rt was added Pd/C (1.5 g, 4.12 mmol). The reaction was stirred under 1 atm $H_2$ at rt for 3 h, then the mixture was filtered, and the filtrate was concentrated to afford Intermediate A49 (26 g, 97% yield) as a white solid.

LCMS: T=1.80 min, [M−1]=323.05

$^1$H NMR: (400 MHz, DMSO) δ 10.97 (s, 1H), 7.02 (d, J=7.6 Hz, 1H), 4.76 (d, J=0.8 Hz, 2H), 0.86 (s, 9H), 0.08 (s, 6H).

Intermediate A50

Synthesis of 4-(((tert-butyldimethylsilyl)oxy) methyl)-3,5-dichloro-2-fluorophenyl trifluorometh-anesulfonate (A50)

A50

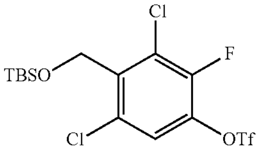

To a solution of A49 (26.8 g, 82.3 mmol, 1.0 eq) in DCM (200 mL) at rt were added pyridine (13.0 g, 165 mmol, 2.0 eq), $K_2CO_3$ (20.9 g, 153 mmol, 1.3 eq) and $Tf_2O$ (27.9 g, 98.8 mmol, 1.2 eq). The reaction was stirred at rt for 10 min, then the mixture was poured into water (200 mL), and extracted with DCM (300 mL*3). The combined organic phase was concentrated in vacuo to afford Intermediate A50 (36.2 g, 96.1% yield) as a colorless oil.

$^1$H NMR: (400 MHz, DMSO) δ 8.16 (d, J=6.8 Hz, 1H), 4.89 (s, 2H), 0.88 (d, J=0.8 Hz, 9H), 0.12 (d, J=0.8 Hz, 6H).

Intermediate A51

Synthesis of methyl (E)-3-(4-(((tert-butyldimethylsilyl)oxy)methyl)-3,5-dichloro-2-fluorophenyl)acrylate (A51)

A51

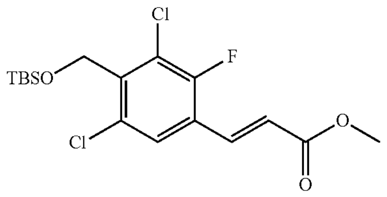

To a solution of A50 (10.5 g, 23.0 mmol, 1.0 eq) and methyl prop-2-enoate (4.9 g, 57.4 mmol, 2.5 eq) in DMF (50 mL) at rt were added $Et_3N$ (5.8 g, 57 mmol, 2.5 eq), $Pd(OAc)_2$ (257.7 mg, 1.15 mmol, 0.05 eq) and dppp (521 mg, 1.26 mmol, 0.06 eq) under $N_2$. The reaction was heated to 100° C. for 6 h, then the mixture was cooled to rt and diluted with EtOAc (50 mL). The organic phase was washed with brine (50 mL*2), dried over $Na_2SO_4$ and concentrated under reduced pressure. The crude material was purified by silica gel column chromatography (EtOAc/pet. ether-1/200) to afford Intermediate A51 (1.6 g, 18% yield) as a light yellow solid.

$^1H$ NMR: (400 MHz, DMSO) δ 7.63 (d, J=16.0 Hz, 1H), 4.89-4.85 (m, 2H), 0.88 (s, 10H), 0.13-0.10 (m, 7H).

Intermediate A52

Synthesis of methyl 3-(4-(((tert-butyldimethylsilyl)oxy)methyl)-3,5-dichloro-2-fluorophenyl)propanoate (A52)

A52

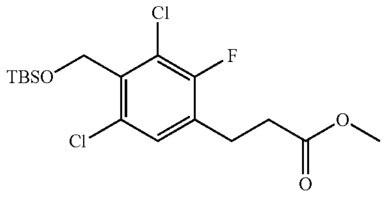

To a solution of A51 (750 mg, 1.9 mmol) in THE (5 mL) at rt was added Pd/C (75 mg, 191 μmol) and the reaction was stirred under 1 atm $H_2$ atmosphere at rt 3 h. The mixture was filtered and concentrated to afford Intermediate A52 (560 mg, 74% yield).

$^1H$ NMR: (400 MHz, DMSO) δ 7.50 (d, J=6.8 Hz, 1H), 4.83 (d, J=1.2 Hz, 2H), 3.58 (s, 3H), 2.90 (t, J=7.6 Hz, 2H), 2.68 (t, J=7.6 Hz, 2H), 0.87 (s, 9H), 0.10 (s, 6H).

Intermediate A53

Synthesis of methyl 3-(3,5-dichloro-2-fluoro-4-(hydroxymethyl)phenyl)propanoate (A53)

A53

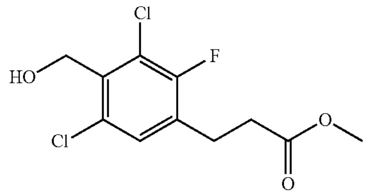

To a solution of A52 (560 mg, 1.4 mmol, 1.0 eq) in THF (5 mL) at rt was added TBAF (2.1 mL, 2.1 mmol, 1.5 eq), and the reaction was stirred for 1 h. The reaction mixture was poured into water (20 mL), extracted with EtOAc (30 mL*3) and concentrated in vacuo to afford Intermediate A53 (470 mg, 99% yield) as a white solid.

$^1H$ NMR: (400 MHz, DMSO) δ 7.47 (d, J=6.8 Hz, 1H), 5.31-5.25 (m, 1H), 4.65 (dd, J=5.2, 1.2 Hz, 2H), 3.59 (s, 3H), 2.90 (s, 2H), 2.67 (s, 2H).

Intermediate A54

Synthesis of methyl 3-(3,5-dichloro-4-(chloromethyl)-2-fluorophenyl)propanoate (A54)

A54

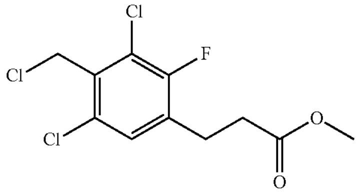

To a solution of A53 (470 mg, 1.67 mmol, 1.0 eq) in DCM (5 mL) at rt was added $SOCl_2$ (298 mg, 2.51 mmol, 1.5 eq) and the mixture was stirred for 2 h. The reaction mixture was concentrated in vacuo to afford Intermediate A54 (500 mg, 99.8% yield) as a white solid.

TLC: EtOAc/pet. ether=1/3 (v/v), $R_f$=0.48.

Intermediate A55

Synthesis of tert-butyl((2,6-dichloro-3-fluoro-4-((trimethylsilyl)ethynyl)benzyl)oxy)dimethylsilane (A55)

A55

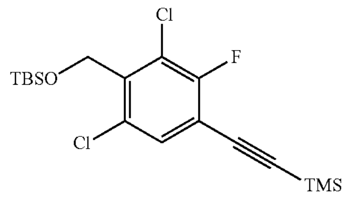

A mixture of A50 (36.0 g, 78.7 mmol, 1.0 eq), ethynyl (trimethyl)silane (8.5 g, 87 mmol, 1.1 eq), $Pd(PPh_3)_2Cl_2$ (2.8 g, 3.94 mmol, 0.05 eq), triethylamine (15.9 g, 157 mmol, 2.0 eq) and CuI (15 mg, 42 μmol, 0.001 eq) in DMF (200 mL) was stirred at 100° C. for 2 h. Water (800 mL) was added and the mixture was extracted with EtOAc (250 mL*2). The combined organic phase was washed with water (500 mL*3) and brine (500 mL), dried over $Na_2SO_4$ and concentrated in vacuo. The residue was purified by silica gel column chromatography (pet. ether) to afford Intermediate A55 (31.0 g, 97.1% yield) as a brown oil.

$^1H$ NMR: (400 MHz, DMSO-$d_6$) δ 7.71 (d, J=6.3 Hz, 1H), 4.84 (s, 2H), 0.86 (s, 9H), 0.25 (s, 9H), 0.09 (s, 6H).

Intermediate A56

Synthesis of tert-butyl((2,6-dichloro-4-ethynyl-3-fluorobenzyl)oxy)dimethylsilane (A56)

A56

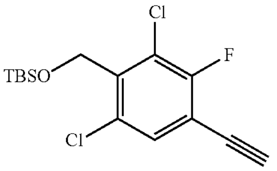

To a solution of A55 (31.0 g, 76.5 mmol, 1.0 eq) in THF (100 mL) cooled to −30° C., TBAF (1 M in THF, 76.5 mmol, 76.5 mL, 1.0 eq) was added dropwise. The reaction was stirred at rt for 1 h then water (500 mL) was added and the mixture extracted with EtOAc (150 mL*2). The combined organic phase was washed with brine (150 mL*2), dried over $Na_2SO_4$ and concentrated in vacuo. The residue was purified by silica gel column chromatography (pet. ether) to afford Intermediate A56 (11.0 g, 43.2% yield) as a light yellow solid.

$^1H$ NMR: (400 MHz, DMSO-$d_6$) δ 7.76 (d, J=6.3 Hz, 1H), 4.85 (s, 2H), 4.80 (s, 1H), 0.86 (s, 9H), 0.10 (s, 6H).

Intermediate A57

Synthesis of 2-(4-(((tert-butyldimethylsilyl)oxymethyl)-3,5-dichloro-2-fluorophenyl)acetic acid (A57)

A57

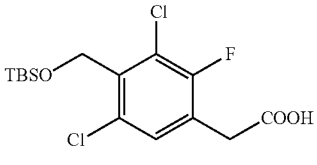

To a solution of A56 (8.4 g, 25 mmol, 1.0 eq) and 4-methylpyridine-N-oxide (5.5 g, 50.4 mmol, 2.0 eq) in MeCN (50 mL) and water (3 mL) at rt was added [Rh(cod)Cl]$_2$ (621 mg, 1.26 mmol, 0.05 eq) and tris(4-fluorophenyl)phosphine (1.6 g, 5.0 mmol, 0.2 eq). The reaction was stirred at 60° C. overnight, then cooled and the pH was adjusted to pH=9 with aqueous $NaHCO_3$. The mixture was washed with ether (100 mL*2) and the organic phase was discarded. The aqueous phase was then adjusted to pH=3-4 with aqueous HCl (2N), and was extracted with EtOAc (100 mL*2). The combined organic phase was washed with brine (100 mL), dried over $Na_2SO_4$ and concentrated in vacuo to afford Intermediate A57 (4.0 g, 43% yield) as a white solid.

$^1H$ NMR: (400 MHz, DMSO-$d_6$) δ 12.69 (s, 1H), 7.55 (s, 1H), 4.85 (s, 2H), 3.72 (s, 2H), 0.88 (s, 9H), 0.11 (s, 6H).

Intermediate A58

Synthesis of methyl 2-(3,5-dichloro-4-(chloromethyl)-2-fluorophenyl)acetate (A58)

A58

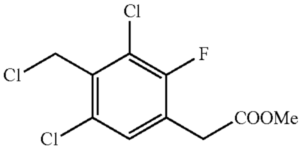

To a solution of A57 (3.9 g, 11 mmol, 1.0 eq) in MeOH (40 mL) was added $SOCl_2$ (2.5 g, 21 mmol, 2.0 eq). The reaction was refluxed for 2 h, then the mixture was concentrated in vacuo. The resulting residue was dissolved in DCM (40 mL), $SOCl_2$ (2.5 g, 21 mmol, 2.0 eq) was added, and the reaction was stirred at rt for another 2 h. The mixture was concentrated in vacuo and the residue purified by silica gel column flash chromatography (pet. ether/EtOAc=10/1) to afford Intermediate A58 (2.5 g, 83% yield) as a white solid.

$^1H$ NMR: (400 MHz, DMSO-$d_6$) δ 7.65 (d, J=6.5 Hz, 1H), 4.90 (d, J=0.8 Hz, 2H), 3.87 (d, J=1.6 Hz, 2H), 3.65 (s, 3H).

Intermediate A59

Synthesis of N-(3,5-dichloro-4-methylphenyl)acetamide (A59)

A59

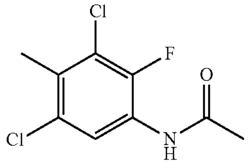

To a solution of 3,5-dichloro-4-methylaniline (15.0 g, 85.2 mmol, 1.0 eq) in DCM (30 mL) and TEA (17.2 g, 170 mmol, 1.0 eq) was added acetyl chloride (8.0 g, 100 mmol, 1.2 eq). The reaction was stirred at rt overnight, then diluted with EtOAc (100 mL). The organic phase was washed with brine (50 mL*2), dried over $Na_2SO_4$ and concentrated in vacuo to afford Intermediate A59 (17.0 g, 91.5% yield) as a yellow solid.

TLC: Pet. ether/EtOAc=3/1 (v/v), Rf=0.16

LCMS: T=1.959 min, [M−1]=216.0

$^1H$ NMR: (400 MHz, DMSO-$d_6$) δ 10.16 (s, 1H), 7.66 (s, 2H), 2.33 (s, 3H), 2.04 (s, 3H).

Intermediate A60

Synthesis of N-(3,5-dichloro-2-fluoro-4-methylphenyl)acetamide (A60)

A60

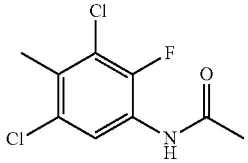

To a solution of A59 (7.0 g, 32 mmol, 1.0 eq) in MeCN (100 mL) was added Selectfluor (11.4 g, 32.1 mmol, 1.0 eq). The mixture was stirred at 80° C. overnight, then the mixture was cooled and diluted with EtOAc (20 mL). The organic phase was washed with brine (10 mL*2), dried over $Na_2SO_4$ and concentrated in vacuo. The crude material was purified with silica gel column chromatography (pet. ether/EtOAc=100/1 to 10/1) to afford Intermediate A60 (1.5 g, 20% yield) as a yellow solid.

TLC: Pet. ether/EtOAc=3/1 (v/v), Rf=0.40

$^1$H NMR: (400 MHz, DMSO-$d_6$) δ 10.01 (s, 1H), 8.05 (d, J=7.2 Hz, 1H), 2.38 (s, 3H), 2.10 (s, 3H).

Intermediate A61

Synthesis of N-(4-(bromomethyl)-3,5-dichloro-2-fluorophenyl)acetamide (A61)

A61

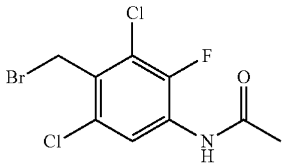

A solution of A60 (800 mg, 3.39 mmol, 1.0 eq), N-bromosuccinimide (844 mg, 4.74 mmol, 1.3 eq) and benzoyl peroxide (246 mg, 1.02 mmol, 0.3 eq) in $CCl_4$ (20 mL) was stirred at 50° C. for 15 min, then at 100° C. overnight. The reaction mixture was concentrated and the crude material purified with silica gel column chromatography (pet. ether/EtOAc=30/1 to 10/1) to afford Intermediate A61 (880 mg, 82.4% yield) as a yellow solid.

TLC: Pet. ether/EtOAc=3/1 (v/v), Rf=0.44

LCMS: T=2.135 min, [M+1]=313.9

HNMR: $^1$H NMR (400 MHz, DMSO-$d_6$) δ 10.19 (s, 1H), 8.21 (d, J=6.8 Hz, 1H), 4.76 (d, J=0.8 Hz, 2H), 2.13 (s, 3H).

Intermediate A62

Synthesis of (4-(benzyloxy)-2,6-dichlorophenyl)(3-isopropyl-4-((triisopropylsilyl)oxy)phenyl)methanol (A62)

A62

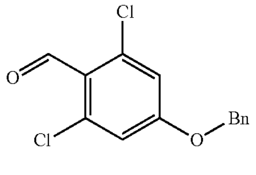

To a solution of 2,6-dichloro-4-hydroxybenzaldehyde (20 g, 0.10 mol, 1.0 eq) and benzyl bromide (18 g, 0.10 mol, 1.0 eq) in DMF (200 mL) at rt was added $K_2CO_3$ (29 g, 0.20 mol, 2.0 eq). The mixture was stirred for 20 h and was filtered. The filtrate was diluted with water (500 mL) and extracted with EtOAc (150 mL*2). The combined organic phase was washed with brine (100 mL*2), dried over $Na_2SO_4$ and concentrated under reduced pressure. The crude residue was triturated with hexane (50 mL*2) to afford Intermediate A62 (26.0 g, 88.3% yield) as a light brown solid.

TLC: EtOAc/pet. ether=1/10, Rf=0.78

$^1$H NMR: (400 MHz, DMSO-$d_6$) δ 10.28 (s, 1H), 7.49-7.34 (m, 5H), 7.30 (s, 2H), 5.27 (s, 2H).

Intermediate A63

Synthesis of 2,6-dichloro-4-(methoxymethoxy)benzaldehyde (A63)

A63

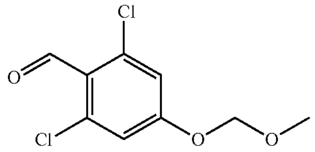

To a solution of 2,6-dichloro-4-hydroxybenzaldehyde (10.0 g, 52.4 mmol, 1.0 eq) in DMF (100 mL) at rt were added $Cs_2CO_3$ (51.2 g, 157 mmol, 3.0 eq) and chloromethyl methyl ether (12.6 g, 157 mmol, 3.0 eq). The reaction was stirred at rt 1 h, then water (300 mL) was added and the mixture was extracted with EtOAc (150 mL*2). The combined organic phase was washed with brine (50 mL*2), dried over $Na_2SO_4$ and concentrated in vacuo to afford Intermediate A63 (12.0 g, 97.6% yield) as a white solid.

Intermediate B1

Synthesis of 3-fluoro-2-(prop-1-en-2-yl)phenol (BI)

B1

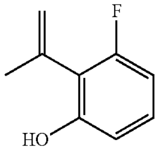

To a mixture of 2-bromo-3-fluorophenol (38.0 g, 200 mmol, 1.0 eq), isopropenyl-2-boron(pinacolate) (50.4 g, 300 mmol, 1.5 eq) and Pd(dppf)$Cl_2$·$CH_2Cl_2$ (16 g, 20 mmol, 0.1 eq) in 1,4-dioxane (300 mL) and water (30 mL) at rt was added $K_2CO_3$ (55.3 g, 400 mmol, 2.0 eq). The mixture was heated to 70° C. and stirred overnight. The reaction mixture was cooled to rt, quenched with water (100 mL) and extracted with EtOAc (100 mL*3). The combined organic phase was washed with brine (200 mL), dried over $Na_2SO_4$, and concentrated in vacuo. The crude material was purified by silica gel column chromatography (EtOAc/pet. ether=1/100 to 1/20) to afford Intermediate B1 (23 g, 76% yield) as a white solid.

TLC: EtOAc/pet. ether=1/10 (v/v), Rf=0.55

$^1$H NMR: (400 MHz, DMSO-$d_6$) δ 9.72 (s, 1H), 7.06 (td, J=8.4, 6.8 Hz, 1H), 6.66 (td, J=8.4, 1.2 Hz, 1H), 6.59 (m, 1.0 Hz, 1H), 5.28 (m, 1H), 4.89 (m, 1H), 1.98 (s, 3H).

Intermediate B2

Synthesis of 3-fluoro-2-isopropylphenol (B2)

B2

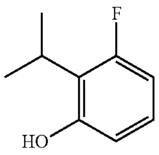

To a solution of B1 (23.0 g, 151 mmol) in MeOH (300 mL) was added Pd/C (10%) (6.0 g). The reaction mixture was stirred under a hydrogen atmosphere at 60° C. overnight. The mixture was cooled to 0° C., filtered and concentrated in vacuo to afford Intermediate B2 (21.0 g, 90% yield) as a yellow oil.

TLC: EtOAc/pet. ether=1/50 (v/v), $R_f$=0.25

$^1$H NMR: (400 MHz, DMSO-$d_6$) δ 9.69 (s, 1H), 7.00-6.93 (m, 1H), 6.65-6.60 (m, 1H), 6.52 (ddd, J=10.8, 8.0, 1.2 Hz, 1H), 3.40 (m, 1H), 1.25 (dd, J=7.2, 1.2 Hz, 6H).

Intermediate B3

Synthesis of 2-(1-(4-fluorophenyl)-1-hydroxyethyl) phenol (B3)

B3

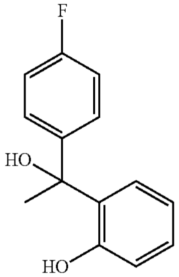

2-Bromophenol (20.0 g, 116 mmol, 1.0 eq) in THF (100 mL) was cooled to −78° C. n-BuLi (232 mmol, 92.5 mL of 2.5 M, 2.0 eq) was added; the mixture was stirred at rt for 1 h and was then cooled to −78° C. 4-Fluoroacetophenone (16.0 g, 116 mmol, 1.0 eq) in THF (10 mL) was added; the mixture was stirred at rt for 16 h. The reaction mixture was acidified to pH~6-7 with 2N HCl and then was extracted with EtOAc (50 mL*3). The combined organic phase was washed with brine (100 mL), dried over $Na_2SO_4$, concentrated in vacuo and purified by reversed-phase column chromatography to afford Intermediate B3 (2.0 g, 7.3% yield).

TLC: EtOAc/pet. ether=1/5 (v/v), Rf=0.3

LCMS: T=3.46 min; [M−1]=231.1.

Intermediate B4

Synthesis of 2-(1-(4-fluorophenyl)ethyl)phenol (B4)

B4

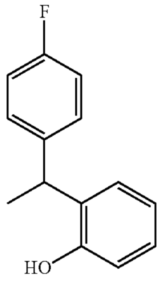

To a solution of B3 (5.7 g, 25 mmol, 1.0 eq) in DCM (50 mL) at 0° C. were added $Et_3SiH$ (11.4 g, 98.0 mmol, 4.0 eq) and TFA (84.0 g, 735 mmol, 30 eq). The mixture was stirred at rt for 2 h, then the reaction was concentrated in vacuo and purified by silica gel column chromatography (pet. ether/EtOAc=10/1) to afford Intermediate B4 (5.0 g, 94% yield).

TLC: EtOAc/pet. ether=1/5 (v/v), Rf=0.25

$^1$H NMR: (400 MHz, DMSO) δ 9.33 (s, 1H), 7.28-7.19 (m, 2H), 7.12-7.02 (m, 3H), 6.99 (m, 1H), 6.79-6.71 (m, 2H), 4.44 (d, J=7.3 Hz, 1H), 1.49 (d, J=7.3 Hz, 3H).

Intermediate B5

Synthesis of 1-(1-bromovinyl)-4-fluorobenzene (B5)

B5

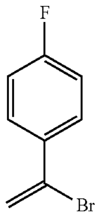

To a solution of 4-fluoroacetophenone (10.0 g, 72.4 mmol), $P(OPh)_3$ (35.4 g, 109 mmol) and TEA (11.7 g, 116 mmol) in DCM (100 mL) at −15° C. was added $Br_2$ (17.4 g, 109 mmol) dropwise. The mixture was stirred at rt for 1 h. The mixture was concentrated to dryness and purified by silica gel column chromatography (pet. ether eluant) to afford Intermediate B5 (8.0 g, 55% yield) as a colorless oil that is best stored at 0° C.

TLC: Pet. ether, $R_f$=0.91

$^1$H NMR: (400 MHz, Chloroform-d) δ 7.63-7.50 (m, 2H), 7.03 (t, J=8.7 Hz, 2H), 6.05 (d, J=2.1 Hz, 1H), 5.76 (d, J=2.0 Hz, 1H).

Intermediate B6

Synthesis of 2-(1-(4-fluorophenyl)vinyl)-4,4,5,5-tetramethyl-1,3,2-dioxaborolane (B6)

B6

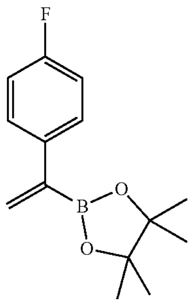

A solution of B5 (3.0 g, 15 mmol), bis(pinacolato)-diboron (5.7 g, 22 mmol), $Pd(PPh_3)_2Cl_2$ (1.1 g, 1.5 mmol), KOAc (4.4 g, 45 mmol) and $PPh_3$ (1.2 g, 4.5 mmol) in toluene (50 mL) was stirred at 100° C. overnight. The mixture was concentrated in vacuo. Water (30 mL) was added, and the mixture was extracted with EtOAc (25 mL*2). The combined organic phase was washed with brine (50 mL), dried over $Na_2SO_4$, concentrated in vacuo, and purified by silica gel column chromatography (pet. ether/EtOAc=20/1) to afford Intermediate B6 (1.5 g, 410% yield) as a yellow oil.

TLC: Pet. ether, $R_f$=0.69

$^1$H NMR: (400 MHz, Chloroform-d) δ 7.45 (dd, J=8.7, 5.6 Hz, 2H), 7.00 (t, J=8.8 Hz, 2H), 6.04 (s, 2H), 1.32 (s, 12H).

Intermediate B7

Synthesis of 2-bromo-4-(difluoromethoxy)-1-fluorobenzene (B7)

B7

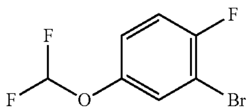

To a solution of 3-bromo-4-fluorophenol (12 g, 63 mmol, 1.0 eq) and ethyl 2-bromo-2,2-difluoroacetate (20.40 g, 100.5 mmol, 1.6 eq) in DMF (100 mL) at rt was added $K_2CO_3$ (10.4 g, 75.4 mmol, 1.2 eq). The mixture was heated to 100° C. overnight then the reaction was cooled to rt, diluted with EtOAc (500 mL), and filtered. The filtrate was washed with water (500 mL*2) and brine (200 mL*2), dried over $Na_2SO_4$ and concentrated under reduced pressure. The crude product was purified by silica gel column flash chromatography (pet. ether) to afford Intermediate B7 (4.0 g, 26% yield) as a colorless oil.

TLC: EtOAc/pet. ether=1/20 (v/v), Rf=0.70

$^1$H NMR: (400 MHz, DMSO-$d_6$) δ 7.61 (dd, J=5.7, 2.9 Hz, 1H), 7.48-7.43 (m, 1H), 7.30-7.24 (m, 1H), 7.24 (t, J=73.6 Hz, 1H).

Intermediate B8

Synthesis of 2-(5-(difluoromethoxy)-2-fluorophenyl)-4,4,5,5-tetramethyl-1,3,2-dioxaborolan (B8)

B8

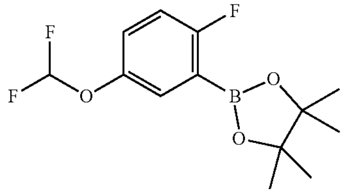

To a mixture of B7 (300 mg, 1.24 mmol, 1.0 eq), bis(pinacolato)diboron (632 mg, 2.49 mmol, 1.0 eq) and $Pd(dppf)Cl_2{\cdot}CH_2Cl_2$ (100 mg, 0.12 mmol, 0.1 eq) in 1,4-dioxane (10 mL) at rt was added potassium acetate (367 mg, 3.73 mmol, 3.0 eq). The mixture was heated to 85° C. overnight then the reaction mixture was cooled to rt, quenched with water (30 mL) and extracted with EtOAc (30 mL*3). The combined organic phase was washed with brine (20 mL), dried over $Na_2SO_4$ and concentrated to dryness to afford crude Intermediate B8 (300 mg, 83.7% yield) as a brown oil.

TLC: EtOAc/pet. ether=1/20 (v/v), Rf=0.86.

Intermediate B9

Synthesis of (4-iodo-2-isopropylphenoxy)triisopropylsilane (B9)

B9

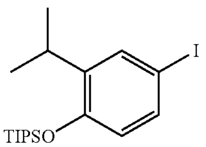

To a solution of 2-isopropyl-4-iodophenol (20.0 g, 76.3 mmol, 1.0 eq), TEA (15.4 g, 153 mmol, 2.0 eq) and DMAP (0.90 g, 7.6 mmol, 0.1 eq) in DCM (200 mL) at rt was added dropwise TIPSCl (22.8 g, 99.2 mmol, 1.3 eq) in DCM (50 mL). The reaction was stirred at rt overnight, then diluted with water (200 mL) and extracted with DCM (100 mL*2). The combined organic phase washed with brine (100 mL*2), dried over $Na_2SO_4$ and concentrated under reduce pressure. The crude product was purified using silica gel column chromatography (pet. ether) to afford Intermediate B9 (26.0 g, 81.5% yield) as a colorless oil.

TLC: EtOAc/pet. ether=1/20, Rf=0.74

$^1$H NMR: (400 MHz, DMSO-$d_6$) δ 7.44 (d, J=2.2 Hz, 1H), 7.38 (dd, J=8.4, 2.3 Hz, 1H), 6.61 (d, J=8.4 Hz, 1H), 3.23 (p, J=6.9 Hz, 1H), 1.30 (q, J=7.5 Hz, 3H), 1.14 (d, J=6.9 Hz, 6H), 1.06 (d, J=7.4 Hz, 18H).

Intermediate B10

Synthesis of 1-(benzyloxy)-4-iodo-2-isopropylbenzene (B10)

B10

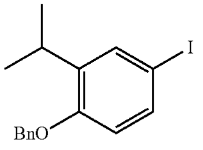

To a solution of 4-iodo-2-isopropylphenol (20.0 g, 76.3 mmol, 1.0 eq) and $K_2CO_3$ (15.8 g, 114 mmol, 1.5 eq) in DMF (200 mL) at rt was added benzyl bromide (13.1 g, 76.3 mmol, 1.0 eq). The reaction was stirred overnight, then water (500 mL) was added and the mixture was extracted with EtOAc (200 mL*2). The combined organic phase was washed with brine (300 mL), dried over $Na_2SO_4$ and concentrated in vacuo to afford Intermediate B10 (21 g, 78% yield) as a yellow liquid.

Intermediate B11

Synthesis of 4-iodo-2-isopropylphenol (B11)

B11

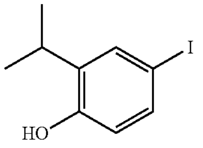

To a solution of 2-isopropylphenol (840 g, 6.17 mol, 1.0 eq) in methanol (10 L) were added NaI (925 g, 6.17 mol, 1.0 eq) and NaOH (247 g, 6.17 mol, 1.0 eq). The mixture was cooled to −10° C. and sodium hypochlorite (9.6 L, 6.2 mol, 15% in water) was added dropwise over 4 h. The mixture was quenched by slowly adding 10% aq. $Na_2S_2O_3$ solution (5 L) with stirring; the mixture was acidified with concentrated aqueous HCl. The mixture was extracted with EtOAc (5 L*2). The combined organic phase was washed with brine (5 L), dried over $Na_2SO_4$, and concentrated in vacuo. The residue was purified by silica gel column chromatography (pet. ether/EtOAc=100/1 to 20/1) to afford Intermediate B11 (800 g, 49% yield) as a reddish oil.

$^1$H NMR: (400 MHz, DMSO-$d_6$) δ 10.08 (s, 1H), 7.85 (d, J=2.3 Hz, 1H), 7.80 (dd, J=8.4, 2.3 Hz, 1H), 7.13 (d, J=8.4 Hz, 1H), 3.64 (m, 1H), 1.64 (d, J=6.9 Hz, 6H).

Intermediate B12

Synthesis of 4-iodo-2-isopropyl-1-(methoxymethoxy)benzene (B12)

B12

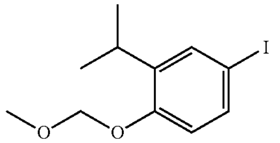

To a solution of B11 (283 g, 1.08 mol, 1.0 eq) in DMF (3.28 L) were added MOM-Cl (258 g, 3.24 mol, 3.0 eq) and $Cs_2CO_3$ (1.05 kg, 3.24 mol, 3.0 eq). The mixture was stirred at rt for 3 h under $N_2$ atmosphere. The mixture was diluted with water (10 L) and extracted with EtOAc (5 L*2). The combined organic layers were dried over $Na_2SO_4$ and concentrated in vacuo. The residue was purified by silica gel column chromatography (pet. ether/EtOAc=100/1 to 30/1) to afford Intermediate B12 (250 g, 76% yield) as a reddish oil.

$^1$H NMR: (400 MHz, DMSO-$d_6$) δ7.45 (d, J=8.0 Hz, 2H), 6.87 (d, J=8.0 Hz, 1H), 5.20 (s, 2H), 3.37 (s, 3H), 3.26-3.18 (m, 1H), 1.14 (d, J=8.0 Hz, 6H)

Intermediate C1

Synthesis of 4-(4-(dibenzylamino)-2,6-dimethylbenzyl)-2-(1-(4-fluorophenyl)ethyl)phenol (C1)

C1

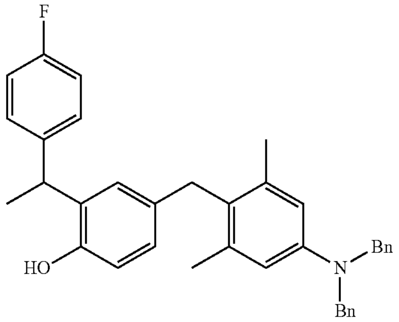

To a solution of A12 (371 mg, 1.06 mmol, 1.0 eq) and B4 (688 mg, 3.18 mmol, 3.0 eq) in DCE (5 mL) was added $ZnCl_2$ (1 M in THF, 2.1 mL, 2.1 mmol, 2.0 eq) and the reaction was stirred at 75° C. overnight. The reaction was cooled to rt, quenched with water (10 mL), and extracted with DCM (10 mL*2). The combined organic phase was washed with brine (20 mL), dried over $Na_2SO_4$ and concentrated in vacuo. The residue was purified by silica gel column chromatography (pet. ether/EtOAc=30/1 to 5/1) to afford Intermediate C1 (410 mg, 73% yield) as a yellow oil.

TLC: Pet. ether/EtOAc=1/1 (v/v), Rf=0.15

$^1$H NMR: (400 MHz, DMSO-$d_6$) δ 9.07 (s, 1H), 7.34-7.28 (m, 4H), 7.27-7.21 (m, 6H), 7.16 (s, 2H), 7.06-6.97 (m, 2H), 6.80 (d, J=2.1 Hz, 1H), 6.61 (d, J=8.2 Hz, 1H), 6.51 (d, J=8.2 Hz, 1H), 6.42 (s, 2H), 4.61 (s, 4H), 4.34 (s, 1H), 3.68 (s, 2H), 2.01 (s, 6H), 1.41 (s, 3H).

Intermediate C2

Synthesis of 4-(4-amino-2,6-dimethylbenzyl)-2-(1-(4-fluorophenyl)ethyl)phenol (C2)

C2

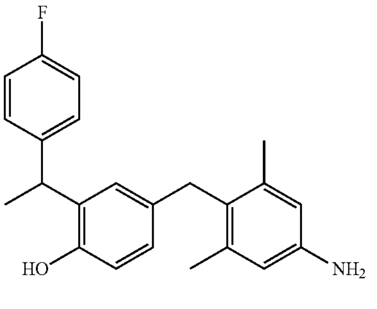

To a solution of C1 (400 mg, 0.75 mmol) in THE (10 mL) was added Pd/C (100 mg) and the reaction was stirred under 1 atm $H_2$ overnight. The mixture was filtered and concentrated in vacuo to afford Intermediate C2 (200 mg, 76% yield) as a yellow solid.

TLC: Pet. ether/EtOAc=1/1 (v/v), Rf=0.1

$^1H$ NMR: (400 MHz, DMSO-$d_6$) δ 9.09 (s, 1H), 7.19 (s, 2H), 7.07 (s, 2H), 6.84 (s, 1H), 6.61 (s, 1H), 6.51 (d, J=8.3 Hz, 1H), 6.24 (s, 2H), 4.69 (s, 2H), 4.37 (q, J=7.3 Hz, 1H), 3.67 (s, 2H), 2.01 (s, 6H), 1.44 (s, 3H).

Intermediate C3

Synthesis of 4-(4-bromo-2,6-dichlorobenzyl)-2-isopropylphenol (C3)

C3

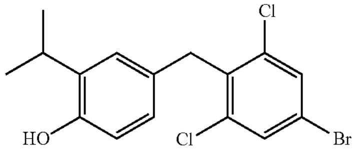

To a solution of A21 (3.0 g, 9.4 mmol, 1.0 eq) in chlorobenzene (4 mL) at rt were added 2-isopropylphenol (2.6 g, 19 mmol, 2.0 eq) and $ZnCl_2$ (2.57 g, 18.8 mmol, 2.0 eq). The reaction was heated to 150° C. and stirred 2 h under microwave irradiation. After cooling the reaction mixture was diluted with EtOAc (80 mL), washed with brine (40 mL*2), dried over $Na_2SO_4$ and concentrated under reduced pressure. The crude product was purified through silica gel column flash chromatography (EtOAc/pet. ether=1/50) to afford Intermediate C3 (2.2 g, 630% yield) as a brown oil.

$^1H$ NMR: (400 MHz, DMSO-$d_6$) δ 9.12 (s, 1H), 7.79 (s, 2H), 6.98 (d, J=2.0 Hz, 1H), 6.68-6.63 (m, 2H), 4.09 (s, 2H), 3.13 (p, J=6.8 Hz, 1H), 1.10 (d, J=6.8 Hz, 6H).

Intermediate C4

Synthesis of 2-(4-(4-bromo-2,6-dichlorobenzyl)-2-isopropylphenoxy)tetrahydro-2H-pyran (C4)

C4

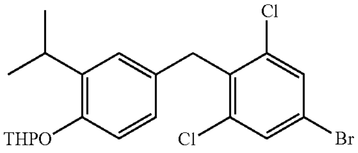

To solution of C3 (1.2 g, 3.21 mmol, 1.0 eq) in THE (15 mL) were added 3,4-dihydro-2H-pyran (324 mg, 3.85 mmol, 1.2 eq), and PPTS (151 mg, 3.85 mmol, 1.2 eq). The reaction mixture was stirred at rt overnight. Water (30 mL) was added, and the resultant mixture was extracted with EtOAc (15 mL*2). The combined organic phase was washed with brine (30 mL), dried over $Na_2SO_4$ and concentrated in vacuo. The residue was purified by silica gel column chromatography (pet. ether/EtOAc=1 to 30/1) to afford Intermediate C4 (1.2 g, 82% yield).

TLC: Pet. ether/EtOAc=10/1 (v/v), Rf=0.75

$^1H$ NMR: (400 MHz, DMSO-$d_6$) δ 7.81 (s, 2H), 7.07 (d, J=2.3 Hz, 1H), 6.93 (d, J=8.5 Hz, 1H), 6.80 (dd, J=8.4, 2.3 Hz, 1H), 5.40 (s, 1H), 4.14 (s, 2H), 3.71 (s, 1H), 3.51 (s, 1H), 3.21 (d, J=20.7 Hz, 1H), 1.77 (d, J=15.7 Hz, 3H), 1.59 (dd, J=37.3, 10.5 Hz, 4H), 1.15 (dd, J=6.9, 5.2 Hz, 6H).

Intermediate C5

Synthesis of methyl (E)-4-(3,5-dichloro-4-(3-isopropyl-4-((tetrahydro-2H-pyran-2-yl)oxy)benzyl)phenyl)but-3-enoate (C5)

C5

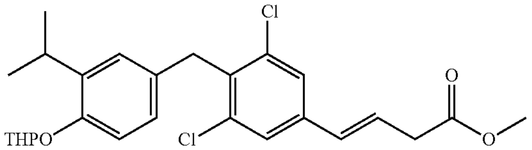

To a mixture of C4 (150 mg, 327 μmol, 1.0 eq) and methyl but-3-enoate (82 mg, 818 mol, 2.5 eq) in $Et_3N$ (2.0 mL) at rt was added $Pd(OAc)_2$ (7 mg, 33 μmol, 0.1 eq) and tris-o-tolylphosphane (20 mg, 65 μmol, 0.2 eq). The reaction was heated to 100° C. overnight under $N_2$, then water (20 mL) was added and the mixture was extracted with EtOAc (10 mL*3). The combined organic phase was washed with brine (20 mL), dried over $Na_2SO_4$ and concentrated in vacuo. The crude material was purified by Prep-TLC (EtOAc/pet. ether-1/20) to afford Intermediate C5 (70 mg, 45% yield) as a yellow oil.

TLC: EtOAc/pet. ether=1/20 (v/v), Rf=0.40

$^1H$ NMR: (400 MHz, DMSO-$d_6$) δ 7.59 (s, 2H), 7.07 (d, J=2.4 Hz, 1H), 6.93 (d, J=8.4 Hz, 1H), 6.81 (dd, J=8.4, 2.4 Hz, 1H), 6.52-6.47 (m, 2H), 5.40 (t, J=2.8 Hz, 1H), 4.15 (s, 2H), 3.74-3.67 (m, 1H), 3.64 (s, 3H), 3.53 (dd, J=10.0, 5.2 Hz, 2H), 3.30 (dd, J=4.0, 1.6 Hz, 2H), 3.21 (q, J=6.8 Hz, 1H), 1.86-1.70 (m, 3H), 1.65-1.50 (m, 4H), 1.14 (dd, J=6.8, 5.6 Hz, 6H).

Intermediate C6

Synthesis of methyl 3-(4-(3-bromo-2-fluoro-4-hydroxybenzyl)-3,5-dichlorophenyl)propanoate (C6)

C6

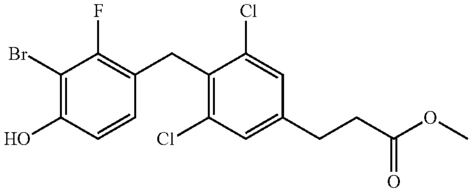

To a solution of 2-bromo-3-fluorophenol (407 mg, 2.13 mmol, 3.0 eq) in DCE (5 mL) at rt was added A26 (200 mg, 0.71 μmol, 1.0 eq) and $ZnCl_2$ (194 mg, 1.42 mmol, 2.0 eq). The reaction was heated to 105° C. overnight and was then cooled and diluted with DCM (20 mL). The organic phase was washed with brine (2*10 mL), dried over $Na_2SO_4$ and concentrated under reduced pressure. The crude product was purified through silica gel column chromatography (EtOAc/pet. ether=1/10) to afford Intermediate C6 (200 mg, 64.5% yield) as a colorless oil.

$^1H$ NMR: (400 MHz, DMSO-$d_6$) δ 10.57 (d, J=1.6 Hz, 1H), 7.42 (s, 2H), 6.68 (dd, J=8.4, 1.6 Hz, 1H), 6.56 (t, J=8.4 Hz, 1H), 4.13 (s, 2H), 3.59 (s, 3H), 2.85 (t, J=7.6 Hz, 2H), 2.69 (t, J=7.2 Hz, 2H).

Intermediate C7

Synthesis of methyl 3-(3,5-dichloro-4-(2-fluoro-3-(1-(4-fluorophenyl)vinyl)-4-hydroxybenzyl)phenyl) propanoate (C7)

C7

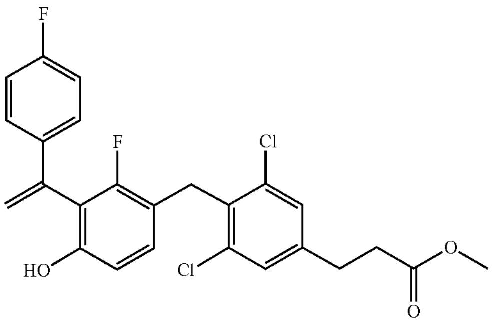

To a solution of C3 (50 mg, 120 μmol, 1.0 eq) and B6 (85 mg, 340 μmol, 3.0 eq) in 1,4-dioxane/water (3 mL/0.5 mL) at rt were added $NaHCO_3$ (29 mg, 340 μmol, 3.0 eq) and $Pd(dppf)Cl_2$ (9.0 mg, 12 μmol, 0.1 eq). The reaction mixture was heated to 95° C. under $N_2$ overnight, and was then cooled, diluted with EtOAc (100 mL) and filtered. The filtrate was washed with water (50 mL*2) and brine (50 mL*2), dried over $Na_2SO_4$ and concentrated under reduced pressure. The crude product was purified using Prep-TLC (EtOAc/pet. ether-1/5) to afford Intermediate C7 (30 mg, 55% yield) as a colorless oil.

$^1$H NMR: (400 MHz, DMSO-$d_6$) δ 9.57 (d, J=1.6 Hz, 1H), 7.42 (s, 2H), 7.31 (dd, J=9.2, 5.6 Hz, 2H), 7.14 (t, J=8.8 Hz, 2H), 6.60 (d, J=8.0 Hz, 1H), 6.53 (t, J=8.4 Hz, 1H), 5.97 (s, 1H), 5.22 (s, 1H), 4.09 (d, J=2.0 Hz, 2H), 3.59 (d, J=1.2 Hz, 3H), 2.85 (d, J=8.0 Hz, 2H), 2.69 (t, J=7.6 Hz, 2H).

Intermediate C8

Synthesis of (2,6-dichloro-4-(dibenzylamino)phenyl)(3-isopropyl-4-(methoxymethoxy)phenyl)methanol (C8)

C8

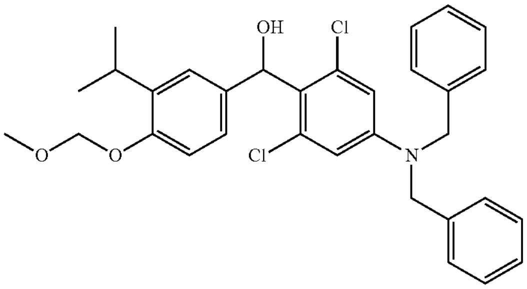

A solution of Intermediate B12 (1.1 g, 3.5 mmol) in THF (10 mL) was cooled to −20° C.; iPr-MgCl (2.7 mL of 2M solution in THF, 5.4 mmol) was added dropwise. The mixture was stirred at rt for 2 h. The mixture was cooled to −78° C. and Intermediate A28 (1.0 g, 2.70 mmol) in THF (4 mL) was added dropwise. The resultant mixture was stirred at −78° C. for 2 h. Aqueous $NH_4Cl$ (30 mL) was added to quench reaction, and the mixture was extracted with EtOAc (10 mL*3). The combined organic layers were washed with brine (30 mL), dried over $Na_2SO_4$, and concentrated in vacuo to give a brown oil. The crude product was purified by silica gel column chromatography (pet. ether/EtOAc=30:1) to afford Intermediate C8 (700 mg, 47% yield) as a colorless oil.

TLC: Pet. ether/EtOAc=5/1 (v/v), Rf=0.5

$^1$H NMR: (400 MHz, DMSO-$d_6$) δ 7.38-7.32 (m, 4H), 7.26 (t, J=6.6 Hz, 7H), 6.92-6.81 (m, 2H), 6.65 (s, 2H), 6.25 (d, J=4.4 Hz, 1H), 5.74 (t, J=5.6 Hz, 1H), 5.15 (s, 2H), 4.74 (s, 4H), 3.37 (s, 3H), 3.25-3.19 (m, 1H), 1.12 (t, J=6.4 Hz, 6H).

Intermediate C9

Synthesis of (4-amino-2,6-dichlorophenyl)(3-isopropyl-4-(methoxymethoxy)phenyl)methanol (C9)

C9

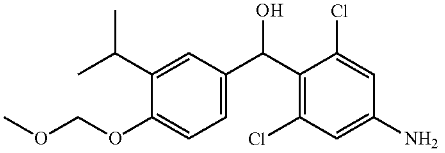

To a solution of C8 (2.1 g, 3.8 mmol) in THF (20 mL) was added Pd/C (400 mg). The mixture was degassed in vacuo and purged with $H_2$ three times. The mixture was stirred under $H_2$ gas (1 atmosphere) at rt for 2 h. The mixture was filtered and concentrated in vacuo to afford Intermediate C9 (1.4 g, 97% yield) as a gray solid.

TLC: Pet. ether/EtOAc=3/1 (v/v), Rf=0.3

$^1$H NMR: (400 MHz, DMSO-$d_6$) δ 7.23 (s, 1H), 6.90 (d, J=1.2 Hz, 2H), 6.57 (s, 2H), 6.23 (s, 1H), 5.17 (s, 2H), 3.27-3.22 (m, 1H), 1.13 (t, J=6.8 Hz, 6H).

Intermediate C10

Synthesis of 4-(4-amino-2,6-dichlorobenzyl)-2-isopropylphenol (C10)

C10

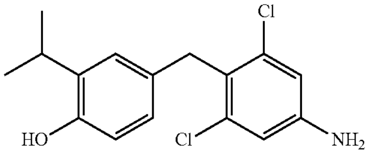

To a solution of C9 (1.0 g, 2.70 mmol) in DCM (10 mL) at 0° C. was added $Et_3SiH$ (13.5 mmol, 1.6 g); TFA (81 mmol, 9.2 g) was added dropwise to the resultant solution. The mixture was stirred at rt overnight, then concentrated in vacuo to remove solvent. Water (20 mL) was added and the resultant mixture was extracted with EtOAc (20 mL*3). The combined organic layer was washed with brine (30 mL), dried over $Na_2SO_4$, and concentrated in vacuo to give a yellow oil. The crude product was purified by silica gel column chromatography (pet. ether/EtOAc=20:1) to afford Intermediate C10 (200 mg, 23.9% yield) as a yellow solid.

TLC: Pet. ether/EtOAc=3/1 (v/v), Rf=0.4

$^1$H NMR (400 MHz, DMSO-$d_6$) δ 9.02 (s, 1H), 6.95 (s, 1H), 6.72-6.57 (m, 4H), 5.53 (s, 2H), 3.92 (s, 2H), 3.16-3.09 (m, 1H), 1.10 (d, J=6.8 Hz, 6H).

Intermediate C11

Synthesis of (4-(((tert-butyldimethylsilyl)oxy) methyl)-2,6-dichlorophenyl) dibenzylamino) phenyl)methanol (C11)

C11

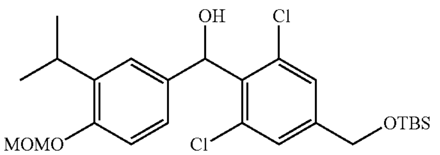

To a solution of B12 (2.9 g, 9.4 mmol, 1.5 eq) in THF (40 mL) at −20° C. was added iPrMgCl (1 M in THF, 13 mL, 13 mmol, 2.1 eq) dropwise. The mixture was stirred at rt for 2 h, then cooled to −70° C. and a solution of A36 (2.0 g, 6.3 mmol, 1.0 eq) in THF (40 mL) was added dropwise. The reaction was stirred at −70° C. for 2 h, then the reaction was quenched with saturated aqueous $NH_4Cl$ (50 mL), and extracted with EtOAc (50 mL*2). The combined organic phase was washed with brine (50 mL), dried over $Na_2SO_4$ and concentrated in vacuo. The crude material was purified by silica gel column chromatography (pet. ether/EtOAc=30:1) to afford Intermediate C11 (1.8 g, 58% yield) as a colorless oil.

TLC: EtOAc/pet. ether=1/5, Rf=0.46

$^1H$ NMR: (400 MHz, DMSO-$d_6$) δ 7.33 (s, 2H), 7.24 (s, 1H), 6.92 (d, J=1.2 Hz, 2H), 6.41 (d, J=5.0 Hz, 1H), 6.05 (d, J=5.0 Hz, 1H), 5.17 (s, 2H), 4.70 (s, 2H), 3.37 (s, 3H), 3.24 (p, J=7.0 Hz, 1H), 1.12 (dd, J=10.1, 6.9 Hz, 6H), 0.90 (s, 9H), 0.08 (d, J=2.3 Hz, 6H).

Intermediate C12

Synthesis of tert-butyl((3,5-dichloro-4-(3-isopropyl-4-(methoxymethoxy)benzyl)benzyl)oxy)dimethylsilane (C12)

C12

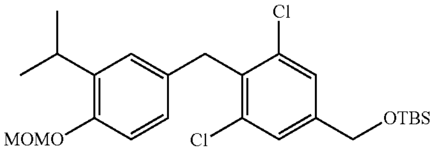

To a solution of C11 (1.6 g, 3.4 mmol, 1.0 eq) in DCM (15 mL) at 0° C. was added triethylsilane (1.9 g, 17 mmol, 5.0 eq) followed by TFA (0.40 g, 3.4 mmol), dropwise. The reaction was stirred at rt for 3 h, then the pH was adjusted to pH=7 by addition of aq. $NaHCO_3$ and the mixture was extracted with EtOAc (20 mL*2). The combined organic phase was washed with brine (20 mL), dried over $Na_2SO_4$ and concentrated in vacuo. The crude material was purified by silica gel column chromatography (pet. ether/EtOAc=30:1) to afford Intermediate C12 (1.5 g, 94% yield) as a yellow oil.

TLC: EtOAc/pet. ether=1/5, Rf=0.52

$^1H$ NMR: (400 MHz, DMSO-$d_6$) δ 7.40 (s, 2H), 7.07 (d, J=2.2 Hz, 1H), 6.90 (s, 1H), 6.82 (dd, J=8.4, 2.3 Hz, 1H), 5.16 (s, 2H), 4.71 (s, 2H), 4.16 (s, 2H), 3.36 (s, 3H), 3.21 (p, J=7.0 Hz, 1H), 1.12 (d, J=6.9 Hz, 6H), 0.90 (s, 9H), 0.08 (s, 6H).

Intermediate C13

Synthesis of (3,5-dichloro-4-(3-isopropyl-4-(methoxymethoxy)benzyl)phenyl)methanol (C13)

C13

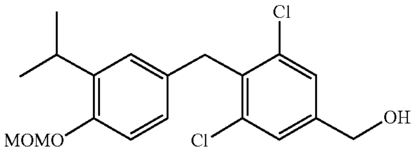

To a solution of C12 (1.5 g, 3.1 mmol, 1.0 eq) in THF (10 mL) was added TBAF (1 M in THF, 3.1 mL, 3.1 mmol, 1.0 eq) and the reaction was stirred at rt for 30 min. The mixture was washed with water (20 mL) and brine (20 mL), dried over $Na_2SO_4$ and concentrated in vacuo to afford Intermediate C13 (0.80 g, 71% yield) as a yellow oil.

TLC: EtOAc/pet. ether=1/5, Rf=0.35

$^1H$ NMR: (400 MHz, DMSO-$d_6$) δ 7.42 (s, 2H), 7.10 (d, J=2.2 Hz, 1H), 6.91 (d, J=8.4 Hz, 1H), 6.81 (dd, J=8.3, 2.3 Hz, 1H), 5.42 (t, J=5.9 Hz, 1H), 5.16 (s, 2H), 4.49 (d, J=5.8 Hz, 2H), 4.16 (s, 2H), 3.36 (s, 3H), 3.22 (p, J=7.0 Hz, 1H), 1.13 (d, J=6.9 Hz, 6H).

Intermediate C14

Synthesis of 1,3-dichloro-5-(chloromethyl)-2-(3-isopropyl-4-(methoxymethoxy)benzyl)benzene (C14)

C14

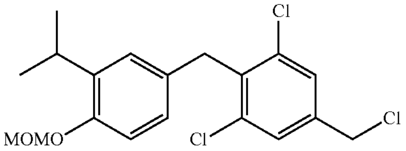

To a solution of C13 (0.0 g, 1.9 mmol, 1.0 eq) in DCM (5 mL) at 0° C. was added $SOCl_2$ (0.20 g, 1.9 mmol, 1.0 eq) and the mixture was concentrated in vacuo to afford Intermediate C14 (600 mg, yield 79.4%) which was used in the next step without purification.

TLC: EtOAc/pet. ether=1/5, Rf=0.67

Intermediate C15

Synthesis of ethyl (3,5-dichloro-4-(3-isopropyl-4-(methoxymethoxy)benzyl)benzyl)glycinate (C15)

C15

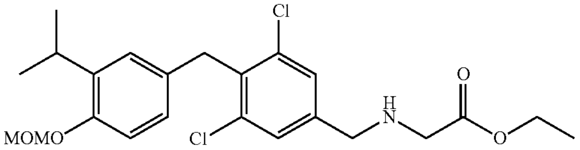

To a solution of C14 (0.90 g, 2.3 mmol, 1.0 eq) in DMF (5 mL) was added ethyl glycinate (0.7 g, 6.8 mmol, 3.0 eq) and TEA (1.2 g, 11.4 mmol, 5.0 eq) and the reaction was stirred at rt overnight. Water (20 mL) was added and the mixture was extracted with EtOAc (20 mL*2). The combined organic phase was washed with brine (20 mL), dried over $Na_2SO_4$ and concentrated in vacuo to afford crude Intermediate C15 (800 mg, yield 77.3%) that was used directly in the next reaction without purification.

TLC: EtOAc/pet. ether=1/5, Rf=0.23.

Intermediate C16

Synthesis of methyl 2-(4-(3-bromo-2-fluoro-4-hydroxybenzyl)-3,5-dichlorophenyl)acetate (C16)

C16

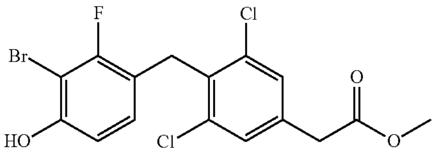

To a solution of A17 (400 mg, 1.28 mmol, 1.0 eq) in chlorobenzene (6 mL) at rt was added 2-bromo-3-fluorophenol (735 mg, 3.85 mmol, 3.0 eq) and $ZnCl_2$ (437 mg, 3.21 mmol, 2.5 eq). The reaction was heated to 160° C. under microwave for 2 h. The reaction mixture was diluted with DCM (20 mL), washed with brine (10 mL*2), dried over $Na_2SO_4$ and concentrated under reduce pressure. The crude product was purified by silica gel column chromatography (EtOAc/pet. ether-1/3) to afford Intermediate C16 (100 mg, 18.5% yield) as a light yellow oil.

TLC: EtOAc/pet. ether=1/3 (v/v), $R_f$=0.25

$^1$H NMR: (400 MHz, DMSO-$d_6$) δ 10.58 (d, J=2.0 Hz, 1H), 7.46 (s, 2H), 6.69 (dd, J=8.4, 1.2 Hz, 1H), 6.58 (t, J=8.4 Hz, 1H), 4.15 (s, 2H), 3.77 (s, 2H), 3.64 (s, 2H).

Intermediate C17

Synthesis of 4-(2,6-dichloro-4-(dibenzylamino)benzyl)-3-fluoro-2-isopropylphenol (C17)

C17

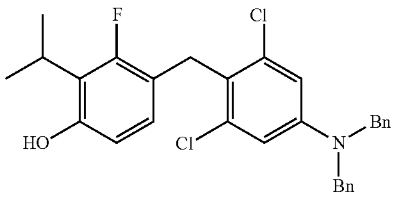

To a solution of A30 (523 mg, 1.34 mmol, 1.0 eq) in DCE (5.0 mL) was added B2 (619 mg, 4.02 mmol, 3.0 eq) and $ZnCl_2$ (365 mg, 2.68 mmol, 2.0 eq). The mixture was stirred at 80° C. overnight, then cooled and diluted with DCM (30 mL). The organic phase was washed with water (20 mL*2) and brine (30 mL), dried over $Na_2SO_4$ and concentrated in vacuo. The residue was purified by silica gel column chromatography (pet. ether/EtOAc=100/1 to 30/1) to afford Intermediate C17 (244 mg, 35.9% yield) as a colorless oil.

TLC: Pet. ether/EtOAc=1/5 (v/v), Rf=0.45

$^1$H NMR: (400 MHz, DMSO-$d_6$) δ 9.48 (s, 1H), 7.39-7.32 (m, 4H), 7.29-7.23 (m, 7H), 6.74 (s, 2H), 6.46 (s, 1H), 6.28 (s, 1H), 4.74 (s, 4H), 3.90 (s, 2H), 3.37 (d, J=7.2 Hz, 1H), 1.24 (d, J=7.2 Hz, 6H).

Intermediate C18

Synthesis of 4-(4-amino-2,6-dichlorobenzyl)-3-fluoro-2-isopropylphenol (C18)

C18

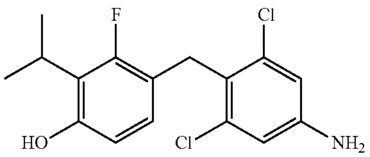

To a solution of C17 (800 mg, 1.75 mmol) in THF (10.0 mL) was added Pd/C (500 mg). The mixture was degassed under reduced pressure and refilled with $H_2$ three times, then the reaction was stirred under 1 atm $H_2$ at rt overnight. The mixture was filtered and concentrated in vacuo to afford Intermediate C18 (330 mg, 63.9% yield) as a yellow solid.

TLC: Pet. ether/EtOAc=1/3 (v/v), Rf=0.50

$^1$H NMR: (400 MHz, DMSO-$d_6$) δ 9.46 (s, 1H), 6.65 (s, 2H), 6.47 (d, J=8.4 Hz, 1H), 6.29 (t, J=8.4 Hz, 1H), 5.61 (s, 2H), 3.90 (s, 2H), 3.38 (d, J=7.2 Hz, 1H), 1.26 (d, J=7.2 Hz, 7H).

Intermediate C19

Synthesis of 2-bromo-4-(2,6-dichloro-4-(dibenzylamino)benzyl)-3-fluorophenol (C19)

C19

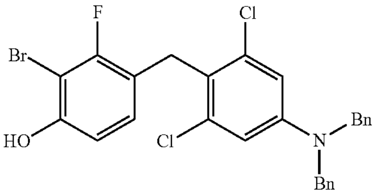

To a solution of 2-bromo-3-fluorophenol (9.2 g, 48 mmol, 3.0 eq) in DCE (50 mL) were added A30 (6.3 g, 16 mmol, 1.0 eq) and $ZnCl_2$ (1 Min THF, 32 mmol, 2.0 eq). The mixture was stirred at 70° C. overnight, then was diluted with DCM (20 mL). The organic phase was washed with water (20 mL) and brine (20 mL), dried over $Na_2SO_4$ and concentrated in vacuo. The residue was purified by silica gel column chromatography (pet. ether/EtOAc=30:1) to afford Intermediate C19 (4.79 g, 54.5% yield) as a red oil.

TLC: Pet. ether:EtOAc=5:1 (v/v), $R_F$=0.5

$^1$H NMR: (400 MHz, DMSO-$d_6$) δ 10.50 (d, J=2.0, 1H), 7.42-7.30 (m, 4H), 7.25 (m, 6H), 6.72 (s, 2H), 6.66 (dd, J=8.8, 1.6 Hz, 1H), 6.56 (t, J=8.4 Hz, 1H), 4.73 (s, 4H), 3.96 (s, 2H).

Intermediate C20

Synthesis of 4-(2,6-dichloro-4-(dibenzylamino)benzyl)-3-fluoro-2-(1-(4-fluorophenyl)vinyl)phenol (C20)

C20

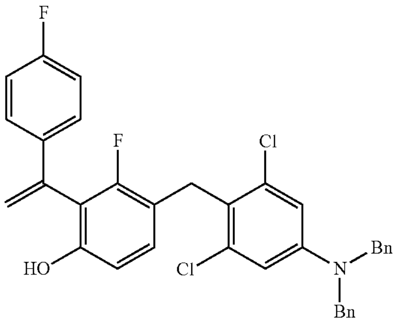

To a solution of B6 (1.1 g, 4.4 mmol, 2.0 eq) in 1,4-dioxane (10 mL) and water (2 mL) at rt were added C19 (1.2 g, 2.2 mmol, 1.0 eq), Pd(dppf)$Cl_2$ (161 mg, 220 μmol, 0.1 eq) and $NaHCO_3$ (555 mg, 6.60 mmol, 3.0 eq). The mixture was stirred at 95° C. overnight, then was diluted with EtOAc (20 mL) and filtered. The filtrate was washed with brine (30 mL), dried over $Na_2SO_4$ and concentrated in vacuo. The residue was purified by silica gel column chromatography (pet. ether/EtOAc=20:1) to afford Intermediate C20 (1.2 g, 93% yield) as a yellow solid TLC: Pet. ether/EtOAc=5/1 (v/v), Rf=0.36.

Intermediate C21

Synthesis of 4-(4-amino-2,6-dichlorobenzyl)-3-fluoro-2-(1-(4-fluorophenyl)ethyl)phenol (C21)

C21

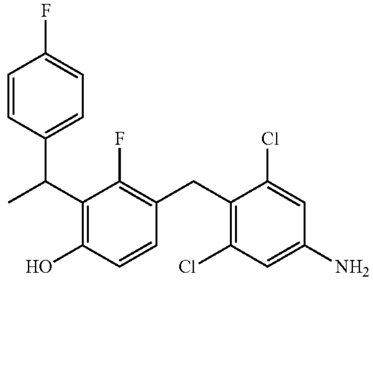

To a solution of C20 (1.2 g, 2.1 mmol) in THF (12 mL) was added Pd/C (382 mg). The mixture was stirred under 1 atm $H_2$ at rt overnight, then filtered and concentrated in vacuo to afford Intermediate C21 (800 mg, 93.9% yield) as a yellow oil.

TLC: Pet. ether/EtOAc=3/1 (v/v), Rf=0.3.

Intermediate C22

Synthesis of N-(3,5-dichloro-2-fluoro-4-(4-hydroxy-3-isopropylbenzyl)phenyl)acetamide (C22)

C22

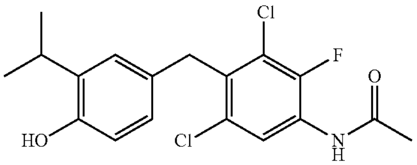

To a solution of A61 (800 mg, 2.54 mmol, 1.0 eq) in DCE (5 mL) at rt were added 2-isopropylphenol (692 mg, 5.08 mmol, 2.0 eq) and $ZnCl_2$ (865 mg, 6.35 mmol, 2.5 eq). The reaction was heated to 90° C. overnight, then the mixture was cooled and diluted with DCM (30 mL). The organic phase was washed with brine (20 mL*2), dried over $Na_2SO_4$ and concentrated under reduce pressure. The crude material was purified by Prep-TLC (pet. ether/EtOAc=5/1) to afford Intermediate C22 (180 mg, 19.1% yield) as a yellow solid.

TLC: Pet. ether/EtOAc=5/1 (v/v), Rf=0.24

LCMS: T=1.672 min, [M−1]=367.9

$^1H$ NMR: (400 MHz, DMSO-$d_6$) δ 9.11 (s, 1H), 8.11 (d, J=6.8 Hz, 1H), 6.99 (d, J=2.0 Hz, 1H), 6.68 (dd, J=8.4, 2.0 Hz, 1H), 6.65 (d, J=8.4 Hz, 2H), 4.09 (s, 2H), 3.13 (m, 1H), 2.12 (s, 3H), 1.11 (d, J=6.8 Hz, 6H).

Intermediate C23

Synthesis of 4-(4-amino-2,6-dichloro-3-fluorobenzyl)-2-isopropylphenol (C23)

C23

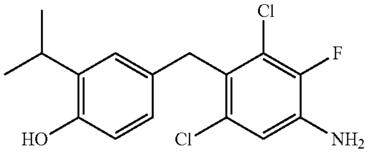

To a solution of C22 (180 mg, 0.49 mmol, 1.0 eq) in $H_2O$/THF (1 mL/3 mL) was added NaOH (190 mg, 4.9 mmol, 10 eq) and the reaction was stirred at 100° C. overnight. The mixture was diluted with water (20 mL), acidified to pH=6-8 with 2 N HCl and extracted with EtOAc (20 mL*2). The combined organic phase was washed with brine (10 mL*2), dried over $Na_2SO_4$ and concentrated under reduced pressure. The crude material was purified by Prep-HPLC to afford Intermediate C23 (66 mg, 410% yield) as a yellow solid.

TLC: Pet. ether/EtOAc=3/1 (v/v), Rf=0.48

LCMS: T=1.864 min, [M+1]=328.0

$^1H$ NMR: (400 MHz, DMSO-$d_6$) δ 9.06 (s, 1H), 6.95 (d, J=1.6 Hz, 1H), 6.84 (d, J=8.0 Hz, 1H), 6.66 (dd, J=8.4, 2.0 Hz, 1H), 6.63 (d, J=8.0 Hz, 1H), 3.95 (s, 2H), 3.12 (p, J=6.8 Hz, 1H), 1.10 (d, J=6.8 Hz, 6H).

Intermediate C24

Synthesis of N-(3,5-dichloro-2-fluoro-4-(2-fluoro-4-hydroxy-3-isopropylbenzyl)phenyl)acetamide (C24)

C24

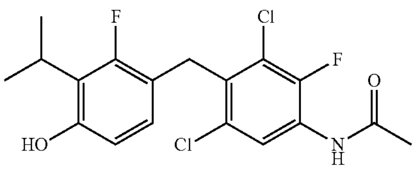

To a solution of A61 (600 mg, 1.90 mmol, 1.0 eq) in DCE (10 mL) at rt were added B2 (587 mg, 3.81 mmol, 2.0 eq) and $ZnCl_2$ (649 mg, 4.76 mmol, 2.5 eq). The reaction was heated to 90° C. and stirred overnight, then the mixture was cooled and diluted with DCM (50 mL). The organic phase was washed with brine (20 mL*2), dried over $Na_2SO_4$ and concentrated under reduced pressure. The crude material was purified by Prep-TLC (pet. ether/EtOAc=3/1) to afford Intermediate C24 (170 mg, 23.0% yield) as a white solid.

TLC: Pet. ether/EtOAc=5/1 (v/v), Rf=0.23

LCMS: T=1.888 min, [M−1]=386.0

$^1$H NMR: (400 MHz, DMSO-$d_6$) δ 10.11 (s, 1H), 9.59 (d, J=1.6 Hz, 1H), 8.14 (d, J=6.8 Hz, 1H), 6.48 (dd, J=8.4, 1.2 Hz, 1H), 6.31 (t, J=8.8 Hz, 1H), 4.07 (s, 2H), 3.41-3.36 (m, 1H), 2.13 (s, 3H), 1.25 (d, J=7.2 Hz 6H).

Intermediate C25

Synthesis of 4-(4-amino-2,6-dichloro-3-fluorobenzyl)-3-fluoro-2-isopropylphenol (C25)

C25

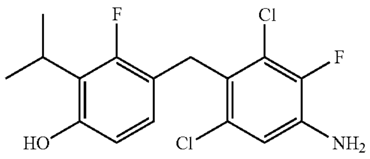

To a solution of C24 (170 mg, 0.44 mmol, 1.0 eq) in water/THF (1 mL/3 mL) was added NaOH (175 mg, 4.38 mmol, 10 eq) and the reaction was stirred at 100° C. overnight. The mixture was diluted with EtOAc (20 mL), washed with brine (10 mL*2), dried over $Na_2SO_4$ and concentrated under reduce pressure. The crude material was purified by Prep-TLC (pet. ether/EtOAc=3/1) to afford Intermediate C25 (120 mg, 79.2% yield) as a yellow solid.

TLC: Pet. ether/EtOAc=3/1 (v/v), Rf=0.50

LCMS: T=2.792 min, [M−1]=344.0

$^1$H NMR: (400 MHz, DMSO-$d_6$) δ 9.52 (d, J=1.2 Hz, 1H), 6.86 (d, J=8.0 Hz, 1H), 6.47 (dd, J=8.4, 1.2 Hz, 1H), 6.28 (t, J=8.4 Hz, 1H), 5.74 (s, 2H), 3.93 (s, 2H), 3.41-3.36 (m, 1H), 1.25 (d, J=6.8 Hz, 6H).

Intermediate C26

Synthesis of (4-(benzyloxy)-2,6-dichlorophenyl)(3-isopropyl-4-((triisopropylsilyl)oxy)phenyl)methanol (C26)

C26

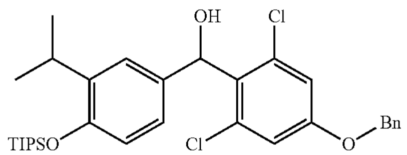

To a solution of B9 (16.0 g, 38.2 mmol, 1.1 eq) in THE (100 mL) at −20° C. was added dropwise iPrMgCl (1 M, 77 mL, 77 mmol, 2.2 eq). The reaction was stirred for 3 h at ~−20° C. then cooled to −50° C. A solution of A62 (9.7 g, 34.7 mmol, 1.0 eq) in THE (25 mL) was added dropwise and the reaction stirred for 1 h at −50° C. The reaction was quenched by the addition of saturated, aqueous $NH_4Cl$ (200 mL) and extracted with EtOAc (100 mL*2). The combined organic phase was washed with brine (100 mL*2), dried over $Na_2SO_4$ and concentrated under reduced pressure. The crude product was purified using silica gel column chromatography (EtOAc/pet. ether-1/200~1/10) to afford Intermediate C26 (7.5 g, 38% yield) as a light yellow oil.

TLC: EtOAc/pet. ether=1/10, Rf=0.46

$^1$H NMR: (400 MHz, DMSO-$d_6$) δ 7.47-7.29 (m, 6H), 7.24 (d, J=2.3 Hz, 1H), 7.10 (s, 2H), 6.82 (dd, J=8.3, 1.7 Hz, 1H), 6.66 (d, J=8.4 Hz, 1H), 6.34 (d, J=5.0 Hz, 1H), 5.92 (d, J=5.0 Hz, 1H), 5.14 (s, 2H), 3.32-3.24 (m, 1H), 1.31-1.24 (m, 3H), 1.11 (dd, J=8.3, 6.9 Hz, 6H), 1.05 (d, J=7.4 Hz, 18H).

Intermediate C27

Synthesis of 3,5-dichloro-4-(3-isopropyl-4-((triisopropylsilyl)oxy)benzyl)phenol (C27)

C27

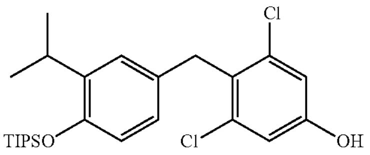

To a solution of C26 (3.0 g, 5.2 mmol) in THF (30 mL) was added Pd/C (0.3 g) and the mixture was heated to 70° C. under 1 atm $H_2$ for 7 h. The reaction mixture was filtered and the filtrate concentrated under reduced pressure. The residue was purified through silica gel column chromatography (EtOAc/pet. ether=1/200-1/30) to afford Intermediate C27 (1.6 g, 65% yield) as a white solid.

TLC: EtOAc/pet. ether=1/10, Rf=0.15

$^1$H NMR: (400 MHz, DMSO-$d_6$) δ 10.23 (s, 1H), 7.05 (d, J=2.2 Hz, 1H), 6.87 (s, 2H), 6.74 (dd, J=8.3, 2.2 Hz, 1H), 6.65 (d, J=8.3 Hz, 1H), 4.03 (s, 2H), 3.30-3.22 (m, 1H), 1.28 (p, J=7.5 Hz, 3H), 1.12 (d, J=6.9 Hz, 6H), 1.05 (d, J=7.4 Hz, 18H).

Intermediate C28

Synthesis of ethyl 2-(3,5-dichloro-4-(3-isopropyl-4-((triisopropylsilyl)oxy)benzyl)phenoxy)-2-fluoroacetate (C28)

C28

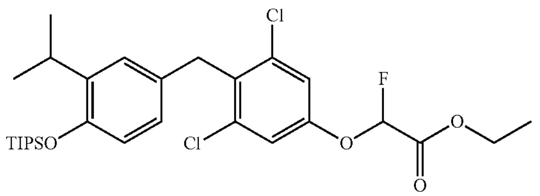

To a solution of C27 (200 mg, 0.43 mmol, 1.0 eq) and ethyl 2-bromo-2-fluoroacetate (79 mg, 0.43 mmol, 1.0 eq) in DMF (3 mL) at rt was added $K_2CO_3$ (120 mg, 0.86 mmol, 2.0 eq) and the mixture was allowed to stir overnight. The reaction was diluted with EtOAc (20 mL), washed with water (20 mL*2) and brine (10 mL*2), dried over $Na_2SO_4$ and concentrated under reduced pressure. The crude product was purified through Prep-TLC (EtOAc/pet. ether=1/10) to afford Intermediate C28 (243 mg, 99.5% yield) as a white solid.

TLC: EtOAc/pet. ether=1/10, Rf=0.45.

Intermediate C29

Synthesis of 2-(3,5-dichloro-4-(3-isopropyl-4-((triisopropylsilyl)oxy)benzyl)phenoxy)-2,2-difluoroacetic acid (C29)

C29

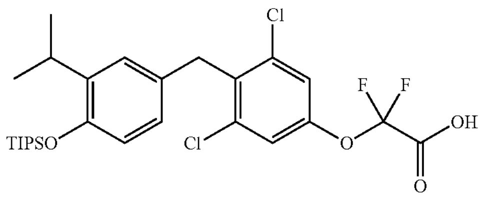

To a solution of C27 (100 mg, 0.21 mol, 1.0 eq) and 2-bromo-2,2-difluoroacetic acid (37 mg, 0.21 mmol, 1.0 eq) in 1,4-dioxane (1 mL) at 0° C. was added NaH (21 mg, 0.53 mmol, 60% purity in mineral oil, 2.5 eq) and the reaction was heated to 100° C. for 3 h. The reaction mixture was carefully quenched with aqueous HCl (2N), diluted with water (2 mL), and extracted with EtOAc (2 mL*2). The combined organic phase was washed with brine (2 mL*2), dried over $Na_2SO_4$ and concentrated under reduce pressure to afford Intermediate C29 (98 mg, 82% yield) as a light yellow oil.

TLC: EtOAc/pet. ether=1/3, Rf=0.34

$^1$H NMR: (400 MHz, DMSO-$d_6$) δ 7.44 (s, 2H), 7.08 (d, J=2.3 Hz, 1H), 6.74 (dd, J=8.3, 2.3 Hz, 1H), 6.67 (d, J=8.3 Hz, 1H), 4.15 (s, 2H), 3.31-3.21 (m, 1H), 1.32-1.23 (m, 3H), 1.12 (d, J=7.0 Hz, 6H), 1.05 (d, J=7.4 Hz, 18H).

Intermediate C30

Synthesis of (4-(benzyloxy)-3-isopropylphenyl)(2,6-dichloro-4-(methoxymethoxy)phenyl)methanol (C30)

C30

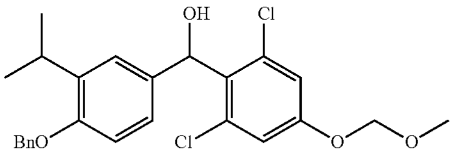

To a solution of B10 (32.0 g, 90.9 mmol, 1.3 eq) in THF (350 mL) at −40° C. was added iPrMgCl (2 M in THF, 70 mL, 140 mmol, 2.0 eq) dropwise. The mixture was stirred at rt for 2 h, then cooled to −70° C., and a solution of A63 (16.4 g, 69.9 mmol, 1.0 eq) in THF (20 mL) was added dropwise. The reaction was stirred at −70° C. for 2 h, then quenched with $NH_4Cl$ (sat. aq., 10 mL) and the resulting mixture was extracted with EtOAc (40 mL*2). The combined organic phase was washed with brine (100 mL), dried over $Na_2SO_4$ and concentrated under reduced pressure. The residue was purified by silica gel column chromatography (pet. ether/EtOAc=100:1 to 10:1) to afford Intermediate C30 (24.0 g, 74.1% yield) as a yellow liquid.

$^1$H NMR: (400 MHz, DMSO-d6) δ 7.47-7.36 (m, 4H), 7.34-7.27 (m, 2H), 7.11 (s, 2H), 6.92 (d, J=2.0 Hz, 2H), 6.37 (d, J=4.8 Hz, 1H), 5.96 (d, J=4.8 Hz, 1H), 5.24 (s, 2H), 5.07 (s, 2H), 3.38 (s, 3H), 3.30-3.22 (m, 1H), 1.14 (dd, J=8.3, 6.8 Hz, 6H).

Intermediate C31

Synthesis of 4-(4-(benzyloxy)-3-isopropylbenzyl)-3,5-dichlorophenol (C31)

C31

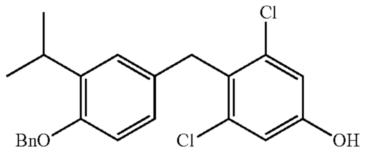

To a solution of C30 (240 g, 52 mmol) in DCM (250 mL) at 0° C. were added $Et_3SiH$ (24.2 g, 208 mmol, 4.0 eq) and TFA (177.9 g, 1.56 mol, 30 eq). The reaction was stirred at rt for 3 h, then washed with brine (100 mL), dried over $Na_2SO_4$ and concentrated under reduced pressure. The crude material was purified by silica gel column chromatography (pet. ether/EtOAc=100:1-30:1) to afford Intermediate C31 (9.5 g, 47% yield) as a yellow oil.

LCMS: T=3.712 min, [M−1]=399.1

$^1$H NMR: (400 MHz, DMSO-$d_6$) δ 10.25 (s, 1H), 7.46-7.28 (m, 5H), 7.06 (s, 1H), 6.92-6.86 (m, 3H), 6.80 (d, J=8.4 Hz, 1H), 5.05 (s, 2H), 4.05 (s, 2H), 3.24 (p, J=6.8 Hz, 1H), 1.13 (d, J=6.8 Hz, 6H).

Intermediate C32

Synthesis of ethyl 2-(4-(4-(benzyloxy)-3-isopropylbenzyl)-3,5-dichlorophenoxy)-2-fluoroacetate (C32)

C32

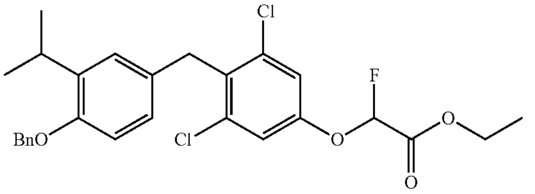

To a solution of C31 (200 mg, 0.50 mmol, 1.0 eq) and $K_2CO_3$ (207 mg, 1.50 mmol, 3.0 eq) in DMF (10 mL) at rt was added ethyl 2-bromo-2-fluoroacetate (101 mg, 0.55 mmol, 1.1 eq). The reaction was stirred at rt overnight, then water (20 mL) was added and the mixture was extracted with EtOAc (20 mL*2). The combined organic phase was washed with brine (30 mL), dried over $Na_2SO_4$ and concentrated in vacuo to afford Intermediate C32 (230 mg, 91.3% yield) as a white solid.

$^1$H NMR: (400 MHz, DMSO-$d_6$) δ 7.45-7.36 (m, 5H), 7.34-7.28 (m, 1H), 7.09 (d, J=2.0 Hz, 1H), 6.91 (d, J=8.4 Hz, 1H), 6.82 (d, J=2.4 Hz, 1H), 6.73 (s, 1H), 6.58 (s, 1H), 5.06 (s, 2H), 4.30 (q, J=7.2 Hz, 2H), 4.14 (s, 2H), 3.24 (p, J=6.8 Hz, 1H), 1.26 (t, J=7.2 Hz, 3H), 1.13 (d, J=6.8 Hz, 6H).

Intermediate C33

Synthesis of 2-(4-(4-(benzyloxy)-3-isopropylbenzyl)-3,5-dichlorophenoxy)-2-fluoro-N-methylacetamide (C33)

C33

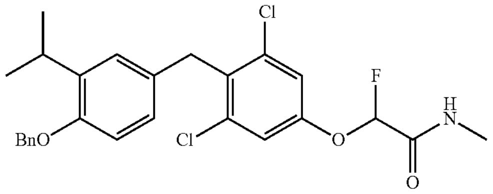

To a solution of C32 (100 mg, 0.20 mmol, 1.0 eq) in THE (8 mL) was added Methylamine (18 mg, 0.60 mmol, 3.0 eq). The reaction mixture was stirred in a sealed tube at 65° C. overnight, then water (10 mL) was added and the mixture was extracted with EtOAc (10 mL*2). The combined organic phase was washed with brine (20 mL), dried over $Na_2SO_4$ and concentrated under reduced pressure. The crude material was purified by Prep-TLC to afford Intermediate C33 (90 mg, 93% yield) as a white solid.

$^1$H NMR: (400 MHz, DMSO-$d_6$) δ 8.57 (d, J=4.8 Hz, 1H), 7.46-7.36 (m, 5H), 7.32 (t, J=7.2 Hz, 1H), 7.09 (d, J=2.0 Hz, 1H), 6.92 (d, J=8.4 Hz, 1H), 6.81 (dd, J=8.4, 2.4 Hz, 1H), 6.46 (s, 1H), 6.32 (s, 1H), 5.06 (s, 2H), 4.14 (s, 2H), 3.21 (s, 1H), 2.69 (d, J=4.8 Hz, 3H), 1.13 (d, J=6.8 Hz, 6H).

Intermediate C34

Synthesis of 2-(4-(4-(benzyloxy)-3-isopropylbenzyl)-3,5-dichlorophenoxy)-2,2-difluoroacetic acid (C34)

C34

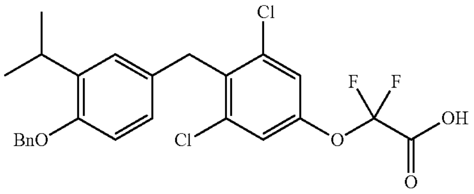

A mixture of 2-bromo-2,2-difluoroacetic acid (200 mg, 1.14 mmol, 1.0 eq) and C31 (459 mg, 1.14 mmol, 1.0 eq) in 1,4-dioxane (5.0 mL) was cooled to 0° C. NaH (60% dispersion in mineral oil, 114 mg, 2.9 mmol, 2.5 eq) was added and the reaction was heated to 100° C. for 2 h. After cooling, water (30 mL) was carefully added and the mixture was acidified to pH=2-3 with 1 N HCl, and extracted with EtOAc (15 mL*3). The combined organic phase was washed with brine (30 mL), dried over $Na_2SO_4$ and concentrated in vacuo to afford Intermediate C34 (420 mg, 74.2% yield) as a light yellow oil.

TLC: MeOH/DCM=1/10 (v/v), Rf=0.40

LCMS: T=4.031 min, [M−1]=493.0

$^1$H NMR: (400 MHz, DMSO-$d_6$) δ 7.45 (s, 2H), 7.45-7.35 (m, 4H), 7.32 (d, J=7.0 Hz, 1H), 7.10 (d, J=2.0 Hz, 1H), 6.92 (d, J=8.8 Hz, 1H), 6.82 (dd, J=8.4, 2.4 Hz, 1H), 5.06 (s, 2H), 4.17 (s, 2H), 3.24 (h, J=6.8 Hz, 1H), 1.14 (d, J=6.8 Hz, 6H).

Intermediate C35

Synthesis of 2-(4-(4-(benzyloxy)-3-isopropylbenzyl)-3,5-dichlorophenoxy)-2,2-difluoroacetyl chloride (C35)

C35

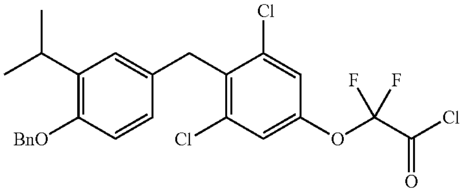

To a solution of C34 (200 mg, 404 μmol, 1.0 eq) in DCM (2.0 mL) was added DMF (0.01 mL). The mixture was cooled to 0° C. and oxalyl chloride (150 mg, 1.2 mmol, 3.0 eq) was added. The reaction was stirred at rt for 30 min and was then concentrated in vacuo to afford crude Intermediate C35 (200 mg, 96.4% yield) as a yellow solid.

TLC: EtOAc/pet. ether=1/5 (v/v), Rf=0.60.

Intermediate C36

Synthesis of 2-(4-(4-(benzyloxy)-3-isopropylbenzyl)-3,5-dichlorophenoxy)-2,2-difluoro-N-methylacetamide (C36)

C36

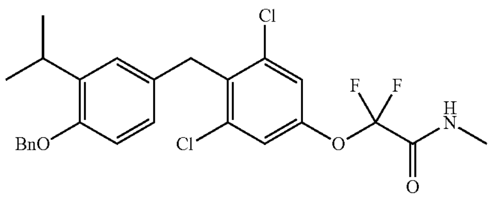

To a solution of C35 (2.0 g, 4.9 mmol) in DCM (5.0 mL) was added $CH_3NH_2$ (2 M, in THF, 2.0 mL). The reaction was stirred at rt for 1 h, then water (20 mL) was added and the mixture extracted with DCM (15 mL*3). The combined organic phase was washed with brine (30 mL), dried over $Na_2SO_4$ and concentrated in vacuo. The crude material was purified by Prep-HPLC to afford Intermediate C36 (190 mg, 95.9% yield) as a white solid.

TLC: EtOAc/pet. ether=1/3 (v/v), Rf=0.45.

Intermediate C37

Synthesis of 3,5-dichloro-4-(3-isopropyl-4-(methoxymethoxy)benzyl)benzaldehyde (C37)

C37

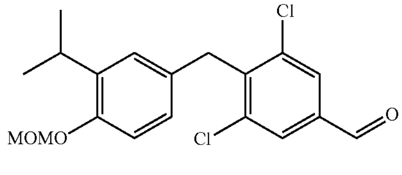

To a solution of C13 (1.0 g, 2.7 mmol, 1.0 eq) in DCM (10.0 mL) was added Dess-Martin periodinane (1.3 g, 3.0 mmol, 1.1 eq). The reaction was stirred at rt for 2 h, then water (30 mL) was added and the mixture was extracted with DCM (20 mL*3). The combined organic phase was washed with $NaHCO_3$ (2 M, 15 mL*2) and brine (30 mL), dried over $Na_2SO_4$ and concentrated in vacuo to afford Intermediate C37 (990 mg, 99.5% yield) as a yellow solid.

TLC: EtOAc/pet. ether=1/10 (v/v), $R_f$=0.60

$^1$H NMR: (400 MHz, DMSO-$d_6$) δ 9.99 (d, J=0.8 Hz, 1H), 8.04 (t, J=1.2 Hz, 2H), 7.16 (d, J=2.4 Hz, 1H), 6.96 (d, J=8.4 Hz, 1H), 6.88 (d, J=2.4 Hz, 1H), 5.20 (s, 2H), 4.30 (s, 2H), 3.40 (s, 3H), 3.26 (s, 1H), 1.17 (d, J=6.8 Hz, 6H).

Intermediate C38

Synthesis of 1-(tert-butyl) 3-ethyl (E)-2-(3,5-dichloro-4-(3-isopropyl-4-(methoxymethoxy)benzyl) benzylidene)malonate (C38)

C38

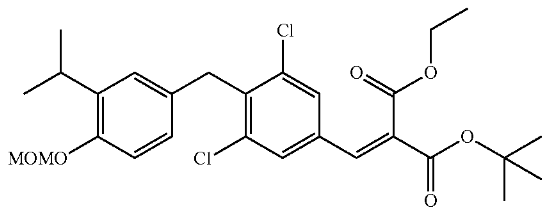

To a solution of C37 (1.1 g, 3.00 mmol, 1.0 eq) in toluene (20 mL) were added tert-butyl ethyl malonate (850 mg, 4.5 mmol, 1.5 eq) and piperidine (102 mg, 1.2 mmol). The reaction was stirred at 110° C. overnight, then water (40 mL) was added and the mixture was extracted with EtOAc (20 mL*3). The combined organic phase was washed with brine (40 mL), dried over $Na_2SO_4$ and concentrated under reduced pressure. The crude material was purified by silica gel column chromatography (EtOAc/pet. ether=1/100 to 1/20) to afford Intermediate C38 (400 mg, 24.9% yield) as a light yellow solid.

TLC: EtOAc/pet. ether=1/15 (v/v), Rf=0.40

$^1$H NMR: (400 MHz, DMSO-$d_6$) δ 7.70 (s, 2H), 7.63 (s, 1H), 7.07 (d, J=2.4 Hz, 1H), 6.93 (d, J=8.4 Hz, 1H), 6.85 (dd, J=8.4, 2.4 Hz, 1H), 5.17 (s, 2H), 4.25 (q, J=7.2 Hz, 2H), 4.21 (s, 2H), 3.37 (s, 3H), 3.22 (p, J=6.8 Hz, 1H), 1.49 (s, 9H), 1.27 (d, J=7.2 Hz, 3H), 1.12 (d, J=6.8 Hz, 6H).

Intermediate C39

Synthesis of methyl 2-((3,5-dichloro-4-(3-isopropyl-4-(methoxymethoxy)benzyl)benzyl)thio)acetate (C39)

C39

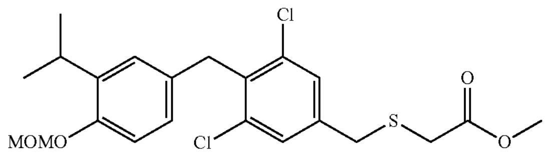

To a solution of C14 (523 mg, 1.35 mmol, 1.0 eq) in EtOH (5 mL) was added methyl 2-mercaptoacetate (287 mg, 2.70 mmol, 2.0 eq) and AcONa (222 mg, 2.70 mmol, 2.0 eq). The reaction was stirred at 90° C. overnight, then cooled to rt and concentrated in vacuo. Water (20 mL) was added and the mixture was extracted with EtOAc (20 mL*2). The combined organic phase was washed with brine (40 mL), dried over $Na_2SO_4$ and concentrated in vacuo to afford crude Intermediate C39 (600 mg, 97.1% yield) as a colorless oil.

Intermediate C40

Synthesis of methyl 3-(3,5-dichloro-4-(3-isopropyl-4-((tetrahydro-2H-pyran-2-yl)oxy)benzyl)phenyl) propiolate (C40)

C40

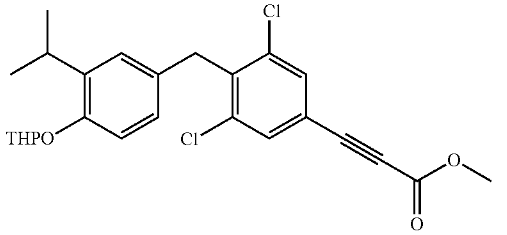

To a mixture of C4 (1.2 g, 2.6 mmol, 1.0 eq), methyl propiolate (661 mg, 7.9 mmol, 3.0 eq), $Pd(PPh_3)_2Cl_2$ (92 mg, 130 μmol, 0.05 eq), CuI (25 mg, 131 μmol, 0.05 eq), $Au(PPh_3)Cl$ (124.16 mg, 262 μmol, 0.1 eq) and TBAI (1.9 g, 5.2 mmol, 2.0 eq) in DMF (10.0 mL) was added $Et_3N$ (800 mg, 7.9 mmol, 3.0 eq). The reaction was stirred at 100° C. for 4 h, and was then cooled to rt, quenched with water (40 mL), and extracted with EtOAc (20 mL*3). The combined organic phase was washed with brine (40 mL), dried over $Na_2SO_4$ and concentrated in vacuo. The crude material was purified by Prep-TLC (pet. ether/EtOAc=20/1) to afford Intermediate C40 (150 mg, 12.4% yield) as a colorless oil.

TLC: EtOAc/pet. ether=1/20 (v/v), $R_f$=0.40

$^1H$ NMR: (400 MHz, DMSO-$d_6$) δ 7.89 (s, 2H), 7.10 (d, J=2.4 Hz, 1H), 6.95 (d, J=8.4 Hz, 1H), 6.82 (dd, J=8.4, 2.4 Hz, 1H), 5.42 (t, J=3.2 Hz, 1H), 4.23 (s, 2H), 3.82 (s, 3H), 3.72 (dt, J=11.4, 4.5 Hz, 1H), 3.54 (dt, J=10.8, 4.0 Hz, 1H), 3.27 3.20 (m, 1H), 1.82 (m, 3H), 1.69-1.49 (m, 3H), 1.16 (dd, J=6.8, 5.2 Hz, 6H).

Intermediate C41

Synthesis of 3,5-dichloro-4-(4-hydroxy-3-isopropyl-benzyl)benzaldehyde (C41)

C41

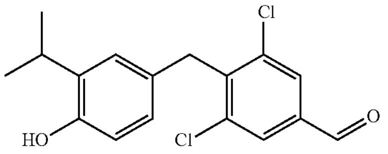

To a solution of C37 (400 mg, 1.1 mmol) in DCM (2.0 mL) was added dropwise HCl/1,4-dioxane (2.0 mL of 4N). The reaction was stirred at rt for 2 h, then water (30 mL) was added and the mixture was extracted with DCM (15 mL*3). The combined organic phase was washed with brine (30 mL), dried over $Na_2SO_4$ and concentrated in vacuo to afford crude Intermediate C41 (60 mg, 17% yield) as a light yellow oil.

TLC: EtOAc/pet. ether=1/5 (v/v), Rf=0.50.

Intermediate C42

Synthesis of 4-(4-bromo-2,6-dichlorobenzyl)-3-fluoro-2-isopropylphenol (C42)

C42

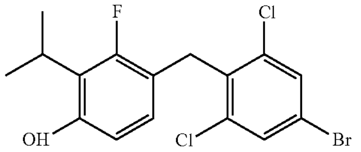

A mixture of Intermediate A21 (500 mg, 1.57 mmol), Intermediate B2 (725 mg, 4.71 mmol) and $Zn(OTf)_2$ (2.8 g, 7905 mmol) was microwaved at 160° C. with stirring for 2 h. The reaction mixture was diluted with DCM (5 mL), washed with brine (5 mL*2), dried over $Na_2SO_4$, concentrated in vacuo and purified by Prep-TLC (EtOAc/pet. ether=1/10) to afford Intermediate C42 (120 mg, 19.5% yield) as a brown oil.

TLC: Pet. ether/EtOAc=5/1 (v/v), Rf=0.21

$^1H$ NMR (400 MHz, DMSO-$d_6$) δ 9.56 (s, 1H), 7.83 (s, 2H), 6.48 (d, J=8.4 Hz, 1H), 6.29 (t, J=8.8 Hz, 1H), 4.07 (s, 2H), 3.38 (d, J=7.2 Hz, 1H), 1.25 (d, J=7.2 Hz, 6H).

Example 1

Synthesis of methyl 2-(4-(3-(1-(4-fluorophenyl) ethyl)-4-hydroxybenzyl)-3,5-dimethylphenyl)acetate (Compound 1)

Compound 1

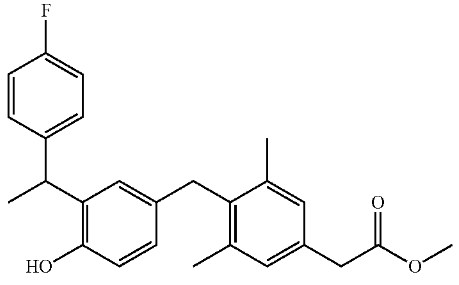

To a solution of A8 (150 mg, 0.66 mmol, 1.0 eq) in DCE (10 mL) at rt were added $ZnCl_2$ (1.99 mmol, 2 mL, 3.0 eq) and B4 (429 mg, 1.99 mmol, 3.0 eq); the mixture was heated to 85° C. for 48 h. The reaction mixture was cooled to rt, quenched with water and extracted with DCM (10 mL*2). The combined organic phase was washed with brine (10 mL*2), dried over $Na_2SO_4$ and concentrated under reduced pressure. The crude material was purified by Prep-TLC (pet. ether/EtOAc=5/1) to afford Compound 1 (85 mg, 32% yield) as a white solid.

$^1H$ NMR: (400 MHz, DMSO-$d_6$) δ 9.10 (s, 1H), 7.17 (dd, J=8.4, 5.6 Hz, 2H), 7.04 (t, J=8.8 Hz, 2H), 6.90 (s, 2H), 6.83 (d, J=2.0 Hz, 1H), 6.62 (d, J=8.0 Hz, 1H), 6.51 6.48 (m, 1H), 4.37 (d, J=7.2 Hz, 1H), 3.82 (s, 2H), 3.60 (s, 3H), 3.55 (s, 2H), 2.14 (s, 6H), 1.43 (d, J=7.2 Hz, 3H).

Example 2

Synthesis of 2-(4-(3-(1-(4-fluorophenyl)ethyl)-4-hydroxybenzyl)-3,5-dimethylphenyl)acetic acid (Compound 2)

Compound 2

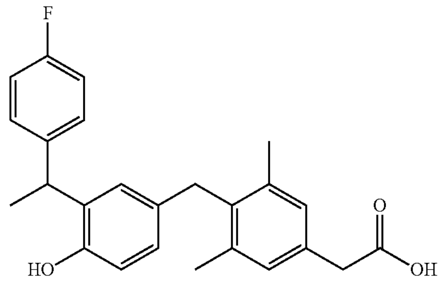

To a solution of Compound 1 (100 mg, 0.25 mmol, 1.0 eq) in THF/water (10 mL/1 mL) at rt was added LiOH·$H_2O$ (59 mg, 2.5 mmol, 10 eq). The mixture was stirred at rt for 1 h, then was adjusted to pH=3-4 with 1 N HCl and extracted with EtOAc (10 mL*3). The combined organic phase was washed with brine (10 mL), dried over $Na_2SO_4$ and concentrated in vacuo. The crude material was purified by Prep-HPLC to afford Compound 2 (50 mg, 52% yield) as a white solid.

LCMS: T=3.909 min, [M−1]=391.2

$^1$H NMR: (400 MHz, DMSO-$d_6$) δ 9.12 (s, 1H), 7.20-7.14 (m, 2H), 7.08-7.01 (m, 2H), 6.89 (s, 2H), 6.85 (d, J=2.0 Hz, 1H), 6.61 (d, J=8.0 Hz, 1H), 6.49 (dd, J=8.0, 2.0 Hz, 1H), 4.37 (d, J=7.2 Hz, 1H), 3.82 (s, 2H), 3.44 (s, 2H), 2.14 (s, 6H), 1.43 (d, J=7.2 Hz, 3H)

$^{19}$F NMR: (376 MHz, DMSO-$d_6$) δ −117.91.

Example 3

Synthesis of ethyl 3-((4-(3-(1-(4-fluorophenyl)ethyl)-4-hydroxybenzyl)-3,5-dimethylphenyl)amino)-3-oxopropanoate (Compound 3)

Compound 3

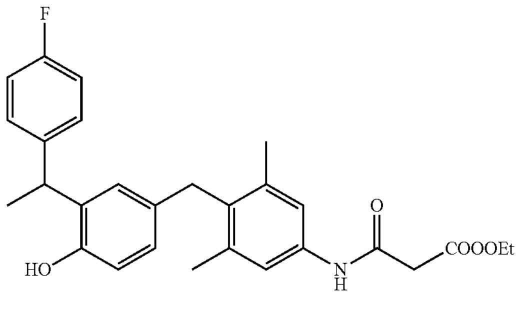

To a solution of C2 (140 mg, 0.39 mmol, 1.0 eq) and TEA (79 mg, 0.78 mmol, 2.0 eq) in DCM (5 mL) at 0° C. was added dropwise, ethyl 3-chloro-3-oxo-propanoate (59 mg, 0.39 mmol, 1.0 eq). The mixture was stirred at rt for 3 h then concentrated in vacuo to afford Compound 3 (180 mg, 99% yield) as a yellow solid that was used in the next step without further purification.

TLC: EtOAc/pet. ether=1/1, Rf=0.50.

Example 4

Synthesis of 3-((4-(3-(1-(4-fluorophenyl)ethyl)-4-hydroxybenzyl)-3,5-dimethylphenyl)amino)-3-oxo-propanoic acid (Compound 4)

Compound 4

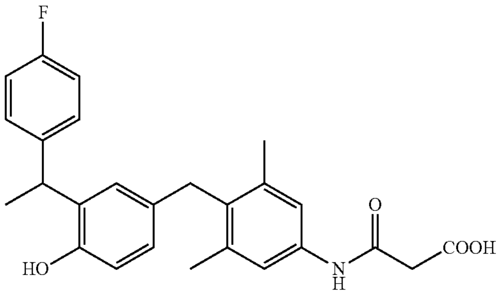

To a solution of Compound 3 (100 mg, 0.21 mmol, 1.0 eq) in THF/$H_2O$ (3/1 mL) at rt was added NaOH (17 mg, 0.42 mmol, 2.0 eq). The mixture was stirred for 2 h, then acidified to pH=4 with 1 N HCl. The aqueous layer was extracted with EtOAc (5 mL*2) and the combined organic phase was washed with brine (10 mL), dried over $Na_2SO_4$ and evaporated to dryness. The crude product was purified by Prep-HPLC to afford Compound 4 (30 mg, 32% yield) as a gray solid.

TLC: EtOAc/pet. ether=1/1 (v/v), Rf=0.05

LCMS: Rt: 3.63 min, M−1=434.1

$^1$H NMR: (400 MHz, DMSO-$d_6$) δ 9.92 (s, 1H), 9.12 (s, 1H), 7.23 (s, 2H), 7.20-7.13 (m, 2H), 7.09-7.01 (m, 2H), 6.84 (s, 1H), 6.61 (d, J=8.2 Hz, 1H), 6.49 (d, J=8.5 Hz, 1H), 4.37 (q, J=7.7, 7.2 Hz, 1H), 3.80 (s, 2H), 3.32 (s, 2H), 2.13 (s, 6H), 1.43 (d, J=7.3 Hz, 3H)

$^{19}$F NMR: (376 MHz, DMSO-$d_6$) δ −117.89.

Example 5

Synthesis of methyl 2-(3,5-dichloro-4-(4-hydroxy-3-isopropylbenzyl)phenyl)acetate (Compound Compound 5

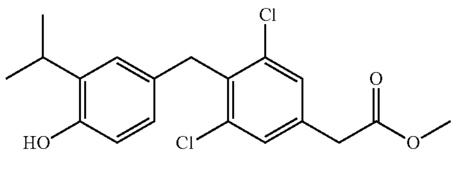

To a solution of A17 (300 mg, 0.96 mmol, 1.0 eq) in DCE (15 mL) at rt were added $ZnCl_2$ (3.36 mmol, 3.4 mL, 3.5 eq) and 2-isopropylphenol (523 mg, 3.84 mmol, 4.0 eq); the reaction mixture was heated to 90° C. overnight. The mixture was cooled to rt, water (10 mL) was added, and the mixture was extracted with DCM (10 mL*2). The combined organic phase was washed with brine (10 mL*2), dried over $Na_2SO_4$ and concentrated under reduced pressure. The crude product was purified by Prep-TLC (pet. ether/EtOAc=3/1) to afford Compound 5 (150 mg, 42.5% yield) as a light yellow oil.

TLC: Pet. ether/EtOAc=3/1 (v/v), Rf=0.19

$^1$H NMR: (400 MHz, DMSO-$d_6$) δ 9.09 (s, 1H), 7.42 (s, 2H), 7.00 (d, J=2.0 Hz, 1H), 6.69 (dd, J=8.4, 2.4 Hz, 1H), 6.64 (d, J=8.0 Hz, 1H), 4.10 (s, 2H), 3.74 (s, 2H), 3.63 (s, 3H), 3.17-3.09 (m, 1H), 1.10 (d, J=6.8 Hz, 6H).

Example 6

Synthesis of 2-(3,5-dichloro-4-(4-hydroxy-3-isopropylbenzyl)phenyl)acetic acid (Compound 6)

Compound 6

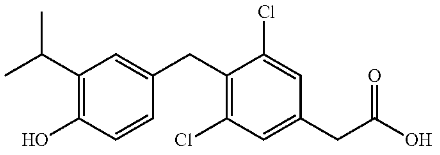

To a solution of Compound 5 (150 mg, 0.41 mmol, 1.0 eq) in water (1 mL) and THF (10 mL) was added LiOH·$H_2O$ (51 mg, 1.23 mmol, 3.0 eq), and the mixture was stirred at rt for 2 h. Water (20 mL) was added and the mixture was adjusted to pH=3-4 with 1 N HCl, then extracted with EtOAc (10 mL*3). The combined organic phase was washed with brine (10 mL), dried over $Na_2SO_4$, concentrated in vacuo to provide a crude product that was purified by Prep-HPLC to afford Compound 6 (100 mg, 69.4% yield) as a white solid.

TLC: DCM/MeOH=5/1 (v/v), Rf=0.34

LCMS: T=3.784 min, [M−1]=353.0

$^1$H NMR: (400 MHz, DMSO-$d_6$) δ 12.50 (s, 1H), 9.09 (s, 1H), 7.40 (s, 2H), 7.00 (d, J=2.0 Hz, 1H), 6.69 (dd, J=8.4, 2.4 Hz, 1H), 6.64 (d, J=8.4 Hz, 1H), 4.10 (s, 2H), 3.63 (s, 2H), 3.31-3.09 (m, 1H), 1.10 (d, J=6.8 Hz, 6H).

Example 7

Synthesis of 2-(3,5-dichloro-4-(4-hydroxy-3-isopropylbenzyl)phenyl)-N-methylacetamide (Compound 7)

Compound 7

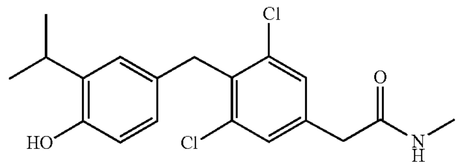

Step 1: Synthesis of 2-(3,5-dichloro-4-(4-hydroxy-3-isopropylbenzyl)phenyl)acetyl chloride (C43)

C43

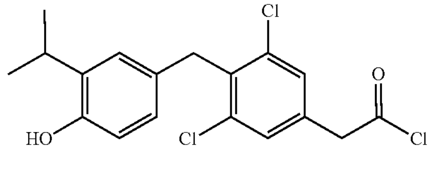

A solution of Compound 6 (60 mg, 0.17 mmol, 1.0 eq) in DCM (5 mL) and DMF (cat) was cooled to 0° C. and $(COCl)_2$ (43 mg, 0.34 mmol, 2.0 eq) was added and the mixture was stirred at rt 30 min. The mixture was concentrated to dryness to afford 2-(3,5-dichloro-4-(4-hydroxy-3-isopropylbenzyl)phenyl)acetyl chloride Intermediate C43 (60 mg, 95% yield) as a yellow solid. The crude product was used directly in the next step without further purification.

TLC: DCM/MeOH=5/1 (v/v), Rf=0.87.

Step 2: Synthesis of 2-(3,5-dichloro-4-(4-hydroxy-3-isopropylbenzyl)phenyl)-N-methylacetamide (Compound 7)

To a solution of C43 (63 mg, 0.17 mmol, 1.0 eq) in DCM (8 mL) was added $CH_3NH_2$ (10 mL) and the mixture was stirred at rt for 1 h. Water (10 mL) was added and the mixture extracted with DCM (5 mL*3). The combined organic phase was washed with brine (10 mL), dried over $Na_2SO_4$ and concentrated in vacuo. The crude product was purified by Prep-HPLC to afford Compound 7 (20 mg, 32% yield) as a white solid.

TLC: DCM/MeOH=5/1 (v/v), Rf=0.28

LCMS: T=3.557 min, [M−1]=364.1

$^1$H NMR: (400 MHz, DMSO-$d_6$) δ 9.09 (s, 1H), 7.99 (s, 1H), 7.36 (s, 2H), 7.01 (s, 1H), 6.67 (d, J=2.0 Hz, 1H), 6.64 (d, J=8.4 Hz, 1H), 4.09 (s, 2H), 3.41 (s, 2H), 3.15-3.10 (m, 1H), 2.58 (d, J=4.4 Hz, 3H), 1.11 (d, J=6.8 Hz, 6H).

Example 8

Synthesis of methyl 2-(3,5-dichloro-4-(3-(1-(4-fluorophenyl)ethyl)-4-hydroxybenzyl)phenyl)acetate (Compound 8)

Compound 8

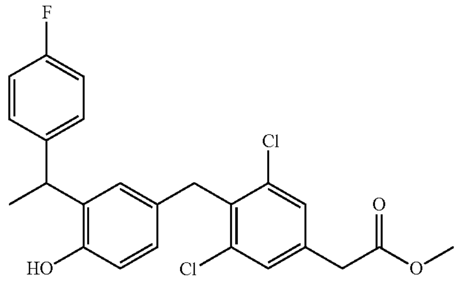

To a solution of B4 (21 mg, 0.96 mmol, 3.0 eq) in DCE (5 mL) at rt were added A17 (100 mg, 0.32 mmol, 1.0 eq) and $ZnCl_2$ (0.8 mL, 0.80 mmol, 2.5 eq); the reaction was heated to 110° C. and stirred overnight. Water (20 mL) was added and the mixture was extracted with DCM (15 mL*3). The combined organic phase was washed with brine (20 mL), dried over $Na_2SO_4$ and concentrated in vacuo. The crude product was purified by Prep-TLC (pet. ether/EtOAc=5/1) to afford Compound 8 (70 mg, 49% yield) as a light yellow oil.

LCMS: T=4.447 min, [M−1]=445.2

$^1$H NMR: (400 MHz, DMSO-$d_6$) δ 9.25 (s, 1H), 7.41 (s, 2H), 7.19 (dd, J=8.8, 5.6 Hz, 2H), 7.09-7.03 (m, 2H), 6.98 (d, J=2.0 Hz, 1H), 6.74 (dd, J=8.4, 2.0 Hz, 1H), 6.66 (d, J=8.4 Hz, 1H), 4.42-4.35 (m, 1H), 4.08 (d, J=2.8 Hz, 2H), 3.74 (s, 2H), 3.63 (s, 3H), 1.45 (d, J=7.2 Hz, 3H).

Example 9

Synthesis of 2-(3,5-dichloro-4-(3-(1-(4-fluorophenyl)ethyl)-4-hydroxybenzyl)phenyl)acetic acid (Compound 9)

Compound 9

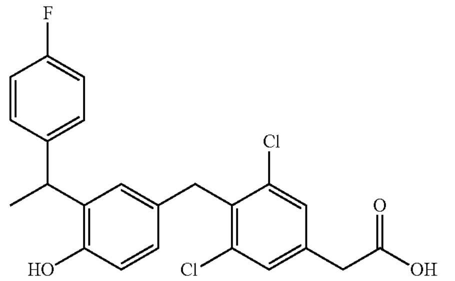

To a solution of Compound 8 (60 mg, 0.13 mmol, 1.0 eq) in THF/water (5 mL/1 mL) at rt was added LiOH·$H_2O$ (3 mg, 0.13 mmol, 1.0 eq). The mixture was stirred at rt for 1 h, then water (10 mL) was added. The mixture was adjusted the pH=3-4 with 1N HCl and extracted with EtOAc (10 mL*2). The combined organic phase was washed with brine (20 mL), dried over $Na_2SO_4$, concentrated in vacuo, and purified by Prep-HPLC to afford Compound 9 (40 mg, 69% yield) as a white solid.

LCMS: T=4.009 min, [M−1]=431.0

$^1$H NMR: (400 MHz, DMSO-$d_6$) δ 12.50 (s, 1H), 9.22 (s, 1H), 7.38 (s, 2H), 7.21-7.16 (m, 2H), 7.07-7.02 (m, 2H), 6.98 (d, J=2.0 Hz, 1H), 6.73 (dd, J=8.4, 2.4 Hz, 1H), 6.65 (d, J=8.4 Hz, 1H), 4.38 (q, J=7.2 Hz, 1H), 4.07 (d, J=3.2 Hz, 2H), 3.62 (s, 2H), 1.44 (d, J=7.2 Hz, 3H)

$^{19}$FNMR: (376 MHz, DMSO-$d_6$) δ −117.82.

Example 10

Synthesis of methyl 3-(3,5-dichloro-4-(4-hydroxy-3-isopropylbenzyl)phenyl)propanoate (Compound 10)

Compound 10

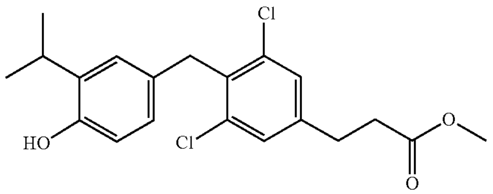

To a solution of A20 (100 mg, 307 μmol, 1.0 eq) in DCE (5.0 mL) at rt were added 2-isopropylphenol (125 mg, 920 μmol, 3.0 eq) and $ZnCl_2$ (767 uL, 767 μmol, 2.5 eq). The reaction was heated to 85° C. and stirred overnight. After cooling to rt, water (20 mL) was added, and the mixture was extracted with DCM (10 mL*3). The combined organic phase was washed with brine (20 mL), dried over $Na_2SO_4$ and concentrated in vacuo. The crude material was purified by Prep-TLC (EtOAc/pet. ether=1/5) to afford Compound 10 (40 mg, 34% yield) as a white solid.

TLC: Pet. ether/EtOAc=5/1 (v/v), Rf=0.20.

Example 11

Synthesis of 3-(3,5-dichloro-4-(4-hydroxy-3-isopropylbenzyl)phenyl)propanoic acid (Compound 11)

Compound 11

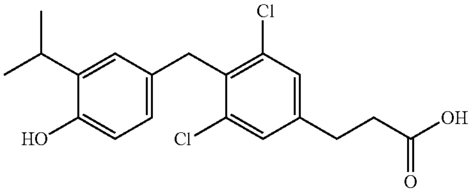

To a mixture of Compound 10 (40 mg, 100 μmol, 1.0 eq) in THF/$H_2O$ (2.0 mL/0.5 mL) at rt was added LiOH·$H_2O$ (13 mg, 300 μmol, 3.0 eq), and the mixture was stirred at rt for 1 h. The mixture was diluted with water (30 mL), acidified to pH=3-4 with 1 N HCl and extracted with EtOAc (15 mL*3). The combined organic phase was washed with brine (30 mL), dried over $Na_2SO_4$ and concentrated under reduced pressure. The crude material was purified by Prep-HPLC to afford Compound 11 (15 mg, 40% yield) as a white solid.

TLC: MeOH/DCM=1/10 (v/v), Rf=0.30

LCMS: T=3.974 min, [M−1]=365.0

$^1$H NMR: (400 MHz, DMSO-$d_6$) δ 12.15 (s, 1H), 9.10 (s, 1H), 7.38 (s, 2H), 7.00 (s, 1H), 6.68 (dd, J=8.0, 2.0 Hz, 1H), 6.64 (d, J=8.4 Hz, 1H), 4.08 (s, 2H), 3.13 (p, J=6.8 Hz, 1H), 2.81 (t, J=7.6 Hz, 2H), 2.57 (t, J=7.6 Hz, 2H), 1.11 (d, J=7.2 Hz, 6H).

Example 12

Synthesis of 3-(3,5-dichloro-4-(4-hydroxy-3-isopropylbenzyl)phenyl)-N-methylpropanamide (Compound 12)

Compound 12

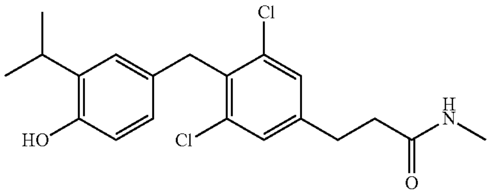

To a solution of Compound 10 (80 mg, 0.21 mmol, 1.0 eq) in THF (5 mL) at rt was added methylamine (13 mg, 0.42 mmol, 2.0 eq). The reaction was stirred in a sealed tube at 70° C. overnight, then water (10 mL) was added and the mixture was extracted with EtOAc (10 mL*2). The combined organic phase was washed with brine (20 mL), dried over $Na_2SO_4$ and concentrated under reduced pressure. The crude material was purified by Prep-HPLC to afford Compound 12 (20 mg, 25% yield) as a white solid.

TLC: Pet. ether/EtOAc=3/1 (v/v), Rf=0.20.

LCMS: T=3.761 min, [M−1]=378.1.

$^1$H NMR: (400 MHz, DMSO-$d_6$) δ 9.09 (s, 1H), 7.74 (d, J=4.8 Hz, 1H), 7.32 (s, 2H), 6.98 (d, J=2.0 Hz, 1H), 6.67 (dd,

J=8.0, 2.0 Hz, 1H), 6.63 (d, J=8.0 Hz, 1H), 4.07 (s, 2H), 3.11 (q, J=6.8 Hz, 1H), 2.79 (t, J=7.6 Hz, 2H), 2.54 (d, J=4.4 Hz, 3H), 2.37 (t, J=7.6 Hz, 2H), 1.10 (d, J=6.8 Hz, 6H).

Example 13

Synthesis of 3-(3,5-dichloro-4-(4-hydroxy-3-isopropylbenzyl)phenyl)-N,N-dimethylpropanamide (Compound 13)

Compound 13

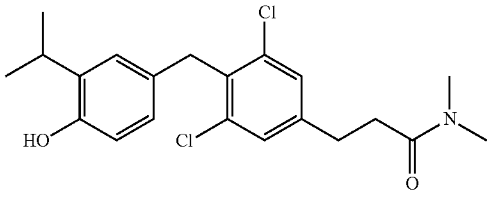

Step 1: Synthesis of 3-(3,5-dichloro-4-(4-hydroxy-3-isopropylbenzyl)phenyl)propanoyl chloride (C44)

C47

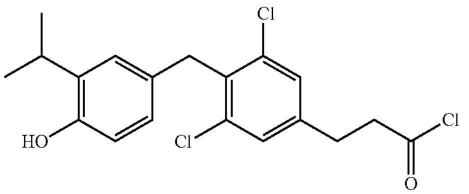

To a solution of Compound 11 (30 mg, 82 µmol, 1.0 eq) in DCM (5 mL) was added oxalyl chloride (21 mg, 0.16 mmol, 2.0 eq) and DMF (0.2 mL). The reaction was stirred at rt for 1 h, then concentrated to dryness to afford Intermediate C44 (30 mg, 93.7% yield) as a colorless oil.

TLC: Pet. ether/EtOAc=3/1 (v/v), Rf=0.32.

Step 2: Synthesis of 3-(3,5-dichloro-4-(4-hydroxy-3-isopropylbenzyl)phenyl)-N,N-dimethylpropanamide (Compound 13)

To a solution of C44 (30 mg, 78 µmol, 1.0 eq) in DCM (5 mL) was added dimethylamine (7.0 mg, 0.15 mmol, 2.0 eq). The reaction was stirred at rt for 30 min, then the mixture was poured into water (20 mL) and extracted with DCM (10 mL*2). The combined organic phase was concentrated to dryness and purified by Prep-HPLC to afford Compound 13 (10 mg, 32% yield) as a white solid.

TLC: DCM/MeOH=3/1 (v/v), Rf=0.39.

LCMS: T=4.072 min, [M−1]=392.1.

$^1$H NMR: (400 MHz, DMSO-$d_6$) δ 9.09 (s, 1H), 7.38 (s, 2H), 7.01 (d, J=2.0 Hz, 1H), 6.68 (dd, J=8.0, 2.0 Hz, 1H), 6.63 (d, J=8.4 Hz, 1H), 4.07 (s, 2H), 3.16-3.09 (m, 1H), 2.93 (s, 3H), 2.80 (s, 3H), 2.77 (d, J=8.0 Hz, 2H), 2.62 (t, J=7.6 Hz, 2H), 1.10 (d, J=7.2 Hz, 6H).

Example 14

Synthesis of methyl (E)-4-(3,5-dichloro-4-(4-hydroxy-3-isopropylbenzyl)phenyl)but-3-enoate (Compound 14)

Compound 14

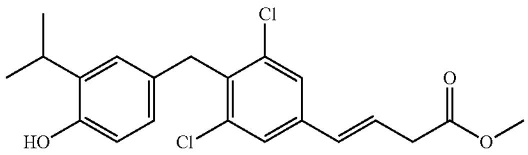

To a solution of C5 (70 mg, 150 µmol, 1.0 eq) in MeOH (2.0 mL) was added TsOH (3 mg, 15 µmol, 0.1 eq). The mixture was stirred at rt for 1 h then the solvent was removed in vacuo. Water (30 mL) was added and the mixture was extracted with EtOAc (15 mL*3). The combined organic phase was washed with brine (30 mL), dried over $Na_2SO_4$ and concentrated in vacuo to afford Compound 14 (58 mg, 95% yield) as a white solid.

TLC: EtOAc/pet. ether=1/20 (v/v), Rf=0.45

LCMS: T=3.303 min, [M−1]=391.0.

Example 15

Synthesis of (E)-4-(3,5-dichloro-4-(4-hydroxy-3-isopropylbenzyl)phenyl)but-3-enoic acid (Compound 15)

Compound 15

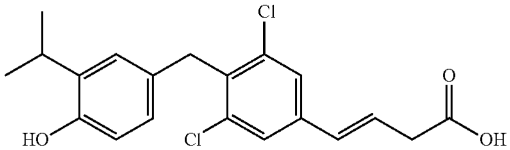

To a mixture of Compound 14 (40 mg, 140 µmol, 1.0 eq) in THF/$H_2O$ (2.0 mL/0.5 mL) at rt was added LiOH·$H_2O$ (10 mg, 420 µmol, 3.0 eq) and the mixture was stirred at rt for 1 h. Water (30 mL) was added, the mixture was acidified with 1 N HCl to pH=3-4, and then extracted with EtOAc (15 mL*3). The combined organic phase was washed with brine (30 mL), dried over $Na_2SO_4$ and concentrated under reduced pressure. The crude product was purified by Prep-HPLC to afford Compound 15 (30 mg, 57% yield) as a white solid.

TLC: MeOH/DCM=1/10 (v/v), Rf=0.30

LCMS: T=4.198 min, [M−1]=377.1; [M−COOH]=333.2

$^1$H NMR: (400 MHz, DMSO-$d_6$) δ 9.12 (s, 1H), 7.56 (s, 2H), 6.99 (d, J=2.4 Hz, 1H), 6.70 6.63 (m, 2H), 6.48-6.45 (m, 2H), 4.10 (s, 2H), 3.21-3.18 (m, 2H), 3.16-3.10 (m, 1H), 1.10 (d, J=6.8 Hz, 6H).

Example 16

Synthesis of 4-(3,5-dichloro-4-(4-hydroxy-3-isopropylbenzyl)phenyl)butanoic acid (Compound 16)

Compound 16

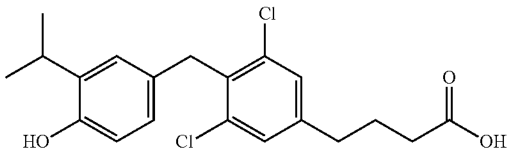

To a solution of Compound 15 (20 mg, 76 μmol) in THE (1.0 mL) was added Pd/C (10%, 5 mg), and the mixture was stirred at rt overnight under $H_2$. The mixture was filtered, then water (20 mL) was added and the mixture was extracted with EtOAc (15 mL*3). The combined organic phase was washed with brine (20 mL), dried over $Na_2SO_4$ and concentrated in vacuo to afford Compound 16 (15 mg, 75% yield) as a white solid.

TLC: DCM/MeOH=1/10, Rf=0.25

LCMS: T=4.142 min, [M−1]=379.1

$^1H$ NMR: (400 MHz, DMSO-$d_6$) δ 9.11 (s, 1H), 7.33 (s, 2H), 6.98 (d, J=2.1 Hz, 1H), 6.70 6.61 (m, 2H), 4.08 (s, 2H), 3.15-3.10 (m, 1H), 2.61-2.55 (m, 2H), 2.17 (t, J=7.2 Hz, 2H), 1.82-1.74 (m, 2H), 1.10 (d, J=6.8 Hz, 6H).

Example 17

Synthesis of methyl 3-(3,5-dichloro-4-(2-fluoro-3-(1-(4-fluorophenyl)ethyl)-4-hydroxybenzyl)phenyl) propanoate (Compound 17)

Compound 17

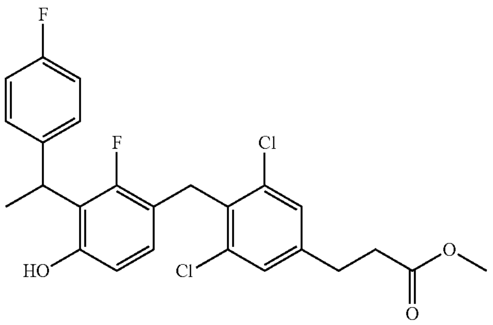

To a solution of C7 (60 mg, 130 μmol) in THF (10 mL) at rt was added Pd/C (15 mg). The mixture was stirred at 55° C. under 1 atm $H_2$ overnight, then the reaction mixture was cooled to rt and filtered through Celite. The filtrate was concentrated under reduced pressure to provide the crude product that was purified by Prep-HPLC to afford Compound 17 (20 mg, 33% yield) as a yellow solid.

$^1H$ NMR: (400 MHz, DMSO-d6) δ 9.75 (s, 1H), 7.40 (s, 2H), 7.32-7.24 (m, 2H), 7.13-7.05 (m, 2H), 6.52 (d, J=8.4 Hz, 1H), 6.33 (t, J=8.4 Hz, 1H), 4.60 (d, J=7.6 Hz, 1H), 4.03 (dd, J=5.6, 1.6 Hz, 2H), 3.59 (s, 3H), 2.85 (t, J=7.6 Hz, 2H), 2.68 (t, J=7.6 Hz, 2H), 1.63 (d, J=7.6 Hz, 3H).

Example 18

Synthesis of 3-(3,5-dichloro-4-(2-fluoro-3-(1-(4-fluorophenyl)ethyl)-4-hydroxybenzyl)phenyl)propanoic acid (Compound 18)

Compound 18

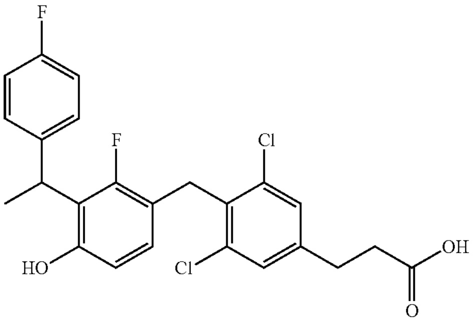

To a solution of Compound 17 (20 mg, 42 μmol, 1.0 eq) in THE (3 mL) and $H_2O$ (1 mL) at rt was added $LiOH·H_2O$ (2.0 mg, 50 μmol, 1.2 eq) and the mixture was stirred for 1 h. Water (5 mL) was added and the mixture was acidified to pH=6 with 1N HCl, and then extracted with EtOAc (5 mL*3). The combined organic phase was washed with brine (10 mL), dried over $Na_2SO_4$ and concentrated under reduced pressure. The crude product was purified by Prep-HPLC to afford Compound 18 (9.0 mg, 46% yield) as an off-white solid.

LCMS: T=4.374 min, [M−1]=463.9

$^1H$ NMR: (400 MHz, DMSO-$d_6$) δ 9.75 (s, 1H), 7.39 (s, 2H), 7.28 (dd, J=8.8, 5.6 Hz, 2H), 7.08 (t, J=8.8 Hz, 2H), 6.52 (d, J=8.4 Hz, 1H), 6.33 (t, J=8.4 Hz, 1H), 4.59 (s, 1H), 4.03 (d, J=4.0 Hz, 2H), 2.81 (t, J=7.6 Hz, 2H), 2.57 (t, J=7.2 Hz, 2H), 1.63 (d, J=7.6 Hz, 3H).

$^{19}F$ NMR: (376 MHz, DMSO-$d_6$) δ −117.8, −118.6

Example 19

Synthesis of ethyl (3,5-dichloro-4-(4-hydroxy-3-isopropylbenzyl)phenyl)glycinate (Compound 19)

Compound 19

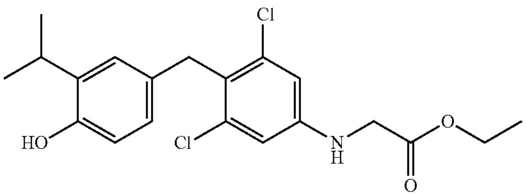

To a solution C10 (300 mg, 0.97 mmol, 1.0 eq) in $CH_3CN$ (5 mL) at rt were added TEA (294 mg, 2.90 mmol, 3.0 eq), NaI (15 mg, 0.97 mmol, 1.0 eq) and ethyl 2-bromoacetate (160 mg, 0.97 mmol, 1.0 eq). The mixture was stirred at 60° C. overnight, then water (30 mL) was added and the mixture extracted with EtOAc (20 mL*2). The combined organic phase was washed with brine (30 mL), dried over $Na_2SO_4$ and concentrated under reduced pressure. The residue was purified by Prep-TLC (pet. ether/EtOAc=3:1) to afford Compound 19 (70 mg, 18% yield) as a yellow oil.

TLC: DCM/MeOH=1/1 (v/v), Rf=0.5

LCMS: T=2.62 min, [M−1]=437.0

$^1$H NMR: (400 MHz, DMSO-$d_6$) δ 9.03 (s, 1H), 6.96 (s, 1H), 6.67 (s, 2H), 6.63 (d, J=8.2 Hz, 1H), 6.45 (s, 1H), 4.14 (s, 2H), 3.94 (t, J=3.0 Hz, 4H), 3.13 (p, J=6.9 Hz, 1H), 1.19 (t, 3H), 1.09 (s, 6H).

Example 20

Synthesis of (3,5-dichloro-4-(4-hydroxy-3-isopropylbenzyl)phenyl)glycine (Compound 20)

Compound 20

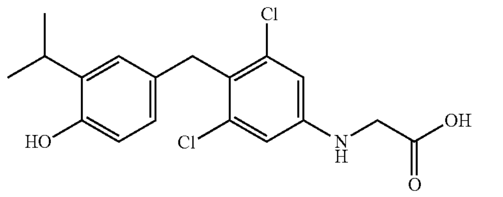

To a solution of Compound 19 (70 mg, 0.17 mmol, 1.0 eq) in THF/$H_2O$ (3 mL/1 mL) was added LiOH·$H_2O$ (14 mg, 0.34 mmol, 2.0 eq) and the mixture was stirred at rt for 2 h. Water (5 mL) was added, the pH was adjusted to 4 with 1 N HCl and the mixture was extracted with EtOAc (5 mL*2). The combined organic phase was washed with brine (20 mL), dried over $Na_2SO_4$ and concentrated under reduced pressure. The residue was purified by Prep-HPLC to afford Compound 20 (26 mg, 40% yield) as a white solid.

TLC: EtOAc/pet. ether=1/1 (v/v), Rf=0.05

LCMS: T=3.83 min, [M−1]=367.1

$^1$H NMR: (400 MHz, DMSO-$d_6$) δ 12.67 (s, 1H), 9.02 (s, 1H), 6.98-6.95 (m, 1H), 6.68 (d, J=1.9 Hz, 1H), 6.66 (s, 2H), 6.63 (d, J=8.2 Hz, 1H), 6.35 (s, 1H), 3.95 (s, 2H), 3.84 (s, 2H), 3.16-3.09 (m, 1H), 1.11 (d, J=6.9 Hz, 6H).

Example 21

Synthesis of methyl 3-((3,5-dichloro-4-(4-hydroxy-3-isopropylbenzyl)phenyl)amino)-3-oxopropanoate (Compound 21)

Compound 21

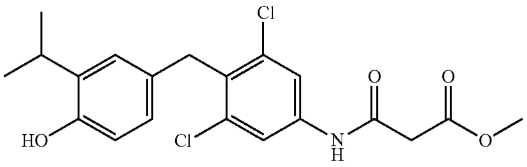

To a solution of C10 (300 mg, 0.97 mmol, 1.0 eq) in DCM (5 mL) at rt was added TEA (294 mg, 2.90 mmol, 3.0 eq), NaI (15 mg, 0.97 mmol, 1.0 eq) and methyl 3-chloro-3-oxopropanoate (130 mg, 0.97 mmol). The mixture was stirred at rt for 2 h, then water (30 mL) was added, and the mixture extracted with DCM (20 mL*2). The combined organic phase was washed with brine (30 mL), dried over $Na_2SO_4$ and concentrated under reduced pressure. The residue was purified by Prep-TLC (pet. ether/EtOAc=3:1) to afford Compound 21 (350 mg, 88.2% yield) as a yellow oil.

TLC: DCM/MeOH=1/1 (v/v), Rf=0.5

$^1$H NMR: (400 MHz, DMSO-$d_6$) δ 10.49 (s, 1H), 9.09 (s, 1H), 7.70 (s, 2H), 6.99 (s, 1H), 6.68 (dd, J=8.2, 2.1 Hz, 1H), 6.64 (s, 1H), 4.07 (s, 2H), 3.67 (s, 3H), 3.50 (s, 2H), 3.18-3.11 (m, 1H), 1.11 (d, J=5.6 Hz, 6H).

Example 22

Synthesis of 3-((3,5-dichloro-4-(4-hydroxy-3-isopropylbenzyl)phenyl)amino)-3-oxopropanoic acid (Compound 22)

Compound 22

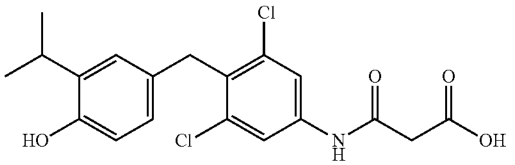

To a solution of Compound 21 (350 mg, 0.17 mmol, 1.0 eq) in THF/$H_2O$ (5 mL/1 mL) was added LiOH·$H_2O$ (107 mg, 2.55 mmol, 15 eq). The mixture was stirred at rt for 2 h, then water (20 mL) was added, the pH was adjusted to 4 with 1 N HCl, and the mixture was extracted with EtOAc (10 mL*2). The combined organic phase was washed with brine (20 mL), dried over $Na_2SO_4$ and concentrated under reduced pressure. The residue was purified by Prep-HPLC to afford Compound 22 (100 mg, 29.5% yield) as a white solid.

TLC: EtOAc/pet. ether=1/1 (v/v), Rf=0.05

LCMS: T=3.52 min, [M−1]=395.07

$^1$H NMR: (400 MHz, DMSO-$d_6$) δ 10.63 (s, 1H), 9.08 (s, 1H), 7.70 (s, 2H), 6.97 (s, 1H), 6.67 (dd, J=8.2, 1.9 Hz, 1H), 6.63 (d, J=8.2 Hz, 1H), 4.06 (s, 2H), 3.15-3.09 (m, 1H), 1.10 (d, J=6.9 Hz, 6H).

Example 23

Synthesis of methyl 4-(3,5-dichloro-4-(4-hydroxy-3-isopropylbenzyl)phenoxy)butanoate (Compound 23)

Compound 23

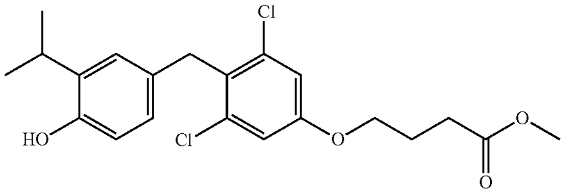

A solution of A32 (300 mg, 0.96 mmol, 1.0 eq), 2-isopropylphenol (394 mg, 2.88 mmol, 3.0 eq) and $ZnCl_2$ (1 M in THF, 1.92 mL, 1.92 mmol, 2.0 eq) in DCE (5 mL) was stirred at 90° C. overnight. After cooling, the mixture was diluted with DCM (20 mL) and washed with brine (20 mL). The organic phase was concentrated in vacuo, and the residue was purified by silica gel column chromatography (pet. ether/EtOAc=10:1) to afford Compound 23 (300 mg, 75.7% yield) as a light yellow oil.

TLC: Pet. ether/EtOAc=1/1 (v/v), Rf=0.15

$^1H$ NMR: (400 MHz, DMSO-$d_6$) δ 9.06 (s, 1H), 7.09 (s, 2H), 6.97 (d, J=2.0 Hz, 1H), 6.66 (dd, J=8.2, 2.0 Hz, 1H), 6.63 (d, J=8.2 Hz, 1H), 4.04 (s, 3H), 4.01 (dd, J=6.8, 3.3 Hz, 2H), 3.60 (s, 3H), 3.15-3.07 (m, 1H), 2.46 (t, J=7.3 Hz, 2H), 1.97-1.91 (m, 2H), 1.09 (d, 6H).

Example 24

Synthesis of 4-(3,5-dichloro-4-(4-hydroxy-3-isopropylbenzyl)phenoxy)butanoic acid (Compound 24)

Compound 24

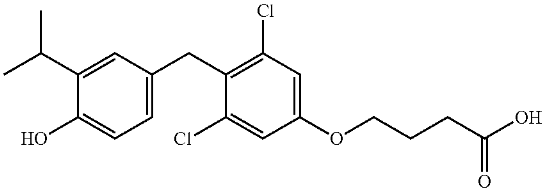

To a solution of Compound 23 (300 mg, 0.73 mmol, 1.0 eq) in THF/$H_2O$ (5 mL/1 mL) was added LiOH·$H_2O$ (92 mg, 2.2 mmol, 3.0 eq). The mixture was stirred at rt for 2 h, then water (20 mL) was added, the pH was adjusted to 4 with 1 N HCl and the mixture was extracted with EtOAc (10 mL*2). The combined organic phase was washed with brine (20 mL), dried over $Na_2SO_4$ and concentrated under reduced pressure. The residue was purified by Prep-HPLC to afford Compound 24 (150 mg, 51.7% yield) as a white solid.

TLC: EtOAc/pet. ether=1/1 (v/v), Rf=0.05

LCMS: T=4.12 min, [M+Na]=420.09

$^1H$ NMR: (400 MHz, DMSO-$d_6$) δ 12.14 (s, 1H), 9.06 (s, 1H), 7.10 (s, 2H), 6.99-6.95 (m, 1H), 6.67 (dd, J=8.3, 1.9 Hz, 1H), 6.64 (d, J=8.2 Hz, 1H), 4.04 (s, 2H), 4.02 (d, J=6.5 Hz, 2H), 3.13 (p, J=7.0 Hz, 1H), 2.37 (t, J=7.3 Hz, 2H), 1.92 (p, J=6.8 Hz, 2H), 1.11 (d, J=6.9 Hz, 6H).

Example 25

Synthesis of methyl 5-(3,5-dichloro-4-(4-hydroxy-3-isopropylbenzyl)phenoxy)pentanoate (Compound 25)

Compound 25

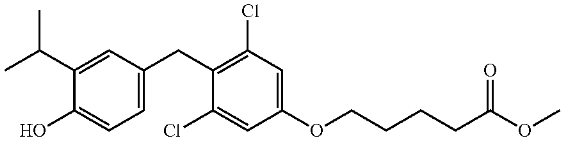

To a solution of A34 (300 mg, 0.92 mmol, 1.0 eq) in DCE (5 mL) at rt were added 2-isopropylphenol (376 mg, 2.76 mmol, 3.0 eq) and $ZnCl_2$ (1.84 mmol, 1.84 mL, 2.0 eq). The mixture was heated to 85° C. for 4 h and cooled to rt. The mixture was concentrated under reduced pressure, and the crude product was purified by silica gel column chromatography (pet. ether/EtOAc=10/1) to afford Compound 25 (230 mg, 58.6% yield) as a colorless oil.

$^1H$ NMR: (400 MHz, DMSO-$d_6$) δ 9.06 (s, 1H), 7.08 (s, 2H), 6.97 (d, J=2.0 Hz, 1H), 6.67 (dd, J=8.0, 2.0 Hz, 1H), 6.63 (d, J=8.0 Hz, 1H), 4.06-3.97 (m, 4H), 3.58 (s, 3H), 3.13 (p, J=6.8 Hz, 1H), 2.38 (t, J=7.2 Hz, 2H), 1.75-1.61 (m, 4H), 1.10 (d, J=7.2 Hz, 6H).

Example 26

Synthesis of 5-(3,5-dichloro-4-(4-hydroxy-3-isopropylbenzyl)phenoxy)pentanoic acid (Compound 26)

Compound 26

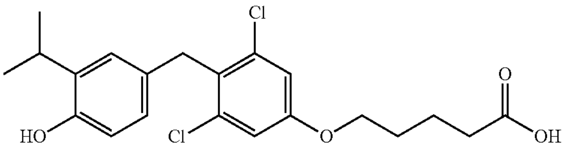

To a solution of Compound 25 (200 mg, 470 μmol, 1.0 eq) in THE (3 mL) at rt was added LiOH·$H_2O$ (29 mg, 700 μmol, 1.5 eq); the mixture was stirred at rt for 2 h. Water (10 mL) was added, the mixture was acidified to pH=4-5 with 1 N HCl, and the mixture was extracted with EtOAc (5 mL*3). The combined organic phase was washed with brine (10 mL), dried over $Na_2SO_4$ and concentrated under reduced pressure to afford Compound 26 (110 mg, 56.8% yield) as a grey solid.

LCMS: T=2.488 min, [M−1]=409.1

$^1H$ NMR: (400 MHz, DMSO-$d_6$) δ 12.02 (s, 1H), 9.06 (s, 1H), 7.09 (s, 2H), 6.97 (s, 1H), 6.65 (td, J=9.6, 2.0 Hz, 2H), 4.02 (d, J=5.6 Hz, 4H), 3.13 (dt, J=13.2, 6.0 Hz, 1H), 2.28 (t, J=7.2 Hz, 2H), 1.67 (dd, J=26.8, 7.6 Hz, 4H), 1.10 (d, J=6.8 Hz, 6H).

Example 27

Synthesis of ethyl 2-((3,5-dichloro-4-(4-hydroxy-3-isopropylbenzyl)benzyl)oxy)acetate (Compound 27)

Compound 27

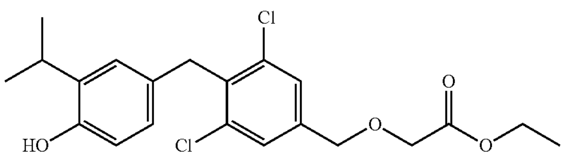

To a solution of A40 (220 mg, 0.70 mmol, 1.0 eq) in DCE (3 mL) were added 2-isopropylphenol (290 mg, 2.1 mmol, 3.0 eq) and $ZnCl_2$ (1 M in THF, 1.4 mL, 1.4 mmol, 2.0 eq); the reaction was stirred at 85° C. overnight. After cooling, the mixture was diluted with DCM (20 mL) and the mixture was washed with water (20 mL) and brine (20 mL), dried over $Na_2SO_4$ and concentrated in vacuo to afford Compound 27 (290 mg, 99.9% yield), which was used in the next step without purification.

TLC: EtOAc/pet. ether=1/10, Rf=0.33.

Example 28

Synthesis of 2-((3,5-dichloro-4-(4-hydroxy-3-isopropylbenzyl)benzyl)oxy)acetic acid (Compound 28)

Compound 28

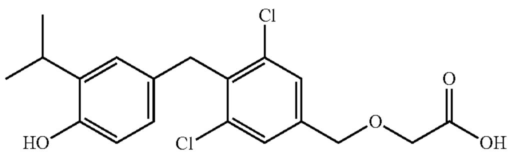

To a solution of Compound 27 (220 mg, 0.53 mol, 1.0 eq) in water/THF (2 mL/3 mL) was added LiOH·$H_2O$ (67 mg, 1.60 mmol, 3.0 eq). The reaction was stirred at rt for 2 h and was then acidified to pH=4 with 1 N HCl and extracted with EtOAc (40 mL*2). The combined organic phase was washed with brine (30 mL), dried over $Na_2SO_4$, and evaporated to dryness. The crude product was purified by Prep-HPLC to afford Compound 28 (10 mg, 4.9% yield) as a white solid.

TLC: Methanol/DCM=1/10, Rf=0.13

LCMS: T=3.72 min; [M−1]=381.0

$^1$H NMR: (400 MHz, DMSO-$d_6$) δ 12.63 (s, 1H), 9.11 (s, 1H), 7.46 (s, 2H), 6.99 (s, 1H), 6.68 (d, J=8.4 Hz, 1H), 6.64 (d, J=8.2 Hz, 1H), 4.54 (s, 2H), 4.11 (s, 2H), 4.11 (s, 2H), 3.17-3.09 (m, 1H), 1.10 (d, J=6.9 Hz, 6H).

Example 29

Synthesis of ethyl (3,5-dichloro-4-(4-hydroxy-3-isopropylbenzyl)benzyl)glycinate (Compound 29)

Compound 29

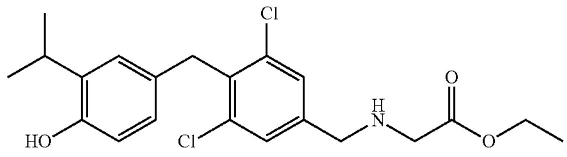

To a solution of C15 (0.80 g, 1.7 mmol, 1.0 eq) in DCM (5 mL) at 0° C. was added TFA (0.20 g, 1.7 mmol, 1.0 eq) and the reaction was stirred at rt for 3 h. The pH was adjusted to ~pH=7 by the addition of aq. $NaHCO_3$ and the mixture was extracted with DCM (20 mL*2). The combined organic phase was washed with brine (20 mL), dried over $Na_2SO_4$ and concentrated in vacuo. The crude product was purified by reverse-phase column chromatography to afford Compound 29 (60 mg, 8.3% yield) as a colorless oil.

TLC: EtOAc/pet. ether=1/10, Rf=0.22

$^1$H NMR: (400 MHz, DMSO-$d_6$) δ 9.09 (s, 1H), 7.43 (s, 2H), 6.98 (d, J=2.1 Hz, 1H), 6.68 (dd, J=8.3, 2.2 Hz, 1H), 6.63 (d, J=8.2 Hz, 1H), 4.09 (s, 2H), 4.08-4.01 (m, 2H), 3.71 (s, 2H), 3.31 (s, 2H), 3.16-3.09 (m, 1H), 1.17 (t, J=7.1 Hz, 3H), 1.09 (d, J=6.9 Hz, 6H).

Example 30

Synthesis of (3,5-dichloro-4-(4-hydroxy-3-isopropylbenzyl)benzyl)glycine (Compound 30)

Compound 30

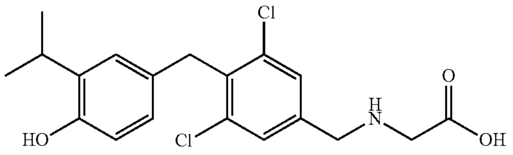

To a solution of Compound 29 (60 mg, 0.14 mol, 1.0 eq) in water/THF (1 mL/2 mL) was added LiOH·$H_2O$ (18 mg, 0.44 mmol, 3.0 eq) and the reaction was stirred at rt for 2 h. The mixture was acidified to pH=3-4 with 1 N HCl and the aqueous layer was extracted with EtOAc (40 mL*2). The combined organic phase was washed with brine (30 mL), dried over $Na_2SO_4$, and evaporated to dryness. The crude product was purified by Prep-HPLC to afford Compound 30 (30 mg 54 yield) as a gray solid.

TLC: Methanol/DCM=1/10, Rf=0.13

LCMS: T=2.77 min; [M−1]=382.1

$^1$H NMR: (400 MHz, DMSO-$d_6$) δ 9.04 (s, 1H), 7.51 (s, 2H), 6.99 (d, J=1.6 Hz, 1H), 6.68 (dd, J=8.2, 2.1 Hz, 2H), 6.64 (d, J=8.2 Hz, 2H), 4.11 (s, 2H), 3.84 (s, 2H), 3.18 (s, 3H), 3.17-3.08 (m, 2H), 1.10 (d, J=6.9 Hz, 6H).

Example 31

Synthesis of methyl 2-(3,5-dichloro-4-(2-fluoro-4-hydroxy-3-isopropylbenzyl)phenyl)acetate (Compound 31)

Compound 31

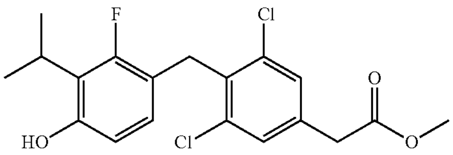

To a solution of A17 (200 mg, 0.64 mmol, 1.0 eq) in DCE (10 mL) at rt were added $ZnCl_2$ (1.92 mmol, 2 mL, 3.0 eq) and Intermediate B2 (296 mg, 1.92 mmol, 3.0 eq). The reaction mixture was heated to 90° C. overnight, then cooled to rt and diluted with DCM (10 mL*2). The combined organic phase was washed with brine (10 mL*2), dried over $Na_2SO_4$ and concentrated under reduced pressure. The crude product was purified by Prep-TLC (pet. ether/EtOAc=5/1) to afford Compound 31 (40 mg, 16% yield) as a white solid.

TLC: Pet. ether/EtOAc=5/1 (v/v), Rf=0.21

$^1$H NMR: (400 MHz, DMSO-$d_6$) δ 9.56 (s, 1H), 7.44 (s, 2H), 6.47 (dd, J=8.4, 1.2 Hz, 1H), 6.27 (t, J=8.4 Hz, 1H), 4.08 (s, 2H), 3.76 (s, 2H), 3.64 (s, 3H), 1.25 (dd, J=7.2, 1.2 Hz, 6H).

Example 32

Synthesis of 2-(3,5-dichloro-4-(2-fluoro-4-hydroxy-3-isopropylbenzyl)phenyl)acetic acid (Compound 32)

Compound 32

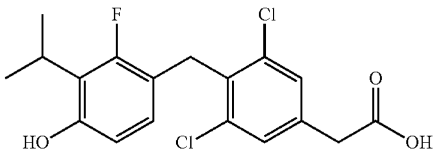

To a solution of Compound 31 (100 mg, 0.26 mmol, 1.0 eq) in water (1 mL) and THF (10 mL) was added $LiOH \cdot H_2O$ (19 mg, 0.78 mmol, 3.0 eq) and the reaction was stirred at rt for 2 h. Water (20 mL) was added, and the mixture was adjusted to pH=3-4 with 1 N HCl then extracted with EtOAc (10 mL*3). The combined organic phase was washed with brine (10 mL), dried over $Na_2SO_4$ and concentrated in vacuo. The crude material was purified by Prep-TLC (DCM/MeOH=5:1) to afford Compound 32 (60 mg, 64% yield) as a white solid.

TLC: Pet. ether/EtOAc=5/1 (v/v), Rf=0.01

LCMS: T=3.976 min, [M−1]=325.0

$^1$H NMR: (400 MHz, DMSO-$d_6$) δ 12.51 (s, 1H), 9.55 (d, J=1.6 Hz, 1H), 7.43 (s, 2H), 6.48 (dd, J=8.8, 1.2 Hz, 1H), 6.27 (t, J=8.8 Hz, 1H), 4.08 (s, 2H), 3.65 (s, 2H), 3.41-3.36 (m, 1H), 1.26 (dd, J=7.2, 0.8 Hz, 6H).

Example 33

Synthesis of 2-(3,5-dichloro-4-(2-fluoro-4-hydroxy-3-isopropylbenzyl)phenyl)-N-methylacetamide (Compound 33)

Compound 33

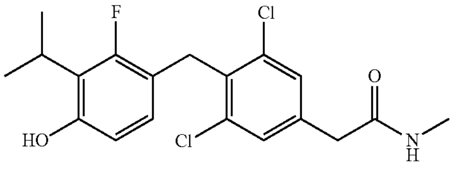

Step 1: Synthesis of 2-(3,5-dichloro-4-(2-fluoro-4-hydroxy-3-isopropylbenzyl)phenyl)acetyl chloride (C45)

C45

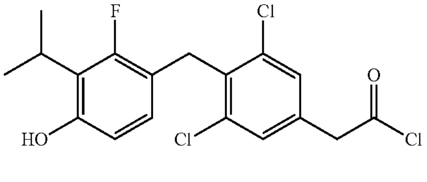

To a solution of Compound 32 (190 mg, 0.51 mmol, 1.0 eq) and DMF (cat) in DCM (10 mL) was added oxalyl chloride (194 mg, 1.54 mmolm 3.0 eq). After stirring at rt for 1 h, the mixture was concentrated in vacuo to afford Intermediate C45 (190 mg, 95% yield).

TLC: EtOAc/pet. ether=1/1; Rf=0.3.

Step 2: Synthesis of 2-(3,5-dichloro-4-(2-fluoro-4-hydroxy-3-isopropylbenzyl)phenyl)-N-methylacetamide (Compound 33)

To a solution of $CH_3NH_2$ (2 Min THF, 0.4 mL, 799 μmol, 3.0 eq) in DCM (6 mL) at rt was added C45 (103 mg, 266 μmol, 1.0 eq). After stirring for 1 h, the mixture was poured into water (20 mL) and extracted with DCM (30 mL*3). The combined organic phase was washed with brine (20 mL), dried over $Na_2SO_4$ and concentrated in vacuo. The crude material was purified by Prep-TLC to afford Compound 33 (15 mg, 14% yield) as a white solid.

TLC: MeOH/DCM=1/10 (v/v), Rf=0.5

LCMS: T=3.861 mins, [M−1]=382.1

$^1$H NMR: (400 MHz, DMSO-$d_6$) δ 9.55 (d, J=1.6 Hz, 1H), 8.02 (s, 1H), 7.39 (s, 2H), 6.48 (d, J=8.4 Hz, 1H), 6.27 (t, J=8.4 Hz, 1H), 4.07 (s, 2H), 3.43 (s, 2H), 3.39 (s, 1H), 2.59 (d, J=4.8 Hz, 3H), 1.27-1.23 (m, 6H)

$^{19}$F NMR: (376 MHz, DMSO-$d_6$) δ −120.13.

Example 34

Synthesis of 2-(3,5-dichloro-4-(2-fluoro-4-hydroxy-3-isopropylbenzyl)phenyl)-N,N-dimethylacetamide (Compound 34)

Compound 34

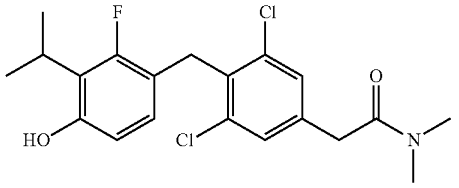

To a solution of dimethylamine (2M in THF, 0.35 mL, 0.69 mmol, 3.0 eq) in DCM (8 mL) at rt was added Intermediate C45 (90 mg, 0.23 mmol, 1.0 eq). After stirring for 1 h, the reaction mixture was poured into water (20 mL) and extracted with DCM (20 mL*2). The combined organic phase was washed with brine (20 mL), dried over $Na_2SO_4$ and concentrated in vacuo. The crude material was purified by Prep-HPLC to afford Compound 34 (25 mg, 27% yield) as a white solid.

TLC: MeOH/DCM=1/10 (v/v), Rf=0.5

LCMS: T=4.080 min, [M−1]=396.0

$^1$H NMR: (400 MHz, DMSO-$d_6$) δ 9.55 (d, J=1.6 Hz, 1H), 7.36 (s, 2H), 6.48 (dd, J=8.4, 1.2 Hz, 1H), 6.27 (t, J=8.4 Hz, 1H), 4.07 (s, 2H), 3.73 (s, 2H), 3.03 (s, 3H), 2.84 (s, 3H), 1.26 (dd, J=7.2, 1.2 Hz, 6H)

$^{19}$F NMR: (376 MHz, DMSO-$d_6$) δ −120.09.

Example 35

Synthesis of methyl 2-(3,5-dichloro-4-(2-fluoro-3-(1-(4-fluorophenyl)vinyl)-4-hydroxybenzyl)phenyl) acetate (Compound 35)

Compound 35

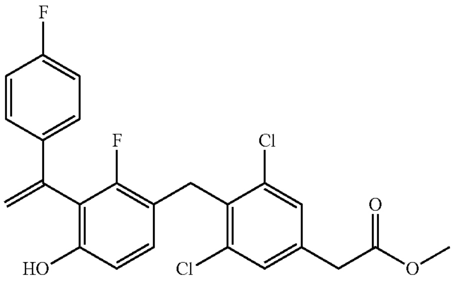

To a solution of C16 (130 mg, 308 μmol, 1.0 eq) and B6 (153 mg, 760 μmol, 2.5 eq) in 1,4-dioxane (5 mL) at rt were added $NaHCO_3$ (78 mg, 920 μmol, 3.0 eq) and Pd(dppf)$Cl_2$ (11 mg, 15.4 μmol, 0.05 eq) under $N_2$. The reaction was heated to 95° C. overnight, then cooled and diluted with EtOAc (5 mL). The mixture was washed with brine (5 mL*2), dried over $Na_2SO_4$ and concentrated under reduced pressure. The crude product was purified through Prep-TLC (EtOAc/pet. ether=1/4) to afford Compound 35 (50 mg, 35% yield) as a light yellow solid.

TLC: EtOAc/pet. ether=1/1 (v/v), Rf=0.24

LCMS: T=2.231 min, [M−1]=461.06.

Example 36

Synthesis of methyl 2-(3,5-dichloro-4-(2-fluoro-3-(1-(4-fluorophenyl)ethyl)-4-hydroxybenzyl)phenyl) acetate (Compound 36)

Compound 36

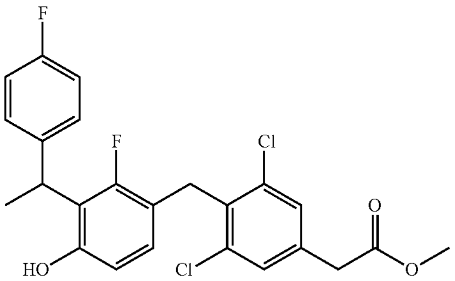

To a solution of Compound 35 (50 mg, 110 μmol) in THF (5 mL) at rt was added Pd/C (5.0 mg, 11 μmol), and the mixture was stirred under 1 atm $H_2$ at 55° C. for 16 h. The reaction was filtered, concentrated and purified by Prep-HPLC to afford Compound 36 (20 mg, 40% yield).

TLC: EtOAc/pet. ether=1/1 (v/v), Rf=0.16

LCMS: T=2.527 min, [M−1]=463.08.

Example 37

Synthesis of 2-(3,5-dichloro-4-(2-fluoro-3-(1-(4-fluorophenyl)ethyl)-4-hydroxybenzyl)phenyl)acetic acid (Compound 37)

Compound 37

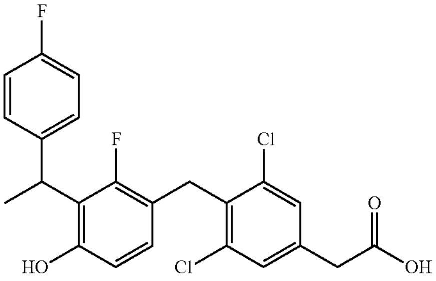

To a solution of Compound 36 (20 mg, 43 μmol, 1.0 eq) in water/THF (5 mL/1 mL) at rt was added LiOH·$H_2O$ (5 mg, 128.9 μmol, 3.0 eq). The mixture was stirred at rt for 1 h, then acidified to pH=6-7 with 2N HCl, and extracted with DCM (20 mL*3). The combined organic phase was concentrated to afford Compound 37 (6.0 mg, 31 yield).

LCMS: T=2.66 min, [M−44]=405.0

$^1$H NMR: (400 MHz, DMSO-$d_6$) δ 9.75 (s, 1H), 7.42 (s, 2H), 7.28 (dd, J=8.4, 5.6 Hz, 2H), 7.08 (t, J=8.8 Hz, 2H), 6.53 (d, J=8.8 Hz, 1H), 6.35 (t, J=8.4 Hz, 1H), 4.60 (d, J=7.6 Hz, 1H), 4.11-3.99 (m, 2H), 3.64 (s, 2H), 1.63 (d, J=7.6 Hz, 3H)

$^{19}$F NMR: (376 MHz, DMSO-$d_6$) δ −117.81, −118.51.

Example 38

Synthesis of methyl (E)-3-(3,5-dichloro-4-(2-fluoro-4-hydroxy-3-isopropylbenzyl)phenyl)acrylate (Compound 38)

Compound 38

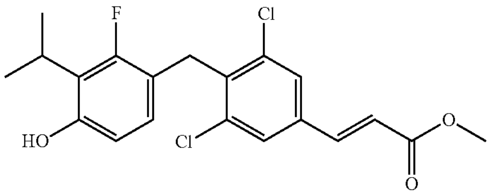

To a solution of A41 (100 mg, 309 μmol, 1.0 eq) in DCE (5.0 mL) at rt was added B2 (142 mg, 956 μmol, 3.0 eq) and $ZnCl_2$ (1M in THF, 773 uL, 773 μmol, 2.5 eq), and the reaction was heated to 85° C. and stirred overnight. The reaction was cooled to rt, water (20 mL) was added and mixture extracted with DCM (10 mL*3). The combined organic phase was washed with brine (20 mL), dried over $Na_2SO_4$ and concentrated in vacuo. The crude product was purified by Prep-TLC (EtOAc/pet. ether=1/5) to afford Compound 38 (30 mg, 24.4% yield) as a white solid.

TLC: Pet. ether/EtOAc=5/1 (v/v), Rf=0.20

$^{1}H$ NMR: (400 MHz, DMSO-$d_6$) δ 9.57 (d, J=1.5 Hz, 1H), 7.64 (d, J=16.0 Hz, 1H), 6.85 (d, J=16.0 Hz, 1H), 6.48 (d, J=8.6 Hz, 1H), 6.29 (t, J=8.6 Hz, 1H), 4.11 (s, 2H), 3.74 (s, 3H), 1.28-1.24 (m, 6H).

Example 39

Synthesis of methyl 3-(3,5-dichloro-4-(2-fluoro-4-hydroxy-3-isopropylbenzyl)phenyl)propanoate (Compound 39)

Compound 39

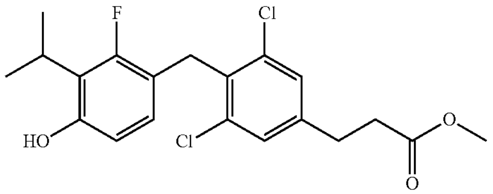

To a solution of Compound 38 (30 mg, 76 μmol) in THF (2 mL) was added Pd/C (10%, 5 mg) and the mixture was stirred at rt overnight under 1 atm $H_2$. The reaction was filtered, water (30 mL) was added and the mixture was extracted with EtOAc (15 mL*3). The combined organic phase was washed with brine (30 mL), dried over $Na_2SO_4$ and concentrated in vacuo to afford Compound 39 (30 mg, 99% yield) as a white solid.

TLC: EtOAc/pet. ether=1/5 (v/v), Rf=0.25

LCMS: T=4.674 min, [M−1]=397.0.

Example 40

Synthesis of 3-(3,5-dichloro-4-(2-fluoro-4-hydroxy-3-isopropylbenzyl)phenyl)propanoic acid (Compound 40)

Compound 40

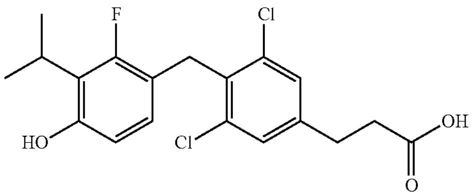

To a mixture of Compound 39 (30 mg, 75 μmol, 1.0 eq) in THF/$H_2O$ (2.0 mL/0.5 mL) at rt was added LiOH·$H_2O$ (5.0 mg, 230-μmol, 3.0 eq) and the reaction was stirred for 1 h. The mixture was diluted with water (30 mL), acidified to pH=3-4 with 1 N HCl, and extracted with EtOAc (15 mL*3). The combined organic phase was washed with brine (30 mL), dried over $Na_2SO_4$ and concentrated under reduced pressure. The crude product was purified by Prep-HPLC to afford Compound 40 (10 mg, 355% yield) as a white solid.

TLC: MeOH/DCM=1/10 (v/v), Rf=0.30

LCMS: T=4.198 min, [M−1]=383.0

$^{1}H$ NMR: (400 MHz, DMSO-$d_6$) δ 12.21 (s, 1H), 9.53 (s, 1H), 7.41 (s, 2H), 6.47 (d, J=8.4 Hz, 1H), 6.25 (t, J=8.4 Hz, 1H), 4.06 (s, 2H), 3.40 (d, J=6.0 Hz, 1H), 2.82 (t, J=7.6 Hz, 2H), 2.58 (t, J=7.6 Hz, 2H), 1.26 (d, J=6.8 Hz, 6H).

$^{19}F$ NMR: (376 MHz, DMSO-$d_6$) δ −120.15.

Example 41

Synthesis of 3-(3,5-dichloro-4-(2-fluoro-4-hydroxy-3-isopropylbenzyl)phenyl)-N-methylpropanamide (Compound 41)

Compound 41

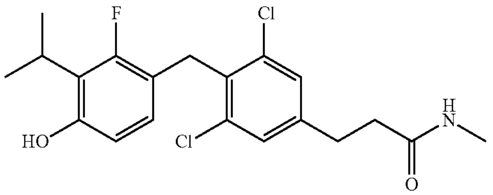

To a solution of Compound 39 (30 mg, 75 μmol, 1.0 eq) in THF (5 mL) at rt was added methylamine (5 mg, 0.15 mmol, 2.0 eq). The reaction was stirred at 70° C. overnight in a sealed tube, then water (10 mL) was added and the mixture extracted with EtOAc (10 mL*2). The combined organic phase was washed with brine (20 mL), dried over $Na_2SO_4$ and concentrated under reduced pressure. The crude material was purified by Prep-TLC (DCM/MeOH=10/1) to afford Compound 41 (8.0 mg, 27% yield) as a white solid.

TLC: DCM/MeOH=10/1 (v/v), Rf=0.42

LCMS: T=3.982 min, [M−1]=396.1

$^{1}H$ NMR: (400 MHz, DMSO-$d_6$) δ 9.53 (d, J=1.6 Hz, 1H), 7.76 (d, J=4.4 Hz, 1H), 7.35 (s, 2H), 6.49-6.43 (m, 1H), 6.24 (t, J=8.4 Hz, 1H), 4.05 (s, 2H), 3.39 (s, 1H), 2.81 (t, J=7.6 Hz, 2H), 2.55 (d, J=4.4 Hz, 3H), 2.39 (t, J=7.6 Hz, 2H), 1.27-1.24 (m, 6H)

$^{19}F$ NMR: (376 MHz, DMSO-$d_6$) δ −124.14.

Example 42

Synthesis of 3-(3,5-dichloro-4-(2-fluoro-4-hydroxy-3-isopropylbenzyl)phenyl)-N,N-dimethylpropanamide (Compound 42)

Compound 42

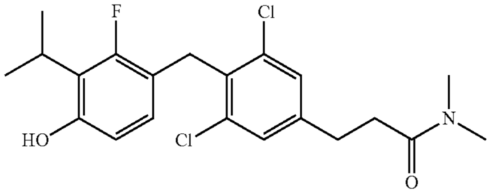

Step 1: Synthesis of 3-(3,5-dichloro-4-(2-fluoro-4-hydroxy-3-isopropylbenzyl)phenyl)propanoyl chloride (C46)

C46

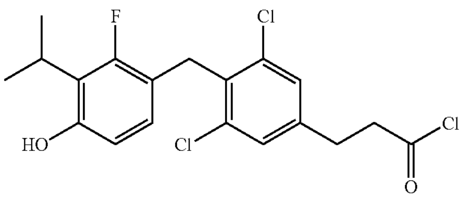

To a solution of Compound 40 (30 mg, 78 μmol, 1.0 eq) in DCM (10 mL) at rt was added $SOCl_2$ (28 mg, 230 μmol, 3.0 eq) and DMF (cat). After 1 h the reaction mixture was concentrated under reduce pressure to afford Intermediate C46 (30 mg, 95% yield) as a light yellow oil that was used in the next step without further purification.

TLC: EtOAc/pet. ether=1/10, Rf=0.78.

Step 2: Synthesis of 3-(3,5-dichloro-4-(2-fluoro-4-hydroxy-3-isopropylbenzyl)phenyl)-N,N-dimethylpropanamide (Compound 42)

To a solution of C46 (100 mg, 0.25 mmol, 1.0 eq) in DCM (5 mL) was added dimethylamine (22 mg, 0.50 mmol, 2.0 eq). The reaction was stirred at rt for 30 min, then poured into water (20 mL) and extracted with DCM (10 mL*2). The combined organic phase was concentrated to dryness and purified by Prep-HPLC to afford Compound 42 (40 mg, 39% yield) as a white solid.

TLC: DCM/MeOH=5/1 (v/v), Rf=0.36.

LCMS: T=4.270 min, [M−1]=410.1

$^1H$ NMR: (400 MHz, DMSO-$d_6$) δ 9.53 (d, J=1.2 Hz, 1H), 7.41 (s, 2H), 6.47 (dd, J=8.4, 1.2 Hz, 1H), 6.26 (t, J=8.8 Hz, 1H), 4.05 (s, 2H), 3.38 (m, 1H), 2.94 (s, 3H), 2.81 (s, 3H), 2.79 (d, J=8.0 Hz, 2H), 2.64 (t, J=7.6 Hz, 2H), 1.26 (dd, J=7.2, 1.2 Hz, 6H)

$^{19}F$ NMR: (376 MHz, DMSO-$d_6$) δ −120.14.

Example 43

Synthesis of methyl 3-(3,5-dichloro-4-((5'-(difluoromethoxy)-2,2'-difluoro-6-hydroxy-[1,1'-biphenyl]-3-yl)methyl)phenyl)propanoate (Compound 43)

Compound 43

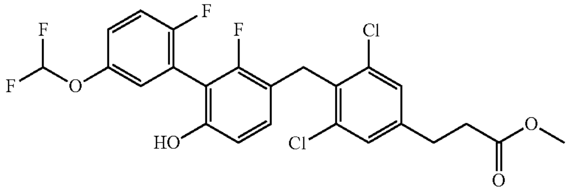

A mixture of Intermediate C8 (90 mg, 0.21 mmol, 1.0 eq), Intermediate B8 (181 mg, 0.63 mmol, 3.0 eq), Pd(dppf)$Cl_2 \cdot CH_2Cl_2$ (16 mg, 0.020 mmol, 0.1 eq), and $K_2CO_3$ (87 mg, 0.63 mmol, 3.0 eq) in water (0.5 mL) and 1,4-dioxane (3 mL) was microwaved at 140° C. for 2 h. The mixture was filtered, concentrated to dryness, and purified by Prep-TLC to afford Compound 43 (50 mg, 97 μmol, 46% yield) as a colorless oil.

TLC: EtOAc/pet. ether=1/5 (v/v), $R_f$=0.41.

Example 44

Synthesis of 3-(3,5-dichloro-4-((5'-(difluoromethoxy)-2,2'-difluoro-6-hydroxy-[1,1'-biphenyl]-3-yl)methyl)phenyl)propanoic acid (Compound 44)

Compound 44

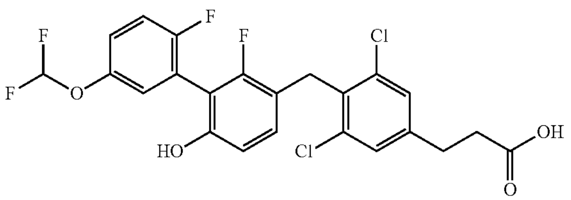

To a solution of Compound 43 (50 mg, 97 mmol, 1.0 eq) in MeOH/$H_2O$ (5 mL/1 mL) at rt was added LiOH·$H_2O$ (12 mg, 300 μmol, 3.0 eq) and the mixture was stirred for 1 h. The mixture was diluted with water (10 mL), acidified to pH=3-4 with 1 N HCl, and extracted with EtOAc (15 mL*3). The combined organic phase was washed with brine (30 mL), dried over $Na_2SO_4$ and concentrated under reduced pressure. The crude product was purified by Prep-HPLC to afford Compound 44 (8.0 mg, 16% yield) as a white solid.

TLC: MeOH/DCM=1/10 (v/v), Rf=0.30

LCMS: T=2.252 min, [M−1]=501.0

$^1H$ NMR: (400 MHz, DMSO-$d_6$) δ 12.20 (s, 1H), 10.00 (d, J=1.6 Hz, 1H), 7.42 (s, 2H), 7.36 (t, J=8.9 Hz, 1H), 7.28-7.19 (m, 2H), 7.23 (t, J=74.1 Hz, 1H), 6.69 (d, J=8.5 Hz, 1H), 6.61 (t, J=8.5 Hz, 1H), 4.12 (s, 2H), 2.83 (t, J=7.5 Hz, 2H), 2.59 (t, J=7.5 Hz, 2H).

Example 45

Synthesis of ethyl (3,5-dichloro-4-(2-fluoro-4-hydroxy-3-isopropylbenzyl)phenyl)glycinate (Compound 45)

Compound 45

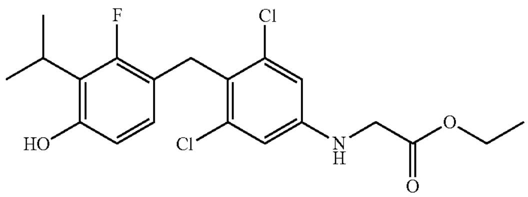

To a solution of C18 (260 mg, 792 μmol, 1.0 eq) in EtOH (5.0 mL) at rt were added AcONa (85 mg, 1.0 mmol, 1.3 eq) and ethyl 2-bromoacetate (132 mg, 792 μmol, 1.0 eq). The mixture was stirred at reflux for 36 h then concentrated in vacuo. Water (30.0 mL) was added and the mixture was extracted with EtOAc (20 mL*2). The combined organic phase was washed with brine (30 mL), dried over $Na_2SO_4$ and concentrated in vacuo. The crude material was purified with Prep-TLC (pet. ether/EtOAc=3/1) to afford Compound 45 (170 mg, 51.8% yield) as a yellow solid.

TLC: EtOAc/pet. ether=1/1, Rf=0.50

$^1H$ NMR: (400 MHz, DMSO-$d_6$) δ 9.47 (d, J=1.2 Hz, 1H), 6.68 (s, 2H), 6.49 (m, 3H), 6.27 (t, J=8.5 Hz, 1H), 4.13 (q, J=7.2 Hz, 2H), 3.95 (d, J=6.4 Hz, 2H), 3.92 (s, 2H), 3.41-3.36 (m, 1H), 1.25 (d, J=7.2 Hz, 7H), 1.19 (t, J=7.2 Hz, 4H).

Example 46

Synthesis of (3,5-dichloro-4-(2-fluoro-4-hydroxy-3-isopropylbenzyl)phenyl)glycine (Compound 46)

Compound 46

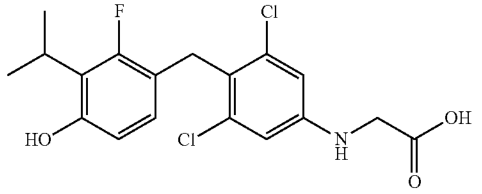

To a solution of Compound 45 (170 mg, 0.41 mmol, 1.0 eq) in THF/$H_2O$ (5.0 mL/1.0 mL) at rt was added LiOH·$H_2O$ (30 mg, 0.71 mmol, 1.7 eq) and the reaction was stirred for 2 h. The mixture was acidified to pH=4 with 1 N HCl, then extracted with EtOAc (40 mL*2). The combined organic phase was washed with brine (50 mL), dried over $Na_2SO_4$ and evaporated to dryness. The crude product was purified by Prep-HPLC to afford Compound 46 (70 mg, 44% yield) as a gray solid.

TLC: DCM/MeOH=10/1 (v/v), Rf=0.3

LCMS: T=4.095 min, [M+1]=386.1

$^1$H NMR: (400 MHz, DMSO-$d_6$) δ 9.75 (s, 1H), 6.62 (s, 2H), 6.48 (d, J=8.3 Hz, 1H), 6.27 (t, J=8.6 Hz, 1H), 5.81 (d, J=5.0 Hz, 1H), 3.90 (s, 2H), 3.41 (d, J=6.1 Hz, 1H), 3.24 (d, J=3.8 Hz, 2H), 1.25 (d, J=7.1 Hz, 6H)

$^{19}$F NMR: (376 MHz, DMSO-$d_6$) δ −120.74.

Example 47

Synthesis of 2-((3,5-dichloro-4-(2-fluoro-4-hydroxy-3-isopropylbenzyl)phenyl)amino)-N-methylacetamide (Compound 47)

Compound 47

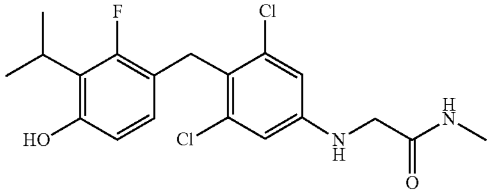

To a solution of Compound 45 (150 mg, 362 μmol) in THE (4.0 mL) was added $MeNH_2$ (55% in water) (2.0 mL). The reaction was stirred at 75° C. in a sealed tube for 2 h then the mixture was concentrated to dryness in vacuo. The residue was purified by Prep-HPLC to afford Compound 47 (50 mg, 35% yield) as a white solid.

TLC: MeOH/DCM=1/10 (v/v), Rf=0.30

LCMS: T=3.961 min, [M−1]=399.1

$^1$H NMR: (400 MHz, DMSO-$d_6$) δ 9.47 (s, 1H), 7.90 (d, J=4.4 Hz, 1H), 6.63 (s, 2H), 6.49 (d, J=6.1 Hz, 1H), 6.47 (d, J=8.4 Hz, 1H), 6.29 (t, J=8.4 Hz, 1H), 3.92 (s, 2H), 3.65 (d, J=6.0 Hz, 2H), 3.39 (s, 1H), 2.61 (d, J=4.4 Hz, 3H), 1.25 (d, J=7.2 Hz, 6H)

$^{19}$F NMR: (376 MHz, DMSO-$d_6$) δ −120.54.

Example 48

Synthesis of 2-((3,5-dichloro-4-(2-fluoro-4-hydroxy-3-isopropylbenzyl)phenyl)amino)-N,N-dimethylacetamide (Compound 48)

Compound 48

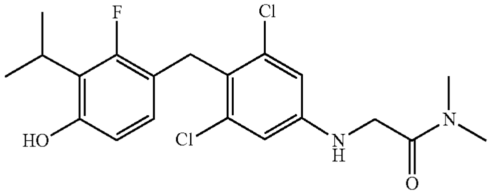

To a solution of Compound 46 (200 mg, 518 μmol, 1.0 eq), EDCI (149 mg, 777 μmol, 1.5 eq) and HOBT (105 mg, 777 μmol, 1.5 eq) in DMF (2 mL) were added dimethylamine (70 mg, 1.6 mmol, 3.1 eq) and DIEA (134 mg, 1.0 mmol, 1.9 eq). The mixture was stirred at rt overnight, then water (30 mL) was added and the mixture extracted with EtOAc (20 mL*3). The combined organic phase was washed with water (20 mL*2) and brine (20 mL), dried over $Na_2SO_4$ and concentrated in vacuo. The crude material was purified by Prep-HPLC to afford Compound 48 (15 mg, 7.0% yield) as a white solid.

TLC: MeOH/DCM=1/10 (v/v), Rf=0.60

LCMS: T=2.576 min, [M−1]=411.1

$^1$H NMR: (400 MHz, DMSO-$d_6$) δ 9.46 (s, 1H), 6.82 (s, 2H), 6.47 (d, J=8.4 Hz, 1H), 6.28 (t, J=8.4 Hz, 1H), 6.14 (t, J=5.2 Hz, 1H), 3.93 (s, 2H), 3.91 (s, 2H), 3.41-3.35 (m, 1H), 3.01 (s, 3H), 2.87 (s, 3H), 1.25 (d, J=7.2 Hz, 6H).

$^{19}$F NMR: (376 MHz, DMSO-$d_6$) δ −73.42, −120.57.

Example 49

Synthesis of ethyl (3,5-dichloro-4-(2-fluoro-3-(1-(4-fluorophenyl)ethyl)-4-hydroxybenzyl) phenyl)glycinate (Compound 49)

Compound 49

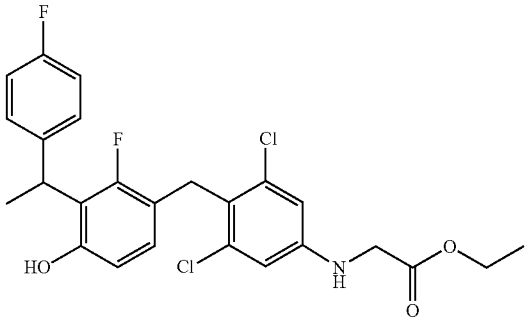

To a solution of C21 (300 mg, 735 μmol, 1.0 eq) in ethanol (5 mL) at rt were added ethyl 2-bromoacetate (123 mg, 735 μmol, 81.3 uL, 1.0 eq) and AcONa (78 mg, 955 μmol, 1.3 eq). The mixture was stirred at 100° C. overnight, then concentrated in vacuo. The crude material was purified by Prep-TLC (pet. ether/EtOAc=3:1) to afford Compound 49 (90 mg, 25% yield) as a yellow solid.

TLC: Pet. ether/EtOAc=3/1 (v/v), Rf=0.52

Example 50

Synthesis of (3,5-dichloro-4-(2-fluoro-3-(1-(4-fluorophenyl)ethyl)-4-hydroxybenzyl)phenyl) glycine (Compound 50)

Compound 50

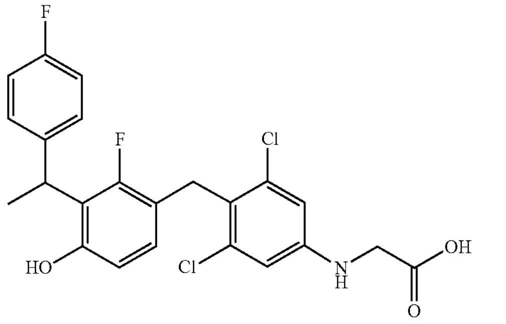

To a solution of Compound 49 (90 mg, 180 μmol, 1.0 eq) in THF (2 mL) was added LiOH·$H_2O$ (23 mg, 550 mol, 3.0 eq) in water (1 mL). The mixture was stirred at rt for 1 h, then the mixture was acidified to pH=3-4 with 1 N HCl and extracted with EtOAc (40 mL*3). The combined organic phase was washed with brine (30 mL), dried over $Na_2SO_4$, and evaporated to dryness. The crude product was purified by Prep-HPLC to afford Compound 50 (35 mg, 40% yield) as a white solid.

TLC: DCM/MeOH=10/1 (v/v), Rf=0.5

LCMS: 2.150 min, [M−1]=497.9

$^1$H NMR: (400 MHz, DMSO-$d_6$) δ 12.63 (s, 1H), 9.68 (s, 1H), 7.27 (dd, J=8.4, 5.6 Hz, 2H), 7.07 (t, J=8.8 Hz, 2H), 6.66 (s, 2H), 6.52 (d, J=8.8 Hz, 1H), 6.41 (s, 1H), 6.35 (t, J=8.8 Hz, 1H), 4.58 (q, J=7.2 Hz, 1H), 3.88 (d, J=4.8 Hz, 2H), 3.84 (s, 2H), 1.62 (d, J=7.6 Hz, 3H)

$^{19}$F NMR: (376 MHz, DMSO-$d_6$) δ −117.86, −119.02.

Example 51

Synthesis of methyl 4-(3,5-dichloro-4-(2-fluoro-4-hydroxy-3-isopropylbenzyl)phenoxy) butanoate (Compound 51)

Compound 51

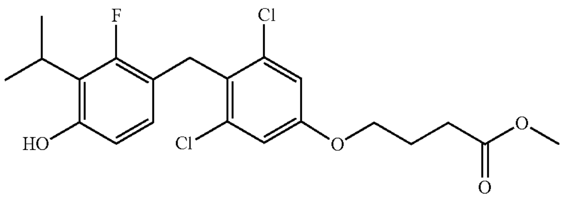

To a solution of Intermediate B2 (300 mg, 1.9 mmol, 3.0 eq) in DCE (5 mL) at rt were added Intermediate A32 (200 mg, 0.6 mmol, 1.0 eq) and $ZnCl_2$ (1 M in THF, 1.3 mL, 1.3 mmol, 2.0 eq); the reaction was heated to 70° C. overnight. The reaction mixture was cooled, diluted with DCM (20 mL), washed with brine (10 mL*2), dried over $Na_2SO_4$ and concentrated under reduce pressure. The crude product was purified through Prep-TLC (EtOAc/pet. ether=1/8) to afford Compound 51 (140 mg, 50.8% yield) as a light yellow oil.

TLC: EtOAc/pet. ether=1/10, Rf=0.34

LCMS: T=3.53 min; [M−1]=427.0.

Example 52

Synthesis of 4-(3,5-dichloro-4-(2-fluoro-4-hydroxy-3-isopropylbenzyl)phenoxy)butanoic acid (Compound 52)

Compound 52

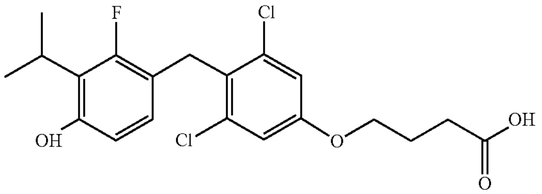

To a solution of Compound 51 (140 mg, 0.32 mmol, 1.0 eq) in water/THF (0.5 mL/3 mL) at rt was added LiOH·$H_2O$ (16 mg, 0.65 mmol, 2.0 eq). The mixture was stirred overnight. The reaction mixture was acidified to pH=3 with HCl (1N), extracted with EtOAc (10 mL*3). The combined organic phase was dried over $Na_2SO_4$ and concentrated under reduced pressure. The crude product was purified through Prep-TLC (methanol/DCM=1/10) to afford Compound 52 (30 mg, 22 yield) as a white solid.

TLC: Methanol/DCM=1/10, Rf=0.13

LCMS: T=4.21 min; [M−$(CH_2)_3$—$CO_2$H]=327.0

$^1$H NMR: (400 MHz, DMSO-$d_6$) δ 9.77 (s, 1H), 7.12 (s, 2H), 6.50 (d, J=8.4 Hz, 1H), 6.25 (t, J=8.6 Hz, 1H), 4.02 (d, J=7.4 Hz, 4H), 3.36 (d, J=7.1 Hz, 1H), 2.22 (t, J=7.2 Hz, 2H), 1.95-1.84 (m, 2H), 1.25 (d, J=7.1 Hz, 6H).

$^{19}$F NMR: (376 MHz, DMSO-$d_6$) δ −120.41.

Example 53

Synthesis of methyl 5-(3,5-dichloro-4-(2-fluoro-4-hydroxy-3-isopropylbenzyl)phenoxy) pentanoate (Compound 53)

Compound 53

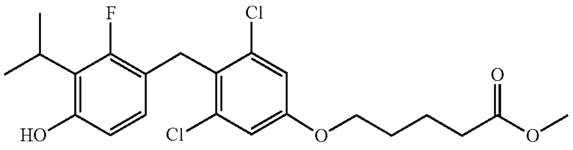

To a solution of Intermediate B2 (284 mg, 1.8 mmol, 3.0 eq) in DCE (5 mL) at rt were added Intermediate A34 (200 mg, 0.6 mmol, 1.0 eq) and $ZnCl_2$ (1 M in THF, 1.2 mL, 1.2 mmol, 2.0 eq). The reaction was heated to 70° C. overnight, cooled, then diluted with DCM (20 mL). The organic phase was washed with brine (10 mL*2), dried over $Na_2SO_4$ and concentrated under reduced pressure. The crude product was purified using Prep-TLC (EtOAc/pet. ether-1/8) to afford Compound 53 (130 mg, 47.7% yield) as a light yellow oil.

TLC: EtOAc/pet. ether=1/10, Rf=0.34

LCMS: T=3.73 min; [M−1]=441.0.

Example 54

Synthesis of 5-(3,5-dichloro-4-(2-fluoro-4-hydroxy-3-isopropylbenzyl)phenoxy)pentanoic acid (Compound 54)

Compound 54

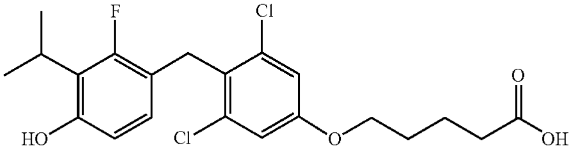

A solution of Compound 53 (130 mg, 0.29 mmol, 1.0 eq) and $LiOH·H_2O$ (25 mg, 0.59 mmol, 2.0 eq) in water/THF (0.5 mL/3 mL) was stirred overnight at rt. The reaction mixture was acidified to pH=3 with HCl (1N), and extracted with EtOAc (10 mL*3). The combined organic phase was dried over $Na_2SO_4$ and concentrated under reduced pressure. The crude product was purified through Prep-TLC (methanol/DCM=1/10) to afford Compound 54 (30 mg, 24% yield) as a white solid.

TLC: Methanol/DCM=1/10, Rf=0.13

LCMS: T=4.33 min; [M−1]=427.1

$^1$H NMR: (400 MHz, DMSO-$d_6$) δ 9.68 (s, 1H), 7.11 (s, 2H), 6.49 (d, J=8.4 Hz, 1H), 6.25 (t, J=8.6 Hz, 1H), 4.01 (s, 4H), 3.37-3.33 (m, 1H), 2.16 (t, J=7.2 Hz, 2H), 1.69 (q, J=6.8, 6.3 Hz, 2H), 1.61 (q, J=7.4 Hz, 2H), 1.25 (d, J=7.1 Hz, 6H)

$^{19}$F NMR: (376 MHz, DMSO-$d_6$) δ −120.38.

Example 55

Synthesis of methyl 3-((3,5-dichloro-4-(2-fluoro-3-(1-(4-fluorophenyl)ethyl)-4-hydroxybenzyl) phenyl) amino)-3-oxopropanoate (Compound 55)

Compound 55

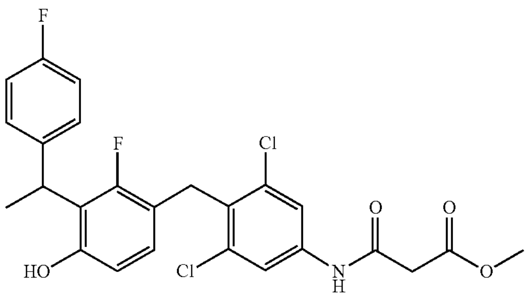

A solution of C21 (100 mg, 245 μmol, 1.0 eq) and TEA (27 mg, 270 μmol, 1.1 eq) in DCM (5 mL) was cooled to 0° C. and methyl 3-chloro-3-oxopropanoate (33 mg, 245 μmol) was added dropwise. The reaction mixture was stirred at rt for 2 h, then it was concentrated in vacuo to provide crude Compound 55 that was used in the next step without purification.

LCMS: T=2.77 min, [M−1]=506.1.

Example 56

Synthesis of 3-((3,5-dichloro-4-(2-fluoro-3-(1-(4-fluorophenyl)ethyl)-4-hydroxybenzyl)phenyl) amino)-3-oxopropanoic acid (Compound 56)

Compound 56

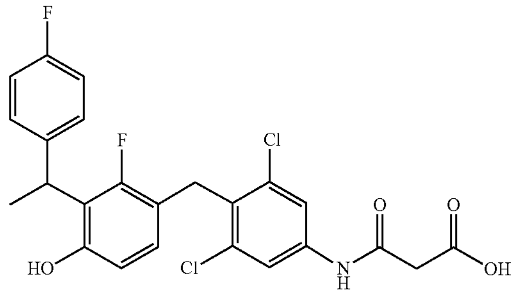

To a solution of crude Compound 55 (100 mg, 197 μmol, 1.0 eq) in THF (2 mL) was added a solution of $LiOH·H_2O$ (25 mg, 590 μmol, 3.0 eq) in water (1 mL) and the mixture was stirred at rt for 2 h. The mixture was acidified to pH=4 with 1 N HCl, then extracted with EtOAc (40 mL*2). The combined organic phase was washed with brine (30 mL), dried over $Na_2SO_4$ and evaporated to dryness. The crude product was purified by Prep-HPLC to afford Compound 56 (30 mg, 29% yield) as a white solid.

TLC: EtOAc/pet. ether=1/1 (v/v), Rf=0.05

LCMS: T=2.487 min, [M−1]=492.0

$^1$H NMR: (400 MHz, DMSO-$d_6$) δ 12.59 (s, 1H), 10.51 (s, 1H), 9.74 (s, 1H), 7.72 (s, 2H), 7.33-7.23 (m, 2H), 7.13-7.05 (m, 2H), 6.53 (d, J=8.4 Hz, 1H), 6.35 (t, J=8.8 Hz, 1H), 4.60 (q, J=7.6 Hz, 1H), 4.02 (d, J=4.8 Hz, 2H), 3.36 (s, 2H), 1.63 (d, J=7.2 Hz, 3H)

$^{19}$F NMR: (376 MHz, DMSO-$d_6$) δ −117.82, −118.70.

Example 57

Synthesis of methyl 2-(3,5-dichloro-4-(2-fluoro-4-hydroxy-3-isopropylbenzyl)phenoxy) propanoate (Compound 57)

Compound 57

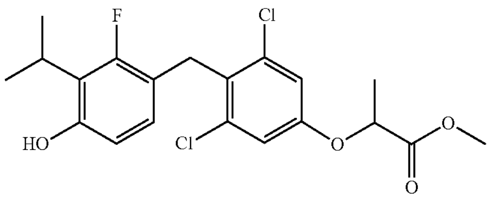

To a solution of Intermediate B2 (310 mg, 2.0 mmol, 1.5 eq) in chlorobenzene (10 mL) at rt was added Intermediate A43 (400 mg, 1.3 mmol, 1.0 eq) and $ZnCl_2$ (370 mg, 2.7 mmol, 2.0 eq). The reaction mixture was stirred overnight at 130° C., then cooled and diluted with DCM (20 mL). The organic phase was washed with brine (10 mL*2), dried over $Na_2SO_4$ and concentrated under reduced pressure. The crude product was purified through Prep-TLC (EtOAc/pet. ether-1/3) to afford Compound 57 (190 mg, 34.1% yield) as a light yellow oil.

TLC: EtOAc/pet. ether=1/10, Rf=0.34

$^1H$ NMR: (400 MHz, DMSO-$d_6$) δ 9.53 (s, 1H), 7.11 (s, 2H), 6.48 (d, J=8.4 Hz, 1H), 6.27 (t, J=8.5 Hz, 1H), 5.18 (d, J=6.8 Hz, 1H), 4.01 (s, 2H), 3.70 (s, 3H), 1.51 (d, J=6.7 Hz, 3H), 1.25 (d, J=7.1 Hz, 7H)

$^{19}F$ NMR: (376 MHz, DMSO-$d_6$) δ −120.21.

Example 58

Synthesis of 2-(3,5-dichloro-4-(2-fluoro-4-hydroxy-3-isopropylbenzyl)phenoxy)propanoic acid (Compound 58)

Compound 58

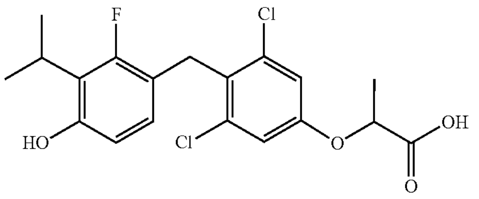

To a solution of Compound 57 (190 mg, 0.45 mmol, 1.0 eq) in water/THF (1 mL/5 mL) at rt was added $LiOH \cdot H_2O$ (38 mg, 0.91 mmol, 2.0 eq). After stirring 3 h, the reaction mixture was diluted with water (10 mL), acidified to pH=3 with aqueous HCl (1N), and extracted with EtOAc (20 mL*2). The combined organic phase was washed with brine (10 mL*2), dried over $Na_2SO_4$ and concentrated under reduced pressure. The crude product was purified through Prep-TLC (methanol/DCM=1/10) to afford Compound 58 (60 mg, 33% yield) as a white solid.

TLC: Methanol/DCM=1/10, Rf=0.13

LCMS: T=2.54 min; [M−1]=399.0

$^1H$ NMR: (400 MHz, DMSO-$d_6$) δ 9.52 (d, J=1.5 Hz, 1H), 7.07 (s, 2H), 6.49-6.46 (m, 1H), 6.27 (t, J=8.4 Hz, 1H), 5.01 (d, J=6.6 Hz, 1H), 4.01 (s, 2H), 3.38 (d, J=7.0 Hz, 1H), 1.50 (d, J=6.8 Hz, 3H), 1.25 (d, J=6.6 Hz, 6H)

$^{19}F$ NMR: (376 MHz, DMSO-$d_6$) δ −120.26.

Example 59

Synthesis of methyl 2-(3,5-dichloro-4-(2-fluoro-4-hydroxy-3-isopropylbenzyl)phenyl)propanoate (Compound 59)

Compound 59

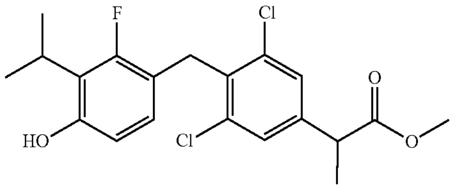

To a solution of Intermediate B2 (354 mg, 2.30 mmol, 3.0 eq) in DCE (6 mL) at rt were added $ZnCl_2$ (313 mg, 2.30 mmol, 3.0 eq) and Intermediate A45 (250 mg, 0.77 mmol, 1.0 eq). The reaction was stirred at 90° C. overnight, then cooled and diluted with DCM (20 mL). The organic phase was washed with brine (10 mL), dried over $Na_2SO_4$ and concentrated under reduced pressure. The crude material was purified by silica gel column chromatography (pet. ether/EtOAc=10/1) to afford Compound 59 (150 mg, 48.9% yield) as a colorless oil.

$^1H$ NMR: (400 MHz, DMSO-$d_6$) δ 9.54 (d, J=1.6 Hz, 1H), 7.44 (s, 2H), 6.48 (dd, J=8.4, 1.2 Hz, 1H), 6.28 (t, J=8.4 Hz, 1H), 4.07 (s, 2H), 3.90 (d, J=7.2 Hz, 1H), 3.62 (s, 3H), 3.44-3.36 (m, 1H), 1.42 (d, J=6.8 Hz, 3H), 1.26 (dd, J=7.2, 1.2 Hz, 6H).

Example 60

Synthesis of 2-(3,5-dichloro-4-(2-fluoro-4-hydroxy-3-isopropylbenzyl)phenyl)propanoic acid (Compound 60)

Compound 60

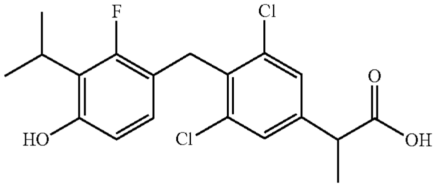

To a solution of Compound 59 (150 mg, 376 μmol, 1.0 eq) in THF (3 mL), $LiOH \cdot H_2O$ (18.9 mg, 451 μmol, 1.2 eq) in water (1 mL) was added and the reaction was stirred at rt for 2 h. Water (5 mL) was added, and the mixture was acidified to pH=3-4 with 1N HCl and extracted with EtOAc (5 ml*3). The combined organic phase was washed with brine (5 mL), dried over $Na_2SO_4$ and concentrated under reduced pressure. The crude product was purified by Prep-HPLC to afford Compound 60 (60 mg, 41 yield) as an off-white solid.

LCMS: T=4.240 min, [M−45]=339.0

$^1H$ NMR: (400 MHz, DMSO-$d_6$) δ 12.43 (s, 1H), 9.54 (d, J=1.2 Hz, 1H), 7.43 (s, 2H), 6.49 (d, J=8.4 Hz, 1H), 6.28 (t, J=8.8 Hz, 1H), 4.07 (s, 2H), 3.77 (d, J=7.2 Hz, 1H), 3.40 (d, J=7.6 Hz, 1H), 1.39 (d, J=7.2 Hz, 3H), 1.28-1.22 (m, 6H)

$^{19}F$ NMR: (376 MHz, DMSO-$d_6$) δ −120.09.

Synthesis of 3,5-dichloro-4-(2-fluoro-4-hydroxy-3-isopropylbenzyl)benzoic acid (Compound 61)

Compound 61

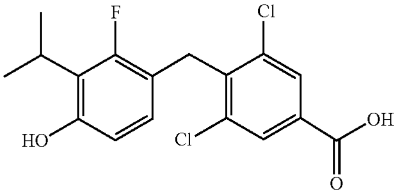

To a solution of B2 (591 mg, 3.84 mmol, 3.0 eq) in PhCl (3 mL) were added A46 (363 mg, 1.28 mmol, 1.0 eq) and $ZnCl_2$ (347.7 mg, 2.56 mmol, 2.0 eq). The reaction was stirred at 160° C. under microwave irradiation for 2 h, then the mixture was concentrated in vacuo and purified by Prep-HPLC to afford Compound 61 (50 mg, 11% yield) as a white solid.

TLC: DCM/MeOH=10/1 (v/v), Rf=0.2

LCMS: (Rt:4.25 min, M−1=355.0)

$^1$H NMR: (400 MHz, DMSO-$d_6$) δ 13.57 (s, 1H), 9.58 (s, 1H), 7.94 (s, 1H), 6.48 (d, J=8.4 Hz, 1H), 6.30 (t, J=8.4 Hz, 1H), 4.16 (s, 1H), 3.39 (dd, J=14.0, 6.8 Hz, 1H), 1.26 (d, J=6.8 Hz, 1H)

$^{19}$F NMR: (376 MHz, DMSO-$d_6$) δ −119.88.

Example 62

Synthesis of ethyl 2-((3,5-dichloro-4-(2-fluoro-4-hydroxy-3-isopropylbenzyl)phenyl)amino)-2-oxoacetate (Compound 62)

Compound 62

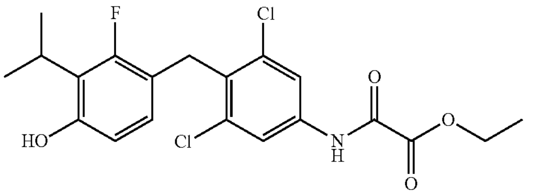

To a solution of C18 (139.0 mg, 424 μmol, 1.0 eq) in DCM (3 mL) at 0° C. were added TEA (85.7 mg, 847 μmol, 2.0 eq) and ethyl 2-chloro-2-oxoacetate (57.8 mg, 424 μmol, 1.0 eq). The mixture was stirred at rt for 2 h, then was diluted with DCM (10 mL) and washed with water (10 mL). The organic phase was dried over $Na_2SO_4$ and concentrated in vacuo. The crude material was purified by Prep-TLC (pet. ether/EtOAc=3:1) to afford Compound 62 (160 mg, 88.2% yield) as a yellow liquid.

Example 63

Synthesis of 2-((3,5-dichloro-4-(2-fluoro-4-hydroxy-3-isopropylbenzyl)phenyl)amino)-2-oxoacetic acid (Compound 63)

Compound 63

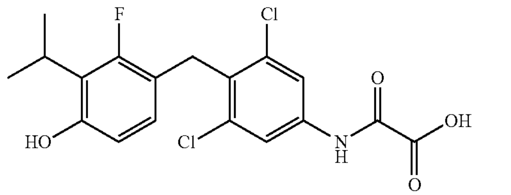

To a solution of Compound 62 (160 mg, 374 μmol, 1.0 eq) in THE (2 mL) was added LiOH·$H_2O$ (26.8 mg, 1.12 mmol, 3.0 eq) in water (1 mL) and the mixture was stirred at rt for 2 h. Water (5 mL) was added and the mixture was adjusted to pH-5 with 1 N HCl and extracted with EtOAc (20 mL*3). The combined organic phase was washed with brine (20 mL), dried over $Na_2SO_4$ and concentrated in vacuo. The crude product was purified by Prep-HPLC to afford Compound 63 (10 mg, 6.7% yield) as a white solid.

TLC: Pet. ether/EtOAc=1/1 (v/v), Rf=0.1

LCMS: T=3.738 min, [M−1]=398.0

$^1$H NMR: (400 MHz, DMSO-$d_6$) $^1$H NMR (400 MHz, DMSO) δ 11.02 (s, 1H), 9.54 (s, 1H), 7.97 (s, 1H), 6.48 (d, J=8.4 Hz, 1H), 6.29 (t, J=8.4 Hz, 1H), 4.06 (s, 1H), 1.26 (d, J=6.8 Hz, 1H).

Example 64

Synthesis of methyl 3-(3,5-dichloro-2-fluoro-4-(4-hydroxy-3-isopropylbenzyl)phenyl)propanoate (Compound 64)

Compound 64

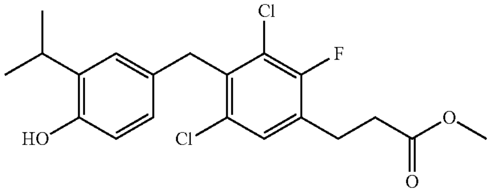

To a solution of Intermediate A54 (150 mg, 500 μmol, 1.0 eq) in DCE (5 mL) at rt were added 2-isopropylphenol (210 mg, 1.5 mmol, 3.0 eq) and $ZnCl_2$ (171 mg, 1.3 mmol, 2.5 eq). The reaction was heated to 105° C. overnight, then the mixture was cooled and diluted with DCM (20 mL). The organic phase was washed with brine (10 mL*2), dried over $Na_2SO_4$ and concentrated under reduced pressure. The crude product was purified through Prep-TLC (EtOAc/pet. ether-1/5) to afford Compound 64 (100 mg, 50.0% yield) as a light yellow oil.

TLC: EtOAc/pet. ether=1/3 (v/v), $R_f$=0.36.

Example 65

Synthesis of 3-(3,5-dichloro-2-fluoro-4-(4-hydroxy-3-isopropylbenzyl)phenyl)propanoic acid (Compound 65)

Compound 65

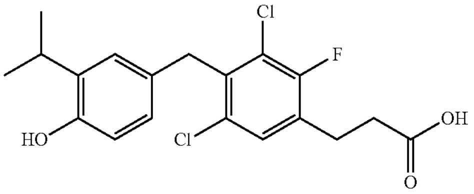

To a solution of Compound 64 (80 mg, 200 μmol, 1.0 eq) in water/THF (5 mL/1 mL) at rt was added LiOH·$H_2O$ (25 mg, 600 μmol, 3.0 eq), and the mixture was stirred at rt for 1 h. The reaction was acidified to pH=3-4 with 2N HCl, concentrated in vacuo and purified by Prep-HPLC to afford Compound 65 (20 mg, 25 yield).

TLC: EtOAc/pet. ether=1/3 (v/v), $R_f$=0.25

$^1$H NMR: (400 MHz, DMSO-$d_6$) δ 9.12 (s, 1H), 7.49 (d, J=6.4 Hz, 1H), 7.00 (d, J=1.6 Hz, 1H), 6.71-6.61 (m, 2H), 4.10 (s, 2H), 3.13 (p, J=7.2 Hz, 1H), 2.86 (t, J=7.2 Hz, 2H), 2.57 (t, J=7.6 Hz, 2H), 1.10 (d, J=6.8 Hz, 6H)

$^{19}$F NMR: (376 MHz, DMSO-$d_6$) δ −118.01.

Example 66

Synthesis of 3-(3,5-dichloro-2-fluoro-4-(4-hydroxy-3-isopropylbenzyl)phenyl)-N-methylpropanamide (Compound 66)

Compound 66

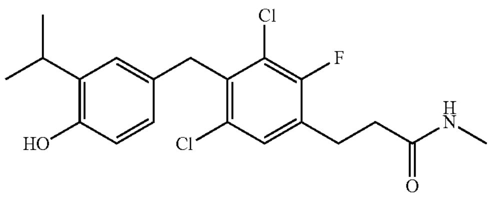

Step 1: Synthesis of 3-(3,5-dichloro-2-fluoro-4-(4-hydroxy-3-isopropylbenzyl)phenyl)propanoyl chloride (C47)

C47

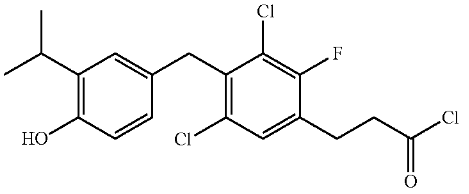

To a solution of Compound 65 (45 mg, 120 μmol, 1.0 eq) in DCM (5 mL) was added oxalyl chloride (44 mg, 350 μmol, 3.0 eq) and DMF (cat.). After stirring at rt for 1 h, the reaction mixture was concentrated in vacuo and crude Intermediate C47 was used directly in the next step.

TLC: DCM/MeOH=10/1 (v/v), Rf=0.36.

Step 2: Synthesis of 3-(3,5-dichloro-2-fluoro-4-(4-hydroxy-3-isopropylbenzyl)phenyl)-N-methylpropanamide (Compound 66)

To a solution of C47 (45 mg, 110 μmol, 1.0 eq) in DCM (5 mL) was added $CH_3NH_2$ (1 M, 1.2 mL, 1.2 mmol, 10 eq). After stirring at room temperature for 1 h, the reaction was poured into water (20 mL) and extracted with DCM (30 mL*3). The combined organic phase was concentrated in vacuo and the residue purified by Prep-TLC (pet. ether: EtOAc=1:1) to afford Compound 66 (20 mg, 90% purity) as a white solid.

TLC: DCM/MeOH=10/1 (v/v), Rf=0.45

LCMS: T=1.997 min, [M−1]=396.10

$^1$H NMR: (400 MHz, DMSO-$d_6$) δ 9.12 (s, 1H), 7.78 (d, J=4.4 Hz, 1H), 7.42 (d, J=6.8 Hz, 1H), 6.99 (d, J=1.6 Hz, 1H), 6.71-6.61 (m, 2H), 4.10 (s, 2H), 3.12 (p, J=6.8 Hz, 1H), 2.85 (t, J=7.6 Hz, 2H), 2.54 (d, J=4.8 Hz, 3H), 2.38 (t, J=7.6 Hz, 2H), 1.10 (d, J=6.8 Hz, 6H)

$^{19}$F NMR: (376 MHz, DMSO-$d_6$) δ −118.14.

Example 67

Synthesis of 3-(3,5-dichloro-2-fluoro-4-(4-hydroxy-3-isopropylbenzyl)phenyl)-N,N-dimethylpropanamide (Compound 67)

Compound 67

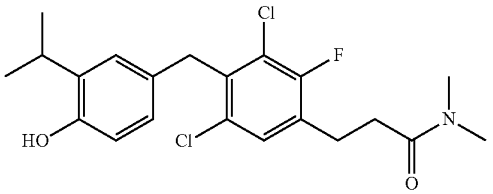

To a solution of C47 (45 mg, 110 μmol, 1.0 eq) in DCM (5 mL) was added dimethylamine (1 Min THF, 1.17 mL, 1.17 mmol, 10 eq). After stirring at room temperature for 2 h, the reaction was poured into water (20 mL) and extracted with DCM (30 mL*3). The combined organic phase was concentrated in vacuo and purified by Prep-TLC (Pet. ether: EtOAc=1:1) to afford Compound 67 (22 mg, 42% yield) as a white solid.

TLC: DCM/MeOH=10/1 (v/v), Rf=0.45

LCMS: T=2.507 min, [M−1]=410.1

$^1$H NMR: (400 MHz, DMSO-$d_6$)) δ 9.12 (s, 1H), 7.51 (d, J=6.4 Hz, 1H), 7.06-6.96 (m, 1H), 6.75-6.59 (m, 2H), 4.10 (s, 2H), 3.13 (p, J=6.8 Hz, 1H), 2.93 (s, 3H), 2.89-2.77 (m, 5H), 2.63 (t, J=7.2 Hz, 2H), 1.11 (d, J=7.2 Hz, 6H)

$^{19}$F NMR: (376 MHz, DMSO-$d_6$) δ −118.06.

Example 68

Synthesis of methyl 2-(3,5-dichloro-2-fluoro-4-(2-fluoro-4-hydroxy-3-isopropylbenzyl)phenyl)acetate (Compound 68)

Compound 68

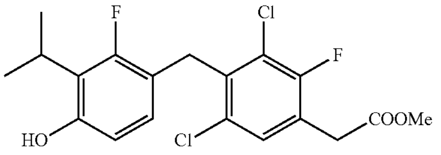

To a solution of Intermediate A58 (500 mg, 1.75 mmol, 1.0 eq) and Intermediate B2 (540 mg, 3.50 mmol, 2.0 eq) in chlorobenzene (5 mL) was added $ZnCl_2$ (1 M in THF, 4.38 mL, 4.38 mmol, 2.5 eq). The reaction was stirred at 115° C. overnight, then the mixture was concentrated to dryness. $H_2O$ (30 mL) was added and the mixture was extracted with EtOAc (25 mL*2). The combined organic phase was washed with brine (50 mL), dried over $Na_2SO_4$ and concentrated to dryness. The crude material was purified by Prep-TLC (pet. ether/EtOAc=5/1) to afford Compound 68 (150 mg, 15.9% yield) as a white solid.

$^1$H NMR: (400 MHz, DMSO-$d_6$) δ 9.58 (d, J=1.6 Hz, 1H), 7.60 (d, J=6.4 Hz, 1H), 6.49 (d, J=8.4 Hz, 1H), 6.30 (t, J=8.4 Hz, 1H), 4.11 (s, 2H), 3.85 (d, J=1.2 Hz, 2H), 3.66 (s, 3H), 3.44-3.34 (m, 1H), 1.26 (d, J=7.2 Hz, 6H).

Example 69

Synthesis of 2-(3,5-dichloro-2-fluoro-4-(2-fluoro-4-hydroxy-3-isopropylbenzyl)phenyl)acetic acid (Compound 69)

Compound 69

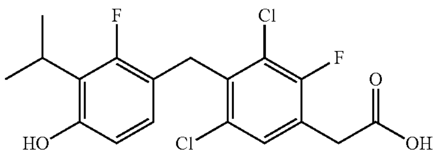

To a solution of Compound 68 (130 mg, 322 μmol, 1.0 eq) in $MeOH/H_2O$ (3 mL/1 mL) at rt was added $LiOH \cdot H_2O$ (23 mg, 552 μmol, 1.7 eq) and the reaction was stirred for 1 h. The mixture was diluted with water (10 mL), acidified to pH=3-4 with 1 N HCl, and extracted with EtOAc (15 mL*2). The combined organic phase was washed with brine (30 mL), dried over $Na_2SO_4$ and concentrated under reduced pressure. The crude product was purified by Prep-HPLC to afford Compound 69 (26 mg, 20% yield) as a white solid.

LCMS: T=1.758 min, [M−1]=342.9

$^1H$ NMR: (400 MHz, DMSO-$d_6$) δ 12.65 (s, 1H), 9.60 (d, J=1.2 Hz, 1H), 7.58 (d, J=6.4 Hz, 1H), 6.49 (d, J=8.4 Hz, 1H), 6.30 (t, J=8.4 Hz, 1H), 4.10 (s, 2H), 3.74 (d, J=1.2 Hz, 2H), 3.42-3.37 (m, 1H), 1.26 (d, J=7.2 Hz, 6H)

$^{19}F$ NMR: (376 MHz, DMSO-$d_6$) δ −116.56, −119.93.

Example 70

Synthesis of methyl 3-(3,5-dichloro-2-fluoro-4-(2-fluoro-4-hydroxy-3-isopropylbenzyl)phenyl)propanoate (Compound 70)

Compound 70

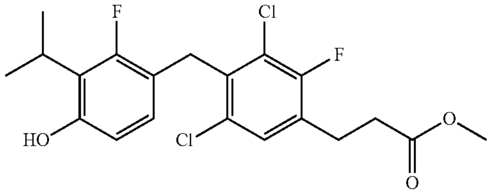

To a solution of Intermediate A54 (77 mg, 500 μmol, 3.0 eq) in DCE (5 mL) at rt were added Intermediate B2 (50 mg, 170 μmol, 1.0 eq) and $ZnCl_2$ (114 mg, 835 μmol, 5.0 eq). The reaction was heated to 105° C. overnight, then the mixture was cooled and diluted with DCM (20 mL). The organic phase was washed with brine (30 mL), dried over $Na_2SO_4$ and concentrated under reduced pressure. The crude product was purified through Prep-TLC (EtOAc/pet. ether=1/3) to afford Compound 70 (50 mg, 72% yield) as a light yellow oil.

TLC: EtOAc/pet. ether=1/3 (v/v), Rf=0.25.

Example 71

Synthesis of 3-(3,5-dichloro-2-fluoro-4-(2-fluoro-4-hydroxy-3-isopropylbenzyl)phenyl)propanoic acid (Compound 71)

Compound 71

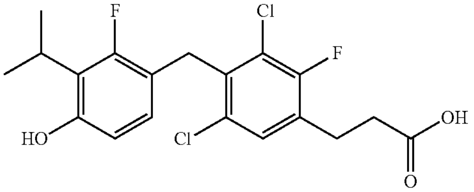

To a solution of Compound 70 (50 mg, 120 μmol, 1.0 eq) in THF/water (5 mL/1 mL) at rt was added $LiOH \cdot H_2O$ (15 mg, 360 μmol, 3.0 eq) and the reaction was stirred for 1 h. The mixture was acidified to pH=3-4 with 2N HCl, and extracted with DCM (20 mL*3). The combined organic phase was dried over $Na_2SO_4$, concentrated in vacuo and purified by Prep-TLC (DCM:MeOH=20:1) to afford Compound 71 (40 mg, 81% yield).

TLC: EtOAc/pet. ether=1/1 (v/v), Rf=0.08

LCMS: T=2.695 min, [M−1]=401.1

$^1$HNMR: (400 MHz, DMSO-$d_6$) δ 9.56 (s, 1H), 7.52 (d, 1H), 6.49 (d, J=1.6 Hz, 1H), 6.28 (t, 1H), 4.08 (s, 2H), 3.36 (m, 1H), 2.88 (t, 2H), 2.59 (t, 2H), 1.25 (d, 6H)

$^{19}F$ NMR: (376 MHz, DMSO-$d_6$) δ −118.08, −119.98.

Example 72

Synthesis of 3-(3,5-dichloro-2-fluoro-4-(2-fluoro-4-hydroxy-3-isopropylbenzyl)phenyl)-N-methylpropanamide (Compound 72)

Compound 72

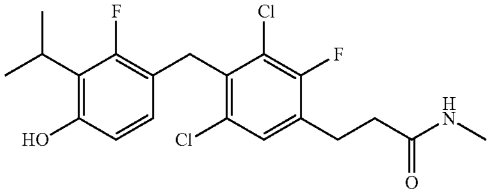

Intermediate C28

Step 1: Synthesis of 3-(3,5-dichloro-2-fluoro-4-(2-fluoro-4-hydroxy-3-isopropylbenzyl)phenyl) propanoyl chloride (C48)

C48

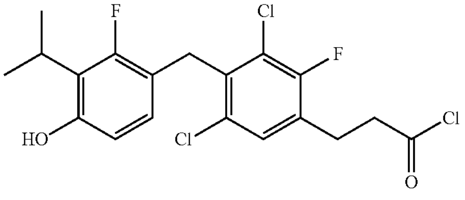

To a solution of Compound 71 (15 mg, 37.20 μmol) in DCM (4 mL) was added $(COCl)_2$ (14 mg, 111.6 μmol) and DMF (cat.). After stirring at RT for 1 h to afford Intermediate C48. The reaction mixture was concentrated in vacuo and used without further purification.

Step 2: Synthesis of 3-(3,5-dichloro-2-fluoro-4-(2-fluoro-4-hydroxy-3-isopropylbenzyl)phenyl)-N-methylpropanamide (Compound 72)

Intermediate C48 (15 mg, 36 μmol) was dissolved in DCM (5 mL); $CH_3NH_2$ (2 M, 178 uL) was added to the solution. After stirring at room temperature for 2 h, the mixture was poured into water (20 mL) and was extracted with DCM (30 mL×3). The combined organic phase was concentrated and purified by prep-TLC (pet. ether: EtOAc=1:1) to afford Compound 72 (8.0 mg, 510% yield) as a white solid.

TLC: DCM/MeOH=10/1 (v/v), Rf=0.45

LCMS: T=0.825 min, [M−1]:414.09

HNMR: $^1H$ NMR (400 MHz, DMSO-$d_6$) δ 9.56 (s, 1H), 7.79 (s, 1H), 7.45 (d, J=6.8 Hz, 1H), 6.48 (d, J=8.2 Hz, 1H), 6.28 (t, J=8.6 Hz, 1H), 4.08 (s, 2H), 3.39 (s, 1H), 2.87 (t, J=7.4 Hz, 2H), 2.55 (d, J=4.6 Hz, 3H), 2.40 (t, J=7.6 Hz, 2H), 1.25 (d, J=7.2 Hz, 6H).

FNMR: $^{19}F$ NMR (377 MHz, DMSO-$d_6$) δ −118.21, −119.98.

Example 73

Synthesis of 3-(3,5-dichloro-2-fluoro-4-(2-fluoro-4-hydroxy-3-isopropylbenzyl)phenyl)-N,N-dimethylpropanamide (Compound 73)

Compound 73

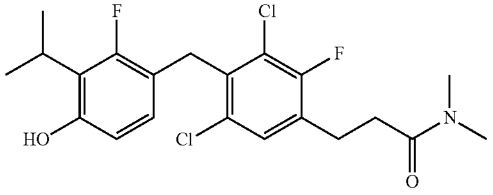

Intermediate C48 (15 mg, 36 μmol) was dissolved in DCM (5 mL); dimethylamine (2 M, 178 uL) was added. After stirring at room temperature for 2 h, the mixture was poured into water (20 mL) and was extracted with DCM (30 mL×3). The combined organic phase was concentrated and purified by prep-TLC (pet. ether:EtOAc=1:1) to afford compound 73 (8.0 mg, 17 μmol, 49% yield) as a white solid.

TLC: DCM/MeOH=10/1 (v/v), Rf=0.45

LCMS: T=1.213 min, [M−1]:428.1

HNMR: $^1H$ NMR (400 MHz, DMSO-$d_6$) δ 9.56 (s, 1H), 7.54 (d, J=6.8 Hz, 1H), 6.48 (d, J=8.4 Hz, 1H), 6.29 (t, J=8.4 Hz, 1H), 4.08 (s, 2H), 3.37 (s, 1H), 2.95 (s, 3H), 2.83 (d, J=14.8 Hz, 6H), 2.66 (t, J=7.2 Hz, 2H), 1.26 (d, J=7.2 Hz, 7H).

FNMR: $^{19}F$ NMR (377 MHz, DMSO-$d_6$) δ −118.16, −119.98.

Example 74

Synthesis of ethyl (3,5-dichloro-2-fluoro-4-(4-hydroxy-3-isopropylbenzyl)phenyl)glycinate (Compound 74)

Compound 74

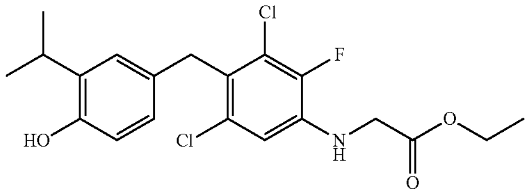

To a solution of C23 (66 mg, 0.20 mmol, 1.0 eq) in MeCN (3 mL) were added AcOH (2 drops) and ethyl glyoxalate (410 mg, 4.0 mmol, 20 eq). The reaction was stirred at 65° C. for 7 h then concentrated in vacuo. The residue was dissolved in THF (3 mL) and Pd/C (24 mg) was added. The reaction was stirred at rt under 1 atm $H_2$ overnight, then the mixture was filtered. The filtrate was concentrated in vacuo to give crude Compound 74 that was used directly in the next step.

TLC: Pet. ether/EtOAc=3/1 (v/v), Rf=0.67

LCMS: T=2.185 min, [M−1]=414.1.

Example 75

Synthesis of (3,5-dichloro-2-fluoro-4-(4-hydroxy-3-isopropylbenzyl)phenyl)glycine (Compound 75)

Compound 75

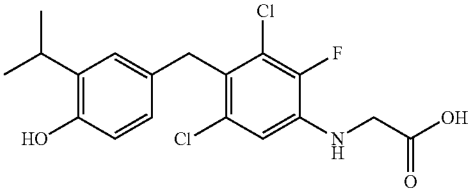

To a solution of Compound 74 (66 mg, 0.16 mmol, 1.0 eq) in MeOH/water (2 mL/1 mL) at rt was added $LiOH{\cdot}H_2O$ (20 mg, 0.48 mmol, 3.0 eq), and the reaction was stirred at rt for 1 h. The mixture was acidified to pH=4-5 with 2 N HCl, and extracted with EtOAc (20 mL). The organic phase was washed with brine (10 mL*2), dried over $Na_2SO_4$ and concentrated in vacuo. The crude material was purified by Prep-HPLC to afford Compound 75 (9.0 mg, 11% yield) as a white solid.

TLC: DCM/MeOH=5/1 (v/v), Rf=0.17

LCMS: T=1.387 min, [M−1]=383.9

$^1H$ NMR: (400 MHz, DMSO-$d_6$) δ 9.05 (s, 1H), 6.97 (d, J=2.0 Hz, 1H), 6.74 (d, J=8.0 Hz, 1H), 6.67 (dd, J=8.0, 2.0 Hz, 1H), 6.63 (d, J=8.0 Hz, 1H), 6.20 (s, 1H), 3.98 (s, 2H), 3.92 (d, J=6.0 Hz, 2H), 3.13 (p, J=6.8 Hz, 1H), 1.11 (d, J=6.8 Hz, 6H)

$^{19}F$ NMR: (376 MHz, DMSO-$d_6$) δ −134.43.

Example 76

Synthesis of 2-((3,5-dichloro-2-fluoro-4-(4-hydroxy-3-isopropylbenzyl)phenyl)amino)-N-methyl-acetamide (Compound 76)

Compound 76

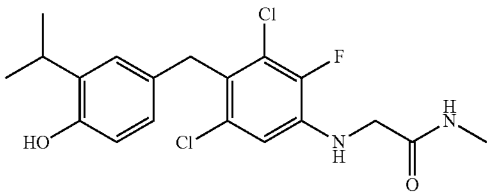

Step 1: Synthesis of (3,5-dichloro-2-fluoro-4-(4-hydroxy-3-isopropylbenzyl)phenyl)glycinoyl chloride (C49)

C49

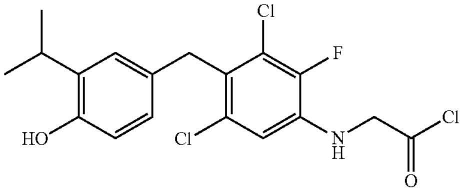

To a solution of Compound 75 (46 mg, 0.12 mmol, 1.0 eq) in DCM (2 mL) was added oxalyl chloride (23 mg, 0.19 mmol, 1.5 eq). The reaction was stirred at rt for 1 h, then the mixture was concentrated to dryness to afford Intermediate C49 (48 mg, 99% yield) as a colorless oil.

TLC: Pet. ether/EtOAc=3/1 (v/v), Rf=0.35.

Step 2: Synthesis of 2-((3,5-dichloro-2-fluoro-4-(4-hydroxy-3-isopropylbenzyl)phenyl)amino)-N-methylacetamide (Compound 76)

To a solution of C49 (46 mg, 0.11 mmol, 1.0 eq) in THF (3 mL) was added $CH_3NH_2$ (2 M in THF, 2 mL, 4 mmol, 36 eq). The reaction was stirred at rt for 30 min, then the mixture was concentrated to dryness. The crude material was purified by Prep-HPLC to afford Compound 76 (11 mg, 19% yield) as a white solid.

TLC: Pet. ether/EtOAc=3/1 (v/v), Rf=0.35

LCMS: T=1.439 min, [M+1]=399.1

$^1H$ NMR: (400 MHz, DMSO-$d_6$) δ 9.05 (s, 1H), 7.89 (d, J=4.8 Hz, 1H), 6.98 (d, J=2.0 Hz, 1H), 6.67 (dd, J=8.4, 2.0 Hz, 1H), 6.63 (d, J=8.0 Hz, 1H), 6.59 (d, J=8.0 Hz, 1H), 6.28 (s, 1H), 3.97 (s, 2H), 3.72 (d, J=4.8 Hz, 2H), 3.13 (p, J=6.8 Hz, 1H), 2.59 (d, J=4.8 Hz, 3H), 1.11 (d, J=6.8 Hz, 6H)

$^{19}F$NMR: (376 MHz, DMSO-$d_6$) δ −133.70.

Example 77

Synthesis of ethyl (3,5-dichloro-2-fluoro-4-(2-fluoro-4-hydroxy-3-isopropylbenzyl)phenyl)glycinate (Compound 77)

Compound 77

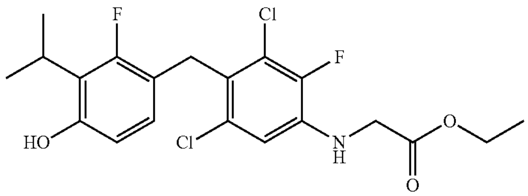

To a solution of C25 (100 mg, 289 μmol, 1.0 eq) in MeCN (3 mL) were added AcOH (3 drops) and ethyl glyoxalate (590 mg, 5.8 mmol, 20 eq). The reaction was stirred at 65° C. for 6 h then concentrated in vacuo. The residue was dissolved in THF (3 mL) and Pd/C (40 mg) was added. The reaction was stirred at rt under 1 atm $H_2$ overnight, then the mixture was filtered. The filtrate was concentrated in vacuo to give crude Compound 77 that was used directly in the next step.

TLC: Pet. ether/EtOAc=3/1 (v/v), Rf=0.67

LCMS: T=2.346 min, [M−1]=429.9.

Example 78

Synthesis of (3,5-dichloro-2-fluoro-4-(2-fluoro-4-hydroxy-3-isopropylbenzyl)phenyl)glycine (Compound 78)

Compound 78

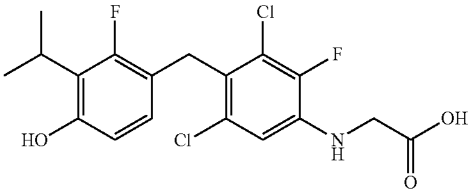

To a solution of Compound 77 (100 mg, 0.23 mmol, 1.0 eq) in MeOH/water (2 mL/1 mL) at rt was added $LiOH \cdot H_2O$ (29 mg, 0.69 mmol, 3.0 eq), and the reaction was stirred at rt for 1 h. The mixture was acidified to pH=4-5 with 2 N HCl, and extracted with EtOAc (20 mL). The organic phase was washed with brine (10 mL*2), dried over $Na_2SO_4$ and concentrated in vacuo. The crude material was purified by Prep-HPLC to afford Compound 78 (14 mg, 15% yield) as a white solid.

TLC: DCM/MeOH=5/1 (v/v), Rf=0.22

LCMS: T=1.721 min, [M−1]=401.9.

$^1H$ NMR: (400 MHz, DMSO-$d_6$) δ 9.50 (s, 1H), 6.76 (d, J=8.0 Hz, 1H), 6.48 (d, J=8.4 Hz, 1H), 6.30 (t, J=8.4 Hz, 2H), 3.96 (s, 2H), 3.93 (s, 2H), 3.40 (s, 1H), 1.26 (d, J=7.2 Hz, 6H)

$^{19}F$ NMR: (376 MHz, DMSO-$d_6$) δ −120.39, −134.52.

Example 79

Synthesis of 2-((3,5-dichloro-2-fluoro-4-(2-fluoro-4-hydroxy-3-isopropylbenzyl)phenyl)amino)-N-methylacetamide (Compound 79)

Compound 79

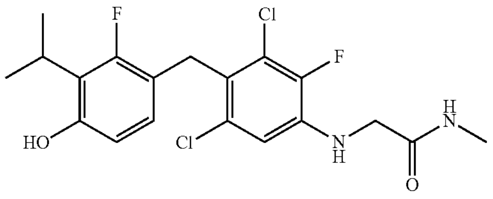

Step 1: Synthesis of (3,5-dichloro-2-fluoro-4-(2-fluoro-4-hydroxy-3-isopropylbenzyl)phenyl) glycinoyl chloride (C50)

C50

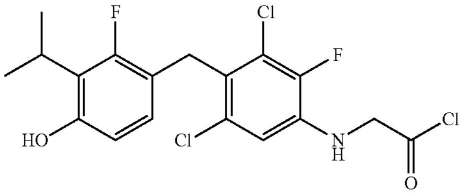

To a solution of Compound 78 (26 mg, 64.3 μmol, 1.0 eq) in DCM (2 mL) was added $SOCl_2$ (11 mg, 97 μmol, 1.5 eq) and DMF (cat). The mixture was stirred at 40° C. for 1 h, then the mixture was concentrated to dryness to afford Intermediate C50 (26 mg, 96% yield) as a colorless oil.

Step 2: Synthesis of 2-((3,5-dichloro-2-fluoro-4-(2-fluoro-4-hydroxy-3-isopropylbenzyl)phenyl) amino)-N-methylacetamide (Compound 79)

To a solution of C50 (26 mg, 62 μmol, 1.0 eq) in DCM (2 mL) was added $CH_3NH_2$ (2 M in THF, 2 mL, 4 mmol, 65 eq). The mixture was stirred at rt for 30 min, then was concentrated to dryness. The crude material was purified by Prep-HPLC to afford Compound 79 (5.0 mg, 20% yield) as a white solid.

TLC: DCM/MeOH=5/1 (v/v), Rf=0.37

LCMS: T=1.647 min, [M+1]=417.0

$^1$H NMR: (400 MHz, DMSO-$d_6$) δ 9.51 (s, 1H), 7.92 (d, J=4.8 Hz, 1H), 6.62 (d, J=8.0 Hz, 1H), 6.48 (d, J=8.0 Hz, 1H), 6.35 (t, J=5.6 Hz, 1H), 6.30 (t, J=8.4 Hz, 1H), 3.96 (s, 2H), 3.74 (d, J=6.0 Hz, 2H), 3.43-3.34 (m, 1H), 2.60 (d, J=4.4 Hz, 3H), 1.25 (d, J=6.8 Hz, 6H)

$^{19}$F NMR: (376 MHz, DMSO-$d_6$) δ −120.39, −133.84.

Example 80

Synthesis of ethyl 2-(3,5-dichloro-4-(4-hydroxy-3-isopropylbenzyl)phenoxy)-2-fluoroacetate (Compound 80)

Compound 80

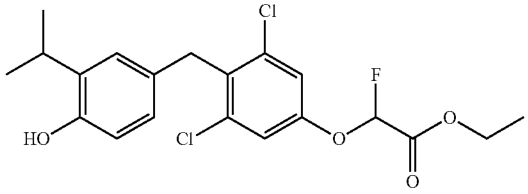

To a solution of C28 (1.0 eq) in THF/Water (40 mL/g) is added TBAF (1.5 eq) and the mixture is stirred for 24 h at rt. The reaction mixture is diluted with water (2.5×), acidified to pH=3 with aqueous HCl (0.1 N), and extracted with EtOAc. The combined organic phase is dried over $Na_2SO_4$ and concentrated under reduce pressure to provide the crude product that is purified through Prep-TLC (Methanol/DCM=1/10) to afford Compound 80.

Example 81

Synthesis of 2-(3,5-dichloro-4-(4-hydroxy-3-isopropylbenzyl)phenoxy)-2-fluoroacetic acid (Compound 81)

Compound 81

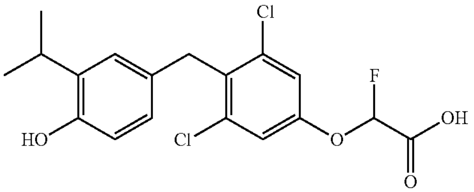

To a solution of C28 (244 mg, 0.43 mmol, 1.0 eq) in THF/water (3 mL/0.5 mL) at rt was added LiOH·$H_2O$ (27 mg, 0.64 mmol, 1.5 eq) and the mixture was stirred overnight. The reaction mixture was acidified to pH=2 with aqueous 2N HCl and stirred for 30 min. The mixture was extracted with EtOAc (10 mL*3), dried over $Na_2SO_4$ and concentrated under reduce pressure. The crude product was purified through Prep-TLC (MeOH/DCM=1/5) to afford Compound 81 (40 mg, 24% yield) as a yellow solid.

TLC: EtOAc/pet. ether=1/10, Rf=0.13

LCMS: T=2.55 min; [M−1]=384.8

$^1$H NMR: (400 MHz, DMSO-$d_6$) δ 9.14 (s, 1H), 7.22 (s, 2H), 6.98 (s, 1H), 6.66 (d, J=1.3 Hz, 2H), 5.79 (d, J=60.4 Hz, 1H), 4.05 (s, 2H), 3.16-3.09 (m, 1H), 1.11 (d, J=6.9 Hz, 6H).

Example 82

Synthesis of 2-(3,5-dichloro-4-(4-hydroxy-3-isopropylbenzyl)phenoxy)-2,2-difluoroacetic acid (Compound 82)

Compound 82

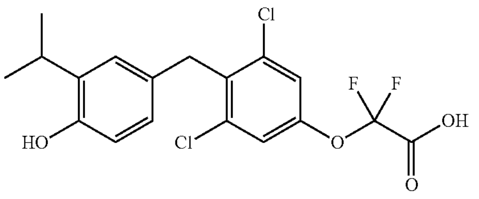

To a solution of C29 (50 mg, 89 µmol, 1.0 eq) in THF/Water (1.0 mL each) was added TBAF (35 mg, 130 µmol, 1.5 eq) and the mixture was stirred for 24 h at rt. The reaction mixture was diluted with water (5 mL), acidified to pH=3 with aqueous HCl (0.1 N), and extracted with EtOAc (5 mL*3). The combined organic phase was dried over $Na_2SO_4$ and concentrated under reduced pressure, then purified through Prep-TLC (Methanol/DCM=1/10) to afford Compound 82 (9.0 mg, 25% yield) as a brown solid.

TLC: EtOAc/pet. ether=1/3, Rf=0.16

LCMS: T=2.29 min; [M−1]=402.8

$^1$H NMR: (400 MHz, DMSO-$d_6$) δ 9.11 (s, 1H), 7.24 (s, 2H), 6.99 (s, 1H), 6.65 (d, J=1.2 Hz, 2H), 4.06 (s, 2H), 3.15-3.08 (m, 1H), 1.11 (d, J=6.9 Hz, 6H)

$^{19}$F NMR: (376 MHz, DMSO-$d_6$) δ −75.21.

Example 83

Synthesis of 2-(3,5-dichloro-4-(4-hydroxy-3-isopropylbenzyl)phenoxy)-2-fluoro-N-methylacetamide (Compound 83)

Compound 83

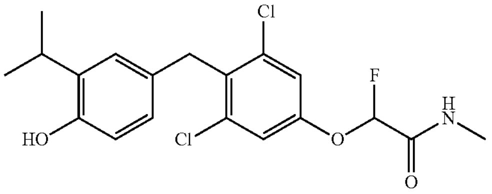

To a solution of C33 (90 mg, 0.18 mmol) in THE (10 mL) was added Pd/C (45 mg) and the reaction was stirred under 1 atm $H_2$ at rt for 16 h. The mixture was filtered, concentrated in vacuo, and purified by Prep-HPLC to afford Compound 83 (25 mg, 34% yield) as a white solid.

LCMS: T=3.888 min, [M+1]=400.1

$^1$H NMR: (400 MHz, DMSO-$d_6$) δ 9.10 (s, 1H), 8.56 (s, 1H), 7.37 (s, 2H), 6.98 (s, 1H), 6.68-6.63 (m, 2H), 6.46 (s, 1H), 6.31 (s, 1H), 4.09 (s, 2H), 3.15-3.10 (m, 1H), 2.69 (d, J=4.4 Hz, 3H), 1.10 (d, J=6.8 Hz, 6H).

Example 84

Synthesis of 2-(3,5-dichloro-4-(4-hydroxy-3-isopropylbenzyl)phenoxy)-2,2-difluoro-N-methylacetamide (Compound 84)

Compound 84

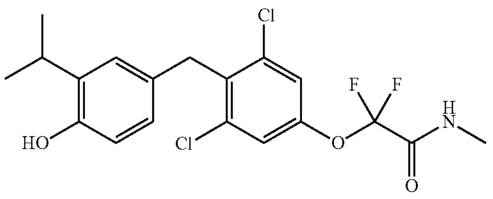

To a solution of C36 (200 mg, 380 µmol) in THE (5.0 mL) was added Pd/C (50 mg). The reaction was flushed repeatedly with $H_2$ then heated to 35° C. and stirred overnight under 1 atm of $H_2$. The mixture was filtered and the filtrate concentrated in vacuo. Water (30 mL) was added, and the mixture was extracted with EtOAc (15 mL*3). The combined organic phase was washed with brine (30 mL), dried over $Na_2SO_4$ and concentrated in vacuo. The crude material was purified by Prep-HPLC to afford Compound 84 (100 mg, 60.3% yield) as a white solid.

TLC: EtOAc/pet. ether=1/3 (v/v), Rf=0.3

LCMS: T=4.100 min, [M−1]=440.1

$^1$H NMR: (400 MHz, DMSO-$d_6$) δ 9.12 (s, 2H), 7.47 (s, 2H), 6.97 (d, J=2.0 Hz, 1H), 6.72-6.63 (m, 2H), 4.12 (s, 2H), 3.13 (p, J=6.9 Hz, 1H), 2.72 (d, J=4.6 Hz, 3H), 1.10 (d, J=6.9 Hz, 6H).

$^{19}$F NMR: (376 MHz, DMSO-$d_6$) δ −76.38.

Example 85

Synthesis of methyl (E)-3-(3,5-dichloro-4-(4-hydroxy-3-isopropylbenzyl)phenyl)acrylate (Compound 85)

Compound 85

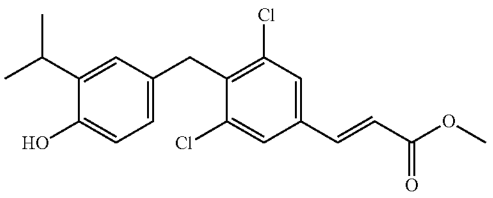

Step 1: Synthesis of methyl (E)-3-(3,5-dichloro-4-(3-isopropyl-4-((tetrahydro-2H-pyran-2-yl)oxy)benzyl)phenyl)acrylate (C51)

C51

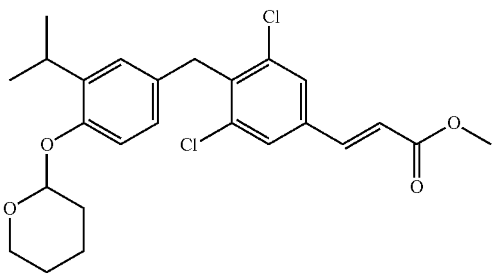

To a mixture of Intermediate C4 (600 mg, 1.31 mmol), $Pd(OAc)_2$ (29 mg, 131 mol) and $K_2CO_3$ (362 mg, 2.62 mmol) in DMF (10 mL) at rt was added methyl acrylate (282 mg, 3.3 mmol, 2.5 eq). The reaction was heated to 100° C. overnight under $N_2$ (g) atmosphere. The reaction mixture was cooled to rt; water (50 mL) was added and the resultant mixture was extracted with EtOAc (20 mL*3). The combined organic phase was washed with brine (30 mL), dried over $Na_2SO_4$, concentrated in vacuo and purified by silica gel column chromatography (EtOAc/pet. ether=1/100 to 1/20) to afford Intermediate C51 (250 mg, 41.2% yield) as a yellow solid.

HNMR: $^1$HNMR (400 MHz, DMSO-$d_6$) δ 7.95 (s, 2H), 7.64 (d, J=16.1 Hz, 1H), 7.11 (d, J=2.3 Hz, 1H), 6.95 (d, J=8.5 Hz, 1H), 6.88-6.81 (m, 2H), 5.41 (s, 1H), 4.21 (s, 2H), 3.75 (s, 3H), 3.71 (s, 1H), 3.54 (dt, J=11.4, 4.4 Hz, 1H), 3.24 (p, J=6.9 Hz, 1H), 1.81 (m, 3H), 1.59 (m, 3H), 1.17 (dd, J=6.9, 5.3 Hz, 6H).

Step 2: Synthesis of methyl (E)-3-(3,5-dichloro-4-(4-hydroxy-3-isopropylbenzyl)phenyl)acrylate (Compound 85)

To a mixture of C51 (250 mg, 540 μmol) in MeOH (5 mL) at rt was added TsOH pyridine (14 mg, 54 μmol). The mixture was heated to 40° C. and stirred overnight. The reaction mixture was concentrated in vacuo; water (40 mL) was added and the mixture was extracted with EtOAc (20 mL*3). The organic phase was washed with brine (30 mL), dried over $Na_2SO_4$, concentrated in vacuo and purified by Prep-TLC (EtOAc/pet. ether=1/5) to afford Compound 85 (130 mg, 63.5% yield) as a white solid.

Example 86

Synthesis of (E)-3-(3,5-dichloro-4-(4-hydroxy-3-isopropylbenzyl)phenyl)acrylic acid (Compound 86)

Compound 86

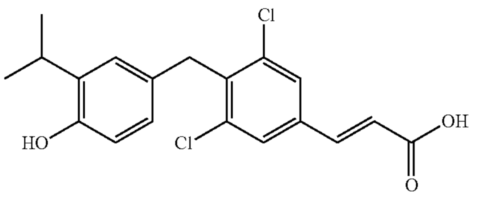

To a solution of Compound 85 (50 mg, 0.13 mmol, 1.0 eq) in THF/water (5 mL/0.2 mL) at rt was added LiOH (19 mg, 0.79 mmol, 6.0 eq) and the reaction was stirred overnight. The mixture was acidified to pH=4-5 with 2N HCl, and extracted with EtOAc (5 mL). The organic phase was washed with brine (5 mL), dried over $Na_2SO_4$ and concentrated in vacuo. The crude material was purified by Prep-TLC (DCM/MeOH=10/1) to afford Compound 86 (35 mg, 73% yield) as a white solid.

TLC: DCM/MeOH=10/1 (v/v), Rf=0.15.

LCMS: T=4.012 min, [M−1]=363.1

$^1$H NMR: (400 MHz, DMSO-$d_6$) δ 12.52 (s, 1H), 9.14 (s, 1H), 7.88 (s, 2H), 7.53 (d, J=16.0 Hz, 1H), 7.00 (d, J=2.0 Hz, 1H), 6.72-6.62 (m, 3H), 4.13 (s, 2H), 3.13 (p, J=6.8 Hz, 1H), 1.10 (d, J=6.8 Hz, 6H).

Example 87

Synthesis of methyl (E)-3-(3,5-dichloro-4-(2-fluoro-4-hydroxy-3-isopropylbenzyl)phenyl)acrylate (Compound 87)

Compound 87

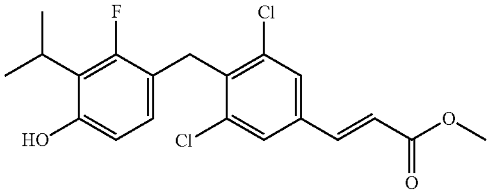

To a solution of Intermediate A41 (100 mg, 309 μmol, 1.0 eq) in DCE (5.0 mL) at rt were added Intermediate B2 (142 mg, 956 μmol, 3.0 eq) and $ZnCl_2$ (1 M in THF, 773 uL, 773 mol, 2.5 eq); the reaction was heated to 85° C. and stirred overnight. The reaction was cooled to rt, water (20 mL) was added and mixture extracted with DCM (10 mL*3). The combined organic phase was washed with brine (20 mL), dried over $Na_2SO_4$ and concentrated in vacuo. The crude product was purified by Prep-TLC (EtOAc/pet. ether=1/5) to afford Compound 87 (30 mg, 24% yield) as a white solid.

TLC: Pet. ether/EtOAc=5/1 (v/v), Rf=0.20

$^1$H NMR: (400 MHz, DMSO-$d_6$) δ 9.57 (d, J=1.5 Hz, 1H), 7.64 (d, J=16.0 Hz, 1H), 6.85 (d, J=16.0 Hz, 1H), 6.48 (d, J=8.6 Hz, 1H), 6.29 (t, J=8.6 Hz, 1H), 4.11 (s, 2H), 3.74 (s, 3H), 1.28-1.24 (m, 6H).

Example 88

Synthesis of (E)-3-(3,5-dichloro-4-(2-fluoro-4-hydroxy-3-isopropylbenzyl)phenyl)acrylic acid (Compound 88)

Compound 88

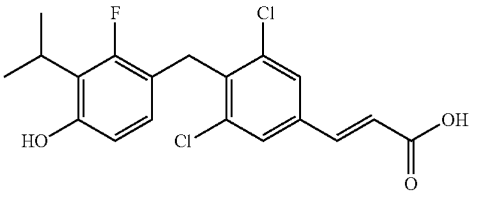

To a solution of Compound 87 (50 mg, 130 μmol, 1.0 eq) in THF/$H_2O$ (2.0 mL/0.5 mL) at rt was added LiOH·$H_2O$ (16 mg, 380 μmol, 3.0 eq) and the mixture was stirred for 1 h. The mixture was diluted with water (20 mL), acidified to pH=3-4 with 1 N HCl, and extracted with EtOAc (15 mL*3). The combined organic phase was washed with brine (20 mL), dried over $Na_2SO_4$ and concentrated under reduced pressure. The crude material was purified by Prep-HPLC to afford Compound 88 (5.0 mg, 10% yield) as a white solid.

TLC: MeOH/DCM=1/10 (v/v), Rf=0.30

LCMS: T=4.282 min, [M−1]=381.1

$^1$H NMR: (400 MHz, DMSO-$d_6$) δ 12.57 (s, 1H), 9.56 (s, 1H), 7.91 (s, 2H), 7.56 (d, J=16.0 Hz, 1H), 6.71 (d, J=16.0 Hz, 1H), 6.48 (dd, J=8.4, 1.1 Hz, 1H), 6.29 (t, J=8.4 Hz, 1H), 4.11 (s, 2H), 3.39 (m, 1H), 1.26 (dd, J=7.2, 0.8 Hz, 6H)

$^{19}$F NMR: (376 MHz, DMSO-$d_6$) δ −120.01.

Example 89

Synthesis of 1-(tert-butyl) 3-ethyl (E)-2-(3,5-dichloro-4-(4-hydroxy-3-isopropylbenzyl)benzylidene) malonate (Compound 89)

Compound 89

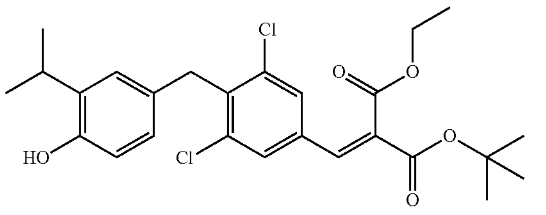

To a solution of C38 (400 mg, 744 μmol) in DCM (2.0 mL) was added dropwise HCl/1,4-dioxane (2.0 mL) and the reaction was stirred at rt for 2 h. Water (30 mL) was added and the mixture was extracted with DCM (15 mL*3). The combined organic phase was washed with brine (30 mL), dried over $Na_2SO_4$ and concentrated in vacuo to afford crude Compound 89 (365 mg, 99.4% yield) as a light yellow oil.

TLC: EtOAc/pet. ether=1/5 (v/v), Rf=0.50.

Example 90

Synthesis of 3-(3,5-dichloro-4-(4-hydroxy-3-isopropylbenzyl)phenyl)-2-(ethoxycarbonyl)acrylic acid (Compound 90)

Compound 90

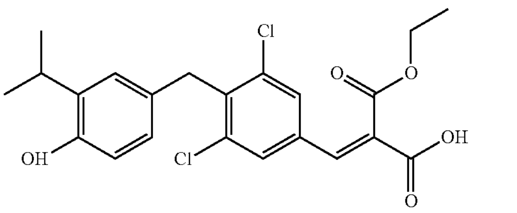

To a solution of Compound 89 (365 mg, 811 μmol, 1.0 eq) in DCE (5.0 mL) at rt was added $ZnCl_2$ (1 M, 0.8 mL, 1.0 eq). The reaction was heated to 85° C. and stirred for 5 h, then water (30 mL) was added and the mixture was extracted with DCM (15 mL*3). The combined organic phase was washed with brine (30 mL), dried over $Na_2SO_4$ and concentrated in vacuo. The crude material was purified by Prep-TLC (DCM/MeOH=1/10) twice and Prep-HPLC to afford Compound 90 (30 mg, 8.1% yield) as a white solid.

TLC: DCM/MeOH=10/1 (v/v), Rf=0.20

LCMS T=1.843 min, [M−45]=391.0

$^1$H NMR: (400 MHz, DMSO-$d_6$) δ 9.19 (s, 1H), 7.75 (s, 1H), 7.68 (s, 1H), 7.61 (s, 2H), 7.00 (d, J=2.0 Hz, 1H), 6.71 (dd, J=8.4, 2.4 Hz, 1H), 6.67 (d, J=8.4 Hz, 2H), 4.32-4.23 (m, 3H), 4.16 (s, 3H), 3.18-3.11 (m, 2H), 1.28 (t, J=7.2 Hz, 2H), 1.23 (t, J=7.2 Hz, 3H), 1.13 (s, 2H), 1.12 (s, 3H), 1.12 (s, 2H), 1.11 (s, 3H).

Example 91

Synthesis of 2-((3,5-dichloro-4-(4-hydroxy-3-isopropylbenzyl)phenyl)thio)acetic acid (Compound 91)

Compound 91

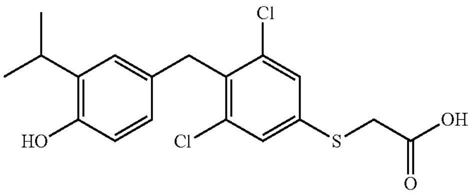

To a solution of C3 (500 mg, 1.34 mmol, 1.0 eq) in DMF (5 mL) at rt were added methyl 2-mercaptoacetate (213 mg, 2.00 mmol, 1.5 eq) and $Cs_2CO_3$ (870 mg, 2.67 mmol, 2.0 eq) under $N_2$. The reaction was heated to 80° C. and stirred overnight, then cooled and acidified to pH=4-5 with 1N HCl, and diluted with EtOAc (20 mL). The organic phase was washed with brine (10 mL*2), dried over $Na_2SO_4$ and concentrated under reduced pressure. The crude product was purified through Prep-HPLC to afford Compound 91 (34 mg, 6.2% yield) as a white solid.

TLC: Pet. ether/EtOAc=10/1 (v/v), Rf=0.35.

LCMS: T=1.608 min, [M−1]=382.8

$^1$H NMR: (400 MHz, DMSO-$d_6$) δ 12.87 (s, 1H), 9.08 (s, 1H), 7.45 (d, J=1.2 Hz, 2H), 6.99 (s, 1H), 6.65 (t, J=6.8 Hz, 2H), 4.07 (s, 2H), 3.93 (s, 2H), 3.13 (p, J=6.8 Hz, 1H), 1.10 (d, J=6.8 Hz, 6H).

Example 92

Synthesis of 2-((3,5-dichloro-4-(4-hydroxy-3-isopropylbenzyl)phenyl)sulfinyl)acetic acid (Compound 92)

Compound 92

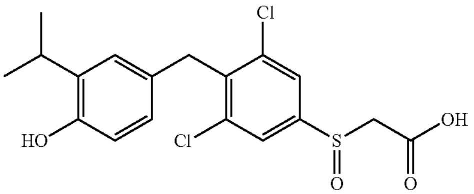

To a solution of Compound 91 (20 mg, 0.05 mmol, 1.0 eq) in DCM (5 mL) was added m-CPBA (9 mg, 0.05 mmol, 1.0 eq) and the reaction was stirred at rt for 2 h. The mixture was diluted with EtOAc (15 mL), washed with brine (10 mL*2), dried over $Na_2SO_4$ and concentrated under reduced pressure. The crude product was purified through Prep-HPLC to afford Compound 92 (3.0 mg, 14% yield) as a white solid.

LCMS: T=2.889 min, $[M+1]^-$=401.0

$^1$H NMR: (400 MHz, DMSO-$d_6$) δ 9.19 (s, 1H), 7.80 (s, 2H), 7.02 (d, J=2.0 Hz, 1H), 6.71-6.64 (m, 2H), 4.17 (s, 2H), 4.11 (d, J=14.8 Hz, 1H), 3.85 (d, J=14.4 Hz, 1H), 3.16-3.10 (m, 1H), 1.11 (d, J=6.8 Hz, 6H).

Example 93

Synthesis of 2-((3,5-dichloro-4-(4-hydroxy-3-isopropylbenzyl)phenyl)sulfonyl)acetic acid (Compound 93)

Compound 93

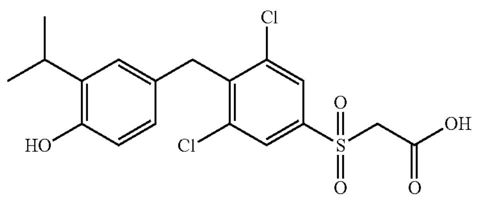

To a solution of Compound 91 (65 mg, 0.17 mmol, 1.0 eq) in AcOH (7 mL) at rt was added $H_2O_2$ (30%, 1.7 mL, 1.7 mmol, 10 eq). The reaction was stirred at rt for 3 d, then diluted with water (15 mL), and extracted with EtOAc (10 ml*2). The combined organic phase was washed with brine (15 mL), dried over $Na_2SO_4$ and concentrated under reduced pressure. The crude product was purified by Prep-HPLC to afford Compound 93 (9.0 mg, 13 yield) as a white solid.

LCMS: T=3.174 min, [M−45]=370.9

$^1$H NMR: (400 MHz, DMSO-$d_6$) δ 9.21 (s, 1H), 7.99 (s, 2H), 7.01 (d, J=2.0 Hz, 1H), 6.71-6.62 (m, 2H), 4.72 (s, 2H), 4.21 (s, 2H), 3.13 (p, J=6.8 Hz, 1H), 1.10 (d, J=6.8 Hz, 6H).

$^1$H NMR: (400 MHz, Chloroform-d) δ 7.87 (s, 2H), 7.26 (s, 2H), 7.06 (d, J=2.4 Hz, 1H), 6.74 (dd, J=8.4, 2.4 Hz, 1H), 6.60 (d, J=8.0 Hz, 1H), 4.25 (s, 2H), 4.10 (s, 2H), 3.18 (p, J=6.8 Hz, 1H), 1.16 (d, J=6.8 Hz, 6H).

Example 94

Synthesis of methyl 2-((3,5-dichloro-4-(4-hydroxy-3-isopropylbenzyl)benzyl)thio)acetate (Compound 94)

Compound 94

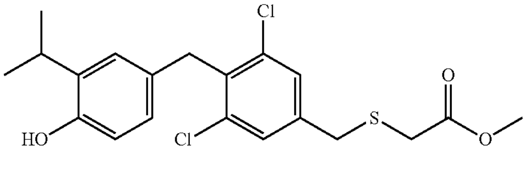

To a solution of C39 (600 mg, 1.31 mmol, 1.0 eq) in DCM (5 mL) was added TFA (150 mg, 1.31 mmol, 1.0 eq). The reaction was stirred at rt for 2 h then the mixture was concentrated in vacuo to afford crude Compound 94 (500 mg, 92.2% yield) as a colorless oil.

Example 95

Synthesis of 2-((3,5-dichloro-4-(4-hydroxy-3-isopropylbenzyl)benzyl)thio)acetic acid (Compound 95)

Compound 95

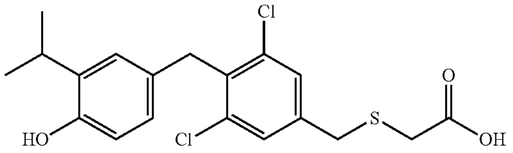

To a mixture of Compound 94 (500 mg, 1.21 μmol, 1.0 eq) in THF/$H_2O$ (4.0 mL/1.0 mL) at rt was added LiOH·$H_2O$ (149 mg, 3.63 mmol, 3.0 eq) and the reaction was stirred for 1 h. The mixture was diluted with water (40 mL), acidified to pH=3-4 with 1 N HCl and extracted with EtOAc (20 mL*3). The combined organic phase was washed with brine (50 mL), dried over $Na_2SO_4$ and concentrated under reduced pressure. The crude product was purified by Prep-HPLC to afford Compound 95 (20 mg, 4.1% yield) as a white solid.

LCMS: T=3.130 min, [M−1]=396.9

$^1$H NMR: (400 MHz, DMSO-$d_6$) δ 12.62 (s, 1H), 9.11 (s, 1H), 7.43 (s, 2H), 6.98 (d, J=2.4 Hz, 1H), 6.68 (dd, J=8.2, 2.2 Hz, 1H), 6.64 (d, J=8.4 Hz, 1H), 4.10 (s, 2H), 3.80 (s, 2H), 3.15 (d, J=3.0 Hz, 2H), 3.14-3.07 (m, 1H), 1.10 (d, J=6.8 Hz, 6H).

Example 96

Synthesis of 2-((3,5-dichloro-4-(4-hydroxy-3-isopropylbenzyl)benzyl)sulfinyl)acetic acid (Compound 96)

Compound 96

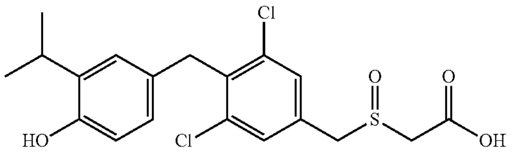

To a solution of Compound 95 (100 mg, 250 μmol, 1.0 eq) in DCM (3 mL) at rt was added m-CPBA (43 mg, 250 μmol, 1.0 eq) and the reaction was stirred for 2 h. Water (30 mL) was added and the mixture extracted with DCM (20 mL*2). The combined organic phase was washed with brine (30 mL), dried over $Na_2SO_4$ and concentrated in vacuo. The crude material was purified by Prep-HPLC to afford Compound 96 (20 mg, 19% yield) as a white solid.

LCMS: T=1.941 min, [M+1]=414.8

$^1$H NMR: (400 MHz, DMSO-$d_6$) δ 9.09 (s, 1H), 7.45 (s, 2H), 6.99 (s, 1H), 6.69 (d, J=8.3 Hz, 1H), 6.65 (d, J=8.2 Hz, 1H), 4.25 (d, J=12.8 Hz, 1H), 4.13 (s, 2H), 4.08 (d, J=12.8 Hz, 1H), 3.88 (d, J=14.3 Hz, 1H), 3.53 (d, J=14.3 Hz, 1H), 3.13 (p, J=6.9 Hz, 1H), 1.10 (d, J=6.8 Hz, 6H).

Example 97

Synthesis of 2-((3,5-dichloro-4-(4-hydroxy-3-isopropylbenzyl)benzyl)sulfonyl)acetic acid (Compound 97)

Compound 97

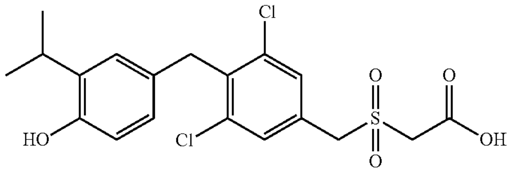

To a solution of Compound 95 (90 mg, 0.23 mmol, 1.0 eq) in AcOH (9 mL) was added $H_2O_2$ (30%, 78 mg, 2.25 mmol, 10 eq) and the reaction was stirred at rt overnight. The mixture was concentrated and purified by Prep-HPLC to afford Compound 97 (30 mg, 30% yield) as a colorless oil.

LCMS: T=2.056 min, [M+23]=453.0

$^1$H NMR: (400 MHz, DMSO-$d_6$) δ 9.13 (s, 1H), 7.51 (s, 2H), 7.04-6.99 (m, 1H), 6.69 (dd, J=8.4, 2.4 Hz, 1H), 6.65 (d, J=8.0 Hz, 1H), 4.68 (s, 2H), 4.24 (s, 2H), 4.13 (s, 2H), 3.17-3.09 (m, 1H), 1.11 (d, J=7.2 Hz, 6H).

Example 98

Synthesis of methyl 3-(3,5-dichloro-4-(4-hydroxy-3-isopropylbenzyl)phenyl)propiolate (Compound 98)

Compound 98

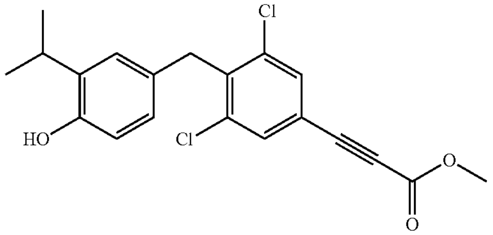

A solution of C40 (100 mg, 217 μmol, 1.0 eq) in MeOH (2.0 mL) at rt was added PPTS (6.0 mg, 22 μmol, 0.1 eq). The reaction was stirred at 30° C. overnight, and was then concentrated in vacuo. Water (30 mL) was added and the mixture extracted with EtOAc (15 mL*3). The combined organic phase was washed with brine (30 mL), dried over $Na_2SO_4$ and concentrated in vacuo. The crude material was purified by Prep-TLC (pet. ether/EtOAc=20/1) to afford Compound 98 (60 mg, 73% yield) as a yellow oil.

TLC: EtOAc/pet. ether=1/15 (v/v), Rf=0.25

Synthesis of 3-(3,5-dichloro-4-(4-hydroxy-3-isopropylbenzyl)phenyl)propiolic acid (Compound 99)

Compound 99

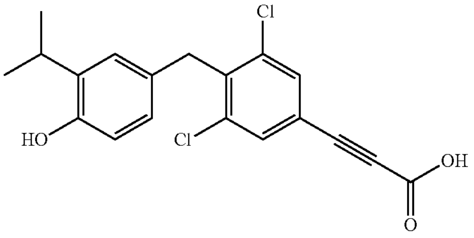

To a mixture of Compound 98 (60 mg, 160 μmol, 1.0 eq) in THF/$H_2O$ (2.0 mL/0.5 mL) at rt was added LiOH·$H_2O$ (20 mg, 477 μmol, 3.0 eq) and the reaction was stirred for 1 h. The mixture was diluted with water (30 mL), acidified to pH=3-4 with 1 N HCl and extracted with EtOAc (15 mL*3). The combined organic phase was washed with brine (30 mL), dried over $Na_2SO_4$ and concentrated under reduced pressure to afford crude Compound 99 (55 mg, 97% yield) as a white solid.

TLC: MeOH/DCM=1/10 (v/v), Rf=0.30.

Example 100

Synthesis of (Z)-3-(3,5-dichloro-4-(4-hydroxy-3-isopropylbenzyl)phenyl)acrylic acid (Compound 100)

Compound 100

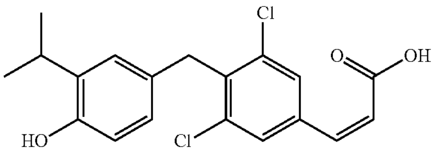

To a solution of Compound 99 (55 mg, 150 μmol, 1.0 eq) in THF (2.0 mL) were added Lindlar's catalyst (Pd—$BaSO_4$)(5%, 5 mg) and quinoline (5.0 mg, 39 μmol, 0.25 eq). The mixture was evacuated and filled with $H_2$ three times and then stirred at rt for 3 h under 1 atm $H_2$. The mixture was filtered, the filtrate was concentrated in vacuo, and the crude material purified by Prep-TLC (DCM/MeOH=15/1) to afford Compound 100 (8.0 mg, 17% yield) as a light yellow solid.

TLC: DCM/MeOH=10/1 (v/v), Rf=0.30

LCMS T=1.760 min, [M−1]=362.9

$^1$H NMR: (400 MHz, DMSO-$d_6$) δ 12.72 (s, 1H), 9.13 (s, 1H), 7.77 (s, 2H), 7.03 (d, J=2.0 Hz, 1H), 6.90 (d, J=12.8 Hz, 1H), 6.72 (dd, J=8.4, 2.4 Hz, 1H), 6.67 (d, J=8.4 Hz, 1H), 6.09 (d, J=12.8 Hz, 1H), 4.15 (s, 2H), 3.14 (q, J=7.2 Hz, 1H), 1.13 (d, J=6.8 Hz, 6H).

Example 101

Synthesis of methyl (E)-3-(3,5-dichloro-4-(4-hydroxy-3-isopropylbenzyl)phenyl)-2-methylacrylate (Compound 101)

Compound 101

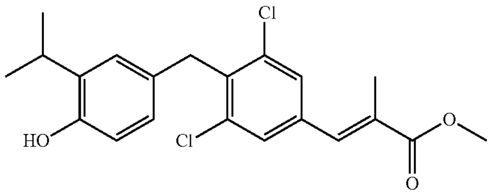

To a solution of Intermediate C3 (200 mg, 0.53 mmol, 1.0 eq) and methyl methacrylate (80 mg, 0.80 mmol, 1.5 eq) in DMF (3 mL) at rt were added $Pd(OAc)_2$ (12 mg, 0.05 mmol, 0.1 eq) and $K_2CO_3$ (148 mg, 1.07 mmol, 2.0 eq). The reaction was heated to 100° C. under $N_2$ for 4 h, then cooled, diluted with EtOAc (15 mL) and filtered. The filtrate was washed with water (15 mL*2) and brine (15 mL*2), dried over $Na_2SO_4$ and concentrated under reduced pressure. The crude product was purified through Prep-TLC (EtOAc/pet. ether=1/5) to afford Compound 101 (70 mg, 33% yield) as a yellow oil.

$^1H$ NMR: (400 MHz, DMSO-$d_6$) δ 9.11 (s, 1H), 7.60 (s, 2H), 7.54 (s, 1H), 7.02 (d, J=2.0 Hz, 1H), 6.71 (dd, J=8.4, 2.4 Hz, 1H), 6.65 (d, J=8.0 Hz, 1H), 4.14 (s, 2H), 3.75 (s, 3H), 3.16-3.10 (m, 1H), 2.05 (d, J=1.6 Hz, 3H), 1.11 (d, J=7.2 Hz, 6H).

Example 102

Synthesis of (E)-3-(3,5-dichloro-4-(4-hydroxy-3-isopropylbenzyl)phenyl)-2-methylacrylic acid (Compound 102)

Compound 102

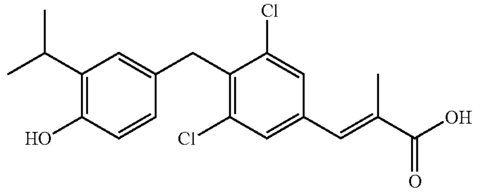

To a solution of Compound 101 (70 mg, 0.18 mmol, 1.0 eq) in THF/water (3 mL/0.5 mL) at rt was added $LiOH \cdot H_2O$ (15 mg, 0.35 mmol, 2.0 eq) and the reaction was stirred at rt for 2 h. The mixture was acidified to pH=4-5 with 2N HCl and extracted with EtOAc (5 mL). The organic phase was washed with brine (5 mL), dried over $Na_2SO_4$ and concentrated in vacuo. The crude material was purified by Prep-TLC (MeOH/DCM=1/10) and Prep-HPLC to afford Compound 102 (20 mg, 29% yield) as a white solid.

LCMS: T=3.669 min, [M−1]=376.9

$^1H$ NMR: (400 MHz, DMSO-$d_6$) δ 9.13 (s, 1H), 7.58 (s, 2H), 7.51 (d, J=1.6 Hz, 1H), 7.02 (d, J=2.4 Hz, 1H), 6.71 (dd, J=8.4, 2.4 Hz, 1H), 6.65 (d, J=8.0 Hz, 1H), 4.14 (s, 2H), 3.13 (p, J=6.8 Hz, 1H), 2.02 (d, J=1.6 Hz, 3H), 1.11 (d, J=6.8 Hz, 6H).

Example 103

Synthesis of 3-((3,5-dichloro-4-(4-hydroxy-3-isopropylbenzyl)phenyl)amino)propanoic acid (Compound 103)

Compound 103

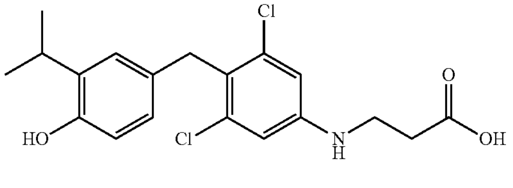

To a solution of C10 (300 mg, 0.96 mmol, 1.0 eq) in ethanol (5 mL) were added 3-bromopropanoic acid (163 mg, 1.06 mmol, 1.1 eq) and NaOAc (103 mg, 1.26 mmol, 1.3 eq). The reaction was heated to reflux for 48 h, then concentrated in vacuo. EtOAc (20 mL) was added; the organic phase was washed with water (20 mL), dried over $Na_2SO_4$ and concentrated in vacuo. The residue was purified by Prep-TLC (MeOH/DCM=1:10) and Prep-HPLC to afford Compound 103 (13 mg, 3.5% yield) as a white solid.

$^1H$ NMR: (400 MHz, DMSO) δ 9.00 (s, 1H), 6.96 (s, 1H), 6.66 (d, J=2.4 Hz, 1H), 6.64 (s, 2H), 6.62 (d, J=8.0 Hz, 1H), 3.94 (s, 2H), 3.23 (t, J=6.4 Hz, 2H), 3.17-3.07 (m, 1H), 2.47 (t, J=6.4 Hz, 2H), 1.10 (d, J=6.8 Hz, 6H).

Example 104

Synthesis of 2-(3,5-dichloro-4-(2-fluoro-4-hydroxy-3-isopropylbenzyl)phenyl)-N-methoxyacetamide (Compound 104)

Compound 104

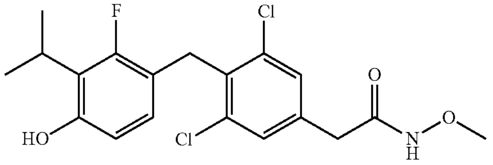

To a solution of Compound 32 (150 mg, 415 μmol, 1.0 eq) and O-methylhydroxylamine hydrochloride (101 mg, 1.3 mmol, 3.0 eq) in DMF (2 mL) at rt were added HATU (230 mg, 606 μmol, 1.5 eq) and DIEA (209 mg, 1.6 mmol, 4.0 eq). The reaction was stirred at rt for 2 h then water (30 mL) was added and the mixture was extracted with EtOAc (15 mL*3). The combined organic phase was washed with brine (30 mL), dried over $Na_2SO_4$ and concentrated under reduced pressure. The crude product was purified by Prep-HPLC to afford Compound 104 (30 mg, 18% yield) as a white solid.

TLC: MeOH/DCM=1/10 (v/v), Rf=0.60

LCMS: T=1.983 min, [M−1]=397.9

$^1H$ NMR: (400 MHz, DMSO-$d_6$) δ 11.29 (s, 1H), 9.54 (s, 1H), 7.39 (s, 2H), 6.48 (d, J=8.4 Hz, 1H), 6.27 (t, J=8.4 Hz, 1H), 4.07 (s, 2H), 3.60 (s, 3H), 3.39 (s, 1H), 1.26 (d, J=7.2 Hz, 6H)

$^{19}F$ NMR: (376 MHz, DMSO-$d_6$) δ −120.10.

Example 105

Synthesis of 2-(3,5-dichloro-4-(2-fluoro-4-hydroxy-3-isopropylbenzyl)phenyl)-N-methoxy-N-methylacetamide (Compound 105)

Compound 105

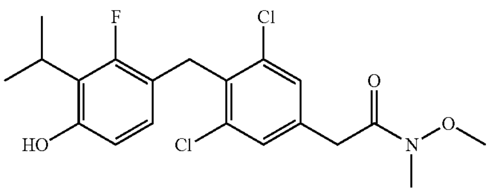

To a solution of Compound 32 (40 mg, 108 μmol, 1.0 eq) and N,O-dimethylhydroxylamine hydrochloride (32 mg, 320 μmol, 3.0 eq) in DMF (2 mL) at rt were added HATU (62 mg, 162 μmol, 1.5 eq) and DIEA (56 mg, 432 mmol, 4.0 eq) and the reaction was stirred for 2 h. Water (10 mL) was added and the mixture was extracted with EtOAc (10 mL*3). The combined organic phase was washed with brine (30 mL), dried over $Na_2SO_4$ and concentrated under reduced pressure. The crude product was purified by Prep-HPLC to afford Compound 105 (5.0 mg, 11% yield) as a white solid.

TLC: MeOH/DCM=1/10 (v/v), Rf=0.60

LCMS: T=2.077 min, [M−1]=411.9

$^1$H NMR: (400 MHz, DMSO-$d_6$) δ 9.55 (s, 1H), 7.40 (s, 2H), 6.49 (dd, J=8.4, 0.8 Hz, 1H), 6.28 (t, J=8.4 Hz, 1H), 4.09 (s, 2H), 3.81 (s, 2H), 3.73 (s, 3H), 3.44-3.37 (m, 1H), 3.13 (s, 3H), 1.27 (d, J=7.2 Hz, 6H)

$^{19}$F NMR: (376 MHz, DMSO-$d_6$) δ −120.08.

Example 106

Synthesis of 3-(3,5-dichloro-4-(2-fluoro-4-hydroxy-3-isopropylbenzyl)phenyl)-N-methoxypropanamide (Compound 106)

Compound 106

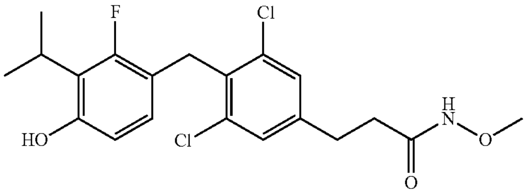

A solution of Compound 39 (30 mg, 75 μmol, 1.0 eq), O-methylhydroxylamine hydrochloride (13 mg, 150 μmol, 2.0 eq) and $K_2CO_3$ (21 mg, 150 μmol, 2.0 eq) in water/THF (1 mL/5 mL) was heated to 50° C. in a sealed tube overnight. After cooling, the reaction mixture was diluted with EtOAc (20 mL), washed with water (10 mL*2), dried over $Na_2SO_4$ and concentrated under reduced pressure. The crude product was purified through Prep-TLC (methanol/DCM=1/10) to afford Compound 106 (10 mg, 32% yield) as a white solid.

TLC: Methanol=1/10, Rf=0.23

LCMS: T=2.39 min; [M−1]=396.9

$^1$H NMR: (400 MHz, DMSO-$d_6$) δ 9.56 (d, J=1.3 Hz, 1H), 7.41 (s, 2H), 6.47 (d, J=8.6 Hz, 1H), 6.24 (t, J=8.6 Hz, 1H), 4.05 (s, 2H), 3.59 (s, 3H), 3.38 (d, J=7.2 Hz, 1H), 2.85 (t, J=7.6 Hz, 2H), 2.69 (t, J=7.6 Hz, 2H), 1.25 (d, J=6.9 Hz, 6H)

$^{19}$F NMR: (376 MHz, DMSO-$d_6$) δ −120.12.

Example 107

Synthesis of 3-(3,5-dichloro-4-(2-fluoro-4-hydroxy-3-isopropylbenzyl)phenyl)-N-methoxy-N-methylpropanamide (Compound 107)

Compound 107

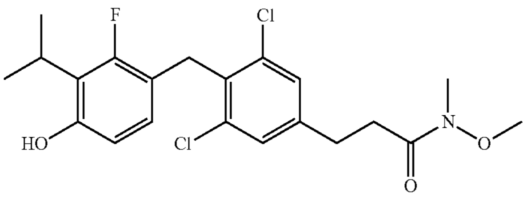

To a solution of N,O-dimethylhydroxylamine hydrochloride (15 mg, 150 μmol, 2.0 eq) and $K_2CO_3$ (30 mg, 110 μmol, 1.5 eq) in DCM (5 mL) at rt was added a solution of C21 (30 mg, 74 μmol, 1.0 eq) in DCM (5 mL); the reaction mixture was stirred overnight. The mixture was diluted with DCM (10 mL), washed with water (5 mL*2), dried over $Na_2SO_4$ and concentrated under reduced pressure. The crude product was purified through Prep-TLC (Methanol/DCM=1/10) to afford Compound 107 (15 mg, 33% yield) as a white solid.

TLC: Methanol=1/10, Rf=0.23

LCMS: T=2.34 min; [M−1]=425.9

$^1$H NMR: (400 MHz, DMSO-$d_6$) δ 9.55 (s, 1H), 7.42 (s, 2H), 6.47 (d, J=8.4 Hz, 1H), 6.25 (t, J=8.6 Hz, 1H), 4.05 (s, 2H), 3.64 (s, 3H), 3.08 (s, 3H), 2.81 (dd, J=8.4, 5.7 Hz, 2H), 2.75 (d, J=7.8 Hz, 2H), 1.25 (d, J=7.1 Hz, 6H)

$^{19}$F NMR: (376 MHz, DMSO-$d_6$) δ −120.15.

Example 108

Synthesis of 2-(3,5-dichloro-4-(4-hydroxy-3-isopropylbenzyl)benzylidene)malonic acid (Compound 108)

Compound 108

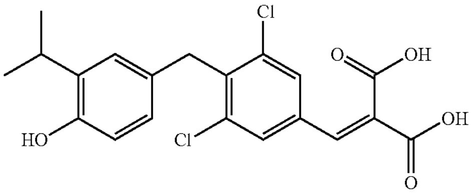

To a solution of C41 (50 mg, 160 μmol, 1.0 eq) in EtOH (3.0 mL) were added malonic acid (19 mg, 186 μmol, 1.2 eq), piperidine (1 mg, 16 μmol, 0.1 eq) and L-homoserine (6 mg, 46 mol, 0.3 eq). The reaction was stirred at 70° C. overnight, then water (20 mL) was added and the mixture was extracted with EtOAc (20 mL*3). The combined organic phase was washed with brine (30 mL), dried over $Na_2SO_4$ and concentrated under reduced pressure. The crude material was purified by reverse phase column chromatography to afford Compound 108 (8.0 mg, 12% yield) as a light yellow solid.

TLC: MeOH/DCM=1/10 (v/v), Rf=0.10

LCMS: T=1.312 min, [M−1]=406.9

$^1H$ NMR: (400 MHz, DMSO-$d_6$) δ 9.14 (s, 1H), 7.88 (s, 2H), 7.63 (s, 1H), 7.04 (d, J=2.0 Hz, 1H), 6.74-6.70 (dd, J=8.4, 1.6 Hz, 1H), 6.67 (d, J=8.4 Hz, 1H), 4.14 (s, 2H), 3.14 (d, J=6.9 Hz, 1H).

Example 109

Synthesis of methyl (3,5-dichloro-4-(2-fluoro-4-hydroxy-3-isopropylbenzyl)benzyl)glycinate (Compound 109)

Compound 109

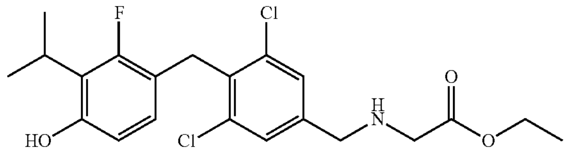

Step 1: Synthesis of 4-(2,6-dichloro-4-(hydroxymethyl)benzyl)-3-fluoro-2-isopropylphenol (C52)

C52

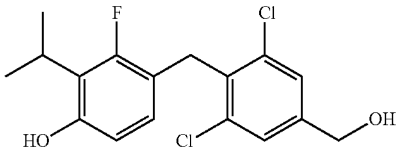

To a solution of Compound 59 (1.0 eq) in THF (10 mL/g —COOH) at 0° C. is added $LiAlH_4$ (2.0 eq) in one portion. The mixture is warmed to rt and stirred for 2 h, then diluted with ether (2×THF). Water is carefully added (1 mL/g $LiAlH_4$), followed by 15% aq. NaOH (1 mL/g $LiAlH_4$), and additional water (3 mL/g $LiAlH_4$). The resulting mixture is filtered through Celite and then concentrated in vacuo to yield crude Intermediate C52 that is used in the next step without further purification.

Step 2: Synthesis of 4-(2,6-dichloro-4-(chloromethyl)benzyl)-3-fluoro-2-isopropylphenol (C53)

C53

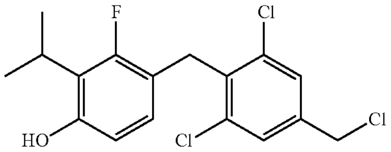

To a solution of C52 (1.0 eq) in DCM (10 mL/g) at rt is added $SOCl_2$ (1.5 eq) and the mixture is stirred for 2 h. The reaction mixture is concentrated in vacuo to afford Intermediate C53.

Step 3: Synthesis of methyl (3,5-dichloro-4-(2-fluoro-4-hydroxy-3-isopropylbenzyl)benzyl)glycinate (Compound 109)

To a solution of C53 in (83 mg, 0.23 mmol, 1.0 eq) in DMF (3 mL) at rt were added ethyl glycinate (71 mg, 0.69 mmol, 3.0 eq) and TEA (116 mg, 1.15 mmol, 5.0 eq). The mixture was stirred at 30° C. overnight, then water (30 mL) was added and the mixture was extracted with EtOAc (20 mL*2). The organic phase was washed with water (20 mL*2) and brine (20 mL), dried over $Na_2SO_4$ and concentrated in vacuo. The crude material was purified by Prep-TLC (pet. ether/EtOAc=1:1) to afford Compound 109 (38 mg, 39% yield) as a yellow oil.

Example 110

Synthesis of (3,5-dichloro-4-(2-fluoro-4-hydroxy-3-isopropylbenzyl)benzyl)glycine (Compound 110)

Compound 110

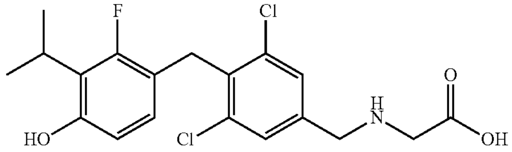

To a solution of Compound 109 (38 mg, 89 μmol, 1.0 eq) in THF (2 mL) and water (1 mL) was added $LiOH \cdot H_2O$ (11 mg, 270 μmol, 3.0 eq) and the reaction was stirred at rt for 2 h. The mixture was acidified to pH=4 with 1 N HCl then extracted with EtOAc (2*40 mL). The combined organic phase was washed with brine (30 mL), dried over $Na_2SO_4$, and evaporated to dryness. The crude material was purified by Prep-HPLC to afford Compound 110 (8.0 mg, 22% yield) as a white solid.

LCMS: T=1.539 min, [M+1]=400.0

$^1H$ NMR: (400 MHz, DMSO-$d_6$) δ 9.51 (s, 1H), 7.52 (s, 2H), 6.48 (d, J=8.4 Hz, 1H), 6.27 (t, J=8.4 Hz, 1H), 4.09 (s, 2H), 3.85 (s, 2H), 3.40 (s, 1H), 3.20 (s, 2H), 1.26 (d, J=7.2 Hz, 6H).

Example 111

Synthesis of 2-((3,5-dichloro-4-(4-hydroxy-3-isopropylbenzyl)benzyl)amino)-N-methylacetamide (Compound 111)

Compound 111

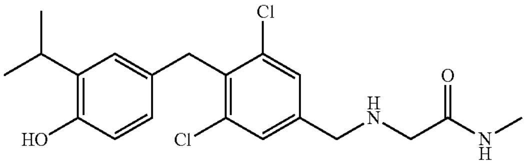

To a solution of Compound 29 (80 mg, 0.19 mmol, 1.0 eq) in THE (3 mL) was added methylamine (2M in THF, 2 mL, 4 mmol, 21 eq) and the reaction was stirred in a sealed tube at 75° C. for 2 h. The mixture was extracted with EtOAc (20 mL*2) and the combined organic phase was washed with brine (10 mL), dried over $Na_2SO_4$ and concentrated in vacuo. The residue was purified by Prep-HPLC to afford Compound 111 (40 mg, 52% yield) as a white solid.

TLC: Methanol/DCM=1/10, Rf=0.33

LCMS: T=1.21 min; [M−1]=395.0

$^1$H NMR: (400 MHz, DMSO-$d_6$) δ 9.07 (s, 1H), 7.76 (s, 1H), 7.47 (s, 2H), 7.00 (s, 1H), 6.68 (d, J=8.6 Hz, 1H), 6.63 (d, J=8.2 Hz, 1H), 4.10 (s, 2H), 3.65 (s, 2H), 3.16-3.10 (m, 1H), 3.04 (s, 2H), 2.64-2.54 (m, 3H), 1.10 (dd, J=7.0, 1.4 Hz, 6H).

Example 112

Synthesis of 2-((3,5-dichloro-4-(4-hydroxy-3-isopropylbenzyl)benzyl)amino)-N,N-dimethylacetamide (Compound 112)

Compound 112

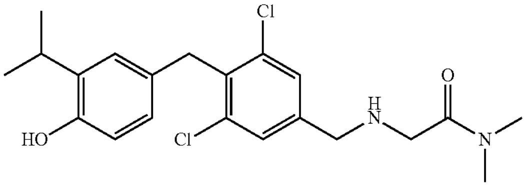

To a solution of Compound 30 (130 mg, 0.34 mmol, 1.0 eq) in DMF (2 mL) were added EDCI (98 mg, 0.51 mmol, 1.5 eq), HOBT (69 mg, 0.51 mmol, 1.5 eq), DIEA (88 mg, 0.68 mmol, 3.0 eq) and dimethylamine (46 mg, 1.0 mmol, 3.0 eq). The reaction was stirred at rt overnight then water (20 mL) was added and the mixture was extracted with EtOAc (10 mL*2). The combined organic phase was washed with water (10 mL) and brine (10 mL), dried over $Na_2SO_4$ and concentrated in vacuo. The residue was purified by Prep-HPLC to afford Compound 112 (10 mg, 7.1% yield) as a white solid.

TLC: Methanol/DCM=1/10, Rf=0.32

LCMS: T=1.27 min; [M−1]=409.0

$^1$H NMR: (400 MHz, DMSO-$d_6$) δ 9.10 (s, 1H), 7.47 (s, 2H), 6.99 (s, 1H), 6.73-6.60 (m, 2H), 4.12 (s, 2H), 3.80 (s, 2H), 3.47 (s, 2H), 3.17-3.09 (m, 1H), 2.86 (d, J=22.4 Hz, 6H), 1.10 (d, J=5.5 Hz, 6H).

Example 113

Synthesis of (E)-3-(3,5-dichloro-4-(4-hydroxy-3-isopropylbenzyl)phenyl)-N-methylacrylamide (Compound 113)

Compound 113

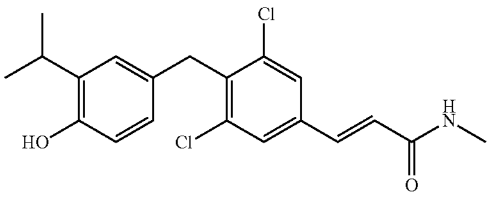

Step 1: Synthesis of (E)-3-(3,5-dichloro-4-(4-hydroxy-3-isopropylbenzyl)phenyl)acryloyl chloride (C54)

C54

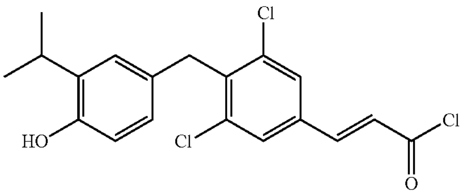

To a mixture of Compound 86 (120 mg, 329 μmol, 1.0 eq) in DCM (2.0 mL) was added oxalyl chloride (63 mg, 490 μmol, 1.5 eq) at 0° C. The reaction was stirred at rt for 30 min, then concentrated in vacuo to afford crude Intermediate C54 (120 mg, 95.2% yield) as a yellow solid.

Step 2: Synthesis of (E)-3-(3,5-dichloro-4-(4-hydroxy-3-isopropylbenzyl)phenyl)-N-methylacrylamide (Compound 113)

A solution of C54 (60 mg, 160 μmol, 1.0 eq) in DCM (2.0 mL) was added to $CH_3NH_2$ (2 M, in THF, 750 uL, 1.56 mmol, 10 eq). The reaction was stirred at rt for 1 h, then water (30 mL) was added and the mixture was extracted with DCM (20 mL*3). The combined organic phase was washed with brine (30 mL), dried over $Na_2SO_4$ and concentrated in vacuo. The crude material was purified by Prep-HPLC to afford Compound 113 (20 mg, 34% yield) as a white solid.

LCMS: T=1.569 min, [M−1]=375.9

$^1$H NMR: (400 MHz, DMSO-$d_6$) δ 9.13 (s, 1H), 8.03 (d, J=4.8 Hz, 1H), 7.72 (s, 2H), 7.38 (d, J=15.8 Hz, 1H), 7.02 (d, J=2.1 Hz, 1H), 6.76-6.69 (m, 2H), 6.67 (d, J=8.2 Hz, 1H), 4.15 (s, 2H), 3.15 (p, J=6.9 Hz, 1H), 2.73 (d, J=4.6 Hz, 3H), 1.13 (d, J=6.9 Hz, 6H).

Example 114

Synthesis of (E)-3-(3,5-dichloro-4-(4-hydroxy-3-isopropylbenzyl)phenyl)-N,N-dimethylacrylamide (Compound 114)

Compound 114

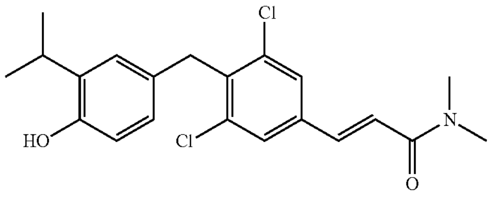

A solution of C54 (60 mg, 160 μmol, 1.0 eq) in DCM (2.0 mL) was added to $(CH_3)_2NH$ (2 M in THF, 782 uL, 1.56 mmol, 10 eq). The reaction was stirred at rt for 1 h, then water (30 mL) was added and the mixture extracted with DCM (20 mL*3). The combined organic phase was washed with brine (30 mL), dried over $Na_2SO_4$ and concentrated in vacuo. The crude material was purified by Prep-HPLC to afford Compound 114 (20 mg, 32% yield) as a white solid.

LCMS: T=2.563 min, [M−1]=390.0

$^1$H NMR: (400 MHz, DMSO-$d_6$) δ 9.12 (s, 1H), 7.93 (s, 2H), 7.45-7.34 (m, 2H), 7.02 (s, 1H), 6.72 (dd, J=8.2, 2.1 Hz, 1H), 6.67 (d, J=8.2 Hz, 1H), 4.15 (s, 2H), 3.18 (s, 3H), 3.17-3.11 (m, 1H), 2.94 (s, 3H), 1.12 (d, J=6.9 Hz, 6H).

Example 115

Synthesis of (E)-3-(3,5-dichloro-4-(2-fluoro-4-hydroxy-3-isopropylbenzyl)phenyl)-N-methylacrylamide (Compound 115)

Compound 115

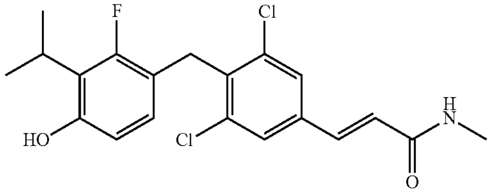

Step 1: Synthesis of (E)-3-(3,5-dichloro-4-(2-fluoro-4-hydroxy-3-isopropylbenzyl)phenyl)acryloyl chloride (C55)

C55

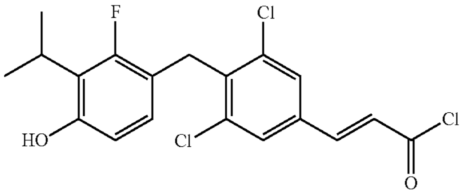

To a mixture of Compound 88 (55 mg, 118 μmol, 1.0 eq) in DCM (2.0 mL) was added oxalyl chloride (30 mg, 235 μmol, 2.0 eq) at 0° C. The reaction was stirred at rt for 30 min, then the mixture was concentrated in vacuo to afford crude product Intermediate C55 (45 mg, 95% yield) as a yellow solid.

Step 2: Synthesis of (E)-3-(3,5-dichloro-4-(2-fluoro-4-hydroxy-3-isopropylbenzyl)phenyl)-N-methylacrylamide (Compound 115)

A solution of C55 (20 mg, 160 μmol, 1.0 eq) in DCM (2.0 mL) was added to $CH_3NH_2$ (2 M in THF, 750 uL, 1.56 mmol, 10 eq). The mixture was stirred at rt for 1 h, then water (30 mL) was added and the mixture extracted with DCM (20 mL*3). The combined organic phase was washed with brine (30 mL), dried over $Na_2SO_4$ and concentrated in vacuo. The crude material was purified by Prep-HPLC to afford Compound 115 (10 mg, 48% yield) as a white solid.

LCMS: T=1.821 min, [M−1]=394.0

$^1$H NMR: (400 MHz, DMSO-$d_6$) δ 9.56 (d, J=1.4 Hz, 1H), 8.04 (d, J=4.9 Hz, 1H), 7.74 (s, 2H), 7.40 (d, J=15.8 Hz, 1H), 6.73 (d, J=15.8 Hz, 1H), 6.50 (d, J=8.4 Hz, 1H), 6.32 (t, J=8.6 Hz, 1H), 4.13 (s, 2H), 3.44-3.37 (m, 1H), 2.73 (d, J=4.7 Hz, 3H), 1.30-1.26 (m, 6H)

$^{19}$F NMR: (376 MHz, DMSO-$d_6$) δ −120.01.

Example 116

Synthesis of (E)-3-(3,5-dichloro-4-(2-fluoro-4-hydroxy-3-isopropylbenzyl)phenyl)-N,N-dimethylacrylamide (Compound 116)

Compound 116

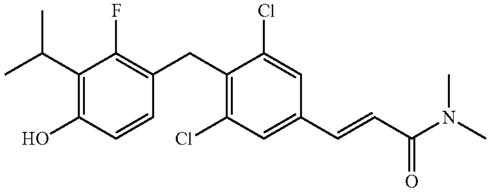

A solution of C55 (25 mg, 62 μmol, 1.0 eq) in DCM (2.0 mL) was added to dimethylamine (2 M, in THF, 310 uL, 0.62 mmol, 10 eq). The reaction was stirred at rt for 1 h, then water (30 mL) was added and the mixture extracted with DCM (20 mL*3). The combined organic phase was washed with brine (30 mL), dried over $Na_2SO_4$ and concentrated in vacuo. The crude material was purified by Prep-HPLC to afford Compound 116 (10 mg, 38% yield) as a white solid.

LCMS: T=2.045 min, [M−1]=408.0

$^1$H NMR: (400 MHz, DMSO-$d_6$) δ 9.56 (d, J=1.5 Hz, 1H), 7.95 (s, 2H), 7.46-7.36 (m, 2H), 6.50 (d, J=8.4 Hz, 1H), 6.32 (t, J=8.6 Hz, 1H), 4.13 (s, 2H), 3.40 (dt, J=14.1, 6.9 Hz, 1H), 3.19 (s, 3H), 2.95 (s, 3H), 1.28 (d, J=7.0 Hz, 6H)

$^{19}$F NMR: (376 MHz, DMSO-$d_6$) δ −120.04.

Example 117

Synthesis of (E)-3-(3,5-dichloro-4-(4-hydroxy-3-isopropylbenzyl)phenyl)-N,2-dimethylacrylamide (Compound 117)

Compound 117

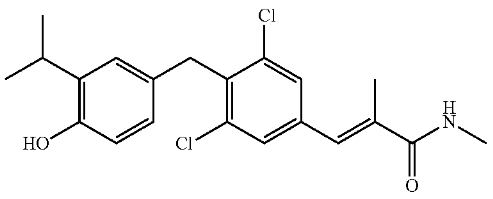

Step 1: Synthesis of (E)-3-(3,5-dichloro-4-(4-hydroxy-3-isopropylbenzyl)phenyl)-2-methylacryloyl chloride (C56)

C56

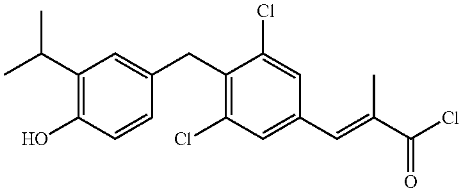

To a solution of Compound 102 (110 mg, 290 μmol, 1.0 eq) in DCM (6 mL) was added oxalyl chloride (36 mg, 290 μmol, 1.0 eq). The reaction was stirred at rt for 1 h, then the mixture was concentrated to dryness to afford Intermediate C56 (110 mg, 95.3% yield) as a brown solid.

Step 2: Synthesis of (E)-3-(3,5-dichloro-4-(4-hydroxy-3-isopropylbenzyl)phenyl)-N,2-dimethylacrylamide (Compound 117)

A solution of C56 (55 mg, 140 μmol, 1.0 eq) in DCM (2 mL) was added to methylamine (2 M in THF, 0.2 mL, 200 μmol, 1.5 eq). The reaction was stirred at rt for 1 h, then water (30 mL) was added and the mixture extracted with DCM (20 mL*3). The combined organic phase was washed with brine (30 mL), dried over $Na_2SO_4$ and concentrated in vacuo. The crude material was purified by Prep-HPLC to afford Compound 117 (16 mg, 29% yield, 97% purity) as a white solid.

LCMS: T=3.505 min, [M+1]=392.0

$^1$H NMR: (400 MHz, DMSO-$d_6$) δ 9.12 (s, 1H), 8.03 (d, J=4.8 Hz, 1H), 7.48 (s, 2H), 7.11 (s, 1H), 7.01 (d, J=2.0 Hz, 1H), 6.71 (dd, J=8.0, 2.4 Hz, 1H), 6.65 (d, J=8.4 Hz, 1H), 4.13 (s, 2H), 3.13 (p, J=6.8 Hz, 1H), 2.69 (d, J=4.4 Hz, 3H), 2.00 (d, J=1.6 Hz, 3H), 1.11 (d, J=6.8 Hz, 6H).

Example 118

Synthesis of (E)-3-(3,5-dichloro-4-(4-hydroxy-3-isopropylbenzyl)phenyl)-N-methoxy-N,2-dimethylacrylamide (Compound 118)

Compound 118

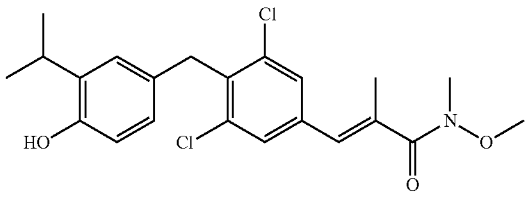

To a solution of C56 (55 mg, 140 μmol, 1.0 eq) in DCM (2 mL) were added N,O-dimethylhydroxylamine hydrochloride (13 mg, 140 μmol, 1.0 eq) and TEA (28 mg, 80 mol, 2.0 eq). The reaction was stirred at rt for 1 h, then water (10 mL) was added and the mixture extracted with DCM (10 mL*3). The combined organic phase was washed with brine (15 mL), dried over $Na_2SO_4$ and concentrated in vacuo. The crude material was purified by Prep-HPLC to afford Compound 118 (15 mg, 25% yield, 98.3% purity) as a white solid.

LCMS: T=2.013 min, [M+1]=422.1

$^1$H NMR: (400 MHz, DMSO-$d_6$) δ 9.10 (s, 1H), 7.51 (s, 2H), 7.02 (d, J=2.4 Hz, 1H), 6.71 (dd, J=8.4, 2.4 Hz, 1H), 6.68-6.62 (m, 2H), 4.13 (s, 2H), 3.65 (s, 3H), 3.19 (s, 3H), 3.13 (p, J=6.8 Hz, 1H), 2.04 (d, J=1.6 Hz, 3H), 1.11 (d, J=6.8 Hz, 6H).

Example 119

Synthesis of methyl (E)-3-(3,5-dichloro-4-(2-fluoro-4-hydroxy-3-isopropylbenzyl)phenyl)-2-methylacrylate (Compound 119)

Compound 119

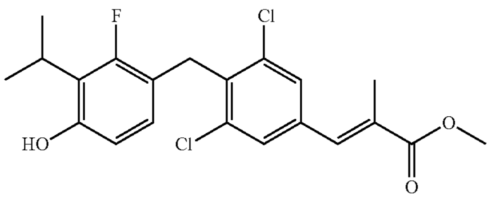

To a solution of C42 (1.0 eq) and methyl methacrylate (1.5 eq) in DMF (15 mL/g C56) at rt were added $Pd(OAc)_2$ (0.1 eq) and $K_2CO_3$ (2.0 eq). The reaction is heated to 100° C. under $N_2$ for 4 h, then cooled, diluted with EtOAc (3×DMF) and filtered. The filtrate is washed with water and brine, dried over $Na_2SO_4$ and concentrated under reduce pressure. The crude product is purified through Prep-TLC (EtOAc/pet. ether=1/5) to afford Compound 119.

Example 120

Synthesis of (E)-3-(3,5-dichloro-4-(2-fluoro-4-hydroxy-3-isopropylbenzyl)phenyl)-2-methylacrylic acid (Compound 120)

Compound 120

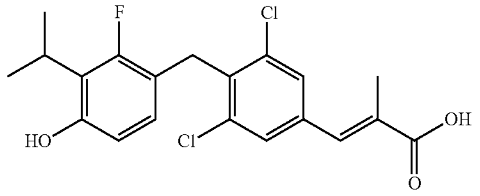

To a solution of Compound 119 (70 mg, 0.18 mmol, 1.0 eq) in THF/water (6:1; 50 mL/g 119) at rt is added $LiOH \cdot H_2O$ (2.0 eq) and the reaction is stirred at rt for 2 h. The mixture is acidified to pH=4-5 with 2N HCl and extracted with EtOAc. The organic phase is washed with brine, dried over $Na_2SO_4$ and concentrated in vacuo. The crude material is purified by Prep-TLC (MeOH/DCM=1/10) and Prep-HPLC to afford Compound 120.

Example 121

Synthesis of (E)-3-(3,5-dichloro-4-(2-fluoro-4-hydroxy-3-isopropylbenzyl)phenyl)-N,2-dimethylacrylamide (Compound 121)

Compound 121

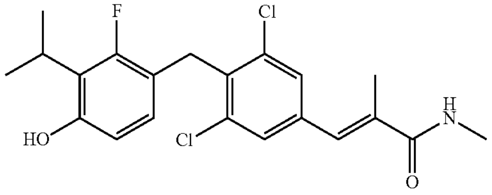

Step 1: Synthesis of (E)-3-(3,5-dichloro-4-(2-fluoro-4-hydroxy-3-isopropylbenzyl)phenyl)-2-methylacryloyl chloride (C57)

C57

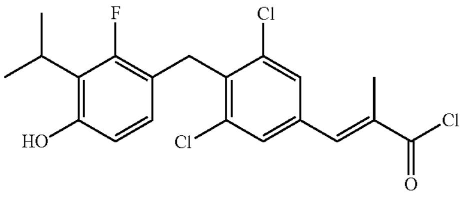

To a solution of Compound 120 (110 mg, 290 µmol, 1.0 eq) in DCM (60 mL/g) is added oxalyl chloride (1.0 eq). The reaction is stirred at rt for 1 h, then the mixture was concentrated to dryness to afford Intermediate C57.

Step 2: Synthesis of (E)-3-(3,5-dichloro-4-(2-fluoro-4-hydroxy-3-isopropylbenzyl)phenyl)-N,2-dimethylacrylamide (Compound 121)

A solution of C57 (1.0 eq) in DCM (40 mL/g) is added to methylamine (2 Min THF, 1.5 eq). The reaction is stirred at rt for 1 h, then water (15×DCM) was added and the mixture extracted with DCM. The combined organic phase is washed with brine, dried over $Na_2SO_4$ and concentrated in vacuo. The crude material is purified by Prep-HPLC to afford Compound 121.

Example 122

Synthesis of (E)-3-(3,5-dichloro-4-(2-fluoro-4-hydroxy-3-isopropylbenzyl)phenyl)-N-methoxy-N,2-dimethylacrylamide (Compound 122)

Compound 122

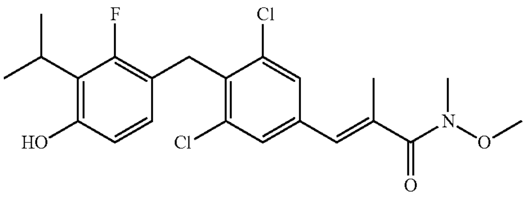

A solution of C57 (1.0 eq) in DCM (40 mL/g) is added N,O-dimethylhydroxylamine hydrochloride (1.0 eq) and TEA (2.0 eq). The reaction is stirred at rt for 1 h, then water (5×DCM) was added and the mixture extracted with DCM. The combined organic phase is washed with brine, dried over $Na_2SO_4$ and concentrated in vacuo. The crude material is purified by Prep-HPLC to afford Compound 122.

Example 123

Synthesis of 2-((3-chloro-4-(4-hydroxy-3-isopropylbenzyl)-5-methylphenyl)thio)acetic acid (Compound 123)

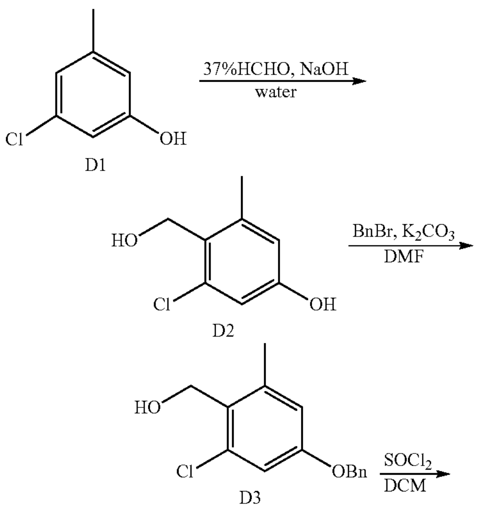

-continued

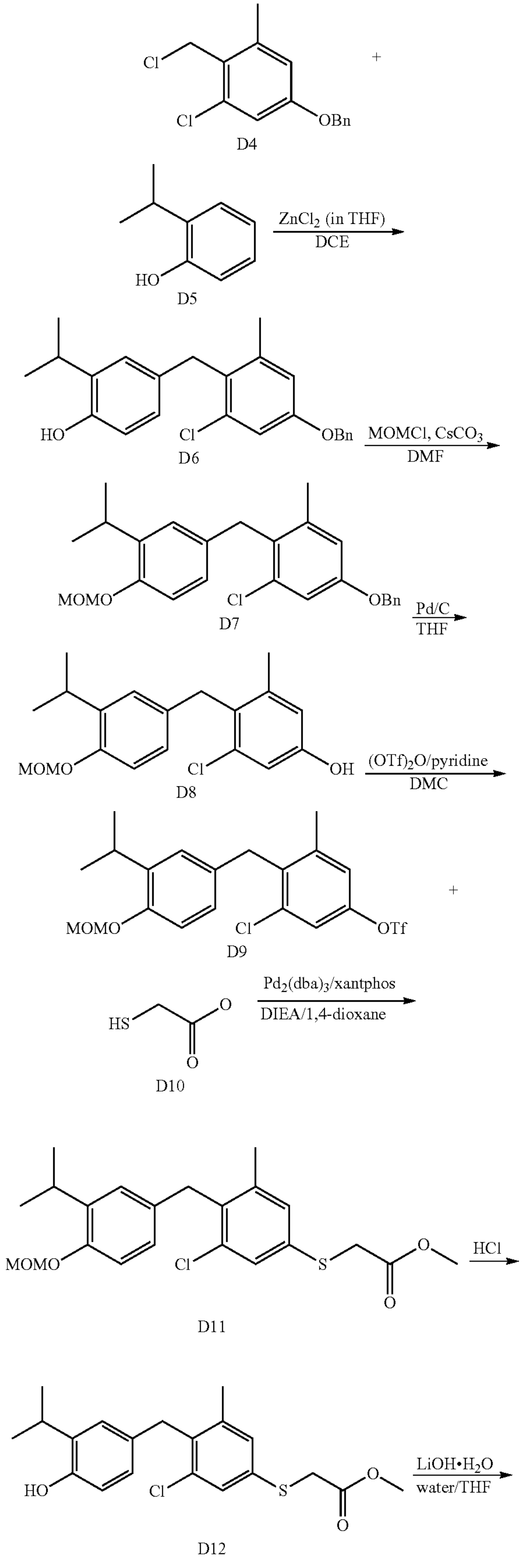

-continued

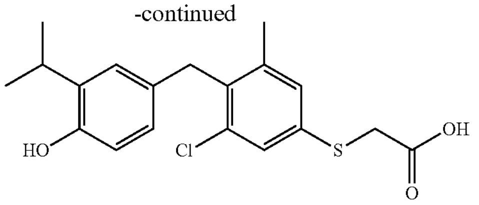

Compound 123

To a solution of NaOH (25.25 g, 631.2 mmol) in water (600 mL) at rt was added compound D1 (75 g, 526.0 mmol). The mixture was heated to 45° C., 37% formaldehyde (46.92 g, 578.5 mmol, 37% purity) was added dropwise. The mixture was stirred at 45° C. overnight. The mixture was cooled down to rt, adjusted the pH=6-7 with 1N HCl and extracted by EtOAc (60 mL*2), the combined organic phase was washed by brine, dried over $Na_2SO_4$, removed most EtOAc, the mixture was filtered and the solid dried to afford compound D2 (14 g, 64.90 mmol, 14.3% yield, 80% purity) as a white solid.

To a solution of compound D2 (13 g, 75.31 mmol) in DMF (130.00 mL) was added potassium carbonate (15.61 g, 112.97 mmol) and BnBr (12.88 g, 75.31 mmol). The mixture was stirred at rt 1 h. Water (130 mL) was added and extracted with EtOAc (100 mL*2). The combined organic layer was washed with water (200 mL*2) and brine (200 mL), dried over $Na_2SO_4$ and concentrated in vacuum to afford compound D3 (19 g, crude) as a yellow oil.

To a solution of compound D3 (11 g, 41.87 mmol) in DCM (100 mL) at 0° C. was added $SOCl_2$ (7.47 g, 62.80 mmol). The mixture was stirred at 0° C. 1 h, concentrated to dryness to afford product compound D4 (11.7 g) as a white solid.

To a solution of compound D4 (10 g, 35.56 mmol), compound D5 (14.53 g, 106.69 mmol) in DCE (110 mL) was added $ZnCl_2$ (1 M/THF, 88.91 mL), the mixture was stirred at 65° C. 1 h. The mixture was cooled down to rt and quenched with water (100 mL), extracted with DCM (25 mL*2). The combined organic layer was washed with water (150 mL), brine (50 mL), dried over $Na_2SO_4$, purified with silica gel column (Pet. ether to Pet. ether/EtOAc=10/1) to afford product compound D6 (10 g, 73.8% yield) as a colorless oil.

To a solution of compound D6 (10 g, 26.25 mmol) and $Cs_2CO_3$ (25.66 g, 78.76 mmol) in DMF (90 mL) at 0° C. was added MOMCl (3.17 g, 39.38 mmol). The mixture was stirred at rt 1 h. The mixture was quenched with water (300 mL), extracted with EtOAc (100 mL*2). The combined organic layer was washed with water (150 mL*2), brine (150 mL), dried over $Na_2SO_4$, concentrated to dryness, purified by silica gel column (pet. ether/EtOAc=20/1 to 5/1) to afford product compound D7 (7 g, 62.7% yield) as a colorless oil.

To a solution of compound D7 (7 g, 16.47 mmol), Pd/C (10%) (1 g) in THF (50 mL) was stirred at rt under 1 atm $H_2$ atmosphere overnight. The mixture was filtered, concentrated to dryness to afford product compound D8 (5.52 g) as a colorless oil.

To a solution of compound D8 (5.5 g, 16.43 mmol) and pyridine (2.60 g, 32.85 mmol) in DCM (50 mL) was added $(OTf)_2O$ (6.02 g, 21.35 mmol) at 0° C. The mixture was stirred at rt 2 h. The mixture was quenched with water (100 mL) and extracted with DCM (20 mL*2), The combined organic phase was washed by water (50 ml*3) and brine (20 ml), dried over $Na_2SO_4$ and concentrated in vacuum to afford compound D9 (7 g, 91.2% yield) as a yellow oil.

A mixture of compound D9 (1.1 g, 2.36 mmol), compound D10 (375.11 mg, 3.53 mmol), xantphos (136.32 mg, 235.60 μmol), N-ethyl-N-isopropyl-propan-2-amine (608.97 mg, 4.71 mmol) and $Pd_2(dba)_3$ (107.87 mg, 117.80 μmol) in 1.4-dioxane (5 mL) was microwaved at 110° C. 1 h. The mixture was quenched with water (30 mL), extracted with EtOAc (25 mL*2). The combined organic layer was washed with water (25 mL*2) and brine (50 mL), dried over $Na_2SO_4$, purified with silica gel column (Pet. ether to Pet. ether/EtOAc=10/1) to afford product compound D11 (600 mg, 60.2% yield) as a colorless oil.

To a solution of compound D11 (600 mg, 1.42 mmol) in HCl/1,4-dioxane (4 M, 5 mL) was stirred at rt 1 h. The mixture was concentrated to dryness to afford product compound D12 (530 mg, 98.6% yield) as a colorless oil.

To a solution of methyl compound D12 (550 mg, 1.45 mmol) in water (2 mL) and THF (10 mL) was added $LiOH \cdot H_2O$ (183.02 mg, 4.35 mmol). The mixture was stirred at rt 1 h. The mixture was acidified to pH=4-5 with 2N HCl, $H_2O$ (30 mL) was added, the mixture was extracted with EtOAc (25 mL*2). The combined organic layer was washed with brine (50 mL), dried over $Na_2SO_4$, purified by Prep-HPLC to afford Compound 123 (150 mg, 27.0% yield) as a white solid.

LCMS: T=1.754 min, [M+1]=362.9

Example 124

Synthesis of 2-((3-chloro-4-(4-hydroxy-3-isopropylbenzyl)-5-methylbenzyl)thio)acetic acid (Compound 124)

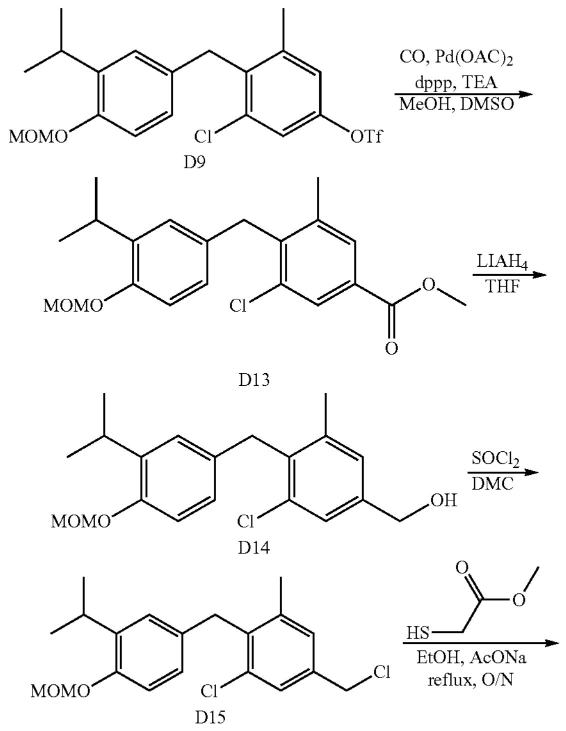

D9

D13

D14

D15

-continued

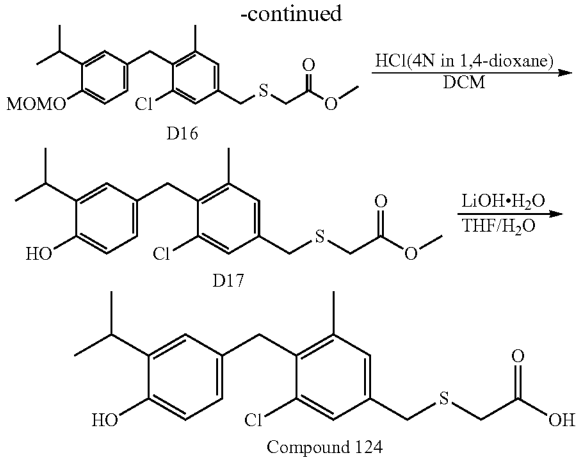

D16

D17

Compound 124

A mixture of compound D9 (5 g, 10.71 mmol), dppp (441.68 mg, 1.07 mmol), $Pd(OAC)_2$ (240.43 mg, 1.07 mmol), TEA (3.25 g, 32.13 mmol) in DMSO (50 mL) and methanol (50 mL) was stirred under 1 atm CO atmosphere at 85° C. overnight. $H_2O$ (300 mL) was added, the mixture was extracted with EtOAc (40 mL*3). The combined organic layer was washed with water (100 mL*2), brine (100 mL), dried over $Na_2SO_4$, purified by silica gel column chromatography (Pet. ether/EtOAc=100/1 to 60/1) to afford product compound D13 (3 g, 74.3% yield) as a light yellow oil.

To a solution of compound D13 (3 g, 7.96 mmol) in THE (30 mL) at 0° C. was added $LiAlH_4$ (362.55 mg, 9.55 mmol). The mixture was stirred at rt for 1 h. $H_2O$ (30 mL) was added, the mixture was extracted with EtOAc (25 mL*2). The combined organic layer was washed with brine (50 mL), dried over $Na_2SO_4$, concentrated to dryness to afford compound D14 (2.7 g, crude) as a white solid.

To a solution of compound D14 (2.6 g, 7.45 mmol) in DCM (25.00 mL) was cooled down to 0° C., thionyl chloride (1.33 g, 11.18 mmol) was added dropwise. The mixture was stirred at rt 3 h and concentrated in vacuum to afford compound D15 (2.25 g, 82.1% yield) as a white solid.

To a solution of compound D15 (2 g, 5.45 mmol) in ethanol (20 mL) at rt was added methyl 2-sulfanylacetate (1.16 g, 10.89 mmol) and NaOAc (893.35 mg, 10.89 mmol). The mixture was stirred at 90° C. overnight. The mixture was concentrated in vacuum. Water (20 mL) was added. The mixture was extracted with EtOAc (3*20 mL). The combined organic layer was washed with brine (50 mL), dried over $Na_2SO_4$ and concentrated in vacuum. The crude product was purified by silica gel column (EtOAc/pet. ether-1/50 to 1/30) to afford product compound D16 (1.4 g, 58.84% yield) as a yellow oil.

A mixture of compound D16 (300 mg, 686.51 μmol) in DCM (3 mL) was added HCl/1,4-dioxane (4 M, 4.29 mL). The mixture was stirred at rt for 1 h. Water (10 mL) was added and extracted with DCM (10 mL*3). The combined organic phase was washed by brine (30 mL), dried over $Na_2SO_4$, concentrated in vacuum to afford crude product compound D17 (250 mg, 92.6% yield) as a light yellow oil.

To a mixture of D17 (300 mg, 763.48 μmol) in THF (3 mL) and water (1.5 mL) was added $LiOH \cdot H_2O$ (96.11 mg, 2.29 mmol). The mixture was stirred at rt for 1 h. Water (15 mL) was added, adjust pH=4-5 with 1 N HCl and extracted with EtOAc (10 mL*3). The combined organic phase was washed by brine (30 mL), dried over $Na_2SO_4$, concentrated in vacuum to afford Compound 124 (280 mg, 96%) as a white solid.

LCMS: T=1.73 min, [M+1]=377.1

Example 125

Synthesis of (3-chloro-4-(4-hydroxy-3-isopropylbenzyl)-5-methylphenyl)glycine (Compound 125)

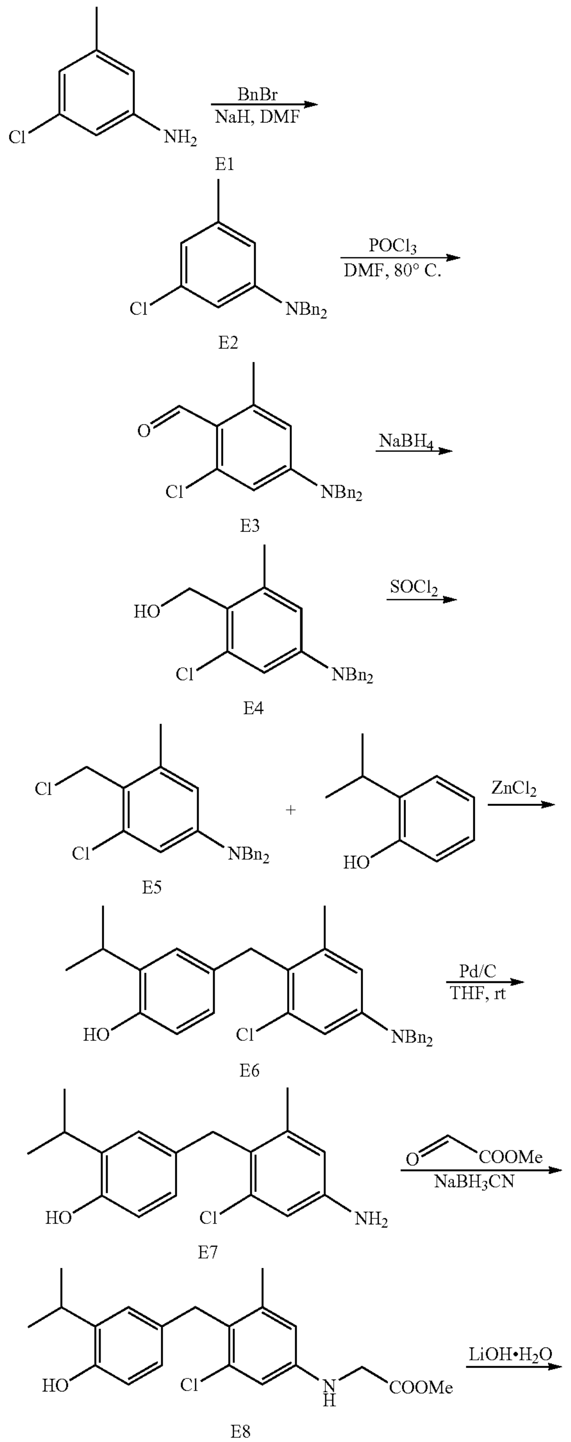

-continued

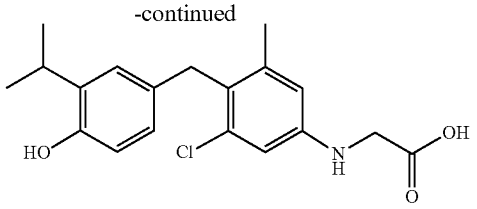

Compound 125

To a solution of compound E1 (10 g, 70.62 mmol) in DMF (100 mL) at 0° C. was added sodium hydride (8.47 g, 211.87 mmol, 60% purity) in portions. The mixture was stirred at rt 1 h. bromomethylbenzene (36.24 g, 211.86 mmol, 25.20 mL) was added dropwise. The mixture was stirred at rt overnight. The mixture was poured into water (80 mL) and extracted with EtOAc (40 mL*3). The combined organic layer was washed with water (50 mL*2) and brine (50 mL), dried over $Na_2SO_4$ and concentrated in vacuum. The crude product was washed by n-hexane to afford compound E2 (15 g, 65.9% yield) as a yellow solid.

$POCl_3$ (21.44 g, 139.82 mmol) was added dropwise to DMF (150 mL) at 0° C. The mixture was stirred at rt 30 min. A solution of compound E2 (15 g, 46.61 mmol) in DMF (150 mL) was added to the previous solution. The mixture was stirred at 90° C. overnight. The mixture was diluted with water (50 mL) and extracted with EtOAc (20 mL*3). The combined organic phase was washed by brine (50 mL), dried over Na2SO4, concentrated in vacuum and purified by silica gel column (pet. ether/EtOAc=200/1 to 50/1) to afford compound E3 (4.2 g, 25.7% yield) as a white solid.

To a solution of compound E3 (4.2 g, 12.01 mmol) in THF (40 mL) at rt was added sodium borohydride (908.36 mg, 24.01 mmol). The mixture was stirred at rt for 2 h. The mixture was added water (50 mL) and extracted with EtOAc (90 mL). The organic layer was washed with brine (50 mL), dried over $Na_2SO_4$ and concentrated in vacuum to afford compound E4 (4.2 g, 99.4% yield) as a yellow oil.

A solution of compound E4 (4.2 g, 11.94 mmol) in DCM (40 mL) was cooled down to 0° C., thionyl chloride (2.13 g, 17.90 mmol) was added dropwise. The mixture was stirred at rt for 1 h. The mixture was concentrated in vacuum to afford crude product compound E5 (4.4 g, 99.5% yield). The crude product was used directly in next step without purification.

To a solution of compound E5 (4.2 g, 11.34 mmol) in DCE (40 mL) at rt was added 3-fluoro-2-isopropyl-phenol (5.25 g, 34.03 mmol) and $ZnCl_2$ (1 M/THF, 28.35 mL). The reaction was heated to 85° C. and stirred for 5 h. Water (50 mL) was added and extracted with DCM (50 mL*3). The combined organic phase was washed by brine (100 mL), dried over $Na_2SO_4$ and concentrated in vacuum. The crude product was purified by silica gel column (EtOAc/pet. ether=1/50 to 1/20) to afford compound E6 (2.3 g, 41.5% yield) as colorless oil.

To a solution of compound E6 (2.3 g, 4.71 mmol) in THE (20 mL) was added Pd/C (400 mg). The mixture was refilled with $H_2$ three times and stirred at rt under 1 atm $H_2$ atmosphere 4 h. The mixture was filtered and the filtrate was concentrated in vacuum and purified by silica gel column (Pet. ether/EtOAc=20/1 to 3/1) to afford product compound E7 (1 g, 68.9% yield) as a yellow oil.

To a solution of compound E7 (300 mg, 1.04 mmol) in MeCN (15 mL) was added ethyl 2-oxoacetate (126.82 mg, 1.24 mmol) and AcOH (6.26 mg, 103.52 umol). The mixture was stirred at 40° C. for 5 h. $NaBH_3CN$ (97.58 mg, 1.55 mmol) was added to the mixture. The reaction mixture was stirred at rt overnight. The mixture was added water (20 mL) and extracted with EtOAc (20 mL*2). The combined organic layer was washed with brine (20 mL), dried over Na2SO4 and concentrated in vacuum. The residue was purified by Prep-TLC (pet. ether/EtOAc=3:1) to afford compound E8 (100 mg, 25.7% yield) as a yellow oil.

To a solution of compound E8 (20 mg, 53.21 umol) in THF (2 mL) was added a solution of $LiOH{\cdot}H_2O$ (6.70 mg, 159.62 umol) in water (1 mL). The mixture was stirred at rt for 2 h. The mixture was acidified with 1 N HCl to pH=3-4. The aqueous layer was extracted with EtOAc (40 mL*2). The organic layer was washed with brine (30 mL), dried over $Na_2SO_4$ and evaporated to dryness. The crude product was purified by prep-HPLC to afford Compound 125 (8 mg, 43.1% yield) as a white solid.

LCMS: T=2.049 min, [M+1]=348.0

Example 126 and Example 127

Synthesis of (E)-3-(3-chloro-4-(2-fluoro-4-hydroxy-3-isopropylbenzyl)-5-methylphenyl)acrylic acid (Compound 126) and 3-(3-chloro-4-(2-fluoro-4-hydroxy-3-isopropylbenzyl)-5-methylphenyl)propanoic acid (Compound 127)

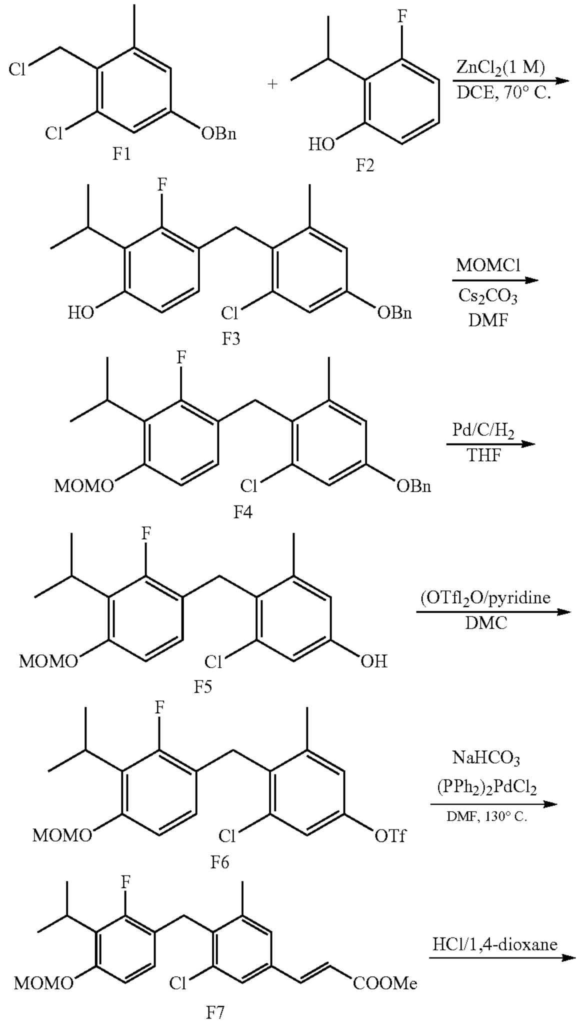

F1 F2 F3 F4 F5 F6 F7

-continued

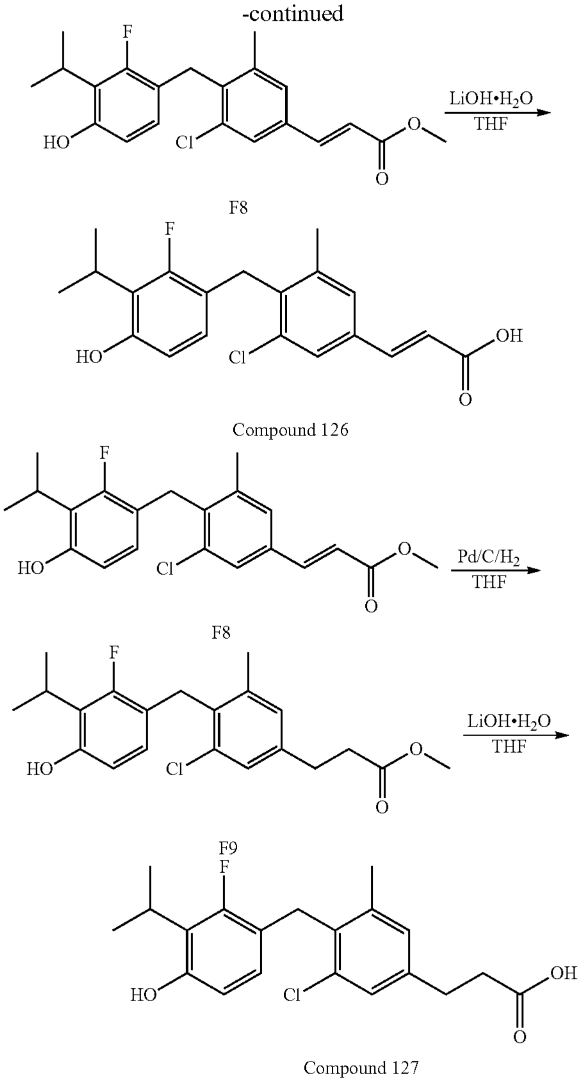

F8

Compound 126

F8

F9

Compound 127

To a solution of compound F1 (3 g, 10.67 mmol) in DCE (40 mL) at rt was added compound F2 (4.94 g, 32.01 mmol) and dichlorozinc (1 M, 21.34 mL). The reaction was heated to 85° C. and stirred for 5 h. Water (30 mL) was added and extracted with DCM (15 mL*3). The combined organic layer was washed by brine (40 mL), dried over $Na_2SO_4$ and concentrated in vacuum. The crude product was purified by silica gel column (EtOAc/pet. ether-1/50 to 1/30) to afford compound F3 (1.6 g, 37.6% yield) as a yellow oil.

To a solution of compound F3 (1.60 g, 4.01 mmol) and $Cs_2CO_3$ (3.94 g, 12.03 mmol) in DMF (15 mL) was added MOMCl (484.4 mg, 6.02 mmol). The mixture was stirred at rt 4 h. Water (50 mL) was added and extracted with EtOAc (30 mL*3). The combined organic phase was washed by water (30 ml*2) and brine (20 mL), dried over $Na_2SO_4$, concentrated in vacuum and purified by silica gel column (EtOAc/pet. ether=1/100 to 1/30) to afford compound F4 (900 mg, 50.7% yield) as a yellow oil.

To a solution of compound F4 (900 mg, 2.03 mmol) in THF (10 mL) was added Pd/C (135 mg, 1.11 mmol). The mixture was refilled with $H_2$ three times and stirred at rt under 1 atm $H_2$ atmosphere 4 h. The mixture was filtered. The filtrate was concentrated in vacuum to afford crude product compound F5 (660 mg, 92.2% yield) as a yellow oil.

To a mixture of compound F5 (660 mg, 1.87 mmol) and pyridine (295.9 mg, 3.74 mmol) in DCM (10 mL) was added $(OTf)_2O$ (686.1 mg, 2.43 mmol, 410 μL). The mixture was stirred at rt 2 h. Water (30 mL) was added and extracted with DCM (20 mL*3). The combined organic phase was washed by water (20 mL*2) and brine (30 mL), dried over $Na_2SO_4$ and concentrated in vacuum to afford compound F6 (800 mg, crude) as a yellow liquid.

To a solution of compound E5 (4.2 g, 11.34 mmol) in DCE (40 mL) at rt was added 3-fluoro-2-isopropyl-phenol (5.25 g, 34.03 mmol) and $ZnCl_2$ (1 M/THF, 28.35 mL). The reaction was heated to 85° C. and stirred for 5 h. Water (50 mL) was added and extracted with DCM (50 mL*3). The combined organic phase was washed by brine (100 mL), dried over $Na_2SO_4$ and concentrated in vacuum. The crude product was purified by silica gel column (EtOAc/pet. ether=1/50 to 1/20) to afford compound E6 (2.3 g, 41.5% yield) as colorless oil.

To a mixture of compound F6 (650 mg, 1.34 mmol), $Pd(PPh_3)Cl_2$ (94.0 mg, 134.1 mol) and sodium bicarbonate (337.9 mg, 4.03 mmol) in DMF (10 mL) was added methyl prop-2-enoate (2.31 g, 26.82 mmol). The mixture was heated to 130° C. and stirred for 3 h. The mixture was cooled down to rt. Water (30 mL) was added and extracted with EtOAc (20 mL*3). The combined organic phase was washed by water (20 ml*2) and brine (10 mL), dried over $Na_2SO_4$, concentrated in vacuum and purified by silica gel column (EtOAc/pet. ether=1/100 to 1/15) to afford product compound F7 (230 mg, 40.8% yield) as a white oil.

To a mixture of compound F7 (230 mg, 546.4 μmol) in DCM (3 mL) was added HCl/1,4-dioxane (4 M, 3 mL). The mixture was stirred at rt for 1 h. Water (15 mL) was added and extracted with DCM (10 mL*3). The combined organic phase was washed by brine (20 mL), dried over $Na_2SO_4$, concentrated in vacuum to afford crude product compound F8 (200 mg, 97.10% yield) as a light yellow oil.

To a mixture of compound F8 (100 mg, 265.36 μmol) in THF (5 mL) and water (1 mL) was added $LiOH·H_2O$ (33.46 mg, 796.08 μmol). The mixture was stirred at rt for 1 h. Water (30 mL) was added, adjust pH=4-5 with 1 M HCl and extracted with EtOAc (20 mL*3). The combined organic phase was washed by brine (30 mL), dried over $Na_2SO_4$, concentrated in vacuum to afford crude product and 100 mg crude product was purified by Prep-HPLC to afford Compound 126 (20 mg, 20.3% yield) as a white solid.

LCMS: T=1.900 min, [M+1]=361.1

To a solution of compound F8 (100 mg, 265.36 μmol) in THF (2 mL) was added Pd/C (20 mg). The mixture was refilled with $H_2$ three times and stirred at 50° C. under 1 atm $H_2$ atmosphere overnight. The reaction was cooled down to rt and filtered. Water (20 mL) was added and extracted with EtOAc (15 mL*3). The combined organic phase was washed by brine (10 mL), dried over $Na_2SO_4$ and concentrated in vacuum to afford crude product compound F9 (100 mg, crude) as a yellow oil.

To a mixture of compound F9 (100 mg, 263.95 umol) in THF (2.0 mL) and water (0.50 mL) was added $LiOH·H_2O$ (33.28 mg, 791.84 umol). The mixture was stirred at rt for 1 h. Water (10 mL) was added, adjust pH=4-5 with 1 M HCl and extracted with EtOAc (10 mL*3). The combined organic phase was washed by brine (10 mL), dried over $Na_2SO_4$, concentrated in vacuum and purified by Prep-HPLC to afford Compound 127 (15 mg, 14.8% yield) as a white solid.

LCMS: T=1.837 min, [M+1]=363.1

Example 128

Synthesis of (E)-3-(5-chloro-2-fluoro-4-(4-hydroxy-3-isopropylbenzyl)-3-methylphenyl)-2-methylacrylic acid (Compound 128)

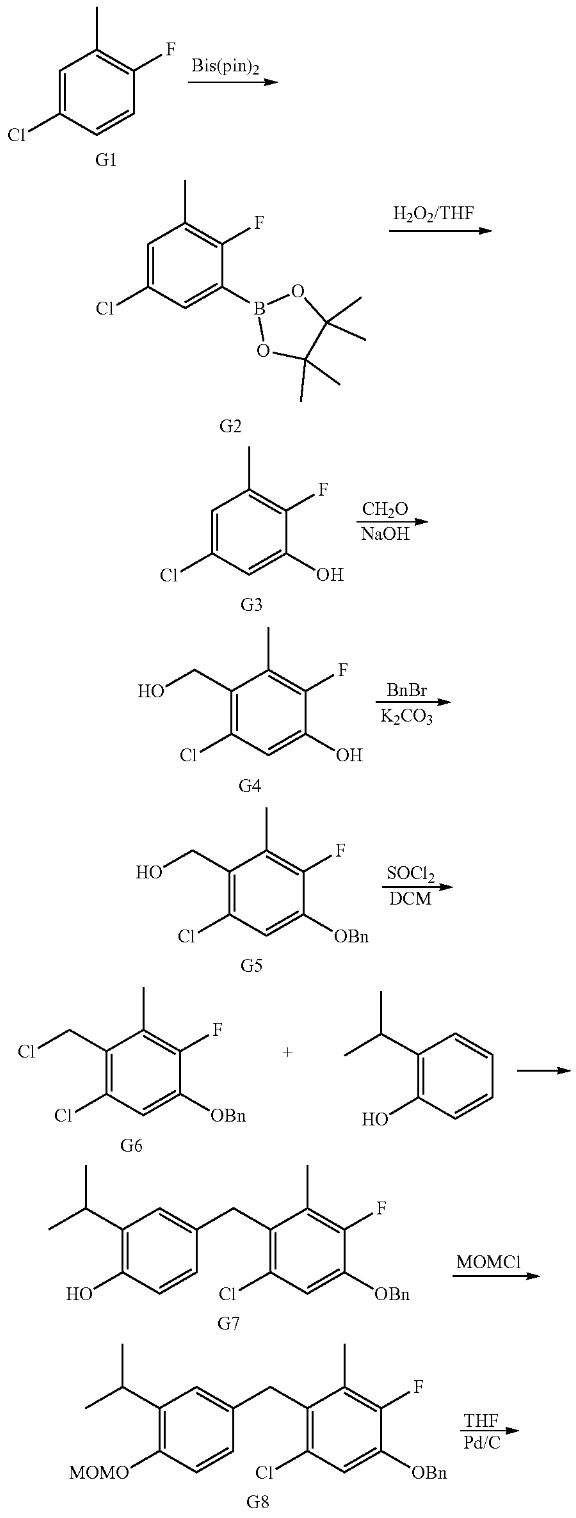

G1
G2
G3
G4
G5
G6
G7
G8

-continued

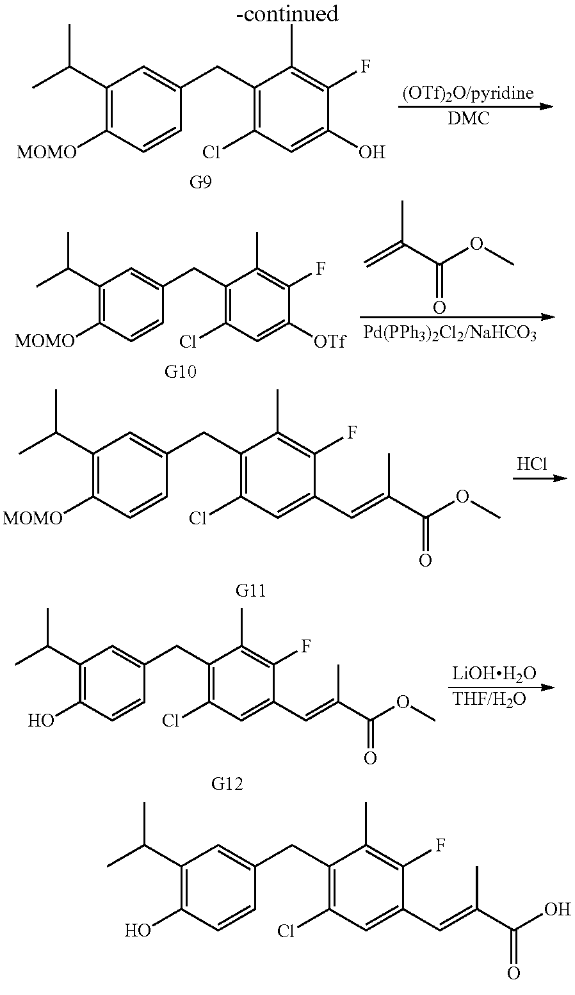

G9, G10, G11, G12, Compound 128

To a mixture of compound GI (10 g, 69.17 mmol, 8.40 mL), 4,4'-di-tert-butyl-2,2'-bipyridine (464 mg, 1.73 mmol) and $[Ir(OMe)(1,5\text{-}cod)]_2$ (917 mg, 1.38 mmol) in THF (100 mL) was added $Bpin_2$ (17.56 g, 69.17 mmol). The mixture was heated to 80° C. overnight. Water (50 mL) was added and extracted with EtOAc (50 mL*3). The combined organic phase was washed brine (50 mL), dried over $Na_2SO_4$ and concentrated in vacuum. The crude product was purified by silica gel column (EtOAc/pet. ether=1/100 to 1/30) to afford compound G2 (16.2 g, 86.5% yield) as a white solid.

To a solution of compound G2 (16 g, 59.14 mmol) in THE (120 mL) was added $H_2O_2$ (33.51 g, 295.71 mmol, 30% purity). The mixture was stirred at rt for 2 h. $Na_2S_2O_3$ (2.0 g) was added and extracted with EtOAc (200 mL*3). The combined organic phase was washed by brine (200 mL), dried over $Na_2SO_4$, concentrated in vacuum to afford compound G3 (9.0 g, 94.7% yield) as colorless liquid.

To a mixture of NaOH (2.74 g, 68.50 mmol) in water (50 mL) at rt was added compound G3 (10 g, 62.28 mmol). The mixture was heated to 45° C., formaldehyde (1.87 g, 62.28 mmol) was added dropwise. The mixture was stirred at 45° C. overnight, diluted with water (10 mL), acidified by 1 N HCl to pH=6-7, extracted with EtOAc (10 mL*3). The combined organic phase was washed by brine (10 mL), dried over $Na_2SO_4$, concentrated under reduce pressure. The crude product was purified by silica gel column (Pet. ether/EtOAc=50/1 to 10/1) to afford compound G4 (8.3 g, 69.9% yield) as a white solid.

To a mixture of compound G4 (8.3 g, 43.55 mmol) in DMF (80 mL) was added potassium carbonate (9.03 g, 65.32 mmol) and BnBr (7.45 g, 43.55 mmol). The mixture was stirred at rt 1 h. Water (30 mL) was added and extracted with EtOAc (60 mL*3). The combined organic layer was washed with water (60 mL*2) and brine (30 mL), dried over $Na_2SO_4$ and concentrated in vacuum to afford compound G5 (12 g, 98.1% yield) as a yellow oil.

A mixture of compound G5 (12 g, 42.75 mmol) in DCM (100 mL) was cooled down to 0° C., thionyl chloride (7.63 g, 64.12 mmol) was added dropwise. The mixture was stirred at rt for 1 h. The mixture was concentrated in vacuum to afford crude compound G6 (12 g, 93.8% yield).

To a solution of compound G6 (13.0 g, 43.45 mmol) in DCE (130 mL) at rt was added 2-isopropylphenol (17.75 g, 130.36 mmol) and $ZnCl_2$ (1M/THF, 65.18 mL). The mixture was heated to 65° C. 4 h. Water (30 mL) was added and extracted with DCM (70 mL*3). The combined was washed brine (70 mL), dried over $Na_2SO_4$ and concentrated in vacuum. The crude product was purified by silica gel column (EtOAc/pet. ether=1/100 to 1/30) to compound G7 (6.13 g, 35.3% yield) as a white solid.

To a solution of compound G7 (5.8 g, 14.54 mmol) in DMF (50 mL) was added $Cs_2CO_3$ (14.21 g, 43.62 mmol), and MOMCl (1.76 g, 21.81 mmol, 1.66 mL). The mixture was stirred at rt overnight. The mixture was quenched with water (200 mL), extracted with EtOAc (50 mL), the organic layer was washed with water (50 mL*2), brine (50 mL), dried over $Na_2SO_4$ and concentrated in vacuum to afford compound G8 (6 g, 93.1% yield) as a yellow oil.

To a solution of compound G8 (4 g, 9.03 mmol) in methanol (20 mL) and THF (20 mL) at rt was added Pd/C (800 mg, 6.59 mmol). The mixture was degassed under reduced pressure and refilled with $H_2$ three times. The mixture was stirred under 1 atm $H_2$ at 50° C. for 7 h. The mixture was filtered and concentrated in vacuum to afford crude compound G9 (2.5 g, 78.4% yield) as a yellow oil.

To a solution of compound G9 (3.3 g, 9.35 mmol) in DCM (30 mL) was added pyridine (1.48 g, 18.71 mmol). The mixture was cooled down to 0° C. and Trifluoromethanesulfonic anhydride (2.90 g, 10.29 mmol, 1.73 mL) was added dropwise. The mixture was stirred at rt for 2 h. The mixture was diluted with DCM (15 mL) and washed with water (20 mL*2). The organic layer was washed with brine (20 mL), dried over $Na_2SO_4$ and concentrated in vacuum to afford crude compound G10 (4 g, 88.2% yield) as a yellow oil.

To a solution of compound G10 (3.8 g, 7.84 mmol), $Pd(PPh_3)_2Cl_2$ (550.07 mg, 783.69 mol) and sodium bicarbonate (1.98 g, 23.51 mmol) in DMF (30 mL) was added methyl 2-methylprop-2-enoate (15.69 g, 156.74 mmol). The mixture was heated to 120° C. and stirred for 3 h. The mixture was cooled down to rt and filtered. The filtrate was concentrated in vacuum and purified by silica gel column (pet. ether/EtOAc=10/1) to afford compound G11 (1 g, 29.3% yield).

To a solution of compound G11 (1 g, 2.30 mmol) in HCl/1,4-dioxane (4 M, 10 mL) was stirred at rt for 1 h. The mixture was concentrated to dryness to afford compound G12 (800 mg, 89.0% yield) as a white solid.

To a solution of compound G12 (800 mg, 2.05 mmol) in methanol (10 mL) was added NaOH (245.59 mg, 6.14 mmol) in water (2 mL). The mixture was stirred at rt for 1 h. The mixture was acidified to pH=4-5 with 2M HCl, $H_2O$ (30 mL) was added, the mixture was extracted with EtOAc (25 mL*2). The combined organic layer was washed with brine (50 mL), dried over $Na_2SO_4$, purified by Prep-HPLC to afford product Compound 128 (100 mg, 12.5% yield) as a white solid.

LCMS: T=2.083 min, [M−1]=375

Example 129

Synthesis of 2-((3-chloro-4-(4-hydroxy-3-isopropylbenzyl)-5-methylbenzyl)sulfinyl)acetic acid (Compound 129)

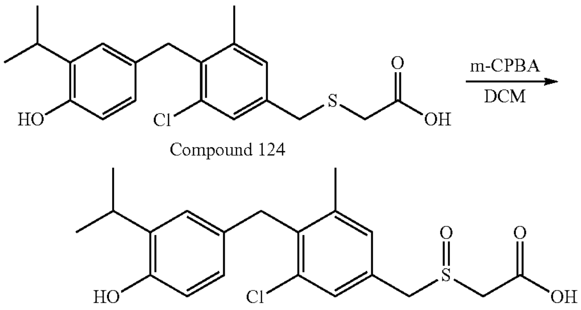

Compound 124

Compound 129

To a solution of Compound 124 (200 mg, 0.53 mmol) in DCM (4 mL) was added m-CPBA (107.0 mg, 0.53 mmol). The mixture was stirred at room temperature overnight. The reaction mixture was diluted with water (20 mL) and extracted with EtOAc (20 mL*2). The combined organic layer was washed with brine (20 mL), dried over $Na_2SO_4$ and concentrated in vacuum. The crude product was purified by Prep-HPLC to afford product Compound 129 (40.0 mg, 19.10% yield) as a white solid.

LCMS: T=1.060 min, [M−1]=393.1

Example 130

Synthesis of 2-((3-chloro-4-(4-hydroxy-3-isopropylbenzyl)-5-methylbenzyl)sulfonyl)acetic acid (Compound 130)

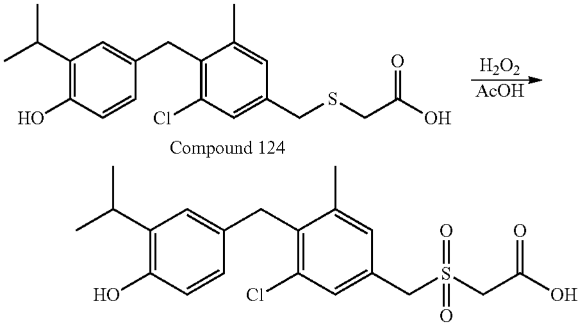

Compound 124

Compound 129

To a solution of Compound 124 (90 mg, 0.24 mmol) in AcOH (1 mL) was added $H_2O_2$ (1 mL, 35% w/w). The mixture was stirred at room temperature overnight. The reaction mixture was diluted with water (20 mL) and extracted with EtOAc (20 mL*2). The combined organic layer was washed with brine (20 mL), dried over $Na_2SO_4$ and concentrated in vacuum. The crude product was purified by Prep-TLC (DCM/MeOH=5/1) to afford product Compound 130 (25.0 mg, 24.4% yield) as a white solid.

LCMS: T=1.256 min, [M−1]=365.1

Example 131

Synthesis of 2-((3-chloro-4-(4-hydroxy-3-isopropylbenzyl)-5-methylbenzyl)thio)-N-cyclohexylacetamide (Compound 131)

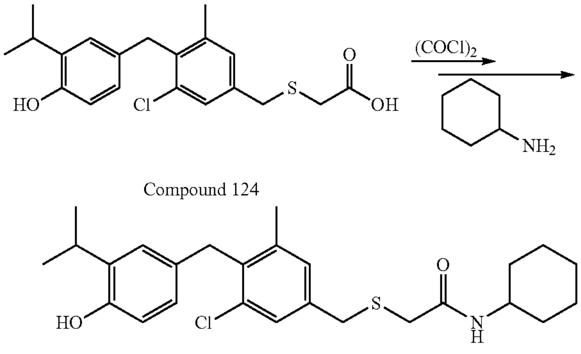

Compound 124

Compound 131

To a mixture of Compound 124 (500 mg, 1.32 mmol) in DCM (5 mL) was added DMF (cat) and oxalyl chloride (251.24 mg, 1.98 mmol). The mixture was stirred at rt for 30 min. The mixture was concentrated in vacuum to afford crude acid chloride as a yellow oil. To a solution of cyclohexanamine (26.21 mg, 264.24 μmol) in DCM (5 mL) was added dropwise the acid chloride (70 mg, 176.16 μmol) in DCM (2 mL). The mixture was stirred at rt for 30 min, water (5 mL) was added and extracted with DCM (10 mL*3). The combined was washed by brine (10 mL), dried over $Na_2SO_4$, concentrated in vacuum and purified by Prep-HPLC to afford product Compound 131 (55 mg, 65.5% yield) as a white solid.

LCMS: T=2.240 min, [M−1]=458

Example 132

Synthesis of (3-chloro-2-fluoro-4-(4-hydroxy-3-isopropylbenzyl)-5-methylbenzyl)glycine (Compound 132)

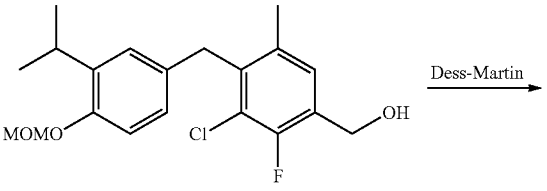

H1

-continued

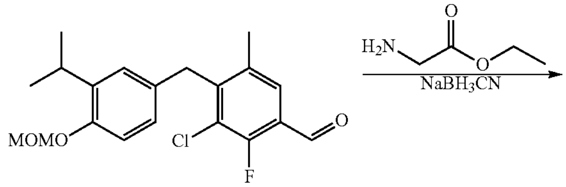

H2

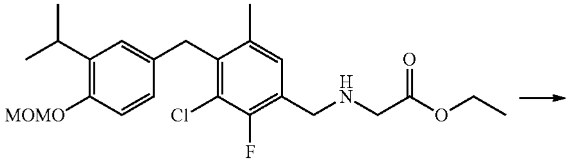

H3

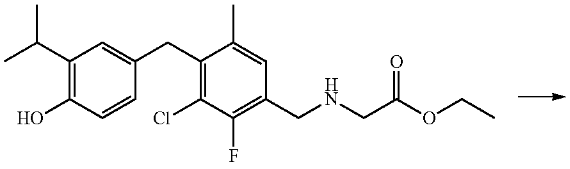

H4

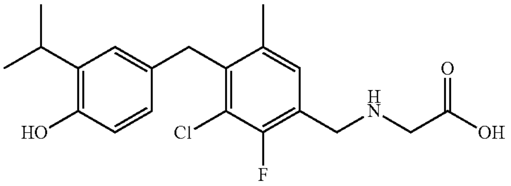

Compound 132

A mixture of compound H1 (260 mg, 708.73 μmol) in DCM (4 mL) at 0° C. was added Dess-Martin periodinane (330.66 mg, 779.60 μmol). The mixture was stirred at rt for 1 h. $H_2O$ (30 mL) was added, the mixture was extracted with EtOAc (25 mL*2). The combined organic layer was washed with water (25 mL*2), brine (50 mL), dried over $Na_2SO_4$, concentrated to afford compound H2 (195 mg, 75.4% yield) as a white solid.

A mixture of compound H2 (150 mg, 411.14 μmol) and ethyl 2-aminoacetate·hydrochloride (114.77 mg, 822.28 μmol) in methanol (3 mL) and THF (3 mL) was stirred at rt for 4 h. $NaBH_3CN$ (77.51 mg, 1.23 mmol) was added. The resulting mixture was stirred at rt overnight. $H_2O$ (30 mL) was added, the mixture was extracted with EtOAc (25 mL*2). The combined organic layer was washed with water (25 mL*2) and brine (50 mL), dried over $Na_2SO_4$, purified with Prep-TLC (Pet. ether/EtOAc=5/1) to afford compound H3 (40 mg, 21.5% yield) as a colorless oil.

A mixture of compound H3 (60 mg, 132.76 μmol) in 1,4-dioxane (2 mL) was added HCl/1,4-dioxane (4 M, 2 mL), the mixture was stirred at rt for 1 h. The mixture was concentrated in vacuum to afford compound H4 (50 mg, 92.3% yield) as a light yellow oil.

A mixture of ethyl compound H4 (50 mg, 122.58 μmol) in MeOH (3 mL)/$H_2O$ (1 mL) at rt was added $LiOH·H_2O$ (15.43 mg, 367.73 μmol). The mixture was stirred at rt 2 h. The reaction was acidified to pH=4-5 with 2 N HCl, extracted with EtOAc (20 mL), washed with brine (10 mL*2), dried over $Na_2SO_4$, concentrated and purified by Prep-HPLC to afford Compound 132 (10 mg, 18.1% yield) as colorless oil.

LCMS: T=1.688 min, [M−1]=378

Example 133

Synthesis of (5-chloro-2-fluoro-4-(2-fluoro-4-hydroxy-3-isopropylbenzyl)-3-methylphenyl)glycine (Compound 133)

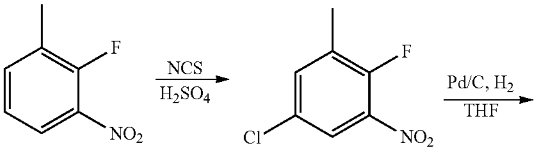

J1 J2

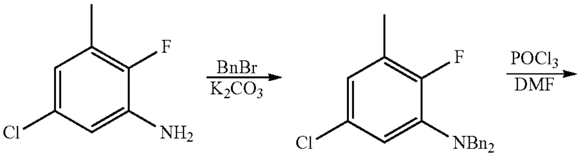

J3 J4

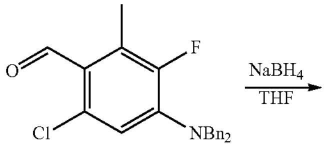

J5

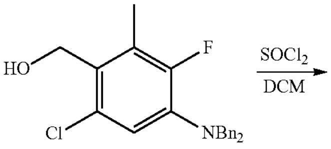

J6

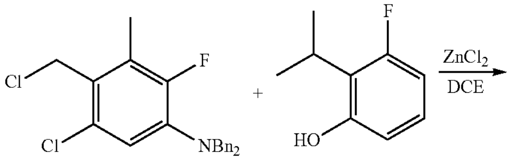

J7 J8

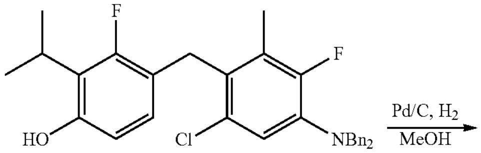

J9

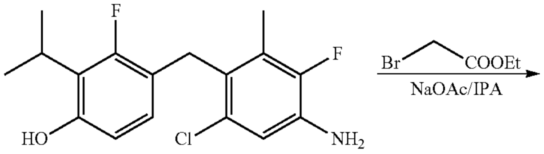

J10

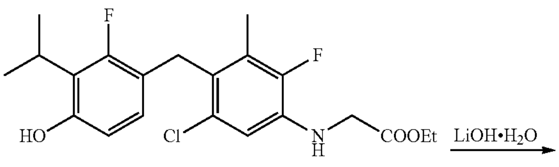

J11

-continued

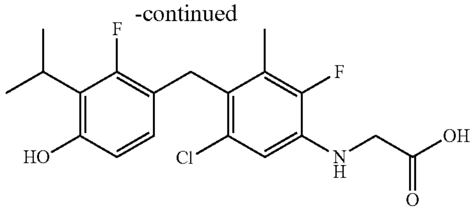

Compound 133

A mixture of compound J1 (50 g, 322.32 mmol) and NCS (51.65 g, 386.78 mmol) in sulfuric acid (250 mL) was stirred at 80° C. over the weekend. The mixture was poured into ice-water (50 mL), extracted with EtOAc (20 mL*2). The organic layer was washed with water (25 mL*2) and brine (50 mL), dried over $Na_2SO_4$, purified with RP column to afford product compound J2 (35 g, 57.2% yield) as a white solid.

A mixture of compound J2 (30 g, 158.25 mmol) and 10% Pd/C (3.0 g) in THF (300 mL) was stirred under 1 atm $H_2$ atmosphere at rt overnight. The mixture was filtered and concentrated in vacuo to afford compound J3 (30 g, 98.9% yield) as a brown oil.

A mixture of compound J3 (45 g, 281.98 mmol), BnBr (144.68 g, 845.93 mmol) and $K_2CO_3$ (194.85 g, 1.41 mol) in DMF (500 mL) was stirred at rt overnight. $H_2O$ (100 mL) was added and extracted with EtOAc (100 mL*2). The combined organic layer was washed with water (100 mL*4) and brine (200 mL), dried over $Na_2SO_4$, purified with silica gel column (Pet. ether) and RP column to afford product compound J4 (40 g, 41.7% yield) as a yellow oil.

To DMF (200 mL) at 0° C. was added dropwise $POCl_3$ (27.07 g, 176.56 mmol). The mixture was stirred at rt for 30 min. A solution of compound J4 (40 g, 117.70 mmol) in DMF (200 mL) was added dropwise to the previous solution. The mixture was stirred at 80° C. for 1 h. The mixture was poured into ice/water and extracted with EtOAc (3*300 mL). The organic layer was washed with water (3*100 mL) and brine (200 mL). The organic layer was concentrated under reduced pressure, purified by silica gel column (pet. ether) to afford compound J5 (4.1 g, 9.4% yield) as a yellow oil.

To a solution of compound J5 (2.7 g, 7.34 mmol) in THF (30 mL) was added $NaBH_4$ (333.23 mg, 8.81 mmol). The mixture was stirred at rt for 1 h. The mixture was quenched with water (100 mL), extracted with EtOAc (50 mL*2). The combined organic layer was washed with water (50 mL*2) and brine (50 mL), dried over $Na_2SO_4$, concentrated to dryness to afford product compound J6 (2.7 g, 99.4% yield) as colorless oil.

To a mixture of compound J6 (2.8 g, 7.57 mmol) in DCM (20 mL) was added thionyl chloride (1.35 g, 11.36 mmol). The mixture was stirred at rt for 2 h. The mixture was concentrated to dryness to afford product compound J7 (2.9 g, 98.6% yield) as white solid.

A mixture of compound J7 (3 g, 7.73 mmol) and compound J8 (3.57 g, 23.18 mmol) in DCE (30 mL) was added $ZnCl_2$ (1 M/THF, 19.31 mL). The mixture was stirred at 85° C. overnight. The mixture was concentrated to dryness, quenched with water (30 mL), extracted with EtOAc (25 mL*2). The combined organic layer was washed with water (25 mL*2) and brine (50 mL), dried over $Na_2SO_4$, purified with silica gel column (Pet. ether to Pet. ether/EtOAc=5/1) to afford product compound J9 (3 g, 76.7% yield) as yellow solid.

A mixture of compound J9 (400 mg, 790.48 μmol) and Pd/C (10%) (40 mg) in MeOH (5 mL) was stirred at rt under 1 atm $H_2$ atmosphere for 6 h. The mixture was filtered, concentrated to dryness purified by silica gel column (pet. ether/EtOAc=3/1) to afford compound J10 (100 mg, 38.83% yield) as a white solid.

To a solution of compound J10 (100 mg, 306.96 μmol) in IPA (3 mL) was added NaOAc (25.18 mg, 306.96 μmol) and ethyl 2-bromoacetate (56.39 mg, 337.65 μmol). The mixture was stirred at 100° C. overnight and cooled down to rt. The mixture was quenched with water (30 mL), extracted with EtOAc (25 mL*2). The combined organic layer was washed with water (25 mL*2) and brine (50 mL), dried over $Na_2SO_4$, concentrated to dryness to afford the crude product compound J11 (100 mg, 79.1%).

A mixture of compound J11 (1.5 g, 3.64 mmol), NaOH (291.33 mg, 7.28 mmol) in methanol (10 mL) and water (1 mL) was stirred at rt 1 h. The mixture was acidified to pH=4-5 with 2M HCl, $H_2O$ (30 mL) was added, the mixture was extracted with EtOAc (25 mL*2). The combined organic layer was washed with brine (50 mL), dried over $Na_2SO_4$, purified by Prep-HPLC to afford product Compound 133 (180 mg, 12.4% yield) as white solid.

LCMS: T=1.774 min, [M+1]=384

Example 134 and Example 135

Synthesis of (3-chloro-2-fluoro-4-(4-hydroxy-3-isopropylbenzyl)-5-methylphenyl)glycine (Compound 134) and 2-((3-chloro-2-fluoro-4-(4-hydroxy-3-isopropylbenzyl)-5-methylphenyl)amino)-N-methylacetamide (Compound 135)

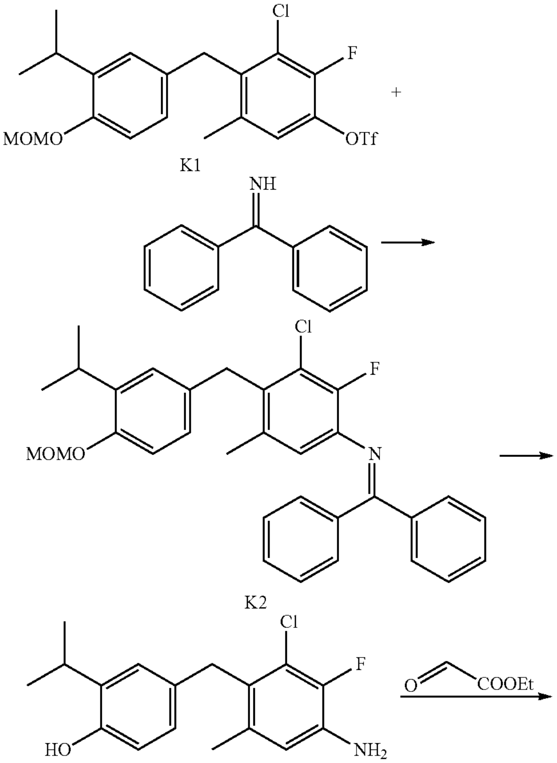

K1

K2

K3

-continued

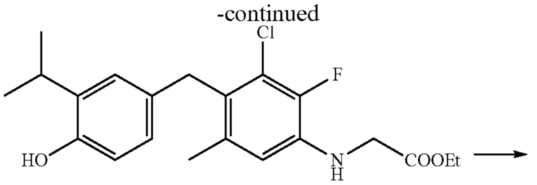

K4

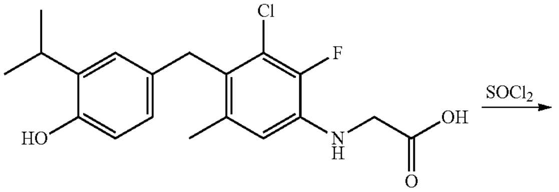

Compound 134

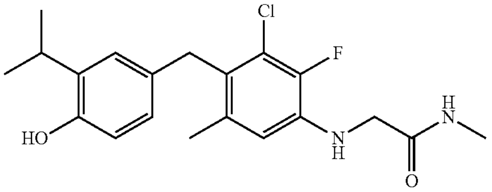

Compound 135

To a mixture of compound K1 (1.2 g, 2.47 mmol) in 1,4-dioxane (4 mL) at rt was added diphenylmethanimine (2.24 g, 12.37 mmol), $Cs_2CO_3$ (1.61 g, 4.95 mmol), $Pd_2(dba)_3$ (113.31 mg, 123.74 μmol) and tBuDavePhos (84.51 mg, 247.48 μmol). The reaction was heated to 110° C. 2 h under microwave condition. The mixture was diluted with water (40 mL) and extracted with EtOAc (20 mL*3) The combine organic phase was washed by brine (30 mL*2), dried over $Na_2SO_4$, concentrated under reduce pressure. The crude product was purified by silica gel column (pet. ether/EtOAc=50/1 to 15/1) to afford compound K2 (210 mg, 16.4% yield) as colorless oil.

To a solution of compound K2 (210 mg, 406.94 μmol) in 1,4-dioane (2 mL) was added HCl/1,4-dioxane (4 M, 2 mL) and stirred at rt overnight. The reaction was extracted with EtOAc (20 mL), washed with brine (10 mL*2), dried over $Na_2SO_4$, concentrated in vacuum and purified by Prep-TLC (Pet. ether/EtOAc=5/1) to afford crude product compound K3 (50 mg, 39.9% yield) as a yellow oil.

To a solution of compound K3 (50 mg, 162.45 μmol) in $CH_3CN$ (4 mL) was added butyl 2-(2,4-dichlorophenoxy) acetate (4.50 mg, 16.24 μmol) and ethyl 2-oxoacetate (663.37 mg, 3.25 mmol, 644.04 μL). The mixture was stirred at 65° C. overnight. The mixture was cooled down to rt and was added Pd/C (10 mg). The mixture was stirred at rt overnight under 1 atm $H_2$ (g) atmosphere. Water (30 mL) was added and extracted with EtOAc (20 mL*3). The combined organic phase was washed by brine (30 mL), dried over $Na_2SO_4$, concentrated in vacuum and purified by Prep-TLC (pet. ether/EtOAc=5/1) to afford compound K4 (40 mg, 62.5% yield) as a white solid.

To a mixture of compound K4 (40 mg, 101.55 μmol) in water (0.5 mL) and THF (2 mL) was added $LiOH{\cdot}H_2O$ (12.78 mg, 304.66 μmol). The mixture was stirred at rt for 1 h. Water (30 mL) was added, adjust pH=4-5 with 1 N HCl and extracted with EtOAc (20 mL*3). The combined organic phase was concentrated in vacuum to afford Compound 134 (37 mg, 99.9% yield) as a colorless oil.

LCMS: T=1.564 min, [M−1]=364

To a mixture of Compound 134 (40 mg, 114.17 μmol) in DCM (2.0 mL) was added DMF (cat) and thionyl chloride (20.37 mg, 171.25 μmol). The mixture was stirred at rt for 30 min. The mixture was concentrated in vacuum and $MeNH_2$ (in THF) (1 M/THF, 1 mL) was added. The mixture was stirred at rt for 30 min. Water (30 mL) was added and diluted with DCM (20 mL*3). The combined was washed by brine (30 mL), dried over $Na_2SO_4$ concentrated in vacuum and purified by Prep-HPLC to afford Compound 135 (5 mg, 12.3% yield) as a white solid.

LCMS: T=1.438 min, [M+1]=379

Example 136

Synthesis of 2-((5-chloro-2-fluoro-4-(2-fluoro-4-hydroxy-3-isopropylbenzyl)-3-methylphenyl) amino)-N-methylacetamide (Compound 136)

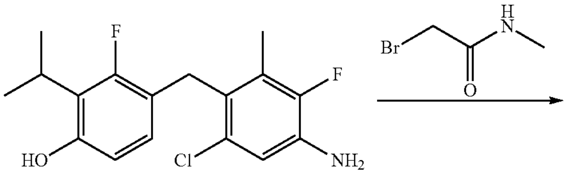

J10

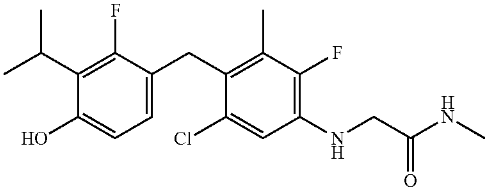

Compound 136

To a solution of methylamine (2 M/THF, 1 mL) was added compound J10 (80 mg, 198.88 μmol). The mixture was stirred at rt 1 h. The mixture was concentrated to dryness, purified by Prep-HPLC to afford product Compound 136 (6 mg, 7.3% yield) as a white solid.

LCMS: T=1.662 min, [M+1]=397

Example 137

Synthesis of 2-(3,5-dichloro-4-(4-hydroxy-3-(piperidine-1-carbonyl)benzyl)phenyl)acetic acid (Compound 137)

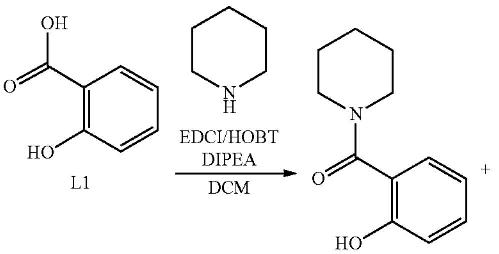

L1

L2

-continued

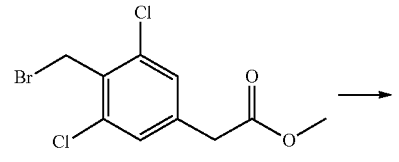

L3

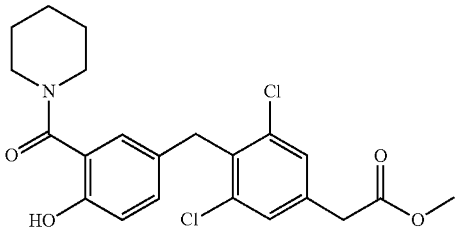

L4

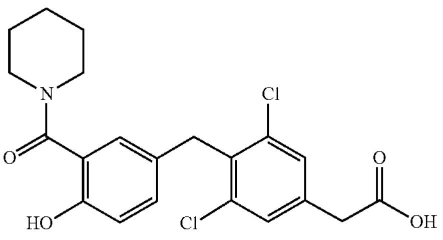

Compound 137

To a solution of compound L1 (2 g, 14.48 mmol) in DCM (20 mL) at 0° C. was added DIPEA (3.74 g, 28.96 mmol), EDCI (4.16 g, 21.72 mmol), and HOBT (2.93 g, 21.72 mmol), the resulting mixture was stirred at 0° C. 5 min and piperidine (3.70 g, 43.44 mmol) at 0° C. was added to the reaction, the resulting mixture was stirred at rt 2 h. The mixture was diluted with water (20 mL) and extracted with DCM (20 mL). The organic phase was dried over $Na_2SO_4$, concentrated and purified by RP column to afford compound L2 (800 mg, 26.9% yield) as a white solid.

To a solution of compound L2 (217.10 mg, 1.06 mmol) in chlorobenzene (5 mL) at rt were added compound L3 (110 mg, 352.58 umol) and $ZnC_2$ (120.14 mg, 881.45 umol). The reaction was heated to 150° C. under microwave and stirred 2 h. The reaction mixture was diluted with DCM (20 mL), washed brine (2*10 mL), dried over Na2SO4, concentrated under reduce pressure. The crude product was purified through Prep-TLC (EtOAc:pet. ether=1:5) to afford compound L4 (50 mg, 32.5% yield).

To a solution of compound L4 (80 mg, 183.35 umol) in THF (1 mL)/water (5 mL) at rt was added $LiOH{\cdot}H_2O$ (13.17 mg, 550.05 umol), the resulting mixture was stirred at rt 1 h. The reaction was acidified to pH=6-7 with 2N HCl, concentrated and purified by Prep-HPLC to afford Compound 137 (30 mg, 38.7% yield).

LCMS: T=3.396 min, [M+1]=422.1

Example 138

Synthesis of 2-(3,5-dichloro-4-(4-hydroxy-3-((2-oxopyrrolidin-1-yl)methyl)benzyl)phenyl)acetic acid (Compound 138)

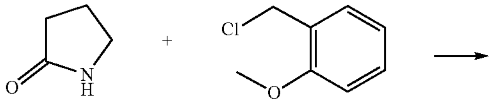

M1 M2

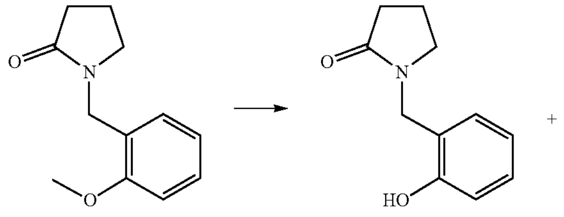

M3 M4

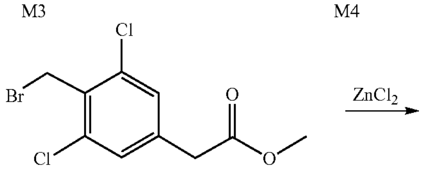

M5

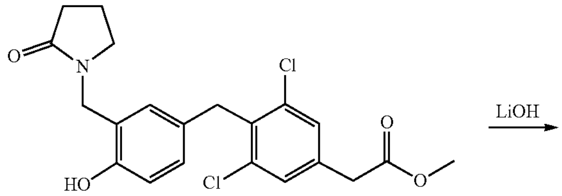

M6

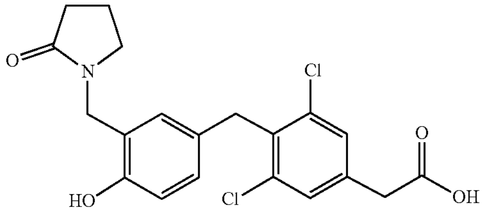

Compound 138

To a solution of compound M1 in DMF (8 mL) at 0° C. was added NaH (60%) (191.56 mg, 4.79 mmol). The mixture was stirred at room temperature 2 h. Compound M2 (500 mg, 3.19 mmol) was added. The mixture was stirred at rt overnight. The mixture was concentrated to dryness. $H_2O$ (30 mL) was added, the mixture was extracted with EtOAc (25 mL*2). The combined organic layer was washed with brine (50 mL), dried over $Na_2SO_4$, concentrated to afford product compound M3 (400 mg, 61.0% yield) as a white solid.

To a solution of compound M3 (300 mg, 1.46 mmol) in DCM (6 mL) was added $BBr_3$ (549.25 mg, 2.19 mmol). The mixture was stirred at rt 2 h. $H_2O$ (30 mL) was added, the mixture was extracted with DCM (25 mL*2). The combined organic layer was washed with brine (50 mL), dried over $Na_2SO_4$, concentrated to dryness to afford product compound M4 (300 mg, 96.6% yield) as a yellow solid.

To solution of compound M4 (202.27 mg, 1.06 mmol), compound M5 (110 mg, 352.58 umol) and $ZnCl_2$ (120.14 mg, 881.45 umol) in chlorobenzene (5 mL) was microwaved at 150° C. 1 h. LCMS showed some SM remained. The mixture was concentrated to dryness. $H_2O$ (10 mL) was added, the mixture was extracted with EtOAc (15 mL*2). The combined organic layer was washed with brine (15 mL), dried over $Na_2SO_4$, purified with Prep-TLC (Pet. ether/EtOAc=5/1) to afford crude product compound M6 (80 mg 53.73% yield) as a yellow solid.

To a solution of compound M6 (80 mg, 189.44 umol) in water (1 mL) and methanol (3 mL) was added $LiOH \cdot H_2O$ (18.15 mg, 757.75 umol). The mixture was stirred for 1 h. The mixture was adjusted to pH=5-6. $H_2O$ (10 mL) was added, the mixture was extracted with EtOAc (10 mL*2). The combined organic layer was washed with brine (10 mL), dried over $Na_2SO_4$, purified with Prep-HPLC to afford product Compound 138 (15 mg, 19.3% yield) as a white solid.

LCMS: T=3.200 min, [M+1]=408.1

Example 139

Synthesis of (3,5-dichloro-4-((5'-(difluoromethoxy)-2,2'-difluoro-6-hydroxy-[1,1'-biphenyl]-3-yl)methyl)phenyl)glycine (Compound 139)

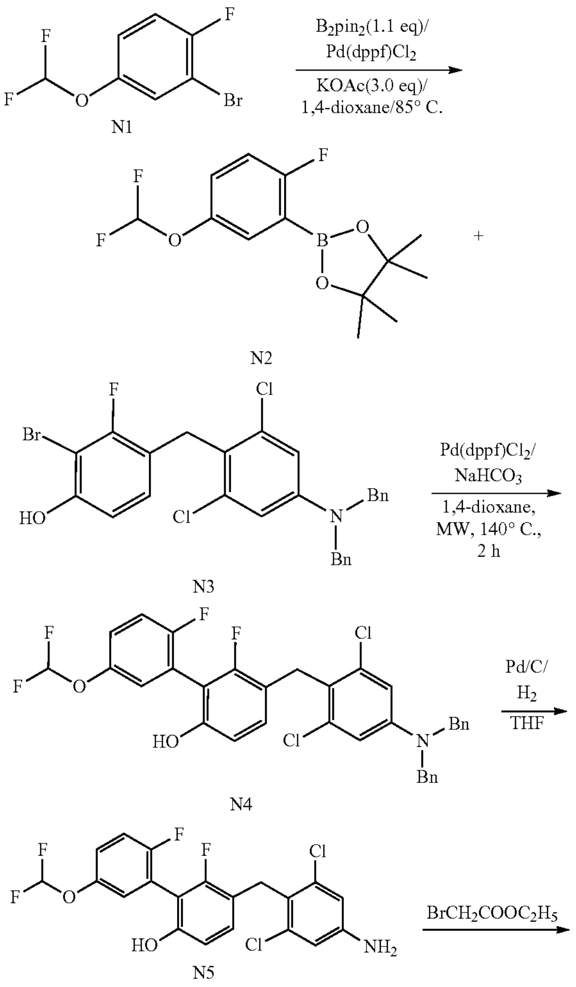

N1

N2

N3

N4

N5

-continued

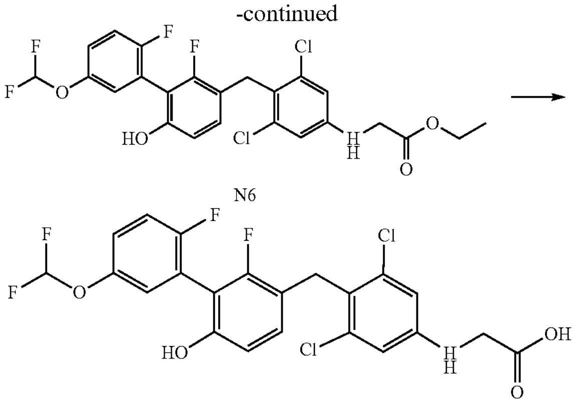
N6

Compound 139

To a solution of 2-bromo-4-(difluoromethoxy)-1-fluorobenzene (1.2 g, 4.98 mmol) in 1,4-dioxane (3 mL) was added pinacol diboride (1.64 g, 6.47 mmol), KOAc (1.47 g, 14.94 mmol) and $Pd(dppf)Cl_2$ (364.33 mg, 497.91 umol). The mixture was stirred at 80° C. overnight. The mixture was filtered and concentrated in vacuum. The residue compound N2 (1.37 g mg, 95.5% yield) was used for the next step without purification.

To a solution of compound N2 (1.37 g, 4.77 mmol) in 1,4-dioxane (10 mL) and water (2 mL) at rt was added compound N3 (1.3 g, 2.38 mmol), $NaHCO_3$ (600.88 mg, 7.15 mmol) and $Pd(dppf)Cl_2$ (174.45 mg, 238.41 umol). The mixture was stirred at 140° C. under microwave condition for 2 h. The mixture was diluted with EtOAc (20 mL) and filtered. The filtrate was washed with brine (30 mL), dried over $Na_2SO_4$ and concentrated in vacuum. The residue was purified by silica gel column (Pet. ether/EtOAc=10:1) and re-purified by Prep-TLC (Pet. ether/EtOAc=5:1) to afford compound N4 (120 mg, 8.0% yield) as a yellow oil.

To a solution of compound N4 (120 mg, 191.55 umol) in THF (4 mL) was added Pd/C (46.53 mg, 383.10 umol). The mixture was degassed under reduced pressure and refilled with $H_2$ three times and stirred at rt under 1 atm $H_2$ for 5 h. The mixture was filtered and concentrated in vacuum. The residue was purified by Prep-TLC (Pet. ether/EtOAc=3:1) to afford compound N5 (70 mg, 81.9% yield) as a yellow oil.

To a solution of compound N5 (70 mg, 156.87 umol) in ethanol (5 mL) was added ethyl 2-bromoacetate (26.20 mg, 156.87 umol) and AcONa (16.73 mg, 203.93 umol). The mixture was stirred at 100° C. for 24 h. The mixture was concentrated and the residue was purified by Prep-TLC (pet. ether/EtOAc=5:1) to afford compound N6 (30 mg, 35.9% yield) as a yellow liquid.

To a solution of compound N6 (30 mg, 56.36 umol) in THF (2 mL) was added a solution of $LiOH \cdot H_2O$ (7.09 mg, 169.07 umol) in water (1 mL). The mixture was stirred at rt for 1 h. The mixture was acidified with 1 N HCl to pH=5. The aqueous layer was extracted with EtOAc (2*40 mL). The organic layer was washed with brine (30 mL), dried over $Na_2SO_4$ and evaporated to dryness. The crude product was purified by Prep-HPLC to afford Compound 139 (11 mg, 38.3% yield) as a white solid.

LCMS: T=3.947 min, [M+1]=502.0

Example 140

Synthesis of N-(3,5-dichloro-4-(2-fluoro-4-hydroxy-3-isopropylbenzyl)phenyl)-N-methylglycine (Compound 140)

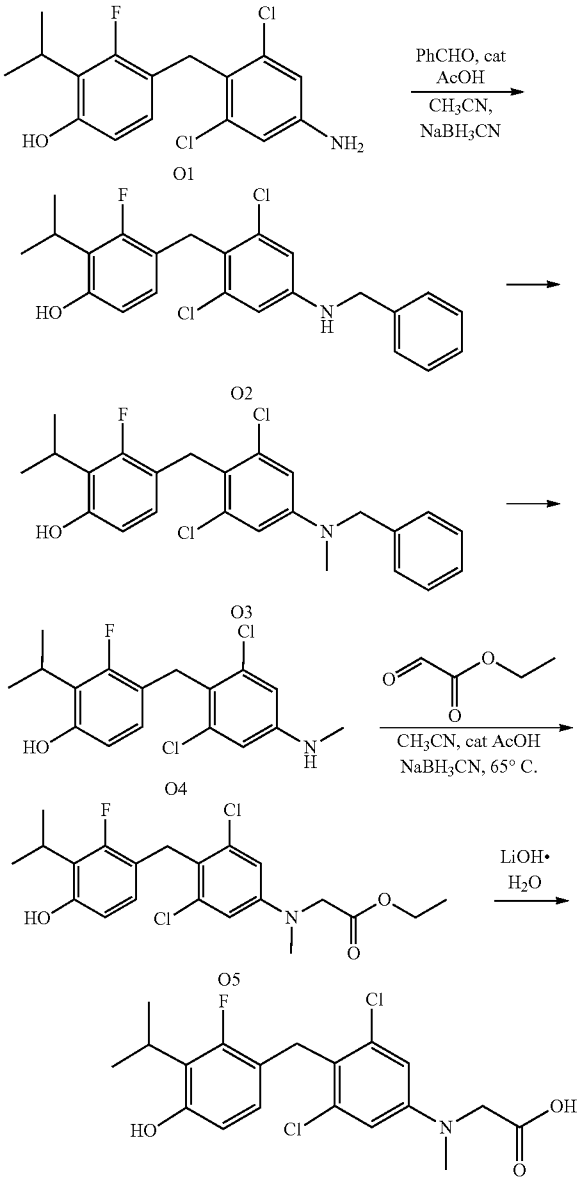

Compound 140

To a solution of compound 01 (827.0 mg, 2.52 mmol) in $CH_3CN$ (8 mL) was added PhCHO (320.9 mg, 3.02 mmol) and AcOH (15.8 mg, 0.25 mmol). The mixture was stirred at room temperature overnight. The reaction mixture was diluted with water (20 mL) and extracted with EtOAc (30 mL*2). The combined organic layer was washed with brine (20 mL), dried over $Na_2SO_4$ and concentrated in vacuum. The crude product was purified by silica gel column (pet. ether/EtOAc=10/1) to afford product compound 02 (699.0 mg, 66.3% yield) as a yellow solid.

To a solution of compound 02 (699 mg, 1.67 mmol) in $CH_3CN$ (7 mL) was added HCHO (101.26 mg, 3.34 mmol) and HCOOH (8.03 mg, 0.17 mmol). The mixture was stirred at room temperature for 5 h. $NaBH_3$ was added, the mixture was stirred at room temperature overnight. The reaction mixture was diluted with water (20 mL) and extracted with EtOAc (30 mL*2). The combined organic layer was washed with brine (20 mL), dried over $Na_2SO_4$ and concentrated in vacuum. The crude product was purified by RP-column to afford product compound 03 (238.0 mg, 32.9% yield) as a yellow solid.

To a solution of compound 03 (238 mg, 0.55 mmol) in THF (5 mL) was added Pd/C (80.0 mg, 0.66 mmol). The mixture was stirred at room temperature with $H_2$ for 1 h. The reaction mixture was filtered and concentrated in vacuum. The crude product was purified by silica gel column (pet. ether/EtOAc=100/1 to 3/1) to afford product compound 04 (120.0 mg, 63.70% yield) as a yellow solid.

To a solution of compound 04 (30.0 mg, 0.09 mmol) in $CH_3CN$ (2 mL) was added AcOH (5.3 mg, 0.09 mmol) and Ethyl glyoxalate (89.5 mg, 0.88 mmol). The mixture was stirred at 65° C. for 5 h. $NaBH_3CN$ was added. The mixture was stirred at room temperature overnight. The reaction mixture was diluted with water (20 mL) and extracted with EtOAc (30 mL*2). The combined organic layer was washed with brine (20 mL), dried over $Na_2SO_4$ and concentrated in vacuum. The crude product was purified by Prep-TLC (pet. ether/EtOAc=5/1) to afford product compound 05 (13.5 mg, 35.9% yield) as a yellow liquid.

To a solution of compound 05 (30.0 mg, 0.07 mmol) in THF (2 mL) was added $LiOH/H_2O$ (8.8 mg, 0.21 mmol) in water (1 mL), the mixture was stirred at room temperature for 2 h. The reaction was acidified to pH=5-6 with 1 N HCl. The reaction mixture was diluted with water (20 mL) and extracted with EtOAc (20 mL*2). The combined organic layer was washed with brine (20 mL), dried over $Na_2SO_4$ and concentrated in vacuum. The crude product was purification by Prep-HPLC to afford product Compound 140 (12.0 mg, 42.7% yield) as a white solid.

LCMS: T=4.226 min, [M−1]=398.0

Example 141 and Example 142

Synthesis of 2-(3,5-dichloro-4-(4-hydroxy-3-isopropylbenzyl)phenyl)-4-ethoxy-4-oxobutanoic acid (Compound 141) and 2-(3,5-dichloro-4-(4-hydroxy-3-isopropylbenzyl)phenyl)succinic acid (Compound 142)

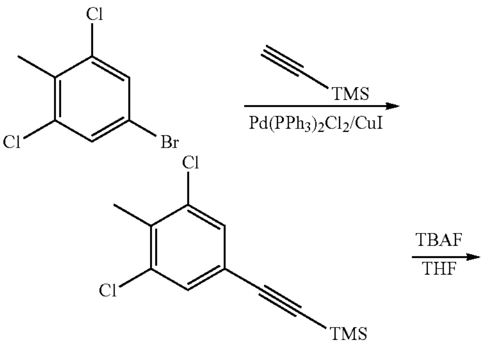

P1

-continued

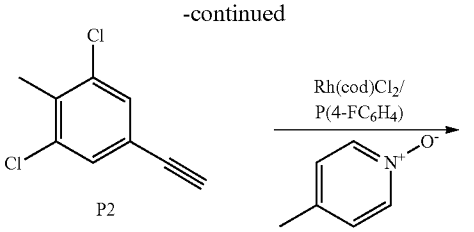

P2

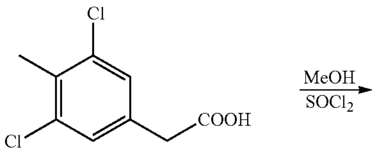

P3

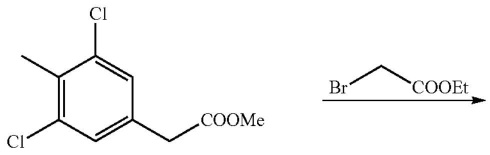

P4

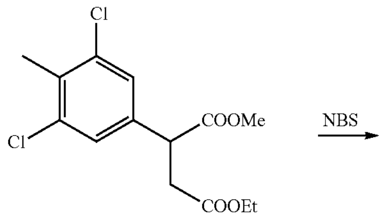

P5

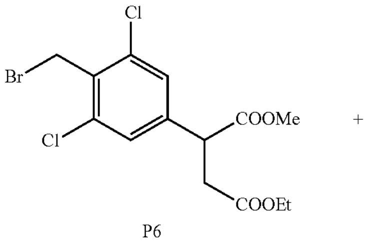

P6

+

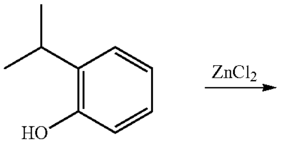

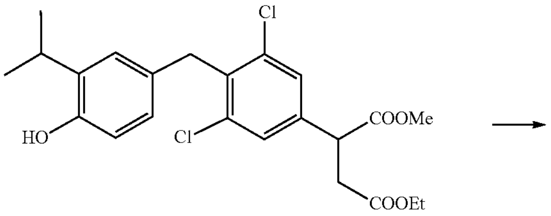

P7

-continued

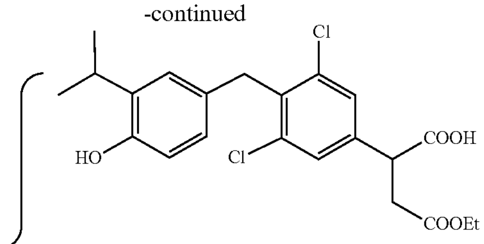

Compound 141

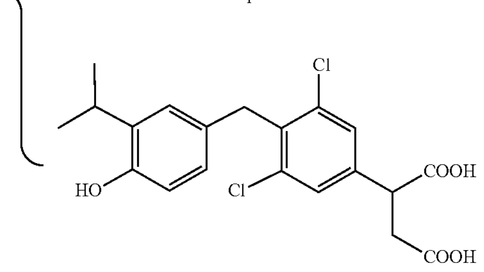

Compound 142

A mixture of 5-bromo-1,3-dichloro-2-methyl-benzene (20.0 g, 83.36 mmol), ethynyl(trimethyl)silane (9.8 g, 100.03 mmol), $Pd(PPh_3)_2Cl_2$ (2.9 g, 4.17 mmol), CuI (16 mg, 83.36 umol) and DIPEA (25.3 g, 250.08 mmol) in DMF (100 mL) was stirred at 100° C. for 2 h. The mixture was cooled to rt, $H_2O$ (200 mL) was added, the mixture was extracted with EtOAc (50 mL*2). The combined organic layer was washed with water (100 mL*3) and brine (50 mL*2), dried over $Na_2SO_4$ and concentrated in vacuum. The residue was purified with silica gel column (Pet. ether) to afford compound P1 (20.0 g, 93.3% yield) as a yellow oil.

To a solution of compound P1 (20.0 g, 77.75 mmol) in THF (100 mL) was added TBAF (1 M/THF, 39 mL). The mixture was stirred at rt for 2 h. The mixture was quenched with water (200 mL), extracted with EtOAc (100 mL*2). The organic layer was washed with brine (100 mL), dried over $Na_2SO_4$ and concentrated to dryness. The residue was purified by silica gel column (pet. ether) to afford compound P2 (10.5 g, 72.9% yield) as a yellow solid.

A mixture of compound P2 (8.5 g, 45.93 mmol), 4-methyl-1-oxido-pyridin-1-ium (10.0 g, 91.87 mmol) and $Rh(cod)Cl_2$ (1.1 g, 2.30 mmol) in water (3 mL) and acetonitrile (50 mL). The mixture was stirred at 60° C. overnight. The mixture was cooled to rt, $NaHCO_3$ (100 mL) was added. The mixture was extracted with diethyl ether (100 mL). The water phase was acidified to pH=5-6, extracted with EtOAc (100 mL). The organic layer was washed with brine (100 mL), dried over $Na_2SO_4$, concentrated to dryness to afford compound P3 (5.8 g, 57.6% yield) as a yellow solid.

To a solution of compound P3 (2.5 g, 11.41 mmol) in methanol (30 mL), was added thionyl chloride (2.0 g, 17.12 mmol). The mixture was refluxed 2 h. The mixture was concentrated and water (20 mL) was added. The mixture was extracted with EtOAc (15 mL*2). The combined EtOAc phase was washed with brine (20 mL), dried over $Na_2SO_4$, concentrated in vacuum to afford compound P4 (2.1 g, 78.9% yield) as a white solid.

To a solution of compound P4 (1.0 g, 4.29 mmol) in THF (15 mL) was added Ethyl bromoacetate (1.1 g, 6.44 mmol), $Cs_2CO_3$ (2.2 g, 6.86 mmol). The reaction was stirred at 70° C. overnight. The reaction was cooled down to rt, water (50 mL) was added. The mixture was extracted with EtOAc (30 mL*2), the combined organic phase was washed by brine (50 mL), dried over $Na_2SO_4$, concentrated in vacuo and purified by silica column (pet. ether/EtOAc=50/1 to 5/1) to afford compound P5 (700 mg, 51.1% yield) as a light yellow oil.

To a solution of compound P5 (700 mg, 2.19 mmol) in CCl4 (15 mL) was added NBS (410 mg, 2.30 mmol), BPO (32 mg, 131.59 umol). The reaction was stirred at reflux for 1 h. The reaction was cooled down to rt, The mixture was concentrated in vacuo and purified by silica column (pet. ether/EtOAc=100/1 to 10/1) to afford compound P6 (500 mg, 57.3% yield) as colorless oil.

A mixture of compound P6 (300 mg, 753.62 umol), 2-isopropylphenol (308 mg, 2.26 mmol) in DCE (10 mL) was added ZnCl2 (257 mg, 1.88 mmol). The reaction was stirred at 80° C. overnight. The mixture was washed by brine (30 mL). The organic layer was dried over $Na_2SO_4$, concentrated in vacuo. The residue was purified by silica column (pet. ether/EtOAc=50/1 to 10/1) to afford compound P7 (100 mg, 29.3% yield) as colorless oil.

To a solution of compound P7 (50 mg, 110.29 umol) in water (0.5 mL) and THE (2 mL) was added $LiOH{\cdot}H_2O$ (6 mg, 132.35 umol). The reaction was stirred at rt overnight. Water (3 mL) was added, adjusted the pH=3-4 with 1N HCl, extracted with EtOAc (3 mL*3). The combined organic phase was washed by brine, dried over $Na_2SO_4$, concentrated in vacuo. The residue was purified by Prep-HPLC to afford Compound 141 (6 mg, 12.4% yield) and Compound 142 (19 mg, 41.9% yield) as a white solid.

Compound 141: LCMS: T=1.824 min, [M+1]=439.0

Compound 142: LCMS: T=1.302 min, [M−1]=408.9

Example 143

Synthesis of 2-amino-3-(3,5-dichloro-4-(4-hydroxy-3-isopropylbenzyl)phenyl)propanoic acid (Compound 143)

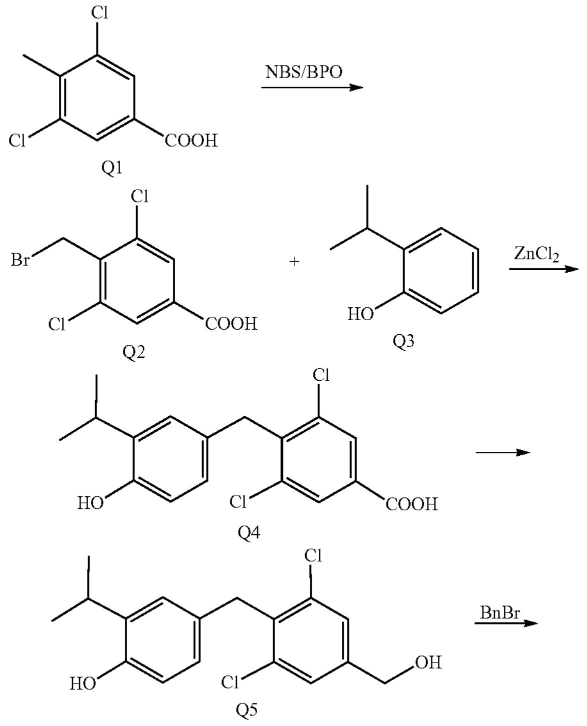

-continued

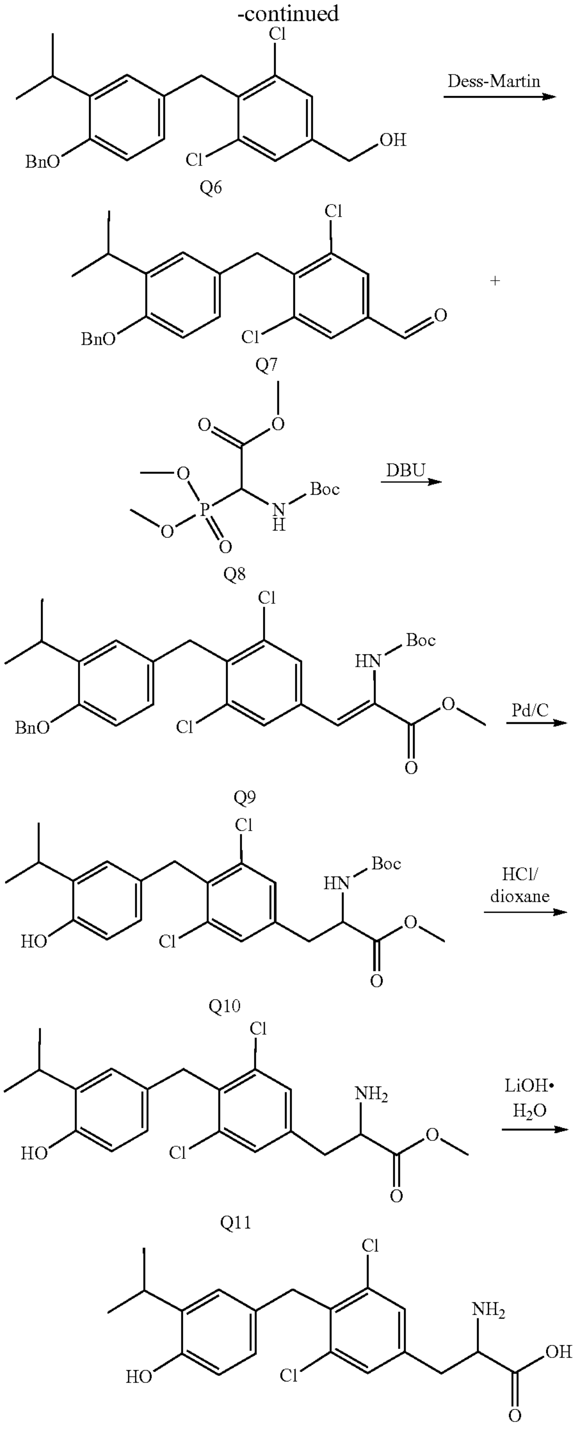

Compound 143

A solution of compound Q1 (5 g, 24.39 mmol) in $CCl_4$ (30 mL) was heated to 60° C., NBS (4.77 g, 26.82 mmol) and BPO (75.37 mg, 1.22 mmol) was added. The mixture was heated at 90° C. overnight. DCM (50 mL) was added and the mixture was washed with water (50 mL), dried over $Na_2SO_4$ and concentrated to afford compound Q2 (6.3 g, 90.9% yield) as a white solid.

To a solution of 2-isopropylphenol (8.63 g, 63.40 mmol) in DCE (60 mL) at rt was added compound Q2 (6.0 g, 21.13 mmol) and $ZnCl_2$ (7.19 g, 52.75 mmol). The reaction was heated to 85° C. and stirred overnight. Water (30 mL) was added and extracted with DCM (50 mL*3). The combined was washed brine (50 mL), dried over $Na_2SO_4$ and concentrated in vacuum. The crude product was purified by silica gel column (EtOAc/pet. ether=1/10 to 1/2) to afford compound Q4 (3.5 g, 48.8% yield) as alight yellow oil.

A solution of compound 4Q (2.5 g, 7.37 mmol) in THF (20 mL) was cooled down to 0° C. and borane-tetrahydrofuran (1 M/THF, 22.11 mL) was added. The mixture was stirred at rt overnight. Water (20 mL) was added and extracted with EtOAc (10 mL*3). The organic phase was washed by brine (30 mL), dried over $Na_2SO_4$ and concentrated in vacuum to afford crude product compound Q5 (2.3 g, 95.9% yield) as a light yellow oil.

To a solution of compound Q5 (1.1 g, 3.38 mmol) in DMF (5 mL) was added $K_2CO_3$ (379.53 mg, 3.38 mmol) and BnBr (578.46 mg, 3.38 mmol). The mixture was stirred at rt overnight and heated to 60° C. 5 h. Water (30 mL) was added. The mixture was extracted with EtOAc (20 mL*3). The combined organic layer was washed with brine (30 mL), dried over $Na_2SO_4$ and concentrated in vacuum. The crude product was purified by prep-TLC (pet. ether/EtOAc=3/1) to afford compound Q6 (1.2 g, 85.4% yield) as a white solid.

To a mixture of compound Q6 (1.2 g, 2.89 mmol) in DCM (20 mL) was added Dess-Martin periodinane (1.35 g, 3.18 mmol). The mixture was stirred at rt for 2 h. The mixture was filtered and extracted with EtOAc (20 mL*3). The combined organic phase was washed by brine (20 mL), $NaHCO_3$ (2 M, 10 mL*2), dried over $Na_2SO_4$, concentrated in vacuum and purified by prep-TLC (pet. ether/EtOAc=1/5) to afford compound Q7 (1.15 g, 96.3% yield) as a yellow solid.

A mixture of compound Q7 (1.2 g, 2.90 mmol) and compound Q8 (1.04 g, 3.48 mmol) in DCM (15 mL) was cooled down to 0° C., DBU (662.98 mg, 4.35 mmol) was added in portion. The mixture was stirred at rt for 2 h. Water (50 mL) was added and extracted with EtOAc (20 mL*3). The combined organic phase was washed by brine (50 mL), dried over $Na_2SO_4$, concentrated in vacuum and purified by silica gel column (EtOAc/pet. ether=1/100 to 1/8) to afford compound Q9 (1.0 g, 58.9% yield) as a white solid.

To a solution of compound Q9 (1.0 g, 1.71 mmol) in THF (20 mL) was added 10% Pd/C (400 mg). The mixture was refilled with $H_2$ three times and stirred under 1 atm $H_2$ at 60° C. overnight. The reaction was cooled down to rt and filtered. Water (20 mL) was added and extracted with EtOAc (10 mL*3). The combined organic phase was washed by brine, dried over $Na_2SO_4$, concentrated in vacuum and purified by Prep-TLC (EtOAc/pet. ether=1/3) to afford product compound Q10 (450 mg, 52.9% yield) as a white solid.

A mixture of compound Q10 (160 mg, 322.3 umol) in DCM (2 mL) was added Chlorine (in dioxane) (4 M, 2 mL). The mixture was stirred at rt for 5 h and concentrated in vacuum. Water (20 mL) was added and extracted with EtOAc (15 mL*3). The combined organic phase was washed by brine (20 mL), dried over $Na_2SO_4$ and concentrated in vacuum to afford crude product compound Q11 (120 mg, 93.9% yield) as a colorless oil.

To a mixture of compound Q11 (100 mg, 252.33 umol) in THE (2 mL) and water (1 mL) was added $LiOH \cdot H_2O$ (31.82 mg, 756.99 umol). The mixture was stirred at rt for 1 h. Water (30 mL) was added, adjust pH=4-5 with 1 MHCl and extracted with EtOAc (20 mL*3). The combined organic phase was washed by brine (30 mL), dried over $Na_2SO_4$, concentrated in vacuum and purified by Prep-HPLC to afford Compound 143 (70 mg, 71.9% yield) as a white solid.

LCMS: T=0.641 min, [M−1]=380

Example 144

Synthesis of 5-(3,5-dichloro-4-(4-hydroxy-3-isopropylbenzyl)benzyl)imidazolidine-2,4-dione (Compound 144)

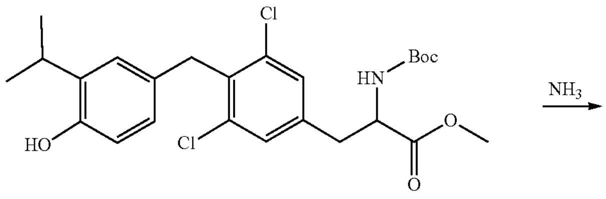

Q9

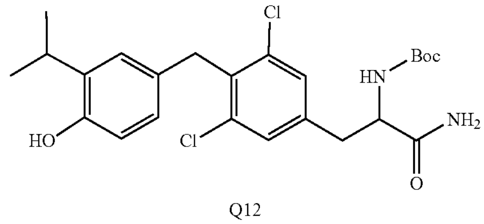

Q12

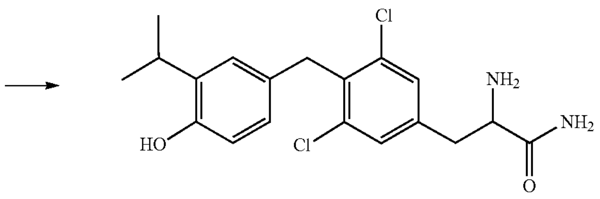

Q13

-continued

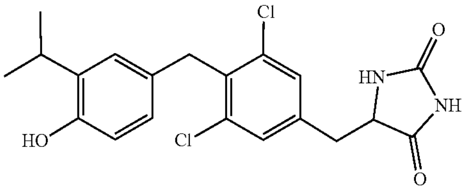

Compound 144

To a reaction mixture of compound Q9 (150 mg, 302.16 umol) in THF (2 mL) was added $NH_3 \cdot H_2O$ (1.35 g, 38.52 mmol) in a sealed tube. The mixture was stirred at 70° C. overnight. Water (20 mL) was added and extracted with EtOAc (15 mL*3). The combined organic phase was washed by brine (20 mL), dried over $Na_2SO_4$ and concentrated in vacuum to afford crude product compound Q12 (100 mg, 68.7% yield) as a light yellow solid.

A mixture of compound Q12 (100 mg, 207.72 umol) in DCM (2 mL) was added HCl/1,4-dioxane (4 M, 3.21 mL). The mixture was stirred at rt for 2 h and concentrated in vacuum. Water (20 mL) was added, adjust pH=4-5 with 1 M HCl and extracted with EtOAc (15 mL*3). The combined organic phase was washed by brine (20 mL), dried over $Na_2SO_4$ and concentrated in vacuum to afford crude product compound Q13 (70 mg, 88.3% yield) as a yellow solid.

To a mixture of compound Q13 (50 mg, 131.13 umol) and (4-nitrophenyl) carbonochloridate (31.72 mg, 157.36 umol) in MeCN (2 mL) was added sodium-hydrogen carbonate (42.96 mg, 511.41 umol). The mixture was stirred at rt overnight. Water (1 mL) was added and the reaction was quickly turned yellow. The mixture was stirred at rt for 6 h and concentrated in vacuum to afford crude product. The crude product was purified by Prep-HPLC to afford Compound 144 (10 mg, 18.2% yield) as a white solid.

LCMS: T=1.513 min, [M−1]=405

Example 145

Synthesis of (E)-3-(3,5-dichloro-4-(2-fluoro-4-hydroxy-3-isopropylbenzyl)phenyl)-2-methylacrylic acid (Compound 145)

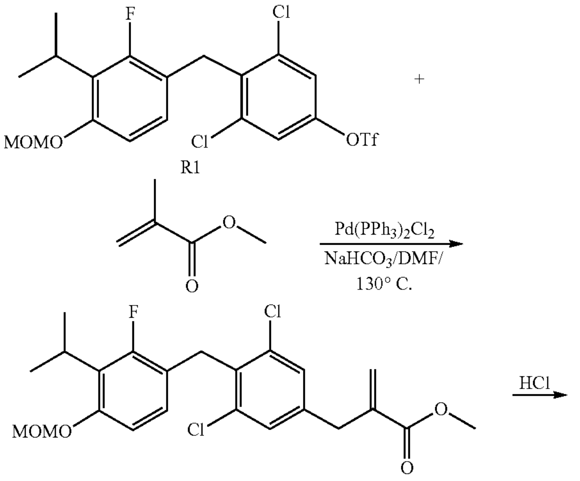

R1

-continued

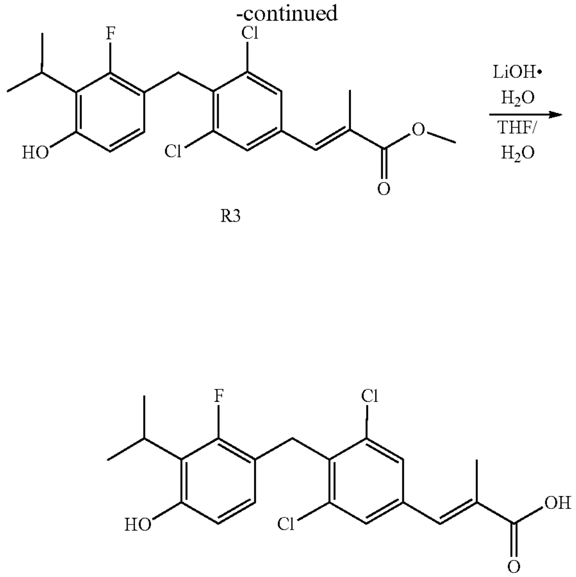

R3

Compound 145

To a mixture of compound R1 (1 g, 1.98 mmol), $Pd(PPh_3)_2Cl_2$ (138.90 mg, 197.90 mol) and sodium bicarbonate (498.75 mg, 5.94 mmol) in DMF (10 mL) was added methyl 2-methylprop-2-enoate (3.96 g, 39.58 mmol). The mixture was heated to 100° C. and stirred for 3 h. The mixture was cooled down to rt and filtered. The filtrate was concentrated in vacuum and purified by Prep-TLC (pet. ether/EtOAc=10/1) to afford crude product compound R2 (450 mg, 49.9% yield).

To a mixture of compound R2 (450 mg, 1.09 mmol) in water (1 mL) and THF (5 mL) was added $LiOH \cdot H_2O$ (137.74 mg, 3.28 mmol). The mixture was stirred at rt for 1 h. Water (30 mL) was added, adjust pH=4-5 with 1 MHCl and extracted with EtOAc (20 mL*3). The combined organic phase was washed by brine (30 mL), dried over $Na_2SO_4$, concentrated in vacuum and purified by Prep-HPLC ($MeCN/H_2O$) to afford compound R3 (100 mg, 23.0% yield) as a white solid.

To a mixture of compound R3 (25 mg, 60.78 μmol) in THE (5 mL) and water (1 mL) was added $LiOH \cdot H_2O$ (12.77 mg, 303.92 μmol). The mixture was stirred at rt for 1 h. Water (30 mL) was added, adjust pH=4-5 with 1 M HCl and extracted with EtOAc (20 mL*3). The combined organic phase was washed by brine (30 mL), dried over $Na_2SO_4$, concentrated in vacuum to afford crude product and 100 mg crude product was purified by Prep-HPLC ($MeCN/H_2O$) to afford Compound 145 (15 mg, 60.3% yield) as a white solid.

LCMS: T=2.184 min, [M−1]=395.0

Example 146

Synthesis of (E)-3-(3,5-dichloro-4-(2-fluoro-4-hydroxy-3-isopropylbenzyl)phenyl)-N,2-dimethylacrylamide (Compound 146)

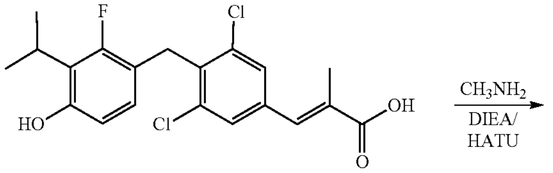

Compound 145

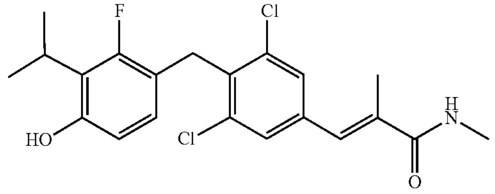

Compound 146

A solution of Compound 145 (50 mg, 125.86 μmol) in DCM (1 mL) was added HATU (71.78 mg, 188.79 μmol), N-ethyl-N-isopropyl-propan-2-amine (32.53 mg, 251.72 mol) and methanamine (1.80 g, 57.89 mmol, 2 mL). The mixture was stirred at rt for 1 h. Water (30 mL) was added and diluted with DCM (20 mL*3). The combined organic phase was washed by brine (30 mL), dried over $Na_2SO_4$, concentrated in vacuum and purified by Prep-HPLC to afford the product Compound 146 (10 mg, 18.9% yield) as a white solid.

LCMS: T=1.984 min, [M−1]=408.1

Example 147

Synthesis of 2-((3,5-dichloro-4-(2-fluoro-4-hydroxy-3-isopropylbenzyl)benzyl)thio)-N-methylacetamide (Compound 147)

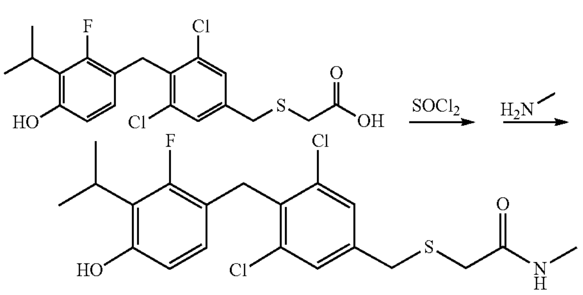

Compound 147

To a solution of 2-((3,5-dichloro-4-(2-fluoro-4-hydroxy-3-isopropylbenzyl)benzyl)thio)acetic acid (25 mg, 59.91 μmol) in DCM (2 mL) was added DMF (cat.) and oxalyl dichloride (11.41 mg, 89.86 μmol). The mixture was stirred at rt 30 minutes. The mixture was concentrated to dryness and methanamine (1M/THF, 1 mL) was added. The mixture was stirred at rt 30 minutes. The mixture was concentrated to dryness and purified by Prep-HPLC to afford Compound 147 (10 mg, 37.5% yield) as a white solid.

LCMS: T=1.828 min, [M−1]=428

Example 148

Synthesis of N-(3,5-dichloro-4-(4-hydroxy-3-isopropylbenzyl)phenyl)-N-methylglycine (Compound 148)

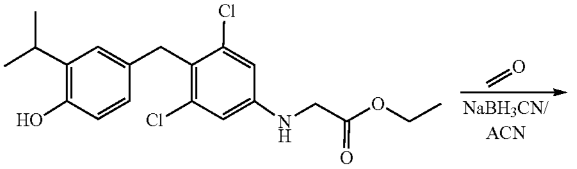

S1

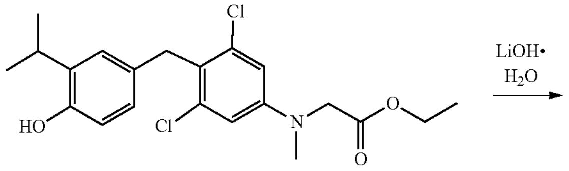

S2

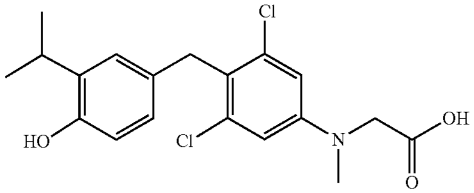

Compund 148

To a solution of compound S1 (550 mg, 1.39 mmol) in $CH_3CN$ (6 mL) was added ACOH (83.34 mg, 1.39 mmol) and formaldehyde (2.25 g, 27.76 mmol). The mixture was stirred at 65° C. overnight and cooled down to rt. The reaction mixture was added Pd/C (16.86 mg, 138.78 μmol) and stirred at rt overnight under 1 atm $H_2$ (g) atmosphere. Water (20 mL) was added and extracted with DCM (10 mL*2). The combined was washed brine (20 mL), dried over $Na_2SO_4$ and concentrated in vacuum. The crude product was purified by silica gel column (EtOAc/pet. ether=1/50 to 1/10) to afford compound S2 (150 mg, 26.3% yield) as a yellow oil.

To a solution of compound S2 (115 mg, 280.26 μmol) in THF (2 mL), $LiOH{\cdot}H_2O$ (23.52 mg, 560.52 μmol) in water (0.5 mL) was added. The mixture was stirred at rt 2 h, diluted with water (5 mL), acidified with 1N HCl to pH=6-7, extracted with EtOAc (3 ml*3). The combined organic phase was washed by brine (5 mL), dried over $Na_2SO_4$, concentrated under reduce pressure. The crude product was purified by Prep-TLC (MeOH/DCM=1/10) and Prep-HPLC to afford Compound 148 (35 mg, 32.5% yield) as a white solid.

LCMS: T=1.732 min, [M−1]=380

Example 149

Synthesis of 2-((3,5-dichloro-4-(4-hydroxy-3-isopropylbenzyl)phenyl)(methyl)amino)-N-methylacetamide (Compound 149)

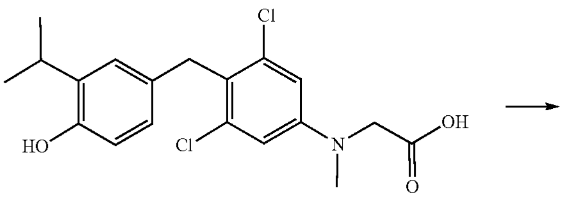

Compound 148

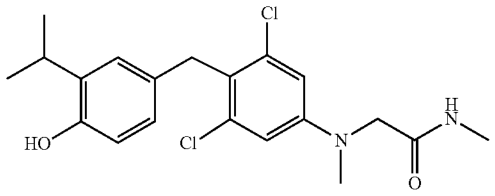

Compound 149

To a solution of Compound 148 (45 mg, 117.71 μmol) in DMF (1 mL) at rt were added N-ethyl-N-isopropyl-propan-2-amine (30.43 mg, 235.43 μmol, 41.01 μL),N,N,N',N'-tetramethyl-1-(3-oxido-2,3-dihydrotriazolo[4,5-b]pyridin-3-ium-1-yl)methanediamine; hexafluorophosphate (67.49 mg, 176.57 μmol) and methanamine (2 M/THF, 1 mL). The reaction was stirred at rt for 1 h. The reaction mixture was diluted with DCM (10 mL), washed with brine (10 mL*2), dried over $Na_2SO_4$, concentrated under reduce pressure. The crude product was purified through Prep-HPLC to afford Compound 149 (23 mg, 48.5% yield) as a white solid.

LCMS: T=1.578 min, [M−1]=395

Example 150

Synthesis of 2-((5-chloro-2,3-difluoro-4-(4-hydroxy-3-isopropylbenzyl)phenyl)amino)-N-methylacetamide (Compound 150)

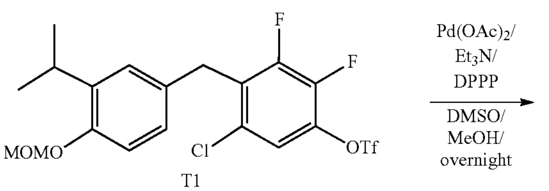

T1

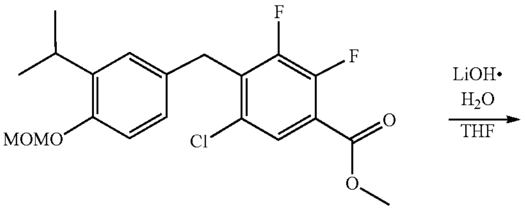

T2

-continued

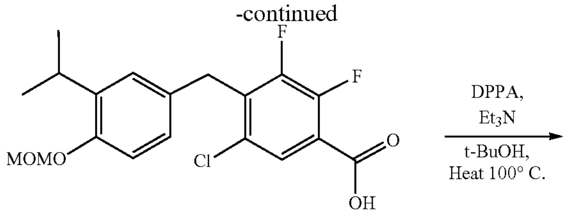

T3

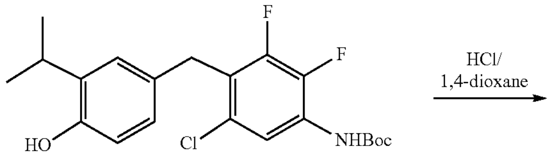

T4

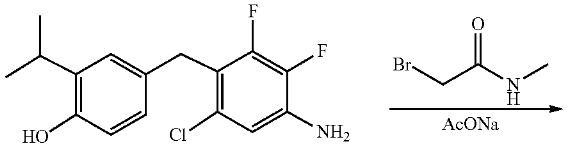

T5

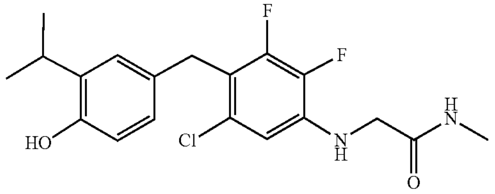

Compound 150

To a solution of compound T1 (500 mg, 1.02 mmol) in MeOH (3 mL) and DMSO (6 mL) was added $Pd(OAc)_2$ (22.96 mg, 102.28 μmol), TEA (310.49 mg, 3.07 mmol) and DPPP (42.18 mg, 102.28 μmol). The mixture was stirred at 80° C. under CO balloon overnight. The mixture was filtered and water (20 mL) was added to the mixture. The mixture was extracted with EtOAc (30 mL*2). The organic layer was dried over $Na_2SO_4$ and concentrated in vacuum. The residue was purified by silica gel column (pet. ether/EtOAc=5:1) to afford compound T2 (300 mg, 73.5% yield) as a yellow oil.

To a solution of compound T2 (300 mg, 752.21 μmol) in $H_2O$ (1 mL) and THF (4 mL) was added $LiOH{\cdot}H_2O$ (126.26 mg, 83.62 μL). The mixture was stirred at rt 30 min. The mixture was acidified with 1 N HCl to pH=6. The aqueous layer was extracted with EtOAc (40 mL*3). The combined organic layer was washed with brine (30 mL), dried over $Na_2SO_4$ and evaporated to afford compound T3 (150 mg, 51.8% yield) as a yellow oil.

To a solution of compound T3 (100 mg, 259.87 μmol) in Toluene (5 mL) was added TEA (52.59 mg, 519.75 μmol) and DPPA (63.20 mg, 229.66 μmol). The mixture was stirred at rt for 30 min. The mixture was concentrated and purified by silica gel column (pet. ether/EtOAc=5:1). The obtained intermediate was dissolved in 2-methylpropan-2-ol (5 mL) and heated to reflux for 2 h. The mixture was cooled to rt. Water (50 mL) was added. The mixture was extracted with EtOAc (2*30 mL). The combined organic layer was washed with brine (30 mL), dried over $Na_2SO_4$ and concentrated in vacuum. The crude product was purified by Prep-TLC (pet. ether/EtOAc=3:1) to afford compound T4 (80 mg, 67.5% yield) as a yellow solid.

To a solution of compound T4 (70 mg, 153.54 μmol) in DCM (2 mL) was added HCl/1,4-dioxane (153.54 μmol, 2 mL). The mixture was stirred at rt for 20 min and aq.

$NaHCO_3$ was added to adjusted pH to 7. The mixture was extracted with DCM (20 mL*2). The organic layer was washed with brine (10 mL), dried over $Na_2SO_4$ and concentrated in vacuum. The crude product was purified by prep-TLC (pet. ether/EtOAc=3:1) to afford compound T5 (25 mg, 52.2% yield) as a colorless oil.

To a solution of compound T5 (25 mg, 80.19 μmol) in ethanol (5 mL) was added 2-bromo-N-methyl-acetamide (12.19 mg, 80.19 μmol) and NaOAc (6.58 mg, 4.31 μL). The mixture was stirred at 100° C. overnight. The mixture was concentrated and purified by Prep-HPLC to afford Compound 150 (10 mg, 31.1% yield) as a white solid.

LCMS: T=1.814 min, [M+42]=424.05

Example 151

Synthesis of 2-(3,5-dichloro-2-fluoro-4-(2-fluoro-4-hydroxy-3-(trimethylsilyl)benzyl)phenyl)acetic acid (Compound 151)

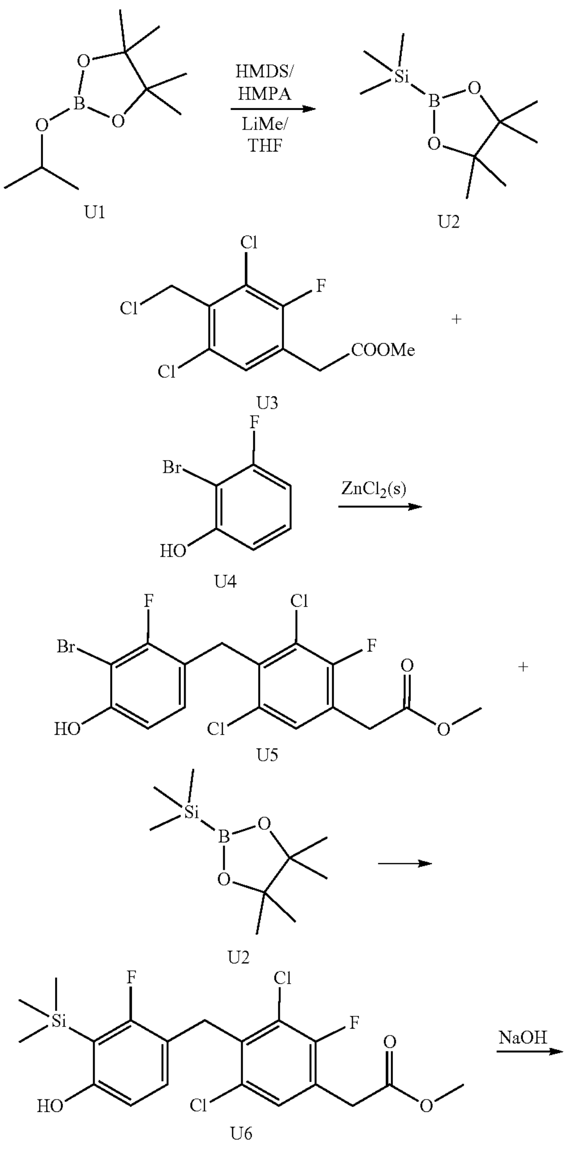

U1
U2
U3
U4
U5
U2
U6

-continued

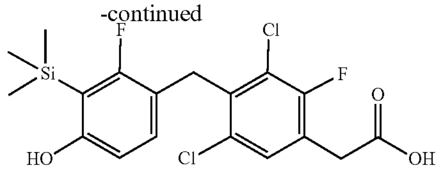

Compund 151

To a solution of HMDS (447.01 mg, 3.05 mmol) in HMPA (2 mL) was added LiMe (53.70 mg, 2.44 mmol) dropwise at 0° C. 15 min, the mixture was added compound U1 (500 mg, 2.69 mmol) in THE (4 mL). The mixture was stirred at −78° C. for 2 h. The reaction mixture was diluted with water (20 mL) and extracted with EtOAc (20 mL*2). The combined organic layer was washed with brine (20 mL), dried over $Na_2SO_4$ and concentrated in vacuum. The crude product was purified by silica gel column to afford product compound U2 (25.0 mg, 43.7% yield) as a white solid.

To a solution of compound U3 (100.0 mg, 0.35 mmol) in $ZnCl_2$ (95 mg, 0.7 mmol) was added compound U4 (134 mg, 0.70 mmol), the mixture was stirred at 85° C. overnight. The reaction mixture was diluted with water (20 mL) and extracted with EtOAc (20 mL*2). The combined organic layer was washed with brine (20 mL), dried over $Na_2SO_4$ and concentrated in vacuum. The crude product was purified by Prep-TLC (pet. ether/EtOAc=10/1) to afford product compound U5 (30.0 mg, 19.4% yield) as a colorless oil.

To a solution of compound U5 (180.0 mg, 0.41 mmol) in THF (5 mL) was added compound U2 (148.0 mg, 0.74 mmol), $K_3PO_4$ (260.5 mg, 1.23 mmol), $Pd(OAc)_2$ (18.4 mg, 0.08 mmol) and PCy3 (34.4 mg, 0.13 mmol). The mixture was stirred at 70° C. overnight. The reaction mixture was diluted with water (20 mL) and extracted with EtOAc (20 mL*2). The combined organic layer was washed with brine (20 mL), dried over $Na_2SO_4$ and concentrated in vacuum. The crude product was purified by Prep-TLC (pet. ether/EtOAc=10/1) to afford product compound U6 (20.0 mg, 11.2% yield) as a colorless oil.

To a solution of compound U6 (20.0 mg, 0.05 mmol) in MeOH (2 mL) was added NaOH (1.85 mg, 0.05 mmol) in $H_2O$ (0.4 mL), the mixture was stirred at room temperature for 1 h. The reaction mixture was acidified to pH=5 with 0.5 N HCl, diluted with water (20 mL) and extracted with DCM (20 mL*2). The combined organic layer was washed with brine (20 mL), dried over $Na_2SO_4$ and concentrated in vacuum. The Na-salt was washed with DCM (1 mL) to afford product Compound 151 (4 mg, 15.4% yield) as a yellow solid.

LCMS: T=2.151 min, [M−1]=372.9

Synthesis of (3,5-dichloro-2-fluoro-4-(4-hydroxy-3-isopropylbenzyl)benzyl)glycine (Compound 152)

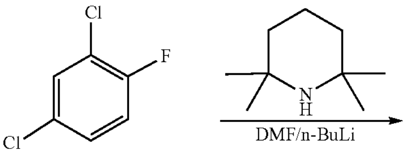

V1

-continued

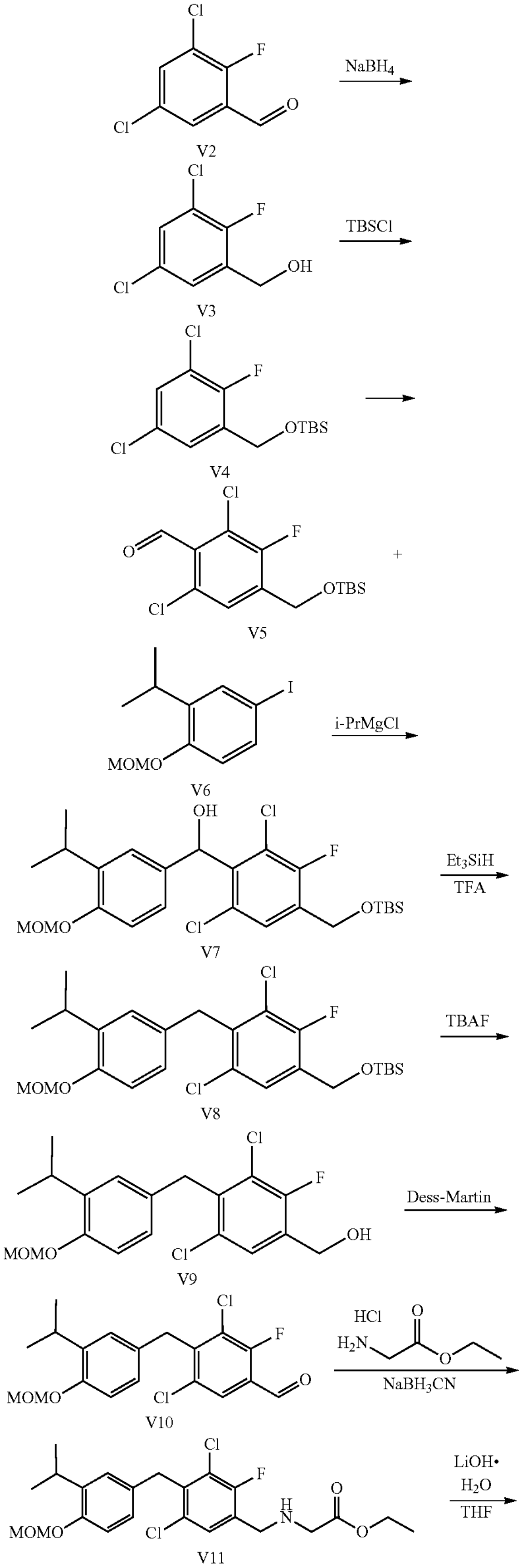

-continued

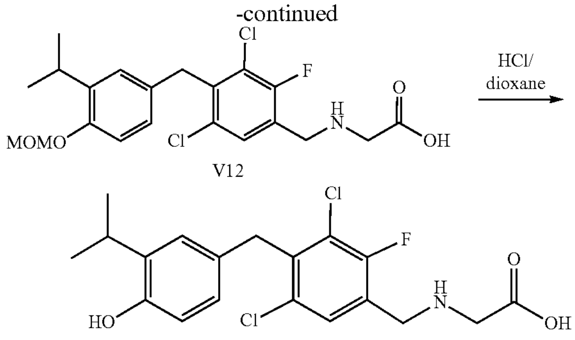

Compound 152

A solution of 2,2,6,6-tetramethylpiperidine (33.39 g, 236.38 mmol) in THF (200 mL) was cooled down to −30° C., n-BuLi (2.5 M/L, 80.00 mL) was added, stirred at −30° C. 30 min and cooled down to −70° C. Compound V1 (30.0 g, 181.83 mmol) in THF (60 mL) was added dropwise, stirred at −70° C. for 1 h. N,N-dimethylformamide (53.16 g, 727.31 mmol) was added, stirred at −70° C. for 30 min. The reaction was warmed to 0° C., quenched with $NH_4Cl$ (aq) (200 mL), extracted with EtOAc (100 mL*2), the combined organic phase was washed by brine (100 mL), dried over $Na_2SO_4$, concentrated in vacuo, the residue was purified by silica gel column (pet. ether/EtOAc=50/1 to 10/1) to afford the product compound V2 (30.0 g, 85.5% yield) as a yellow oil.

To solution of compound V2 (30 g, 155.44 mmol) in THE (200 mL) was cooled down to 0° C., $NaBH_4$ (8.82 g, 233.16 mmol) was added, stirred at rt 1 h. The reaction was quenched by water (200 mL), extracted with EtOAc (100 mL*2), the combined organic phase was washed by brine (100 mL), dried over $Na_2SO_4$, concentrated in vacuo, the residue was purified by silica gel column (pet. ether/EtOAc=2/1) to afford the product compound V3 (20.0 g, 65.9% yield).

To a solution of compound V3 (8.0 g, 41.02 mmol) in DCM (80 mL) was added TBSCl (12.4 g, 82.04 mmol) at 0° C. The reaction was stirred at rt 2 h. The reaction was added water (50 mL), extracted with DCM (100 mL*2), the combined organic phase was washed by brine (100 mL), dried over $Na_2SO_4$, concentrated in vacuo to afford crude product compound V4 (13.0 g).

To a solution of compound V4 (10.5 g, 33.95 mmol) in THE (100 mL) at −78° C. was added dropwise n-butyllithium (7.19 g, 50.92 mL). The mixture was stirred for 60 min at −10° C., DMF (9.93 g, 135.80 mmol) was added at −78° C. The mixture was stirred at −78° C.-20° C. for 1 h. The reaction was quenched by water (100 mL), extracted with EtOAc (100 mL*2), the combined organic phase was washed by brine (100 mL), dried over $Na_2SO_4$, concentrated in vacuo, the residue was purified by silica gel column (pet. ether/EtOAc=2/1) to afford product compound V5 (9.0 g, 78.6% yield).

To a solution of compound V6 (12.71 g, 41.51 mmol) in THF (100 mL) was added iPrMgCl (4.27 g, 41.51 mmol). The reaction was stirred at 80° C. for 1 h. The reaction was cooled to rt. Compound V5 (7.0 g, 20.75 mmol) in THF (70 mL) was added to the reaction. The reaction was stirred at rt for 2 h. The reaction was quenched by $NH_4Cl$ (aq) (100 mL), extracted with EtOAc (100 mL*2), the combined organic phase was washed by brine (100 mL), dried over $Na_2SO_4$, concentrated in vacuo, the residue was purified by silica gel column (Pet. ether/EtOAc=50/1 to 10/1) to afford product compound V7 (6.0 g, 56.1% yield).

A solution of compound V7 (6.0 g, 11.59 mmol) in DCM (60 mL) were added TFA (1.32 g, 11.59 mmol) and triethylsilane (6.72 g, 57.95 mmol). The reaction was stirred at rt for 2 h. The reaction was The reaction was quenched by water (100 mL), extracted with DCM (100 mL*2), the combined organic phase was washed by brine (100 mL), dried over $Na_2SO_4$, concentrated in vacuo, the residue was purified by silica gel column (Pet. ether/EtOAc=50/1 to 10/1) to afford product compound V8 (4.5 g, 68.8% yield).

To a solution of compound V8 (5.0 g, 9.97 mmol) in THF (50 mL) was added TBAF (3.91 g, 14.95 mmol). The reaction was stirred at rt for 2 h. The reaction was quenched by water (50 mL), extracted with EtOAc (50 mL*2), the combined organic phase was washed by brine (50 mL), dried over $Na_2SO_4$, concentrated in vacuo, the residue was purified by silica gel column (Pet. ether/EtOAc=50/1 to 10/1) to afford product compound V9 (3 g, 77.7% yield).

To a solution of compound V9 (3.0 g, 7.75 mmol) in DCM (30 mL) was added Dess-Martin (3.61 g, 8.52 mmol). The reaction was stirred at rt for 2 h. The reaction was quenched by water (50 mL), extracted with DCM (50 mL*2), the combined organic phase was washed by brine (50 mL), dried over $Na_2SO_4$, concentrated in vacuo to afford crude product compound V10 (3 g).

To a solution of compound V10 (1 g, 2.48 mmol) in ACN (10 mL) were added ethyl 2-aminoacetate·hydrochloride (692.28 mg, 4.96 mmol) and cat. AcOH. The reaction was stirred at 80° C. for 2 h. The reaction was cooled to rt and added sodium cyanoboranuide (326.66 mg, 4.96 mmol). The reaction was stirred at rt for overnight. The reaction was quenched by water (20 mL), extracted with EtOAc (50 mL*2), the combined organic phase was washed by brine (50 mL), dried over $Na_2SO_4$, concentrated in vacuo, the residue was purified by silica gel column (Pet. ether/EtOAc=50/1 to 10/1) to afford product compound V11 (400 mg, 32.7% yield).

To a solution of compound V11 (250 mg, 529.24 umol) in THE (3 mL) was added a solution of LiOH·H2O (66.68 mg, 1.59 mmol) in water (1 mL). The mixture was stirred at rt for 2 h. The mixture was acidified with 1 N HCl to pH=5. The aqueous layer was extracted with EtOAc (2*40 mL). The organic layer was washed with brine (30 mL), dried over $Na_2SO_4$ and evaporated to dryness to afford product compound V12 (200 mg, 85.05% yield) as a yellow oil.

To a solution of compound V12 (200 mg, 450.12 umol) was added to HCl/1,4-dioxane (450.12 umol, 4 mL). The mixture was stirred at rt for 2 h. The mixture was concentrated in vacuum and purified by Prep-HPLC to afford Compound 152 (50 mg, 27.45% yield) as a white solid.

LCMS: T=1.170 min, [M+1]=400

Example 153

Synthesis of (3,5-dichloro-2-fluoro-4-(2-fluoro-4-hydroxy-3-isopropylbenzyl)benzyl)glycine (Compound 153)

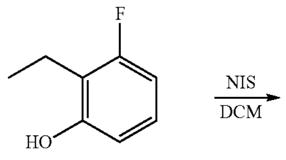

W1

-continued

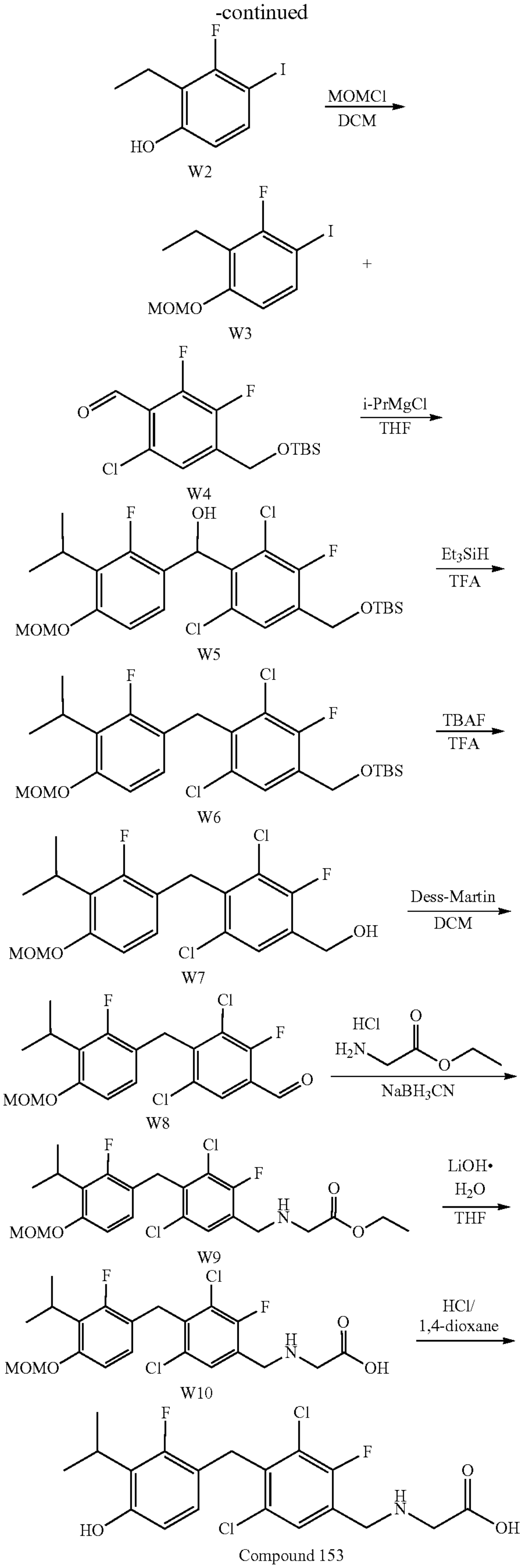

W2, W3, W4, W5, W6, W7, W8, W9, W10, Compound 153

To solution of compound W1 (6.0 g, 38.92 mmol) in DCM (20 mL) was cooled down to 0° C. TsOH (1.48 g, 7.78 mmol) and NIS (8.76 g, 38.92 mmol) was added in portion. The mixture was stirred at 0° C. for 30 min. Water (50 mL) was added and extracted with EtOAc (30 mL*3). The combined organic phase was washed by brine (50 mL), dried over $Na_2SO_4$, concentrated in vacuum and purified by silica gel column (pet. ether/DCM=100/1 to 20/1) twice and Prep-TLC (pet. ether/DCM=2/1) to afford compound W2 (5.0 g, 45.8% yield) as a white solid.

To a solution of compound W2 (5.0 g, 17.85 mmol) in DCM (70 mL) was added MOMCl (2.80 g, 34.81 mmol) and N-ethyl-N-isopropyl-propan-2-amine (6.0 g, 46.42 mmol), the mixture was stirred at RT for 1 h under a $N_2$ atmosphere. The mixture was diluted with water (80 mL) and extracted with EtOAc (30 mL*2). The combined organic phase was washed by brine (40 mL), dried over $Na_2SO_4$, concentrated under reduced pressure to afford compound W3 (5.5 g, 16.97 mmol, 95.0% yield) as a yellow liquid.

To a solution of compound W3 (2.88 g, 8.89 mmol) in THF (10 mL) was cooled to −70° C. and was added dropwise ipr-MgCl (914.79 mg, 8.89 mmol). The mixture was stirred at −70° C. for 0.5 h. Compound W4 (3.0 g, 8.89 mmol) in THF (10 mL) was added dropwise. It was stirred at −70° C. for 2 h. The mixture was quenched with aqueous $NH_4Cl$ (10 mL). The mixture was extracted with EtOAc (50 mL*2). The combined EtOAc phase was washed with brine (80 mL), dried over $Na_2SO_4$, concentrated in vacuum. The crude product was purified by prep-TLC (pet. ether/EtOAc=5/1) to afford compound W5 (3.0 g, 5.60 mmol, 62.9% yield) as a white solid.

To a solution of compound W5 (3.0 g, 5.60 mmol) in DCM (30 mL) was added TFA (638.5 mg, 5.60 mmol) and triethylsilane (3.26 g, 28.0 mmol). The reaction was stirred at rt for 2 h. The reaction was The reaction was quenched by water (100 mL), extracted with DCM (100 mL*2), the combined organic phase was washed by brine (100 mL), dried over $Na_2SO_4$, concentrated in vacuo, the residue was purified by silica gel column (Pet. ether/EtOAc=50/1 to 10/1) to afford product compound W6 (2.5 g, 85.9% yield).

To a solution of compound W6 (2.5 g, 4.81 mmol) in THF (20 mL) was added TBAF (1.89 g, 7.215 mmol). The reaction was stirred at rt for 2 h. The reaction was quenched by water (50 mL), extracted with EtOAc (50 mL*2), the combined organic phase was washed by brine (50 mL), dried over $Na_2SO_4$, concentrated in vacuo, the residue was purified by silica gel column (Pet. ether/EtOAc=50/1 to 10/1) to afford product compound W7 (1.7 g, 87.2% yield).

To a solution of compound W7 (1.7 g, 4.19 mmol) in DCM (20 mL) was added Dess-Martin (1.96 g, 4.61 mmol). The reaction was stirred at rt for 2 h. The reaction was quenched by water (30 mL), extracted with DCM (20 mL*2), the combined organic phase was washed by brine (50 mL), dried over $Na_2SO_4$, concentrated in vacuo to afford crude product compound W8 (1.6 g, 94.7% yield).

To a solution of compound W8 (1.6 g, 3.97 mmol) in ACN (10 mL) were added ethyl 2-aminoacetate·hydrochloride (1.11 g, 7.94 mmol) and cat. AcOH. The reaction was stirred at 80° C. for 2 h. The reaction was cooled to rt and added sodium cyanoboranuide (522.92 mg, 7.94 mmol). The reaction was stirred at rt for overnight. The reaction was quenched by water (20 mL), extracted with EtOAc (50 mL*2), the combined organic phase was washed by brine (50 mL), dried over $Na_2SO_4$, concentrated in vacuo, the residue was purified by silica gel column (Pet. ether/EtOAc=50/1 to 10/1) to afford product compound W9 (800 mg, 41.0% yield).

To a solution of compound W9 (300 mg, 611.8 umol) in THF (3 mL) was added a solution of $LiOH \cdot H_2O$ (77.28 mg, 1.84 mmol) in water (1 mL). The mixture was stirred at rt for 2 h. The mixture was acidified with 1 N HCl to pH=5. The aqueous layer was extracted with EtOAc (2*40 mL). The organic layer was washed with brine (30 mL), dried over $Na_2SO_4$ and evaporated to dryness to afford product compound W10 (250 mg, 88.3% yield) as a yellow oil.

To a solution of compound W10 (250 mg, 540.7 umol) was added to HCl/1,4-dioxane (540.7 umol, 5 mL). The mixture was stirred at rt for 2 h. The mixture was concentrated in vacuum and purified by Prep-HPLC to afford Compound 153 (100 mg, 43.4% yield) as a white solid.

LCMS: T=1.269 min, [M+1]=418.0

Compounds 154-251 in Table 2 were prepared in similar manner as described in the preceding examples.

TABLE 2

| Cmpd | Structure | Name | [M + H]$^+$ |
|---|---|---|---|
| 154 | 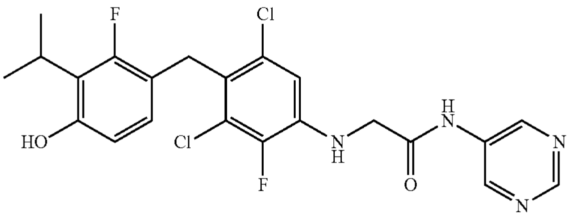 [SMILES: CC(C)c1c(O)ccc(Cc2c(Cl)cc(NCC(=O)Nc3cncnc3)c(F)c2Cl)c1F] | 2-((3,5-dichloro-2-fluoro-4-(2-fluoro-4-hydroxy-3-isopropylbenzyl)phenyl)amino)-N-(pyrimidin-5-yl)acetamide | 481.1 |
| 155 | 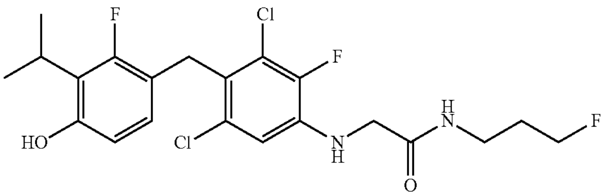 [SMILES: CC(C)c1c(O)ccc(Cc2c(Cl)cc(NCC(=O)NCCCF)c(F)c2Cl)c1F] | 2-((3,5-dichloro-2-fluoro-4-(2-fluoro-4-hydroxy-3-isopropylbenzyl)phenyl)amino)-N-(3-fluoropropyl)acetamide | 461.1 |

TABLE 2-continued

| Cmpd | Structure | Name | [M + H]+ |
|---|---|---|---|
| 156 | 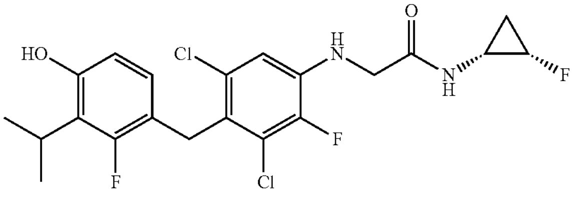 [SMILES: CC(C)c1c(O)ccc(Cc2c(Cl)cc(NCC(=O)N[C@@H]3C[C@@H]3F)c(F)c2Cl)c1F] | 2-((3,5-dichloro-2-fluoro-4-(2-fluoro-4-hydroxy-3-isopropylbenzyl)phenyl)amino)-N-((1R,2S)-2-fluorocyclopropyl)acetamide | 461.2 |
| 157 | 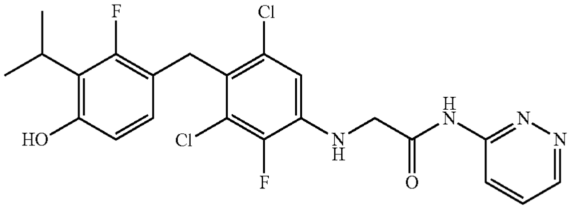 [SMILES: CC(C)c1c(O)ccc(Cc2c(Cl)cc(NCC(=O)Nc3cccnn3)c(F)c2Cl)c1F] | 2-((3,5-dichloro-2-fluoro-4-(2-fluoro-4-hydroxy-3-isopropylbenzyl)phenyl)amino)-N-(pyridazin-3-yl)acetamide | 481.1 |
| 158 | 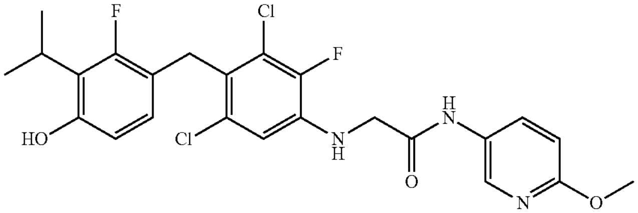 [SMILES: COc1ccc(NC(=O)CNc2cc(Cl)c(Cc3ccc(O)c(C(C)C)c3F)c(Cl)c2F)cn1] | 2-((3,5-dichloro-2-fluoro-4-(2-fluoro-4-hydroxy-3-isopropylbenzyl)phenyl)amino)-N-(6-methoxypyridin-3-yl)acetamide | 510.1 |
| 159 | 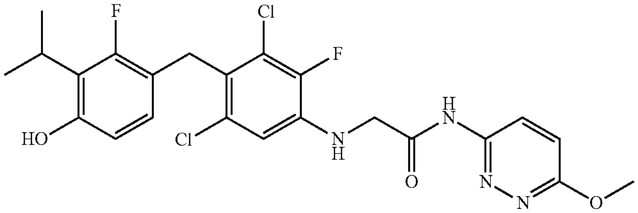 [SMILES: COc1ccc(NC(=O)CNc2cc(Cl)c(Cc3ccc(O)c(C(C)C)c3F)c(Cl)c2F)nn1] | 2-((3,5-dichloro-2-fluoro-4-(2-fluoro-4-hydroxy-3-isopropylbenzyl)phenyl)amino)-N-(6-methoxypyridazin-3-yl)acetamide | 511.1 |
| 160 | 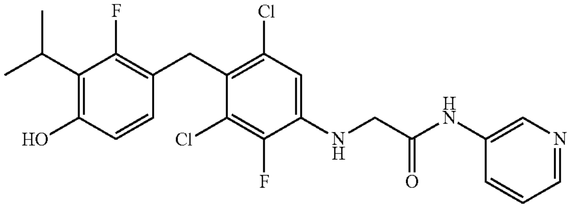 [SMILES: CC(C)c1c(O)ccc(Cc2c(Cl)cc(NCC(=O)Nc3cccnc3)c(F)c2Cl)c1F] | 2-((3,5-dichloro-2-fluoro-4-(2-fluoro-4-hydroxy-3-isopropylbenzyl)phenyl)amino)-N-(pyridin-3-yl)acetamide | 480.1 |
| 161 | 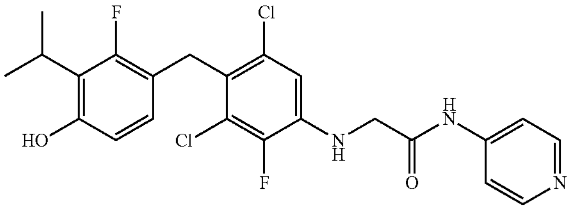 [SMILES: CC(C)c1c(O)ccc(Cc2c(Cl)cc(NCC(=O)Nc3ccncc3)c(F)c2Cl)c1F] | 2-((3,5-dichloro-2-fluoro-4-(2-fluoro-4-hydroxy-3-isopropylbenzyl)phenyl)amino)-N-(pyridin-4-yl)acetamide | 480.1 |
| 162 | 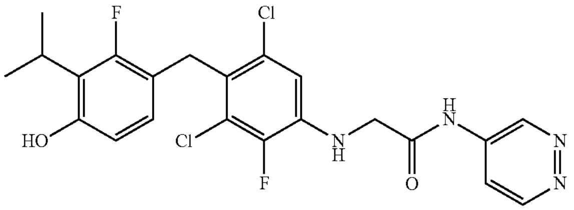 [SMILES: CC(C)c1c(O)ccc(Cc2c(Cl)cc(NCC(=O)Nc3ccnnc3)c(F)c2Cl)c1F] | 2-((3,5-dichloro-2-fluoro-4-(2-fluoro-4-hydroxy-3-isopropylbenzyl)phenyl)amino)-N-(pyridazin-4-yl)acetamide | 481.1 |

TABLE 2-continued

| Cmpd | Structure | Name | [M + H]$^+$ |
| --- | --- | --- | --- |
| 163 | 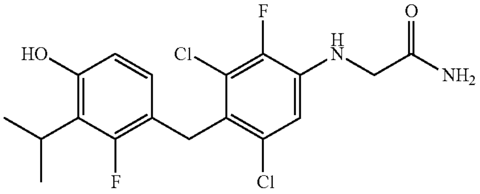 [SMILES: CC(C)c1c(O)ccc(Cc2c(Cl)cc(NCC(N)=O)c(F)c2Cl)c1F] | 2-((3,5-dichloro-2-fluoro-4-(2-fluoro-4-hydroxy-3-isopropylbenzyl)phenyl)amino) acetamide | 400.9 (M − H) |
| 164 | 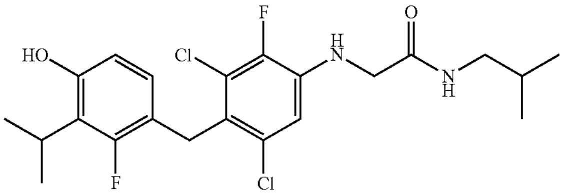 [SMILES: CC(C)CNC(=O)CNc1cc(Cl)c(Cc2ccc(O)c(C(C)C)c2F)c(Cl)c1F] | 2-((3,5-dichloro-2-fluoro-4-(2-fluoro-4-hydroxy-3-isopropylbenzyl)phenyl)amino)-N-isobutylacetamide | 457.0 (M − H) |
| 165 | 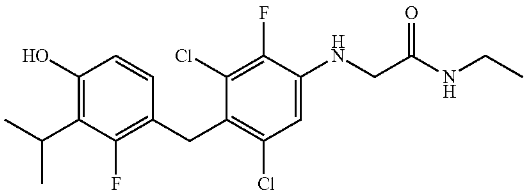 [SMILES: CCNC(=O)CNc1cc(Cl)c(Cc2ccc(O)c(C(C)C)c2F)c(Cl)c1F] | 2-((3,5-dichloro-2-fluoro-4-(2-fluoro-4-hydroxy-3-isopropylbenzyl)phenyl)amino)-N-ethylacetamide | 431.1 |
| 166 | 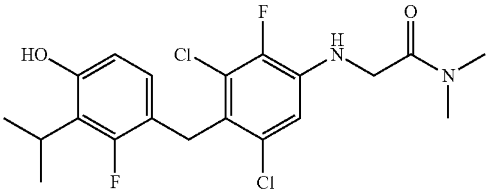 [SMILES: CC(C)c1c(O)ccc(Cc2c(Cl)cc(NCC(=O)N(C)C)c(F)c2Cl)c1F] | 2-((3,5-dichloro-2-fluoro-4-(2-fluoro-4-hydroxy-3-isopropylbenzyl)phenyl)amino)-N,N-dimethylacetamide | 431.1 |
| 167 | 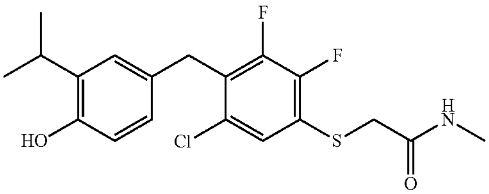 [SMILES: CNC(=O)CSc1cc(Cl)c(Cc2ccc(O)c(C(C)C)c2)c(F)c1F] | 2-((5-chloro-2,3-difluoro-4-(4-hydroxy-3-isopropylbenzyl)phenyl)thio)-N-methylacetamide | 399.8 |
| 168 | 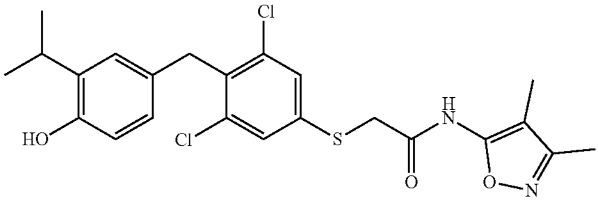 [SMILES: Cc1noc(NC(=O)CSc2cc(Cl)c(Cc3ccc(O)c(C(C)C)c3)c(Cl)c2)c1C] | 2-((3,5-dichloro-4-(4-hydroxy-3-isopropylbenzyl)phenyl)thio)-N-(3,4-dimethylisoxazol-5-yl)acetamide | 479.1 |
| 169 | 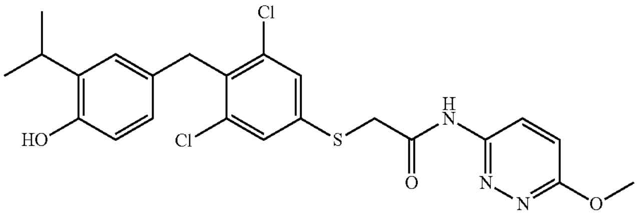 [SMILES: COc1ccc(NC(=O)CSc2cc(Cl)c(Cc3ccc(O)c(C(C)C)c3)c(Cl)c2)nn1] | 2-((3,5-dichloro-4-(4-hydroxy-3-isopropylbenzyl)phenyl)thio)-N-(6-methoxypyridazin-3-yl)acetamide | 490.1 (M − H) |

TABLE 2-continued

| Cmpd | Structure | Name | [M + H]+ |
|---|---|---|---|
| 170 | 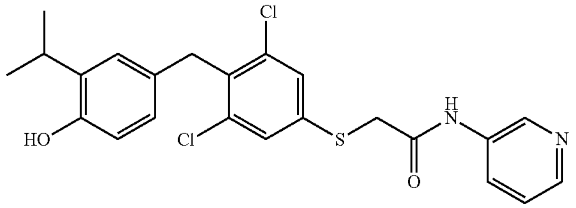 [SMILES: CC(C)c1cc(Cc2c(Cl)cc(SCC(=O)Nc3cccnc3)cc2Cl)ccc1O] | 2-((3,5-dichloro-4-(4-hydroxy-3-isopropylbenzyl)phenyl)thio)-N-(pyridin-3-yl)acetamide | 461.2 |
| 171 | 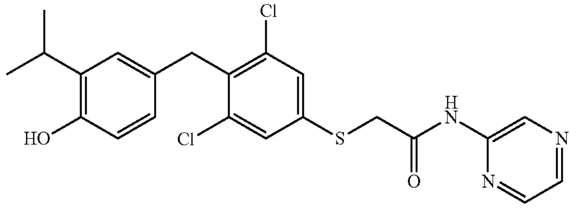 [SMILES: CC(C)c1cc(Cc2c(Cl)cc(SCC(=O)Nc3cnccn3)cc2Cl)ccc1O] | 2-((3,5-dichloro-4-(4-hydroxy-3-isopropylbenzyl)phenyl)thio)-N-(pyrazin-2-yl)acetamide | 462.1 |
| 172 | 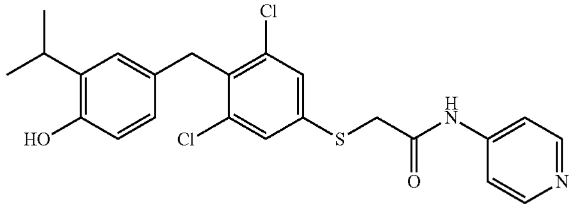 [SMILES: CC(C)c1cc(Cc2c(Cl)cc(SCC(=O)Nc3ccncc3)cc2Cl)ccc1O] | 2-((3,5-dichloro-4-(4-hydroxy-3-isopropylbenzyl)phenyl)thio)-N-(pyridin-4-yl)acetamide | 461.20 |
| 173 | 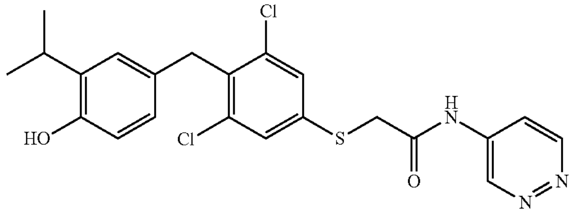 [SMILES: CC(C)c1cc(Cc2c(Cl)cc(SCC(=O)Nc3ccnnc3)cc2Cl)ccc1O] | 2-((3,5-dichloro-4-(4-hydroxy-3-isopropylbenzyl)phenyl)thio)-N-(pyridazin-4-yl)acetamide | 462.05 |
| 174 | 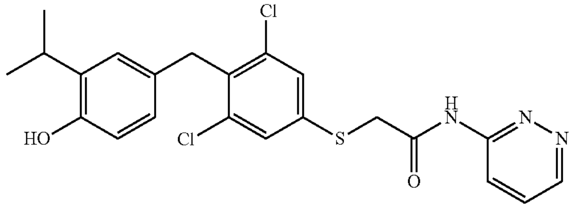 [SMILES: CC(C)c1cc(Cc2c(Cl)cc(SCC(=O)Nc3cccnn3)cc2Cl)ccc1O] | 2-((3,5-dichloro-4-(4-hydroxy-3-isopropylbenzyl)phenyl)thio)-N-(pyridazin-3-yl)acetamide | 462.2 |
| 175 | 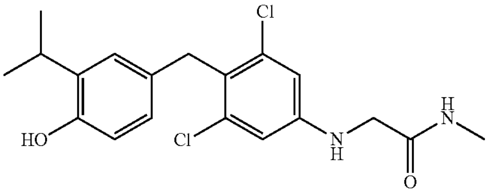 [SMILES: CNC(=O)CNc1cc(Cl)c(Cc2ccc(O)c(C(C)C)c2)c(Cl)c1] | 2-((3,5-dichloro-4-(4-hydroxy-3-isopropylbenzyl)phenyl)amino)-N-methylacetamide | 381.1 |
| 177 | 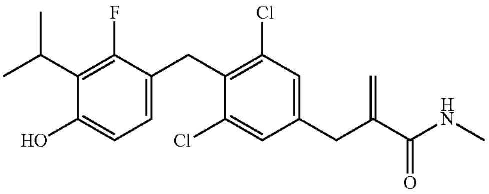 [SMILES: C=C(Cc1cc(Cl)c(Cc2ccc(O)c(C(C)C)c2F)c(Cl)c1)C(=O)NC] | 2-(3,5-dichloro-4-(2-fluoro-4-hydroxy-3-isopropylbenzyl)benzyl)-N-methylacrylamide | 408.1 (M − H) |

TABLE 2-continued

| Cmpd | Structure | Name | [M + H]+ |
|---|---|---|---|
| 178 | 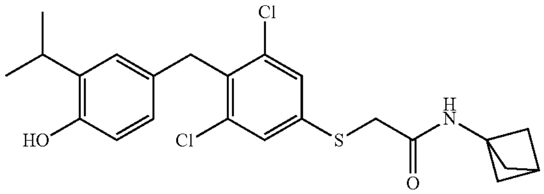 [SMILES: CC(C)c1cc(Cc2c(Cl)cc(SCC(=O)NC34CC(C3)C4)cc2Cl)ccc1O] | N-(bicyclo[1.1.1]pentan-1-yl)-2-((3,5-dichloro-4-(4-hydroxy-3-isopropylbenzyl)phenyl)thio)acetamide | 450.1 |
| 179 | 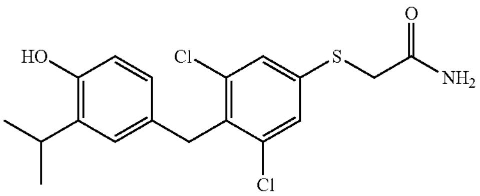 [SMILES: CC(C)c1cc(Cc2c(Cl)cc(SCC(N)=O)cc2Cl)ccc1O] | 2-((3,5-dichloro-4-(4-hydroxy-3-isopropylbenzyl)phenyl)thio)acetamide | 381.9 (M − H) |
| 180 | 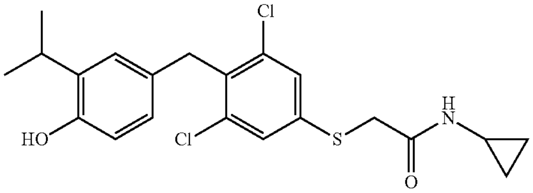 [SMILES: CC(C)c1cc(Cc2c(Cl)cc(SCC(=O)NC3CC3)cc2Cl)ccc1O] | N-cyclopropyl-2-((3,5-dichloro-4-(4-hydroxy-3-isopropylbenzyl)phenyl)thio)acetamide | 424.1 |
| 181 | 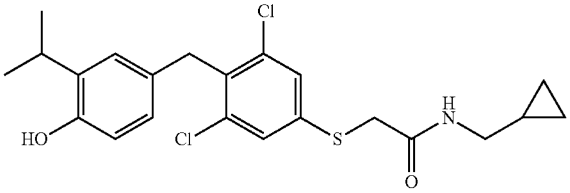 [SMILES: CC(C)c1cc(Cc2c(Cl)cc(SCC(=O)NCC3CC3)cc2Cl)ccc1O] | N-(cyclopropylmethyl)-2-((3,5-dichloro-4-(4-hydroxy-3-isopropylbenzyl)phenyl)thio)acetamide | 438.1 |
| 182 | 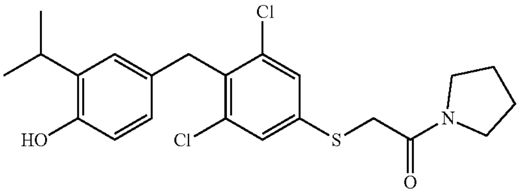 [SMILES: CC(C)c1cc(Cc2c(Cl)cc(SCC(=O)N3CCCC3)cc2Cl)ccc1O] | 2-((3,5-dichloro-4-(4-hydroxy-3-isopropylbenzyl)phenyl)thio)-1-(pyrrolidin-1-yl)ethan-1-one | 438.1 |
| 183 | 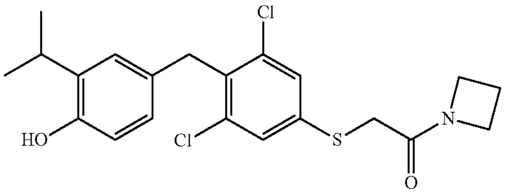 [SMILES: CC(C)c1cc(Cc2c(Cl)cc(SCC(=O)N3CCC3)cc2Cl)ccc1O] | 1-(azetidin-1-yl)-2-((3,5-dichloro-4-(4-hydroxy-3-isopropylbenzyl)phenyl)thio)ethan-1-one | 424.0 |
| 184 | 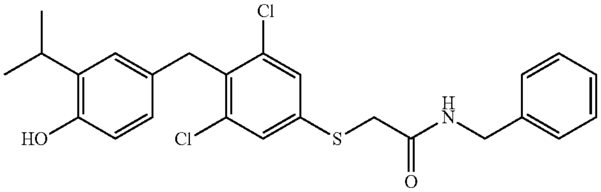 [SMILES: CC(C)c1cc(Cc2c(Cl)cc(SCC(=O)NCc3ccccc3)cc2Cl)ccc1O] | N-benzyl-2-((3,5-dichloro-4-(4-hydroxy-3-isopropylbenzyl)phenyl)thio)acetamide | 474.1 |

TABLE 2-continued

| Cmpd | Structure | Name | [M + H]+ |
|---|---|---|---|
| 185 | 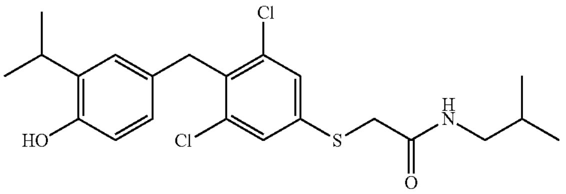 [SMILES: CC(C)CNC(=O)CSc1cc(Cl)c(Cc2ccc(O)c(C(C)C)c2)c(Cl)c1] | 2-((3,5-dichloro-4-(4-hydroxy-3-isopropylbenzyl)phenyl)thio)-N-isobutylacetamide | 440.1 |
| 186 | 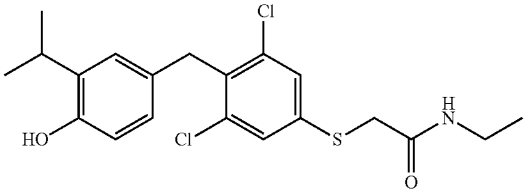 [SMILES: CCNC(=O)CSc1cc(Cl)c(Cc2ccc(O)c(C(C)C)c2)c(Cl)c1] | 2-((3,5-dichloro-4-(4-hydroxy-3-isopropylbenzyl)phenyl)thio)-N-ethylacetamide | 412.1 |
| 187 | 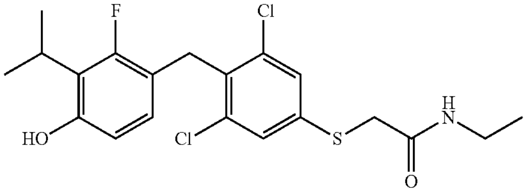 [SMILES: CCNC(=O)CSc1cc(Cl)c(Cc2ccc(O)c(C(C)C)c2F)c(Cl)c1] | 2-((3,5-dichloro-4-(2-fluoro-4-hydroxy-3-isopropylbenzyl)phenyl)thio)-N-ethylacetamide | 429.9 |
| 188 | 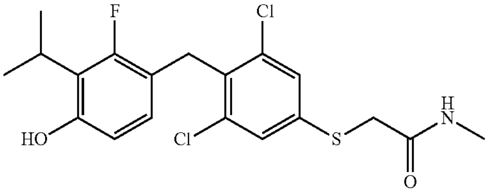 [SMILES: CNC(=O)CSc1cc(Cl)c(Cc2ccc(O)c(C(C)C)c2F)c(Cl)c1] | 2-((3,5-dichloro-4-(2-fluoro-4-hydroxy-3-isopropylbenzyl)phenyl)thio)-N-methylacetamide | 416.0 |
| 189 | 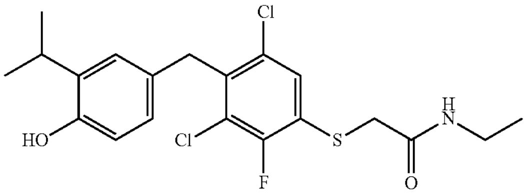 [SMILES: CCNC(=O)CSc1cc(Cl)c(Cc2ccc(O)c(C(C)C)c2)c(Cl)c1F] | 2-((3,5-dichloro-2-fluoro-4-(4-hydroxy-3-isopropylbenzyl)phenyl)thio)-N-ethylacetamide | 430.0 |
| 190 | 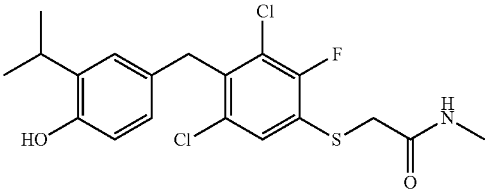 [SMILES: CNC(=O)CSc1cc(Cl)c(Cc2ccc(O)c(C(C)C)c2)c(Cl)c1F] | 2-((3,5-dichloro-2-fluoro-4-(4-hydroxy-3-isopropylbenzyl)phenyl)thio)-N-methylacetamide | 416.0 |
| 191 | 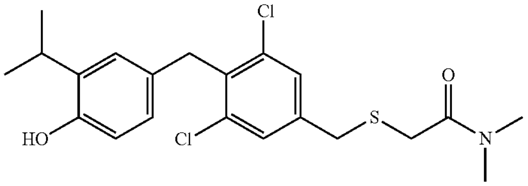 [SMILES: CC(C)c1cc(Cc2c(Cl)cc(CSCC(=O)N(C)C)cc2Cl)ccc1O] | 2-((3,5-dichloro-4-(4-hydroxy-3-isopropylbenzyl)benzyl)thio)-N,N-dimethylacetamide | 424.0 (M − H) |
| 193 | 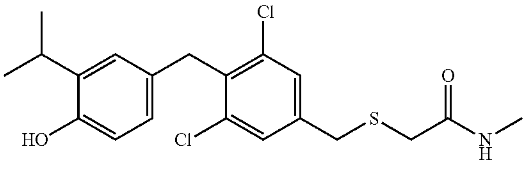 [SMILES: CNC(=O)CSCc1cc(Cl)c(Cc2ccc(O)c(C(C)C)c2)c(Cl)c1] | 2-((3,5-dichloro-4-(4-hydroxy-3-isopropylbenzyl)benzyl)thio)-N-methylacetamide | 410.0 (M − H) |

TABLE 2-continued

| Cmpd | Structure | Name | [M + H]$^+$ |
|---|---|---|---|
| 194 | 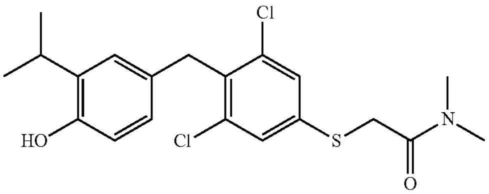 [SMILES: CC(C)c1cc(Cc2c(Cl)cc(SCC(=O)N(C)C)cc2Cl)ccc1O] | 2-((3,5-dichloro-4-(4-hydroxy-3-isopropylbenzyl)phenyl)thio)-N,N-dimethylacetamide | 412.1 |
| 195 | 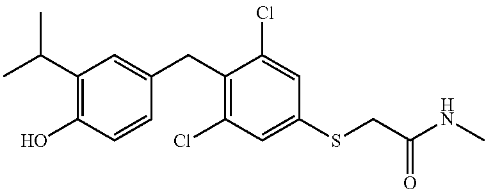 [SMILES: CNC(=O)CSc1cc(Cl)c(Cc2ccc(O)c(C(C)C)c2)c(Cl)c1] | 2-((3,5-dichloro-4-(4-hydroxy-3-isopropylbenzyl)phenyl)thio)-N-methylacetamide | 397.9 |
| 196 | 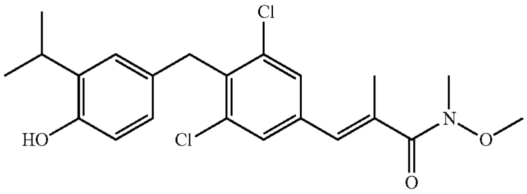 [SMILES: CON(C)C(=O)/C(C)=C/c1cc(Cl)c(Cc2ccc(O)c(C(C)C)c2)c(Cl)c1] | (E)-3-(3,5-dichloro-4-(4-hydroxy-3-isopropylbenzyl)phenyl)-N-methoxy-N,2-dimethylacrylamide | 422.1 |
| 197 | 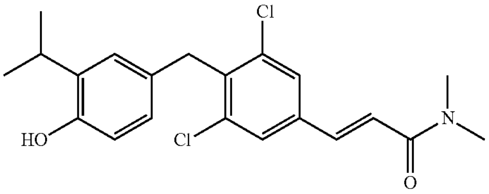 [SMILES: CC(C)c1cc(Cc2c(Cl)cc(/C=C/C(=O)N(C)C)cc2Cl)ccc1O] | (E)-3-(3,5-dichloro-4-(4-hydroxy-3-isopropylbenzyl)phenyl)-N,N-dimethylacrylamide | 390.0 (M − H) |
| 198 | 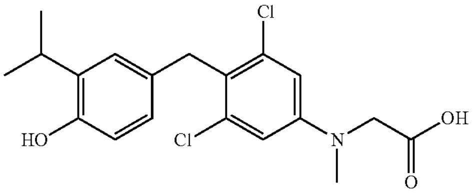 [SMILES: CC(C)c1cc(Cc2c(Cl)cc(N(C)CC(=O)O)cc2Cl)ccc1O] | N-(3,5-dichloro-4-(4-hydroxy-3-isopropylbenzyl)phenyl)-N-methylglycine | 379.9 (M − H) |
| 199 | 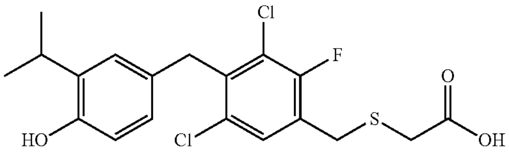 [SMILES: CC(C)c1cc(Cc2c(Cl)cc(CSCC(=O)O)c(F)c2Cl)ccc1O] | 2-((3,5-dichloro-2-fluoro-4-(4-hydroxy-3-isopropylbenzyl)benzyl)thio)acetic acid | 414.9 (M − H) |
| 200 | 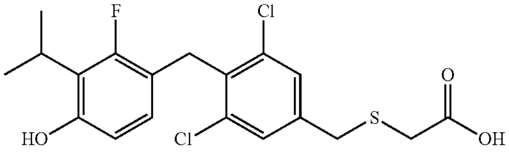 [SMILES: CC(C)c1c(O)ccc(Cc2c(Cl)cc(CSCC(=O)O)cc2Cl)c1F] | 2-((3,5-dichloro-4-(2-fluoro-4-hydroxy-3-isopropylbenzyl)benzyl)thio)acetic acid | 414.8 (M − H) |
| 201 | 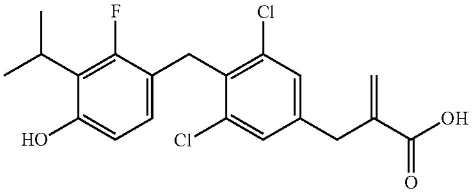 [SMILES: C=C(Cc1cc(Cl)c(Cc2ccc(O)c(C(C)C)c2F)c(Cl)c1)C(=O)O] | 2-(3,5-dichloro-4-(2-fluoro-4-hydroxy-3-isopropylbenzyl)benzyl)acrylic acid | 395.0 (M − H) |

TABLE 2-continued

| Cmpd | Structure | Name | [M + H]+ |
|---|---|---|---|
| 203 | 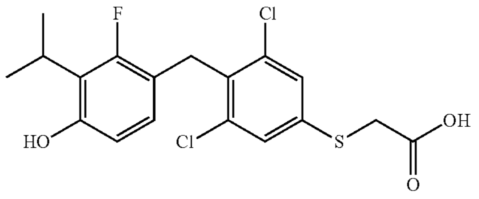 | 2-((3,5-dichloro-4-(2-fluoro-4-hydroxy-3-isopropylbenzyl)phenyl)thio)acetic acid | 401.0 (M − H) |
| 204 | 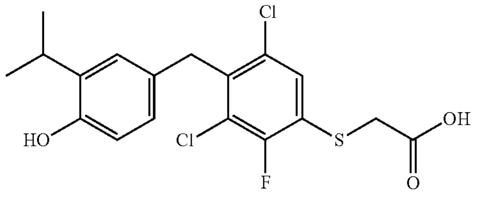 [SMILES: CC(C)c1cc(Cc2c(Cl)cc(SCC(=O)O)c(F)c2Cl)ccc1O] | 2-((3,5-dichloro-2-fluoro-4-(4-hydroxy-3-isopropylbenzyl)phenyl)thio)acetic acid | 401.0 (M − H) |
| 205 | 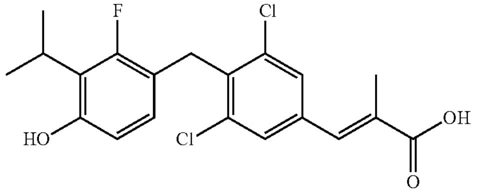 | (E)-3-(3,5-dichloro-4-(2-fluoro-4-hydroxy-3-isopropylbenzyl)phenyl)-2-methylacrylic acid | 395.0 (M − H) |
| 206 | 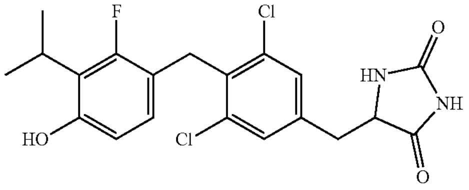 [SMILES: CC(C)c1c(O)ccc(Cc2c(Cl)cc(CC3NC(=O)NC3=O)cc2Cl)c1F] | 5-(3,5-dichloro-4-(2-fluoro-4-hydroxy-3-isopropylbenzyl)benzyl)imidazolidine-2,4-dione | 423.1 (M − H) |
| 207 | 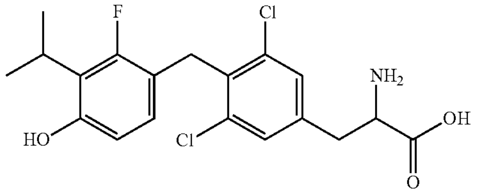 [SMILES: CC(C)c1c(O)ccc(Cc2c(Cl)cc(CC(N)C(=O)O)cc2Cl)c1F] | 2-amino-3-(3,5-dichloro-4-(2-fluoro-4-hydroxy-3-isopropylbenzyl)phenyl)propanoic acid | 398.1 (M − H) |
| 208 | 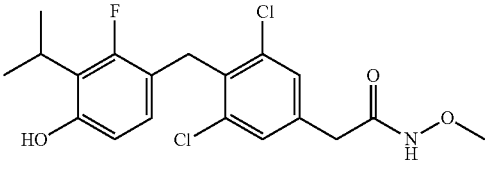 [SMILES: CONC(=O)Cc1cc(Cl)c(Cc2ccc(O)c(C(C)C)c2F)c(Cl)c1] | 2-(3,5-dichloro-4-(2-fluoro-4-hydroxy-3-isopropylbenzyl)phenyl)-N-methoxyacetamide | 397.9 (M − H) |
| 209 | 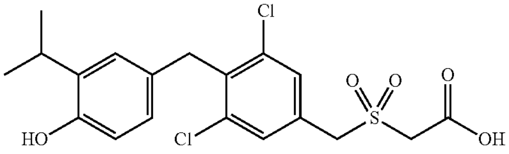 [SMILES: CC(C)c1cc(Cc2c(Cl)cc(CS(=O)(=O)CC(=O)O)cc2Cl)ccc1O] | 2-((3,5-dichloro-4-(4-hydroxy-3-isopropylbenzyl)benzyl)sulfonyl)acetic acid | 453.0 (M + 23) |
| 210 | 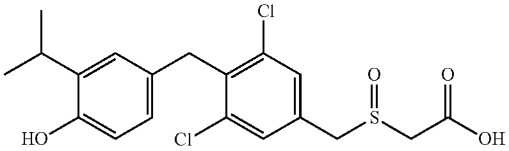 [SMILES: CC(C)c1cc(Cc2c(Cl)cc(CS(=O)CC(=O)O)cc2Cl)ccc1O] | 2-((3,5-dichloro-4-(4-hydroxy-3-isopropylbenzyl)benzyl)sulfinyl)acetic acid | 414.8 |

TABLE 2-continued

| Cmpd | Structure | Name | [M + H]$^+$ |
|---|---|---|---|
| 211 | 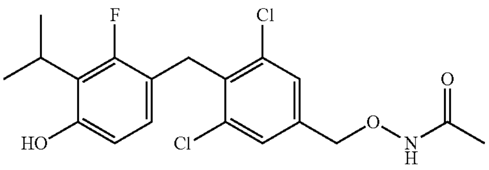 [SMILES: CC(=O)NOCc1cc(Cl)c(Cc2ccc(O)c(C(C)C)c2F)c(Cl)c1] | N-((3,5-dichloro-4-(2-fluoro-4-hydroxy-3-isopropylbenzyl)benzyl)oxy)acetamide | 397.9 (M − H) |
| 212 | 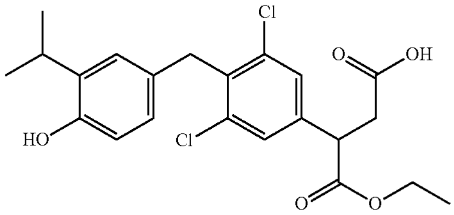 [SMILES: CCOC(=O)C(CC(=O)O)c1cc(Cl)c(Cc2ccc(O)c(C(C)C)c2)c(Cl)c1] | 3-(3,5-dichloro-4-(4-hydroxy-3-isopropylbenzyl)phenyl)-4-ethoxy-4-oxobutanoic acid | 436.9 (M − H) |
| 213 | 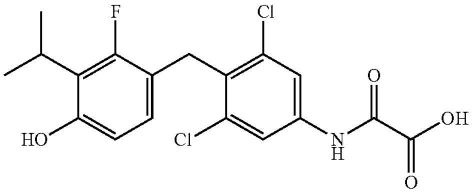 | 2-((3,5-dichloro-4-(2-fluoro-4-hydroxy-3-isopropylbenzyl)phenyl)amino)-2-oxoacetic acid | 398.0 (M − H) |
| 214 | 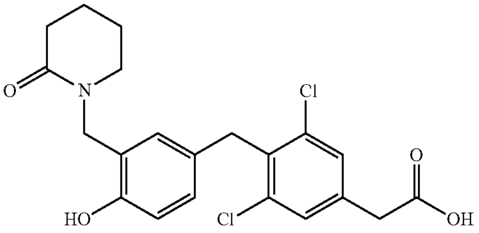 [SMILES: O=C(O)Cc1cc(Cl)c(Cc2ccc(O)c(CN3CCCCC3=O)c2)c(Cl)c1] | 2-(3,5-dichloro-4-(4-hydroxy-3-((2-oxopiperidin-1-yl)methyl)benzyl)phenyl)acetic acid | 422.1 |
| 215 | 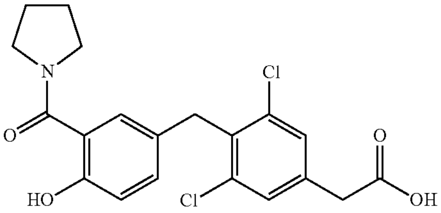 [SMILES: O=C(O)Cc1cc(Cl)c(Cc2ccc(O)c(C(=O)N3CCCC3)c2)c(Cl)c1] | 2-(3,5-dichloro-4-(4-hydroxy-3-(pyrrolidine-1-carbonyl)benzyl)phenyl)acetic acid | 408.1 |
| 216 | 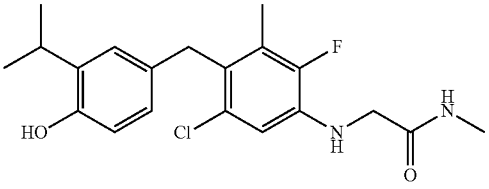 [SMILES: CNC(=O)CNc1cc(Cl)c(Cc2ccc(O)c(C(C)C)c2)c(C)c1F] | 2-((5-chloro-2-fluoro-4-(4-hydroxy-3-isopropylbenzyl)-3-methylphenyl)amino)-N-methylacetamide | 379.1 |
| 217 | 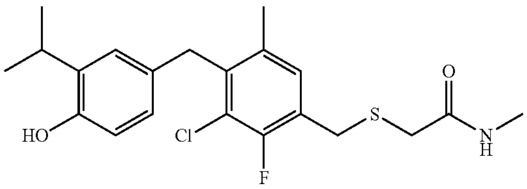 [SMILES: CNC(=O)CSCc1cc(C)c(Cc2ccc(O)c(C(C)C)c2)c(Cl)c1F] | 2-((3-chloro-2-fluoro-4-(4-hydroxy-3-isopropylbenzyl)-5-methylbenzyl)thio)-N-methylacetamide | 410.0 |

TABLE 2-continued

| Cmpd | Structure | Name | [M + H]+ |
|---|---|---|---|
| 218 | 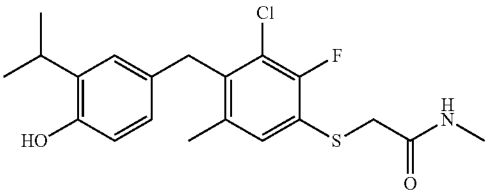 [SMILES: CNC(=O)CSc1cc(C)c(Cc2ccc(O)c(C(C)C)c2)c(Cl)c1F] | 2-((3-chloro-2-fluoro-4-(4-hydroxy-3-isopropylbenzyl)-5-methylphenyl)thio)-N-methylacetamide | 394.0 (M − H) |
| 219 | 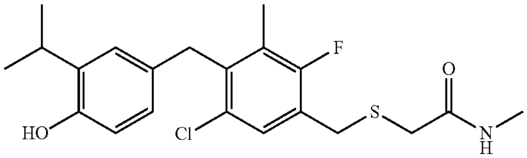 [SMILES: CNC(=O)CSCc1cc(Cl)c(Cc2ccc(O)c(C(C)C)c2)c(C)c1F] | 2-((5-chloro-2-fluoro-4-(4-hydroxy-3-isopropylbenzyl)-3-methylbenzyl)thio)-N-methylacetamide | 410.0 |
| 220 | 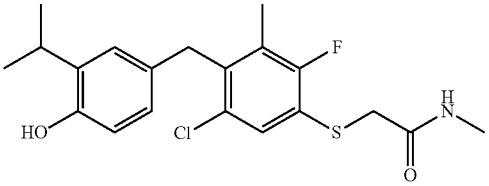 [SMILES: CNC(=O)CSc1cc(Cl)c(Cc2ccc(O)c(C(C)C)c2)c(C)c1F] | 2-((5-chloro-2-fluoro-4-(4-hydroxy-3-isopropylbenzyl)-3-methylphenyl)thio)-N-methylacetamide | 396.0 |
| 221 | 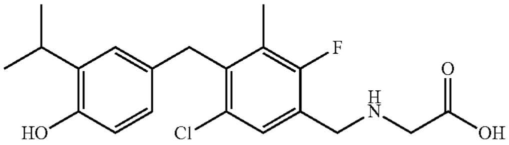 [SMILES: Cc1c(F)c(CNCC(=O)O)cc(Cl)c1Cc1ccc(O)c(C(C)C)c1] | (5-chloro-2-fluoro-4-(4-hydroxy-3-isopropylbenzyl)-3-methylbenzyl)glycine | 380.0 |
| 222 | 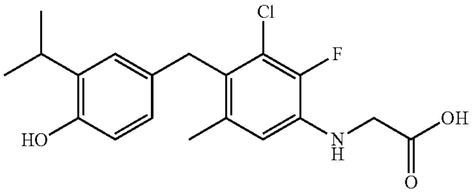 | (3-chloro-2-fluoro-4-(4-hydroxy-3-isopropylbenzyl)-5-methylphenyl)glycine | 364.1 (M − H) |
| 223 | 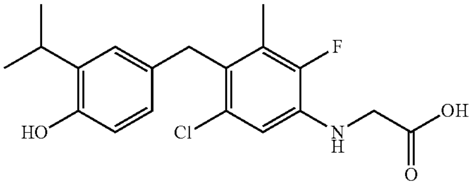 | (5-chloro-2-fluoro-4-(4-hydroxy-3-isopropylbenzyl)-3-methylphenyl)glycine | 364.0 (M − H) |
| 224 | 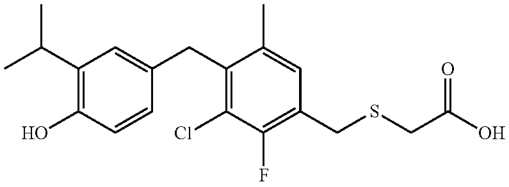 [SMILES: Cc1cc(CSCC(=O)O)c(F)c(Cl)c1Cc1ccc(O)c(C(C)C)c1] | 2-((3-chloro-2-fluoro-4-(4-hydroxy-3-isopropylbenzyl)-5-methylbenzyl)thio)acetic acid | 395.1 (M − H) |
| 225 | 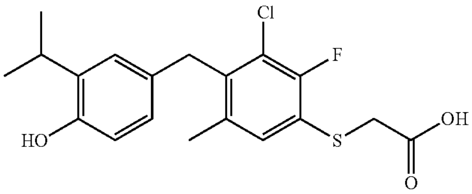 [SMILES: Cc1cc(SCC(=O)O)c(F)c(Cl)c1Cc1ccc(O)c(C(C)C)c1] | 2-((3-chloro-2-fluoro-4-(4-hydroxy-3-isopropylbenzyl)-5-methylphenyl)thio)acetic acid | 381.0 (M − H) |

TABLE 2-continued

| Cmpd | Structure | Name | [M + H]$^+$ |
|---|---|---|---|
| 226 | 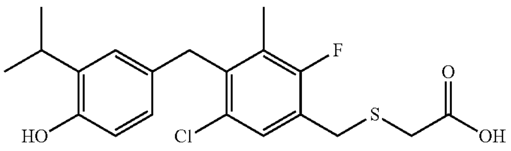 [SMILES: Cc1c(F)c(CSCC(=O)O)cc(Cl)c1Cc1ccc(O)c(C(C)C)c1] | 2-((5-chloro-2-fluoro-4-(4-hydroxy-3-isopropylbenzyl)-3-methylbenzyl)thio)acetic acid | 395.0 (M − H) |
| 227 | 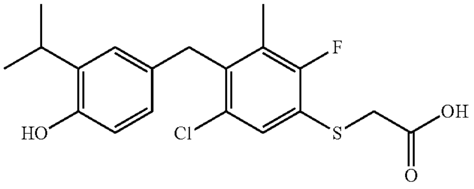 [SMILES: Cc1c(F)c(SCC(=O)O)cc(Cl)c1Cc1ccc(O)c(C(C)C)c1] | 2-((5-chloro-2-fluoro-4-(4-hydroxy-3-isopropylbenzyl)-3-methylphenyl)thio)acetic acid | 381.1 (M − H) |
| 228 | 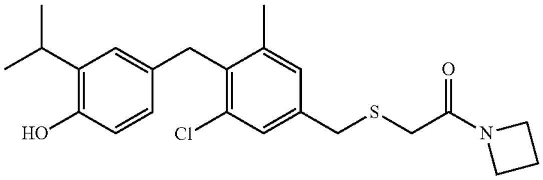 [SMILES: Cc1cc(CSCC(=O)N2CCC2)cc(Cl)c1Cc1ccc(O)c(C(C)C)c1] | 1-(azetidin-1-yl)-2-((3-chloro-4-(4-hydroxy-3-isopropylbenzyl)-5-methylbenzyl)thio)ethan-1-one | 418.2 |
| 229 | 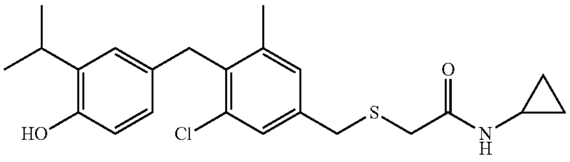 [SMILES: Cc1cc(CSCC(=O)NC2CC2)cc(Cl)c1Cc1ccc(O)c(C(C)C)c1] | 2-((3-chloro-4-(4-hydroxy-3-isopropylbenzyl)-5-methylbenzyl)thio)-N-cyclopropylacetamide | 418.2 |
| 230 | 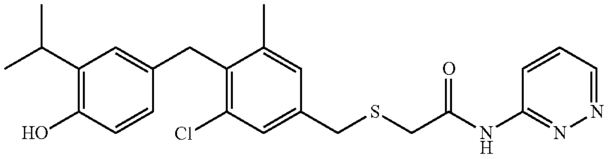 [SMILES: Cc1cc(CSCC(=O)Nc2cccnn2)cc(Cl)c1Cc1ccc(O)c(C(C)C)c1] | 2-((3-chloro-4-(4-hydroxy-3-isopropylbenzyl)-5-methylbenzyl)thio)-N-(pyridazin-3-yl)acetamide | 454.2 (M − H) |
| 231 | 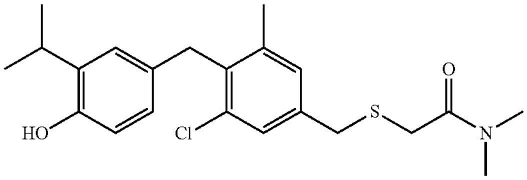 [SMILES: Cc1cc(CSCC(=O)N(C)C)cc(Cl)c1Cc1ccc(O)c(C(C)C)c1] | 2-((3-chloro-4-(4-hydroxy-3-isopropylbenzyl)-5-methylbenzyl)thio)-N,N-dimethylacetamide | 404.2 (M − H) |
| 232 | 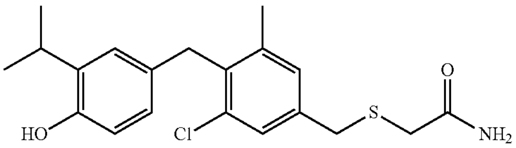 [SMILES: Cc1cc(CSCC(N)=O)cc(Cl)c1Cc1ccc(O)c(C(C)C)c1] | 2-((3-chloro-4-(4-hydroxy-3-isopropylbenzyl)-5-methylbenzyl)thio)acetamide | 378.1 |
| 233 | 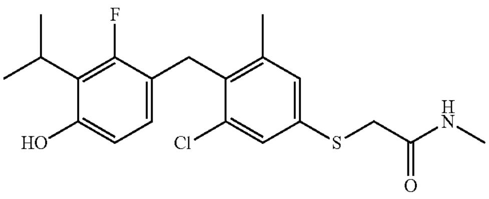 [SMILES: CNC(=O)CSc1cc(C)c(Cc2ccc(O)c(C(C)C)c2F)c(Cl)c1] | 2-((3-chloro-4-(2-fluoro-4-hydroxy-3-isopropylbenzyl)-5-methylphenyl)thio)-N-methylacetamide | 394.0 (M − H) |

TABLE 2-continued

| Cmpd | Structure | Name | [M + H]$^+$ |
| --- | --- | --- | --- |
| 234 | 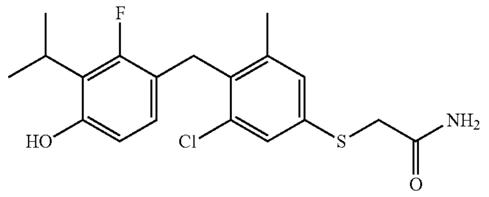 [SMILES: Cc1cc(SCC(N)=O)cc(Cl)c1Cc1ccc(O)c(C(C)C)c1F] | 2-((3-chloro-4-(2-fluoro-4-hydroxy-3-isopropylbenzyl)-5-methylphenyl)thio)acetamide | 380.0 (M − H) |
| 235 | 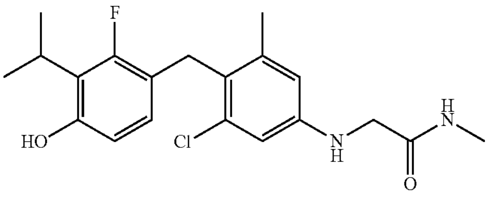 [SMILES: CNC(=O)CNc1cc(C)c(Cc2ccc(O)c(C(C)C)c2F)c(Cl)c1] | 2-((3-chloro-4-(2-fluoro-4-hydroxy-3-isopropylbenzyl)-5-methylphenyl)amino)-N-methylacetamide | 379.0 |
| 236 | 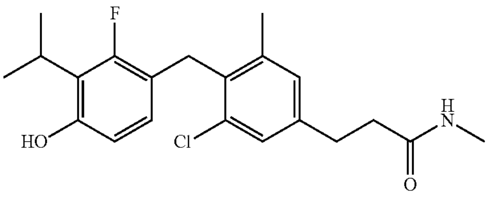 [SMILES: CNC(=O)CCc1cc(C)c(Cc2ccc(O)c(C(C)C)c2F)c(Cl)c1] | 3-(3-chloro-4-(2-fluoro-4-hydroxy-3-isopropylbenzyl)-5-methylphenyl)-N-methylpropanamide | 378.2 |
| 237 | 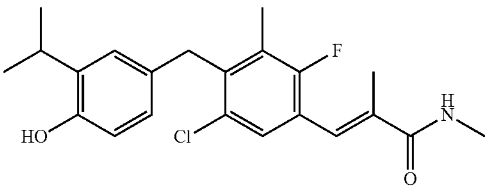 [SMILES: CNC(=O)/C(C)=C/c1cc(Cl)c(Cc2ccc(O)c(C(C)C)c2)c(C)c1F] | (E)-3-(5-chloro-2-fluoro-4-(4-hydroxy-3-isopropylbenzyl)-3-methylphenyl)-N,2-dimethylacrylamide | 388.1 (M − H) |
| 238 | 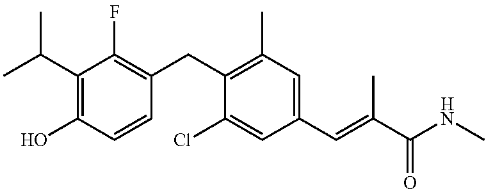 [SMILES: CNC(=O)/C(C)=C/c1cc(C)c(Cc2ccc(O)c(C(C)C)c2F)c(Cl)c1] | (E)-3-(3-chloro-4-(2-fluoro-4-hydroxy-3-isopropylbenzyl)-5-methylphenyl)-N,2-dimethylacrylamide | 388.1 (M − H) |
| 239 | 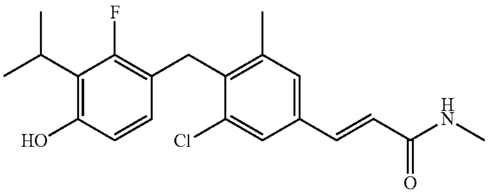 [SMILES: CNC(=O)/C=C/c1cc(C)c(Cc2ccc(O)c(C(C)C)c2F)c(Cl)c1] | (E)-3-(3-chloro-4-(2-fluoro-4-hydroxy-3-isopropylbenzyl)-5-methylphenyl)-N-methylacrylamide | 374.0 (M − H) |
| 240 | 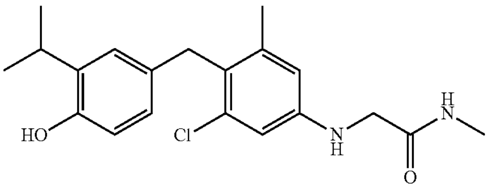 [SMILES: CNC(=O)CNc1cc(C)c(Cc2ccc(O)c(C(C)C)c2)c(Cl)c1] | 2-((3-chloro-4-(4-hydroxy-3-isopropylbenzyl)-5-methylphenyl)amino)-N-methylacetamide | 361.1 |
| 241 | 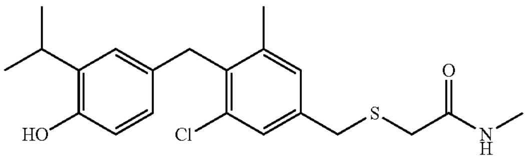 [SMILES: CNC(=O)CSCc1cc(C)c(Cc2ccc(O)c(C(C)C)c2)c(Cl)c1] | 2-((3-chloro-4-(4-hydroxy-3-isopropylbenzyl)-5-methylbenzyl)thio)-N-methylacetamide | 390.2 (M − H) |

TABLE 2-continued

| Cmpd | Structure | Name | [M + H]$^+$ |
|---|---|---|---|
| 242 | 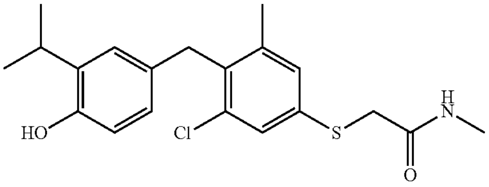 [SMILES: CNC(=O)CSc1cc(C)c(Cc2ccc(O)c(C(C)C)c2)c(Cl)c1] | 2-((3-chloro-4-(4-hydroxy-3-isopropylbenzyl)-5-methylphenyl)thio)-N-methylacetamide | 378.2 |
| 244 | 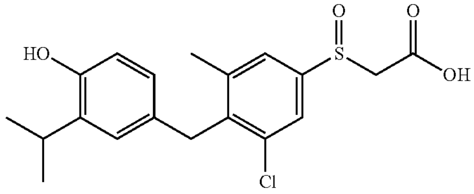 [SMILES: Cc1cc(S(=O)CC(=O)O)cc(Cl)c1Cc1ccc(O)c(C(C)C)c1] | 2-((3-chloro-4-(4-hydroxy-3-isopropylbenzyl)-5-methylphenyl)sulfinyl)acetic acid | 335.1 (M − COOH) |
| 245 | 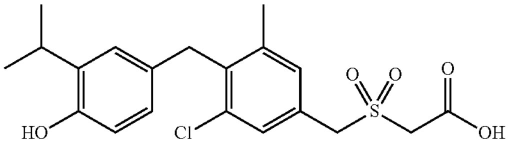 [SMILES: Cc1cc(CS(=O)(=O)CC(=O)O)cc(Cl)c1Cc1ccc(O)c(C(C)C)c1] | 2-((3-chloro-4-(4-hydroxy-3-isopropylbenzyl)-5-methylbenzyl)sulfonyl)acetic acid | 365.1 M − COOH |
| 246 | 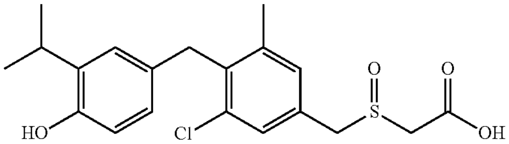 [SMILES: Cc1cc(CS(=O)CC(=O)O)cc(Cl)c1Cc1ccc(O)c(C(C)C)c1] | 2-((3-chloro-4-(4-hydroxy-3-isopropylbenzyl)-5-methylbenzyl)sulfinyl)acetic acid | 393.1 (M − H) |
| 247 | 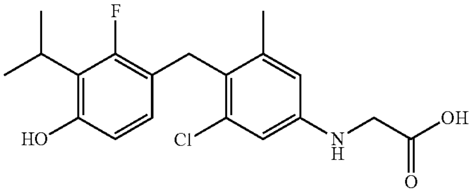 | (3-chloro-4-(2-fluoro-4-hydroxy-3-isopropylbenzyl)-5-methylphenyl)glycine | 364.0 (M − H) |
| 248 | 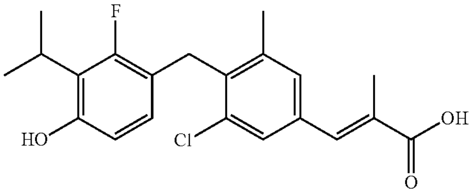 [SMILES: C/C(=C\c1cc(C)c(Cc2ccc(O)c(C(C)C)c2F)c(Cl)c1)C(=O)O] | (E)-3-(3-chloro-4-(2-fluoro-4-hydroxy-3-isopropylbenzyl)-5-methylphenyl)-2-methylacrylic acid | 375.0 (M − H) |
| 249 | 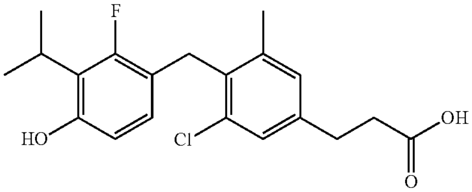 [SMILES: Cc1cc(CCC(=O)O)cc(Cl)c1Cc1ccc(O)c(C(C)C)c1F] | 3-(3-chloro-4-(2-fluoro-4-hydroxy-3-isopropylbenzyl)-5-methylphenyl)propanoic acid | 363.1 (M − H) |
| 250 | 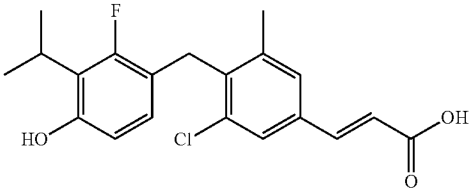 | (E)-3-(3-chloro-4-(2-fluoro-4-hydroxy-3-isopropylbenzyl)-5-methylphenyl)acrylic acid | 361.1 (M − H) |

TABLE 2-continued

| Cmpd | Structure | Name | [M + H]$^+$ |
|---|---|---|---|
| 251 | 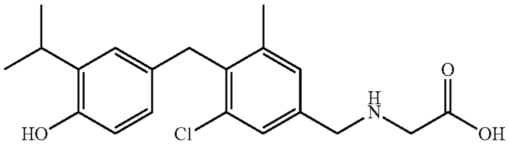 [SMILES: Cc1cc(CNCC(=O)O)cc(Cl)c1Cc1ccc(O)c(C(C)C)c1] | (3-chloro-4-(4-hydroxy-3-isopropylbenzyl)-5-methylbenzyl)glycine | 362.1 |

Example 154

Biological Testing: Thyroid-Hormone Reporter-Gene Assays

Compounds were tested for thyroid-hormone receptor activity using TR reporter-gene assays. Reporter cells used in the assays express a TR-receptor hybrid (either TRα or TRβ) in which the native N-terminal DNA binding domain (DBD) has been replaced with that of the yeast Gal4 DBD. The reporter gene, firefly luciferase, is functionally linked to the Gal4 upstream activation sequence (UAS). Both cell lines were derived from human embryonic kidney (HEK293).

Step 1: A suspension of reporter cells was prepared in cell recovery medium containing 10% charcoal-stripped FBS, and dispensed into assay plates. The plates were pre-incubated for 6 hours in a cell culture incubator (37° C./5% CO2/85% humidity).

Step 2: Test compound master stocks and triiodothyronine were diluted in DMSO to generate solutions at "1,000×-concentration" relative to each final treatment concentration. These intermediate stocks were subsequently diluted directly into compound screening medium containing 10% charcoal-stripped FBS to generate "2×-concentration" treatment media (containing 0.2, 0.4 or 0.8% DMSO).

Step 3: At the end of the pre-incubation period, culture media were discarded from the assay plates, and all wells received 100 μl of compound screening medium. 100 μl of each of the previously prepared "2×-concentration" treatment media were dispensed into duplicate assay wells, thereby achieving the desired final treatment concentrations. The final concentration of DMSO in all assay wells was 0.1, 0.2 or 0.4%. Assay plates were incubated for 24 hr in a cell culture incubator (37° C./5% CO2/85% humidity).

Step 4: At the 24 h assay endpoint, treatment media were discarded and 100 l/well of luciferase detection reagent was added. Relative luminometer units (RLUs) were quantified from each assay well. The performance of the TRα and TRβ assays was validated using the reference agonist triiodothyronine (T3).

The results of these assays are presented in Table 3 below, wherein data are reported as EC50 values determined for TRα and TRβ receptors, and the selectivity index (SI) is calculated as EC50 (TRα)/EC50 (TRβ). To this end, EC50 and SI values are expressed as follows:

TABLE 3

ACTIVITY DATA

| Cpd. No. | TRα | TRβ | T3-SI |
|---|---|---|---|
| T3 | ++++ | +++ | + |
| 2 | ++ | +++ | ++ |
| 4 | ++ | +++ | ++ |
| 6 | ++ | ++ | ++ |

TABLE 3-continued

ACTIVITY DATA

| Cpd. No. | TRα | TRβ | T3-SI |
|---|---|---|---|
| 9 | +++ | ++++ | ++ |
| 11 | +++ | +++ | ++ |
| 15 | +++ | +++ | ++ |
| 16 | + | ++ | +++ |
| 18 | +++ | +++ | + |
| 20 | +++ | +++ | ++ |
| 22 | ++ | ++ | ++ |
| 24 | ++ | ++ | + |
| 26 | ++ | ++ | + |
| 28 | +++ | +++ | ++ |
| 30 | ++ | ++ | + |
| 32 | +++ | ++++ | ++ |
| 37 | +++ | ++++ | ++ |
| 40 | ++++ | ++++ | ++ |
| 44 | +++ | ++++ | ++ |
| 46 | +++ | ++++ | ++ |
| 50 | +++ | ++++ | ++ |
| 52 | ++ | ++ | + |
| 54 | +++ | +++ | + |
| 56 | ++ | +++ | ++ |
| 58 | ++ | +++ | ++ |
| 60 | ++ | ++ | ++ |
| 61 | + | + | ++ |
| 63 | ++ | ++ | ++ |
| 65 | +++ | +++ | ++ |
| 69 | +++ | ++++ | ++ |
| 71 | +++ | +++ | ++ |
| 75 | +++ | +++ | ++ |
| 78 | ++++ | ++++ | ++ |
| 81 | ++ | ++ | ++ |
| 82 | + | ++ | ++ |
| 84 | ++ | ++ | + |
| 86 | +++ | +++ | + |
| 88 | ++++ | ++++ | + |
| 90 | + | + | ++ |
| 91 | ++ | ++ | ++ |
| 92 | + | + | +++ |
| 93 | + | + | ++ |
| 95 | +++ | ++ | ++ |
| 96 | + | + | + |
| 97 | + | + | ++ |
| 100 | ++ | + | + |
| 102 | ++ | ++ | ++ |
| 103 | +++ | +++ | ++ |
| 104 | + | ++ | +++ |
| 105 | ND | + | ND |
| 106 | +++ | +++ | ++ |
| 107 | ++ | ++ | ++ |
| 108 | ++ | + | + |
| 110 | +++ | ++ | + |
| 123 | ++ | ++ | ++ |
| 124 | +++ | +++ | ++ |
| 125 | +++ | +++ | ++ |
| 126 | +++ | +++ | + |
| 127 | +++ | +++ | ++ |
| 128 | +++ | +++ | ++ |
| 129 | + | + | ++ |
| 130 | + | + | ++ |
| 131 | ND | ND | ND |
| 132 | ND | ND | ND |
| 133 | ++++ | ++++ | ++ |
| 134 | +++ | +++ | ++ |

TABLE 3-continued

| ACTIVITY DATA | | | |
|---|---|---|---|
| Cpd. No. | TRα | TRβ | T3-SI |
| 135 | ND | ND | ND |
| 136 | ND | ND | ND |
| 137 | ND | + | ND |
| 138 | + | ND | ND |
| 139 | +++ | ND | ND |
| 140 | + | ND | ND |
| 141 | ND | ND | ND |
| 142 | + | ND | ND |
| 143 | +++ | +++ | + |
| 144 | ++ | + | + |
| 145 | ND | ND | ND |
| 146 | ND | ND | ND |
| 147 | ND | ND | ND |
| 148 | + | + | + |
| 149 | ND | ND | ND |
| 150 | ND | ND | ND |
| 151 | ++ | ++ | ++ |
| 152 | ++ | ++ | ++ |
| 153 | +++ | +++ | ++ |
| 198 | + | + | + |
| 200 | ++++ | ++++ | ++ |
| 201 | ++++ | ++++ | ++ |
| 203 | +++ | +++ | ++ |
| 204 | +++ | +++ | ++ |
| 205 | ++++ | ++++ | ++ |
| 206 | + | + | +++ |
| 207 | + | ++ | + |
| 208 | + | ++ | ++ |
| 209 | + | + | ++ |
| 210 | + | + | ++ |
| 211 | ++ | ND | ND |
| 213 | ++ | ++ | 7.15 |
| 217 | + | + | ++ |
| 221 | ++ | ++ | ++ |
| 222 | +++ | +++ | ++ |
| 223 | +++ | +++ | ++ |
| 224 | ++ | ++ | ++ |
| 225 | ++ | ++ | ++ |
| 226 | ++ | ++ | ++ |
| 227 | ++ | ++ | ++ |
| 244 | + | + | ++ |
| 245 | + | + | ++ |
| 246 | + | + | ++ |
| 247 | +++ | +++ | ++ |
| 248 | +++ | +++ | + |
| 249 | +++ | +++ | ++ |
| 250 | +++ | +++ | + |
| 251 | ++ | + | + |

Potency:
+ $EC_{50}$ > 1,000 nM
++ 100 nM < $EC_{50}$ ≤ 1,000 nM
+++ 10 nM < $EC_{50}$ ≤ 100 nM
++++ $EC_{50}$ ≤ 10 nM
ND Not determined
Selectivity:
+ T3-SI ≤ 3x
++ 3x < T3-SI ≤ 30x
+++ T3-SI > 30x
ND Not determined

Example 155

FAAH Substrate Evaluation

Purified recombinant human FAAH (rhFAAH) was purchased from Cayman Chemical (Ann Arbor, MI, USA). The total volume for each incubation was 400 μL containing a final 0.5 ng/μL rhFAAH, 1 μM test compound, 1.25% ethanol or 1 μM PF-3845 (FAAH inhibitor), and 0.1% bovine serum albumin in Tris-EDTA buffer at pH 8.0). The positive control was LL-341001. The incubation was conducted at the room temperature. At 0, 5, 15, 30 and 60 minutes, an aliquot of 30 μL reaction mixtures was removed and mixed with 300 μL acetonitrile containing 5 ng/mL terfenadine and 10 ng/mL tolbutamide as internal standards to quench the reaction. The resulting mixture was centrifuged at 4000 rpm, 4° C. for 15 minutes, and 100 μL supernatant was ready for LC-MS/MS analysis to measure the formation of acid metabolite.

LC-MS/MS Analysis

Acquity Ultra Performance LC system from Waters was used for sample analysis. The chromatography was performed on a reverse phase Kinetex 2.6 μm C18 column, 2.1×30 mm, 100 Å. The mobile phase A comprised of 0.1% formic acid in water and mobile phase B comprised of 0.1% formic acid in acetonitrile with a 2-min run time at the flow rate of 0.8 mL/min for the acid metabolite from positive control or a 1.5 min run time at the flow rate of 0.9 mL/min for the acid metabolite of test compounds. The mass spectrometer (API-5500 and API Q Trap 4000 Applied Biosystems/MDS SCIEX Instruments, Framingham, MA, USA) was operated under ESI positive or negative ion MRM mode.

Data Analysis

The formation of acid metabolite was monitored and quantified using one calibration point of 1 μM. The observed rate constant (ke) for the acid metabolite formation was calculated by plotting the metabolite concentration versus time of incubation with the slope being ke and is shown in Table 4.

TABLE 4

| Compound | ke |
|---|---|
| 7 | NC |
| 12 | A |
| 33 | NC |
| 34 | NC |
| 41 | A |
| 47 | A |
| 66 | A |
| 72 | A |
| 76 | A |
| 79 | A |
| 105 | NC |
| 111 | A |
| 115 | NC |
| 122 | A |
| 131 | NC |
| 135 | A |
| 136 | A |
| 146 | A |
| 147 | C |
| 149 | NC |
| 155 | A |
| 156 | A |
| 157 | B |
| 158 | B |
| 159 | B |
| 160 | B |
| 161 | B |
| 162 | C |
| 163 | A |
| 164 | NC |
| 165 | A |
| 166 | NC |
| 168 | B |
| 169 | A |
| 170 | C |
| 171 | B |
| 172 | C |
| 173 | C |
| 174 | C |
| 175 | A |
| 177 | NC |
| 178 | NC |
| 179 | C |

TABLE 4-continued

| Compound | ke |
|---|---|
| 180 | C |
| 181 | A |
| 182 | A |
| 183 | A |
| 184 | A |
| 185 | NC |
| 186 | A |
| 187 | A |
| 188 | B |
| 189 | A |
| 190 | B |
| 190 | B |
| 191 | NC |
| 193 | NC |
| 194 | NC |
| 195 | B |
| 208 | A |
| 216 | A |
| 217 | C |
| 218 | B |
| 219 | A |
| 220 | NC |
| 228 | A |
| 229 | C |
| 230 | B |
| 231 | A |
| 232 | C |
| 233 | C |
| 234 | C |
| 235 | A |
| 236 | B |
| 237 | A |
| 238 | B |
| 239 | NC |
| 240 | NC |
| 241 | B |
| 242 | B |

A = ke is equal to or less than 1.0,
B = ke is greater than 1.0 and less than or equal to 2.5,
C = ke is greater than 2.5,
NC = no conversion.

As indicated by the above experiments, modification of the linker region leads to a wide range of activity profiles, with compounds of the present invention exhibiting high potency against TRa receptor, TRb, receptor, or both. Receptor selectivity values can range from highly selective for TRb, to TRa/TRb balanced. Thus, agonists and prodrugs of the present invention, when appropriately targeted, may find utility against indications which require selective modulation of TRb receptor, or where activation of both receptor subtypes is preferred.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the structure of Formula (I-D):

(I-D)

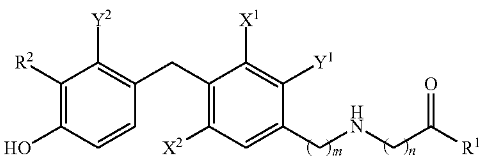

or a tautomer, hydrate, solvate, isotope, or pharmaceutically acceptable salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

m is 0 or 1;

n is 1 or 2;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^{1c}$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, —CN, —OR', —NR'R", =O, =S, —C(O) OR', —C(O) NR'R", —$S(O)_2R'$ or —$S(O)_2OR'$, wherein R' and R" are each, independently, H, lower alkyl, or lower haloalkyl.

2. The compound of claim 1, or a tautomer, hydrate, solvate, isotope, or pharmaceutically acceptable salt thereof, wherein $R^2$ is unsubstituted lower alkyl.

3. The compound of claim 1, or a tautomer, hydrate, solvate, isotope, or pharmaceutically acceptable salt thereof, wherein $R^2$ is isopropyl.

4. The compound of claim 1, or a tautomer, hydrate, solvate, isotope, or pharmaceutically acceptable salt thereof, wherein $R^1$ is —$NR^{1a}R^{1b}$.

5. The compound of claim 4, or a tautomer, hydrate, solvate, isotope, or pharmaceutically acceptable salt thereof, wherein $R^{1a}$ is lower alkyl.

6. The compound of claim 4, or a tautomer, hydrate, solvate, isotope, or pharmaceutically acceptable salt thereof, wherein $R^{1b}$ is H.

7. The compound of claim 1, or a tautomer, hydrate, solvate, isotope, or pharmaceutically acceptable salt thereof, wherein $R^1$ is —$OR^{1c}$.

8. The compound of claim 7, or a tautomer, hydrate, solvate, isotope, or pharmaceutically acceptable salt thereof, wherein $R^{1c}$ is H.

9. The compound of claim 7, or a tautomer, hydrate, solvate, isotope, or pharmaceutically acceptable salt thereof, wherein $R^{1c}$ is lower alkyl.

10. The compound of claim 1, or a tautomer, hydrate, solvate, isotope, or pharmaceutically acceptable salt thereof, wherein $X^1$ is lower alkyl or halo and $X^2$ is halo.

11. The compound of claim 1, or a tautomer, hydrate, solvate, isotope, or pharmaceutically acceptable salt thereof, wherein $Y^1$ is H or halogen and $Y^2$ is H or halogen.
12. A compound, or a tautomer, hydrate, solvate, isotope, or pharmaceutically acceptable salt thereof, selected from:
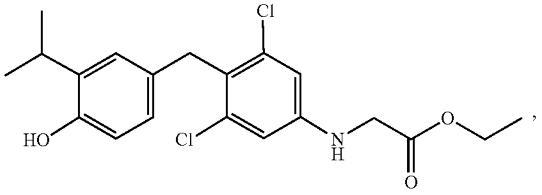
,
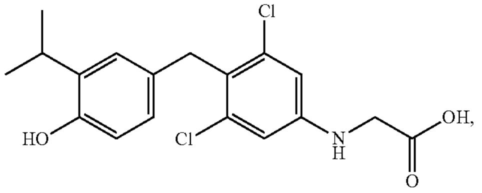
,
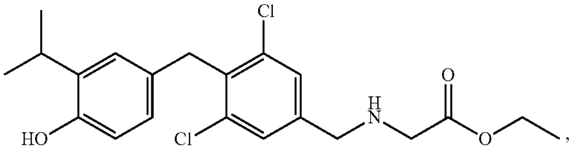
,
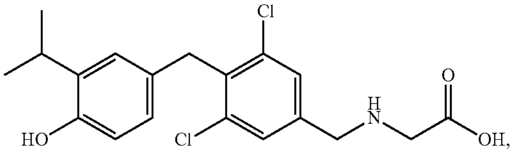
,
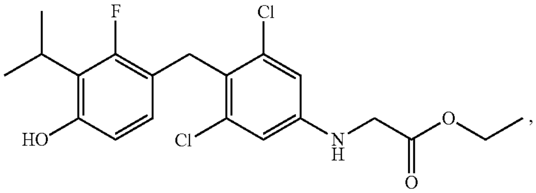
,
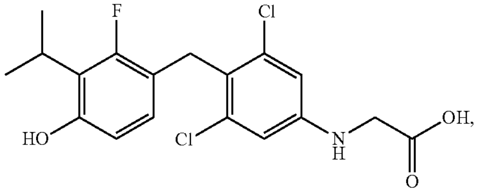
,
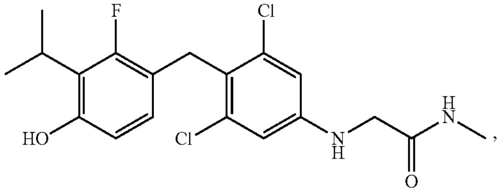
,
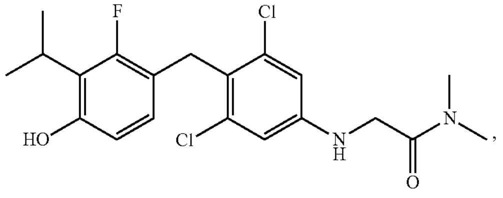
,
-continued
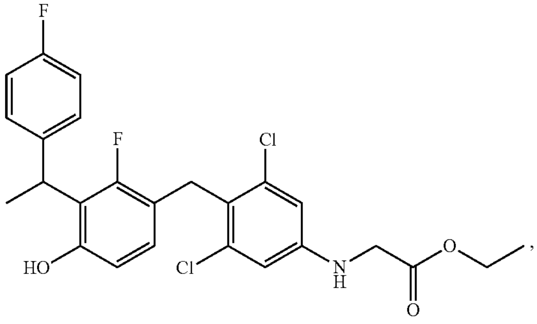
,
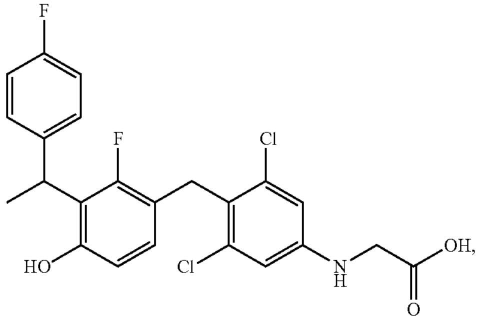
,
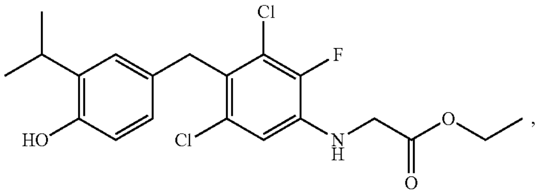
,
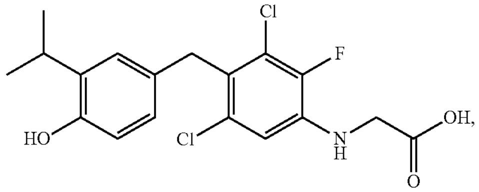
,
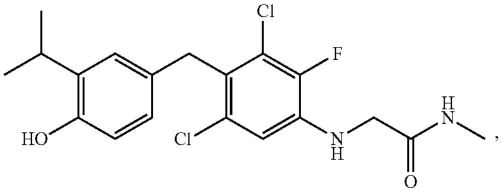
,
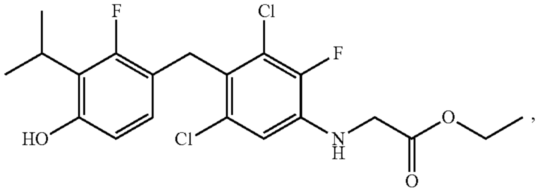
,
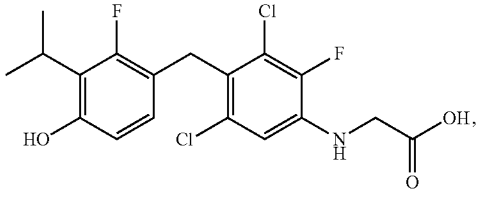
, -continued
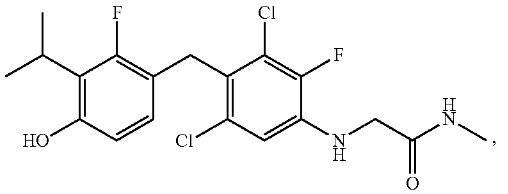
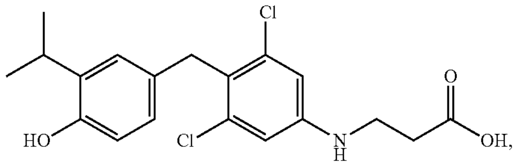
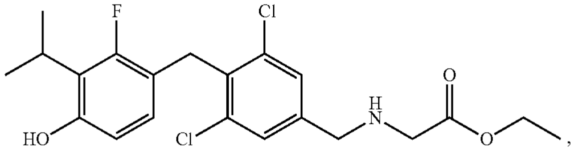
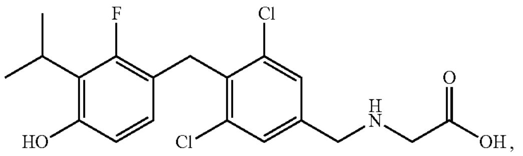
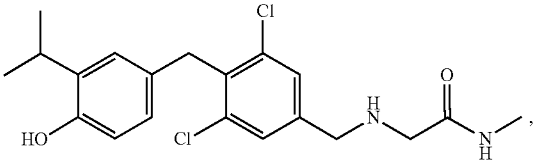
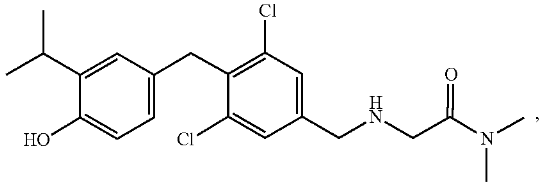
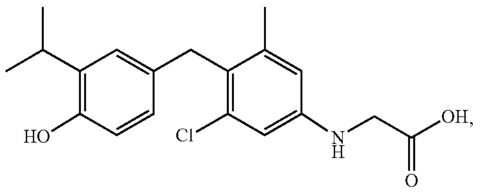
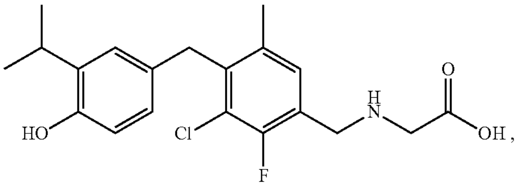
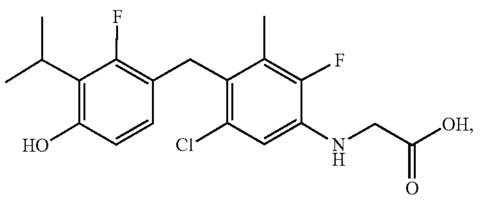
-continued
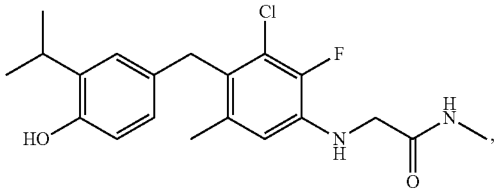
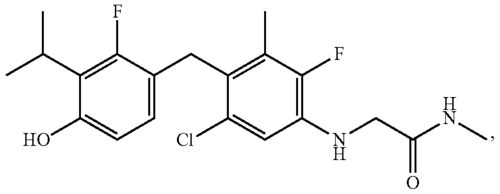
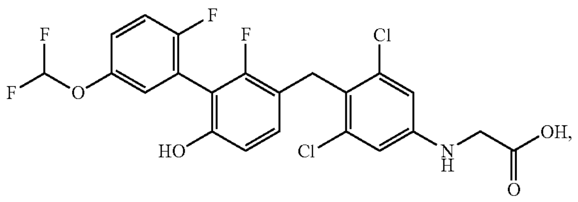
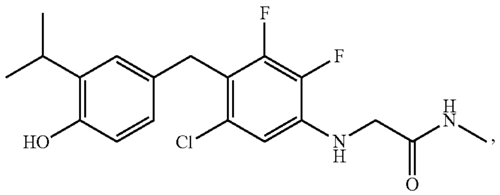
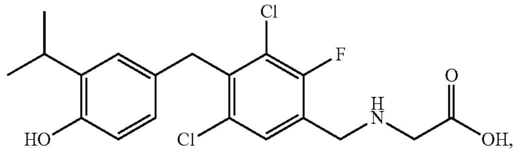
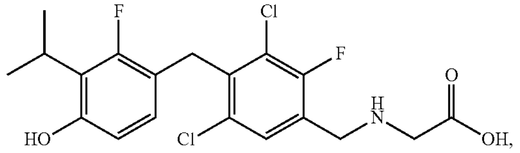
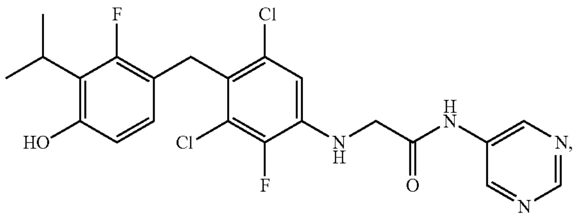
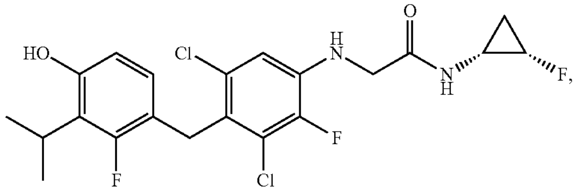
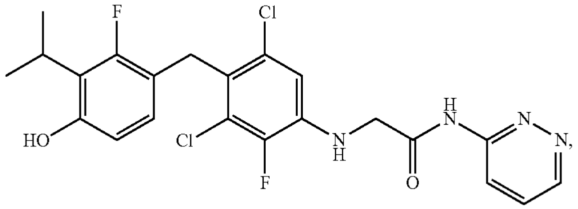

-continued
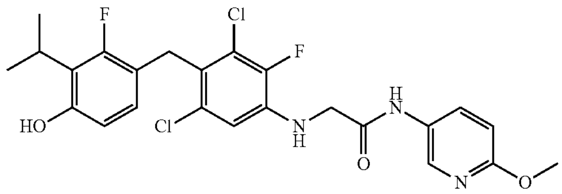
,
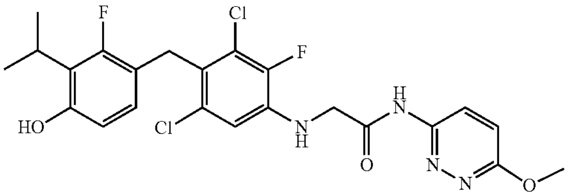
,
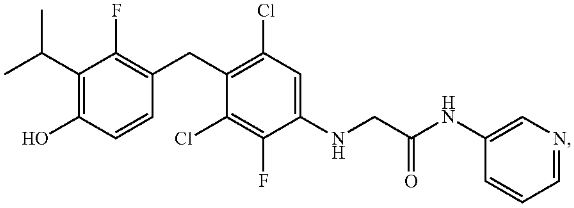
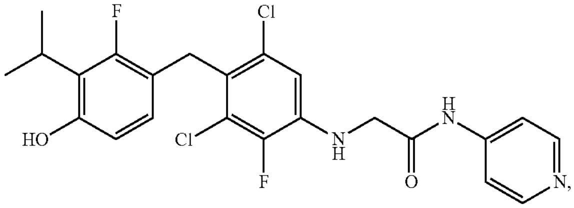
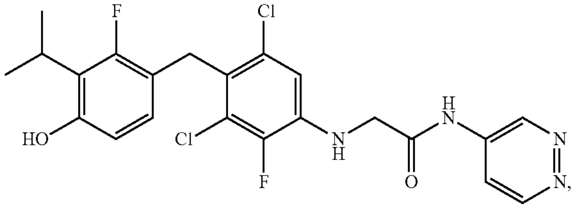
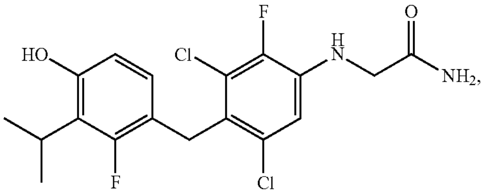
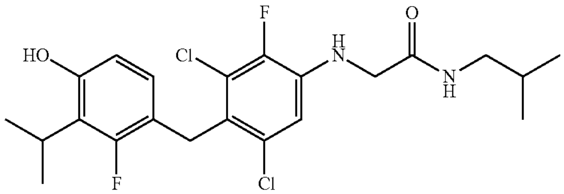
,
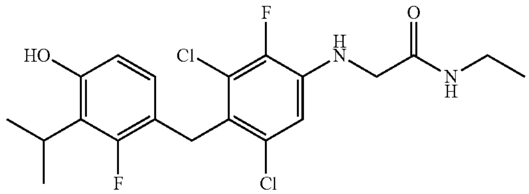
,
-continued
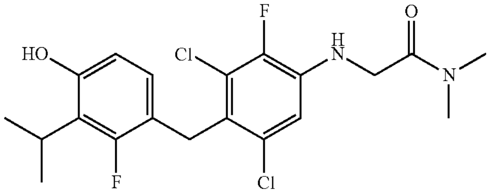
,
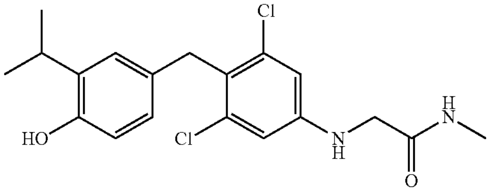
,
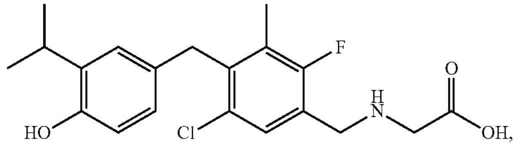
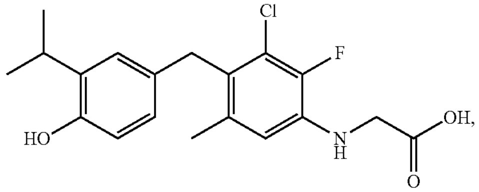
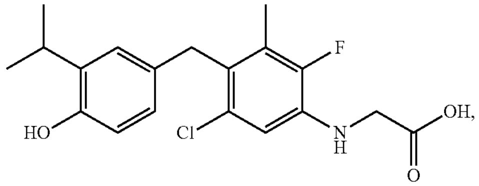
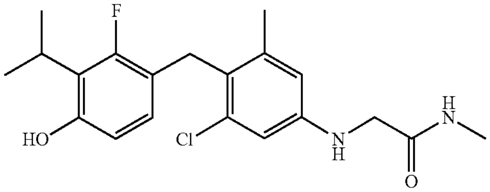
,
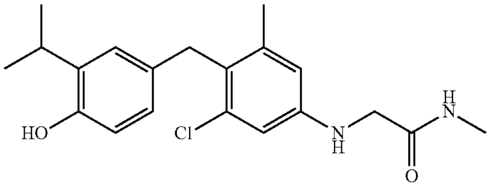
,
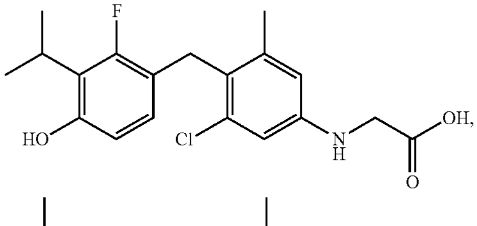
and
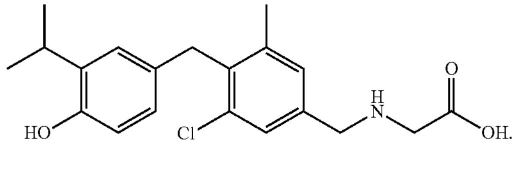 [SMILES: Cc1cc(CNCC(=O)O)cc(Cl)c1Cc1ccc(O)c(C(C)C)c1]
13. A pharmaceutical composition comprising a compound of claim 1, or a hydrate, solvate, isotope, or pharmaceutically acceptable salt thereof, and a pharmaceutically acceptable excipient.

14. A method of treating a subject having a neurodegenerative disease comprising administering to the subject in need thereof a pharmaceutically effective amount of the compound of claim 1, or a pharmaceutically salt or composition thereof, wherein the neurodegenerative disease is multiple sclerosis, MCT8 deficiency, X-linked adrenoleukodystrophy (ALD), amyotrophic lateral sclerosis (ALS), Alzheimer's disease, frontotemporal dementia, lacunar stroke, adult Refsum disease, Alexander disease, Balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, idiopathic inflammatory demyelinating disease, infantile Refsum disease, Krabbe disease, Leber hereditary optic neuropathy, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, or Zellweger syndrome.

* * * * *